US009151756B2

(12) United States Patent
Grandi et al.

(10) Patent No.: US 9,151,756 B2
(45) Date of Patent: Oct. 6, 2015

(54) CHLAMYDIA ANTIGENS

(71) Applicant: Novartis AG, Basel (CH)

(72) Inventors: Guido Grandi, segrate (IT); Renata Maria Grifantini, Siena (IT); Oretta Finco, Siena (IT)

(73) Assignee: Glaxosmithkline Biologicals SA, Rixensart (BE)

( * ) Notice: Subject to any disclaimer, the term of this patent is extended or adjusted under 35 U.S.C. 154(b) by 0 days.

(21) Appl. No.: 14/035,750

(22) Filed: Sep. 24, 2013

(65) Prior Publication Data

US 2014/0093510 A1 Apr. 3, 2014

Related U.S. Application Data

(63) Continuation of application No. 13/255,002, filed as application No. PCT/IB2010/050988 on Mar. 8, 2010, now Pat. No. 8,568,732.

(60) Provisional application No. 61/157,921, filed on Mar. 6, 2009.

(51) Int. Cl.

| | |
|---|---|
| ***A61K 39/118*** | (2006.01) |
| ***C07K 14/195*** | (2006.01) |
| ***G01N 33/569*** | (2006.01) |
| ***A61K 39/395*** | (2006.01) |
| *A61K 39/00* | (2006.01) |

(52) U.S. Cl.

CPC ........ *G01N 33/56927* (2013.01); *A61K 39/118* (2013.01); *A61K 39/3955* (2013.01); *A61K 2039/543* (2013.01); *A61K 2039/545* (2013.01); *A61K 2039/55544* (2013.01); *A61K 2039/55561* (2013.01)

(58) Field of Classification Search

CPC .................. A61K 39/118; A61K 2039/55544; A61K 2039/55561; A61K 2039/543; A61K 2039/545; A61K 39/3955; A61K 2039/522; A61K 2039/523; A61K 2039/55505; A61K 2039/6068; A61K 39/00; C07K 14/295; C07K 14/245

USPC ........ 424/164.1, 197.11, 263.1, 9.1; 530/350, 530/324, 300, 325, 326, 327, 328, 387.9, 530/389.5

See application file for complete search history.

(56) References Cited

U.S. PATENT DOCUMENTS

| | | | |
|---|---|---|---|
| 6,248,329 B1 | 6/2001 | Chandrashekar et al. | |
| 7,041,490 B1 * | 5/2006 | Griffais et al. ............ | 435/252.3 |

FOREIGN PATENT DOCUMENTS

| | | |
|---|---|---|
| WO | WO 99/27105 | 6/1999 |
| WO | WO 99/28475 | 6/1999 |
| WO | WO 00/27994 | 5/2000 |
| WO | WO 00/34483 | 6/2000 |
| WO | WO 00/37494 | 6/2000 |
| WO | WO 00/46359 | 8/2000 |
| WO | WO 00/66739 | 11/2000 |
| WO | WO 01/21804 | 3/2001 |
| WO | WO 01/21811 | 3/2001 |
| WO | WO 01/40474 | 6/2001 |
| WO | WO 01/46224 | 6/2001 |
| WO | WO 01/81379 | 11/2001 |
| WO | WO 01/85972 | 11/2001 |
| WO | WO 02/02606 | 1/2002 |
| WO | WO 02/08267 | 1/2002 |
| WO | WO 2007/110700 | 10/2007 |
| WO | WO 2009/109860 | 9/2009 |

OTHER PUBLICATIONS

Goodall et al., "Identification of Chlamydia Trachomatis Antigens Recongnized by Human CD4+ T Lymphocytes by Screening an Expression Library," Eur. J. Immunol. 31(5):1513-1522 (2001).

Goodall et al., "Recognition of the 60 Kilodalton Cysteine-Rich Outer Membrane Protein OMP2 by CD4+ T Cells From Humans Infected With Chlamydia Trachomatis," Clin. Exp. Immunol. , 126(3):488-493 (2001).

Hassell et al., "Identification of T-Call Stimulatory Antigens of Chlamydia Trachomatis Using Synovial Fluid-Derived T-Cell Clones," Immunology, 79(4):513-519 (1993).

Kalman et al., "Comparative Genomes of Chlamydia Pneumoniae and C. Trachomatis," Nature Genetics, vol. 21, pp. 385-389 (1999).

Stephens et al., "Genome Sequence of an Obligate Intracellular Pathogen of Humans: Chlamydia Trachomatis," Science, American Association for the Advancement of Science, 282(5389):754-759 (1998).

"Putative Uncharacterized Protein", XP002585081, Database Accession No. 084738, Nov. 11, 1998.

Li et al. (Proc. Natl. Acad. Sci. USA 77:3211-3214 (1980).

Brunham, R. C. in Chlamydia: Intracellular Biology, Pathogenesis, and Immunity ed. Stephens, 211-238 American Society for Microbiology Press, Washington DC, 1999.

Read et al 2000 Nucleic Acids Res. 28, 1397-1406.

Caldwell et al 2003. J. Clin. Invest. 111, 1757-1769.

Lederman et al. (Molecular Immunology 28:1171-1181, 1991).

* cited by examiner

*Primary Examiner* — Padma V Baskar

(74) *Attorney, Agent, or Firm* — Roberta L. Robins; Robins Law Group

(57) ABSTRACT

The invention provides *Chlamydia* antigens for use in the treatment, prevention and/or diagnosis of *Chlamydia* infection. In particular, the invention provides antigens CT733, CT153, CT601, CT279, CT443, CT372, CT456, CT381, CT255, CT341, CT716, CT745, CT387, CT812, CT869, CT166, CT175, CT163, CT214, CT721, CT127, CT043, CT823 and/or CT600 from *C. trachomatis* for the treatment, prevention or diagnosis of *Chlamydia* infection.

6 Claims, 12 Drawing Sheets

FIGURE 1
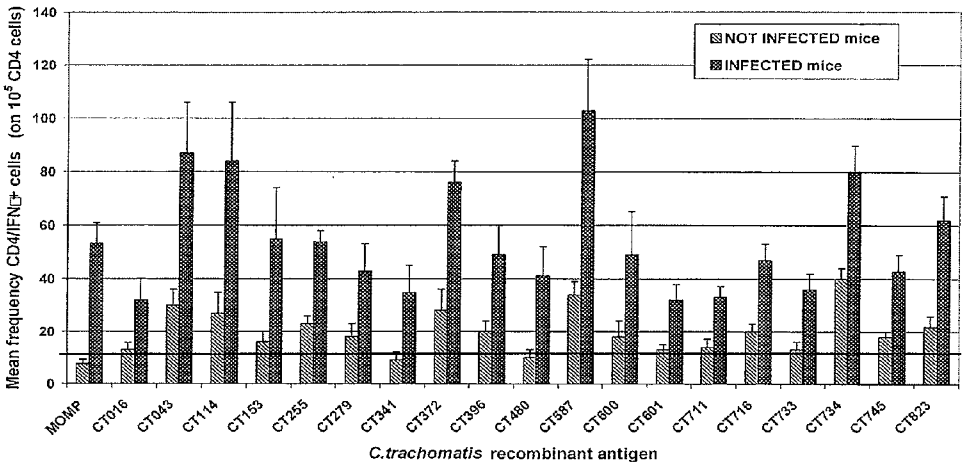
FIGURE 2
FIGURE 2A
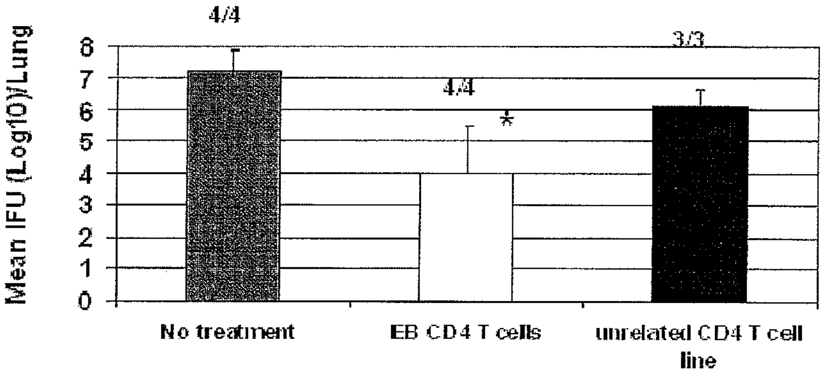

FIGURE 10
FIGURE 10A
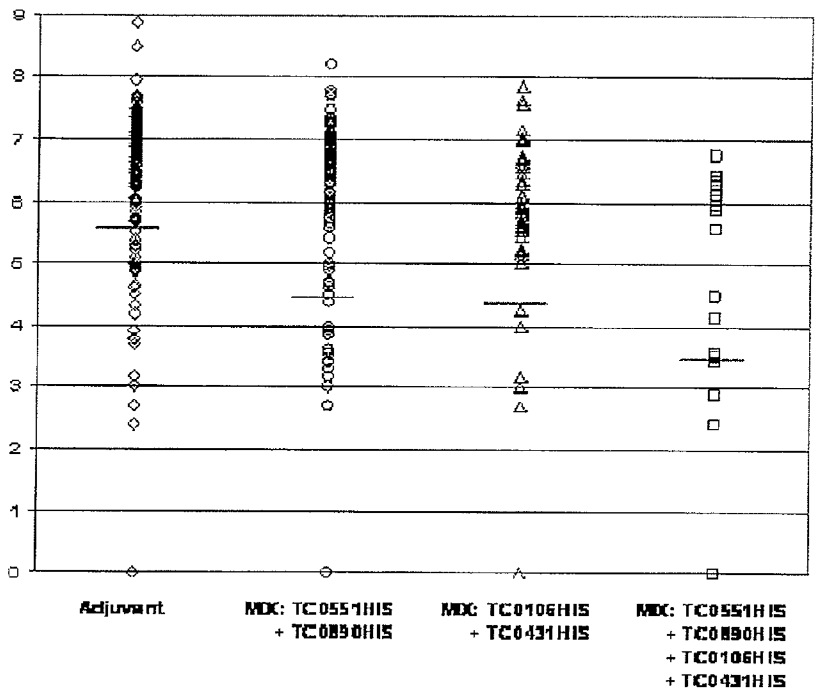
FIGURE 10B
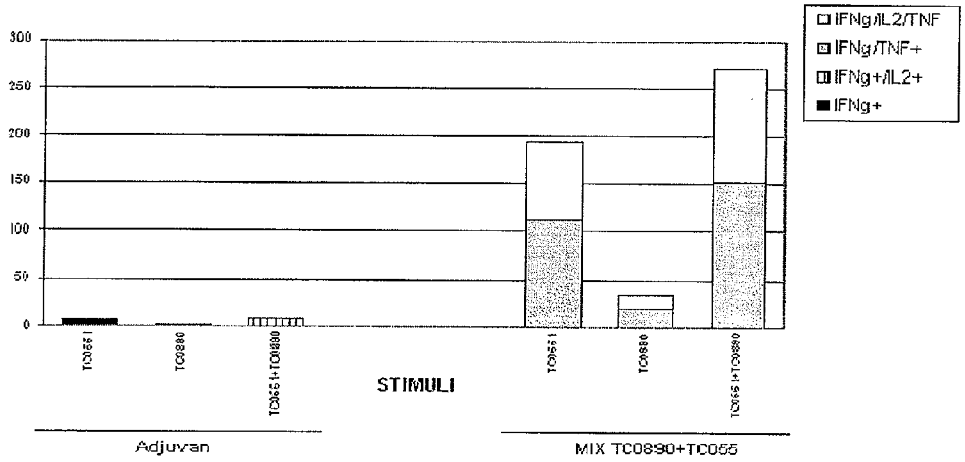

FIGURE 12
FIGURE 12A
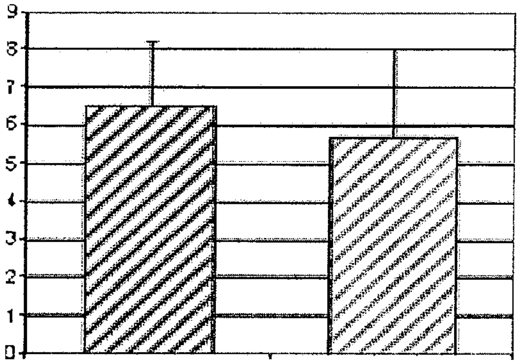
FIGURE 12B
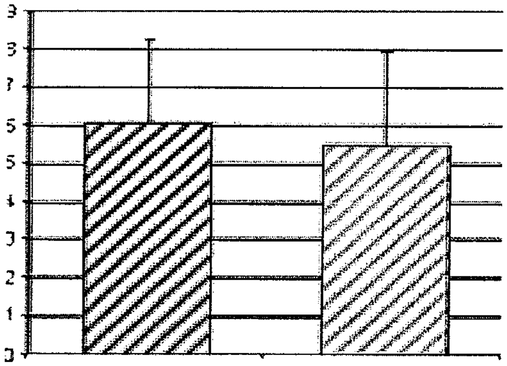
FIGURE 12C
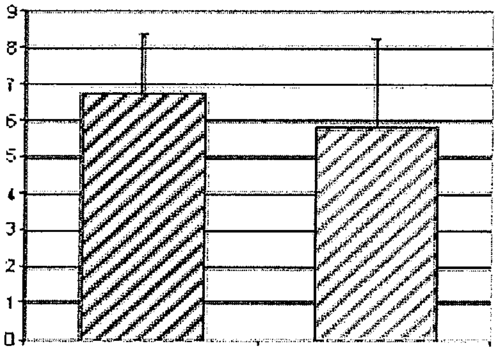
FIGURE 12D
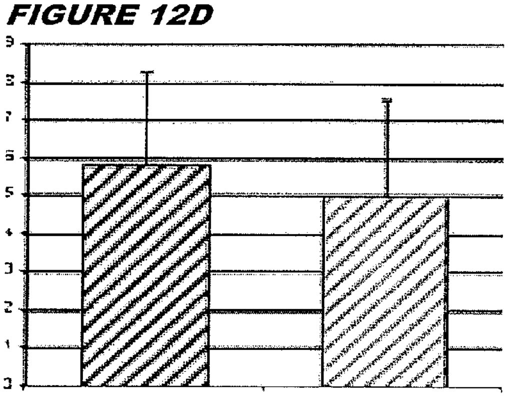
FIGURE 12E
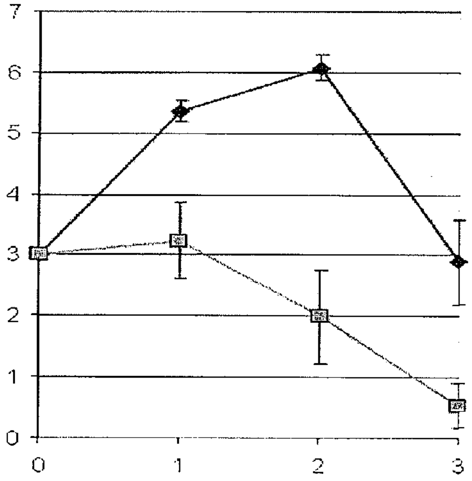

SEQUENCE LISTING

<160> NUMBER OF SEQ ID NOS: 171

<210> SEQ ID NO 1
<211> LENGTH: 1347
<212> TYPE: DNA
<213> ORGANISM: Chlamydia trachomatis

<400> SEQUENCE: 1
atgttaataa actttacctt tcgcaactgt cttttgttcc ttgtcacact gtctagtgtc 60
cctgttttct cagcacctca acctcgcgga acgcttccta gctcgaccac aaaaattgga 120
tcagaagttt ggattgaaca aaaagtccgc caatatccag agcttttatg gttagtagag 180
ccgtcctcta cgggagcctc tttaaaatct ccttcaggag ccatcttttc tccaacatta 240
ttccaaaaaa aggtccctgc tttcgatatc gcagtgcgca gtttgattca cttacattta 300
ttaatccagg gttcccgcca agcctatgct caactgatcc aactacagac cagcgaatcc 360
cctctaacat ttaagcaatt ccttgcattg cataagcaat taactctatt tttaaattcc 420
cctaaggaat tttatgactc tgttaaagtg ttagagacag ctatcgtctt acgtcactta 480
ggctgttcaa ctaaggctgt tgctgcgttt aaaccttatt tctcagaaat gcaaagagag 540
gctttttaca ctaaggctct gcatgtacta cacaccttcc cagagctaag cccatcattt 600
gctcgcctct ctccggagca gaaaactctc ttcttctcct tgagaaaatt ggcgaattac 660
gatgagttac tctcgctgac gaacacccca agttttcagc ttctgtctgc tgggcgctcg 720
caacgagctc ttttagctct ggacttgtac ctctatgctt tggattcctg tggagaacag 780
gggatgtcct ctcaattcca cacaaacttc gcacctctac agtccatgtt gcaacaatac 840
gctactgtag aagaggcctt ttctcgttat tttacttacc gagctaatcg attaggattt 900
gatggctctt ctcgatccga gatggcttta gtaagaatgg ccaccttgat gaacttgtct 960
ccttccgaag ctgcgatttt aaccacaagc ttcaaaaccc ttcctacaga agaagcggat 1020
actttgatca atagtttcta taccaataag ggcgattcgt tggctctttc tctgcgaggg 1080

```
ttgcctacac ttgtatccga actgacgcga actgcccatg gcaataccaa tgcagaagct   1140

cgatctcagc aaatttatgc aactacccta tcgctagtag taaagagtct gaaagcgcac   1200

aaagaaatgc taaacaagca aattctttct aaggaaattg ttttagattt ctcagaaact   1260

gcagcttctt gccaaggatt ggatatcttt tccgagaatg tcgctgttca aattcactta   1320

aatggaaccg ttagtatcca tttataa                                        1347


<210> SEQ ID NO 2
<211> LENGTH: 448
<212> TYPE: PRT
<213> ORGANISM: Chlamydia trachomatis

<400> SEQUENCE: 2

Met Leu Ile Asn Phe Thr Phe Arg Asn Cys Leu Leu Phe Leu Val Thr
1               5                   10                  15

Leu Ser Ser Val Pro Val Phe Ser Ala Pro Gln Pro Arg Gly Thr Leu
            20                  25                  30

Pro Ser Ser Thr Thr Lys Ile Gly Ser Glu Val Trp Ile Glu Gln Lys
        35                  40                  45

Val Arg Gln Tyr Pro Glu Leu Leu Trp Leu Val Glu Pro Ser Ser Thr
    50                  55                  60

Gly Ala Ser Leu Lys Ser Pro Ser Gly Ala Ile Phe Ser Pro Thr Leu
65                  70                  75                  80

Phe Gln Lys Lys Val Pro Ala Phe Asp Ile Ala Val Arg Ser Leu Ile
                85                  90                  95

His Leu His Leu Leu Ile Gln Gly Ser Arg Gln Ala Tyr Ala Gln Leu
            100                 105                 110

Ile Gln Leu Gln Thr Ser Glu Ser Pro Leu Thr Phe Lys Gln Phe Leu
        115                 120                 125

Ala Leu His Lys Gln Leu Thr Leu Phe Leu Asn Ser Pro Lys Glu Phe
    130                 135                 140

Tyr Asp Ser Val Lys Val Leu Glu Thr Ala Ile Val Leu Arg His Leu
145                 150                 155                 160

Gly Cys Ser Thr Lys Ala Val Ala Ala Phe Lys Pro Tyr Phe Ser Glu
                165                 170                 175

Met Gln Arg Glu Ala Phe Tyr Thr Lys Ala Leu His Val Leu His Thr
            180                 185                 190

Phe Pro Glu Leu Ser Pro Ser Phe Ala Arg Leu Ser Pro Glu Gln Lys
        195                 200                 205

Thr Leu Phe Phe Ser Leu Arg Lys Leu Ala Asn Tyr Asp Glu Leu Leu
    210                 215                 220

Ser Leu Thr Asn Thr Pro Ser Phe Gln Leu Leu Ser Ala Gly Arg Ser
225                 230                 235                 240

Gln Arg Ala Leu Leu Ala Leu Asp Leu Tyr Leu Tyr Ala Leu Asp Ser
                245                 250                 255

Cys Gly Glu Gln Gly Met Ser Ser Gln Phe His Thr Asn Phe Ala Pro
            260                 265                 270

Leu Gln Ser Met Leu Gln Gln Tyr Ala Thr Val Glu Glu Ala Phe Ser
        275                 280                 285

Arg Tyr Phe Thr Tyr Arg Ala Asn Arg Leu Gly Phe Asp Gly Ser Ser
    290                 295                 300

Arg Ser Glu Met Ala Leu Val Arg Met Ala Thr Leu Met Asn Leu Ser
305                 310                 315                 320

Pro Ser Glu Ala Ala Ile Leu Thr Thr Ser Phe Lys Thr Leu Pro Thr
```

```
                325                 330                 335

Glu Glu Ala Asp Thr Leu Ile Asn Ser Phe Tyr Thr Asn Lys Gly Asp
            340                 345                 350

Ser Leu Ala Leu Ser Leu Arg Gly Leu Pro Thr Leu Val Ser Glu Leu
        355                 360                 365

Thr Arg Thr Ala His Gly Asn Thr Asn Ala Glu Ala Arg Ser Gln Gln
    370                 375                 380

Ile Tyr Ala Thr Thr Leu Ser Leu Val Val Lys Ser Leu Lys Ala His
385                 390                 395                 400

Lys Glu Met Leu Asn Lys Gln Ile Leu Ser Lys Glu Ile Val Leu Asp
                405                 410                 415

Phe Ser Glu Thr Ala Ala Ser Cys Gln Gly Leu Asp Ile Phe Ser Glu
            420                 425                 430

Asn Val Ala Val Gln Ile His Leu Asn Gly Thr Val Ser Ile His Leu
        435                 440                 445


<210> SEQ ID NO 3
<211> LENGTH: 2433
<212> TYPE: DNA
<213> ORGANISM: Chlamydia trachomatis

<400> SEQUENCE: 3

atgactaagc cttctttctt atacgttatt caaccttttt ccgtatttaa tccacgatta     60

ggacgtttct ctacagactc agatacttat atcgaagaag aaaaccgcct agcatcgttc    120

attgagagtt tgccactgga gatcttcgat ataccttctt tcatggaaac cgcgatttcc    180

aatagcccct atattttatc ttgggagaca actaaagacg gcgctctgtt cactattctt    240

gaacccaaac tctcagcttg cgcagccact tgcctggtag ccccttctat acaaatgaaa    300

tccgatgcgg agctcctaga agaaattaag caagcgttat tacgcagctc tcatgacggt    360

gtgaaatatc gcatcaccag agaatccttc tctccagaaa agaaaactcc taaggttgct    420

ctagtcgatg acgatattga attgattcgc aatgtcgact tttgggtag agctgttgac     480

attgtcaaat tagaccctat taatattctg aataccgtaa gcgaagagaa tattctagat    540

tactctttta caagagaaac ggctcagctg agcgcggatg gtcgttttgg tattcctcca    600

gggactaagc tattccctaa accttctttt gatgtagaaa tcagtacctc cattttcgaa    660

gaaacaactt catttactcg aagtttttct gcatcggtta cttttagtgt accagacctc    720

gcggcgacta tgcctcttca aagccctccc atggtagaaa atggtcaaaa agaaatttgt    780

gtcattcaaa aacacttatt cccaagctac tctcctaaac tagtcgatat tgttaaacga    840

tacaaaagag aggctaagat cttgattaac aagcttgcct ttggaatgtt atggcgacat    900

cgggctaaaa gccaaatcct caccgaggga agcgtacgtc tagacttaca aggattcaca    960

gaatcgaagt acaattacca gattcaagta ggatcccata cgattgcagc tgtattaatc   1020

gatatggata tttccaagat tcaatccaaa tcagaacaag cttatgcaat taggaaaatc   1080

aaatcaggct ttcaacgtag cttggatgac tatcatattt atcaaattga aagaaaacaa   1140

accttttctt tttctccgaa gcatcgcagc ctctcatcca catcccattc cgaagattct   1200

gatttggatc tttctgaagc agccgccttt tcaggaagtc ttacctgcga gtttgtaaaa   1260

aaaagcactc aacatgccaa gaataccgtc acatgttcca cagccgctca ttccctatac   1320

acactcaaag aagatgacag ctcgaacccc tctgaaaaac gattagatag ttgtttccgc   1380

aattggattg aaaacaaact aagcgccaat tctccagatt cctggtcagc gtttattcaa   1440
```

-continued

```
aaattcggaa cacactatat tgcatcagca acttttggag ggataggttt ccaagtgctc   1500

aaactatctt ttgaacaggt ggaggatcta catagcaaaa agatctcctt agaaaccgca   1560

gcagccaact ctctattaaa aggttctgta tccagcagca cagaatctgg atactccagc   1620

tatagctcca cgtcttcttc tcatacggta tttttaggag gaacggtctt accttcggtt   1680

catgatgaac gtttagactt taaagattgg tcggaaagtg tgcacctgga acctgttcct   1740

atccaggttt ctttacaacc tataacgaat ttactagttc ctctccattt tcctaatatc   1800

ggtgctgcag agctctctaa taaacgagaa tctcttcaac aagcgattcg agtctatctc   1860

aaagaacata aagtagatga gcaaggagaa cgtactacat ttacatcagg aatcgataat   1920

ccttcttcct ggtttacctt agaagctgcc cactctcctc ttatagtcag tactccttac   1980

attgcttcgt ggtctacgct tccttatttg ttcccaacat taagagaacg ttcttcggca   2040

acccctatcg ttttctattt ttgtgtagat aataatgaac atgcttcgca aaaaatatta   2100

aaccaatcgt attgcttcct cgggtccttg cctattcgac aaaaaatttt tggtagcgaa   2160

tttgctagtt tcccctatct atctttctat ggaaatgcaa aagaggcgta ctttgataac   2220

acgtactacc caacgcgttg tgggtggatt gttgaaaagt taaatactac acaagatcaa   2280

ttcctccggg atggagacga ggtgcgacta aaacatgttt ccagcggaaa gtatctagca   2340

acaactcctc ttaaggatac ccatggtaca ctcacgcgta caacgaactg tgaagatgct   2400

atctttatta ttaaaaaatc ttcaggttat tga                                2433
```

<210> SEQ ID NO 4
<211> LENGTH: 810
<212> TYPE: PRT
<213> ORGANISM: Chlamydia trachomatis

<400> SEQUENCE: 4

```
Met Thr Lys Pro Ser Phe Leu Tyr Val Ile Gln Pro Phe Ser Val Phe
1               5                   10                  15

Asn Pro Arg Leu Gly Arg Phe Ser Thr Asp Ser Asp Thr Tyr Ile Glu
            20                  25                  30

Glu Glu Asn Arg Leu Ala Ser Phe Ile Glu Ser Leu Pro Leu Glu Ile
        35                  40                  45

Phe Asp Ile Pro Ser Phe Met Glu Thr Ala Ile Ser Asn Ser Pro Tyr
    50                  55                  60

Ile Leu Ser Trp Glu Thr Thr Lys Asp Gly Ala Leu Phe Thr Ile Leu
65                  70                  75                  80

Glu Pro Lys Leu Ser Ala Cys Ala Ala Thr Cys Leu Val Ala Pro Ser
                85                  90                  95

Ile Gln Met Lys Ser Asp Ala Glu Leu Leu Glu Glu Ile Lys Gln Ala
            100                 105                 110

Leu Leu Arg Ser Ser His Asp Gly Val Lys Tyr Arg Ile Thr Arg Glu
        115                 120                 125

Ser Phe Ser Pro Glu Lys Lys Thr Pro Lys Val Ala Leu Val Asp Asp
    130                 135                 140

Asp Ile Glu Leu Ile Arg Asn Val Asp Phe Leu Gly Arg Ala Val Asp
145                 150                 155                 160

Ile Val Lys Leu Asp Pro Ile Asn Ile Leu Asn Thr Val Ser Glu Glu
                165                 170                 175

Asn Ile Leu Asp Tyr Ser Phe Thr Arg Glu Thr Ala Gln Leu Ser Ala
            180                 185                 190

Asp Gly Arg Phe Gly Ile Pro Pro Gly Thr Lys Leu Phe Pro Lys Pro
```

```
        195                 200                 205

Ser Phe Asp Val Glu Ile Ser Thr Ser Ile Phe Glu Glu Thr Thr Ser
    210                 215                 220

Phe Thr Arg Ser Phe Ser Ala Ser Val Thr Phe Ser Val Pro Asp Leu
225                 230                 235                 240

Ala Ala Thr Met Pro Leu Gln Ser Pro Pro Met Val Glu Asn Gly Gln
                245                 250                 255

Lys Glu Ile Cys Val Ile Gln Lys His Leu Phe Pro Ser Tyr Ser Pro
            260                 265                 270

Lys Leu Val Asp Ile Val Lys Arg Tyr Lys Arg Glu Ala Lys Ile Leu
        275                 280                 285

Ile Asn Lys Leu Ala Phe Gly Met Leu Trp Arg His Arg Ala Lys Ser
    290                 295                 300

Gln Ile Leu Thr Glu Gly Ser Val Arg Leu Asp Leu Gln Gly Phe Thr
305                 310                 315                 320

Glu Ser Lys Tyr Asn Tyr Gln Ile Gln Val Gly Ser His Thr Ile Ala
                325                 330                 335

Ala Val Leu Ile Asp Met Asp Ile Ser Lys Ile Gln Ser Lys Ser Glu
            340                 345                 350

Gln Ala Tyr Ala Ile Arg Lys Ile Lys Ser Gly Phe Gln Arg Ser Leu
        355                 360                 365

Asp Asp Tyr His Ile Tyr Gln Ile Glu Arg Lys Gln Thr Phe Ser Phe
    370                 375                 380

Ser Pro Lys His Arg Ser Leu Ser Ser Thr Ser His Ser Glu Asp Ser
385                 390                 395                 400

Asp Leu Asp Leu Ser Glu Ala Ala Ala Phe Ser Gly Ser Leu Thr Cys
                405                 410                 415

Glu Phe Val Lys Lys Ser Thr Gln His Ala Lys Asn Thr Val Thr Cys
            420                 425                 430

Ser Thr Ala Ala His Ser Leu Tyr Thr Leu Lys Glu Asp Asp Ser Ser
        435                 440                 445

Asn Pro Ser Glu Lys Arg Leu Asp Ser Cys Phe Arg Asn Trp Ile Glu
    450                 455                 460

Asn Lys Leu Ser Ala Asn Ser Pro Asp Ser Trp Ser Ala Phe Ile Gln
465                 470                 475                 480

Lys Phe Gly Thr His Tyr Ile Ala Ser Ala Thr Phe Gly Gly Ile Gly
                485                 490                 495

Phe Gln Val Leu Lys Leu Ser Phe Glu Gln Val Glu Asp Leu His Ser
            500                 505                 510

Lys Lys Ile Ser Leu Glu Thr Ala Ala Ala Asn Ser Leu Leu Lys Gly
        515                 520                 525

Ser Val Ser Ser Ser Thr Glu Ser Gly Tyr Ser Ser Tyr Ser Ser Thr
    530                 535                 540

Ser Ser Ser His Thr Val Phe Leu Gly Gly Thr Val Leu Pro Ser Val
545                 550                 555                 560

His Asp Glu Arg Leu Asp Phe Lys Asp Trp Ser Glu Ser Val His Leu
                565                 570                 575

Glu Pro Val Pro Ile Gln Val Ser Leu Gln Pro Ile Thr Asn Leu Leu
            580                 585                 590

Val Pro Leu His Phe Pro Asn Ile Gly Ala Ala Glu Leu Ser Asn Lys
        595                 600                 605

Arg Glu Ser Leu Gln Gln Ala Ile Arg Val Tyr Leu Lys Glu His Lys
    610                 615                 620
```

Val Asp Glu Gln Gly Glu Arg Thr Thr Phe Thr Ser Gly Ile Asp Asn
625 630 635 640

Pro Ser Ser Trp Phe Thr Leu Glu Ala Ala His Ser Pro Leu Ile Val
645 650 655

Ser Thr Pro Tyr Ile Ala Ser Trp Ser Thr Leu Pro Tyr Leu Phe Pro
660 665 670

Thr Leu Arg Glu Arg Ser Ser Ala Thr Pro Ile Val Phe Tyr Phe Cys
675 680 685

Val Asp Asn Asn Glu His Ala Ser Gln Lys Ile Leu Asn Gln Ser Tyr
690 695 700

Cys Phe Leu Gly Ser Leu Pro Ile Arg Gln Lys Ile Phe Gly Ser Glu
705 710 715 720

Phe Ala Ser Phe Pro Tyr Leu Ser Phe Tyr Gly Asn Ala Lys Glu Ala
725 730 735

Tyr Phe Asp Asn Thr Tyr Tyr Pro Thr Arg Cys Gly Trp Ile Val Glu
740 745 750

Lys Leu Asn Thr Thr Gln Asp Gln Phe Leu Arg Asp Gly Asp Glu Val
755 760 765

Arg Leu Lys His Val Ser Ser Gly Lys Tyr Leu Ala Thr Thr Pro Leu
770 775 780

Lys Asp Thr His Gly Thr Leu Thr Arg Thr Thr Asn Cys Glu Asp Ala
785 790 795 800

Ile Phe Ile Ile Lys Lys Ser Ser Gly Tyr
805 810

<210> SEQ ID NO 5
<211> LENGTH: 603
<212> TYPE: DNA
<213> ORGANISM: Chlamydia trachomatis

<400> SEQUENCE: 5
atgctcgcta atcgcttatt cttaataacc cttttagggt taagttcgtc tgtttacggc 60
gcaggtaaag caccgtcttt gcaggctatt ctagccgaag tcgaagacac ctcctctcgt 120
ctacacgctc atcacaatga gcttgctatg atctctgaac gcctcgatga gcaagacacg 180
aaactacagc aactttcgtc aacacaagat cataacctac ctcgacaagt tcagcgacta 240
gaaacggacc aaaaagcttt ggcaaaaaca ctggcgattc tttcgcaatc cgtccaagat 300
attcggtctt ctgtacaaaa taaattacaa gaaatccaac aagaacaaaa aaaattagca 360
caaaatttgc gagcgcttcg taactcttta caagctctcg ttgatggctc ttctccagaa 420
aattatattg atttcctaac tggtgaaacc ccggaacata ttcatattgt taaacaagga 480
gagaccctga gcaagatcgc gagtaaatat aacatccccg tcgtagaatt aaaaaaactt 540
aataaactaa attcggatac tatttttaca gatcaaagaa ttcgccttcc gaaaaagaaa 600
tag 603

<210> SEQ ID NO 6
<211> LENGTH: 200
<212> TYPE: PRT
<213> ORGANISM: Chlamydia trachomatis

<400> SEQUENCE: 6

Met Leu Ala Asn Arg Leu Phe Leu Ile Thr Leu Leu Gly Leu Ser Ser
1 5 10 15

Ser Val Tyr Gly Ala Gly Lys Ala Pro Ser Leu Gln Ala Ile Leu Ala

-continued

```
            20                  25                  30

Glu Val Glu Asp Thr Ser Ser Arg Leu His Ala His His Asn Glu Leu
        35                  40                  45

Ala Met Ile Ser Glu Arg Leu Asp Glu Gln Asp Thr Lys Leu Gln Gln
    50                  55                  60

Leu Ser Ser Thr Gln Asp His Asn Leu Pro Arg Gln Val Gln Arg Leu
65                  70                  75                  80

Glu Thr Asp Gln Lys Ala Leu Ala Lys Thr Leu Ala Ile Leu Ser Gln
                85                  90                  95

Ser Val Gln Asp Ile Arg Ser Ser Val Gln Asn Lys Leu Gln Glu Ile
            100                 105                 110

Gln Gln Glu Gln Lys Lys Leu Ala Gln Asn Leu Arg Ala Leu Arg Asn
        115                 120                 125

Ser Leu Gln Ala Leu Val Asp Gly Ser Ser Pro Glu Asn Tyr Ile Asp
    130                 135                 140

Phe Leu Thr Gly Glu Thr Pro Glu His Ile His Ile Val Lys Gln Gly
145                 150                 155                 160

Glu Thr Leu Ser Lys Ile Ala Ser Lys Tyr Asn Ile Pro Val Val Glu
                165                 170                 175

Leu Lys Lys Leu Asn Lys Leu Asn Ser Asp Thr Ile Phe Thr Asp Gln
            180                 185                 190

Arg Ile Arg Leu Pro Lys Lys Lys
        195                 200
```

<210> SEQ ID NO 7
<211> LENGTH: 951
<212> TYPE: DNA
<213> ORGANISM: Chlamydia trachomatis

<400> SEQUENCE: 7

```
atggcatcca agtctcgcca ttatcttaat cagccttggt acattatctt attcatcttt     60

gttcttagtt taattgctgg taccctcctg tcttctgtgt attatgtcct tgcacctatc    120

caacagcaag ctgcggaatt cgatcgcaat caacaaatgc taatggctgc acaagtaatt    180

tcttccgata acacattcca agtctatgaa aagggagatt ggcacccagc cctatataat    240

actaaaaagc agttgctaga gatctcctct actcctccta aagtaaccgt gacaacttta    300

agctcatatt ttcaaaactt tgttagagtc ttgcttacag atacacaagg aaatctttct    360

tcattcgaag accataatct caatctagaa gaatttttat ctcaaccaac tcctgtaata    420

catggtcttg ccctttatgt ggtctacgct atcctacaca acgatgcagc ttcctctaaa    480

ttatctgctt cccaagtagc gaaaaatcca acagctatag aatctatagt tcttcctata    540

gaaggttttg gtttgtgggg acctatctat ggattccttg ctctagaaaa agacgggaat    600

actgttcttg gtacttcttg gtatcaacat ggcgagactc ctggattagg agcaaatatc    660

gctaaccctc aatggcaaaa aaatttcaga ggcaaaaaag tatttctagt ctcagcttct    720

ggagaaacag attttgctaa gacaacccta ggactggaag ttataaaagg atctgtatct    780

gcagcattag gagactcacc taaagctgct tcttccatcg acggaatttc aggagctact    840

ttgacttgta atggtgttac cgaatccttc tctcattctc tagctcccta ccgcgctttg    900

ttgactttct tcgccaactc taaacctagt ggagagtctc atgaccacta a             951
```

<210> SEQ ID NO 8
<211> LENGTH: 316
<212> TYPE: PRT

<213> ORGANISM: Chlamydia trachomatis

<400> SEQUENCE: 8

```
Met Ala Ser Lys Ser Arg His Tyr Leu Asn Gln Pro Trp Tyr Ile Ile
1               5                   10                  15

Leu Phe Ile Phe Val Leu Ser Leu Ile Ala Gly Thr Leu Leu Ser Ser
            20                  25                  30

Val Tyr Tyr Val Leu Ala Pro Ile Gln Gln Gln Ala Ala Glu Phe Asp
        35                  40                  45

Arg Asn Gln Gln Met Leu Met Ala Ala Gln Val Ile Ser Ser Asp Asn
    50                  55                  60

Thr Phe Gln Val Tyr Glu Lys Gly Asp Trp His Pro Ala Leu Tyr Asn
65                  70                  75                  80

Thr Lys Lys Gln Leu Leu Glu Ile Ser Ser Thr Pro Pro Lys Val Thr
                85                  90                  95

Val Thr Thr Leu Ser Ser Tyr Phe Gln Asn Phe Val Arg Val Leu Leu
            100                 105                 110

Thr Asp Thr Gln Gly Asn Leu Ser Ser Phe Glu Asp His Asn Leu Asn
        115                 120                 125

Leu Glu Glu Phe Leu Ser Gln Pro Thr Pro Val Ile His Gly Leu Ala
    130                 135                 140

Leu Tyr Val Val Tyr Ala Ile Leu His Asn Asp Ala Ala Ser Ser Lys
145                 150                 155                 160

Leu Ser Ala Ser Gln Val Ala Lys Asn Pro Thr Ala Ile Glu Ser Ile
                165                 170                 175

Val Leu Pro Ile Glu Gly Phe Gly Leu Trp Gly Pro Ile Tyr Gly Phe
            180                 185                 190

Leu Ala Leu Glu Lys Asp Gly Asn Thr Val Leu Gly Thr Ser Trp Tyr
        195                 200                 205

Gln His Gly Glu Thr Pro Gly Leu Gly Ala Asn Ile Ala Asn Pro Gln
    210                 215                 220

Trp Gln Lys Asn Phe Arg Gly Lys Lys Val Phe Leu Val Ser Ala Ser
225                 230                 235                 240

Gly Glu Thr Asp Phe Ala Lys Thr Thr Leu Gly Leu Glu Val Ile Lys
                245                 250                 255

Gly Ser Val Ser Ala Ala Leu Gly Asp Ser Pro Lys Ala Ala Ser Ser
            260                 265                 270

Ile Asp Gly Ile Ser Gly Ala Thr Leu Thr Cys Asn Gly Val Thr Glu
        275                 280                 285

Ser Phe Ser His Ser Leu Ala Pro Tyr Arg Ala Leu Leu Thr Phe Phe
    290                 295                 300

Ala Asn Ser Lys Pro Ser Gly Glu Ser His Asp His
305                 310                 315
```

<210> SEQ ID NO 9
<211> LENGTH: 1662
<212> TYPE: DNA
<213> ORGANISM: Chlamydia trachomatis

<400> SEQUENCE: 9

```
atgcgaatag gagatcctat gaacaaactc atcagacgag cagtgacgat cttcgcggtg      60

actagtgtgg cgagtttatt tgctagcggg gtgttagaga cctctatggc agagtctctc     120

tctacaaacg ttattagctt agctgacacc aaagcgaaag acaacacttc tcataaaagc     180

aaaaaagcaa gaaaaaacca cagcaaagag actcccgtag accgtaaaga ggttgctccg     240
```

```
gttcatgagt ctaaagctac aggacctaaa caggattctt gctttggcag aatgtataca    300

gtcaaagtta atgatgatcg caatgttgaa atcacacaag ctgttcctga atatgctacg    360

gtaggatctc cctatcctat tgaaattact gctacaggta aaagggattg tgttgatgtt    420

atcattactc agcaattacc atgtgaagca gagttcgtac gcagtgatcc agcgacaact    480

cctactgctg atggtaagct agtttggaaa attgaccgct taggacaagg cgaaaagagt    540

aaaattactg tatgggtaaa acctcttaaa gaaggttgct gctttacagc tgcaacagta    600

tgcgcttgtc cagagatccg ttcggttaca aaatgtggac aacctgctat ctgtgttaaa    660

caagaaggcc cagagaatgc ttgtttgcgt tgcccagtag tttacaaaat taatatagtg    720

aaccaaggaa cagcaacagc tcgtaacgtt gttgttgaaa atcctgttcc agatggttac    780

gctcattctt ctggacagcg tgtactgacg tttactcttg gagatatgca acctggagag    840

cacagaacaa ttactgtaga gttttgtccg cttaaacgtg gtcgtgctac caatatagca    900

acggtttctt actgtggagg acataaaaat acagcaagcg taacaactgt gatcaacgag    960

ccttgcgtac aagtaagtat tgcaggagca gattggtctt atgtttgtaa gcctgtagaa   1020

tatgtgatct ccgtttccaa tcctggagat cttgtgttgc gagatgtcgt cgttgaagac   1080

actctttctc ccggagtcac agttcttgaa gctgcaggag ctcaaatttc ttgtaataaa   1140

gtagtttgga ctgtgaaaga actgaatcct ggagagtctc tacagtataa agttctagta   1200

agagcacaaa ctcctggaca attcacaaat aatgttgttg tgaagagctg ctctgactgt   1260

ggtacttgta cttcttgcgc agaagcgaca acttactgga aaggagttgc tgctactcat   1320

atgtgcgtag tagatacttg tgaccctgtt tgtgtaggag aaaatactgt ttaccgtatt   1380

tgtgtcacca acagaggttc tgcagaagat acaaatgttt ctttaatgct taaattctct   1440

aaagaactgc aacctgtatc cttctctgga ccaactaaag gaacgattac aggcaataca   1500

gtagtattcg attcgttacc tagattaggt tctaaagaaa ctgtagagtt ttctgtaaca   1560

ttgaaagcag tatcagctgg agatgctcgt ggggaagcga ttctttcttc cgatacattg   1620

actgttccag tttctgatac agagaataca cacatctatt aa                      1662
```

<210> SEQ ID NO 10
<211> LENGTH: 553
<212> TYPE: PRT
<213> ORGANISM: Chlamydia trachomatis

<400> SEQUENCE: 10

```
Met Arg Ile Gly Asp Pro Met Asn Lys Leu Ile Arg Arg Ala Val Thr
1               5                   10                  15

Ile Phe Ala Val Thr Ser Val Ala Ser Leu Phe Ala Ser Gly Val Leu
            20                  25                  30

Glu Thr Ser Met Ala Glu Ser Leu Ser Thr Asn Val Ile Ser Leu Ala
        35                  40                  45

Asp Thr Lys Ala Lys Asp Asn Thr Ser His Lys Ser Lys Lys Ala Arg
    50                  55                  60

Lys Asn His Ser Lys Glu Thr Pro Val Asp Arg Lys Glu Val Ala Pro
65                  70                  75                  80

Val His Glu Ser Lys Ala Thr Gly Pro Lys Gln Asp Ser Cys Phe Gly
                85                  90                  95

Arg Met Tyr Thr Val Lys Val Asn Asp Asp Arg Asn Val Glu Ile Thr
            100                 105                 110

Gln Ala Val Pro Glu Tyr Ala Thr Val Gly Ser Pro Tyr Pro Ile Glu
```

-continued

```
        115                 120                 125

Ile Thr Ala Thr Gly Lys Arg Asp Cys Val Asp Val Ile Ile Thr Gln
    130                 135                 140

Gln Leu Pro Cys Glu Ala Glu Phe Val Arg Ser Asp Pro Ala Thr Thr
145                 150                 155                 160

Pro Thr Ala Asp Gly Lys Leu Val Trp Lys Ile Asp Arg Leu Gly Gln
                165                 170                 175

Gly Glu Lys Ser Lys Ile Thr Val Trp Val Lys Pro Leu Lys Glu Gly
            180                 185                 190

Cys Cys Phe Thr Ala Ala Thr Val Cys Ala Cys Pro Glu Ile Arg Ser
        195                 200                 205

Val Thr Lys Cys Gly Gln Pro Ala Ile Cys Val Lys Gln Glu Gly Pro
    210                 215                 220

Glu Asn Ala Cys Leu Arg Cys Pro Val Val Tyr Lys Ile Asn Ile Val
225                 230                 235                 240

Asn Gln Gly Thr Ala Thr Ala Arg Asn Val Val Val Glu Asn Pro Val
                245                 250                 255

Pro Asp Gly Tyr Ala His Ser Ser Gly Gln Arg Val Leu Thr Phe Thr
            260                 265                 270

Leu Gly Asp Met Gln Pro Gly Glu His Arg Thr Ile Thr Val Glu Phe
        275                 280                 285

Cys Pro Leu Lys Arg Gly Arg Ala Thr Asn Ile Ala Thr Val Ser Tyr
    290                 295                 300

Cys Gly Gly His Lys Asn Thr Ala Ser Val Thr Thr Val Ile Asn Glu
305                 310                 315                 320

Pro Cys Val Gln Val Ser Ile Ala Gly Ala Asp Trp Ser Tyr Val Cys
                325                 330                 335

Lys Pro Val Glu Tyr Val Ile Ser Val Ser Asn Pro Gly Asp Leu Val
            340                 345                 350

Leu Arg Asp Val Val Val Glu Asp Thr Leu Ser Pro Gly Val Thr Val
        355                 360                 365

Leu Glu Ala Ala Gly Ala Gln Ile Ser Cys Asn Lys Val Val Trp Thr
    370                 375                 380

Val Lys Glu Leu Asn Pro Gly Glu Ser Leu Gln Tyr Lys Val Leu Val
385                 390                 395                 400

Arg Ala Gln Thr Pro Gly Gln Phe Thr Asn Asn Val Val Val Lys Ser
                405                 410                 415

Cys Ser Asp Cys Gly Thr Cys Thr Ser Cys Ala Glu Ala Thr Thr Tyr
            420                 425                 430

Trp Lys Gly Val Ala Ala Thr His Met Cys Val Val Asp Thr Cys Asp
        435                 440                 445

Pro Val Cys Val Gly Glu Asn Thr Val Tyr Arg Ile Cys Val Thr Asn
    450                 455                 460

Arg Gly Ser Ala Glu Asp Thr Asn Val Ser Leu Met Leu Lys Phe Ser
465                 470                 475                 480

Lys Glu Leu Gln Pro Val Ser Phe Ser Gly Pro Thr Lys Gly Thr Ile
                485                 490                 495

Thr Gly Asn Thr Val Val Phe Asp Ser Leu Pro Arg Leu Gly Ser Lys
            500                 505                 510

Glu Thr Val Glu Phe Ser Val Thr Leu Lys Ala Val Ser Ala Gly Asp
        515                 520                 525

Ala Arg Gly Glu Ala Ile Leu Ser Ser Asp Thr Leu Thr Val Pro Val
    530                 535                 540
```

```
Ser Asp Thr Glu Asn Thr His Ile Tyr
545                 550

<210> SEQ ID NO 11
<211> LENGTH: 1329
<212> TYPE: DNA
<213> ORGANISM: Chlamydia trachomatis

<400> SEQUENCE: 11

atgcaggctg cacaccatca ctatcaccgc tacacagata aactgcacag acaaaaccat     60

aaaaaagatc tcatctctcc caaacctacc gaacaagagg cgtgcaatac ttcttccctt    120

agtaaggaat taatccctct atcagaacaa agaggccttt tatcccccat ctgtgacttt    180

atttcggaac gcccttgctt acacggagtt tctgttagaa atctcaagca agcgctaaaa    240

aattctgcag gaacccaaat tgcactggat tggtctattc tccctcaatg gttcaatcct    300

cgggtctctc atgcccctaa gctttctatc cgagactttg ggtatagcgc acaccaaact    360

gttaccgaag ccactcctcc ttgctggcaa aactgcttta atccatctgc ggccgttact    420

atctatgatt cctcatatgg gaaaggggtc tttcaaatat cctataccct tgtccgctat    480

tggagagaga atgctgcgac tgctggcgat gctatgatgc tcgcagggag tatcaatgat    540

tatccctctc gtcagaacat tttctctcag tttactttct cccaaaactt cccaaatgaa    600

cgggtgagtc tgacaattgg tcagtactca ctctatgcaa tagacggaac attatacaat    660

aacgatcaac aacttggatt cattagttac gcattatcac aaaatccaac agcaacttat    720

tcctctggaa gtcttggagc ttacctacaa gtcgctccta ccgcaagcac aagtcttcaa    780

ataggatttc aagacgctta taatatctcc ggatcctcta tcaaatggag taaccttaca    840

aaaaatagat acaattttca cggttttgct tcctgggctc cccgctgttg cttaggatct    900

ggccagtact ccgtgcttct ttatgtgact agacaagttc cagaacagat ggaacaaaca    960

atgggatggt cagtcaatgc gagtcaacac atatcttcta aactgtatgt gtttggaaga   1020

tacagcggtg ttacaggaca tgtgttcccg attaaccgca cgtattcatt cggtatggcc   1080

tctgcaaatt tatttaaccg taacccacaa gatttatttg gaattgcttg cgcattcaat   1140

aatgtacacc tctctgcttc tccaaatact aaaagaaaat acgaaactgt aatcgaaggg   1200

tttgcaacta tcggttgcgg cccctatctt tctttcgctc cagacttcca actctacctc   1260

tacccagctc ttcgtccaaa caaacaatct gcccgtgttt atagcgtgcg agctaattta   1320

gctatctaa                                                            1329

<210> SEQ ID NO 12
<211> LENGTH: 442
<212> TYPE: PRT
<213> ORGANISM: Chlamydia trachomatis

<400> SEQUENCE: 12

Met Gln Ala Ala His His His Tyr His Arg Tyr Thr Asp Lys Leu His
1               5                   10                  15

Arg Gln Asn His Lys Lys Asp Leu Ile Ser Pro Lys Pro Thr Glu Gln
            20                  25                  30

Glu Ala Cys Asn Thr Ser Ser Leu Ser Lys Glu Leu Ile Pro Leu Ser
        35                  40                  45

Glu Gln Arg Gly Leu Leu Ser Pro Ile Cys Asp Phe Ile Ser Glu Arg
    50                  55                  60

Pro Cys Leu His Gly Val Ser Val Arg Asn Leu Lys Gln Ala Leu Lys
```

-continued

```
65                  70                  75                  80

Asn Ser Ala Gly Thr Gln Ile Ala Leu Asp Trp Ser Ile Leu Pro Gln
                85                  90                  95

Trp Phe Asn Pro Arg Val Ser His Ala Pro Lys Leu Ser Ile Arg Asp
            100                 105                 110

Phe Gly Tyr Ser Ala His Gln Thr Val Thr Glu Ala Thr Pro Pro Cys
        115                 120                 125

Trp Gln Asn Cys Phe Asn Pro Ser Ala Ala Val Thr Ile Tyr Asp Ser
    130                 135                 140

Ser Tyr Gly Lys Gly Val Phe Gln Ile Ser Tyr Thr Leu Val Arg Tyr
145                 150                 155                 160

Trp Arg Glu Asn Ala Ala Thr Ala Gly Asp Ala Met Met Leu Ala Gly
                165                 170                 175

Ser Ile Asn Asp Tyr Pro Ser Arg Gln Asn Ile Phe Ser Gln Phe Thr
            180                 185                 190

Phe Ser Gln Asn Phe Pro Asn Glu Arg Val Ser Leu Thr Ile Gly Gln
        195                 200                 205

Tyr Ser Leu Tyr Ala Ile Asp Gly Thr Leu Tyr Asn Asn Asp Gln Gln
    210                 215                 220

Leu Gly Phe Ile Ser Tyr Ala Leu Ser Gln Asn Pro Thr Ala Thr Tyr
225                 230                 235                 240

Ser Ser Gly Ser Leu Gly Ala Tyr Leu Gln Val Ala Pro Thr Ala Ser
                245                 250                 255

Thr Ser Leu Gln Ile Gly Phe Gln Asp Ala Tyr Asn Ile Ser Gly Ser
            260                 265                 270

Ser Ile Lys Trp Ser Asn Leu Thr Lys Asn Arg Tyr Asn Phe His Gly
        275                 280                 285

Phe Ala Ser Trp Ala Pro Arg Cys Cys Leu Gly Ser Gly Gln Tyr Ser
    290                 295                 300

Val Leu Leu Tyr Val Thr Arg Gln Val Pro Glu Gln Met Glu Gln Thr
305                 310                 315                 320

Met Gly Trp Ser Val Asn Ala Ser Gln His Ile Ser Ser Lys Leu Tyr
                325                 330                 335

Val Phe Gly Arg Tyr Ser Gly Val Thr Gly His Val Phe Pro Ile Asn
            340                 345                 350

Arg Thr Tyr Ser Phe Gly Met Ala Ser Ala Asn Leu Phe Asn Arg Asn
        355                 360                 365

Pro Gln Asp Leu Phe Gly Ile Ala Cys Ala Phe Asn Asn Val His Leu
    370                 375                 380

Ser Ala Ser Pro Asn Thr Lys Arg Lys Tyr Glu Thr Val Ile Glu Gly
385                 390                 395                 400

Phe Ala Thr Ile Gly Cys Gly Pro Tyr Leu Ser Phe Ala Pro Asp Phe
                405                 410                 415

Gln Leu Tyr Leu Tyr Pro Ala Leu Arg Pro Asn Lys Gln Ser Ala Arg
            420                 425                 430

Val Tyr Ser Val Arg Ala Asn Leu Ala Ile
        435                 440


<210> SEQ ID NO 13
<211> LENGTH: 3018
<212> TYPE: DNA
<213> ORGANISM: Chlamydia trachomatis

<400> SEQUENCE: 13
```

-continued

```
atgacgaatt ctatatcagg ttatcaacct actgttacaa cttctacatc atcaaccact     60
tcggcatcag gtgcttccgg atctctggga gcttcttctg tatctactac cgcaaacgct    120
acagttacac aaacagcaaa cgcaacaaat tcagcggcta catcttctat ccaaacgact    180
ggagagactg tagtaaacta tacgaattca gcctccgccc ccaatgtaac tgtatcgacc    240
tcctcttctt ccacacaagc cacagccact tcgaataaaa cttcccaagc cgttgctgga    300
aaaatcactt ctccagatac ttcagaaagc tcagaaacta gctctacctc atcaagcgat    360
catatcccta gcgattacga tgacgttggt agcaatagtg gagatattag caacaactac    420
gatgacgtag gtagtaacaa cggagatatc agtagcaatt atgacgatgc tgctgctgat    480
tacgagccga taagaactac tgaaaatatt tatgagagta ttggtggctc tagaacaagt    540
ggcccagaaa atacaagtgg tggtgcagca gcagcactca attctctaag aggctcctcc    600
tacagcaatt atgacgatgc tgctgctgat tacgagccga taagaactac tgaaaatatt    660
tatgagagta ttggtggctc tagaacaagt ggcccagaaa atacgagtgg tggtgcagca    720
gcagcactca attctctaag aggctcctcc tacagcaatt atgacgatgc tgctgctgat    780
tacgagccga taagaactac tgaaaatatt tatgagagta ttggtggctc tagaacaagt    840
ggcccagaaa atacgagtga tggtgcagca gcagcagcac tcaattctct aagaggctcc    900
tcctacacaa cagggcctcg taacgagggt gtattcggcc ctggaccgga aggactacca    960
gacatgtctc ttccttcata cgatcctaca aataaaacct cgttattgac tttcctctcc   1020
aaccctcatg taaagtcgaa aatgcttgaa aactcggggc atttcgtctt cattgataca   1080
gatagaagta gtttcattct tgttcctaac ggaaattggg accaagtctg ttcaattaaa   1140
gttcaaaatg gaaagaccaa agaagatctc gacatcaaag acttggaaaa catgtgtgca   1200
aaattctgta cagggtttag caaattctct ggtgactggg acagtcttgt agaacctatg   1260
gtgtcagcca aagctggagt ggccagcgga ggcaatcttc ccaatacagt gattatcaat   1320
aataaattca aaacttgcgt tgcttatggt ccttggaata gccaggaagc aagttctggt   1380
tatacacctt ctgcttggag acgtggtcat cgagtagatt ttggaggaat ttttgagaaa   1440
gccaacgact ttaataaaat caactgggga actcaagccg ggcctagtag cgaagacgat   1500
ggcatttcct tctccaatga aactcctgga gctggtcctg cagctgctcc atcaccaacg   1560
ccatcctcta ttcctatcat caatgtcaat gtcaatgttg gcggaactaa tgtgaatatt   1620
ggagatacga atgtcaacac gactaacacc acaccaacaa ctcaatctac agacgcctct   1680
acagatacaa gcgatatcga tgacataaat accaacaacc aaactgatga tatcaatacg   1740
acagacaaag actctgacgg agctggtgga gtcaatggcg atatatccga aacagaatcc   1800
tcttctggag atgattcagg aagtgtctct tcctcagaat cagacaagaa tgcctctgtc   1860
ggaaatgacg gacctgctat gaaagatatc ctttctgccg tgcgtaaaca cctagacgtc   1920
gtttaccctg gcgaaaatgg cggttctaca gaagggcctc tcccagctaa ccaaactctc   1980
ggagacgtaa tctctgatgt agagaataaa ggctccgctc aggatacaaa attgtcagga   2040
aatacaggag ctggggatga cgatccaaca accacagctg ctgtaggtaa tggagcggaa   2100
gagatcactc tttccgacac agattctggt atcggagatg atgtatccga tacagcgtct   2160
tcatctgggg atgaatccgg aggagtctcc tctccctctt cagaatccaa taaaaatact   2220
gccgttggaa atgacggacc ttctggacta gatatcctcg ctgccgtacg taaacattta   2280
gataaggttt accctggcga caatggtggt tctacagaag ggcctctcca agctaaccaa   2340
actcttggag atatcgtcca ggatatggaa acaacaggga catcccaaga aaccgttgta   2400
```

tccccatgga aaggaagcac ttcttcaacg gaatcagcag gaggaagtgg tagcgtacaa 2460
acactactgc cttcaccacc tccaaccccg tcaactacaa cattaagaac gggcacagga 2520
gctaccacca catccttgat gatgggagga ccaatcaaag ctgacataat aacaactggt 2580
ggcggaggac gaattcctgg aggaggaacg ttagaaaagc tgctccctcg tatacgtgcg 2640
cacttagaca tatcctttga tgcgcaaggc gatctcgtaa gtactgaaga gcctcagctt 2700
ggctcgattg taaacaaatt ccgccaagaa actggttcaa gaggaatctt agctttcgtt 2760
gagagtgctc caggcaagcc gggatctgca caggtcttaa cgggtacagg gggagataaa 2820
ggcaacctat tccaagcagc tgccgcagtc acccaagcct taggaaatgt tgcagggaaa 2880
gtcaaccttg cgatacaagg ccaaaaacta tcatccctag tcaatgacga cgggaagggg 2940
tctgttggaa gagatttatt ccaagcagca gcccaaacaa ctcaagtgct aagcgcactg 3000
attgataccg taggataa 3018

<210> SEQ ID NO 14
<211> LENGTH: 1005
<212> TYPE: PRT
<213> ORGANISM: Chlamydia trachomatis

<400> SEQUENCE: 14

Met Thr Asn Ser Ile Ser Gly Tyr Gln Pro Thr Val Thr Thr Ser Thr
1 5 10 15

Ser Ser Thr Thr Ser Ala Ser Gly Ala Ser Gly Ser Leu Gly Ala Ser
20 25 30

Ser Val Ser Thr Thr Ala Asn Ala Thr Val Thr Gln Thr Ala Asn Ala
35 40 45

Thr Asn Ser Ala Ala Thr Ser Ser Ile Gln Thr Thr Gly Glu Thr Val
50 55 60

Val Asn Tyr Thr Asn Ser Ala Ser Ala Pro Asn Val Thr Val Ser Thr
65 70 75 80

Ser Ser Ser Ser Thr Gln Ala Thr Ala Thr Ser Asn Lys Thr Ser Gln
85 90 95

Ala Val Ala Gly Lys Ile Thr Ser Pro Asp Thr Ser Glu Ser Ser Glu
100 105 110

Thr Ser Ser Thr Ser Ser Ser Asp His Ile Pro Ser Asp Tyr Asp Asp
115 120 125

Val Gly Ser Asn Ser Gly Asp Ile Ser Asn Asn Tyr Asp Asp Val Gly
130 135 140

Ser Asn Asn Gly Asp Ile Ser Ser Asn Tyr Asp Asp Ala Ala Ala Asp
145 150 155 160

Tyr Glu Pro Ile Arg Thr Thr Glu Asn Ile Tyr Glu Ser Ile Gly Gly
165 170 175

Ser Arg Thr Ser Gly Pro Glu Asn Thr Ser Gly Gly Ala Ala Ala Ala
180 185 190

Leu Asn Ser Leu Arg Gly Ser Ser Tyr Ser Asn Tyr Asp Asp Ala Ala
195 200 205

Ala Asp Tyr Glu Pro Ile Arg Thr Thr Glu Asn Ile Tyr Glu Ser Ile
210 215 220

Gly Gly Ser Arg Thr Ser Gly Pro Glu Asn Thr Ser Gly Gly Ala Ala
225 230 235 240

Ala Ala Leu Asn Ser Leu Arg Gly Ser Ser Tyr Ser Asn Tyr Asp Asp
245 250 255

```
Ala Ala Ala Asp Tyr Glu Pro Ile Arg Thr Thr Glu Asn Ile Tyr Glu
            260                 265                 270

Ser Ile Gly Gly Ser Arg Thr Ser Gly Pro Glu Asn Thr Ser Asp Gly
        275                 280                 285

Ala Ala Ala Ala Ala Leu Asn Ser Leu Arg Gly Ser Ser Tyr Thr Thr
    290                 295                 300

Gly Pro Arg Asn Glu Gly Val Phe Gly Pro Gly Pro Glu Gly Leu Pro
305                 310                 315                 320

Asp Met Ser Leu Pro Ser Tyr Asp Pro Thr Asn Lys Thr Ser Leu Leu
                325                 330                 335

Thr Phe Leu Ser Asn Pro His Val Lys Ser Lys Met Leu Glu Asn Ser
            340                 345                 350

Gly His Phe Val Phe Ile Asp Thr Asp Arg Ser Ser Phe Ile Leu Val
        355                 360                 365

Pro Asn Gly Asn Trp Asp Gln Val Cys Ser Ile Lys Val Gln Asn Gly
    370                 375                 380

Lys Thr Lys Glu Asp Leu Asp Ile Lys Asp Leu Glu Asn Met Cys Ala
385                 390                 395                 400

Lys Phe Cys Thr Gly Phe Ser Lys Phe Ser Gly Asp Trp Asp Ser Leu
                405                 410                 415

Val Glu Pro Met Val Ser Ala Lys Ala Gly Val Ala Ser Gly Gly Asn
            420                 425                 430

Leu Pro Asn Thr Val Ile Ile Asn Asn Lys Phe Lys Thr Cys Val Ala
        435                 440                 445

Tyr Gly Pro Trp Asn Ser Gln Glu Ala Ser Ser Gly Tyr Thr Pro Ser
    450                 455                 460

Ala Trp Arg Arg Gly His Arg Val Asp Phe Gly Gly Ile Phe Glu Lys
465                 470                 475                 480

Ala Asn Asp Phe Asn Lys Ile Asn Trp Gly Thr Gln Ala Gly Pro Ser
                485                 490                 495

Ser Glu Asp Asp Gly Ile Ser Phe Ser Asn Glu Thr Pro Gly Ala Gly
            500                 505                 510

Pro Ala Ala Ala Pro Ser Pro Thr Pro Ser Ser Ile Pro Ile Ile Asn
        515                 520                 525

Val Asn Val Asn Val Gly Gly Thr Asn Val Asn Ile Gly Asp Thr Asn
    530                 535                 540

Val Asn Thr Thr Asn Thr Thr Pro Thr Thr Gln Ser Thr Asp Ala Ser
545                 550                 555                 560

Thr Asp Thr Ser Asp Ile Asp Asp Ile Asn Thr Asn Asn Gln Thr Asp
                565                 570                 575

Asp Ile Asn Thr Thr Asp Lys Asp Ser Asp Gly Ala Gly Gly Val Asn
            580                 585                 590

Gly Asp Ile Ser Glu Thr Glu Ser Ser Ser Gly Asp Asp Ser Gly Ser
        595                 600                 605

Val Ser Ser Ser Glu Ser Asp Lys Asn Ala Ser Val Gly Asn Asp Gly
    610                 615                 620

Pro Ala Met Lys Asp Ile Leu Ser Ala Val Arg Lys His Leu Asp Val
625                 630                 635                 640

Val Tyr Pro Gly Glu Asn Gly Gly Ser Thr Glu Gly Pro Leu Pro Ala
                645                 650                 655

Asn Gln Thr Leu Gly Asp Val Ile Ser Asp Val Glu Asn Lys Gly Ser
            660                 665                 670

Ala Gln Asp Thr Lys Leu Ser Gly Asn Thr Gly Ala Gly Asp Asp Asp
```

```
        675                 680                 685

Pro Thr Thr Thr Ala Ala Val Gly Asn Gly Ala Glu Glu Ile Thr Leu
    690                 695                 700

Ser Asp Thr Asp Ser Gly Ile Gly Asp Asp Val Ser Asp Thr Ala Ser
705                 710                 715                 720

Ser Ser Gly Asp Glu Ser Gly Gly Val Ser Ser Pro Ser Ser Glu Ser
                725                 730                 735

Asn Lys Asn Thr Ala Val Gly Asn Asp Gly Pro Ser Gly Leu Asp Ile
            740                 745                 750

Leu Ala Ala Val Arg Lys His Leu Asp Lys Val Tyr Pro Gly Asp Asn
        755                 760                 765

Gly Gly Ser Thr Glu Gly Pro Leu Gln Ala Asn Gln Thr Leu Gly Asp
    770                 775                 780

Ile Val Gln Asp Met Glu Thr Thr Gly Thr Ser Gln Glu Thr Val Val
785                 790                 795                 800

Ser Pro Trp Lys Gly Ser Thr Ser Ser Thr Glu Ser Ala Gly Gly Ser
                805                 810                 815

Gly Ser Val Gln Thr Leu Leu Pro Ser Pro Pro Pro Thr Pro Ser Thr
            820                 825                 830

Thr Thr Leu Arg Thr Gly Thr Gly Ala Thr Thr Thr Ser Leu Met Met
        835                 840                 845

Gly Gly Pro Ile Lys Ala Asp Ile Ile Thr Thr Gly Gly Gly Gly Arg
    850                 855                 860

Ile Pro Gly Gly Gly Thr Leu Glu Lys Leu Leu Pro Arg Ile Arg Ala
865                 870                 875                 880

His Leu Asp Ile Ser Phe Asp Ala Gln Gly Asp Leu Val Ser Thr Glu
                885                 890                 895

Glu Pro Gln Leu Gly Ser Ile Val Asn Lys Phe Arg Gln Glu Thr Gly
            900                 905                 910

Ser Arg Gly Ile Leu Ala Phe Val Glu Ser Ala Pro Gly Lys Pro Gly
        915                 920                 925

Ser Ala Gln Val Leu Thr Gly Thr Gly Gly Asp Lys Gly Asn Leu Phe
    930                 935                 940

Gln Ala Ala Ala Ala Val Thr Gln Ala Leu Gly Asn Val Ala Gly Lys
945                 950                 955                 960

Val Asn Leu Ala Ile Gln Gly Gln Lys Leu Ser Ser Leu Val Asn Asp
                965                 970                 975

Asp Gly Lys Gly Ser Val Gly Arg Asp Leu Phe Gln Ala Ala Ala Gln
            980                 985                 990

Thr Thr Gln Val Leu Ser Ala Leu  Ile Asp Thr Val Gly
        995                 1000                1005
```

<210> SEQ ID NO 15
<211> LENGTH: 774
<212> TYPE: DNA
<213> ORGANISM: Chlamydia trachomatis

<400> SEQUENCE: 15

```
atgtgcataa aaagaaaaaa aacatggata gctttttttag cagttgtctg tagtttttgt     60

ttgacgggtt gtttaaaaga agggggagac tccaatagtg aaaaatttat tgtagggact    120

aatgcaacct accctccttt tgagtttgtt gataagcgag gagaggttgt aggcttcgat    180

atagacttgg ctagagagat tagtaacaag ctggggaaaa cgctggacgt tcgggagttt    240

tcctttgatg cactcattct aaacctaaaa cagcatcgga ttgatgcggt tataacaggg    300
```

```
atgtccatta ctccttctag attgaaggaa attcttatga ttccctatta tggggaggaa    360

ataaaacact tggttttagt gtttaaagga gagaataagc atccattgcc actcactcaa    420

tatcgttctg tagctgttca aacaggaacc tatcaagagg cctatttaca gtctctttct    480

gaagttcata ttcgctcttt tgatagcact ctagaagtac tcatggaagt catgcatggt    540

aaatctcccg tcgctgtttt agagccatct atcgctcaag ttgtcttgaa agatttcccg    600

gctctttcta cagcaaccat agatctccct gaagatcagt gggttttagg atacgggatt    660

ggcgttgctt cagatcgccc agctttagcc ttgaaaatcg aggcagctgt gcaagagatc    720

cgaaaagaag gagtgctagc agagttggaa cagaagtggg gtttgaacaa ctaa          774


<210> SEQ ID NO 16
<211> LENGTH: 257
<212> TYPE: PRT
<213> ORGANISM: Chlamydia trachomatis

<400> SEQUENCE: 16

Met Cys Ile Lys Arg Lys Lys Thr Trp Ile Ala Phe Leu Ala Val Val
1               5                   10                  15

Cys Ser Phe Cys Leu Thr Gly Cys Leu Lys Glu Gly Gly Asp Ser Asn
            20                  25                  30

Ser Glu Lys Phe Ile Val Gly Thr Asn Ala Thr Tyr Pro Pro Phe Glu
        35                  40                  45

Phe Val Asp Lys Arg Gly Glu Val Val Gly Phe Asp Ile Asp Leu Ala
    50                  55                  60

Arg Glu Ile Ser Asn Lys Leu Gly Lys Thr Leu Asp Val Arg Glu Phe
65                  70                  75                  80

Ser Phe Asp Ala Leu Ile Leu Asn Leu Lys Gln His Arg Ile Asp Ala
                85                  90                  95

Val Ile Thr Gly Met Ser Ile Thr Pro Ser Arg Leu Lys Glu Ile Leu
            100                 105                 110

Met Ile Pro Tyr Tyr Gly Glu Glu Ile Lys His Leu Val Leu Val Phe
        115                 120                 125

Lys Gly Glu Asn Lys His Pro Leu Pro Leu Thr Gln Tyr Arg Ser Val
    130                 135                 140

Ala Val Gln Thr Gly Thr Tyr Gln Glu Ala Tyr Leu Gln Ser Leu Ser
145                 150                 155                 160

Glu Val His Ile Arg Ser Phe Asp Ser Thr Leu Glu Val Leu Met Glu
                165                 170                 175

Val Met His Gly Lys Ser Pro Val Ala Val Leu Glu Pro Ser Ile Ala
            180                 185                 190

Gln Val Val Leu Lys Asp Phe Pro Ala Leu Ser Thr Ala Thr Ile Asp
        195                 200                 205

Leu Pro Glu Asp Gln Trp Val Leu Gly Tyr Gly Ile Gly Val Ala Ser
    210                 215                 220

Asp Arg Pro Ala Leu Ala Leu Lys Ile Glu Ala Ala Val Gln Glu Ile
225                 230                 235                 240

Arg Lys Glu Gly Val Leu Ala Glu Leu Glu Gln Lys Trp Gly Leu Asn
                245                 250                 255

Asn


<210> SEQ ID NO 17
<211> LENGTH: 504
<212> TYPE: DNA
```

<213> ORGANISM: Chlamydia trachomatis

<400> SEQUENCE: 17

```
atgtccaggc agaatgctga ggaaaatcta aaaaattttg ctaaagagct taaactcccc     60
gacgtggcct tcgatcagaa taatacgtgc attttgtttg ttgatggaga gttttctctt    120
cacctgacct acgaagaaca ctctgatcgc ctttatgttt acgcacctct tcttgacgga    180
ctgccagaca atccgcaaag aaggttagct ctatatgaga agttgttaga aggctctatg    240
ctcggaggcc aaatggctgg tggaggggta ggagtcgcta ctaaggaaca gttgatctta    300
atgcactgcg tgttagacat gaagtatgca gagaccaacc tactcaaagc ttttgcacag    360
ctttttattg aaaccgttgt gaaatggcga actgtttgtt ctgatatcag cgctggacga    420
gaacccactg ttgataccat gccacaaatg cctcaagggg gtggcggagg aattcaacct    480
cctccagcag gaatccgtgc ataa                                          504
```

<210> SEQ ID NO 18
<211> LENGTH: 167
<212> TYPE: PRT
<213> ORGANISM: Chlamydia trachomatis

<400> SEQUENCE: 18

```
Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30

Phe Val Asp Gly Glu Phe Ser Leu His Leu Thr Tyr Glu Glu His Ser
        35                  40                  45

Asp Arg Leu Tyr Val Tyr Ala Pro Leu Leu Asp Gly Leu Pro Asp Asn
    50                  55                  60

Pro Gln Arg Arg Leu Ala Leu Tyr Glu Lys Leu Leu Glu Gly Ser Met
65                  70                  75                  80

Leu Gly Gly Gln Met Ala Gly Gly Gly Val Gly Val Ala Thr Lys Glu
                85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125

Trp Arg Thr Val Cys Ser Asp Ile Ser Ala Gly Arg Glu Pro Thr Val
    130                 135                 140

Asp Thr Met Pro Gln Met Pro Gln Gly Gly Gly Gly Gly Ile Gln Pro
145                 150                 155                 160

Pro Pro Ala Gly Ile Arg Ala
                165
```

<210> SEQ ID NO 19
<211> LENGTH: 767
<212> TYPE: PRT
<213> ORGANISM: Chlamydia trachomatis

<400> SEQUENCE: 19

```
Met Ser Ile Gln Pro Thr Ser Ile Ser Leu Thr Lys Asn Ile Thr Ala
1               5                   10                  15

Ala Leu Ala Gly Glu Gln Val Asp Ala Ala Ala Val Tyr Met Pro Gln
            20                  25                  30

Ala Val Phe Phe Phe Gln Gln Leu Asp Glu Lys Ser Lys Gly Leu Lys
        35                  40                  45
```

```
Gln Ala Leu Gly Leu Leu Glu Glu Val Asp Leu Glu Lys Phe Ile Pro
    50                  55                  60

Ser Leu Glu Lys Ser Pro Thr Pro Ile Thr Thr Gly Thr Thr Ser Lys
65                  70                  75                  80

Ile Ser Ala Asp Gly Ile Glu Ile Val Gly Glu Leu Ser Ser Glu Thr
                85                  90                  95

Ile Leu Ala Asp Pro Asn Lys Ala Ala Ala Gln Val Phe Gly Glu Gly
            100                 105                 110

Leu Ala Asp Ser Phe Asp Asp Trp Leu Arg Leu Ser Glu Asn Gly Gly
        115                 120                 125

Ile Gln Asp Pro Thr Ala Ile Glu Glu Glu Ile Val Thr Lys Tyr Gln
    130                 135                 140

Thr Glu Leu Asn Thr Leu Arg Asn Lys Leu Lys Gln Gln Ser Leu Thr
145                 150                 155                 160

Asp Asp Glu Tyr Thr Lys Leu Tyr Ala Ile Pro Gln Asn Phe Val Lys
                165                 170                 175

Glu Ile Glu Ser Leu Lys Asn Glu Asn Asn Val Arg Leu Ile Pro Lys
            180                 185                 190

Ser Lys Val Thr Asn Phe Trp Gln Asn Ile Met Leu Thr Tyr Asn Ser
        195                 200                 205

Val Thr Ser Leu Ser Glu Pro Val Thr Asp Ala Met Asn Thr Thr Met
    210                 215                 220

Ala Glu Tyr Ser Leu Tyr Ile Glu Arg Ala Thr Glu Ala Ala Lys Leu
225                 230                 235                 240

Ile Arg Glu Ile Thr Asn Thr Ile Lys Asp Ile Phe Asn Pro Val Trp
                245                 250                 255

Asp Val Arg Glu Gln Thr Gly Ile Phe Gly Leu Lys Gly Ala Glu Tyr
            260                 265                 270

Asn Ala Leu Glu Gly Asn Met Ile Gln Ser Leu Leu Ser Phe Ala Gly
        275                 280                 285

Leu Phe Arg Gln Leu Met Ser Arg Thr Ala Thr Val Asp Glu Ile Gly
    290                 295                 300

Ala Leu Tyr Pro Lys Asn Asp Lys Asn Glu Asp Val Ile His Thr Ala
305                 310                 315                 320

Ile Asp Asp Tyr Val Asn Ser Leu Ala Asp Leu Lys Ala Asn Glu Gln
                325                 330                 335

Val Lys Leu Asn Gly Leu Leu Ser Leu Val Tyr Ala Tyr Tyr Ala Ser
            340                 345                 350

Thr Leu Gly Phe Ala Lys Lys Asp Val Phe Asn Asn Ala Gln Ala Ser
        355                 360                 365

Phe Thr Asp Tyr Thr Asn Phe Leu Asn Gln Glu Ile Gln Tyr Trp Thr
    370                 375                 380

Pro Arg Glu Thr Ser Ser Phe Asn Ile Ser Asn Gln Ala Leu Gln Thr
385                 390                 395                 400

Phe Lys Asn Lys Pro Ser Ala Asp Tyr Asn Gly Val Tyr Leu Phe Asp
                405                 410                 415

Asn Lys Gly Leu Glu Thr Asn Leu Phe Asn Pro Thr Phe Phe Phe Asp
            420                 425                 430

Val Val Ser Leu Met Thr Ala Asp Pro Thr Lys Thr Met Ser Arg Gln
        435                 440                 445

Asp Tyr Asn Lys Val Ile Thr Ala Ser Glu Ser Ser Ile Gln Lys Ile
    450                 455                 460
```

Asn Gln Ala Ile Thr Ala Trp Glu Leu Ala Ile Ala Glu Cys Gly Thr
465 470 475 480

Lys Lys Ala Lys Leu Glu Pro Ser Ser Leu Asn Tyr Phe Asn Ala Met
485 490 495

Val Glu Ala Lys Lys Thr Phe Val Glu Thr Ser Pro Ile Gln Met Val
500 505 510

Tyr Ser Ser Leu Met Leu Asp Lys Tyr Leu Pro Asn Gln Gln Tyr Ile
515 520 525

Leu Glu Thr Leu Gly Ser Gln Met Thr Phe Ser Asn Lys Ala Ala Arg
530 535 540

Tyr Leu Asn Asp Ile Ile Ala Tyr Ala Val Ser Phe Gln Thr Ala Asp
545 550 555 560

Val Tyr Tyr Ser Leu Gly Met Tyr Leu Arg Gln Met Asn Gln Gln Glu
565 570 575

Phe Pro Glu Val Ile Ser Arg Ala Asn Asp Thr Val Lys Lys Glu Ile
580 585 590

Asp Arg Ser Arg Ala Asp Leu Phe His Cys Lys Lys Ala Ile Glu Lys
595 600 605

Ile Lys Glu Leu Val Thr Ser Val Asn Ala Asp Thr Glu Leu Thr Ser
610 615 620

Ser Gln Arg Ala Glu Leu Leu Glu Thr Leu Ala Ser Tyr Ala Phe Glu
625 630 635 640

Phe Glu Asn Leu Tyr His Asn Leu Ser Asn Val Tyr Val Met Val Ser
645 650 655

Lys Val Gln Ile Ser Gly Val Ser Lys Pro Asp Glu Val Asp Glu Ala
660 665 670

Phe Thr Ala Lys Ile Gly Ser Lys Glu Phe Asp Thr Trp Ile Gln Gln
675 680 685

Leu Thr Thr Phe Glu Ser Ala Val Ile Glu Gly Gly Arg Asn Gly Val
690 695 700

Met Pro Gly Gly Glu Gln Gln Val Leu Gln Ser Leu Glu Ser Lys Gln
705 710 715 720

Gln Asp Tyr Thr Ser Phe Asn Gln Asn Gln Gln Leu Ala Leu Gln Met
725 730 735

Glu Ser Ala Ala Ile Gln Gln Glu Trp Thr Met Val Ala Ala Ala Leu
740 745 750

Ala Leu Met Asn Gln Ile Phe Ala Lys Leu Ile Arg Arg Phe Lys
755 760 765

<210> SEQ ID NO 20
<211> LENGTH: 486
<212> TYPE: PRT
<213> ORGANISM: Chlamydia trachomatis

<400> SEQUENCE: 20

Met Cys Phe Ile Gly Ile Gly Ser Leu Leu Leu Pro Thr Ala Leu Arg
1 5 10 15

Ala Thr Glu Arg Met Arg Lys Glu Pro Ile Pro Leu Leu Asp Lys Gln
20 25 30

Gln Ser Phe Trp Asn Val Asp Pro Tyr Cys Leu Glu Ser Ile Cys Ala
35 40 45

Cys Phe Val Ala His Arg Asp Pro Leu Ser Ala Lys Gln Leu Met Tyr
50 55 60

Leu Phe Pro Gln Leu Ser Glu Glu Asp Val Ser Val Phe Ala Arg Cys
65 70 75 80

-continued

```
Ile Leu Ser Ser Lys Arg Pro Glu Tyr Leu Phe Ser Lys Ser Glu Glu
                85                  90                  95

Glu Leu Phe Ala Lys Leu Ile Leu Pro Arg Val Ser Leu Gly Val His
            100                 105                 110

Arg Asp Asp Asp Leu Ala Arg Val Leu Val Leu Ala Glu Pro Ser Ala
        115                 120                 125

Glu Glu Gln Lys Ala Arg Tyr Tyr Ser Leu Tyr Leu Asp Val Leu Ala
    130                 135                 140

Leu Arg Ala Tyr Val Glu Arg Glu Arg Leu Ala Ser Ala Ala His Gly
145                 150                 155                 160

Asp Pro Glu Arg Ile Asp Leu Ala Thr Ile Glu Ala Ile Asn Thr Ile
                165                 170                 175

Leu Phe Gln Glu Glu Gly Trp Arg Tyr Pro Ser Lys Gln Glu Met Phe
            180                 185                 190

Glu Asn Arg Phe Ser Glu Leu Ala Ala Val Thr Asp Ser Lys Phe Gly
        195                 200                 205

Val Cys Leu Gly Thr Val Val Leu Tyr Gln Ala Val Ala Gln Arg Leu
    210                 215                 220

Asp Leu Ser Leu Asp Pro Val Thr Pro Pro Gly His Ile Tyr Leu Arg
225                 230                 235                 240

Tyr Lys Asp Lys Val Asn Ile Glu Thr Thr Ser Gly Gly Arg His Leu
                245                 250                 255

Pro Thr Glu Arg Tyr Cys Glu Cys Ile Lys Glu Ser Gln Leu Lys Val
            260                 265                 270

Arg Ser Gln Met Glu Leu Ile Gly Leu Thr Phe Met Asn Arg Gly Ala
        275                 280                 285

Phe Phe Leu Gln Lys Gly Glu Phe Leu Gln Ala Ser Leu Ala Tyr Glu
    290                 295                 300

Gln Ala Gln Ser Tyr Leu Ser Asp Glu Gln Ile Ser Asp Leu Leu Gly
305                 310                 315                 320

Ile Thr Tyr Val Leu Leu Gly Lys Lys Ala Ala Gly Glu Ala Leu Leu
                325                 330                 335

Lys Lys Ser Ala Glu Lys Thr Arg Arg Gly Ser Ser Ile Tyr Asp Tyr
            340                 345                 350

Phe Gln Gly Tyr Ile Ser Pro Glu Ile Leu Gly Val Leu Phe Ala Asp
        355                 360                 365

Ser Gly Val Thr Tyr Gln Glu Thr Leu Glu Tyr Arg Lys Lys Leu Val
    370                 375                 380

Met Leu Ser Lys Lys Tyr Pro Lys Ser Gly Ser Leu Arg Leu Arg Leu
385                 390                 395                 400

Ala Thr Thr Ala Leu Glu Leu Gly Leu Val Lys Glu Gly Val Gln Leu
                405                 410                 415

Leu Glu Glu Ser Val Lys Asp Ala Pro Glu Asp Leu Ser Leu Arg Leu
            420                 425                 430

Gln Phe Cys Lys Ile Leu Cys Asn Arg His Asp Tyr Val Arg Ala Lys
        435                 440                 445

Tyr His Phe Asp Gln Ala Gln Ala Leu Leu Ile Lys Glu Gly Leu Phe
    450                 455                 460

Ser Glu Lys Thr Ser Tyr Thr Leu Leu Lys Thr Ile Gly Lys Lys Leu
465                 470                 475                 480

Ser Leu Phe Ala Pro Ser
                485
```

<210> SEQ ID NO 21
<211> LENGTH: 696
<212> TYPE: PRT
<213> ORGANISM: Chlamydia trachomatis

<400> SEQUENCE: 21

Met Ile Asp Lys Ile Ile Arg Thr Ile Leu Val Leu Ser Leu Phe Leu
1 5 10 15

Leu Tyr Trp Ser Ser Asp Leu Leu Glu Lys Asp Val Lys Ser Ile Lys
20 25 30

Arg Glu Leu Lys Ala Leu His Glu Asp Val Leu Glu Leu Val Arg Ile
35 40 45

Ser His Gln Gln Lys Asn Trp Val Gln Ser Thr Asp Phe Ser Val Ser
50 55 60

Pro Glu Ile Ser Val Leu Lys Asp Cys Gly Asp Pro Ala Phe Pro Asn
65 70 75 80

Leu Leu Cys Glu Asp Pro Tyr Val Glu Lys Val Val Pro Ser Leu Leu
85 90 95

Lys Glu Gly Phe Val Pro Lys Gly Ile Leu Arg Thr Ala Gln Val Gly
100 105 110

Arg Pro Asp Asn Leu Ser Pro Phe Asn Gly Phe Val Asn Ile Val Arg
115 120 125

Phe Tyr Glu Leu Cys Val Pro Asn Leu Ala Val Glu His Val Gly Lys
130 135 140

Tyr Glu Glu Phe Ala Pro Ser Leu Ala Leu Lys Ile Glu Glu His Tyr
145 150 155 160

Val Glu Asp Gly Ser Gly Asp Lys Glu Phe His Ile Tyr Leu Arg Pro
165 170 175

Asn Met Phe Trp Glu Pro Ile Asp Pro Thr Leu Phe Pro Lys Asn Ile
180 185 190

Thr Leu Ala Asp Ser Phe Leu Arg Pro His Pro Val Thr Ala His Asp
195 200 205

Val Lys Phe Tyr Tyr Asp Val Val Met Asn Pro Tyr Val Ala Glu Met
210 215 220

Arg Ala Val Ala Met Arg Ser Tyr Phe Glu Asp Met Val Ser Val Arg
225 230 235 240

Val Glu Asn Asp Leu Lys Leu Ile Val Arg Trp Arg Ala His Thr Val
245 250 255

Arg Asn Glu Gln Gly Glu Glu Glu Lys Lys Val Leu Tyr Ser Ala Phe
260 265 270

Ala Asn Thr Leu Ala Leu Gln Pro Leu Pro Cys Phe Val Tyr Gln His
275 280 285

Phe Ala Asn Gly Glu Lys Ile Val Pro Glu Asp Ser Asp Pro Asp Thr
290 295 300

Tyr Arg Lys Asp Ser Val Trp Ala Gln Asn Phe Ser Ser His Trp Ala
305 310 315 320

Tyr Asn Tyr Ile Val Ser Cys Gly Ala Phe Arg Phe Ala Gly Met Asp
325 330 335

Asp Glu Lys Ile Thr Leu Val Arg Asn Pro Asn Tyr His Asn Pro Phe
340 345 350

Ala Ala Leu Val Glu Lys Arg Tyr Ile Tyr Met Lys Asp Ser Thr Asp
355 360 365

Ser Leu Phe Gln Asp Phe Lys Ala Gly Lys Val Asp Ile Ala Tyr Phe
370 375 380

```
Pro Pro Asn His Val Asp Asn Leu Ala Ser Phe Met Gln Thr Ser Ala
385                 390                 395                 400

Tyr Lys Glu Gln Ala Ala Arg Gly Glu Ala Ile Leu Glu Lys Asn Ser
                405                 410                 415

Ser Asp Arg Ser Tyr Ser Tyr Ile Gly Trp Asn Cys Leu Ser Leu Phe
            420                 425                 430

Phe Asn Asn Arg Ser Val Arg Gln Ala Met Asn Met Leu Ile Asp Arg
        435                 440                 445

Asp Arg Ile Ile Glu Gln Cys Leu Asp Gly Arg Gly Val Ser Val Ser
    450                 455                 460

Gly Pro Phe Ser Leu Cys Ser Pro Ser Tyr Asn Arg Asp Val Glu Gly
465                 470                 475                 480

Trp Gln Tyr Ser Pro Glu Glu Ala Ala Arg Lys Leu Glu Glu Glu Gly
                485                 490                 495

Trp Ile Asp Ala Asp Gly Asp Gly Ile Arg Glu Lys Val Ile Asp Gly
            500                 505                 510

Val Val Val Pro Phe Arg Phe Arg Leu Cys Tyr Tyr Val Lys Ser Val
        515                 520                 525

Thr Ala Arg Thr Ile Ala Glu Tyr Val Ala Thr Val Cys Lys Glu Val
    530                 535                 540

Gly Ile Glu Cys Cys Leu Leu Gly Leu Asp Met Ala Asp Tyr Ser Gln
545                 550                 555                 560

Ala Leu Glu Glu Lys Asn Phe Asp Ala Ile Leu Ser Gly Trp Cys Leu
                565                 570                 575

Gly Thr Pro Pro Glu Asp Pro Arg Ala Leu Trp His Ser Glu Gly Ala
            580                 585                 590

Leu Glu Lys Gly Ser Ala Asn Ala Val Gly Phe Cys Asn Glu Glu Ala
        595                 600                 605

Asp Arg Ile Ile Glu Gln Leu Ser Tyr Glu Tyr Asp Ser Asn Lys Arg
    610                 615                 620

Gln Ala Leu Tyr His Arg Phe His Glu Val Ile His Glu Glu Ser Pro
625                 630                 635                 640

Tyr Ala Phe Leu Tyr Ser Arg Gln Tyr Ser Leu Val Tyr Lys Glu Phe
                645                 650                 655

Val Lys Asn Ile Phe Val Pro Thr Glu His Gln Asp Leu Ile Pro Gly
            660                 665                 670

Ala Gln Asp Glu Thr Val Asn Leu Ser Met Leu Trp Val Asp Lys Glu
        675                 680                 685

Glu Gly Arg Cys Ser Ala Ile Ser
    690                 695


<210> SEQ ID NO 22
<211> LENGTH: 421
<212> TYPE: PRT
<213> ORGANISM: Chlamydia trachomatis

<400> SEQUENCE: 22

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
```

-continued

```
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420
```

<210> SEQ ID NO 23
<211> LENGTH: 221
<212> TYPE: PRT
<213> ORGANISM: Chlamydia trachomatis

<400> SEQUENCE: 23

```
Met Lys Lys Phe Ile Tyr Lys Tyr Ser Phe Gly Ala Leu Leu Leu Leu
1               5                   10                  15

Ser Gly Leu Ser Gly Leu Ser Ser Cys Cys Ala Asn Ser Tyr Gly Ser
            20                  25                  30

Thr Leu Ala Lys Asn Thr Ala Glu Ile Lys Glu Glu Ser Val Thr Leu
        35                  40                  45

Arg Glu Lys Pro Asp Ala Gly Cys Lys Lys Lys Ser Ser Cys Tyr Leu
    50                  55                  60

Arg Lys Phe Phe Ser Arg Lys Lys Pro Lys Glu Lys Thr Glu Pro Val
65                  70                  75                  80

Leu Pro Asn Phe Lys Ser Tyr Ala Asp Pro Met Thr Asp Ser Glu Arg
                85                  90                  95

Lys Asp Leu Ser Phe Val Val Ser Ala Ala Ala Asp Lys Ser Ser Ile
            100                 105                 110

Ala Leu Ala Met Ala Gln Gly Glu Ile Lys Gly Ala Leu Ser Arg Ile
        115                 120                 125

Arg Glu Ile His Pro Leu Ala Leu Leu Gln Ala Leu Ala Glu Asp Pro
    130                 135                 140

Ala Leu Ile Ala Gly Met Lys Lys Met Gln Gly Arg Asp Trp Val Trp
145                 150                 155                 160

Asn Ile Phe Ile Thr Glu Leu Ser Lys Val Phe Ser Gln Ala Ala Ser
                165                 170                 175

Leu Gly Ala Phe Ser Val Ala Asp Val Ala Ala Phe Ala Ser Thr Leu
            180                 185                 190

Gly Leu Asp Ser Gly Thr Val Thr Ser Ile Val Asp Gly Glu Arg Trp
        195                 200                 205

Ala Glu Leu Ile Asp Val Val Ile Gln Asn Pro Ala Ile
    210                 215                 220
```

<210> SEQ ID NO 24
<211> LENGTH: 242
<212> TYPE: PRT
<213> ORGANISM: Chlamydia trachomatis

<400> SEQUENCE: 24

```
Met Lys Val Lys Ile Asn Asp Gln Phe Ile Cys Ile Ser Pro Tyr Ile
1               5                   10                  15

Ser Ala Arg Trp Asn Gln Ile Ala Phe Ile Glu Ser Cys Asp Gly Gly
            20                  25                  30

Thr Glu Gly Gly Ile Thr Leu Lys Leu His Leu Ile Asp Gly Glu Thr
        35                  40                  45

Val Ser Ile Pro Asn Leu Gly Gln Ala Ile Val Asp Glu Val Phe Gln
    50                  55                  60

Glu His Leu Leu Tyr Leu Glu Ser Thr Ala Pro Gln Lys Asn Lys Glu
65                  70                  75                  80

Glu Glu Lys Ile Ser Ser Leu Leu Gly Ala Val Gln Gln Met Ala Lys
                85                  90                  95

Gly Cys Glu Val Gln Val Phe Ser Gln Lys Gly Leu Val Ser Met Leu
            100                 105                 110

Leu Gly Gly Ala Gly Ser Ile Asn Val Leu Leu Gln His Ser Pro Glu
        115                 120                 125

His Lys Asp His Pro Asp Leu Pro Thr Asp Leu Leu Glu Arg Ile Ala
    130                 135                 140

Gln Met Met Arg Ser Leu Ser Ile Gly Pro Thr Ser Ile Leu Ala Lys
145                 150                 155                 160
```

Pro Glu Pro His Cys Asn Cys Leu His Cys Gln Ile Gly Arg Ala Thr
165 170 175

Val Glu Glu Glu Asp Ala Gly Val Ser Asp Glu Asp Leu Thr Phe Arg
180 185 190

Ser Trp Asp Ile Ser Gln Ser Gly Glu Lys Met Tyr Thr Val Thr Asp
195 200 205

Pro Leu Asn Pro Glu Glu Gln Phe Asn Val Tyr Leu Gly Thr Pro Ile
210 215 220

Gly Cys Thr Cys Gly Gln Pro Tyr Cys Glu His Val Lys Ala Val Leu
225 230 235 240

Tyr Thr

<210> SEQ ID NO 25
<211> LENGTH: 957
<212> TYPE: DNA
<213> ORGANISM: Chlamydia muridarum

<400> SEQUENCE: 25
atggcatcca agtctcgtca ttatcttaac cagccttggt acattatctt attcatcttt 60
gttcttagtc tggttgctgg tacccttctt tcttcagttt cctatgttct atctccaatc 120
caaaaacaag ctgcagaatt tgatcgtaat cagcaaatgt tgatggccgc acaaattatt 180
tcctatgaca ataaattcca aatatatgct gaaggggatt ggcaacctgc tgtctataat 240
acaaaaaaac agatactaga aaaaagctct tccactccac cacaagtgac tgtggcgact 300
ctatgctctt attttcaaaa ttttgttaga gttttgctta cagactccca agggaatctt 360
tcttcttttg aagatcacaa tcttaaccta gaagagttct tatcccaccc cacatcttca 420
gtacaagatc actctctgca tgtaatttat gctattctag caaacgatga atcctctaaa 480
aagttatcat cctcccaagt agcaaaaaat ccggtatcca tagagtctat tattcttcct 540
ataaaaggat ttggtttatg gggaccaatc tatggatttc ttgctttaga aaaggacggt 600
aatacggttc tagggacatg ctggtatcaa catggtgaga ctccaggatt aggagcaaat 660
ataactaatc cccaatggca acaaaatttc agaggaaaaa aagtatttct cgcttcctct 720
tccggagaaa ccgattttgc taaaacaact ctaggactag aagttataaa aggatctgtt 780
tctgcattat taggggactc tcccaaagct aattccgctg ttgatggaat ttcaggagct 840
acactgacct gtaatggagt tactgaagct tttgctaatt cgctagctcc ttaccgcccc 900
ttattgactt tcttcgccaa tcttaactct agtggagaat ctcatgacaa ccaataa 957

<210> SEQ ID NO 26
<211> LENGTH: 318
<212> TYPE: PRT
<213> ORGANISM: Chlamydia muridarum

<400> SEQUENCE: 26

Met Ala Ser Lys Ser Arg His Tyr Leu Asn Gln Pro Trp Tyr Ile Ile
1 5 10 15

Leu Phe Ile Phe Val Leu Ser Leu Val Ala Gly Thr Leu Leu Ser Ser
20 25 30

Val Ser Tyr Val Leu Ser Pro Ile Gln Lys Gln Ala Ala Glu Phe Asp
35 40 45

Arg Asn Gln Gln Met Leu Met Ala Ala Gln Ile Ile Ser Tyr Asp Asn
50 55 60

Lys Phe Gln Ile Tyr Ala Glu Gly Asp Trp Gln Pro Ala Val Tyr Asn

```
65                  70                  75                  80

Thr Lys Lys Gln Ile Leu Glu Lys Ser Ser Ser Thr Pro Pro Gln Val
                85                  90                  95

Thr Val Ala Thr Leu Cys Ser Tyr Phe Gln Asn Phe Val Arg Val Leu
            100                 105                 110

Leu Thr Asp Ser Gln Gly Asn Leu Ser Ser Phe Glu Asp His Asn Leu
        115                 120                 125

Asn Leu Glu Glu Phe Leu Ser His Pro Thr Ser Ser Val Gln Asp His
    130                 135                 140

Ser Leu His Val Ile Tyr Ala Ile Leu Ala Asn Asp Glu Ser Ser Lys
145                 150                 155                 160

Lys Leu Ser Ser Ser Gln Val Ala Lys Asn Pro Val Ser Ile Glu Ser
                165                 170                 175

Ile Ile Leu Pro Ile Lys Gly Phe Gly Leu Trp Gly Pro Ile Tyr Gly
            180                 185                 190

Phe Leu Ala Leu Glu Lys Asp Gly Asn Thr Val Leu Gly Thr Cys Trp
        195                 200                 205

Tyr Gln His Gly Glu Thr Pro Gly Leu Gly Ala Asn Ile Thr Asn Pro
    210                 215                 220

Gln Trp Gln Gln Asn Phe Arg Gly Lys Lys Val Phe Leu Ala Ser Ser
225                 230                 235                 240

Ser Gly Glu Thr Asp Phe Ala Lys Thr Thr Leu Gly Leu Glu Val Ile
                245                 250                 255

Lys Gly Ser Val Ser Ala Leu Leu Gly Asp Ser Pro Lys Ala Asn Ser
            260                 265                 270

Ala Val Asp Gly Ile Ser Gly Ala Thr Leu Thr Cys Asn Gly Val Thr
        275                 280                 285

Glu Ala Phe Ala Asn Ser Leu Ala Pro Tyr Arg Pro Leu Leu Thr Phe
    290                 295                 300

Phe Ala Asn Leu Asn Ser Ser Gly Glu Ser His Asp Asn Gln
305                 310                 315


<210> SEQ ID NO 27
<211> LENGTH: 1416
<212> TYPE: DNA
<213> ORGANISM: Chlamydia muridarum

<400> SEQUENCE: 27

atgaatggaa aagttctgtg tgaggtttct gtgtccttcc gttcgattct gctgacggct      60

ctgctttcac tttcttttac aaacactatg caggctgcac accatcatta tcaccgttat     120

gatgataaac tacgcagaca ataccataaa aaggacttgc ccactcaaga gaatgttcgg     180

aaagagtttt gtaatcccta ctctcatagt agtgatccta tccctttgtc acaacaacga     240

ggagtcctat ctcctatctg tgatttagtc tcagagtgct cgtttttgaa cgggatttcc     300

gttaggagtc ttaaacaaac actgaaaaat tctgctggga ctcaagttgc tttagactgg     360

tctatccttc ctcaatggtt caatcctaga tcctcttggg ctcctaagct ctctattcga     420

gatcttggat atggtaaacc ccagtccctt attgaagcag attccccttg ttgtcaaacc     480

tgcttcaacc catctgctgc tattacgatt tacgattctt catgtgggaa gggtgttgtc     540

caagtgtcat acacccttgt tcgttattgg agagaaacgg ctgcacttgc agggcaaact     600

atgatgcttg caggaagtat taatgattat cctgctcgcc aaaacatatt ctctcaactt     660

acattttccc aaactttccc taatgagaga gtaaatctaa ctgttggtca atactctctt     720
```

-continued

```
tactcgatag acggaacgct gtacaacaat gatcagcagc taggatttat tagttatgcg    780

ttgtcgcaaa atccaacagc gacttattcc tctggaagcc ttggcgccta tctacaagtc    840

gctccaacag aaagcacctg tcttcaagtt gggttccaag atgcctataa tatttcaggt    900

tcctcgatca aatggaataa tcttacaaaa aataagtata acttccatgg ctatgcatct    960

tgggctccac actgttgctt aggacctgga caatactctg ttcttcttta tgtaaccaga   1020

aaggttcctg agcaaatgat gcagacaatg ggctggtctg tgaatgcaag tcaatacatc   1080

tcttctaaac tttatgtatt tggaagatac agcggagtca caggccaatt gtctcctatt   1140

aaccgaacct attcatttgg cttagtctct cctaatttat tgaaccgtaa cccacaagac   1200

ttatttggag tagcttgcgc attcaataat atacacgcct ccgcctttca aaatgctcaa   1260

agaaaatatg aaactgtgat cgagggattt gcaactattg gttgcggacc ttacatctcc   1320

tttgctccag atttccaact ttacctctat cctgctctgc gtccaaataa acaaagcgcc   1380

cgagtctata gcgttcgcgc aaacctagct atttag                             1416


<210> SEQ ID NO 28
<211> LENGTH: 471
<212> TYPE: PRT
<213> ORGANISM: Chlamydia muridarum

<400> SEQUENCE: 28

Met Asn Gly Lys Val Leu Cys Glu Val Ser Val Ser Phe Arg Ser Ile
1               5                   10                  15

Leu Leu Thr Ala Leu Leu Ser Leu Ser Phe Thr Asn Thr Met Gln Ala
            20                  25                  30

Ala His His His Tyr His Arg Tyr Asp Asp Lys Leu Arg Arg Gln Tyr
        35                  40                  45

His Lys Lys Asp Leu Pro Thr Gln Glu Asn Val Arg Lys Glu Phe Cys
    50                  55                  60

Asn Pro Tyr Ser His Ser Ser Asp Pro Ile Pro Leu Ser Gln Gln Arg
65                  70                  75                  80

Gly Val Leu Ser Pro Ile Cys Asp Leu Val Ser Glu Cys Ser Phe Leu
                85                  90                  95

Asn Gly Ile Ser Val Arg Ser Leu Lys Gln Thr Leu Lys Asn Ser Ala
            100                 105                 110

Gly Thr Gln Val Ala Leu Asp Trp Ser Ile Leu Pro Gln Trp Phe Asn
        115                 120                 125

Pro Arg Ser Ser Trp Ala Pro Lys Leu Ser Ile Arg Asp Leu Gly Tyr
    130                 135                 140

Gly Lys Pro Gln Ser Leu Ile Glu Ala Asp Ser Pro Cys Cys Gln Thr
145                 150                 155                 160

Cys Phe Asn Pro Ser Ala Ala Ile Thr Ile Tyr Asp Ser Ser Cys Gly
                165                 170                 175

Lys Gly Val Val Gln Val Ser Tyr Thr Leu Val Arg Tyr Trp Arg Glu
            180                 185                 190

Thr Ala Ala Leu Ala Gly Gln Thr Met Met Leu Ala Gly Ser Ile Asn
        195                 200                 205

Asp Tyr Pro Ala Arg Gln Asn Ile Phe Ser Gln Leu Thr Phe Ser Gln
    210                 215                 220

Thr Phe Pro Asn Glu Arg Val Asn Leu Thr Val Gly Gln Tyr Ser Leu
225                 230                 235                 240

Tyr Ser Ile Asp Gly Thr Leu Tyr Asn Asn Asp Gln Gln Leu Gly Phe
                245                 250                 255
```

```
Ile Ser Tyr Ala Leu Ser Gln Asn Pro Thr Ala Thr Tyr Ser Ser Gly
            260                 265                 270

Ser Leu Gly Ala Tyr Leu Gln Val Ala Pro Thr Glu Ser Thr Cys Leu
        275                 280                 285

Gln Val Gly Phe Gln Asp Ala Tyr Asn Ile Ser Gly Ser Ser Ile Lys
    290                 295                 300

Trp Asn Asn Leu Thr Lys Asn Lys Tyr Asn Phe His Gly Tyr Ala Ser
305                 310                 315                 320

Trp Ala Pro His Cys Cys Leu Gly Pro Gly Gln Tyr Ser Val Leu Leu
                325                 330                 335

Tyr Val Thr Arg Lys Val Pro Glu Gln Met Met Gln Thr Met Gly Trp
            340                 345                 350

Ser Val Asn Ala Ser Gln Tyr Ile Ser Ser Lys Leu Tyr Val Phe Gly
        355                 360                 365

Arg Tyr Ser Gly Val Thr Gly Gln Leu Ser Pro Ile Asn Arg Thr Tyr
    370                 375                 380

Ser Phe Gly Leu Val Ser Pro Asn Leu Leu Asn Arg Asn Pro Gln Asp
385                 390                 395                 400

Leu Phe Gly Val Ala Cys Ala Phe Asn Asn Ile His Ala Ser Ala Phe
                405                 410                 415

Gln Asn Ala Gln Arg Lys Tyr Glu Thr Val Ile Glu Gly Phe Ala Thr
            420                 425                 430

Ile Gly Cys Gly Pro Tyr Ile Ser Phe Ala Pro Asp Phe Gln Leu Tyr
        435                 440                 445

Leu Tyr Pro Ala Leu Arg Pro Asn Lys Gln Ser Ala Arg Val Tyr Ser
    450                 455                 460

Val Arg Ala Asn Leu Ala Ile
465                 470
```

<210> SEQ ID NO 29
<211> LENGTH: 1665
<212> TYPE: DNA
<213> ORGANISM: Chlamydia muridarum

<400> SEQUENCE: 29

```
atgcgaatag gagatcctat gaacaaactc atcagacgag ctgtgacgat cttcgcggtg      60

actagtgtgg cgagtttatt tgctagcggg gtgttagaga cctctatggc agagtctctc     120

tctaccaacg ttattagctt agctgacacc aaagcgaaag agaccacttc tcatcaaaaa     180

gacagaaaag caagaaaaaa tcatcaaaat aggacttccg tagtccgtaa agaggttact     240

gcagttcgtg atactaaagc tgtagagcct agacaggatt cttgctttgg caaaatgtat     300

acagtcaaag ttaatgatga tcgtaatgta gaaatcgtgc agtccgttcc tgaatatgct     360

acggtaggat ctccatatcc tattgagatt actgctatag ggaaaagaga ctgtgttgat     420

gtaatcatta cacagcaatt accatgcgaa gcagagtttg ttagcagtga tccagctact     480

actcctactg ctgatggtaa gctagtttgg aaaattgatc ggttaggaca gggcgaaaag     540

agtaaaatta ctgtatgggt aaaacctctt aaagaaggtt gctgctttac agctgcaacg     600

gtttgtgctt gtccagagat ccgttcggtt acgaaatgtg gccagcctgc tatctgtgtt     660

aaacaggaag gtccagaaag cgcatgtttg cgttgcccag taacttatag aattaatgta     720

gtcaaccaag gaacagcaac agcacgtaat gttgttgtgg aaaatcctgt tccagatggc     780

tatgctcatg catccggaca gcgtgtattg acatatactc ttggggatat gcaacctgga     840
```

```
gaacagagaa caatcaccgt ggagttttgt ccgcttaaac gtggtcgagt cacaaatatt    900

gctacagttt cttactgtgg tggacacaaa aatactgcta gcgtaacaac agtgatcaat    960

gagccttgcg tgcaagttaa catcgaggga gcagattggt cttatgtttg taagcctgta   1020

gaatatgtta tctctgtttc taaccctggt gacttagttt tacgagacgt tgtaattgaa   1080

gatacgcttt ctcctggaat aactgttgtt gaagcagctg gagctcagat ttcttgtaat   1140

aaattggttt ggactttgaa ggaactcaat cctggagagt ctttacaata taaggttcta   1200

gtaagagctc aaactccagg gcaattcaca aacaacgttg ttgtgaaaag ttgctctgat   1260

tgcggtattt gtacttcttg cgcagaagca acaacttact ggaaaggagt tgctgctact   1320

catatgtgcg tagtagatac ttgtgatcct atttgcgtag gagagaacac tgtttatcgt   1380

atctgtgtga caaacagagg ttctgctgaa gatacaaatg tgtccttaat tttgaaattc   1440

tctaaagaat tacaacctat atctttctct ggaccaacta aaggaaccat tacaggaaac   1500

acggtagtgt ttgattcgtt acctagatta ggttctaaag aaactgtaga gttttctgta   1560

acgttgaaag cagtatccgc tggagatgct cgtggggaag ctattctttc ttccgataca   1620

ttgacagttc ctgtatctga tacggagaat acacatatct attaa                   1665
```

```
<210> SEQ ID NO 30
<211> LENGTH: 554
<212> TYPE: PRT
<213> ORGANISM: Chlamydia muridarum

<400> SEQUENCE: 30

Met Arg Ile Gly Asp Pro Met Asn Lys Leu Ile Arg Arg Ala Val Thr
1               5                   10                  15

Ile Phe Ala Val Thr Ser Val Ala Ser Leu Phe Ala Ser Gly Val Leu
            20                  25                  30

Glu Thr Ser Met Ala Glu Ser Leu Ser Thr Asn Val Ile Ser Leu Ala
        35                  40                  45

Asp Thr Lys Ala Lys Glu Thr Thr Ser His Gln Lys Asp Arg Lys Ala
    50                  55                  60

Arg Lys Asn His Gln Asn Arg Thr Ser Val Val Arg Lys Glu Val Thr
65                  70                  75                  80

Ala Val Arg Asp Thr Lys Ala Val Glu Pro Arg Gln Asp Ser Cys Phe
                85                  90                  95

Gly Lys Met Tyr Thr Val Lys Val Asn Asp Asp Arg Asn Val Glu Ile
            100                 105                 110

Val Gln Ser Val Pro Glu Tyr Ala Thr Val Gly Ser Pro Tyr Pro Ile
        115                 120                 125

Glu Ile Thr Ala Ile Gly Lys Arg Asp Cys Val Asp Val Ile Ile Thr
    130                 135                 140

Gln Gln Leu Pro Cys Glu Ala Glu Phe Val Ser Ser Asp Pro Ala Thr
145                 150                 155                 160

Thr Pro Thr Ala Asp Gly Lys Leu Val Trp Lys Ile Asp Arg Leu Gly
                165                 170                 175

Gln Gly Glu Lys Ser Lys Ile Thr Val Trp Val Lys Pro Leu Lys Glu
            180                 185                 190

Gly Cys Cys Phe Thr Ala Ala Thr Val Cys Ala Cys Pro Glu Ile Arg
        195                 200                 205

Ser Val Thr Lys Cys Gly Gln Pro Ala Ile Cys Val Lys Gln Glu Gly
    210                 215                 220

Pro Glu Ser Ala Cys Leu Arg Cys Pro Val Thr Tyr Arg Ile Asn Val
```

```
225                 230                 235                 240

Val Asn Gln Gly Thr Ala Thr Ala Arg Asn Val Val Val Glu Asn Pro
                245                 250                 255

Val Pro Asp Gly Tyr Ala His Ala Ser Gly Gln Arg Val Leu Thr Tyr
            260                 265                 270

Thr Leu Gly Asp Met Gln Pro Gly Glu Gln Arg Thr Ile Thr Val Glu
        275                 280                 285

Phe Cys Pro Leu Lys Arg Gly Arg Val Thr Asn Ile Ala Thr Val Ser
    290                 295                 300

Tyr Cys Gly Gly His Lys Asn Thr Ala Ser Val Thr Thr Val Ile Asn
305                 310                 315                 320

Glu Pro Cys Val Gln Val Asn Ile Glu Gly Ala Asp Trp Ser Tyr Val
                325                 330                 335

Cys Lys Pro Val Glu Tyr Val Ile Ser Val Ser Asn Pro Gly Asp Leu
            340                 345                 350

Val Leu Arg Asp Val Val Ile Glu Asp Thr Leu Ser Pro Gly Ile Thr
        355                 360                 365

Val Val Glu Ala Ala Gly Ala Gln Ile Ser Cys Asn Lys Leu Val Trp
    370                 375                 380

Thr Leu Lys Glu Leu Asn Pro Gly Glu Ser Leu Gln Tyr Lys Val Leu
385                 390                 395                 400

Val Arg Ala Gln Thr Pro Gly Gln Phe Thr Asn Asn Val Val Val Lys
                405                 410                 415

Ser Cys Ser Asp Cys Gly Ile Cys Thr Ser Cys Ala Glu Ala Thr Thr
            420                 425                 430

Tyr Trp Lys Gly Val Ala Ala Thr His Met Cys Val Val Asp Thr Cys
        435                 440                 445

Asp Pro Ile Cys Val Gly Glu Asn Thr Val Tyr Arg Ile Cys Val Thr
    450                 455                 460

Asn Arg Gly Ser Ala Glu Asp Thr Asn Val Ser Leu Ile Leu Lys Phe
465                 470                 475                 480

Ser Lys Glu Leu Gln Pro Ile Ser Phe Ser Gly Pro Thr Lys Gly Thr
                485                 490                 495

Ile Thr Gly Asn Thr Val Val Phe Asp Ser Leu Pro Arg Leu Gly Ser
            500                 505                 510

Lys Glu Thr Val Glu Phe Ser Val Thr Leu Lys Ala Val Ser Ala Gly
        515                 520                 525

Asp Ala Arg Gly Glu Ala Ile Leu Ser Ser Asp Thr Leu Thr Val Pro
    530                 535                 540

Val Ser Asp Thr Glu Asn Thr His Ile Tyr
545                 550
```

<210> SEQ ID NO 31
<211> LENGTH: 504
<212> TYPE: DNA
<213> ORGANISM: Chlamydia muridarum

<400> SEQUENCE: 31

```
atgtccagac agaatgctga ggaaaatcta aaaaattttg ctaaagagct caagctcccc      60

gacgtggcct tcgatcagaa taatacgtgc attttgtttg ttgatggaga gttttctctt     120

cacctgacct acgaagagca ctctgatcgc ctttatgttt acgcacctct ccttgacgga     180

ctcccagata atccgcaaag aaagttggct ctgtatgaga aattgttgga aggctctatg     240

ctcggaggcc aaatggctgg tggaggagta ggagttgcta ctaaagaaca gttgatccta     300
```

```
atgcattgcg tgttagatat gaaatatgca gagactaatc tattgaaagc ttttgcacag    360

cttttcattg aaactgttgt gaaatggcga acggtctgtt ctgatatcag cgctggacga    420

gaaccttccg ttgacactat gcctcaaatg cctcaaggag gcagcggagg aattcaacct    480

cctccaacag gaattcgtgc gtag                                           504


<210> SEQ ID NO 32
<211> LENGTH: 167
<212> TYPE: PRT
<213> ORGANISM: Chlamydia muridarum

<400> SEQUENCE: 32

Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30

Phe Val Asp Gly Glu Phe Ser Leu His Leu Thr Tyr Glu Glu His Ser
        35                  40                  45

Asp Arg Leu Tyr Val Tyr Ala Pro Leu Leu Asp Gly Leu Pro Asp Asn
    50                  55                  60

Pro Gln Arg Lys Leu Ala Leu Tyr Glu Lys Leu Leu Glu Gly Ser Met
65                  70                  75                  80

Leu Gly Gly Gln Met Ala Gly Gly Gly Val Gly Val Ala Thr Lys Glu
                85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125

Trp Arg Thr Val Cys Ser Asp Ile Ser Ala Gly Arg Glu Pro Ser Val
    130                 135                 140

Asp Thr Met Pro Gln Met Pro Gln Gly Gly Ser Gly Gly Ile Gln Pro
145                 150                 155                 160

Pro Pro Thr Gly Ile Arg Ala
                165


<210> SEQ ID NO 33
<211> LENGTH: 609
<212> TYPE: DNA
<213> ORGANISM: Chlamydia muridarum

<400> SEQUENCE: 33

atgctcgcta atcggttatt tctaatcacc cttataggtt ttggctattc tgcttacggt     60

gccagcacag ggaaatcacc ttctttacag gttattttag ctgaagtcga ggatacatct    120

tcgcgcttac aagctcatca gaatgagctt gttatgctct cggaacgttt agatgagcaa    180

gacacaaaac ttcaacaact ctcgtcaact caggcccgta atcttcctca acaagttcaa    240

cggcttgaga ttgatctgag agctctggct aaaacagctg ctgtgctctc gcaatctgtt    300

caggatatcc gatcatccgt gcaaaataaa ttacaagaaa tccaacaaga acaaaaaaat    360

ttagctcaaa atttacgagc gcttcgcaac tccttacaag cactagttga tggctcttcc    420

ccagaaaatt atattgattt tttggccggg gagacacctg aacatattca cgttgttaaa    480

caaggagaaa ccctgagtaa aatcgctagt aagtacaata tccctgtcgc agaattgaaa    540

aaacttaata aattaaattc cgatactatt tttactgatc aaagaatccg acttccaaaa    600

aagaaataa                                                            609
```

<210> SEQ ID NO 34
<211> LENGTH: 202
<212> TYPE: PRT
<213> ORGANISM: Chlamydia muridarum

<400> SEQUENCE: 34

```
Met Leu Ala Asn Arg Leu Phe Leu Ile Thr Leu Ile Gly Phe Gly Tyr
1               5                   10                  15

Ser Ala Tyr Gly Ala Ser Thr Gly Lys Ser Pro Ser Leu Gln Val Ile
            20                  25                  30

Leu Ala Glu Val Glu Asp Thr Ser Ser Arg Leu Gln Ala His Gln Asn
        35                  40                  45

Glu Leu Val Met Leu Ser Glu Arg Leu Asp Glu Gln Asp Thr Lys Leu
    50                  55                  60

Gln Gln Leu Ser Ser Thr Gln Ala Arg Asn Leu Pro Gln Gln Val Gln
65                  70                  75                  80

Arg Leu Glu Ile Asp Leu Arg Ala Leu Ala Lys Thr Ala Ala Val Leu
                85                  90                  95

Ser Gln Ser Val Gln Asp Ile Arg Ser Ser Val Gln Asn Lys Leu Gln
            100                 105                 110

Glu Ile Gln Gln Glu Gln Lys Asn Leu Ala Gln Asn Leu Arg Ala Leu
        115                 120                 125

Arg Asn Ser Leu Gln Ala Leu Val Asp Gly Ser Ser Pro Glu Asn Tyr
    130                 135                 140

Ile Asp Phe Leu Ala Gly Glu Thr Pro Glu His Ile His Val Val Lys
145                 150                 155                 160

Gln Gly Glu Thr Leu Ser Lys Ile Ala Ser Lys Tyr Asn Ile Pro Val
                165                 170                 175

Ala Glu Leu Lys Lys Leu Asn Lys Leu Asn Ser Asp Thr Ile Phe Thr
            180                 185                 190

Asp Gln Arg Ile Arg Leu Pro Lys Lys Lys
        195                 200
```

<210> SEQ ID NO 35
<211> LENGTH: 3024
<212> TYPE: DNA
<213> ORGANISM: Chlamydia muridarum

<400> SEQUENCE: 35

```
atgacgactc caataagtaa ttctccatct tctattccaa ctgttacagt atcaactact     60

acagcatctt ctggatctct cggaacttct actgtatcat caacgactac aagtacttca    120

gtcgcacaaa cagcaacaac aacatcttct gcttctacat ctataattca gtctagtgga    180

gaaaacatcc aatccactac aggtacccct tctcctatta cgtctagtgt ttcaacatcc    240

gctccatctc ctaaagcctc cgccactgca aacaaaactt caagcgctgt ttctgggaaa    300

attacctcac aagaaacttc tgaggaatcc gaaacccaag ccactacatc tgatggagaa    360

gttagtagta attacgatga tgttgatacc ccgaccaatt cgtccgattc gacagttgat    420

agtgattacc aagatgttga gactcagtac aaaacaatta gcaacaatgg tgaaaacact    480

tatgaaacaa tcggaagtca tggtgagaaa aacacacacg tccaggaaag ccatgcatcc    540

ggaacaggaa atcccataaa taatcagcaa gaagctatta gacagctccg atcatctacc    600

tatacaacca gccctcgtaa tgagaatata tttagtccag gaccggaagg tctacctaat    660

atgtctcttc ctagttacag ccctacagat aaaagttctc tactagcttt cctatctaat    720
```

-continued

```
cccaatacaa aagcaaaaat gctcgaacac tccgggcatt tagtctttat agacacaact    780
agaagtagct ttatctttgt tccgaatgga aattgggatc aagtctgttc catgaaggtt    840
cagaatggga aaactaaaga agaccttggc ttaaaggact tagaagatat gtgtgcaaag    900
ttttgcacag gatacaataa attctcctct gattggggaa atcgagttga ccccttggtc    960
tcttctaagg ccgggataga aagtgggggg cacctcccaa gctcagttat catcaacaac   1020
aaatttagaa cctgtgttgc ctatgggccg tggaacccca aagaaaacgg ccccaattat   1080
actccttcag cctggagacg tggcatcga gtagattttg gaaagatctt tgatggaaca   1140
gcgccgttta ataaaatcaa ctggggctct tcccctaccc ctggtgatga cggcatctcc   1200
ttctctaatg aaactattgg gtctgaacca ttcgcgacac ctccctcatc cccatcgcaa   1260
acccccgtta tcaacgtcaa tgttaatgtc ggtggaacca atgttaatat tggggataca   1320
aacgtatcta aaggatccgg cacaccaaca tcttctcaat ctgtggacat gtctacagat   1380
actagcgatt tagataccag tgatattgat acaaacaacc aaactaacgg cgatatcaac   1440
acgaatgaca actccaataa tgtcgatgga agtttatctg acgttgattc aagggtggaa   1500
gacgatgacg gtgtatcgga tacagagtcc actaatggca atgactctgg taaaactact   1560
tccacagaag aaaatggtga cccaagcgga ccagacatcc tggctgctgt acgtaaacac   1620
ctagacactg tctatccagg agaaaatggc ggatctacag aaggacctct ccctgctaat   1680
caaaatctgg ggaacgttat ccatgatgtg gagcagaatg gatctgctaa agaaactatt   1740
atcactccag gagatacagg gcctacagac tcaagctcct ctgtagatgc tgatgcagac   1800
gttgaagata cttctgatac tgactctgga atcggagacg acgacggtgt atcggataca   1860
gagtccacta atggtaataa ctctggtaaa actacttcca cagaagaaaa tggtgaccca   1920
agcggaccag acatcctggc tgctgtacgt aaacacctag acactgtcta tccaggagaa   1980
aatggcggat ctacagaagg acctctccct gctaatcaaa atctggggaa cgttatccat   2040
gatgtagaac aaaacggagc cgctcaagaa actattatca ctccaggaga tacggaatct   2100
acagacacaa gctctagtgt aaatgctaat gcagacttag aagatgtttc tgatgctgat   2160
tcaggattcg gggatgatga cggtatatcg gatacagagt ccactaatgg taacgactct   2220
ggaaaaaata ctcctgtagg ggatggtggt acaccaagcg gaccagatat cctagctgct   2280
gtacgcaaac atctagacac tgtctatcca ggagaaaatg gtggatctac agagagacct   2340
ttacccgcta atcaaaattt aggagatatc attcatgatg tagaacaaaa cggaagcgct   2400
aaagaaactg tagtatcgcc ttatcgagga ggaggaggaa atacatcttc cccaattgga   2460
ttagcctccc tgcttccagc aacaccatcc acacctttga tgacaacacc tagaacaaat   2520
gggaaagctg cagcttcttc tttgatgata aaaggaggag aaactcaagc caagctagtt   2580
aagaatggcg gcaatatccc tggagaaacc acattagcag aattactccc tcgtttaaga   2640
ggacaccttg acaaagtctt tacttcagac gggaagttta caaatcttaa tggacctcaa   2700
cttggagcca tcatagacca attccgcaaa gaaacgggtt ccggaggaat catagctcat   2760
acagatagtg ttccaggaga gaacggaaca gcctctcctc tcacaggaag ttcaggggaa   2820
aaagtctctc tctatgatgc agcgaaaaac gtcactcaag ctttaacaag tgttacgaac   2880
aaagtaaccc tagcaatgca aggacaaaaa ctggaaggaa ttataaacaa caacaatacc   2940
ccctcttcta ttggacaaaa tcttttcgca gcagcgaggg caacgacaca atccctcagt   3000
tcattaattg gaaccgtaca ataa                                          3024
```

<210> SEQ ID NO 36
<211> LENGTH: 1007
<212> TYPE: PRT
<213> ORGANISM: Chlamydia muridarum

<400> SEQUENCE: 36

Met Thr Thr Pro Ile Ser Asn Ser Pro Ser Ser Ile Pro Thr Val Thr
1 5 10 15

Val Ser Thr Thr Thr Ala Ser Ser Gly Ser Leu Gly Thr Ser Thr Val
20 25 30

Ser Ser Thr Thr Thr Ser Thr Ser Val Ala Gln Thr Ala Thr Thr Thr
35 40 45

Ser Ser Ala Ser Thr Ser Ile Ile Gln Ser Ser Gly Glu Asn Ile Gln
50 55 60

Ser Thr Thr Gly Thr Pro Ser Pro Ile Thr Ser Ser Val Ser Thr Ser
65 70 75 80

Ala Pro Ser Pro Lys Ala Ser Ala Thr Ala Asn Lys Thr Ser Ser Ala
85 90 95

Val Ser Gly Lys Ile Thr Ser Gln Glu Thr Ser Glu Glu Ser Glu Thr
100 105 110

Gln Ala Thr Thr Ser Asp Gly Glu Val Ser Ser Asn Tyr Asp Asp Val
115 120 125

Asp Thr Pro Thr Asn Ser Ser Asp Ser Thr Val Asp Ser Asp Tyr Gln
130 135 140

Asp Val Glu Thr Gln Tyr Lys Thr Ile Ser Asn Asn Gly Glu Asn Thr
145 150 155 160

Tyr Glu Thr Ile Gly Ser His Gly Glu Lys Asn Thr His Val Gln Glu
165 170 175

Ser His Ala Ser Gly Thr Gly Asn Pro Ile Asn Asn Gln Gln Glu Ala
180 185 190

Ile Arg Gln Leu Arg Ser Ser Thr Tyr Thr Thr Ser Pro Arg Asn Glu
195 200 205

Asn Ile Phe Ser Pro Gly Pro Glu Gly Leu Pro Asn Met Ser Leu Pro
210 215 220

Ser Tyr Ser Pro Thr Asp Lys Ser Ser Leu Leu Ala Phe Leu Ser Asn
225 230 235 240

Pro Asn Thr Lys Ala Lys Met Leu Glu His Ser Gly His Leu Val Phe
245 250 255

Ile Asp Thr Thr Arg Ser Ser Phe Ile Phe Val Pro Asn Gly Asn Trp
260 265 270

Asp Gln Val Cys Ser Met Lys Val Gln Asn Gly Lys Thr Lys Glu Asp
275 280 285

Leu Gly Leu Lys Asp Leu Glu Asp Met Cys Ala Lys Phe Cys Thr Gly
290 295 300

Tyr Asn Lys Phe Ser Ser Asp Trp Gly Asn Arg Val Asp Pro Leu Val
305 310 315 320

Ser Ser Lys Ala Gly Ile Glu Ser Gly Gly His Leu Pro Ser Ser Val
325 330 335

Ile Ile Asn Asn Lys Phe Arg Thr Cys Val Ala Tyr Gly Pro Trp Asn
340 345 350

Pro Lys Glu Asn Gly Pro Asn Tyr Thr Pro Ser Ala Trp Arg Arg Gly
355 360 365

His Arg Val Asp Phe Gly Lys Ile Phe Asp Gly Thr Ala Pro Phe Asn
370 375 380

-continued

```
Lys Ile Asn Trp Gly Ser Ser Pro Thr Pro Gly Asp Asp Gly Ile Ser
385                 390                 395                 400

Phe Ser Asn Glu Thr Ile Gly Ser Glu Pro Phe Ala Thr Pro Pro Ser
                405                 410                 415

Ser Pro Ser Gln Thr Pro Val Ile Asn Val Asn Val Asn Val Gly Gly
            420                 425                 430

Thr Asn Val Asn Ile Gly Asp Thr Asn Val Ser Lys Gly Ser Gly Thr
        435                 440                 445

Pro Thr Ser Ser Gln Ser Val Asp Met Ser Thr Asp Thr Ser Asp Leu
    450                 455                 460

Asp Thr Ser Asp Ile Asp Thr Asn Asn Gln Thr Asn Gly Asp Ile Asn
465                 470                 475                 480

Thr Asn Asp Asn Ser Asn Asn Val Asp Gly Ser Leu Ser Asp Val Asp
                485                 490                 495

Ser Arg Val Glu Asp Asp Asp Gly Val Ser Asp Thr Glu Ser Thr Asn
            500                 505                 510

Gly Asn Asp Ser Gly Lys Thr Thr Ser Thr Glu Glu Asn Gly Asp Pro
        515                 520                 525

Ser Gly Pro Asp Ile Leu Ala Ala Val Arg Lys His Leu Asp Thr Val
    530                 535                 540

Tyr Pro Gly Glu Asn Gly Gly Ser Thr Glu Gly Pro Leu Pro Ala Asn
545                 550                 555                 560

Gln Asn Leu Gly Asn Val Ile His Asp Val Glu Gln Asn Gly Ser Ala
                565                 570                 575

Lys Glu Thr Ile Ile Thr Pro Gly Asp Thr Gly Pro Thr Asp Ser Ser
            580                 585                 590

Ser Ser Val Asp Ala Asp Ala Asp Val Glu Asp Thr Ser Asp Thr Asp
        595                 600                 605

Ser Gly Ile Gly Asp Asp Asp Gly Val Ser Asp Thr Glu Ser Thr Asn
    610                 615                 620

Gly Asn Asn Ser Gly Lys Thr Thr Ser Thr Glu Glu Asn Gly Asp Pro
625                 630                 635                 640

Ser Gly Pro Asp Ile Leu Ala Ala Val Arg Lys His Leu Asp Thr Val
                645                 650                 655

Tyr Pro Gly Glu Asn Gly Gly Ser Thr Glu Gly Pro Leu Pro Ala Asn
            660                 665                 670

Gln Asn Leu Gly Asn Val Ile His Asp Val Glu Gln Asn Gly Ala Ala
        675                 680                 685

Gln Glu Thr Ile Ile Thr Pro Gly Asp Thr Glu Ser Thr Asp Thr Ser
    690                 695                 700

Ser Ser Val Asn Ala Asn Ala Asp Leu Glu Asp Val Ser Asp Ala Asp
705                 710                 715                 720

Ser Gly Phe Gly Asp Asp Asp Gly Ile Ser Asp Thr Glu Ser Thr Asn
                725                 730                 735

Gly Asn Asp Ser Gly Lys Asn Thr Pro Val Gly Asp Gly Gly Thr Pro
            740                 745                 750

Ser Gly Pro Asp Ile Leu Ala Ala Val Arg Lys His Leu Asp Thr Val
        755                 760                 765

Tyr Pro Gly Glu Asn Gly Gly Ser Thr Glu Arg Pro Leu Pro Ala Asn
    770                 775                 780

Gln Asn Leu Gly Asp Ile Ile His Asp Val Glu Gln Asn Gly Ser Ala
785                 790                 795                 800
```

```
Lys Glu Thr Val Val Ser Pro Tyr Arg Gly Gly Gly Gly Asn Thr Ser
                805                 810                 815

Ser Pro Ile Gly Leu Ala Ser Leu Leu Pro Ala Thr Pro Ser Thr Pro
            820                 825                 830

Leu Met Thr Thr Pro Arg Thr Asn Gly Lys Ala Ala Ala Ser Ser Leu
        835                 840                 845

Met Ile Lys Gly Gly Glu Thr Gln Ala Lys Leu Val Lys Asn Gly Gly
    850                 855                 860

Asn Ile Pro Gly Glu Thr Thr Leu Ala Glu Leu Leu Pro Arg Leu Arg
865                 870                 875                 880

Gly His Leu Asp Lys Val Phe Thr Ser Asp Gly Lys Phe Thr Asn Leu
                885                 890                 895

Asn Gly Pro Gln Leu Gly Ala Ile Ile Asp Gln Phe Arg Lys Glu Thr
            900                 905                 910

Gly Ser Gly Gly Ile Ile Ala His Thr Asp Ser Val Pro Gly Glu Asn
        915                 920                 925

Gly Thr Ala Ser Pro Leu Thr Gly Ser Ser Gly Glu Lys Val Ser Leu
    930                 935                 940

Tyr Asp Ala Ala Lys Asn Val Thr Gln Ala Leu Thr Ser Val Thr Asn
945                 950                 955                 960

Lys Val Thr Leu Ala Met Gln Gly Gln Lys Leu Glu Gly Ile Ile Asn
                965                 970                 975

Asn Asn Asn Thr Pro Ser Ser Ile Gly Gln Asn Leu Phe Ala Ala Ala
            980                 985                 990

Arg Ala Thr Thr Gln Ser Leu Ser  Ser Leu Ile Gly Thr  Val Gln
        995                 1000                1005
```

<210> SEQ ID NO 37
<211> LENGTH: 780
<212> TYPE: DNA
<213> ORGANISM: Chlamydia muridarum

<400> SEQUENCE: 37

```
gtgagtatgt atataaaaag aaagaaagct tggatgactt tcttagcaat tgtctgtagt      60

ttctgtttgg cgggctgttc aaaagagagc aaagactctg ttagtgaaaa atttattgta     120

ggaactaacg caacgtatcc tccttttgag tttgttgatg aaagaggtga gacggttggc     180

tttgatattg atttagctag ggagattagt aaaaagctag ggaaaaaatt agaagtccga     240

gaatttgctt ttgatgcact cgttctcaat ttaaaacagc atcgtattga tgcaattatg     300

gcaggggtgt ccattacgtc ttctcgattg aaagaaattt tgatgattcc ctactatggc     360

gaagaaataa agagtttggt tttagtgttt aaggatggag actcaaagtc tttaccacta     420

gatcagtata attctgttgc tgttcaaact ggcacgtacc aagaggaata tttacagtct     480

cttccagggg tgcgtattcg ctcttttgat agtactttag aagtgcttat ggaagttttg     540

catagcaagt ctcctatagc tgttttagaa ccgtctattg cgcaggtcgt tttaaaagat     600

tttccgacgc tcactactga aacgatagat cttcctgaag ataaatgggt tttagggtat     660

ggaattggag ttgcttctga tcgaccatct ctagcttctg atatagaagc tgctgtacaa     720

gagatcaaga aagaaggagt gttagcagag ttagagcaaa aatggggttt gaacggctaa     780
```

<210> SEQ ID NO 38
<211> LENGTH: 259
<212> TYPE: PRT
<213> ORGANISM: Chlamydia muridarum

<400> SEQUENCE: 38

```
Met Ser Met Tyr Ile Lys Arg Lys Lys Ala Trp Met Thr Phe Leu Ala
1               5                   10                  15

Ile Val Cys Ser Phe Cys Leu Ala Gly Cys Ser Lys Glu Ser Lys Asp
            20                  25                  30

Ser Val Ser Glu Lys Phe Ile Val Gly Thr Asn Ala Thr Tyr Pro Pro
        35                  40                  45

Phe Glu Phe Val Asp Glu Arg Gly Glu Thr Val Gly Phe Asp Ile Asp
    50                  55                  60

Leu Ala Arg Glu Ile Ser Lys Lys Leu Gly Lys Lys Leu Glu Val Arg
65                  70                  75                  80

Glu Phe Ala Phe Asp Ala Leu Val Leu Asn Leu Lys Gln His Arg Ile
                85                  90                  95

Asp Ala Ile Met Ala Gly Val Ser Ile Thr Ser Ser Arg Leu Lys Glu
            100                 105                 110

Ile Leu Met Ile Pro Tyr Tyr Gly Glu Glu Ile Lys Ser Leu Val Leu
        115                 120                 125

Val Phe Lys Asp Gly Asp Ser Lys Ser Leu Pro Leu Asp Gln Tyr Asn
    130                 135                 140

Ser Val Ala Val Gln Thr Gly Thr Tyr Gln Glu Glu Tyr Leu Gln Ser
145                 150                 155                 160

Leu Pro Gly Val Arg Ile Arg Ser Phe Asp Ser Thr Leu Glu Val Leu
                165                 170                 175

Met Glu Val Leu His Ser Lys Ser Pro Ile Ala Val Leu Glu Pro Ser
            180                 185                 190

Ile Ala Gln Val Val Leu Lys Asp Phe Pro Thr Leu Thr Thr Glu Thr
        195                 200                 205

Ile Asp Leu Pro Glu Asp Lys Trp Val Leu Gly Tyr Gly Ile Gly Val
    210                 215                 220

Ala Ser Asp Arg Pro Ser Leu Ala Ser Asp Ile Glu Ala Ala Val Gln
225                 230                 235                 240

Glu Ile Lys Lys Glu Gly Val Leu Ala Glu Leu Glu Gln Lys Trp Gly
                245                 250                 255

Leu Asn Gly
```

<210> SEQ ID NO 39
<211> LENGTH: 384
<212> TYPE: DNA
<213> ORGANISM: Chlamydia trachomatis

<400> SEQUENCE: 39

```
atggaagaaa aaggcatctt acaattggtt gaaatttcgc gagcaatggc tttacaggga      60

gtttgtcctt ggactaattt acagagtgtg gagtctatgt tgcagtatat agcaggggag     120

tgtcaggagt tggctgatgc tgtacaagaa aataaagctt cgttggaaat cgcttcggaa     180

gccggagacg tacttacttt agtattgacc ttgtgtttct tgctagaaag agaaggaaag     240

cttaaagctg aagaagtatt tgtagaagct ttggctaagt tgcgtcgtcg atctcctcat     300

gtttttgatc ctcataatca aatttcttta gaacaggctg aagaatactg ggctcgtatg     360

aaacagcaag aaaaaatttc ttaa                                            384
```

<210> SEQ ID NO 40
<211> LENGTH: 127
<212> TYPE: PRT
<213> ORGANISM: Chlamydia trachomatis

<400> SEQUENCE: 40

Met Glu Glu Lys Gly Ile Leu Gln Leu Val Glu Ile Ser Arg Ala Met
1               5                   10                  15

Ala Leu Gln Gly Val Cys Pro Trp Thr Asn Leu Gln Ser Val Glu Ser
            20                  25                  30

Met Leu Gln Tyr Ile Ala Gly Glu Cys Gln Glu Leu Ala Asp Ala Val
        35                  40                  45

Gln Glu Asn Lys Ala Ser Leu Glu Ile Ala Ser Glu Ala Gly Asp Val
    50                  55                  60

Leu Thr Leu Val Leu Thr Leu Cys Phe Leu Leu Glu Arg Glu Gly Lys
65                  70                  75                  80

Leu Lys Ala Glu Glu Val Phe Val Glu Ala Leu Ala Lys Leu Arg Arg
                85                  90                  95

Arg Ser Pro His Val Phe Asp Pro His Asn Gln Ile Ser Leu Glu Gln
            100                 105                 110

Ala Glu Glu Tyr Trp Ala Arg Met Lys Gln Gln Glu Lys Ile Ser
        115                 120                 125

<210> SEQ ID NO 41
<211> LENGTH: 1179
<212> TYPE: DNA
<213> ORGANISM: Chlamydia trachomatis

<400> SEQUENCE: 41
atggattact acacgatatt gggtgtagcg aagactgcta ctcctgaaga aataaagaaa 60
gcttaccgta agctcgctgt aaagtaccat ccagataaga atcctgggga tgctgaagcg 120
gagcgacgct ttaaagaagt ttctgaagcc tatgaagtat taggtgatgc gcagaagcgg 180
gagtcatatg atcgttacgg caaagacggt ccatttgctg gtgctggagg attcggtggc 240
gctggcatgg ggaatatgga agacgctttg cgaacattta tgggagcttt tggcggcgat 300
ttcggtggta atggaggcgg tttctttgaa gggctttttg gaggacttgg agaagctttc 360
ggaatgcgtg gaggctcaga aagttctcga caaggagcta gtaagaaggt gcatattacg 420
ctgtccttcg aggaggcggc aaaaggtgtt gaaaaagaac ttcttgtttc aggctataaa 480
tcttgtgatg cttgttctgg tagtggagcc aatactgcta aaggtgtaaa agtttgtgat 540
cgatgcaagg gctctggtca ggtagtgcaa agccgaggct tttctccat ggcttctact 600 tgccctgatt gtagtggtga aggtcgggtt atcacagatc cttgttcagt ttgtcgtggg 660
cagggacgta tcaaggataa acgtagcgtc catgttaata tcccagctgg agtcgattct 720
gggatgagat taaagatgga aggctatgga gatgctggcc aaaatggagc gcctgcaggg 780
gatctgtatg tttttattga tgtagagcct catcctgttt tcgagcgcca tggggatgat 840
ttagttttag agcttcctat tggatttgtt gatgcggctt tagggatcaa gaaggaaatc 900
cctacactct taaaagaagg tacttgccgt ttgagtatcc cagaagggat tcagagcgga 960
acagttctta aagttagagg gcagggattc cctaatgtgc atgggaaatc cagaggagat 1020
cttttagtaa gagtatctgt ggagactccc cagcacctat ctaatgaaca aaaagattta 1080
ttgagacagt ttgctgctac ggagaaggct gaaaatttcc ctaagaaacg gagtttctta 1140
gacaaaatca aaggtttttt ttctgacttt gctgtatag 1179

<210> SEQ ID NO 42
<211> LENGTH: 392
<212> TYPE: PRT

<213> ORGANISM: Chlamydia trachomatis

<400> SEQUENCE: 42

Met Asp Tyr Tyr Thr Ile Leu Gly Val Ala Lys Thr Ala Thr Pro Glu
1 5 10 15

Glu Ile Lys Lys Ala Tyr Arg Lys Leu Ala Val Lys Tyr His Pro Asp
20 25 30

Lys Asn Pro Gly Asp Ala Glu Ala Glu Arg Arg Phe Lys Glu Val Ser
35 40 45

Glu Ala Tyr Glu Val Leu Gly Asp Ala Gln Lys Arg Glu Ser Tyr Asp
50 55 60

Arg Tyr Gly Lys Asp Gly Pro Phe Ala Gly Ala Gly Gly Phe Gly Gly
65 70 75 80

Ala Gly Met Gly Asn Met Glu Asp Ala Leu Arg Thr Phe Met Gly Ala
85 90 95

Phe Gly Gly Asp Phe Gly Gly Asn Gly Gly Gly Phe Phe Glu Gly Leu
100 105 110

Phe Gly Gly Leu Gly Glu Ala Phe Gly Met Arg Gly Gly Ser Glu Ser
115 120 125

Ser Arg Gln Gly Ala Ser Lys Lys Val His Ile Thr Leu Ser Phe Glu
130 135 140

Glu Ala Ala Lys Gly Val Glu Lys Glu Leu Leu Val Ser Gly Tyr Lys
145 150 155 160

Ser Cys Asp Ala Cys Ser Gly Ser Gly Ala Asn Thr Ala Lys Gly Val
165 170 175

Lys Val Cys Asp Arg Cys Lys Gly Ser Gly Gln Val Val Gln Ser Arg
180 185 190

Gly Phe Phe Ser Met Ala Ser Thr Cys Pro Asp Cys Ser Gly Glu Gly
195 200 205

Arg Val Ile Thr Asp Pro Cys Ser Val Cys Arg Gly Gln Gly Arg Ile
210 215 220

Lys Asp Lys Arg Ser Val His Val Asn Ile Pro Ala Gly Val Asp Ser
225 230 235 240

Gly Met Arg Leu Lys Met Glu Gly Tyr Gly Asp Ala Gly Gln Asn Gly
245 250 255

Ala Pro Ala Gly Asp Leu Tyr Val Phe Ile Asp Val Glu Pro His Pro
260 265 270

Val Phe Glu Arg His Gly Asp Asp Leu Val Leu Glu Leu Pro Ile Gly
275 280 285

Phe Val Asp Ala Ala Leu Gly Ile Lys Lys Glu Ile Pro Thr Leu Leu
290 295 300

Lys Glu Gly Thr Cys Arg Leu Ser Ile Pro Glu Gly Ile Gln Ser Gly
305 310 315 320

Thr Val Leu Lys Val Arg Gly Gln Gly Phe Pro Asn Val His Gly Lys
325 330 335

Ser Arg Gly Asp Leu Leu Val Arg Val Ser Val Glu Thr Pro Gln His
340 345 350

Leu Ser Asn Glu Gln Lys Asp Leu Leu Arg Gln Phe Ala Ala Thr Glu
355 360 365

Lys Ala Glu Asn Phe Pro Lys Lys Arg Ser Phe Leu Asp Lys Ile Lys
370 375 380

Gly Phe Phe Ser Asp Phe Ala Val
385 390

<210> SEQ ID NO 43
<211> LENGTH: 366
<212> TYPE: DNA
<213> ORGANISM: Chlamydia trachomatis

<400> SEQUENCE: 43
atgaataaaa aactccaaga tctgtctaaa ctgctcacta ttgagctttt caagaaacgt 60
acacggttgg aaacagtaaa aaaagcgctc tccacaatag aacatcgctt acaacaaata 120
caggagcaca tcgcgaaaat ttccttaaca aggcacaaac aattcctatg tcggtcatat 180
acccatgaat atgaccaaca tttagaacat ttacaaagag agcaaacttc tctatataaa 240
cagcatcaga ccctgaaaac gtctttgaaa gatgcttatg gcgacataca aaaacaacta 300
gaccaaagaa aaattatcga aaagatccat gacagtaaat atcctataaa gagcgcgaat 360
aactaa 366

<210> SEQ ID NO 44
<211> LENGTH: 121
<212> TYPE: PRT
<213> ORGANISM: Chlamydia trachomatis

<400> SEQUENCE: 44

Met Asn Lys Lys Leu Gln Asp Leu Ser Lys Leu Leu Thr Ile Glu Leu
1 5 10 15

Phe Lys Lys Arg Thr Arg Leu Glu Thr Val Lys Lys Ala Leu Ser Thr
20 25 30

Ile Glu His Arg Leu Gln Gln Ile Gln Glu His Ile Ala Lys Ile Ser
35 40 45

Leu Thr Arg His Lys Gln Phe Leu Cys Arg Ser Tyr Thr His Glu Tyr
50 55 60

Asp Gln His Leu Glu His Leu Gln Arg Glu Gln Thr Ser Leu Tyr Lys
65 70 75 80

Gln His Gln Thr Leu Lys Thr Ser Leu Lys Asp Ala Tyr Gly Asp Ile
85 90 95

Gln Lys Gln Leu Asp Gln Arg Lys Ile Ile Glu Lys Ile His Asp Ser
100 105 110

Lys Tyr Pro Ile Lys Ser Ala Asn Asn
115 120

<210> SEQ ID NO 45
<211> LENGTH: 1275
<212> TYPE: DNA
<213> ORGANISM: Chlamydia trachomatis

<400> SEQUENCE: 45
atgaaacatg ctctcattgt tggctcaggt attgccggcc tttctgccgc gtggtggcta 60
cacaaacgat tccctcatgt gcagctgtct attctagaaa aagagtctcg atctggaggg 120
ctaattgtca cagagaaaca acaagggttt tccctcaata tgggccctaa aggttttgtt 180
ttagctcatg atgggcaaca cacccttcac ctcattcagt ctttaggcct agcagacgag 240
ctattatata gctctccaga ggctaaaaac cgctttatcc actataataa taaaacccga 300
aaagtctcgc cttggactat tttcaaacaa aatctccctc tctcttttgc taaggatttc 360
tttgcgcgtc cttacaaaca agacagctcc gtggaagcct tctttaaaag acacagttct 420
tccaagctta gaagaaatct tttaaatccc attagcattg ctattcgtgc aggacatagt 480
catatattgt ctgcacagat ggcttaccca gaattaacac gaagagaagc tcaaacagga 540

```
tcgttgttac gtagttatct caaagatttt cctaaagaga aacgcacagg cccttattta    600

gctaccttgc ggtctgggat gggaatgcta acccaggctt tgcatgataa attgcctgct    660

acctggtatt tttctgcacc cgtcagcaaa atccgtcagt tggcgaatgg gaaaatttct    720

ctttcatctc ctcaaggaga aataacggga gatatgctca tttatgctgg gtccgtgcac    780

gatctccctt cctgtctaga agggatccct gaaaccaagc ttatcaagca aacgacttca    840

tcttgggatc tctcttgtgt atctttagga tggcatgcat ccttccctat ccctcatgga    900

tatggcatgc ttttcgctga tacgcctccc ttattaggga tcgtgtttaa tacggaagtg    960

ttccctcaac ccgagcggcc taatacaata gtctctcttc ttttagaagg tcgatggcac   1020

caagaagaag cgtatgcttt ctcactagca gctatttctg agtacctgca aatttacact   1080

cctccccaag ctttctcact attctctcct cgagagggac ttccccaaca ccatgttgga   1140

tttatccaat cccgccaacg ccttctatct aaacttcctc acaatataaa aattgtaggg   1200

cagaattttg caggtccagg tctcaaccgc gctacagcgt ctgcttataa agctatagct   1260

tctttactat catga                                                    1275
```

<210> SEQ ID NO 46
<211> LENGTH: 424
<212> TYPE: PRT
<213> ORGANISM: Chlamydia trachomatis

<400> SEQUENCE: 46

```
Met Lys His Ala Leu Ile Val Gly Ser Gly Ile Ala Gly Leu Ser Ala
1               5                   10                  15

Ala Trp Trp Leu His Lys Arg Phe Pro His Val Gln Leu Ser Ile Leu
            20                  25                  30

Glu Lys Glu Ser Arg Ser Gly Gly Leu Ile Val Thr Glu Lys Gln Gln
        35                  40                  45

Gly Phe Ser Leu Asn Met Gly Pro Lys Gly Phe Val Leu Ala His Asp
    50                  55                  60

Gly Gln His Thr Leu His Leu Ile Gln Ser Leu Gly Leu Ala Asp Glu
65                  70                  75                  80

Leu Leu Tyr Ser Ser Pro Glu Ala Lys Asn Arg Phe Ile His Tyr Asn
                85                  90                  95

Asn Lys Thr Arg Lys Val Ser Pro Trp Thr Ile Phe Lys Gln Asn Leu
            100                 105                 110

Pro Leu Ser Phe Ala Lys Asp Phe Phe Ala Arg Pro Tyr Lys Gln Asp
        115                 120                 125

Ser Ser Val Glu Ala Phe Phe Lys Arg His Ser Ser Ser Lys Leu Arg
    130                 135                 140

Arg Asn Leu Leu Asn Pro Ile Ser Ile Ala Ile Arg Ala Gly His Ser
145                 150                 155                 160

His Ile Leu Ser Ala Gln Met Ala Tyr Pro Glu Leu Thr Arg Arg Glu
                165                 170                 175

Ala Gln Thr Gly Ser Leu Leu Arg Ser Tyr Leu Lys Asp Phe Pro Lys
            180                 185                 190

Glu Lys Arg Thr Gly Pro Tyr Leu Ala Thr Leu Arg Ser Gly Met Gly
        195                 200                 205

Met Leu Thr Gln Ala Leu His Asp Lys Leu Pro Ala Thr Trp Tyr Phe
    210                 215                 220

Ser Ala Pro Val Ser Lys Ile Arg Gln Leu Ala Asn Gly Lys Ile Ser
225                 230                 235                 240
```

-continued

```
Leu Ser Ser Pro Gln Gly Glu Ile Thr Gly Asp Met Leu Ile Tyr Ala
                245                 250                 255

Gly Ser Val His Asp Leu Pro Ser Cys Leu Glu Gly Ile Pro Glu Thr
            260                 265                 270

Lys Leu Ile Lys Gln Thr Thr Ser Ser Trp Asp Leu Ser Cys Val Ser
        275                 280                 285

Leu Gly Trp His Ala Ser Phe Pro Ile Pro His Gly Tyr Gly Met Leu
    290                 295                 300

Phe Ala Asp Thr Pro Pro Leu Leu Gly Ile Val Phe Asn Thr Glu Val
305                 310                 315                 320

Phe Pro Gln Pro Glu Arg Pro Asn Thr Ile Val Ser Leu Leu Leu Glu
                325                 330                 335

Gly Arg Trp His Gln Glu Glu Ala Tyr Ala Phe Ser Leu Ala Ala Ile
            340                 345                 350

Ser Glu Tyr Leu Gln Ile Tyr Thr Pro Pro Gln Ala Phe Ser Leu Phe
        355                 360                 365

Ser Pro Arg Glu Gly Leu Pro Gln His His Val Gly Phe Ile Gln Ser
    370                 375                 380

Arg Gln Arg Leu Leu Ser Lys Leu Pro His Asn Ile Lys Ile Val Gly
385                 390                 395                 400

Gln Asn Phe Ala Gly Pro Gly Leu Asn Arg Ala Thr Ala Ser Ala Tyr
                405                 410                 415

Lys Ala Ile Ala Ser Leu Leu Ser
            420
```

<210> SEQ ID NO 47
<211> LENGTH: 2076
<212> TYPE: DNA
<213> ORGANISM: Chlamydia trachomatis

<400> SEQUENCE: 47

```
atgacgctct ttcattctca tcatgatgcc gtctctccag acagctacct atgttcttcc     60

cttcagttag ttggtactgg cgtatacgaa ggagaaatcg agattcaaaa tatcccctct    120

tatttccttg gattccaatt accctctcat tgcatacacc ttaatttaaa gagctctcta    180

gctcaattag gaatagatgc ctcccttctt cactgcgaat tgagcaaaaa tcaacatcga    240

gcacatatac atgctcaatt taccggtcat ggccccattg ctgaatctat gctagccctt    300

ctccaaccag gagatcgtgt agcaaaacta tttgctgcag acgatcgcag actggtccga    360

tctccagatt acctcgaaag catgctgaaa aatacagata aagctggcca tcctttgctc    420

tgttttggga aaaaattaga acacttgatt tcttttgatg tggtagatga tcgccttgtc    480

gtctcccttc ctaccctgcc gggagttgtt cgttatgatt cggatattta tggactcctt    540

cctcttattc aaaaatcact cagtaatccc aaactcagca ttcgtcactt tttagctctg    600

taccaacaga ttgtggaagg gcaacatgtc tcttgcggaa accatattct tctgatcaaa    660

acagaaccgc tgcacatccg cactgtattt gctcgcgtgg taaatcaact cctccctcaa    720

ggtctctccc acacttctgc caatattttg gaaccaacca ctcgagaatc cggggatatc    780

tttgaatttt ttgggaaccc ttctgcacag atagaaagaa ttcctttaga atttttcact    840

atcgaaccct ataaagaaca ttcttacttc tgtaatcggg atttattaca aaccatctta    900

caatcagaaa gcgaaatcaa aaaaatattc gaaacagcgc ccaaagaacc tgtcaaagct    960

gccacctatt tatcaaaagg cagtgaaatc tcttccctgc acacagactc ttggctcaca   1020
```

-continued

```
ggatccgcag ctgcctatca atatagtgag caagcagata aaaacgagta cactcatgct   1080

caaccttgct atcctttctt agaagcaatg gaaatgggcc tgatcaatag cgaaggagcc   1140

ttactcactc gttatttccc ttcagctagc ttaaaaggaa tgttgatttc ctaccatgtg   1200

cgccactatc tcaaacaaat ctactttcaa gttccctctt atacacatgg aaactatttc   1260

tctcataatg acagaggttt gctattagat ctgcagcaag cagatattga tgttttctgg   1320

gcagatgaag aaagcggccg tgtgttgcaa tatacaaaac gacgcgataa gaatagcggt   1380

atgttcgtga tcaaaaatcg tgttgaagag tttcgatcag cttattttat tgctatttat   1440

ggctctcgtc tccttgagaa taatttctct gctcagctcc ataccctcct agcgggctta   1500

cagcaagcag cacatactct cggcattcct ggattctcaa agcctacccc acttgcagtc   1560

atcaccggag gcggcactgg agttatggcc acaggaaatc gtgtagctaa agaactagga   1620

atcctatctt gtggaaccgt tcttgattta gaagcttctc cagcacaaat cgaccaacct   1680

accaatgaat tcttagatgc taaaatgaca taccgcctac ctcaacttat agaaaggcaa   1740

gaacactttt atgcagacct tcctatcctt gtagttggcg gtgtaggaac cgatttcgaa   1800

ctctacctag aacttgtcta tctcaaaaca ggagctaaac caccgactcc cattttccta   1860

attggaccta ttgaatactg gaaagaaaaa gtggcccacg cctacgagat caacctcaaa   1920

gcaggaacca tccgtggatc cgaatggatc agcaactgcc tatattgtat cacttctccg   1980

gaagctggaa ttgccgtatt cgaacaattc ctagctggag aactccctat aggatacgac   2040

tatcctccag ctccagatgg attagtgatc gtctaa                             2076
```

```
<210> SEQ ID NO 48
<211> LENGTH: 691
<212> TYPE: PRT
<213> ORGANISM: Chlamydia trachomatis

<400> SEQUENCE: 48

Met Thr Leu Phe His Ser His His Asp Ala Val Ser Pro Asp Ser Tyr
1               5                   10                  15

Leu Cys Ser Ser Leu Gln Leu Val Gly Thr Gly Val Tyr Glu Gly Glu
            20                  25                  30

Ile Glu Ile Gln Asn Ile Pro Ser Tyr Phe Leu Gly Phe Gln Leu Pro
        35                  40                  45

Ser His Cys Ile His Leu Asn Leu Lys Ser Ser Leu Ala Gln Leu Gly
    50                  55                  60

Ile Asp Ala Ser Leu Leu His Cys Glu Leu Ser Lys Asn Gln His Arg
65                  70                  75                  80

Ala His Ile His Ala Gln Phe Thr Gly His Gly Pro Ile Ala Glu Ser
                85                  90                  95

Met Leu Ala Leu Leu Gln Pro Gly Asp Arg Val Ala Lys Leu Phe Ala
            100                 105                 110

Ala Asp Asp Arg Arg Leu Val Arg Ser Pro Asp Tyr Leu Glu Ser Met
        115                 120                 125

Leu Lys Asn Thr Asp Lys Ala Gly His Pro Leu Leu Cys Phe Gly Lys
    130                 135                 140

Lys Leu Glu His Leu Ile Ser Phe Asp Val Val Asp Asp Arg Leu Val
145                 150                 155                 160

Val Ser Leu Pro Thr Leu Pro Gly Val Val Arg Tyr Asp Ser Asp Ile
                165                 170                 175

Tyr Gly Leu Leu Pro Leu Ile Gln Lys Ser Leu Ser Asn Pro Lys Leu
            180                 185                 190
```

-continued

```
Ser Ile Arg His Phe Leu Ala Leu Tyr Gln Gln Ile Val Glu Gly Gln
        195                 200                 205

His Val Ser Cys Gly Asn His Ile Leu Leu Ile Lys Thr Glu Pro Leu
    210                 215                 220

His Ile Arg Thr Val Phe Ala Arg Val Val Asn Gln Leu Leu Pro Gln
225                 230                 235                 240

Gly Leu Ser His Thr Ser Ala Asn Ile Leu Glu Pro Thr Thr Arg Glu
                245                 250                 255

Ser Gly Asp Ile Phe Glu Phe Phe Gly Asn Pro Ser Ala Gln Ile Glu
            260                 265                 270

Arg Ile Pro Leu Glu Phe Phe Thr Ile Glu Pro Tyr Lys Glu His Ser
        275                 280                 285

Tyr Phe Cys Asn Arg Asp Leu Leu Gln Thr Ile Leu Gln Ser Glu Ser
    290                 295                 300

Glu Ile Lys Lys Ile Phe Glu Thr Ala Pro Lys Glu Pro Val Lys Ala
305                 310                 315                 320

Ala Thr Tyr Leu Ser Lys Gly Ser Glu Ile Ser Ser Leu His Thr Asp
                325                 330                 335

Ser Trp Leu Thr Gly Ser Ala Ala Ala Tyr Gln Tyr Ser Glu Gln Ala
            340                 345                 350

Asp Lys Asn Glu Tyr Thr His Ala Gln Pro Cys Tyr Pro Phe Leu Glu
        355                 360                 365

Ala Met Glu Met Gly Leu Ile Asn Ser Glu Gly Ala Leu Leu Thr Arg
    370                 375                 380

Tyr Phe Pro Ser Ala Ser Leu Lys Gly Met Leu Ile Ser Tyr His Val
385                 390                 395                 400

Arg His Tyr Leu Lys Gln Ile Tyr Phe Gln Val Pro Ser Tyr Thr His
                405                 410                 415

Gly Asn Tyr Phe Ser His Asn Asp Arg Gly Leu Leu Leu Asp Leu Gln
            420                 425                 430

Gln Ala Asp Ile Asp Val Phe Trp Ala Asp Glu Glu Ser Gly Arg Val
        435                 440                 445

Leu Gln Tyr Thr Lys Arg Arg Asp Lys Asn Ser Gly Met Phe Val Ile
    450                 455                 460

Lys Asn Arg Val Glu Glu Phe Arg Ser Ala Tyr Phe Ile Ala Ile Tyr
465                 470                 475                 480

Gly Ser Arg Leu Leu Glu Asn Asn Phe Ser Ala Gln Leu His Thr Leu
                485                 490                 495

Leu Ala Gly Leu Gln Gln Ala Ala His Thr Leu Gly Ile Pro Gly Phe
            500                 505                 510

Ser Lys Pro Thr Pro Leu Ala Val Ile Thr Gly Gly Gly Thr Gly Val
        515                 520                 525

Met Ala Thr Gly Asn Arg Val Ala Lys Glu Leu Gly Ile Leu Ser Cys
    530                 535                 540

Gly Thr Val Leu Asp Leu Glu Ala Ser Pro Ala Gln Ile Asp Gln Pro
545                 550                 555                 560

Thr Asn Glu Phe Leu Asp Ala Lys Met Thr Tyr Arg Leu Pro Gln Leu
                565                 570                 575

Ile Glu Arg Gln Glu His Phe Tyr Ala Asp Leu Pro Ile Leu Val Val
            580                 585                 590

Gly Gly Val Gly Thr Asp Phe Glu Leu Tyr Leu Glu Leu Val Tyr Leu
        595                 600                 605
```

-continued

Lys Thr Gly Ala Lys Pro Pro Thr Pro Ile Phe Leu Ile Gly Pro Ile
    610                 615                 620

Glu Tyr Trp Lys Glu Lys Val Ala His Ala Tyr Glu Ile Asn Leu Lys
625                 630                 635                 640

Ala Gly Thr Ile Arg Gly Ser Glu Trp Ile Ser Asn Cys Leu Tyr Cys
                645                 650                 655

Ile Thr Ser Pro Glu Ala Gly Ile Ala Val Phe Glu Gln Phe Leu Ala
            660                 665                 670

Gly Glu Leu Pro Ile Gly Tyr Asp Tyr Pro Pro Ala Pro Asp Gly Leu
        675                 680                 685

Val Ile Val
    690

<210> SEQ ID NO 49
<211> LENGTH: 4596
<212> TYPE: DNA
<213> ORGANISM: Chlamydia trachomatis

<400> SEQUENCE: 49
atgagttccg agaaagatat aaaaagcacc tgttctaagt tttctttgtc tgtagtagca 60
gctatccttg cctctgttag cgggttagct agttgcgtag atcttcatgc tggaggacag 120
tctgtaaatg agctggtata tgtaggccct caagcggttt tattgttaga ccaaattcga 180
gatctattcg ttgggtctaa agatagtcag gctgaaggac agtataggtt aattgtagga 240
gatccaagtt ctttccaaga gaaagatgcg gatactcttc ccgggaaggt agagcaaagt 300
actttgttct cagtaaccaa tcccgtggtt ttccaaggtg tggaccaaca ggatcaagtc 360
tcttcccaag ggttaatttg tagttttacg agcagcaacc ttgattctcc tcgtgacgga 420
gaatcttttt taggtattgc ttttgttggg gatagtagta aggctggaat cacattaact 480
gacgtgaaag cttctttgtc tggagcggct ttatattcta cagaagatct tatctttgaa 540
aagattaagg gtggattgga atttgcatca tgttcttctc tagaacaggg gggagcttgt 600
gcagctcaaa gtattttgat tcatgattgt caaggattgc aggttaaaca ctgtactaca 660
gccgtgaatg ctgaggggtc tagtgcgaat gatcatcttg gatttggagg aggcgctttc 720
tttgttacgg gttctctttc tggagagaaa agtctctata tgcctgcagg agatatggta 780
gttgcgaatt gtgatggggc tatatctttt gaaggaaaca gcgcgaactt tgctaatgga 840
ggagcgattg ctgcctctgg gaaagtgctt tttgtcgcta atgataaaaa gacttctttt 900
atagagaacc gagctttgtc tggaggagcg attgcagcct cttctgatat tgcctttcaa 960
aactgcgcag aactagtttt caaaggcaat tgtgcaattg gaacagagga taaaggttct 1020
ttaggtggag gggctatatc ttctctaggc accgttcttt tgcaagggaa tcacgggata 1080
acttgtgata agaatgagtc tgcttcgcaa ggaggcgcca tttttggcaa aaattgtcag 1140
atttctgaca acgaggggcc agtggttttc agagatagta cagcttgctt aggaggaggc 1200
gctattgcag ctcaagaaat tgtttctatt cagaacaatc aggctgggat ttccttcgag 1260
ggaggtaagg ctagtttcgg aggaggtatt gcgtgtggat ctttttcttc cgcaggtggt 1320
gcttctgttt tagggaccat tgatatttcg aagaatttag gcgcgatttc gttctctcgt 1380
actttatgta cgacctcaga tttaggacaa atggagtacc agggaggagg agctctattt 1440
ggtgaaaata tttctctttc tgagaatgct ggtgtgctca cctttaaaga caacattgtg 1500 aagactttg cttcgaatgg gaaaattctg ggaggaggag cgattttagc tactggtaag 1560
gtggaaatta ctaataattc cgaaggaatt tcttttacag gaaatgcgag agctccacaa 1620

-continued

```
gctcttccaa ctcaagagga gtttccttta ttcagcaaaa aagaagggcg accactctct   1680
tcaggatatt ctgggggagg agcgatttta ggaagagaag tagctattct ccacaacgct   1740
gcagtagtat ttgagcaaaa tcgtttgcag tgcagcgaag aagaagcgac attattaggt   1800
tgttgtggag gaggcgctgt tcatgggatg gatagcactt cgattgttgg caactcttca   1860
gtaagatttg gtaataatta cgcaatggga caaggagtct caggaggagc tcttttatct   1920
aaaacagtgc agttagctgg gaatggaagc gtcgattttt ctcgaaatat tgctagtttg   1980
ggaggaggag ctcttcaagc ttctgaagga aattgtgagc tagttgataa cggctatgtg   2040
ctattcagag ataatcgagg gagggtttat gggggtgcta tttcttgctt acgtggagat   2100
gtagtcattt ctggaaacaa gggtagagtt gaatttaaag acaacatagc aacacgtctt   2160
tatgtggaag aaactgtaga aaaggttgaa gaggtagagc cagctcctga gcaaaaagac   2220
aataatgagc tttctttctt agggagagca gaacagagtt ttattactgc agctaatcaa   2280
gctcttttcg catctgaaga tggggattta tcacctgagt catccatttc ttctgaagaa   2340
cttgcgaaaa gaagagagtg tgctggagga gctatttttg caaaacgggt tcgtattgta   2400
gataaccaag aggccgttgt attctcgaat aacttctctg atatttatgg cggcgccatt   2460
tttacaggtt ctcttcgaga agaggataag ttagatgggc aaatccctga agtcttgatc   2520
tcaggcaatg caggggatgt tgttttttcc ggaaattcct cgaagcgtga tgagcatctt   2580
cctcatacag gtgggggagc catttgtact caaaatttga cgatttctca gaatacaggg   2640
aatgttctgt tttataacaa cgtggcctgt tcgggaggag ctgttcgtat agaggatcat   2700
ggtaatgttc ttttagaagc ttttggagga gatattgttt ttaaaggaaa ttcttctttc   2760
agagcacaag gatccgatgc tatctatttt gcaggtaaag aatcgcatat tacagccctg   2820
aatgctacgg aaggacatgc tattgttttc cacgacgcat tagtttttga aaatctagaa   2880
gaaaggaaat ctgctgaagt attgttaatc aatagtcgag aaaatccagg ttacactgga   2940
tctattcgat tttagaagc agaaagtaaa gttcctcaat gtattcatgt acaacaagga   3000
agccttgagt tgctaaatgg agccacatta tgtagttatg gttttaaaca agatgctgga   3060
gctaagttgg tattggctgc tggagctaaa ctgaagattt tagattcagg aactcctgta   3120
caacaagggc atgctatcag taaacctgaa gcagaaatcg agtcatcttc tgaaccagag   3180
ggtgcacatt ctctttggat tgcgaagaat gctcaaacaa cagttcctat ggttgatatc   3240
catactattt ctgtagattt agcctccttc tcttctagtc aacaggaggg gacagtagaa   3300
gctcctcagg ttattgttcc tggaggaagt tatgttcgat ctggagagct taatttggag   3360
ttagttaaca caacaggtac tggttatgaa aatcatgctt tattgaagaa tgaggctaaa   3420
gttccattga tgtctttcgt tgcttctggt gatgaagctt cagccgaaat cagtaacttg   3480
tcggtttctg atttacagat tcatgtagta actccagaga ttgaagaaga cacatacggc   3540
catatgggag attggtctga ggctaaaatt caagatggaa ctcttgtcat tagttggaat   3600
cctactggat atcgattaga tcctcaaaaa gcaggggctt tagtatttaa tgcattatgg   3660
gaagaagggg ctgtcttgtc tgctctgaaa aatgcacgct ttgctcataa tctcactgct   3720
cagcgtatgg aattcgatta ttctacaaat gtgtggggat tcgcctttgg tggtttccga   3780
actctatctg cagagaatct ggttgctatt gatggataca aaggagctta tggtggtgct   3840
tctgctggag tcgatattca attgatggaa gattttgttc taggagttag tggagctgct   3900
ttcctaggta aaatggatag tcagaagttt gatgcggagg tttctcggaa gggagttgtt   3960
```

-continued

```
ggttctgtat atacaggatt tttagctgga tcctggttct tcaaaggaca atatagcctt   4020

ggagaaacac agaacgatat gaaaacgcgt tatggagtac taggagagtc gagtgcttct   4080

tggacatctc gaggagtact ggcagatgct ttagttgaat accgaagttt agttggtcct   4140

gtgagaccta ctttttatgc tttgcatttc aatccttatg tcgaagtatc ttatgcttct   4200

atgaaattcc ctggctttac agaacaagga agagaagcgc gttcttttga agacgcttcc   4260

cttaccaata tcaccattcc tttagggatg aagtttgaat tggcgttcat aaaaggacag   4320

ttttcagagg tgaactcttt gggaataagt tatgcatggg aagcttatcg aaaagtagaa   4380

ggaggcgcgg tgcagctttt agaagctggg tttgattggg agggagctcc aatggatctt   4440

cctagacagg agctgcgtgt cgctctggaa aataatacgg aatggagttc ttacttcagc   4500

acagtcttag gattaacagc tttttgtgga ggatttactt ctacagatag taaactagga   4560

tatgaggcga atactggatt gcgattgatc ttttaa                             4596
```

<210> SEQ ID NO 50
<211> LENGTH: 1531
<212> TYPE: PRT
<213> ORGANISM: Chlamydia trachomatis

<400> SEQUENCE: 50

```
Met Ser Ser Glu Lys Asp Ile Lys Ser Thr Cys Ser Lys Phe Ser Leu
1               5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
```

-continued

```
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Gly Ala Leu Phe
465                 470                 475                 480

Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510

Gly Ala Ile Leu Ala Thr Gly Lys Val Glu Ile Thr Asn Asn Ser Glu
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Glu Gly Arg Pro Leu Ser
545                 550                 555                 560

Ser Gly Tyr Ser Gly Gly Gly Ala Ile Leu Gly Arg Glu Val Ala Ile
                565                 570                 575

Leu His Asn Ala Ala Val Val Phe Glu Gln Asn Arg Leu Gln Cys Ser
            580                 585                 590

Glu Glu Glu Ala Thr Leu Leu Gly Cys Cys Gly Gly Gly Ala Val His
        595                 600                 605

Gly Met Asp Ser Thr Ser Ile Val Gly Asn Ser Ser Val Arg Phe Gly
    610                 615                 620

Asn Asn Tyr Ala Met Gly Gln Gly Val Ser Gly Gly Ala Leu Leu Ser
625                 630                 635                 640

Lys Thr Val Gln Leu Ala Gly Asn Gly Ser Val Asp Phe Ser Arg Asn
                645                 650                 655

Ile Ala Ser Leu Gly Gly Gly Ala Leu Gln Ala Ser Glu Gly Asn Cys
            660                 665                 670

Glu Leu Val Asp Asn Gly Tyr Val Leu Phe Arg Asp Asn Arg Gly Arg
        675                 680                 685
```

```
Val Tyr Gly Gly Ala Ile Ser Cys Leu Arg Gly Asp Val Val Ile Ser
    690                 695                 700

Gly Asn Lys Gly Arg Val Glu Phe Lys Asp Asn Ile Ala Thr Arg Leu
705                 710                 715                 720

Tyr Val Glu Glu Thr Val Glu Lys Val Glu Glu Val Glu Pro Ala Pro
                725                 730                 735

Glu Gln Lys Asp Asn Asn Glu Leu Ser Phe Leu Gly Arg Ala Glu Gln
            740                 745                 750

Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
            820                 825                 830

Gly Gln Ile Pro Glu Val Leu Ile Ser Gly Asn Ala Gly Asp Val Val
        835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
            900                 905                 910

Val Phe Lys Gly Asn Ser Ser Phe Arg Ala Gln Gly Ser Asp Ala Ile
        915                 920                 925

Tyr Phe Ala Gly Lys Glu Ser His Ile Thr Ala Leu Asn Ala Thr Glu
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly  Ser Leu Glu Leu Leu  Asn Gly Ala
        995                 1000                1005

Thr Leu  Cys Ser Tyr Gly Phe  Lys Gln Asp Ala Gly  Ala Lys Leu
    1010                1015                1020

Val Leu  Ala Ala Gly Ala Lys  Leu Lys Ile Leu Asp  Ser Gly Thr
    1025                1030                1035

Pro Val  Gln Gln Gly His Ala  Ile Ser Lys Pro Glu  Ala Glu Ile
    1040                1045                1050

Glu Ser  Ser Ser Glu Pro Glu  Gly Ala His Ser Leu  Trp Ile Ala
    1055                1060                1065

Lys Asn  Ala Gln Thr Thr Val  Pro Met Val Asp Ile  His Thr Ile
    1070                1075                1080

Ser Val  Asp Leu Ala Ser Phe  Ser Ser Ser Gln Gln  Glu Gly Thr
    1085                1090                1095
```

```
Val Glu  Ala Pro Gln Val Ile  Val Pro Gly Gly Ser  Tyr Val Arg
    1100                 1105                 1110

Ser Gly  Glu Leu Asn Leu Glu  Leu Val Asn Thr Thr  Gly Thr Gly
    1115                 1120                 1125

Tyr Glu  Asn His Ala Leu Leu  Lys Asn Glu Ala Lys  Val Pro Leu
    1130                 1135                 1140

Met Ser  Phe Val Ala Ser Gly  Asp Glu Ala Ser Ala  Glu Ile Ser
    1145                 1150                 1155

Asn Leu  Ser Val Ser Asp Leu  Gln Ile His Val Val  Thr Pro Glu
    1160                 1165                 1170

Ile Glu  Glu Asp Thr Tyr Gly  His Met Gly Asp Trp  Ser Glu Ala
    1175                 1180                 1185

Lys Ile  Gln Asp Gly Thr Leu  Val Ile Ser Trp Asn  Pro Thr Gly
    1190                 1195                 1200

Tyr Arg  Leu Asp Pro Gln Lys  Ala Gly Ala Leu Val  Phe Asn Ala
    1205                 1210                 1215

Leu Trp  Glu Glu Gly Ala Val  Leu Ser Ala Leu Lys  Asn Ala Arg
    1220                 1225                 1230

Phe Ala  His Asn Leu Thr Ala  Gln Arg Met Glu Phe  Asp Tyr Ser
    1235                 1240                 1245

Thr Asn  Val Trp Gly Phe Ala  Phe Gly Gly Phe Arg  Thr Leu Ser
    1250                 1255                 1260

Ala Glu  Asn Leu Val Ala Ile  Asp Gly Tyr Lys Gly  Ala Tyr Gly
    1265                 1270                 1275

Gly Ala  Ser Ala Gly Val Asp  Ile Gln Leu Met Glu  Asp Phe Val
    1280                 1285                 1290

Leu Gly  Val Ser Gly Ala Ala  Phe Leu Gly Lys Met  Asp Ser Gln
    1295                 1300                 1305

Lys Phe  Asp Ala Glu Val Ser  Arg Lys Gly Val Val  Gly Ser Val
    1310                 1315                 1320

Tyr Thr  Gly Phe Leu Ala Gly  Ser Trp Phe Phe Lys  Gly Gln Tyr
    1325                 1330                 1335

Ser Leu  Gly Glu Thr Gln Asn  Asp Met Lys Thr Arg  Tyr Gly Val
    1340                 1345                 1350

Leu Gly  Glu Ser Ser Ala Ser  Trp Thr Ser Arg Gly  Val Leu Ala
    1355                 1360                 1365

Asp Ala  Leu Val Glu Tyr Arg  Ser Leu Val Gly Pro  Val Arg Pro
    1370                 1375                 1380

Thr Phe  Tyr Ala Leu His Phe  Asn Pro Tyr Val Glu  Val Ser Tyr
    1385                 1390                 1395

Ala Ser  Met Lys Phe Pro Gly  Phe Thr Glu Gln Gly  Arg Glu Ala
    1400                 1405                 1410

Arg Ser  Phe Glu Asp Ala Ser  Leu Thr Asn Ile Thr  Ile Pro Leu
    1415                 1420                 1425

Gly Met  Lys Phe Glu Leu Ala  Phe Ile Lys Gly Gln  Phe Ser Glu
    1430                 1435                 1440

Val Asn  Ser Leu Gly Ile Ser  Tyr Ala Trp Glu Ala  Tyr Arg Lys
    1445                 1450                 1455

Val Glu  Gly Gly Ala Val Gln  Leu Leu Glu Ala Gly  Phe Asp Trp
    1460                 1465                 1470

Glu Gly  Ala Pro Met Asp Leu  Pro Arg Gln Glu Leu  Arg Val Ala
    1475                 1480                 1485

Leu Glu  Asn Asn Thr Glu Trp  Ser Ser Tyr Phe Ser  Thr Val Leu
```

-continued

```
    1490                1495                1500

Gly Leu  Thr Ala Phe Cys Gly  Gly Phe Thr Ser Thr  Asp Ser Lys
    1505                1510                1515

Leu Gly  Tyr Glu Ala Asn Thr  Gly Leu Arg Leu Ile  Phe
    1520                1525                1530


<210> SEQ ID NO 51
<211> LENGTH: 2895
<212> TYPE: DNA
<213> ORGANISM: Chlamydia trachomatis

<400> SEQUENCE: 51

atgaaaaaag cgtttttctt tttccttatc ggaaactccc tatcaggact agctagagag     60

gttccttcta gaatctttct tatgcccaac tcagttccag atcctacgaa agagtcgcta    120

tcaaataaaa ttagtttgac aggagacact cacaatctca ctaactgcta tctcgataac    180

ctacgctaca tactggctat tctacaaaaa actcccaatg aaggagctgc tgtcacaata    240

acagattacc taagcttttt tgatacacaa aaagaaggta tttattttgc aaaaaatctc    300

acccctgaaa gtggtggtgc gattggttat gcgagtccca attctcctac cgtggagatt    360

cgtgatacaa taggtcctgt aatctttgaa aataatactt gttgcagact atttacatgg    420

agaaatcctt atgctgctga taaaataaga gaaggcggag ccattcatgc tcaaaatctt    480

tacataaatc ataatcatga tgtggtcgga tttatgaaga acttttctta tgtccaagga    540

ggagccatta gtaccgctaa tacctttgtt gtgagcgaga atcagtcttg ttttctcttt    600

atggacaaca tctgtattca aactaataca gcaggaaaag gtggcgctat ctatgctgga    660

acgagcaatt cttttgagag taataactgc gatctcttct tcatcaataa cgcctgttgt    720

gcaggaggag cgatcttctc ccctatctgt tctctaacag gaaatcgtgg taacatcgtt    780

ttctataaca atcgctgctt taaaaatgta gaaacagctt cttcagaagc ttctgatgga    840

ggagcaatta aagtaactac tcgcctagat gttacaggca atcgtggtag gatctttttt    900

agtgacaata tcacaaaaaa ttatggcgga gctatttacg ctcctgtagt taccctagtg    960

gataatggcc ctacctactt tataaacaat atcgccaata ataagggggg cgctatctat   1020

atagacggaa ccagtaactc caaaatttct gccgaccgcc atgctattat ttttaatgaa   1080

aatattgtga ctaatgtaac taatgcaaat ggtaccagta cgtcagctaa tcctcctaga   1140

agaaatgcaa taacagtagc aagctcctct ggtgaaattc tattaggagc agggagtagc   1200

caaaatttaa tttttatga tcctattgaa gttagcaatg caggggtctc tgtgtccttc   1260

aataaggaag ctgatcaaac aggctctgta gtattttcag gagctactgt taattctgca   1320

gattttcatc aacgcaattt acaaacaaaa acacctgcac cccttactct cagtaatggt   1380

tttctatgta tcgaagatca tgctcagctt acagtgaatc gattcacaca aactgggggt   1440

gttgtttctc ttgggaatgg agcagttctg agttgctata aaaatggtac aggagattct   1500

gctagcaatg cctctataac actgaagcat attggattga atctttcttc cattctgaaa   1560

agtggtgctg agattccttt attgtgggta gagcctacaa ataacagcaa taactataca   1620

gcagatactg cagctacctt ttcattaagt gatgtaaaac tctcactcat tgatgactac   1680

gggaactctc cttatgaatc cacagatctg acccatgctc tgtcatcaca gcctatgcta   1740

tctatttctg aagctagcga taaccagcta caatcagaaa atatagattt ttcgggacta   1800

aatgtccctc attatggatg gcaaggactt tggacttggg gctgggcaaa aactcaagat   1860

ccagaaccag catcttcagc aacaatcact gatccacaaa aagccaatag atttcataga   1920
```

```
accttactac taacatggct tcctgccggg tatgttccta gcccaaaaca cagaagtccc   1980

ctcatagcta acaccttatg ggggaatatg ctgcttgcaa cagaaagctt aaaaaatagt   2040

gcagagctga cacctagtgg tcatcctttc tggggaatta caggaggagg actaggcatg   2100

atggtttacc aagatcctcg agaaaatcat cctggattcc atatgcgctc ttccggatac   2160

tctgcgggga tgatagcagg gcagacacac accttctcat tgaaattcag tcagacctac   2220

accaaactca atgagcgtta cgcaaaaaac aacgtatctt ctaaaaatta ctcatgccaa   2280

ggagaaatgc tcttctcatt gcaagaaggt ttcttgctga ctaaattagt tgggctttac   2340

agctatggag accataactg tcaccatttc tatactcaag gagaaaatct aacatctcaa   2400

gggacgttcc gcagtcaaac gatgggaggt gctgtctttt ttgatctccc tatgaaaccc   2460

tttggatcaa cgcatatact gacagctccc tttttaggtg ctcttggtat ttattctagc   2520

ctgtctcact ttactgaggt gggagcctat ccgcgaagct tttctacaaa gactcctttg   2580

atcaatgtcc tagtccctat tggagttaaa ggtagcttta tgaatgctac ccacagacct   2640

caagcctgga ctgtagaatt ggcataccaa cccgttctgt atagacaaga accagggatc   2700

gcagcccagc tcctagccag taagggtatt tggttcggta gtggaagccc ctcatcgcgt   2760

catgccatgt cctataaaat ctcacagcaa acacaacctt tgagttggtt aactctccat   2820

ttccagtatc atggattcta ctcctcttca accttctgta attatctcaa tggggaaatt   2880

gctctgcgat tctag                                                    2895


<210> SEQ ID NO 52
<211> LENGTH: 964
<212> TYPE: PRT
<213> ORGANISM: Chlamydia trachomatis

<400> SEQUENCE: 52

Met Lys Lys Ala Phe Phe Phe Phe Leu Ile Gly Asn Ser Leu Ser Gly
1               5                   10                  15

Leu Ala Arg Glu Val Pro Ser Arg Ile Phe Leu Met Pro Asn Ser Val
            20                  25                  30

Pro Asp Pro Thr Lys Glu Ser Leu Ser Asn Lys Ile Ser Leu Thr Gly
        35                  40                  45

Asp Thr His Asn Leu Thr Asn Cys Tyr Leu Asp Asn Leu Arg Tyr Ile
    50                  55                  60

Leu Ala Ile Leu Gln Lys Thr Pro Asn Glu Gly Ala Ala Val Thr Ile
65                  70                  75                  80

Thr Asp Tyr Leu Ser Phe Phe Asp Thr Gln Lys Glu Gly Ile Tyr Phe
                85                  90                  95

Ala Lys Asn Leu Thr Pro Glu Ser Gly Gly Ala Ile Gly Tyr Ala Ser
            100                 105                 110

Pro Asn Ser Pro Thr Val Glu Ile Arg Asp Thr Ile Gly Pro Val Ile
        115                 120                 125

Phe Glu Asn Asn Thr Cys Cys Arg Leu Phe Thr Trp Arg Asn Pro Tyr
    130                 135                 140

Ala Ala Asp Lys Ile Arg Glu Gly Gly Ala Ile His Ala Gln Asn Leu
145                 150                 155                 160

Tyr Ile Asn His Asn His Asp Val Val Gly Phe Met Lys Asn Phe Ser
                165                 170                 175

Tyr Val Gln Gly Gly Ala Ile Ser Thr Ala Asn Thr Phe Val Val Ser
            180                 185                 190
```

```
Glu Asn Gln Ser Cys Phe Leu Phe Met Asp Asn Ile Cys Ile Gln Thr
        195                 200                 205

Asn Thr Ala Gly Lys Gly Gly Ala Ile Tyr Ala Gly Thr Ser Asn Ser
    210                 215                 220

Phe Glu Ser Asn Asn Cys Asp Leu Phe Phe Ile Asn Asn Ala Cys Cys
225                 230                 235                 240

Ala Gly Gly Ala Ile Phe Ser Pro Ile Cys Ser Leu Thr Gly Asn Arg
                245                 250                 255

Gly Asn Ile Val Phe Tyr Asn Asn Arg Cys Phe Lys Asn Val Glu Thr
            260                 265                 270

Ala Ser Ser Glu Ala Ser Asp Gly Gly Ala Ile Lys Val Thr Thr Arg
        275                 280                 285

Leu Asp Val Thr Gly Asn Arg Gly Arg Ile Phe Phe Ser Asp Asn Ile
    290                 295                 300

Thr Lys Asn Tyr Gly Gly Ala Ile Tyr Ala Pro Val Val Thr Leu Val
305                 310                 315                 320

Asp Asn Gly Pro Thr Tyr Phe Ile Asn Asn Ile Ala Asn Asn Lys Gly
                325                 330                 335

Gly Ala Ile Tyr Ile Asp Gly Thr Ser Asn Ser Lys Ile Ser Ala Asp
            340                 345                 350

Arg His Ala Ile Ile Phe Asn Glu Asn Ile Val Thr Asn Val Thr Asn
        355                 360                 365

Ala Asn Gly Thr Ser Thr Ser Ala Asn Pro Pro Arg Arg Asn Ala Ile
    370                 375                 380

Thr Val Ala Ser Ser Ser Gly Glu Ile Leu Leu Gly Ala Gly Ser Ser
385                 390                 395                 400

Gln Asn Leu Ile Phe Tyr Asp Pro Ile Glu Val Ser Asn Ala Gly Val
                405                 410                 415

Ser Val Ser Phe Asn Lys Glu Ala Asp Gln Thr Gly Ser Val Val Phe
            420                 425                 430

Ser Gly Ala Thr Val Asn Ser Ala Asp Phe His Gln Arg Asn Leu Gln
        435                 440                 445

Thr Lys Thr Pro Ala Pro Leu Thr Leu Ser Asn Gly Phe Leu Cys Ile
    450                 455                 460

Glu Asp His Ala Gln Leu Thr Val Asn Arg Phe Thr Gln Thr Gly Gly
465                 470                 475                 480

Val Val Ser Leu Gly Asn Gly Ala Val Leu Ser Cys Tyr Lys Asn Gly
                485                 490                 495

Thr Gly Asp Ser Ala Ser Asn Ala Ser Ile Thr Leu Lys His Ile Gly
            500                 505                 510

Leu Asn Leu Ser Ser Ile Leu Lys Ser Gly Ala Glu Ile Pro Leu Leu
        515                 520                 525

Trp Val Glu Pro Thr Asn Asn Ser Asn Asn Tyr Thr Ala Asp Thr Ala
    530                 535                 540

Ala Thr Phe Ser Leu Ser Asp Val Lys Leu Ser Leu Ile Asp Asp Tyr
545                 550                 555                 560

Gly Asn Ser Pro Tyr Glu Ser Thr Asp Leu Thr His Ala Leu Ser Ser
                565                 570                 575

Gln Pro Met Leu Ser Ile Ser Glu Ala Ser Asp Asn Gln Leu Gln Ser
            580                 585                 590

Glu Asn Ile Asp Phe Ser Gly Leu Asn Val Pro His Tyr Gly Trp Gln
        595                 600                 605

Gly Leu Trp Thr Trp Gly Trp Ala Lys Thr Gln Asp Pro Glu Pro Ala
```

610 615 620

Ser Ser Ala Thr Ile Thr Asp Pro Gln Lys Ala Asn Arg Phe His Arg
625 630 635 640

Thr Leu Leu Leu Thr Trp Leu Pro Ala Gly Tyr Val Pro Ser Pro Lys
645 650 655

His Arg Ser Pro Leu Ile Ala Asn Thr Leu Trp Gly Asn Met Leu Leu
660 665 670

Ala Thr Glu Ser Leu Lys Asn Ser Ala Glu Leu Thr Pro Ser Gly His
675 680 685

Pro Phe Trp Gly Ile Thr Gly Gly Gly Leu Gly Met Met Val Tyr Gln
690 695 700

Asp Pro Arg Glu Asn His Pro Gly Phe His Met Arg Ser Ser Gly Tyr
705 710 715 720

Ser Ala Gly Met Ile Ala Gly Gln Thr His Thr Phe Ser Leu Lys Phe
725 730 735

Ser Gln Thr Tyr Thr Lys Leu Asn Glu Arg Tyr Ala Lys Asn Asn Val
740 745 750

Ser Ser Lys Asn Tyr Ser Cys Gln Gly Glu Met Leu Phe Ser Leu Gln
755 760 765

Glu Gly Phe Leu Leu Thr Lys Leu Val Gly Leu Tyr Ser Tyr Gly Asp
770 775 780

His Asn Cys His His Phe Tyr Thr Gln Gly Glu Asn Leu Thr Ser Gln
785 790 795 800

Gly Thr Phe Arg Ser Gln Thr Met Gly Gly Ala Val Phe Phe Asp Leu
805 810 815

Pro Met Lys Pro Phe Gly Ser Thr His Ile Leu Thr Ala Pro Phe Leu
820 825 830

Gly Ala Leu Gly Ile Tyr Ser Ser Leu Ser His Phe Thr Glu Val Gly
835 840 845

Ala Tyr Pro Arg Ser Phe Ser Thr Lys Thr Pro Leu Ile Asn Val Leu
850 855 860

Val Pro Ile Gly Val Lys Gly Ser Phe Met Asn Ala Thr His Arg Pro
865 870 875 880

Gln Ala Trp Thr Val Glu Leu Ala Tyr Gln Pro Val Leu Tyr Arg Gln
885 890 895

Glu Pro Gly Ile Ala Ala Gln Leu Leu Ala Ser Lys Gly Ile Trp Phe
900 905 910

Gly Ser Gly Ser Pro Ser Ser Arg His Ala Met Ser Tyr Lys Ile Ser
915 920 925

Gln Gln Thr Gln Pro Leu Ser Trp Leu Thr Leu His Phe Gln Tyr His
930 935 940

Gly Phe Tyr Ser Ser Ser Thr Phe Cys Asn Tyr Leu Asn Gly Glu Ile
945 950 955 960

Ala Leu Arg Phe

<210> SEQ ID NO 53
<211> LENGTH: 1920
<212> TYPE: DNA
<213> ORGANISM: Chlamydia trachomatis

<400> SEQUENCE: 53
gtgaacgttc gtacgtactc tgttcagagg ggggggtaa aaacgatttc tgctagtgca 60
gttcctccta cagcagctgt tttatcgaga aaaaagcgtg ctatagaaga gaagaaggag 120

```
gaagcttctt ctggaaagat agaaaatctt gatgctagca aatacgatct tactcccaag    180
aacatagaag aaaaactagg aattactcct gaacagaaat ctactgttaa agacctatta    240
aataaactga aaaaggtcat tagtgcttac aactctatgc cagataaaaa ttcggaagcg    300
ggacagaatt ccttgattca acaaggaaaa tacgtcgatg ccattcagaa gaagcttcca    360
gcatcatcgc aggctcagcc taaacaggca aaagctaagg aacagaaagc cgaagaaaaa    420
cctaagacga ctccgattga aggtgttctt gaaaccatca aaacagaatt taaaggccat    480
cgtgtacctg ttgagaaaat catccatgga atatggatcg caggagcgcc tccggatggt    540
atcgaagatt atatgcgagt ctttttagat acttatgaag gttttgactt ctacttctgg    600
gtagatgaga atgcttatgc agcagctaaa ttttctagca ttttgaagaa ggtcgctttc    660
gatgcggcta ttcaagatct acgatctgcc acagatgagt ctacgaaggc ctttgttaaa    720
gactacgatg aattaaaaca gaaatatgaa aagaaagttg cggagacgac ttctcaagca    780
gaaaaagacc aatatctcaa agatctaaag gatcttttag agaaatttac aaaaatcagt    840
gatgagattc gtggaaaatt tgatcggctg tttcttaaga atgtgattgt tgctcagaac    900
ggattcttta atttctgctt gctgaaaggc ctcggcaata tcaatgacga aacgcgtgca    960
gagtatttag agaaagaact caaacttcct actgaggaga tcgaacagta taaaaagctt   1020
aaagagacga acaaagagaa gatagccgct attgtaaaac aactaaacga gaaacttgga   1080
tcggatcggg taaaaatcaa agacattaaa gagctgcaat ctatgaagca agctcgaaat   1140
gtctacaatt atgaacagga aatgtttctg cgctggaact atgcagccgc aacagatcag   1200
attcgtatgt atatgttgga ggaacttgga ggtctttata ctgatctgga tatgatgcct   1260
tcatactctc aggaagtatt ggagcttatc aaaaagcaca gtgatggaaa ccgaatgttt   1320
gaggatatga gctctagacg ggcgatttct gatgcggttt taaagatggc tgtaggtaag   1380
gcgacaacag tttccatgga agaggtagca aaggatatcg atgtttctcg cttaacagaa   1440
gaggataaga caaaattaaa tgctctattt aaggatctag agccatttgc aaaaccggat   1500
tctaaaggag ctgaagcaga agggggtgaa ggagcaaaag gtatgaaaaa gagctttttc   1560
cagcccatag atctgaatat tgtcagaaat accatgccta tcttgagacg ctatcatcac   1620
tatcctgagt taggatggtt tattcgagga ttgaacggat tgatggtctc tcataaggga   1680
agcactgcgg tttctgctgt cattgtaggg caacaggctg cctaccagga actagcagca   1740
cttagacaag atgtcctttc aggggagttt ttccattctt tagaaaattt gacacataga   1800
aaccataagg agcgtattgg aaatcatctc gtcgctaatt atttggctaa aagtctcttt   1860
tttgattact gccaagattc agtgatgccg gaggctgtaa gtaccttagg tattagatga   1920
```

<210> SEQ ID NO 54
<211> LENGTH: 639
<212> TYPE: PRT
<213> ORGANISM: Chlamydia trachomatis

<400> SEQUENCE: 54

```
Met Asn Val Arg Thr Tyr Ser Val Gln Arg Gly Gly Val Lys Thr Ile
1               5                   10                  15

Ser Ala Ser Ala Val Pro Pro Thr Ala Ala Val Leu Ser Arg Lys Lys
            20                  25                  30

Arg Ala Ile Glu Glu Lys Lys Glu Glu Ala Ser Ser Gly Lys Ile Glu
        35                  40                  45

Asn Leu Asp Ala Ser Lys Tyr Asp Leu Thr Pro Lys Asn Ile Glu Glu
    50                  55                  60
```

-continued

```
Lys Leu Gly Ile Thr Pro Glu Gln Lys Ser Thr Val Lys Asp Leu Leu
65                  70                  75                  80

Asn Lys Leu Lys Lys Val Ile Ser Ala Tyr Asn Ser Met Pro Asp Lys
                85                  90                  95

Asn Ser Glu Ala Gly Gln Asn Ser Leu Ile Gln Gln Gly Lys Tyr Val
            100                 105                 110

Asp Ala Ile Gln Lys Lys Leu Pro Ala Ser Ser Gln Ala Gln Pro Lys
        115                 120                 125

Gln Ala Lys Ala Lys Glu Gln Lys Ala Glu Glu Lys Pro Lys Thr Thr
    130                 135                 140

Pro Ile Glu Gly Val Leu Glu Thr Ile Lys Thr Glu Phe Lys Gly His
145                 150                 155                 160

Arg Val Pro Val Glu Lys Ile Ile His Gly Ile Trp Ile Ala Gly Ala
                165                 170                 175

Pro Pro Asp Gly Ile Glu Asp Tyr Met Arg Val Phe Leu Asp Thr Tyr
            180                 185                 190

Glu Gly Phe Asp Phe Tyr Phe Trp Val Asp Glu Asn Ala Tyr Ala Ala
        195                 200                 205

Ala Lys Phe Ser Ser Ile Leu Lys Lys Val Ala Phe Asp Ala Ala Ile
    210                 215                 220

Gln Asp Leu Arg Ser Ala Thr Asp Glu Ser Thr Lys Ala Phe Val Lys
225                 230                 235                 240

Asp Tyr Asp Glu Leu Lys Gln Lys Tyr Glu Lys Lys Val Ala Glu Thr
                245                 250                 255

Thr Ser Gln Ala Glu Lys Asp Gln Tyr Leu Lys Asp Leu Lys Asp Leu
            260                 265                 270

Leu Glu Lys Phe Thr Lys Ile Ser Asp Glu Ile Arg Gly Lys Phe Asp
        275                 280                 285

Arg Leu Phe Leu Lys Asn Val Ile Val Ala Gln Asn Gly Phe Phe Asn
    290                 295                 300

Phe Cys Leu Leu Lys Gly Leu Gly Asn Ile Asn Asp Glu Thr Arg Ala
305                 310                 315                 320

Glu Tyr Leu Glu Lys Glu Leu Lys Leu Pro Thr Glu Glu Ile Glu Gln
                325                 330                 335

Tyr Lys Lys Leu Lys Glu Thr Asn Lys Glu Lys Ile Ala Ala Ile Val
            340                 345                 350

Lys Gln Leu Asn Glu Lys Leu Gly Ser Asp Arg Val Lys Ile Lys Asp
        355                 360                 365

Ile Lys Glu Leu Gln Ser Met Lys Gln Ala Arg Asn Val Tyr Asn Tyr
    370                 375                 380

Glu Gln Glu Met Phe Leu Arg Trp Asn Tyr Ala Ala Ala Thr Asp Gln
385                 390                 395                 400

Ile Arg Met Tyr Met Leu Glu Glu Leu Gly Gly Leu Tyr Thr Asp Leu
                405                 410                 415

Asp Met Met Pro Ser Tyr Ser Gln Glu Val Leu Glu Leu Ile Lys Lys
            420                 425                 430

His Ser Asp Gly Asn Arg Met Phe Glu Asp Met Ser Ser Arg Arg Ala
        435                 440                 445

Ile Ser Asp Ala Val Leu Lys Met Ala Val Gly Lys Ala Thr Thr Val
    450                 455                 460

Ser Met Glu Glu Val Ala Lys Asp Ile Asp Val Ser Arg Leu Thr Glu
465                 470                 475                 480
```

```
Glu Asp Lys Thr Lys Leu Asn Ala Leu Phe Lys Asp Leu Glu Pro Phe
                485                 490                 495

Ala Lys Pro Asp Ser Lys Gly Ala Glu Ala Glu Gly Gly Glu Gly Ala
            500                 505                 510

Lys Gly Met Lys Lys Ser Phe Phe Gln Pro Ile Asp Leu Asn Ile Val
        515                 520                 525

Arg Asn Thr Met Pro Ile Leu Arg Arg Tyr His His Tyr Pro Glu Leu
    530                 535                 540

Gly Trp Phe Ile Arg Gly Leu Asn Gly Leu Met Val Ser His Lys Gly
545                 550                 555                 560

Ser Thr Ala Val Ser Ala Val Ile Val Gly Gln Gln Ala Ala Tyr Gln
                565                 570                 575

Glu Leu Ala Ala Leu Arg Gln Asp Val Leu Ser Gly Glu Phe Phe His
            580                 585                 590

Ser Leu Glu Asn Leu Thr His Arg Asn His Lys Glu Arg Ile Gly Asn
        595                 600                 605

His Leu Val Ala Asn Tyr Leu Ala Lys Ser Leu Phe Phe Asp Tyr Cys
    610                 615                 620

Gln Asp Ser Val Met Pro Glu Ala Val Ser Thr Leu Gly Ile Arg
625                 630                 635
```

<210> SEQ ID NO 55
<211> LENGTH: 1590
<212> TYPE: DNA
<213> ORGANISM: Chlamydia trachomatis

<400> SEQUENCE: 55

```
atgcatcaca ggaagttttt agcagtttcc attgctttcg taagtttagc ttttgggcta     60

acatcttgtt atcataaaaa agaagaacca aaagatgttt tgcggattgc gatctgtcat    120

gatccaatgt ctttagatcc gcgtcaggtt tttttaagca aagatgtttc tattgtaaaa    180

gctctctatg aagggttagt ccgggaaaaa gaagctgcgt tccagctagc tttggcagaa    240

agatatcatc aatctgatga tggttgtgtt tatacttttt ttctaaaaaa tacattctgg    300

agcaacggag atgttgtaac agcatatgat tttgaagagt ctattaaaca aatttatttc    360

cgagaaattg ataacccttc gttacgctct cttgcattaa ttaaaaattc tcatgctgtt    420

ttaacaggag ctctccctgt tgaagattta ggtgttagag ctttgaatgc gaaaactcta    480

gaaattgttt tagaaaaccc gtttccttat tttctagaga tattggcgca cccggttttt    540

tatccggtgc acacctcttt acgagaatat tacaaagata agcgtaacaa acgcgttttc    600

ccgataattt ctaatggtcc ttttgcgatt caatgttatg agccgcaaag atatttacta    660

atcaacaaaa accctctgta tcatgccaag cacgatgttc tgttaaattc ggtatgtttg    720

cagatagttc ctgatatcca tacagctatg cagttattcc aaaaaaatca tatcgattta    780

gttgggttac cctggagctc ctccttttct ttagaagaac aaagaaatct ccctagagaa    840

aaattatttg attatcctgt attgagttgc tctgttttat tctgtaacat tcatcaaaca    900

cctttaaata atccctcgct gagaacagcc ctctctttag caatcaatcg agaaacttta    960

ttaaaactag caggtaaagg ctgtagcgct acgagctttg ttcacccaca attatctcag   1020

atacctgcta ctactttgtc tcaagatgag cggattgctt tagcaaaagg ctacttgacc   1080

gaagctttaa agactttatc tcaagaagat ttagaaaaaa ttacattaat ttatcctata   1140

gaatctgttt gcttacgagc cgttgttcaa gaaattcgcc aacaattatt tgatgtactg   1200

ggatttaaaa tttctacatt aggattagaa tatcattgtt ttttagacaa acgttccaga   1260
```

```
ggagaattct ccttagcaac tggtaattgg attgcagact atcatcaagc tagtgctttc   1320

ctgtctgtcc taggtaatgg gacaagatat aaagactttc aattgattaa ctggcagaac   1380

caaaagtaca caaatatagt tgctcaactt ctgattcaag aatcaagcga cctacagctt   1440

atggcagagc agttgttgct taaagaaagt cctcttattc ctctatacca cctcgattat   1500

gtgtatgcga aacagcctcg ggtgtctgat ctccaaacct cttctcgtgg agaaattgat   1560

ttaaaaagag tttcattagc tgaaggatag                                   1590


<210> SEQ ID NO 56
<211> LENGTH: 529
<212> TYPE: PRT
<213> ORGANISM: Chlamydia trachomatis

<400> SEQUENCE: 56

Met His His Arg Lys Phe Leu Ala Val Ser Ile Ala Phe Val Ser Leu
1               5                   10                  15

Ala Phe Gly Leu Thr Ser Cys Tyr His Lys Lys Glu Glu Pro Lys Asp
            20                  25                  30

Val Leu Arg Ile Ala Ile Cys His Asp Pro Met Ser Leu Asp Pro Arg
        35                  40                  45

Gln Val Phe Leu Ser Lys Asp Val Ser Ile Val Lys Ala Leu Tyr Glu
    50                  55                  60

Gly Leu Val Arg Glu Lys Glu Ala Ala Phe Gln Leu Ala Leu Ala Glu
65                  70                  75                  80

Arg Tyr His Gln Ser Asp Asp Gly Cys Val Tyr Thr Phe Phe Leu Lys
                85                  90                  95

Asn Thr Phe Trp Ser Asn Gly Asp Val Val Thr Ala Tyr Asp Phe Glu
            100                 105                 110

Glu Ser Ile Lys Gln Ile Tyr Phe Arg Glu Ile Asp Asn Pro Ser Leu
        115                 120                 125

Arg Ser Leu Ala Leu Ile Lys Asn Ser His Ala Val Leu Thr Gly Ala
    130                 135                 140

Leu Pro Val Glu Asp Leu Gly Val Arg Ala Leu Asn Ala Lys Thr Leu
145                 150                 155                 160

Glu Ile Val Leu Glu Asn Pro Phe Pro Tyr Phe Leu Glu Ile Leu Ala
                165                 170                 175

His Pro Val Phe Tyr Pro Val His Thr Ser Leu Arg Glu Tyr Tyr Lys
            180                 185                 190

Asp Lys Arg Asn Lys Arg Val Phe Pro Ile Ile Ser Asn Gly Pro Phe
        195                 200                 205

Ala Ile Gln Cys Tyr Glu Pro Gln Arg Tyr Leu Leu Ile Asn Lys Asn
    210                 215                 220

Pro Leu Tyr His Ala Lys His Asp Val Leu Leu Asn Ser Val Cys Leu
225                 230                 235                 240

Gln Ile Val Pro Asp Ile His Thr Ala Met Gln Leu Phe Gln Lys Asn
                245                 250                 255

His Ile Asp Leu Val Gly Leu Pro Trp Ser Ser Ser Phe Ser Leu Glu
            260                 265                 270

Glu Gln Arg Asn Leu Pro Arg Glu Lys Leu Phe Asp Tyr Pro Val Leu
        275                 280                 285

Ser Cys Ser Val Leu Phe Cys Asn Ile His Gln Thr Pro Leu Asn Asn
    290                 295                 300

Pro Ser Leu Arg Thr Ala Leu Ser Leu Ala Ile Asn Arg Glu Thr Leu
```

```
305                 310                 315                 320

Leu Lys Leu Ala Gly Lys Gly Cys Ser Ala Thr Ser Phe Val His Pro
                325                 330                 335

Gln Leu Ser Gln Ile Pro Ala Thr Thr Leu Ser Gln Asp Glu Arg Ile
            340                 345                 350

Ala Leu Ala Lys Gly Tyr Leu Thr Glu Ala Leu Lys Thr Leu Ser Gln
        355                 360                 365

Glu Asp Leu Glu Lys Ile Thr Leu Ile Tyr Pro Ile Glu Ser Val Cys
    370                 375                 380

Leu Arg Ala Val Val Gln Glu Ile Arg Gln Gln Leu Phe Asp Val Leu
385                 390                 395                 400

Gly Phe Lys Ile Ser Thr Leu Gly Leu Glu Tyr His Cys Phe Leu Asp
                405                 410                 415

Lys Arg Ser Arg Gly Glu Phe Ser Leu Ala Thr Gly Asn Trp Ile Ala
            420                 425                 430

Asp Tyr His Gln Ala Ser Ala Phe Leu Ser Val Leu Gly Asn Gly Thr
        435                 440                 445

Arg Tyr Lys Asp Phe Gln Leu Ile Asn Trp Gln Asn Gln Lys Tyr Thr
    450                 455                 460

Asn Ile Val Ala Gln Leu Leu Ile Gln Glu Ser Ser Asp Leu Gln Leu
465                 470                 475                 480

Met Ala Glu Gln Leu Leu Leu Lys Glu Ser Pro Leu Ile Pro Leu Tyr
                485                 490                 495

His Leu Asp Tyr Val Tyr Ala Lys Gln Pro Arg Val Ser Asp Leu Gln
            500                 505                 510

Thr Ser Ser Arg Gly Glu Ile Asp Leu Lys Arg Val Ser Leu Ala Glu
        515                 520                 525

Gly
```

<210> SEQ ID NO 57
<211> LENGTH: 2091
<212> TYPE: DNA
<213> ORGANISM: Chlamydia muridarum

<400> SEQUENCE: 57

```
atgaggattc caatgacact ctttcacact catcacgatg ccgtctctcc ggacggctac      60

ttatgttctt cccttcagtt agttggctct ggcacatatg aaggagaaat cgaaatccaa     120

aatattcctt cttatttcct tggattccga ttacccaccc attgcgttca tcttaatttg     180

aagagttctc tagcccagtt aggagtagat gcatctcttc ttcactgcga actaagcaaa     240

aatcaacaac gtgcacatat gcacgtgcag ttcaccggct atggccctat cgctgagtcc     300

atgctatctc ttctcaaacc cggagatcga gtagccaaac tgtttgctgc agatgatcgt     360

agactagtcc gctcccctga ttatcttgaa agcatgctaa aaaatactga taagacagga     420

catcctctgc tccgatttgg aaaaaaactc gagcatctta tctcttttga tgtggtggac     480

gatcgcctcg ttgtatcact ccccaccttg ccaggcatag tcaattatga cccagacatc     540

tatggacttc ttcccttaat tcaaaaatca ctaagcaatc ctaaattgag tattcgccac     600

ttcttgtctc tctatcagaa gatcgtagaa ggaccacaca tcccttatga aggaaacatt     660

ttgttaatca aaacagagcc tcttcatatc cgcacagtat ttgctcgcgt ggtcgatcaa     720

atgctccctc aaggtctatt tcacacttct gccaacattt tagaacccac aacgcgagag     780

tctggagata tttttgaatt ttttggaaat ccctccactc ttgtagaaag aatccctcta     840
```

-continued

```
gaattcttca ctatcgaacc ctacaaagaa cactcttact tctgtaatcg agatctattg    900

caaactacct tgcaatcgga aagtgaaatc aaaaaaatat tcgatacagc tcctcaagag    960

cctgtaaaag ccgccactta tttatcaaaa ggaagtgaaa tttcttctct tgatgcagat   1020

tcttggctta cgggatccgc agctgcatac caatgtagcg aaaaacaggc agctaaagac   1080

gaatacatcc acgctcaacc ctgttatcca tttttggaag caatggaaac gggactcatc   1140

aatagcgaag gagctttact cactcggttt ttcccctctt ccagcttaaa agggatgttg   1200

atctcctatc atgtacgcca ctatcttaag caaatttact ttcaagttcc ttcttataca   1260

tatggagact acttctctca taatgaccga ggattactgt tagatctata tcaggcgaac   1320

attgatgtgt tctgggctga tgaagagagc ggccgtgtat tgcaatatac aaaacggcgc   1380

gacaaaaata gtggaatgtt cgtcgttaaa aatcgagtag aagagttcca atcagcatat   1440

ttcgtagcga tttatggatc acgtctcctg gaaaataatt tctcggccca actaaacacg   1500

cttcttgcag ggttacaaaa agctgcacac actctaggca ttccaggctt ctcaaaaccc   1560

actcctcttg ccgtaatcac aggaggaggg actggcgtta tggctacagg aaatcgtgtt   1620

gcaaaagagt tgggaattct ttcttgcggg accgttctcg atttggaagc ttcacctgca   1680

caaatagatc agcctgcaaa cgaattttta gatgccaaaa tgacataccg tctaccgcaa   1740

cttatagaaa gacaagaaca tttttattca gaccttgcca ttttagttgt tggtggtgtt   1800

ggaacagatt tcgaacttta cctagaactc gtctacttga aacaggcgc caaacctcct    1860

actccaattt tccttattgg gcctgttgaa tactggaaag agaaagttgc tcatgcctat   1920

gagattaatc ttaaagcagg aactattcgt ggttctgagt ggatcagcaa ctgcttattc   1980

tgcattacat ctcctgaagc aggaattgct gtattcgaac agttcctcgc tggagaactt   2040

cccataggat atgattatcc tccagctcca gacggattag ttatcgtcta a            2091
```

<210> SEQ ID NO 58
<211> LENGTH: 696
<212> TYPE: PRT
<213> ORGANISM: Chlamydia muridarum

<400> SEQUENCE: 58

```
Met Arg Ile Pro Met Thr Leu Phe His Thr His His Asp Ala Val Ser
1               5                   10                  15

Pro Asp Gly Tyr Leu Cys Ser Ser Leu Gln Leu Val Gly Ser Gly Thr
            20                  25                  30

Tyr Glu Gly Glu Ile Glu Ile Gln Asn Ile Pro Ser Tyr Phe Leu Gly
        35                  40                  45

Phe Arg Leu Pro Thr His Cys Val His Leu Asn Leu Lys Ser Ser Leu
    50                  55                  60

Ala Gln Leu Gly Val Asp Ala Ser Leu Leu His Cys Glu Leu Ser Lys
65                  70                  75                  80

Asn Gln Gln Arg Ala His Met His Val Gln Phe Thr Gly Tyr Gly Pro
                85                  90                  95

Ile Ala Glu Ser Met Leu Ser Leu Leu Lys Pro Gly Asp Arg Val Ala
            100                 105                 110

Lys Leu Phe Ala Ala Asp Asp Arg Arg Leu Val Arg Ser Pro Asp Tyr
        115                 120                 125

Leu Glu Ser Met Leu Lys Asn Thr Asp Lys Thr Gly His Pro Leu Leu
    130                 135                 140

Arg Phe Gly Lys Lys Leu Glu His Leu Ile Ser Phe Asp Val Val Asp
145                 150                 155                 160
```

Asp Arg Leu Val Val Ser Leu Pro Thr Leu Pro Gly Ile Val Asn Tyr
165 170 175

Asp Pro Asp Ile Tyr Gly Leu Leu Pro Leu Ile Gln Lys Ser Leu Ser
180 185 190

Asn Pro Lys Leu Ser Ile Arg His Phe Leu Ser Leu Tyr Gln Lys Ile
195 200 205

Val Glu Gly Pro His Ile Pro Tyr Glu Gly Asn Ile Leu Leu Ile Lys
210 215 220

Thr Glu Pro Leu His Ile Arg Thr Val Phe Ala Arg Val Val Asp Gln
225 230 235 240

Met Leu Pro Gln Gly Leu Phe His Thr Ser Ala Asn Ile Leu Glu Pro
245 250 255

Thr Thr Arg Glu Ser Gly Asp Ile Phe Glu Phe Phe Gly Asn Pro Ser
260 265 270

Thr Leu Val Glu Arg Ile Pro Leu Glu Phe Phe Thr Ile Glu Pro Tyr
275 280 285

Lys Glu His Ser Tyr Phe Cys Asn Arg Asp Leu Leu Gln Thr Thr Leu
290 295 300

Gln Ser Glu Ser Glu Ile Lys Lys Ile Phe Asp Thr Ala Pro Gln Glu
305 310 315 320

Pro Val Lys Ala Ala Thr Tyr Leu Ser Lys Gly Ser Glu Ile Ser Ser
325 330 335

Leu Asp Ala Asp Ser Trp Leu Thr Gly Ser Ala Ala Ala Tyr Gln Cys
340 345 350

Ser Glu Lys Gln Ala Ala Lys Asp Glu Tyr Ile His Ala Gln Pro Cys
355 360 365

Tyr Pro Phe Leu Glu Ala Met Glu Thr Gly Leu Ile Asn Ser Glu Gly
370 375 380

Ala Leu Leu Thr Arg Phe Phe Pro Ser Ser Ser Leu Lys Gly Met Leu
385 390 395 400

Ile Ser Tyr His Val Arg His Tyr Leu Lys Gln Ile Tyr Phe Gln Val
405 410 415

Pro Ser Tyr Thr Tyr Gly Asp Tyr Phe Ser His Asn Asp Arg Gly Leu
420 425 430

Leu Leu Asp Leu Tyr Gln Ala Asn Ile Asp Val Phe Trp Ala Asp Glu
435 440 445

Glu Ser Gly Arg Val Leu Gln Tyr Thr Lys Arg Arg Asp Lys Asn Ser
450 455 460

Gly Met Phe Val Val Lys Asn Arg Val Glu Glu Phe Gln Ser Ala Tyr
465 470 475 480

Phe Val Ala Ile Tyr Gly Ser Arg Leu Leu Glu Asn Asn Phe Ser Ala
485 490 495

Gln Leu Asn Thr Leu Leu Ala Gly Leu Gln Lys Ala Ala His Thr Leu
500 505 510

Gly Ile Pro Gly Phe Ser Lys Pro Thr Pro Leu Ala Val Ile Thr Gly
515 520 525

Gly Gly Thr Gly Val Met Ala Thr Gly Asn Arg Val Ala Lys Glu Leu
530 535 540

Gly Ile Leu Ser Cys Gly Thr Val Leu Asp Leu Glu Ala Ser Pro Ala
545 550 555 560

Gln Ile Asp Gln Pro Ala Asn Glu Phe Leu Asp Ala Lys Met Thr Tyr
565 570 575

```
Arg Leu Pro Gln Leu Ile Glu Arg Gln Glu His Phe Tyr Ser Asp Leu
            580                 585                 590

Ala Ile Leu Val Val Gly Gly Val Gly Thr Asp Phe Glu Leu Tyr Leu
        595                 600                 605

Glu Leu Val Tyr Leu Lys Thr Gly Ala Lys Pro Pro Thr Pro Ile Phe
    610                 615                 620

Leu Ile Gly Pro Val Glu Tyr Trp Lys Glu Lys Val Ala His Ala Tyr
625                 630                 635                 640

Glu Ile Asn Leu Lys Ala Gly Thr Ile Arg Gly Ser Glu Trp Ile Ser
                645                 650                 655

Asn Cys Leu Phe Cys Ile Thr Ser Pro Glu Ala Gly Ile Ala Val Phe
            660                 665                 670

Glu Gln Phe Leu Ala Gly Glu Leu Pro Ile Gly Tyr Asp Tyr Pro Pro
        675                 680                 685

Ala Pro Asp Gly Leu Val Ile Val
    690                 695
```

<210> SEQ ID NO 59
<211> LENGTH: 4563
<212> TYPE: DNA
<213> ORGANISM: Chlamydia muridarum

<400> SEQUENCE: 59

```
atgagttccg agaaagataa aaaaaactcc tgttctaagt tttccttatc ggtagtagca     60
gctattctcg cttctatgag tggtttatcg aattgttccg atctttatgc cgtaggaagt    120
tctgcagacc atcctgccta cttgattcct caagcggggt tattattgga tcatattaag    180
gatatattca ttggccctaa agatagtcag gataaggggc agtataagtt gattattggt    240
gaggctggct ctttccaaga tagtaatgca gagactcttc ctcaaaaggt agagcacagc    300
actttgtttt cagttacaac acctataatt gtgcaaggaa tagatcaaca agatcaggtc    360
tcttcgcagg gattggtctg taatttttca ggagatcatt cagaggagat tttgagaga     420 gaatcctttt tagggatcgc tttcctaggg aatggtagca aggatggaat cacgttaaca    480
gatataaaat cttcgttatc tggtgctgcc ttgtattctt cagatgatct tatttttgaa    540
agaattaagg gagatataga gctttcttct tgttcatctt tagaaagagg aggagcttgt    600
tcagctcaaa gtattttaat tcatgattgt caaggattaa cggtaaaaca ttgtgccgca    660
ggggtgaatg ttgaaggagt tagtgctagc gaccatctcg gatttggggg cggggccttc    720
tctactacaa gttctctttc tggagagaag agtttgtata tgcctgcagg cgatattgtg    780
gtggctacct gcgatggtcc tgtgtgtttc gaaggaaata gtgctcagtt agcaaatggt    840
ggcgctattg ccgcttctgg taaagttctt tttgtagcta acgaaaaaaa gatttccttt    900
acagacaacc aagctttgtc tggaggagct atttctgcat cttctagtat ttctttccaa    960
aattgtgctg agcttgtgtt caagagtaat cttgcaaaag gagttaaaga taaatgttct   1020
ttgggaggag gtgctttagc ctctttagaa tccgtagttt tgaaagataa tctcggtatt   1080
acttatgaaa aaaatcagtc ctattcggaa ggaggggcta tttttgggaa ggattgtgag   1140
atttttgaaa acagggggcc tgttgtattc agagataata cagctgcttt aggaggcgga   1200
gctattttgg cgcaacaaac tgtggcgatt tgtggtaata agtctggaat atcttttgaa   1260
ggaagtaagt ctagttttgg aggggccatt gcttgtggaa atttctcttc tgagaataat   1320
tcttcagctt tgggatcaat tgatatctct aacaatctag gagatatctc ttttcttcgg   1380
actctgtgta ctacttcgga tttagggcaa acggattacc aagggggagg ggccttattc   1440
```

-continued

```
gctgaaaata tttctctttc tgagaatgct ggtgcaatta ctttcaaaga caatattgtg   1500
aagacatttg cctcaaatgg aaaaatgttg ggtggagggg caattttagc ttcaggaaat   1560
gttttgatta gcaaaaactc tggagagatt tcttttgtag ggaatgctcg agctcctcag   1620
gctattccga ctcgttcatc tgacgaattg tcttttggcg cacaattaac tcaaactact   1680
tcaggatgtt ctggaggagg agctcttttt ggtaaagagg ttgccattgt tcaaaatgcc   1740
actgttgtat tcgagcaaaa tcgcttacag tgtggcgagc aggaaacaca tggtggaggc   1800
ggtgctgttt atggtatgga gagtgcctct attattggaa actcttttgt gagattcgga   1860
aataattacg ctgtagggaa tcagatttct ggaggagctc ttttatccaa gaaggtccgt   1920
ttagctgaaa atacaagggt agatttttct cgaaatatcg ctactttctg cggcggggct   1980
gttcaagttt ctgatggaag ttgcgaattg atcaacaatg ggtatgtgct attcagagat   2040
aaccgagggc agacatttgg tggggctatt tcttgcttga aaggagatgt gatcatttcc   2100
ggaaataaag atagggttga gtttagagat aacattgtga cgcggcctta ttttgaagaa   2160
aatgaagaaa aagttgagac agcagatatt aattcagata agcaagaagc agaagagcgc   2220
tctttattag agaacattga gcagagcttt attactgcaa ctaatcagac ctttttctta   2280
gaggaagaga aactcccatc agaagctttt atctctgctg aagaactttc aaagagaaga   2340
gaatgtgctg gtggggcgat tttgcaaaa cgggtctaca ttacggataa taaagaacct   2400
atcttgtttt cgcataattt ttctgatgtt tatgggggag ctatttttac gggttctcta   2460
caggaaactg ataaacaaga tgttgtaact cctgaagttg tgatatcagg caacgatggg   2520
gatgtcattt tttctggaaa tgcagctaaa catgataagc atttacctga tacaggtggt   2580
ggagccattt gtacacagaa tttgacgatt tcccaaaaca atgggaatgt cttgttcttg   2640
aacaattttg cttgttctgg tggagcagtt cgcatagagg atcatggaga agttctttta   2700
gaggcttttg gggagatat tattttcaat ggaaactctt ctttcagagc tcaaggatcg   2760
gatgcgatct attttgctgg taaggactct agaattaaag ctttaaatgc tactgaagga   2820
catgcgattg tgttccaaga tgcattggtg tttgaaaata tagaagaaag aaagtcttcg   2880
ggactattgg tgattaactc tcaggaaaat gagggttata cgggatccgt ccgattttta   2940
ggatctgaaa gtaaggttcc tcaatggatt catgtgcaac agggaggtct tgagttgcta   3000
catggagcta ttttatgtag ttatggggtt aaacaagatc ctagagctaa aatagtatta   3060
tctgctggat ctaaattgaa gattctagat tcagagcaag aaaataacgc agaaattgga   3120
gatcttgaag attctgttaa ttcagaaaaa acaccatctc tttggattgg gaagaacgct   3180
caagcaaaag tccctctggt tgatatccat actatttcta ttgatttagc atcattttct   3240
tctaaagctc aggaaacccc tgaggaagct ccacaagtca tcgtccctaa gggaagttgt   3300
gtccactcgg gagagttaag tttggagttg gttaatacaa caggaaaagg ttatgagaat   3360
catgcgttgt taaaaaatga tactcaggtt tctctcatgt ctttcaaaga ggaaaatgat   3420
ggatctttag aagatttgag taagttgtct gtttcggatt tacgcattaa agtttctact   3480
ccagatattg tagaagaaac ttatggccat atgggggatt ggtctgaagc tacaattcaa   3540
gatggggctc ttgtcattaa ttggcatcct actggatata aattagatcc gcaaaaagct   3600
ggttctttgg tattcaatgc attatgggag gaagaggctg tattgtctac tctaaaaaat   3660
gctcggattg cccataacct taccattcag agaatggaat ttgattattc tacaaatgct   3720
tggggattag cttttagtag ctttagagag ctatcttcag agaagcttgt ttctgttgat   3780
```

-continued

```
ggatatagag gctcttatat aggggcttct gcaggcattg atactcagtt gatggaagat   3840

tttgttttgg gaatcagcac ggcttccttc ttcgggaaaa tgcatagtca gaattttgat   3900

gcagagattt ctcgacatgg ttttgttggt tcggtctata caggcttcct agctggggcc   3960

tggttcttca aggggcagta cagtcttggc gaaacacata acgatatgac aactcgttac   4020

ggggttttgg gagaatctaa tgctacttgg aagtctcgag gagtactagc agatgcttta   4080

gttgaatatc gtagtttagt cggtccagca cgacctaaat tttatgcttt gcattttaat   4140

ccttatgtcg aggtatctta tgcatctgcg aagttcccta gttttgtaga acaaggagga   4200

gaagctcgtg cttttgaaga aacctcttta acaaacatta ccgttccctt tggtatgaaa   4260

tttgaactat cttttacaaa aggacagttt tcagagacta attctcttgg aataggttgt   4320

gcatgggaaa tgtatcggaa agtcgaagga agatctgtag agctactaga agctggtttt   4380

gattgggaag gatctcctat agatctccct aaacaagagc tgagagtggc tttagaaaac   4440

aatacggaat ggagttcgta ttttagtaca gctctaggag taacagcatt ttgtggagga   4500

ttttcttcta tggataataa actaggatac gaagcgaatg ctggaatgcg tttgattttc   4560

tag                                                                 4563
```

<210> SEQ ID NO 60
<211> LENGTH: 1520
<212> TYPE: PRT
<213> ORGANISM: Chlamydia muridarum

<400> SEQUENCE: 60

```
Met Ser Ser Glu Lys Asp Lys Lys Asn Ser Cys Ser Lys Phe Ser Leu
1               5                   10                  15

Ser Val Val Ala Ala Ile Leu Ala Ser Met Ser Gly Leu Ser Asn Cys
            20                  25                  30

Ser Asp Leu Tyr Ala Val Gly Ser Ser Ala Asp His Pro Ala Tyr Leu
        35                  40                  45

Ile Pro Gln Ala Gly Leu Leu Leu Asp His Ile Lys Asp Ile Phe Ile
    50                  55                  60

Gly Pro Lys Asp Ser Gln Asp Lys Gly Gln Tyr Lys Leu Ile Ile Gly
65                  70                  75                  80

Glu Ala Gly Ser Phe Gln Asp Ser Asn Ala Glu Thr Leu Pro Gln Lys
                85                  90                  95

Val Glu His Ser Thr Leu Phe Ser Val Thr Thr Pro Ile Ile Val Gln
            100                 105                 110

Gly Ile Asp Gln Gln Asp Gln Val Ser Ser Gln Gly Leu Val Cys Asn
        115                 120                 125

Phe Ser Gly Asp His Ser Glu Glu Ile Phe Glu Arg Glu Ser Phe Leu
    130                 135                 140

Gly Ile Ala Phe Leu Gly Asn Gly Ser Lys Asp Gly Ile Thr Leu Thr
145                 150                 155                 160

Asp Ile Lys Ser Ser Leu Ser Gly Ala Ala Leu Tyr Ser Ser Asp Asp
                165                 170                 175

Leu Ile Phe Glu Arg Ile Lys Gly Asp Ile Glu Leu Ser Ser Cys Ser
            180                 185                 190

Ser Leu Glu Arg Gly Gly Ala Cys Ser Ala Gln Ser Ile Leu Ile His
        195                 200                 205

Asp Cys Gln Gly Leu Thr Val Lys His Cys Ala Ala Gly Val Asn Val
    210                 215                 220

Glu Gly Val Ser Ala Ser Asp His Leu Gly Phe Gly Gly Gly Ala Phe
```

-continued

```
225                 230                 235                 240

Ser Thr Thr Ser Ser Leu Ser Gly Glu Lys Ser Leu Tyr Met Pro Ala
                245                 250                 255

Gly Asp Ile Val Val Ala Thr Cys Asp Gly Pro Val Cys Phe Glu Gly
            260                 265                 270

Asn Ser Ala Gln Leu Ala Asn Gly Gly Ala Ile Ala Ala Ser Gly Lys
        275                 280                 285

Val Leu Phe Val Ala Asn Glu Lys Lys Ile Ser Phe Thr Asp Asn Gln
    290                 295                 300

Ala Leu Ser Gly Gly Ala Ile Ser Ala Ser Ser Ser Ile Ser Phe Gln
305                 310                 315                 320

Asn Cys Ala Glu Leu Val Phe Lys Ser Asn Leu Ala Lys Gly Val Lys
                325                 330                 335

Asp Lys Cys Ser Leu Gly Gly Gly Ala Leu Ala Ser Leu Glu Ser Val
            340                 345                 350

Val Leu Lys Asp Asn Leu Gly Ile Thr Tyr Glu Lys Asn Gln Ser Tyr
        355                 360                 365

Ser Glu Gly Gly Ala Ile Phe Gly Lys Asp Cys Glu Ile Phe Glu Asn
    370                 375                 380

Arg Gly Pro Val Val Phe Arg Asp Asn Thr Ala Ala Leu Gly Gly Gly
385                 390                 395                 400

Ala Ile Leu Ala Gln Gln Thr Val Ala Ile Cys Gly Asn Lys Ser Gly
                405                 410                 415

Ile Ser Phe Glu Gly Ser Lys Ser Ser Phe Gly Gly Ala Ile Ala Cys
            420                 425                 430

Gly Asn Phe Ser Ser Glu Asn Asn Ser Ser Ala Leu Gly Ser Ile Asp
        435                 440                 445

Ile Ser Asn Asn Leu Gly Asp Ile Ser Phe Leu Arg Thr Leu Cys Thr
    450                 455                 460

Thr Ser Asp Leu Gly Gln Thr Asp Tyr Gln Gly Gly Gly Ala Leu Phe
465                 470                 475                 480

Ala Glu Asn Ile Ser Leu Ser Glu Asn Ala Gly Ala Ile Thr Phe Lys
                485                 490                 495

Asp Asn Ile Val Lys Thr Phe Ala Ser Asn Gly Lys Met Leu Gly Gly
            500                 505                 510

Gly Ala Ile Leu Ala Ser Gly Asn Val Leu Ile Ser Lys Asn Ser Gly
        515                 520                 525

Glu Ile Ser Phe Val Gly Asn Ala Arg Ala Pro Gln Ala Ile Pro Thr
    530                 535                 540

Arg Ser Ser Asp Glu Leu Ser Phe Gly Ala Gln Leu Thr Gln Thr Thr
545                 550                 555                 560

Ser Gly Cys Ser Gly Gly Gly Ala Leu Phe Gly Lys Glu Val Ala Ile
                565                 570                 575

Val Gln Asn Ala Thr Val Val Phe Glu Gln Asn Arg Leu Gln Cys Gly
            580                 585                 590

Glu Gln Glu Thr His Gly Gly Gly Gly Ala Val Tyr Gly Met Glu Ser
        595                 600                 605

Ala Ser Ile Ile Gly Asn Ser Phe Val Arg Phe Gly Asn Asn Tyr Ala
    610                 615                 620

Val Gly Asn Gln Ile Ser Gly Gly Ala Leu Leu Ser Lys Lys Val Arg
625                 630                 635                 640

Leu Ala Glu Asn Thr Arg Val Asp Phe Ser Arg Asn Ile Ala Thr Phe
                645                 650                 655
```

```
Cys Gly Gly Ala Val Gln Val Ser Asp Gly Ser Cys Glu Leu Ile Asn
            660                 665                 670

Asn Gly Tyr Val Leu Phe Arg Asp Asn Arg Gly Gln Thr Phe Gly Gly
        675                 680                 685

Ala Ile Ser Cys Leu Lys Gly Asp Val Ile Ile Ser Gly Asn Lys Asp
    690                 695                 700

Arg Val Glu Phe Arg Asp Asn Ile Val Thr Arg Pro Tyr Phe Glu Glu
705                 710                 715                 720

Asn Glu Glu Lys Val Glu Thr Ala Asp Ile Asn Ser Asp Lys Gln Glu
                725                 730                 735

Ala Glu Glu Arg Ser Leu Leu Glu Asn Ile Glu Gln Ser Phe Ile Thr
            740                 745                 750

Ala Thr Asn Gln Thr Phe Phe Leu Glu Glu Glu Lys Leu Pro Ser Glu
        755                 760                 765

Ala Phe Ile Ser Ala Glu Glu Leu Ser Lys Arg Arg Glu Cys Ala Gly
    770                 775                 780

Gly Ala Ile Phe Ala Lys Arg Val Tyr Ile Thr Asp Asn Lys Glu Pro
785                 790                 795                 800

Ile Leu Phe Ser His Asn Phe Ser Asp Val Tyr Gly Gly Ala Ile Phe
                805                 810                 815

Thr Gly Ser Leu Gln Glu Thr Asp Lys Gln Asp Val Val Thr Pro Glu
            820                 825                 830

Val Val Ile Ser Gly Asn Asp Gly Asp Val Ile Phe Ser Gly Asn Ala
        835                 840                 845

Ala Lys His Asp Lys His Leu Pro Asp Thr Gly Gly Gly Ala Ile Cys
    850                 855                 860

Thr Gln Asn Leu Thr Ile Ser Gln Asn Asn Gly Asn Val Leu Phe Leu
865                 870                 875                 880

Asn Asn Phe Ala Cys Ser Gly Gly Ala Val Arg Ile Glu Asp His Gly
                885                 890                 895

Glu Val Leu Leu Glu Ala Phe Gly Gly Asp Ile Ile Phe Asn Gly Asn
            900                 905                 910

Ser Ser Phe Arg Ala Gln Gly Ser Asp Ala Ile Tyr Phe Ala Gly Lys
        915                 920                 925

Asp Ser Arg Ile Lys Ala Leu Asn Ala Thr Glu Gly His Ala Ile Val
    930                 935                 940

Phe Gln Asp Ala Leu Val Phe Glu Asn Ile Glu Glu Arg Lys Ser Ser
945                 950                 955                 960

Gly Leu Leu Val Ile Asn Ser Gln Glu Asn Glu Gly Tyr Thr Gly Ser
                965                 970                 975

Val Arg Phe Leu Gly Ser Glu Ser Lys Val Pro Gln Trp Ile His Val
            980                 985                 990

Gln Gln Gly Gly Leu Glu Leu Leu  His Gly Ala Ile Leu  Cys Ser Tyr
        995                 1000                 1005

Gly Val  Lys Gln Asp Pro Arg  Ala Lys Ile Val Leu  Ser Ala Gly
    1010                 1015                 1020

Ser Lys  Leu Lys Ile Leu Asp  Ser Glu Gln Glu Asn  Asn Ala Glu
    1025                 1030                 1035

Ile Gly  Asp Leu Glu Asp Ser  Val Asn Ser Glu Lys  Thr Pro Ser
    1040                 1045                 1050

Leu Trp  Ile Gly Lys Asn Ala  Gln Ala Lys Val Pro  Leu Val Asp
    1055                 1060                 1065
```

```
Ile His  Thr Ile Ser Ile Asp  Leu Ala Ser Phe Ser  Ser Lys Ala
    1070                 1075                 1080

Gln Glu  Thr Pro Glu Glu Ala  Pro Gln Val Ile Val  Pro Lys Gly
    1085                 1090                 1095

Ser Cys  Val His Ser Gly Glu  Leu Ser Leu Glu Leu  Val Asn Thr
    1100                 1105                 1110

Thr Gly  Lys Gly Tyr Glu Asn  His Ala Leu Leu Lys  Asn Asp Thr
    1115                 1120                 1125

Gln Val  Ser Leu Met Ser Phe  Lys Glu Glu Asn Asp  Gly Ser Leu
    1130                 1135                 1140

Glu Asp  Leu Ser Lys Leu Ser  Val Ser Asp Leu Arg  Ile Lys Val
    1145                 1150                 1155

Ser Thr  Pro Asp Ile Val Glu  Glu Thr Tyr Gly His  Met Gly Asp
    1160                 1165                 1170

Trp Ser  Glu Ala Thr Ile Gln  Asp Gly Ala Leu Val  Ile Asn Trp
    1175                 1180                 1185

His Pro  Thr Gly Tyr Lys Leu  Asp Pro Gln Lys Ala  Gly Ser Leu
    1190                 1195                 1200

Val Phe  Asn Ala Leu Trp Glu  Glu Glu Ala Val Leu  Ser Thr Leu
    1205                 1210                 1215

Lys Asn  Ala Arg Ile Ala His  Asn Leu Thr Ile Gln  Arg Met Glu
    1220                 1225                 1230

Phe Asp  Tyr Ser Thr Asn Ala  Trp Gly Leu Ala Phe  Ser Ser Phe
    1235                 1240                 1245

Arg Glu  Leu Ser Ser Glu Lys  Leu Val Ser Val Asp  Gly Tyr Arg
    1250                 1255                 1260

Gly Ser  Tyr Ile Gly Ala Ser  Ala Gly Ile Asp Thr  Gln Leu Met
    1265                 1270                 1275

Glu Asp  Phe Val Leu Gly Ile  Ser Thr Ala Ser Phe  Phe Gly Lys
    1280                 1285                 1290

Met His  Ser Gln Asn Phe Asp  Ala Glu Ile Ser Arg  His Gly Phe
    1295                 1300                 1305

Val Gly  Ser Val Tyr Thr Gly  Phe Leu Ala Gly Ala  Trp Phe Phe
    1310                 1315                 1320

Lys Gly  Gln Tyr Ser Leu Gly  Glu Thr His Asn Asp  Met Thr Thr
    1325                 1330                 1335

Arg Tyr  Gly Val Leu Gly Glu  Ser Asn Ala Thr Trp  Lys Ser Arg
    1340                 1345                 1350

Gly Val  Leu Ala Asp Ala Leu  Val Glu Tyr Arg Ser  Leu Val Gly
    1355                 1360                 1365

Pro Ala  Arg Pro Lys Phe Tyr  Ala Leu His Phe Asn  Pro Tyr Val
    1370                 1375                 1380

Glu Val  Ser Tyr Ala Ser Ala  Lys Phe Pro Ser Phe  Val Glu Gln
    1385                 1390                 1395

Gly Gly  Glu Ala Arg Ala Phe  Glu Glu Thr Ser Leu  Thr Asn Ile
    1400                 1405                 1410

Thr Val  Pro Phe Gly Met Lys  Phe Glu Leu Ser Phe  Thr Lys Gly
    1415                 1420                 1425

Gln Phe  Ser Glu Thr Asn Ser  Leu Gly Ile Gly Cys  Ala Trp Glu
    1430                 1435                 1440

Met Tyr  Arg Lys Val Glu Gly  Arg Ser Val Glu Leu  Leu Glu Ala
    1445                 1450                 1455

Gly Phe  Asp Trp Glu Gly Ser  Pro Ile Asp Leu Pro  Lys Gln Glu
```

1460 1465 1470

Leu Arg Val Ala Leu Glu Asn Asn Thr Glu Trp Ser Ser Tyr Phe
1475 1480 1485

Ser Thr Ala Leu Gly Val Thr Ala Phe Cys Gly Gly Phe Ser Ser
1490 1495 1500

Met Asp Asn Lys Leu Gly Tyr Glu Ala Asn Ala Gly Met Arg Leu
1505 1510 1515

Ile Phe
1520

<210> SEQ ID NO 61
<211> LENGTH: 2931
<212> TYPE: DNA
<213> ORGANISM: Chlamydia muridarum
<400> SEQUENCE: 61
atgaaaaaac tgttcttttt tgtccttatt ggaagctcta tactgggatt tactcgagaa 60
gtccctcctt cgattctttt aaagcctata ctaaatccat accatatgac cgggttattt 120
tttcccaagg ttaatttgct tggagacaca cataatctca ctgattacca tttggataat 180
ctaaaatgca ttctggcttg cctacaaaga actccttatg aaggagctgc tttcacagta 240
accgattact taggtttttc agatacacaa aaggatggta ttttttgttt taaaaatctt 300
actccagaga gtggaggggt tattggttcc ccaactcaaa acactcctac tataaaaatt 360
cataatacaa tcggccccgt tcttttcgaa aataatacct gtcatagact gtggacacag 420
accgatcccg aaaatgaagg aaacaaagca cgcgaaggcg gggcaattca tgctggggac 480
gtttacataa gcaataacca gaaccttgtc ggattcataa agaactttgc ttatgttcaa 540
ggtggagcta ttagtgctaa tacttttgcc tataaagaaa ataaatcgag ctttctttgc 600
ctaaataact cttgtataca aactaagacg ggagggaaag gtggtgctat ttacgttagt 660
acgagctgct ctttcgagaa caataacaag gatctgcttt tcatccaaaa ctccggctgt 720
gcaggaggag ctatcttctc tccaacctgt tctctaatag gaaaccaagg agatattgtt 780
ttttacagca accacggttt taaaaatgtt gataatgcaa ctaacgaatc tggggatgga 840
ggagctatta aagtaactac ccgcttggac atcaccaata atggtagtca aatctttttt 900
tctgataata tctcaagaaa ttttggagga gctattcatg ctccttgtct tcatcttgtt 960
ggtaatgggc caacctattt tacaaacaat atagctaatc acacaggtgg ggctatttat 1020
ataacaggaa cagaaacctc aaagatttct gcagatcacc atgctattat ttttgataat 1080
aacatttctg caaacgccac caatgcggac ggatctagca gcaacactaa tcctcctcac 1140
agaaatgcga tcactatgga caattccgct ggaggaatag aacttggtgc agggaagagc 1200
cagaatctta ttttctatga tcctattcaa gtgacgaatg ctggagttac cgtagacttc 1260
aataaggatg cctcccaaac cggatgtgta gttttctctg gagcgactgt cctttctgca 1320
gatatttctc aggctaattt gcaaactaaa acacctgcaa cgcttactct cagtcacggt 1380
cttctgtgta tcgaagatcg tgctcagctc acagtgaaca attttacaca aacaggaggg 1440
attgtagcct taggaaatgg agcagtttta agcagctacc aacacagcac tacagacgcc 1500
actcaaactc cccctacaac caccactaca gatgcttccg taactcttaa tcacattgga 1560
ttaaatctcc cctctattct taaggatgga gcagagatgc ctctattatg ggtagaacct 1620
ataagcacaa ctcaaggtaa cactacaaca tatacgtcag ataccgcggc ttccttctca 1680
ttaaatggag ccacactctc tctcattgat gaagatggaa attctcccta tgaaaacacg 1740
gacctctctc gtgcattgta cgctcaacct atgctagcaa tttctgaggc cagtgataac 1800
caattgcaat ccgaaagcat ggacttttct aaagttaatg ttcctcacta tggatggcaa 1860
ggactttgga cctgggggtg ggcaaaaact gaaaatccaa caacaactcc tccagcaaca 1920
attactgatc cgaaaaaagc taatcagttt catagaactt tattattaac gtggctccct 1980
gctggttata tccccagccc taaacataaa agccctttaa tagctaatac cttgtggggg 2040
aatatacttt ttgcaacgga aaacttaaaa aatagctcag ggcaagaact tcttgatcgt 2100
cctttctggg gaattacagg agggggcttg ggatgatgg tctatcaaga acctagaaaa 2160
gaccatcctg gattccacat gcatacctcc ggatattcag caggaatgat tacaggaaac 2220
acacatacct tctcattacg attcagccag tcctatacaa aactcaatga acgttatgcc 2280
aagaactatg tgtcttctaa aaattactct tgccaagggg aaatgctttt gtccttacaa 2340
gaaggactca tgctgactaa actaattggt ctctatagtt atgggaatca caacagccac 2400
catttctata cccaaggaga agacctatcg tctcaagggg agttccatag tcagactttt 2460
ggaggggctg tctttttga tctacctctg aaacctttg gaagaacaca catacttaca 2520
gctcctttct taggtgccat tggtatgtat tctaagctgt ctagctttac agaagtagga 2580
gcctatccaa gaacctttat tacagaaacg cctttaatca atgtcctgat tcctatcgga 2640
gtaaaaggta gcttcatgaa tgccacccat agacctcagg cctggactgt agagcttgct 2700
taccaacctg ttctttacag acaagaacct agtatctcta cccaattact cgctggtaaa 2760
ggtatgtggt ttgggcatgg aagtcctgca tctcgccacg ctctagctta taaaatttca 2820
cagaaaacac agcttttgcg atttgcaaca cttcaactcc agtatcacgg atactattcg 2880
tcttccactt tctgtaatta tctgaatgga gaggtatctt tacgtttcta a 2931

<210> SEQ ID NO 62
<211> LENGTH: 976
<212> TYPE: PRT
<213> ORGANISM: Chlamydia muridarum

<400> SEQUENCE: 62

Met Lys Lys Leu Phe Phe Phe Val Leu Ile Gly Ser Ser Ile Leu Gly
1 5 10 15

Phe Thr Arg Glu Val Pro Pro Ser Ile Leu Leu Lys Pro Ile Leu Asn
20 25 30

Pro Tyr His Met Thr Gly Leu Phe Phe Pro Lys Val Asn Leu Leu Gly
35 40 45

Asp Thr His Asn Leu Thr Asp Tyr His Leu Asp Asn Leu Lys Cys Ile
50 55 60

Leu Ala Cys Leu Gln Arg Thr Pro Tyr Glu Gly Ala Ala Phe Thr Val
65 70 75 80

Thr Asp Tyr Leu Gly Phe Ser Asp Thr Gln Lys Asp Gly Ile Phe Cys
85 90 95

Phe Lys Asn Leu Thr Pro Glu Ser Gly Gly Val Ile Gly Ser Pro Thr
100 105 110

Gln Asn Thr Pro Thr Ile Lys Ile His Asn Thr Ile Gly Pro Val Leu
115 120 125

Phe Glu Asn Asn Thr Cys His Arg Leu Trp Thr Gln Thr Asp Pro Glu
130 135 140

Asn Glu Gly Asn Lys Ala Arg Glu Gly Gly Ala Ile His Ala Gly Asp
145 150 155 160

```
Val Tyr Ile Ser Asn Asn Gln Asn Leu Val Gly Phe Ile Lys Asn Phe
                165                 170                 175

Ala Tyr Val Gln Gly Gly Ala Ile Ser Ala Asn Thr Phe Ala Tyr Lys
            180                 185                 190

Glu Asn Lys Ser Ser Phe Leu Cys Leu Asn Asn Ser Cys Ile Gln Thr
        195                 200                 205

Lys Thr Gly Gly Lys Gly Gly Ala Ile Tyr Val Ser Thr Ser Cys Ser
    210                 215                 220

Phe Glu Asn Asn Asn Lys Asp Leu Leu Phe Ile Gln Asn Ser Gly Cys
225                 230                 235                 240

Ala Gly Gly Ala Ile Phe Ser Pro Thr Cys Ser Leu Ile Gly Asn Gln
                245                 250                 255

Gly Asp Ile Val Phe Tyr Ser Asn His Gly Phe Lys Asn Val Asp Asn
            260                 265                 270

Ala Thr Asn Glu Ser Gly Asp Gly Gly Ala Ile Lys Val Thr Thr Arg
        275                 280                 285

Leu Asp Ile Thr Asn Asn Gly Ser Gln Ile Phe Phe Ser Asp Asn Ile
    290                 295                 300

Ser Arg Asn Phe Gly Gly Ala Ile His Ala Pro Cys Leu His Leu Val
305                 310                 315                 320

Gly Asn Gly Pro Thr Tyr Phe Thr Asn Asn Ile Ala Asn His Thr Gly
                325                 330                 335

Gly Ala Ile Tyr Ile Thr Gly Thr Glu Thr Ser Lys Ile Ser Ala Asp
            340                 345                 350

His His Ala Ile Ile Phe Asp Asn Asn Ile Ser Ala Asn Ala Thr Asn
        355                 360                 365

Ala Asp Gly Ser Ser Ser Asn Thr Asn Pro Pro His Arg Asn Ala Ile
    370                 375                 380

Thr Met Asp Asn Ser Ala Gly Gly Ile Glu Leu Gly Ala Gly Lys Ser
385                 390                 395                 400

Gln Asn Leu Ile Phe Tyr Asp Pro Ile Gln Val Thr Asn Ala Gly Val
                405                 410                 415

Thr Val Asp Phe Asn Lys Asp Ala Ser Gln Thr Gly Cys Val Val Phe
            420                 425                 430

Ser Gly Ala Thr Val Leu Ser Ala Asp Ile Ser Gln Ala Asn Leu Gln
        435                 440                 445

Thr Lys Thr Pro Ala Thr Leu Thr Leu Ser His Gly Leu Leu Cys Ile
    450                 455                 460

Glu Asp Arg Ala Gln Leu Thr Val Asn Asn Phe Thr Gln Thr Gly Gly
465                 470                 475                 480

Ile Val Ala Leu Gly Asn Gly Ala Val Leu Ser Ser Tyr Gln His Ser
                485                 490                 495

Thr Thr Asp Ala Thr Gln Thr Pro Pro Thr Thr Thr Thr Thr Asp Ala
            500                 505                 510

Ser Val Thr Leu Asn His Ile Gly Leu Asn Leu Pro Ser Ile Leu Lys
        515                 520                 525

Asp Gly Ala Glu Met Pro Leu Leu Trp Val Glu Pro Ile Ser Thr Thr
    530                 535                 540

Gln Gly Asn Thr Thr Thr Tyr Thr Ser Asp Thr Ala Ala Ser Phe Ser
545                 550                 555                 560

Leu Asn Gly Ala Thr Leu Ser Leu Ile Asp Glu Asp Gly Asn Ser Pro
                565                 570                 575

Tyr Glu Asn Thr Asp Leu Ser Arg Ala Leu Tyr Ala Gln Pro Met Leu
```

```
            580                 585                 590

Ala Ile Ser Glu Ala Ser Asp Asn Gln Leu Gln Ser Glu Ser Met Asp
        595                 600                 605

Phe Ser Lys Val Asn Val Pro His Tyr Gly Trp Gln Gly Leu Trp Thr
    610                 615                 620

Trp Gly Trp Ala Lys Thr Glu Asn Pro Thr Thr Thr Pro Pro Ala Thr
625                 630                 635                 640

Ile Thr Asp Pro Lys Lys Ala Asn Gln Phe His Arg Thr Leu Leu Leu
                645                 650                 655

Thr Trp Leu Pro Ala Gly Tyr Ile Pro Ser Pro Lys His Lys Ser Pro
            660                 665                 670

Leu Ile Ala Asn Thr Leu Trp Gly Asn Ile Leu Phe Ala Thr Glu Asn
        675                 680                 685

Leu Lys Asn Ser Ser Gly Gln Glu Leu Leu Asp Arg Pro Phe Trp Gly
    690                 695                 700

Ile Thr Gly Gly Gly Leu Gly Met Met Val Tyr Gln Glu Pro Arg Lys
705                 710                 715                 720

Asp His Pro Gly Phe His Met His Thr Ser Gly Tyr Ser Ala Gly Met
                725                 730                 735

Ile Thr Gly Asn Thr His Thr Phe Ser Leu Arg Phe Ser Gln Ser Tyr
            740                 745                 750

Thr Lys Leu Asn Glu Arg Tyr Ala Lys Asn Tyr Val Ser Ser Lys Asn
        755                 760                 765

Tyr Ser Cys Gln Gly Glu Met Leu Leu Ser Leu Gln Glu Gly Leu Met
    770                 775                 780

Leu Thr Lys Leu Ile Gly Leu Tyr Ser Tyr Gly Asn His Asn Ser His
785                 790                 795                 800

His Phe Tyr Thr Gln Gly Glu Asp Leu Ser Ser Gln Gly Glu Phe His
                805                 810                 815

Ser Gln Thr Phe Gly Gly Ala Val Phe Phe Asp Leu Pro Leu Lys Pro
            820                 825                 830

Phe Gly Arg Thr His Ile Leu Thr Ala Pro Phe Leu Gly Ala Ile Gly
        835                 840                 845

Met Tyr Ser Lys Leu Ser Ser Phe Thr Glu Val Gly Ala Tyr Pro Arg
    850                 855                 860

Thr Phe Ile Thr Glu Thr Pro Leu Ile Asn Val Leu Ile Pro Ile Gly
865                 870                 875                 880

Val Lys Gly Ser Phe Met Asn Ala Thr His Arg Pro Gln Ala Trp Thr
                885                 890                 895

Val Glu Leu Ala Tyr Gln Pro Val Leu Tyr Arg Gln Glu Pro Ser Ile
            900                 905                 910

Ser Thr Gln Leu Leu Ala Gly Lys Gly Met Trp Phe Gly His Gly Ser
        915                 920                 925

Pro Ala Ser Arg His Ala Leu Ala Tyr Lys Ile Ser Gln Lys Thr Gln
    930                 935                 940

Leu Leu Arg Phe Ala Thr Leu Gln Leu Gln Tyr His Gly Tyr Tyr Ser
945                 950                 955                 960

Ser Ser Thr Phe Cys Asn Tyr Leu Asn Gly Glu Val Ser Leu Arg Phe
                965                 970                 975
```

<210> SEQ ID NO 63
<211> LENGTH: 1272
<212> TYPE: DNA
<213> ORGANISM: Chlamydia trachomatis

<400> SEQUENCE: 63

```
gcacctcaac ctcgcggaac gcttcctagc tcgaccacaa aaattggatc agaagtttgg      60
attgaacaaa aagtccgcca atatccagag cttttatggt tagtagagcc gtcctctacg     120
ggagcctctt taaaatctcc ttcaggagcc atcttttctc caacattatt ccaaaaaaag     180
gtccctgctt tcgatatcgc agtgcgcagt ttgattcact tacatttatt aatccagggt     240
tcccgccaag cctatgctca actgatccaa ctacagacca gcgaatcccc tctaacattt     300
aagcaattcc ttgcattgca taagcaatta actctatttt taaattcccc taaggaattt     360
tatgactctg ttaaagtgtt agagacagct atcgtcttac gtcacttagg ctgttcaact     420
aaggctgttg ctgcgtttaa accttatttc tcagaaatgc aaagagaggc tttttacact     480
aaggctctgc atgtactaca caccttccca gagctaagcc catcatttgc tcgcctctct     540
ccggagcaga aaactctctt cttctccttg agaaaattgg cgaattacga tgagttactc     600
tcgctgacga acaccccaag ttttcagctt ctgtctgctg ggcgctcgca acgagctctt     660
ttagctctgg acttgtacct ctatgctttg gattcctgtg gagaacaggg gatgtcctct     720
caattccaca caaacttcgc acctctacag tccatgttgc aacaatacgc tactgtagaa     780
gaggcctttt ctcgttattt tacttaccga gctaatcgat taggatttga tggctcttct     840
cgatccgaga tggctttagt aagaatggcc accttgatga acttgtctcc ttccgaagct     900
gcgattttaa ccacaagctt caaaaccctt cctacagaag aagcggatac tttgatcaat     960
agtttctata ccaataaggg cgattcgttg gctctttctc tgcgagggtt gcctacactt    1020
gtatccgaac tgacgcgaac tgcccatggc aataccaatg cagaagctcg atctcagcaa    1080
atttatgcaa ctaccctatc gctagtagta aagagtctga aagcgcacaa agaaatgcta    1140
aacaagcaaa ttctttctaa ggaaattgtt ttagatttct cagaaactgc agcttcttgc    1200
caaggattgg atatcttttc cgagaatgtc gctgttcaaa ttcacttaaa tggaaccgtt    1260
agtatccatt ta                                                        1272
```

<210> SEQ ID NO 64
<211> LENGTH: 424
<212> TYPE: PRT
<213> ORGANISM: Chlamydia trachomatis

<400> SEQUENCE: 64

```
Ala Pro Gln Pro Arg Gly Thr Leu Pro Ser Ser Thr Thr Lys Ile Gly
1               5                   10                  15

Ser Glu Val Trp Ile Glu Gln Lys Val Arg Gln Tyr Pro Glu Leu Leu
            20                  25                  30

Trp Leu Val Glu Pro Ser Ser Thr Gly Ala Ser Leu Lys Ser Pro Ser
        35                  40                  45

Gly Ala Ile Phe Ser Pro Thr Leu Phe Gln Lys Lys Val Pro Ala Phe
    50                  55                  60

Asp Ile Ala Val Arg Ser Leu Ile His Leu His Leu Leu Ile Gln Gly
65                  70                  75                  80

Ser Arg Gln Ala Tyr Ala Gln Leu Ile Gln Leu Gln Thr Ser Glu Ser
                85                  90                  95

Pro Leu Thr Phe Lys Gln Phe Leu Ala Leu His Lys Gln Leu Thr Leu
            100                 105                 110

Phe Leu Asn Ser Pro Lys Glu Phe Tyr Asp Ser Val Lys Val Leu Glu
        115                 120                 125
```

```
Thr Ala Ile Val Leu Arg His Leu Gly Cys Ser Thr Lys Ala Val Ala
    130                 135                 140

Ala Phe Lys Pro Tyr Phe Ser Glu Met Gln Arg Glu Ala Phe Tyr Thr
145                 150                 155                 160

Lys Ala Leu His Val Leu His Thr Phe Pro Glu Leu Ser Pro Ser Phe
                165                 170                 175

Ala Arg Leu Ser Pro Glu Gln Lys Thr Leu Phe Phe Ser Leu Arg Lys
            180                 185                 190

Leu Ala Asn Tyr Asp Glu Leu Leu Ser Leu Thr Asn Thr Pro Ser Phe
        195                 200                 205

Gln Leu Leu Ser Ala Gly Arg Ser Gln Arg Ala Leu Leu Ala Leu Asp
    210                 215                 220

Leu Tyr Leu Tyr Ala Leu Asp Ser Cys Gly Glu Gln Gly Met Ser Ser
225                 230                 235                 240

Gln Phe His Thr Asn Phe Ala Pro Leu Gln Ser Met Leu Gln Gln Tyr
                245                 250                 255

Ala Thr Val Glu Glu Ala Phe Ser Arg Tyr Phe Thr Tyr Arg Ala Asn
            260                 265                 270

Arg Leu Gly Phe Asp Gly Ser Ser Arg Ser Glu Met Ala Leu Val Arg
        275                 280                 285

Met Ala Thr Leu Met Asn Leu Ser Pro Ser Glu Ala Ala Ile Leu Thr
    290                 295                 300

Thr Ser Phe Lys Thr Leu Pro Thr Glu Glu Ala Asp Thr Leu Ile Asn
305                 310                 315                 320

Ser Phe Tyr Thr Asn Lys Gly Asp Ser Leu Ala Leu Ser Leu Arg Gly
                325                 330                 335

Leu Pro Thr Leu Val Ser Glu Leu Thr Arg Thr Ala His Gly Asn Thr
            340                 345                 350

Asn Ala Glu Ala Arg Ser Gln Gln Ile Tyr Ala Thr Thr Leu Ser Leu
        355                 360                 365

Val Val Lys Ser Leu Lys Ala His Lys Glu Met Leu Asn Lys Gln Ile
    370                 375                 380

Leu Ser Lys Glu Ile Val Leu Asp Phe Ser Glu Thr Ala Ala Ser Cys
385                 390                 395                 400

Gln Gly Leu Asp Ile Phe Ser Glu Asn Val Ala Val Gln Ile His Leu
                405                 410                 415

Asn Gly Thr Val Ser Ile His Leu
            420
```

```
<210> SEQ ID NO 65
<211> LENGTH: 2427
<212> TYPE: DNA
<213> ORGANISM: Chlamydia trachomatis

<400> SEQUENCE: 65

actaagcctt ctttcttata cgttattcaa cctttttccg tatttaatcc acgattagga     60

cgtttctcta cagactcaga tacttatatc gaagaagaaa accgcctagc atcgttcatt    120

gagagtttgc cactggagat cttcgatata ccttctttca tggaaaccgc gatttccaat    180

agcccctata ttttatcttg ggagacaact aaagacggcg ctctgttcac tattcttgaa    240

cccaaactct cagcttgcgc agccacttgc ctggtagccc cttctataca aatgaaatcc    300

gatgcggagc tcctagaaga aattaagcaa gcgttattac gcagctctca tgacggtgtg    360

aaatatcgca tcaccagaga atccttctct ccagaaaaga aaactcctaa ggttgctcta    420
```

-continued

```
gtcgatgacg atattgaatt gattcgcaat gtcgactttt tgggtagagc tgttgacatt    480
gtcaaattag accctattaa tattctgaat accgtaagcg aagagaatat tctagattac    540
tcttttacaa gagaaacggc tcagctgagc gcggatggtc gttttggtat tcctccaggg    600
actaagctat tccctaaacc ttcttttgat gtagaaatca gtacctccat tttcgaagaa    660
acaacttcat ttactcgaag tttttctgca tcggttactt ttagtgtacc agacctcgcg    720
gcgactatgc ctcttcaaag ccctcccatg gtagaaaatg gtcaaaaaga aatttgtgtc    780
attcaaaaac acttattccc aagctactct cctaaactag tcgatattgt taaacgatac    840
aaaagagagg ctaagatctt gattaacaag cttgcctttg gaatgttatg gcgacatcgg    900
gctaaaagcc aaatcctcac cgagggaagc gtacgtctag acttacaagg attcacagaa    960
tcgaagtaca attaccagat tcaagtagga tcccatacga ttgcagctgt attaatcgat   1020
atggatattt ccaagattca atccaaatca gaacaagctt atgcaattag gaaaatcaaa   1080
tcaggctttc aacgtagctt ggatgactat catatttatc aaattgaaag aaaacaaacc   1140
ttttcttttt ctccgaagca tcgcagcctc tcatccacat cccattccga agattctgat   1200
ttggatcttt ctgaagcagc cgccttttca ggaagtctta cctgcgagtt tgtaaaaaaa   1260
agcactcaac atgccaagaa taccgtcaca tgttccacag ccgctcattc cctatacaca   1320
ctcaaagaag atgacagctc gaacccctct gaaaaacgat tagatagttg tttccgcaat   1380
tggattgaaa acaaactaag cgccaattct ccagattcct ggtcagcgtt tattcaaaaa   1440
ttcggaacac actatattgc atcagcaact tttggaggga taggtttcca agtgctcaaa   1500
ctatcttttg aacaggtgga ggatctacat agcaaaaaga tctccttaga aaccgcagca   1560
gccaactctc tattaaaagg ttctgtatcc agcagcacag aatctggata ctccagctat   1620
agctccacgt cttcttctca tacggtattt ttaggaggaa cggtcttacc ttcggttcat   1680
gatgaacgtt tagactttaa agattggtcg gaaagtgtgc acctggaacc tgttcctatc   1740
caggtttctt tacaacctat aacgaattta ctagttcctc tccattttcc taatatcggt   1800
gctgcagagc tctctaataa acgagaatct cttcaacaag cgattcgagt ctatctcaaa   1860
gaacataaag tagatgagca aggagaacgt actacattta catcaggaat cgataatcct   1920
tcttcctggt ttaccttaga agctgcccac tctcctctta tagtcagtac tccttacatt   1980
gcttcgtggt ctacgcttcc ttatttgttc ccaacattaa gagaacgttc ttcggcaacc   2040
cctatcgttt tctatttttg tgtagataat aatgaacatg cttcgcaaaa aatattaaac   2100
caatcgtatt gcttcctcgg gtccttgcct attcgacaaa aaatttttgg tagcgaattt   2160
gctagtttcc cctatctatc tttctatgga aatgcaaaag aggcgtactt tgataacacg   2220
tactacccaa cgcgttgtgg gtggattgtt gaaaagttaa atactacaca agatcaattc   2280
ctccgggatg gagacgaggt gcgactaaaa catgtttcca gcggaaagta tctagcaaca   2340
actcctctta aggataccca tggtacactc acgcgtacaa cgaactgtga agatgctatc   2400
tttattatta aaaaatcttc aggttat                                       2427
```

<210> SEQ ID NO 66
<211> LENGTH: 809
<212> TYPE: PRT
<213> ORGANISM: Chlamydia trachomatis

<400> SEQUENCE: 66

```
Thr Lys Pro Ser Phe Leu Tyr Val Ile Gln Pro Phe Ser Val Phe Asn
1               5                   10                  15
```

-continued

```
Pro Arg Leu Gly Arg Phe Ser Thr Asp Ser Asp Thr Tyr Ile Glu Glu
            20                  25                  30

Glu Asn Arg Leu Ala Ser Phe Ile Glu Ser Leu Pro Leu Glu Ile Phe
        35                  40                  45

Asp Ile Pro Ser Phe Met Glu Thr Ala Ile Ser Asn Ser Pro Tyr Ile
    50                  55                  60

Leu Ser Trp Glu Thr Thr Lys Asp Gly Ala Leu Phe Thr Ile Leu Glu
65                  70                  75                  80

Pro Lys Leu Ser Ala Cys Ala Ala Thr Cys Leu Val Ala Pro Ser Ile
                85                  90                  95

Gln Met Lys Ser Asp Ala Glu Leu Leu Glu Glu Ile Lys Gln Ala Leu
            100                 105                 110

Leu Arg Ser Ser His Asp Gly Val Lys Tyr Arg Ile Thr Arg Glu Ser
        115                 120                 125

Phe Ser Pro Glu Lys Lys Thr Pro Lys Val Ala Leu Val Asp Asp Asp
    130                 135                 140

Ile Glu Leu Ile Arg Asn Val Asp Phe Leu Gly Arg Ala Val Asp Ile
145                 150                 155                 160

Val Lys Leu Asp Pro Ile Asn Ile Leu Asn Thr Val Ser Glu Glu Asn
                165                 170                 175

Ile Leu Asp Tyr Ser Phe Thr Arg Glu Thr Ala Gln Leu Ser Ala Asp
            180                 185                 190

Gly Arg Phe Gly Ile Pro Pro Gly Thr Lys Leu Phe Pro Lys Pro Ser
        195                 200                 205

Phe Asp Val Glu Ile Ser Thr Ser Ile Phe Glu Glu Thr Thr Ser Phe
    210                 215                 220

Thr Arg Ser Phe Ser Ala Ser Val Thr Phe Ser Val Pro Asp Leu Ala
225                 230                 235                 240

Ala Thr Met Pro Leu Gln Ser Pro Pro Met Val Glu Asn Gly Gln Lys
                245                 250                 255

Glu Ile Cys Val Ile Gln Lys His Leu Phe Pro Ser Tyr Ser Pro Lys
            260                 265                 270

Leu Val Asp Ile Val Lys Arg Tyr Lys Arg Glu Ala Lys Ile Leu Ile
        275                 280                 285

Asn Lys Leu Ala Phe Gly Met Leu Trp Arg His Arg Ala Lys Ser Gln
    290                 295                 300

Ile Leu Thr Glu Gly Ser Val Arg Leu Asp Leu Gln Gly Phe Thr Glu
305                 310                 315                 320

Ser Lys Tyr Asn Tyr Gln Ile Gln Val Gly Ser His Thr Ile Ala Ala
                325                 330                 335

Val Leu Ile Asp Met Asp Ile Ser Lys Ile Gln Ser Lys Ser Glu Gln
            340                 345                 350

Ala Tyr Ala Ile Arg Lys Ile Lys Ser Gly Phe Gln Arg Ser Leu Asp
        355                 360                 365

Asp Tyr His Ile Tyr Gln Ile Glu Arg Lys Gln Thr Phe Ser Phe Ser
    370                 375                 380

Pro Lys His Arg Ser Leu Ser Ser Thr Ser His Ser Glu Asp Ser Asp
385                 390                 395                 400

Leu Asp Leu Ser Glu Ala Ala Ala Phe Ser Gly Ser Leu Thr Cys Glu
                405                 410                 415

Phe Val Lys Lys Ser Thr Gln His Ala Lys Asn Thr Val Thr Cys Ser
            420                 425                 430

Thr Ala Ala His Ser Leu Tyr Thr Leu Lys Glu Asp Asp Ser Ser Asn
```

-continued

```
        435                 440                 445

Pro Ser Glu Lys Arg Leu Asp Ser Cys Phe Arg Asn Trp Ile Glu Asn
    450                 455                 460

Lys Leu Ser Ala Asn Ser Pro Asp Ser Trp Ser Ala Phe Ile Gln Lys
465                 470                 475                 480

Phe Gly Thr His Tyr Ile Ala Ser Ala Thr Phe Gly Gly Ile Gly Phe
                485                 490                 495

Gln Val Leu Lys Leu Ser Phe Glu Gln Val Glu Asp Leu His Ser Lys
            500                 505                 510

Lys Ile Ser Leu Glu Thr Ala Ala Ala Asn Ser Leu Leu Lys Gly Ser
        515                 520                 525

Val Ser Ser Ser Thr Glu Ser Gly Tyr Ser Ser Tyr Ser Ser Thr Ser
    530                 535                 540

Ser Ser His Thr Val Phe Leu Gly Gly Thr Val Leu Pro Ser Val His
545                 550                 555                 560

Asp Glu Arg Leu Asp Phe Lys Asp Trp Ser Glu Ser Val His Leu Glu
                565                 570                 575

Pro Val Pro Ile Gln Val Ser Leu Gln Pro Ile Thr Asn Leu Leu Val
            580                 585                 590

Pro Leu His Phe Pro Asn Ile Gly Ala Ala Glu Leu Ser Asn Lys Arg
        595                 600                 605

Glu Ser Leu Gln Gln Ala Ile Arg Val Tyr Leu Lys Glu His Lys Val
    610                 615                 620

Asp Glu Gln Gly Glu Arg Thr Thr Phe Thr Ser Gly Ile Asp Asn Pro
625                 630                 635                 640

Ser Ser Trp Phe Thr Leu Glu Ala Ala His Ser Pro Leu Ile Val Ser
                645                 650                 655

Thr Pro Tyr Ile Ala Ser Trp Ser Thr Leu Pro Tyr Leu Phe Pro Thr
            660                 665                 670

Leu Arg Glu Arg Ser Ser Ala Thr Pro Ile Val Phe Tyr Phe Cys Val
        675                 680                 685

Asp Asn Asn Glu His Ala Ser Gln Lys Ile Leu Asn Gln Ser Tyr Cys
    690                 695                 700

Phe Leu Gly Ser Leu Pro Ile Arg Gln Lys Ile Phe Gly Ser Glu Phe
705                 710                 715                 720

Ala Ser Phe Pro Tyr Leu Ser Phe Tyr Gly Asn Ala Lys Glu Ala Tyr
                725                 730                 735

Phe Asp Asn Thr Tyr Tyr Pro Thr Arg Cys Gly Trp Ile Val Glu Lys
            740                 745                 750

Leu Asn Thr Thr Gln Asp Gln Phe Leu Arg Asp Gly Asp Glu Val Arg
        755                 760                 765

Leu Lys His Val Ser Ser Gly Lys Tyr Leu Ala Thr Thr Pro Leu Lys
    770                 775                 780

Asp Thr His Gly Thr Leu Thr Arg Thr Thr Asn Cys Glu Asp Ala Ile
785                 790                 795                 800

Phe Ile Ile Lys Lys Ser Ser Gly Tyr
                805
```

<210> SEQ ID NO 67
<211> LENGTH: 537
<212> TYPE: DNA
<213> ORGANISM: Chlamydia trachomatis

<400> SEQUENCE: 67

```
ggtaaagcac cgtctttgca ggctattcta gccgaagtcg aagacacctc ctctcgtcta     60

cacgctcatc acaatgagct tgctatgatc tctgaacgcc tcgatgagca agacacgaaa    120

ctacagcaac tttcgtcaac acaagatcat aacctacctc gacaagttca gcgactagaa    180

acggaccaaa aagctttggc aaaaacactg gcgattcttt cgcaatccgt ccaagatatt    240

cggtcttctg tacaaaataa attacaagaa atccaacaag aacaaaaaaa attagcacaa    300

aatttgcgag cgcttcgtaa ctctttacaa gctctcgttg atggctcttc tccagaaaat    360

tatattgatt tcctaactgg tgaaaccccg gaacatattc atattgttaa acaaggagag    420

accctgagca agatcgcgag taaatataac atccccgtcg tagaattaaa aaacttaat     480

aaactaaatt cggatactat ttttacagat caaagaattc gccttccgaa aaagaaa       537
```

<210> SEQ ID NO 68
<211> LENGTH: 179
<212> TYPE: PRT
<213> ORGANISM: Chlamydia trachomatis

<400> SEQUENCE: 68

```
Gly Lys Ala Pro Ser Leu Gln Ala Ile Leu Ala Glu Val Glu Asp Thr
1               5                   10                  15

Ser Ser Arg Leu His Ala His His Asn Glu Leu Ala Met Ile Ser Glu
            20                  25                  30

Arg Leu Asp Glu Gln Asp Thr Lys Leu Gln Gln Leu Ser Ser Thr Gln
        35                  40                  45

Asp His Asn Leu Pro Arg Gln Val Gln Arg Leu Glu Thr Asp Gln Lys
    50                  55                  60

Ala Leu Ala Lys Thr Leu Ala Ile Leu Ser Gln Ser Val Gln Asp Ile
65                  70                  75                  80

Arg Ser Ser Val Gln Asn Lys Leu Gln Glu Ile Gln Gln Glu Gln Lys
                85                  90                  95

Lys Leu Ala Gln Asn Leu Arg Ala Leu Arg Asn Ser Leu Gln Ala Leu
            100                 105                 110

Val Asp Gly Ser Ser Pro Glu Asn Tyr Ile Asp Phe Leu Thr Gly Glu
        115                 120                 125

Thr Pro Glu His Ile His Ile Val Lys Gln Gly Glu Thr Leu Ser Lys
    130                 135                 140

Ile Ala Ser Lys Tyr Asn Ile Pro Val Val Glu Leu Lys Lys Leu Asn
145                 150                 155                 160

Lys Leu Asn Ser Asp Thr Ile Phe Thr Asp Gln Arg Ile Arg Leu Pro
                165                 170                 175

Lys Lys Lys
```

<210> SEQ ID NO 69
<211> LENGTH: 780
<212> TYPE: DNA
<213> ORGANISM: Chlamydia trachomatis

<400> SEQUENCE: 69

```
gcacaagtaa tttcttccga taacacattc caagtctatg aaaagggaga ttggcaccca     60

gccctatata atactaaaaa gcagttgcta gagatctcct ctactcctcc taaagtaacc    120

gtgacaactt taagctcata ttttcaaaac tttgttagag tcttgcttac agatacacaa    180

ggaaatcttt cttcattcga agaccataat ctcaatctag aagaattttt atctcaacca    240

actcctgtaa tacatggtct tgccctttat gtggtctacg ctatcctaca caacgatgca    300
```

-continued gcttcctcta aattatctgc ttcccaagta gcgaaaaatc caacagctat agaatctata 360
gttcttccta tagaaggttt tggtttgtgg ggacctatct atggattcct tgctctagaa 420
aaagacggga atactgttct tggtacttct tggtatcaac atggcgagac tcctggatta 480
ggagcaaata tcgctaaccc tcaatggcaa aaaaatttca gaggcaaaaa agtatttcta 540
gtctcagctt ctggagaaac agattttgct aagacaaccc taggactgga agttataaaa 600
ggatctgtat ctgcagcatt aggagactca cctaaagctg cttcttccat cgacggaatt 660
tcaggagcta ctttgacttg taatggtgtt accgaatcct tctctcattc tctagctccc 720
taccgcgctt tgttgacttt cttcgccaac tctaaaccta gtggagagtc tcatgaccac 780

<210> SEQ ID NO 70
<211> LENGTH: 260
<212> TYPE: PRT
<213> ORGANISM: Chlamydia trachomatis

<400> SEQUENCE: 70

```
Ala Gln Val Ile Ser Ser Asp Asn Thr Phe Gln Val Tyr Glu Lys Gly
1               5                   10                  15

Asp Trp His Pro Ala Leu Tyr Asn Thr Lys Lys Gln Leu Leu Glu Ile
            20                  25                  30

Ser Ser Thr Pro Pro Lys Val Thr Val Thr Thr Leu Ser Ser Tyr Phe
        35                  40                  45

Gln Asn Phe Val Arg Val Leu Leu Thr Asp Thr Gln Gly Asn Leu Ser
    50                  55                  60

Ser Phe Glu Asp His Asn Leu Asn Leu Glu Glu Phe Leu Ser Gln Pro
65                  70                  75                  80

Thr Pro Val Ile His Gly Leu Ala Leu Tyr Val Val Tyr Ala Ile Leu
                85                  90                  95

His Asn Asp Ala Ala Ser Ser Lys Leu Ser Ala Ser Gln Val Ala Lys
            100                 105                 110

Asn Pro Thr Ala Ile Glu Ser Ile Val Leu Pro Ile Glu Gly Phe Gly
        115                 120                 125

Leu Trp Gly Pro Ile Tyr Gly Phe Leu Ala Leu Glu Lys Asp Gly Asn
    130                 135                 140

Thr Val Leu Gly Thr Ser Trp Tyr Gln His Gly Glu Thr Pro Gly Leu
145                 150                 155                 160

Gly Ala Asn Ile Ala Asn Pro Gln Trp Gln Lys Asn Phe Arg Gly Lys
                165                 170                 175

Lys Val Phe Leu Val Ser Ala Ser Gly Glu Thr Asp Phe Ala Lys Thr
            180                 185                 190

Thr Leu Gly Leu Glu Val Ile Lys Gly Ser Val Ser Ala Ala Leu Gly
        195                 200                 205

Asp Ser Pro Lys Ala Ala Ser Ser Ile Asp Gly Ile Ser Gly Ala Thr
    210                 215                 220

Leu Thr Cys Asn Gly Val Thr Glu Ser Phe Ser His Ser Leu Ala Pro
225                 230                 235                 240

Tyr Arg Ala Leu Leu Thr Phe Phe Ala Asn Ser Lys Pro Ser Gly Glu
                245                 250                 255

Ser His Asp His
            260
```

<210> SEQ ID NO 71
<211> LENGTH: 1572
<212> TYPE: DNA

<213> ORGANISM: Chlamydia trachomatis

<400> SEQUENCE: 71

```
ggggtgttag agacctctat ggcagagtct ctctctacaa acgttattag cttagctgac      60
accaaagcga aagacaacac ttctcataaa agcaaaaaag caagaaaaaa ccacagcaaa     120
gagactcccg tagaccgtaa agaggttgct ccggttcatg agtctaaagc tacaggacct     180
aaacaggatt cttgctttgg cagaatgtat acagtcaaag ttaatgatga tcgcaatgtt     240
gaaatcacac aagctgttcc tgaatatgct acggtaggat ctccctatcc tattgaaatt     300
actgctacag gtaaaaggga ttgtgttgat gttatcatta ctcagcaatt accatgtgaa     360
gcagagttcg tacgcagtga tccagcgaca actcctactg ctgatggtaa gctagtttgg     420
aaaattgacc gcttaggaca aggcgaaaag agtaaaatta ctgtatgggt aaaacctctt     480
aaagaaggtt gctgctttac agctgcaaca gtatgcgctt gtccagagat ccgttcggtt     540
acaaaatgtg gacaacctgc tatctgtgtt aaacaagaag gcccagagaa tgcttgtttg     600
cgttgcccag tagtttacaa aattaatata gtgaaccaag gaacagcaac agctcgtaac     660
gttgttgttg aaaatcctgt tccagatggt tacgctcatt cttctggaca gcgtgtactg     720
acgtttactc ttggagatat gcaacctgga gagcacagaa caattactgt agagttttgt     780
ccgcttaaac gtggtcgtgc taccaatata gcaacggttt cttactgtgg aggacataaa     840
aatacagcaa gcgtaacaac tgtgatcaac gagccttgcg tacaagtaag tattgcagga     900
gcagattggt cttatgtttg taagcctgta gaatatgtga tctccgtttc caatcctgga     960
gatcttgtgt tgcgagatgt cgtcgttgaa gacactcttt ctcccggagt cacagttctt    1020
gaagctgcag gagctcaaat ttcttgtaat aaagtagttt ggactgtgaa agaactgaat    1080
cctggagagt ctctacagta taaagttcta gtaagagcac aaactcctgg acaattcaca    1140
aataatgttg ttgtgaagag ctgctctgac tgtggtactt gtacttcttg cgcagaagcg    1200
acaacttact ggaaaggagt tgctgctact catatgtgcg tagtagatac ttgtgaccct    1260
gtttgtgtag gagaaaatac tgtttaccgt atttgtgtca ccaacagagg ttctgcagaa    1320
gatacaaatg tttctttaat gcttaaattc tctaaagaac tgcaacctgt atccttctct    1380
ggaccaacta aaggaacgat tacaggcaat acagtagtat tcgattcgtt acctagatta    1440
ggttctaaag aaactgtaga gttttctgta acattgaaag cagtatcagc tggagatgct    1500
cgtggggaag cgattctttc ttccgataca ttgactgttc cagtttctga tacagagaat    1560
acacacatct at                                                        1572
```

<210> SEQ ID NO 72
<211> LENGTH: 524
<212> TYPE: PRT
<213> ORGANISM: Chlamydia trachomatis

<400> SEQUENCE: 72

```
Gly Val Leu Glu Thr Ser Met Ala Glu Ser Leu Ser Thr Asn Val Ile
1               5                   10                  15

Ser Leu Ala Asp Thr Lys Ala Lys Asp Asn Thr Ser His Lys Ser Lys
            20                  25                  30

Lys Ala Arg Lys Asn His Ser Lys Glu Thr Pro Val Asp Arg Lys Glu
        35                  40                  45

Val Ala Pro Val His Glu Ser Lys Ala Thr Gly Pro Lys Gln Asp Ser
    50                  55                  60

Cys Phe Gly Arg Met Tyr Thr Val Lys Val Asn Asp Asp Arg Asn Val
```

```
65                  70                  75                  80

Glu Ile Thr Gln Ala Val Pro Glu Tyr Ala Thr Val Gly Ser Pro Tyr
                85                  90                  95

Pro Ile Glu Ile Thr Ala Thr Gly Lys Arg Asp Cys Val Asp Val Ile
            100                 105                 110

Ile Thr Gln Gln Leu Pro Cys Glu Ala Glu Phe Val Arg Ser Asp Pro
        115                 120                 125

Ala Thr Thr Pro Thr Ala Asp Gly Lys Leu Val Trp Lys Ile Asp Arg
    130                 135                 140

Leu Gly Gln Gly Glu Lys Ser Lys Ile Thr Val Trp Val Lys Pro Leu
145                 150                 155                 160

Lys Glu Gly Cys Cys Phe Thr Ala Ala Thr Val Cys Ala Cys Pro Glu
                165                 170                 175

Ile Arg Ser Val Thr Lys Cys Gly Gln Pro Ala Ile Cys Val Lys Gln
            180                 185                 190

Glu Gly Pro Glu Asn Ala Cys Leu Arg Cys Pro Val Val Tyr Lys Ile
        195                 200                 205

Asn Ile Val Asn Gln Gly Thr Ala Thr Ala Arg Asn Val Val Val Glu
    210                 215                 220

Asn Pro Val Pro Asp Gly Tyr Ala His Ser Ser Gly Gln Arg Val Leu
225                 230                 235                 240

Thr Phe Thr Leu Gly Asp Met Gln Pro Gly Glu His Arg Thr Ile Thr
                245                 250                 255

Val Glu Phe Cys Pro Leu Lys Arg Gly Arg Ala Thr Asn Ile Ala Thr
            260                 265                 270

Val Ser Tyr Cys Gly Gly His Lys Asn Thr Ala Ser Val Thr Thr Val
        275                 280                 285

Ile Asn Glu Pro Cys Val Gln Val Ser Ile Ala Gly Ala Asp Trp Ser
    290                 295                 300

Tyr Val Cys Lys Pro Val Glu Tyr Val Ile Ser Val Ser Asn Pro Gly
305                 310                 315                 320

Asp Leu Val Leu Arg Asp Val Val Val Glu Asp Thr Leu Ser Pro Gly
                325                 330                 335

Val Thr Val Leu Glu Ala Ala Gly Ala Gln Ile Ser Cys Asn Lys Val
            340                 345                 350

Val Trp Thr Val Lys Glu Leu Asn Pro Gly Glu Ser Leu Gln Tyr Lys
        355                 360                 365

Val Leu Val Arg Ala Gln Thr Pro Gly Gln Phe Thr Asn Asn Val Val
    370                 375                 380

Val Lys Ser Cys Ser Asp Cys Gly Thr Cys Thr Ser Cys Ala Glu Ala
385                 390                 395                 400

Thr Thr Tyr Trp Lys Gly Val Ala Ala Thr His Met Cys Val Val Asp
                405                 410                 415

Thr Cys Asp Pro Val Cys Val Gly Glu Asn Thr Val Tyr Arg Ile Cys
            420                 425                 430

Val Thr Asn Arg Gly Ser Ala Glu Asp Thr Asn Val Ser Leu Met Leu
        435                 440                 445

Lys Phe Ser Lys Glu Leu Gln Pro Val Ser Phe Ser Gly Pro Thr Lys
    450                 455                 460

Gly Thr Ile Thr Gly Asn Thr Val Val Phe Asp Ser Leu Pro Arg Leu
465                 470                 475                 480

Gly Ser Lys Glu Thr Val Glu Phe Ser Val Thr Leu Lys Ala Val Ser
                485                 490                 495
```

```
Ala Gly Asp Ala Arg Gly Glu Ala Ile Leu Ser Ser Asp Thr Leu Thr
            500                 505                 510

Val Pro Val Ser Asp Thr Glu Asn Thr His Ile Tyr
        515                 520
```

<210> SEQ ID NO 73
<211> LENGTH: 1323
<212> TYPE: DNA
<213> ORGANISM: Chlamydia trachomatis

<400> SEQUENCE: 73

```
caggctgcac accatcacta tcaccgctac acagataaac tgcacagaca aaaccataaa      60

aaagatctca tctctcccaa acctaccgaa caagaggcgt gcaatacttc ttcccttagt     120

aaggaattaa tccctctatc agaacaaaga ggccttttat cccccatctg tgactttatt     180

tcggaacgcc cttgcttaca cggagtttct gttagaaatc tcaagcaagc gctaaaaaat     240

tctgcaggaa cccaaattgc actggattgg tctattctcc ctcaatggtt caatcctcgg     300

gtctctcatg cccctaagct ttctatccga gactttgggt atagcgcaca ccaaactgtt     360

accgaagcca ctcctccttg ctggcaaaac tgctttaatc catctgcggc cgttactatc     420

tatgattcct catatgggaa aggggtcttt caaatatcct atacccttgt ccgctattgg     480

agagagaatg ctgcgactgc tggcgatgct atgatgctcg cagggagtat caatgattat     540

ccctctcgtc agaacatttt ctctcagttt actttctccc aaaacttccc aaatgaacgg     600

gtgagtctga caattggtca gtactcactc tatgcaatag acggaacatt atacaataac     660

gatcaacaac ttggattcat tagttacgca ttatcacaaa atccaacagc aacttattcc     720

tctggaagtc ttggagctta cctacaagtc gctcctaccg caagcacaag tcttcaaata     780

ggatttcaag acgcttataa tatctccgga tcctctatca aatggagtaa ccttacaaaa     840

aatagataca attttcacgg ttttgcttcc tgggctcccc gctgttgctt aggatctggc     900

cagtactccg tgcttcttta tgtgactaga caagttccag aacagatgga acaaacaatg     960

ggatggtcag tcaatgcgag tcaacacata tcttctaaac tgtatgtgtt tggaagatac    1020

agcggtgtta caggacatgt gttcccgatt aaccgcacgt attcattcgg tatggcctct    1080

gcaaatttat ttaaccgtaa cccacaagat ttatttggaa ttgcttgcgc attcaataat    1140

gtacacctct ctgcttctcc aaatactaaa agaaaatacg aaactgtaat cgaagggttt    1200

gcaactatcg gttgcggccc ctatctttct ttcgctccag acttccaact ctacctctac    1260

ccagctcttc gtccaaacaa acaatctgcc cgtgtttata gcgtgcgagc taatttagct    1320

atc                                                                  1323
```

<210> SEQ ID NO 74
<211> LENGTH: 441
<212> TYPE: PRT
<213> ORGANISM: Chlamydia trachomatis

<400> SEQUENCE: 74

```
Gln Ala Ala His His His Tyr His Arg Tyr Thr Asp Lys Leu His Arg
1               5                   10                  15

Gln Asn His Lys Lys Asp Leu Ile Ser Pro Lys Pro Thr Glu Gln Glu
            20                  25                  30

Ala Cys Asn Thr Ser Ser Leu Ser Lys Glu Leu Ile Pro Leu Ser Glu
        35                  40                  45

Gln Arg Gly Leu Leu Ser Pro Ile Cys Asp Phe Ile Ser Glu Arg Pro
```

```
    50                  55                  60

Cys Leu His Gly Val Ser Val Arg Asn Leu Lys Gln Ala Leu Lys Asn
65                  70                  75                  80

Ser Ala Gly Thr Gln Ile Ala Leu Asp Trp Ser Ile Leu Pro Gln Trp
                85                  90                  95

Phe Asn Pro Arg Val Ser His Ala Pro Lys Leu Ser Ile Arg Asp Phe
            100                 105                 110

Gly Tyr Ser Ala His Gln Thr Val Thr Glu Ala Thr Pro Pro Cys Trp
        115                 120                 125

Gln Asn Cys Phe Asn Pro Ser Ala Ala Val Thr Ile Tyr Asp Ser Ser
    130                 135                 140

Tyr Gly Lys Gly Val Phe Gln Ile Ser Tyr Thr Leu Val Arg Tyr Trp
145                 150                 155                 160

Arg Glu Asn Ala Ala Thr Ala Gly Asp Ala Met Met Leu Ala Gly Ser
                165                 170                 175

Ile Asn Asp Tyr Pro Ser Arg Gln Asn Ile Phe Ser Gln Phe Thr Phe
            180                 185                 190

Ser Gln Asn Phe Pro Asn Glu Arg Val Ser Leu Thr Ile Gly Gln Tyr
        195                 200                 205

Ser Leu Tyr Ala Ile Asp Gly Thr Leu Tyr Asn Asn Asp Gln Gln Leu
    210                 215                 220

Gly Phe Ile Ser Tyr Ala Leu Ser Gln Asn Pro Thr Ala Thr Tyr Ser
225                 230                 235                 240

Ser Gly Ser Leu Gly Ala Tyr Leu Gln Val Ala Pro Thr Ala Ser Thr
                245                 250                 255

Ser Leu Gln Ile Gly Phe Gln Asp Ala Tyr Asn Ile Ser Gly Ser Ser
            260                 265                 270

Ile Lys Trp Ser Asn Leu Thr Lys Asn Arg Tyr Asn Phe His Gly Phe
        275                 280                 285

Ala Ser Trp Ala Pro Arg Cys Cys Leu Gly Ser Gly Gln Tyr Ser Val
    290                 295                 300

Leu Leu Tyr Val Thr Arg Gln Val Pro Glu Gln Met Glu Gln Thr Met
305                 310                 315                 320

Gly Trp Ser Val Asn Ala Ser Gln His Ile Ser Ser Lys Leu Tyr Val
                325                 330                 335

Phe Gly Arg Tyr Ser Gly Val Thr Gly His Val Phe Pro Ile Asn Arg
            340                 345                 350

Thr Tyr Ser Phe Gly Met Ala Ser Ala Asn Leu Phe Asn Arg Asn Pro
        355                 360                 365

Gln Asp Leu Phe Gly Ile Ala Cys Ala Phe Asn Asn Val His Leu Ser
    370                 375                 380

Ala Ser Pro Asn Thr Lys Arg Lys Tyr Glu Thr Val Ile Glu Gly Phe
385                 390                 395                 400

Ala Thr Ile Gly Cys Gly Pro Tyr Leu Ser Phe Ala Pro Asp Phe Gln
                405                 410                 415

Leu Tyr Leu Tyr Pro Ala Leu Arg Pro Asn Lys Gln Ser Ala Arg Val
            420                 425                 430

Tyr Ser Val Arg Ala Asn Leu Ala Ile
        435                 440


<210> SEQ ID NO 75
<211> LENGTH: 2871
<212> TYPE: DNA
<213> ORGANISM: Chlamydia trachomatis
```

<400> SEQUENCE: 75
acaaattcag cggctacatc ttctatccaa acgactggag agactgtagt aaactatacg 60
aattcagcct ccgcccccaa tgtaactgta tcgacctcct cttcttccac acaagccaca 120
gccacttcga ataaaacttc ccaagccgtt gctggaaaaa tcacttctcc agatacttca 180
gaaagctcag aaactagctc tacctcatca agcgatcata tccctagcga ttacgatgac 240
gttggtagca atagtggaga tattagcaac aactacgatg acgtaggtag taacaacgga 300
gatatcagta gcaattatga cgatgctgct gctgattacg agccgataag aactactgaa 360
aatatttatg agagtattgg tggctctaga acaagtggcc cagaaaatac aagtggtggt 420
gcagcagcag cactcaattc tctaagaggc tcctcctaca gcaattatga cgatgctgct 480
gctgattacg agccgataag aactactgaa aatatttatg agagtattgg tggctctaga 540
acaagtggcc cagaaaatac gagtggtggt gcagcagcag cactcaattc tctaagaggc 600
tcctcctaca gcaattatga cgatgctgct gctgattacg agccgataag aactactgaa 660
aatatttatg agagtattgg tggctctaga acaagtggcc cagaaaatac gagtgatggt 720
gcagcagcag cagcactcaa ttctctaaga ggctcctcct acacaacagg gcctcgtaac 780
gagggtgtat tcggccctgg accggaagga ctaccagaca tgtctcttcc ttcatacgat 840
cctacaaata aaacctcgtt attgactttc ctctccaacc ctcatgtaaa gtcgaaaatg 900
cttgaaaact cggggcattt cgtcttcatt gatacagata gaagtagttt cattcttgtt 960
cctaacggaa attgggacca agtctgttca attaaagttc aaaatggaaa gaccaaagaa 1020
gatctcgaca tcaaagactt ggaaaacatg tgtgcaaaat tctgtacagg gtttagcaaa 1080
ttctctggtg actgggacag tcttgtagaa cctatggtgt cagccaaagc tggagtggcc 1140
agcggaggca atcttcccaa tacagtgatt atcaataata aattcaaaac ttgcgttgct 1200
tatggtcctt ggaatagcca ggaagcaagt tctggttata caccttctgc ttggagacgt 1260
ggtcatcgag tagattttgg aggaattttt gagaaagcca acgactttaa taaaatcaac 1320
tggggaactc aagccgggcc tagtagcgaa gacgatggca tttccttctc caatgaaact 1380
cctggagctg gtcctgcagc tgctccatca ccaacgccat cctctattcc tatcatcaat 1440
gtcaatgtca atgttggcgg aactaatgtg aatattggag atacgaatgt caacacgact 1500
aacaccacac caacaactca atctacagac gcctctacag atacaagcga tatcgatgac 1560
ataaatacca acaaccaaac tgatgatatc aatacgacag acaaagactc tgacggagct 1620
ggtggagtca atggcgatat atccgaaaca gaatcctctt ctggagatga ttcaggaagt 1680
gtctcttcct cagaatcaga caagaatgcc tctgtcggaa atgacggacc tgctatgaaa 1740
gatatccttt ctgccgtgcg taaacaccta gacgtcgttt accctggcga aaatggcggt 1800
tctacagaag ggcctctccc agctaaccaa actctcggag acgtaatctc tgatgtagag 1860
aataaaggct ccgctcagga tacaaaattg tcaggaaata caggagctgg ggatgacgat 1920
ccaacaacca cagctgctgt aggtaatgga gcggaagaga tcactctttc cgacacagat 1980
tctggtatcg gagatgatgt atccgataca gcgtcttcat ctggggatga atccggagga 2040
gtctcctctc cctcttcaga atccaataaa aatactgccg ttggaaatga cggaccttct 2100
ggactagata tcctcgctgc cgtacgtaaa catttagata aggtttaccc tggcgacaat 2160
ggtggttcta cagaagggcc tctccaagct aaccaaactc ttggagatat cgtccaggat 2220
atggaaacaa cagggacatc ccaagaaacc gttgtatccc catggaaagg aagcacttct 2280

```
tcaacggaat cagcaggagg aagtggtagc gtacaaacac tactgccttc accacctcca   2340

accccgtcaa ctacaacatt aagaacgggc acaggagcta ccaccacatc cttgatgatg   2400

ggaggaccaa tcaaagctga cataataaca actggtggcg gaggacgaat tcctggagga   2460

ggaacgttag aaaagctgct ccctcgtata cgtgcgcact tagacatatc ctttgatgcg   2520

caaggcgatc tcgtaagtac tgaagagcct cagcttggct cgattgtaaa caaattccgc   2580

caagaaactg gttcaagagg aatcttagct ttcgttgaga gtgctccagg caagccggga   2640

tctgcacagg tcttaacggg tacaggggga gataaaggca acctattcca agcagctgcc   2700

gcagtcaccc aagccttagg aaatgttgca gggaaagtca accttgcgat acaaggccaa   2760

aaactatcat ccctagtcaa tgacgacggg aaggggtctg ttggaagaga tttattccaa   2820

gcagcagccc aaacaactca agtgctaagc gcactgattg ataccgtagg a            2871


<210> SEQ ID NO 76
<211> LENGTH: 957
<212> TYPE: PRT
<213> ORGANISM: Chlamydia trachomatis

<400> SEQUENCE: 76

Thr Asn Ser Ala Ala Thr Ser Ser Ile Gln Thr Thr Gly Glu Thr Val
1               5                   10                  15

Val Asn Tyr Thr Asn Ser Ala Ser Ala Pro Asn Val Thr Val Ser Thr
            20                  25                  30

Ser Ser Ser Ser Thr Gln Ala Thr Ala Thr Ser Asn Lys Thr Ser Gln
        35                  40                  45

Ala Val Ala Gly Lys Ile Thr Ser Pro Asp Thr Ser Glu Ser Ser Glu
    50                  55                  60

Thr Ser Ser Thr Ser Ser Ser Asp His Ile Pro Ser Asp Tyr Asp Asp
65                  70                  75                  80

Val Gly Ser Asn Ser Gly Asp Ile Ser Asn Asn Tyr Asp Asp Val Gly
                85                  90                  95

Ser Asn Asn Gly Asp Ile Ser Ser Asn Tyr Asp Asp Ala Ala Ala Asp
            100                 105                 110

Tyr Glu Pro Ile Arg Thr Thr Glu Asn Ile Tyr Glu Ser Ile Gly Gly
        115                 120                 125

Ser Arg Thr Ser Gly Pro Glu Asn Thr Ser Gly Gly Ala Ala Ala Ala
    130                 135                 140

Leu Asn Ser Leu Arg Gly Ser Ser Tyr Ser Asn Tyr Asp Asp Ala Ala
145                 150                 155                 160

Ala Asp Tyr Glu Pro Ile Arg Thr Thr Glu Asn Ile Tyr Glu Ser Ile
                165                 170                 175

Gly Gly Ser Arg Thr Ser Gly Pro Glu Asn Thr Ser Gly Gly Ala Ala
            180                 185                 190

Ala Ala Leu Asn Ser Leu Arg Gly Ser Ser Tyr Ser Asn Tyr Asp Asp
        195                 200                 205

Ala Ala Ala Asp Tyr Glu Pro Ile Arg Thr Thr Glu Asn Ile Tyr Glu
    210                 215                 220

Ser Ile Gly Gly Ser Arg Thr Ser Gly Pro Glu Asn Thr Ser Asp Gly
225                 230                 235                 240

Ala Ala Ala Ala Ala Leu Asn Ser Leu Arg Gly Ser Ser Tyr Thr Thr
                245                 250                 255

Gly Pro Arg Asn Glu Gly Val Phe Gly Pro Gly Pro Glu Gly Leu Pro
            260                 265                 270
```

```
Asp Met Ser Leu Pro Ser Tyr Asp Pro Thr Asn Lys Thr Ser Leu Leu
        275                 280                 285

Thr Phe Leu Ser Asn Pro His Val Lys Ser Lys Met Leu Glu Asn Ser
    290                 295                 300

Gly His Phe Val Phe Ile Asp Thr Asp Arg Ser Ser Phe Ile Leu Val
305                 310                 315                 320

Pro Asn Gly Asn Trp Asp Gln Val Cys Ser Ile Lys Val Gln Asn Gly
                325                 330                 335

Lys Thr Lys Glu Asp Leu Asp Ile Lys Asp Leu Glu Asn Met Cys Ala
            340                 345                 350

Lys Phe Cys Thr Gly Phe Ser Lys Phe Ser Gly Asp Trp Asp Ser Leu
        355                 360                 365

Val Glu Pro Met Val Ser Ala Lys Ala Gly Val Ala Ser Gly Gly Asn
    370                 375                 380

Leu Pro Asn Thr Val Ile Ile Asn Asn Lys Phe Lys Thr Cys Val Ala
385                 390                 395                 400

Tyr Gly Pro Trp Asn Ser Gln Glu Ala Ser Ser Gly Tyr Thr Pro Ser
                405                 410                 415

Ala Trp Arg Arg Gly His Arg Val Asp Phe Gly Gly Ile Phe Glu Lys
            420                 425                 430

Ala Asn Asp Phe Asn Lys Ile Asn Trp Gly Thr Gln Ala Gly Pro Ser
        435                 440                 445

Ser Glu Asp Asp Gly Ile Ser Phe Ser Asn Glu Thr Pro Gly Ala Gly
    450                 455                 460

Pro Ala Ala Ala Pro Ser Pro Thr Pro Ser Ser Ile Pro Ile Ile Asn
465                 470                 475                 480

Val Asn Val Asn Val Gly Gly Thr Asn Val Asn Ile Gly Asp Thr Asn
                485                 490                 495

Val Asn Thr Thr Asn Thr Thr Pro Thr Thr Gln Ser Thr Asp Ala Ser
            500                 505                 510

Thr Asp Thr Ser Asp Ile Asp Asp Ile Asn Thr Asn Asn Gln Thr Asp
        515                 520                 525

Asp Ile Asn Thr Thr Asp Lys Asp Ser Asp Gly Ala Gly Gly Val Asn
    530                 535                 540

Gly Asp Ile Ser Glu Thr Glu Ser Ser Ser Gly Asp Asp Ser Gly Ser
545                 550                 555                 560

Val Ser Ser Ser Glu Ser Asp Lys Asn Ala Ser Val Gly Asn Asp Gly
                565                 570                 575

Pro Ala Met Lys Asp Ile Leu Ser Ala Val Arg Lys His Leu Asp Val
            580                 585                 590

Val Tyr Pro Gly Glu Asn Gly Gly Ser Thr Glu Gly Pro Leu Pro Ala
        595                 600                 605

Asn Gln Thr Leu Gly Asp Val Ile Ser Asp Val Glu Asn Lys Gly Ser
    610                 615                 620

Ala Gln Asp Thr Lys Leu Ser Gly Asn Thr Gly Ala Gly Asp Asp Asp
625                 630                 635                 640

Pro Thr Thr Thr Ala Ala Val Gly Asn Gly Ala Glu Glu Ile Thr Leu
                645                 650                 655

Ser Asp Thr Asp Ser Gly Ile Gly Asp Asp Val Ser Asp Thr Ala Ser
            660                 665                 670

Ser Ser Gly Asp Glu Ser Gly Gly Val Ser Ser Pro Ser Ser Glu Ser
        675                 680                 685

Asn Lys Asn Thr Ala Val Gly Asn Asp Gly Pro Ser Gly Leu Asp Ile
```

```
    690                 695                 700

Leu Ala Ala Val Arg Lys His Leu Asp Lys Val Tyr Pro Gly Asp Asn
705                 710                 715                 720

Gly Gly Ser Thr Glu Gly Pro Leu Gln Ala Asn Gln Thr Leu Gly Asp
                725                 730                 735

Ile Val Gln Asp Met Glu Thr Thr Gly Thr Ser Gln Glu Thr Val Val
            740                 745                 750

Ser Pro Trp Lys Gly Ser Thr Ser Ser Thr Glu Ser Ala Gly Gly Ser
        755                 760                 765

Gly Ser Val Gln Thr Leu Leu Pro Ser Pro Pro Pro Thr Pro Ser Thr
    770                 775                 780

Thr Thr Leu Arg Thr Gly Thr Gly Ala Thr Thr Thr Ser Leu Met Met
785                 790                 795                 800

Gly Gly Pro Ile Lys Ala Asp Ile Ile Thr Thr Gly Gly Gly Gly Arg
                805                 810                 815

Ile Pro Gly Gly Gly Thr Leu Glu Lys Leu Leu Pro Arg Ile Arg Ala
            820                 825                 830

His Leu Asp Ile Ser Phe Asp Ala Gln Gly Asp Leu Val Ser Thr Glu
        835                 840                 845

Glu Pro Gln Leu Gly Ser Ile Val Asn Lys Phe Arg Gln Glu Thr Gly
    850                 855                 860

Ser Arg Gly Ile Leu Ala Phe Val Glu Ser Ala Pro Gly Lys Pro Gly
865                 870                 875                 880

Ser Ala Gln Val Leu Thr Gly Thr Gly Gly Asp Lys Gly Asn Leu Phe
                885                 890                 895

Gln Ala Ala Ala Ala Val Thr Gln Ala Leu Gly Asn Val Ala Gly Lys
            900                 905                 910

Val Asn Leu Ala Ile Gln Gly Gln Lys Leu Ser Ser Leu Val Asn Asp
        915                 920                 925

Asp Gly Lys Gly Ser Val Gly Arg Asp Leu Phe Gln Ala Ala Ala Gln
    930                 935                 940

Thr Thr Gln Val Leu Ser Ala Leu Ile Asp Thr Val Gly
945                 950                 955
```

<210> SEQ ID NO 77
<211> LENGTH: 702
<212> TYPE: DNA
<213> ORGANISM: Chlamydia trachomatis

<400> SEQUENCE: 77

```
tgtttaaaag aaggggaga ctccaatagt gaaaaattta ttgtagggac taatgcaacc      60

taccctcctt ttgagtttgt tgataagcga ggagaggttg taggcttcga tatagacttg    120

gctagagaga ttagtaacaa gctggggaaa acgctggacg ttcgggagtt ttcctttgat    180

gcactcattc taaacctaaa acagcatcgg attgatgcgg ttataacagg gatgtccatt    240

actccttcta gattgaagga aattcttatg attccctatt atggggagga aataaaacac    300

ttggttttag tgtttaaagg agagaataag catccattgc cactcactca atatcgttct    360

gtagctgttc aaacaggaac ctatcaagag gcctatttac agtctctttc tgaagttcat    420

attcgctctt ttgatagcac tctagaagta ctcatggaag tcatgcatgg taaatctccc    480

gtcgctgttt tagagccatc tatcgctcaa gttgtcttga aagatttccc ggctctttct    540

acagcaacca tagatctccc tgaagatcag tgggttttag gatacgggat tggcgttgct    600

tcagatcgcc cagctttagc cttgaaaatc gaggcagctg tgcaagagat ccgaaaagaa    660
```

ggagtgctag cagagttgga acagaagtgg ggtttgaaca ac 702

<210> SEQ ID NO 78
<211> LENGTH: 234
<212> TYPE: PRT
<213> ORGANISM: Chlamydia trachomatis

<400> SEQUENCE: 78

Cys Leu Lys Glu Gly Gly Asp Ser Asn Ser Glu Lys Phe Ile Val Gly
1 5 10 15

Thr Asn Ala Thr Tyr Pro Pro Phe Glu Phe Val Asp Lys Arg Gly Glu
20 25 30

Val Val Gly Phe Asp Ile Asp Leu Ala Arg Glu Ile Ser Asn Lys Leu
35 40 45

Gly Lys Thr Leu Asp Val Arg Glu Phe Ser Phe Asp Ala Leu Ile Leu
50 55 60

Asn Leu Lys Gln His Arg Ile Asp Ala Val Ile Thr Gly Met Ser Ile
65 70 75 80

Thr Pro Ser Arg Leu Lys Glu Ile Leu Met Ile Pro Tyr Tyr Gly Glu
85 90 95

Glu Ile Lys His Leu Val Leu Val Phe Lys Gly Glu Asn Lys His Pro
100 105 110

Leu Pro Leu Thr Gln Tyr Arg Ser Val Ala Val Gln Thr Gly Thr Tyr
115 120 125

Gln Glu Ala Tyr Leu Gln Ser Leu Ser Glu Val His Ile Arg Ser Phe
130 135 140

Asp Ser Thr Leu Glu Val Leu Met Glu Val Met His Gly Lys Ser Pro
145 150 155 160

Val Ala Val Leu Glu Pro Ser Ile Ala Gln Val Val Leu Lys Asp Phe
165 170 175

Pro Ala Leu Ser Thr Ala Thr Ile Asp Leu Pro Glu Asp Gln Trp Val
180 185 190

Leu Gly Tyr Gly Ile Gly Val Ala Ser Asp Arg Pro Ala Leu Ala Leu
195 200 205

Lys Ile Glu Ala Ala Val Gln Glu Ile Arg Lys Glu Gly Val Leu Ala
210 215 220

Glu Leu Glu Gln Lys Trp Gly Leu Asn Asn
225 230

<210> SEQ ID NO 79
<211> LENGTH: 498
<212> TYPE: DNA
<213> ORGANISM: Chlamydia trachomatis

<400> SEQUENCE: 79
tccaggcaga atgctgagga aaatctaaaa aattttgcta aagagcttaa actccccgac 60
gtggccttcg atcagaataa tacgtgcatt ttgtttgttg atggagagtt ttctcttcac 120
ctgacctacg aagaacactc tgatcgcctt tatgtttacg cacctcttct tgacggactg 180
ccagacaatc cgcaaagaag gttagctcta tatgagaagt tgttagaagg ctctatgctc 240
ggaggccaaa tggctggtgg aggggtagga gtcgctacta aggaacagtt gatcttaatg 300
cactgcgtgt tagacatgaa gtatgcagag accaacctac tcaaagcttt tgcacagctt 360
tttattgaaa ccgttgtgaa atggcgaact gtttgttctg atatcagcgc tggacgagaa 420
cccactgttg ataccatgcc acaaatgcct caagggggtg gcggaggaat tcaacctcct 480
ccagcaggaa tccgtgca 498

<210> SEQ ID NO 80
<211> LENGTH: 166
<212> TYPE: PRT
<213> ORGANISM: Chlamydia trachomatis

<400> SEQUENCE: 80

Ser Arg Gln Asn Ala Glu Glu Asn Leu Lys Asn Phe Ala Lys Glu Leu
1 5 10 15

Lys Leu Pro Asp Val Ala Phe Asp Gln Asn Asn Thr Cys Ile Leu Phe
20 25 30

Val Asp Gly Glu Phe Ser Leu His Leu Thr Tyr Glu Glu His Ser Asp
35 40 45

Arg Leu Tyr Val Tyr Ala Pro Leu Leu Asp Gly Leu Pro Asp Asn Pro
50 55 60

Gln Arg Arg Leu Ala Leu Tyr Glu Lys Leu Leu Glu Gly Ser Met Leu
65 70 75 80

Gly Gly Gln Met Ala Gly Gly Gly Val Gly Val Ala Thr Lys Glu Gln
85 90 95

Leu Ile Leu Met His Cys Val Leu Asp Met Lys Tyr Ala Glu Thr Asn
100 105 110

Leu Leu Lys Ala Phe Ala Gln Leu Phe Ile Glu Thr Val Val Lys Trp
115 120 125

Arg Thr Val Cys Ser Asp Ile Ser Ala Gly Arg Glu Pro Thr Val Asp
130 135 140

Thr Met Pro Gln Met Pro Gln Gly Gly Gly Gly Gly Ile Gln Pro Pro
145 150 155 160

Pro Ala Gly Ile Arg Ala
165

<210> SEQ ID NO 81
<211> LENGTH: 2298
<212> TYPE: DNA
<213> ORGANISM: Chlamydia trachomatis

<400> SEQUENCE: 81
tcaatacaac ctacatccat ttctttaact aagaatataa cggcagcttt agccggagag 60
caggtcgatg ctgctgcagt gtatatgccg caggctgttt ttttctttca gcaactggat 120
gaaaaaagca aggggctgaa acaggcttta ggattgctcg aagaggttga tctagaaaaa 180
tttataccgt ctttagaaaa atcacctaca cctatcacta cgggaacaac gagtaaaatt 240
tccgctgatg ggattgagat tgttggagag ctttcttcag aaacaatttt ggcagatcct 300
aataaagctg cagctcaggt ttttggagag gggcttgcag atagttttga tgattggctc 360
agattatctg aaaatggggg gattcaagat cctacagcaa tagaagaaga gattgttact 420
aagtatcaaa cagaactcaa tactctgcgc aataaactca agcaacaatc tttaacagac 480
gatgagtata cgaagcttta tgctattcct caaaactttg ttaaagagat agaaagctta 540
aagaatgaaa ataatgtgag gttaattccc aaaagtaaag tcactaactt ttggcagaat 600
atcatgctca cttacaactc ggtaacctcg ttatcagaac ctgttaccga tgcgatgaat 660
acgactatgg cggagtactc tctttatatt gagagagcta cagaggctgc caagttgata 720
cgggagataa ccaacacgat caaagacatt ttcaatccag tttgggatgt gcgtgaacaa 780
acaggaattt ttgggttaaa aggagctgag tataacgctt tagaaggcaa tatgattcaa 840

-continued

```
agcttgctta gctttgcggg tctattccgg cagttaatga gtcgtactgc aacagttgat     900

gagataggcg cactttatcc taaaaatgat aaaaacgaag acgtcattca tactgctatt     960

gatgattatg tgaattcttt agctgatttg aaagccaatg aacaggtcaa actcaacggt    1020

ctgttgagtt tagtatatgc ttattatgct agtactttag gttttgctaa gaaggatgta    1080

ttcaataatg cacaagcttc ttttacagat tatactaatt ttctaaacca agagatccaa    1140

tattggacgc ctagagagac ttcaagtttt aatatctcca atcaagcatt gcaaaccttt    1200

aaaaataagc cttcggctga ttataacggc gtatatcttt ttgataataa aggattagag    1260

actaatctct ttaatcctac gttcttcttt gatgttgtga gtctcatgac agctgatcct    1320

acgaagacta tgtctcgaca ggattacaat aaggtgatta cagcctcgga atccagtatt    1380

cagaagatta atcaggctat taccgcttgg gaactagcta ttgcagaatg tgggactaaa    1440

aaagcgaagc tcgaaccatc cagtttaaat tattttaatg ctatggtcga agcgaagaag    1500

accttcgtag agacctctcc aatacagatg gtctattcat ctttgatgtt ggataagtat    1560

cttccgaatc agcagtacat attagagaca ttaggaagtc agatgacttt ctctaacaag    1620

gctgctcggt atttaaatga tatcattgcg tatgcagtta gcttccaaac agctgacgtc    1680

tattattctt tagggatgta tcttcgacaa atgaaccagc aggaatttcc tgaggtgatt    1740

tctcgtgcta acgatactgt gaaaaaagag atagatcgga gtcgtgcgga tctctttcac    1800

tgtaaaaaag ctatcgaaaa gattaaagaa ttagtgactt ctgtaaatgc ggatactgaa    1860

ttgacctcat ctcagcgtgc agagttatta gagacgttag ctagttatgc ttttgaattt    1920

gagaatctct atcacaacct ctctaatgtt tacgtcatgg tttctaaggt acagatttct    1980

ggcgtaagca agcctgatga agtggatgag gcttttactg ctaagattgg atcgaaggaa    2040

ttcgatactt ggattcagca gcttacaaca tttgaaagtg ctgtgattga aggtgggcgt    2100

aatggtgtga tgcctggggg agagcagcag gttttacaga gtttagagag caagcagcaa    2160

gattacacgt cgttcaacca gaatcagcaa ttagctctac aaatggagtc cgcagcgatt    2220

caacaagagt ggactatggt agcagcagcc ttagcattaa tgaatcagat tttgctaag     2280

ttgatccgta gatttaaa                                                  2298
```

```
<210> SEQ ID NO 82
<211> LENGTH: 766
<212> TYPE: PRT
<213> ORGANISM: Chlamydia trachomatis

<400> SEQUENCE: 82

Ser Ile Gln Pro Thr Ser Ile Ser Leu Thr Lys Asn Ile Thr Ala Ala
1               5                   10                  15

Leu Ala Gly Glu Gln Val Asp Ala Ala Ala Val Tyr Met Pro Gln Ala
            20                  25                  30

Val Phe Phe Phe Gln Gln Leu Asp Glu Lys Ser Lys Gly Leu Lys Gln
        35                  40                  45

Ala Leu Gly Leu Leu Glu Glu Val Asp Leu Glu Lys Phe Ile Pro Ser
    50                  55                  60

Leu Glu Lys Ser Pro Thr Pro Ile Thr Thr Gly Thr Thr Ser Lys Ile
65                  70                  75                  80

Ser Ala Asp Gly Ile Glu Ile Val Gly Glu Leu Ser Ser Glu Thr Ile
                85                  90                  95

Leu Ala Asp Pro Asn Lys Ala Ala Ala Gln Val Phe Gly Glu Gly Leu
            100                 105                 110
```

```
Ala Asp Ser Phe Asp Asp Trp Leu Arg Leu Ser Glu Asn Gly Gly Ile
        115                 120                 125

Gln Asp Pro Thr Ala Ile Glu Glu Glu Ile Val Thr Lys Tyr Gln Thr
    130                 135                 140

Glu Leu Asn Thr Leu Arg Asn Lys Leu Lys Gln Gln Ser Leu Thr Asp
145                 150                 155                 160

Asp Glu Tyr Thr Lys Leu Tyr Ala Ile Pro Gln Asn Phe Val Lys Glu
                165                 170                 175

Ile Glu Ser Leu Lys Asn Glu Asn Asn Val Arg Leu Ile Pro Lys Ser
            180                 185                 190

Lys Val Thr Asn Phe Trp Gln Asn Ile Met Leu Thr Tyr Asn Ser Val
        195                 200                 205

Thr Ser Leu Ser Glu Pro Val Thr Asp Ala Met Asn Thr Thr Met Ala
    210                 215                 220

Glu Tyr Ser Leu Tyr Ile Glu Arg Ala Thr Glu Ala Ala Lys Leu Ile
225                 230                 235                 240

Arg Glu Ile Thr Asn Thr Ile Lys Asp Ile Phe Asn Pro Val Trp Asp
                245                 250                 255

Val Arg Glu Gln Thr Gly Ile Phe Gly Leu Lys Gly Ala Glu Tyr Asn
            260                 265                 270

Ala Leu Glu Gly Asn Met Ile Gln Ser Leu Leu Ser Phe Ala Gly Leu
        275                 280                 285

Phe Arg Gln Leu Met Ser Arg Thr Ala Thr Val Asp Glu Ile Gly Ala
    290                 295                 300

Leu Tyr Pro Lys Asn Asp Lys Asn Glu Asp Val Ile His Thr Ala Ile
305                 310                 315                 320

Asp Asp Tyr Val Asn Ser Leu Ala Asp Leu Lys Ala Asn Glu Gln Val
                325                 330                 335

Lys Leu Asn Gly Leu Leu Ser Leu Val Tyr Ala Tyr Tyr Ala Ser Thr
            340                 345                 350

Leu Gly Phe Ala Lys Lys Asp Val Phe Asn Asn Ala Gln Ala Ser Phe
        355                 360                 365

Thr Asp Tyr Thr Asn Phe Leu Asn Gln Glu Ile Gln Tyr Trp Thr Pro
    370                 375                 380

Arg Glu Thr Ser Ser Phe Asn Ile Ser Asn Gln Ala Leu Gln Thr Phe
385                 390                 395                 400

Lys Asn Lys Pro Ser Ala Asp Tyr Asn Gly Val Tyr Leu Phe Asp Asn
                405                 410                 415

Lys Gly Leu Glu Thr Asn Leu Phe Asn Pro Thr Phe Phe Phe Asp Val
            420                 425                 430

Val Ser Leu Met Thr Ala Asp Pro Thr Lys Thr Met Ser Arg Gln Asp
        435                 440                 445

Tyr Asn Lys Val Ile Thr Ala Ser Glu Ser Ser Ile Gln Lys Ile Asn
    450                 455                 460

Gln Ala Ile Thr Ala Trp Glu Leu Ala Ile Ala Glu Cys Gly Thr Lys
465                 470                 475                 480

Lys Ala Lys Leu Glu Pro Ser Ser Leu Asn Tyr Phe Asn Ala Met Val
                485                 490                 495

Glu Ala Lys Lys Thr Phe Val Glu Thr Ser Pro Ile Gln Met Val Tyr
            500                 505                 510

Ser Ser Leu Met Leu Asp Lys Tyr Leu Pro Asn Gln Gln Tyr Ile Leu
        515                 520                 525
```

Glu Thr Leu Gly Ser Gln Met Thr Phe Ser Asn Lys Ala Ala Arg Tyr
530 535 540

Leu Asn Asp Ile Ile Ala Tyr Ala Val Ser Phe Gln Thr Ala Asp Val
545 550 555 560

Tyr Tyr Ser Leu Gly Met Tyr Leu Arg Gln Met Asn Gln Gln Glu Phe
565 570 575

Pro Glu Val Ile Ser Arg Ala Asn Asp Thr Val Lys Lys Glu Ile Asp
580 585 590

Arg Ser Arg Ala Asp Leu Phe His Cys Lys Lys Ala Ile Glu Lys Ile
595 600 605

Lys Glu Leu Val Thr Ser Val Asn Ala Asp Thr Glu Leu Thr Ser Ser
610 615 620

Gln Arg Ala Glu Leu Leu Glu Thr Leu Ala Ser Tyr Ala Phe Glu Phe
625 630 635 640

Glu Asn Leu Tyr His Asn Leu Ser Asn Val Tyr Val Met Val Ser Lys
645 650 655

Val Gln Ile Ser Gly Val Ser Lys Pro Asp Glu Val Asp Glu Ala Phe
660 665 670

Thr Ala Lys Ile Gly Ser Lys Glu Phe Asp Thr Trp Ile Gln Gln Leu
675 680 685

Thr Thr Phe Glu Ser Ala Val Ile Glu Gly Gly Arg Asn Gly Val Met
690 695 700

Pro Gly Gly Glu Gln Gln Val Leu Gln Ser Leu Glu Ser Lys Gln Gln
705 710 715 720

Asp Tyr Thr Ser Phe Asn Gln Asn Gln Gln Leu Ala Leu Gln Met Glu
725 730 735

Ser Ala Ala Ile Gln Gln Glu Trp Thr Met Val Ala Ala Ala Leu Ala
740 745 750

Leu Met Asn Gln Ile Phe Ala Lys Leu Ile Arg Arg Phe Lys
755 760 765

<210> SEQ ID NO 83
<211> LENGTH: 1296
<212> TYPE: DNA
<213> ORGANISM: Chlamydia trachomatis

<400> SEQUENCE: 83
gatcctttga gtgcaaaaca gttaatgtat ctgtttcctc agctctcaga agaggatgta 60
tctgtttttg ctcgatgcat tttgtcttca aagcgtccag aatacctctt ttcaaaatcg 120
gaggaagagc tctttgcaaa attgattttg ccaagggttt ctctaggtgt tcatcgggac 180
gatgatttag cgagagtgtt ggtgttagcg gagccttctg cagaagagca gaaggctcga 240
tactattcat tgtatctgga tgttttagct ttgcgtgcat acgttgaaag agagcgtttg 300
gcgagtgctg cacacggaga tcctgagcgg atagatttgg caaccataga agctattaat 360
accatccttt ttcaggaaga aggatggagg tatccttcaa aacaagagat gtttgaaaac 420
aggttttctg agttagctgc tgttacagat agtaagtttg gagtttgctt gggaactgta 480
gtgctttatc aagctgtcgc ccagcggctt gatttgtctc tggaccctgt cacccctcct 540
ggacatattt acttacgcta taaggacaag gtgaatattg aaaccacttc tggaggaagg 600
catcttccta ctgaaaggta ttgtgaatgc ataaaagagt cgcagttaaa ggtgcgttcg 660
cagatggagc ttatagggtt aacttttatg aatagaggag ctttcttttt gcaaaaagga 720
gagtttcttc aggcgtcctt agcttatgag caagctcaat catatttatc agacgagcag 780

-continued

```
atttctgatt tgttagggat tacttatgtt cttttaggaa agaaggcggc gggagaggct    840

cttttaaaga aatctgcaga aaagactcgg cgagggtcat ctatctatga ctatttccaa    900

ggatatattt cccccgaaat cctaggggtg ttgtttgccg attcaggggt gacctatcaa    960

gaaactttgg agtatcgaaa aaaactagtg atgctttcca agaagtatcc aaaaagtgga   1020

tctcttaggt tgaggttggc gacaacagca ttggagctag ggctggtcaa ggagggggtg   1080

cagttgttag aagagagtgt taaggatgcc ccagaggacc tctctttacg tctgcagttt   1140

tgtaaaattc tttgcaatcg acatgattat gtccgagcaa aatatcattt tgatcaagcg   1200

caagctcttc tcattaaaga agggttgttt tccgaaaaaa cttcctatac tctcttaaaa   1260

actatcggga aaaagctatc tctttttgct ccgagt                             1296


<210> SEQ ID NO 84
<211> LENGTH: 432
<212> TYPE: PRT
<213> ORGANISM: Chlamydia trachomatis

<400> SEQUENCE: 84

Asp Pro Leu Ser Ala Lys Gln Leu Met Tyr Leu Phe Pro Gln Leu Ser
1               5                   10                  15

Glu Glu Asp Val Ser Val Phe Ala Arg Cys Ile Leu Ser Ser Lys Arg
            20                  25                  30

Pro Glu Tyr Leu Phe Ser Lys Ser Glu Glu Glu Leu Phe Ala Lys Leu
        35                  40                  45

Ile Leu Pro Arg Val Ser Leu Gly Val His Arg Asp Asp Leu Ala
    50                  55                  60

Arg Val Leu Val Leu Ala Glu Pro Ser Ala Glu Glu Gln Lys Ala Arg
65                  70                  75                  80

Tyr Tyr Ser Leu Tyr Leu Asp Val Leu Ala Leu Arg Ala Tyr Val Glu
                85                  90                  95

Arg Glu Arg Leu Ala Ser Ala Ala His Gly Asp Pro Glu Arg Ile Asp
            100                 105                 110

Leu Ala Thr Ile Glu Ala Ile Asn Thr Ile Leu Phe Gln Glu Glu Gly
        115                 120                 125

Trp Arg Tyr Pro Ser Lys Gln Glu Met Phe Glu Asn Arg Phe Ser Glu
    130                 135                 140

Leu Ala Ala Val Thr Asp Ser Lys Phe Gly Val Cys Leu Gly Thr Val
145                 150                 155                 160

Val Leu Tyr Gln Ala Val Ala Gln Arg Leu Asp Leu Ser Leu Asp Pro
                165                 170                 175

Val Thr Pro Pro Gly His Ile Tyr Leu Arg Tyr Lys Asp Lys Val Asn
            180                 185                 190

Ile Glu Thr Thr Ser Gly Gly Arg His Leu Pro Thr Glu Arg Tyr Cys
        195                 200                 205

Glu Cys Ile Lys Glu Ser Gln Leu Lys Val Arg Ser Gln Met Glu Leu
    210                 215                 220

Ile Gly Leu Thr Phe Met Asn Arg Gly Ala Phe Phe Leu Gln Lys Gly
225                 230                 235                 240

Glu Phe Leu Gln Ala Ser Leu Ala Tyr Glu Gln Ala Gln Ser Tyr Leu
                245                 250                 255

Ser Asp Glu Gln Ile Ser Asp Leu Leu Gly Ile Thr Tyr Val Leu Leu
            260                 265                 270

Gly Lys Lys Ala Ala Gly Glu Ala Leu Leu Lys Lys Ser Ala Glu Lys
        275                 280                 285
```

```
Thr Arg Arg Gly Ser Ser Ile Tyr Asp Tyr Phe Gln Gly Tyr Ile Ser
    290                 295                 300

Pro Glu Ile Leu Gly Val Leu Phe Ala Asp Ser Gly Val Thr Tyr Gln
305                 310                 315                 320

Glu Thr Leu Glu Tyr Arg Lys Lys Leu Val Met Leu Ser Lys Lys Tyr
                325                 330                 335

Pro Lys Ser Gly Ser Leu Arg Leu Arg Leu Ala Thr Thr Ala Leu Glu
            340                 345                 350

Leu Gly Leu Val Lys Glu Gly Val Gln Leu Leu Glu Glu Ser Val Lys
        355                 360                 365

Asp Ala Pro Glu Asp Leu Ser Leu Arg Leu Gln Phe Cys Lys Ile Leu
    370                 375                 380

Cys Asn Arg His Asp Tyr Val Arg Ala Lys Tyr His Phe Asp Gln Ala
385                 390                 395                 400

Gln Ala Leu Leu Ile Lys Glu Gly Leu Phe Ser Glu Lys Thr Ser Tyr
                405                 410                 415

Thr Leu Leu Lys Thr Ile Gly Lys Lys Leu Ser Leu Phe Ala Pro Ser
            420                 425                 430


<210> SEQ ID NO 85
<211> LENGTH: 2031
<212> TYPE: DNA
<213> ORGANISM: Chlamydia trachomatis

<400> SEQUENCE: 85

tcttcagatc tacttgaaaa agatgtgaaa tcgatcaaaa gagaactcaa ggctttacat     60

gaagatgttc ttgagttagt ccggatctcg catcagcaaa aaaattgggt ccagtctaca    120

gatttttctg tttctccaga gatcagtgta ttgaaggatt gcggagatcc tgcgttccct    180

aatttattat gcgaagaccc ttatgttgaa aaagtggtcc cttcgttgtt aaaggaaggt    240

tttgttccga aaggtatttt gcgtacagct caagtaggaa ggcctgataa cctaagtccg    300

tttaatggct ttgttaatat cgttcgattt tatgaattgt gcgttcctaa tttggctgtt    360

gagcatgttg gtaaatacga ggagtttgcg cctagtttag ccttaaagat agaagagcat    420

tatgtagagg atgggtctgg ggataaagaa tttcatattt atttgcgtcc taatatgttt    480

tgggagccga tagatcctac gctgttccct aaaaatataa ctttagcaga cagcttctta    540

agaccacatc ctgtcaccgc tcatgatgtg aagttctatt acgatgtagt catgaatccc    600

tatgttgcag aaatgcgtgc agtggctatg agatcttatt ttgaggatat ggtttcggtt    660

cgggtagaaa acgatttgaa attaatcgtt cgttggagag ctcatactgt acgtaatgaa    720

cagggagagg aagagaaaaa agtgctctat tctgctttcg cgaatacatt ggcactccaa    780

ccgttacctt gtttcgtgta tcagcatttc gcaaatggag agaagatcgt tccagaagat    840

tctgatcccg atacgtatcg caaagattcg gtatgggcgc aaaacttttc ttcacattgg    900

gcgtataatt acatagtgag ctgtggagca ttccgatttg cagggatgga tgatgagaaa    960

attactttag ttcgtaatcc taattatcat aatccgtttg cggctcttgt ggagaagcgc   1020

tatatctata tgaaagatag tacagattct ctcttccaag atttcaaagc tgggaaggtg   1080

gatattgcgt atttccctcc taaccatgtc gataatctag cgagcttcat gcaaacctct   1140

gcttataagg aacaagctgc tagaggagag gcaattttag aaaaaaattc atcagaccgg   1200

tcctattctt acatcggatg gaattgtctt tctcttttct ttaacaatcg ttcggtacga   1260

caagccatga atatgttgat cgatcgggat cgcattattg agcagtgctt ggatggtcgt   1320
```

ggagtctctg tgagtgggcc tttttctctc tgctctccat catacaacag agatgtagag 1380
ggatggcaat actctccgga agaggccgca cgtaaattag aggaagaggg ctggatcgat 1440
gctgatggag atggtattcg tgagaaagta atcgatggag ttgtagtgcc tttccgtttc 1500
cggttatgct actatgtgaa aagtgtaaca gcacgaacga ttgccgaata tgtagctacg 1560
gtatgtaaag aggtgggtat cgagtgttgc ttactcgggt tagatatggc ggattattca 1620
caagccctcg aggagaaaaa tttcgatgct attctttccg gatggtgttt aggaacccct 1680
ccagaagatc ctcgtgctct atggcattcg gaaggagctt tggagaaagg atctgccaat 1740
gctgttggat tttgtaatga ggaagcagac cgtatcatcg aacagctcag ttacgagtat 1800
gattctaata agcgccaagc cttgtatcac cgttttcacg aggtgattca tgaggaatct 1860
ccttacgcgt ttctctattc aagacagtac tcccttgtct ataaggagtt tgtaaaaaat 1920
atttttgtgc caacagaaca tcaggatttg attcctggag ctcaagatga gacagtgaat 1980
ttatccatgt tgtgggtaga taaagaggag ggtcgatgct ccgctatatc t 2031

<210> SEQ ID NO 86
<211> LENGTH: 677
<212> TYPE: PRT
<213> ORGANISM: Chlamydia trachomatis

<400> SEQUENCE: 86

Ser Ser Asp Leu Leu Glu Lys Asp Val Lys Ser Ile Lys Arg Glu Leu
1 5 10 15

Lys Ala Leu His Glu Asp Val Leu Glu Leu Val Arg Ile Ser His Gln
20 25 30

Gln Lys Asn Trp Val Gln Ser Thr Asp Phe Ser Val Ser Pro Glu Ile
35 40 45

Ser Val Leu Lys Asp Cys Gly Asp Pro Ala Phe Pro Asn Leu Leu Cys
50 55 60

Glu Asp Pro Tyr Val Glu Lys Val Val Pro Ser Leu Leu Lys Glu Gly
65 70 75 80

Phe Val Pro Lys Gly Ile Leu Arg Thr Ala Gln Val Gly Arg Pro Asp
85 90 95

Asn Leu Ser Pro Phe Asn Gly Phe Val Asn Ile Val Arg Phe Tyr Glu
100 105 110

Leu Cys Val Pro Asn Leu Ala Val Glu His Val Gly Lys Tyr Glu Glu
115 120 125

Phe Ala Pro Ser Leu Ala Leu Lys Ile Glu Glu His Tyr Val Glu Asp
130 135 140

Gly Ser Gly Asp Lys Glu Phe His Ile Tyr Leu Arg Pro Asn Met Phe
145 150 155 160

Trp Glu Pro Ile Asp Pro Thr Leu Phe Pro Lys Asn Ile Thr Leu Ala
165 170 175

Asp Ser Phe Leu Arg Pro His Pro Val Thr Ala His Asp Val Lys Phe
180 185 190

Tyr Tyr Asp Val Val Met Asn Pro Tyr Val Ala Glu Met Arg Ala Val
195 200 205

Ala Met Arg Ser Tyr Phe Glu Asp Met Val Ser Val Arg Val Glu Asn
210 215 220

Asp Leu Lys Leu Ile Val Arg Trp Arg Ala His Thr Val Arg Asn Glu
225 230 235 240

Gln Gly Glu Glu Glu Lys Lys Val Leu Tyr Ser Ala Phe Ala Asn Thr

-continued

```
                245                 250                 255

Leu Ala Leu Gln Pro Leu Pro Cys Phe Val Tyr Gln His Phe Ala Asn
            260                 265                 270

Gly Glu Lys Ile Val Pro Glu Asp Ser Asp Pro Asp Thr Tyr Arg Lys
        275                 280                 285

Asp Ser Val Trp Ala Gln Asn Phe Ser Ser His Trp Ala Tyr Asn Tyr
    290                 295                 300

Ile Val Ser Cys Gly Ala Phe Arg Phe Ala Gly Met Asp Asp Glu Lys
305                 310                 315                 320

Ile Thr Leu Val Arg Asn Pro Asn Tyr His Asn Pro Phe Ala Ala Leu
                325                 330                 335

Val Glu Lys Arg Tyr Ile Tyr Met Lys Asp Ser Thr Asp Ser Leu Phe
            340                 345                 350

Gln Asp Phe Lys Ala Gly Lys Val Asp Ile Ala Tyr Phe Pro Pro Asn
        355                 360                 365

His Val Asp Asn Leu Ala Ser Phe Met Gln Thr Ser Ala Tyr Lys Glu
    370                 375                 380

Gln Ala Ala Arg Gly Glu Ala Ile Leu Glu Lys Asn Ser Ser Asp Arg
385                 390                 395                 400

Ser Tyr Ser Tyr Ile Gly Trp Asn Cys Leu Ser Leu Phe Phe Asn Asn
                405                 410                 415

Arg Ser Val Arg Gln Ala Met Asn Met Leu Ile Asp Arg Asp Arg Ile
            420                 425                 430

Ile Glu Gln Cys Leu Asp Gly Arg Gly Val Ser Val Ser Gly Pro Phe
        435                 440                 445

Ser Leu Cys Ser Pro Ser Tyr Asn Arg Asp Val Glu Gly Trp Gln Tyr
    450                 455                 460

Ser Pro Glu Glu Ala Ala Arg Lys Leu Glu Glu Glu Gly Trp Ile Asp
465                 470                 475                 480

Ala Asp Gly Asp Gly Ile Arg Glu Lys Val Ile Asp Gly Val Val Val
                485                 490                 495

Pro Phe Arg Phe Arg Leu Cys Tyr Tyr Val Lys Ser Val Thr Ala Arg
            500                 505                 510

Thr Ile Ala Glu Tyr Val Ala Thr Val Cys Lys Glu Val Gly Ile Glu
        515                 520                 525

Cys Cys Leu Leu Gly Leu Asp Met Ala Asp Tyr Ser Gln Ala Leu Glu
    530                 535                 540

Glu Lys Asn Phe Asp Ala Ile Leu Ser Gly Trp Cys Leu Gly Thr Pro
545                 550                 555                 560

Pro Glu Asp Pro Arg Ala Leu Trp His Ser Glu Gly Ala Leu Glu Lys
                565                 570                 575

Gly Ser Ala Asn Ala Val Gly Phe Cys Asn Glu Glu Ala Asp Arg Ile
            580                 585                 590

Ile Glu Gln Leu Ser Tyr Glu Tyr Asp Ser Asn Lys Arg Gln Ala Leu
        595                 600                 605

Tyr His Arg Phe His Glu Val Ile His Glu Glu Ser Pro Tyr Ala Phe
    610                 615                 620

Leu Tyr Ser Arg Gln Tyr Ser Leu Val Tyr Lys Glu Phe Val Lys Asn
625                 630                 635                 640

Ile Phe Val Pro Thr Glu His Gln Asp Leu Ile Pro Gly Ala Gln Asp
                645                 650                 655

Glu Thr Val Asn Leu Ser Met Leu Trp Val Asp Lys Glu Glu Gly Arg
            660                 665                 670
```

Cys Ser Ala Ile Ser
675

<210> SEQ ID NO 87
<211> LENGTH: 1194
<212> TYPE: DNA
<213> ORGANISM: Chlamydia trachomatis

<400> SEQUENCE: 87
gctgcagcta ctcaagatgc acaagaggtt atcggctctc aggaagcttc tgaggcaagt 60
atgctcaaag gatgtgagga tctcataaat cctgcagctg caacccgaat caaaaaaaaa 120
ggagagaagt ttgaatcatt agaagctcgt cgcaaaccaa cagcggataa agcagaaaag 180
aaatccgaga gcacagagga aaaaggcgat actcctcttg aagatcgttt cacagaagat 240
ctttccgaag tctccggaga agattttcga ggattgaaaa attcgttcga tgatgattct 300
tctcctgacg aaattctcga tgcgctcaca agtaaatttt ctgatcccac aataaaggat 360
ctagctcttg attatctaat tcaaacagct ccctctgatg ggaaacttaa gtccactctc 420
attcaggcaa agcatcaact gatgagccag aatcctcagg cgattgttgg aggacgcaat 480
gttctgttag cttcagaaac ctttgcttcc agagcaaata catctccttc atcgcttcgc 540
tccttatatt tccaagtaac ctcatccccc tctaattgcg ctaatttaca tcaaatgctt 600
gcttcttact tgccatcaga gaaaaccgct gttatggagt ttctagtaaa tggcatggta 660
gcagatttaa aatcggaggg cccttccatt cctcctgcaa aattgcaagt atatatgacg 720
gaactaagca atctccaagc cttacactct gtaaatagct tttttgatag aaatattggg 780
aacttggaaa atagcttaaa gcatgaagga catgccccta ttccatcctt aacgacagga 840
aatttaacta aaaccttctt acaattagta gaagataaat tcccttcctc ttccaaagct 900
caaaaggcat taaatgaact ggtaggccca gatactggtc ctcaaactga agttttaaac 960
ttattcttcc gcgctcttaa tggctgttcg cctagaatat tctctggagc tgaaaaaaaa 1020
cagcagctgg catcggttat cacaaatacg ctagatgcga taaatgcgga taatgaggat 1080
tatcctaaac caggtgactt cccacgatct tccttctcta gtacgcctcc tcatgctcca 1140
gtacctcaat ctgagattcc aacgtcacct acctcaacac agcctccatc accc 1194

<210> SEQ ID NO 88
<211> LENGTH: 398
<212> TYPE: PRT
<213> ORGANISM: Chlamydia trachomatis

<400> SEQUENCE: 88

Ala Ala Ala Thr Gln Asp Ala Gln Glu Val Ile Gly Ser Gln Glu Ala
1 5 10 15

Ser Glu Ala Ser Met Leu Lys Gly Cys Glu Asp Leu Ile Asn Pro Ala
20 25 30

Ala Ala Thr Arg Ile Lys Lys Lys Gly Glu Lys Phe Glu Ser Leu Glu
35 40 45

Ala Arg Arg Lys Pro Thr Ala Asp Lys Ala Glu Lys Lys Ser Glu Ser
50 55 60

Thr Glu Glu Lys Gly Asp Thr Pro Leu Glu Asp Arg Phe Thr Glu Asp
65 70 75 80

Leu Ser Glu Val Ser Gly Glu Asp Phe Arg Gly Leu Lys Asn Ser Phe
85 90 95

Asp Asp Asp Ser Ser Pro Asp Glu Ile Leu Asp Ala Leu Thr Ser Lys

```
            100                 105                 110
Phe Ser Asp Pro Thr Ile Lys Asp Leu Ala Leu Asp Tyr Leu Ile Gln
        115                 120                 125

Thr Ala Pro Ser Asp Gly Lys Leu Lys Ser Thr Leu Ile Gln Ala Lys
    130                 135                 140

His Gln Leu Met Ser Gln Asn Pro Gln Ala Ile Val Gly Gly Arg Asn
145                 150                 155                 160

Val Leu Leu Ala Ser Glu Thr Phe Ala Ser Arg Ala Asn Thr Ser Pro
                165                 170                 175

Ser Ser Leu Arg Ser Leu Tyr Phe Gln Val Thr Ser Ser Pro Ser Asn
            180                 185                 190

Cys Ala Asn Leu His Gln Met Leu Ala Ser Tyr Leu Pro Ser Glu Lys
        195                 200                 205

Thr Ala Val Met Glu Phe Leu Val Asn Gly Met Val Ala Asp Leu Lys
    210                 215                 220

Ser Glu Gly Pro Ser Ile Pro Pro Ala Lys Leu Gln Val Tyr Met Thr
225                 230                 235                 240

Glu Leu Ser Asn Leu Gln Ala Leu His Ser Val Asn Ser Phe Phe Asp
                245                 250                 255

Arg Asn Ile Gly Asn Leu Glu Asn Ser Leu Lys His Glu Gly His Ala
            260                 265                 270

Pro Ile Pro Ser Leu Thr Thr Gly Asn Leu Thr Lys Thr Phe Leu Gln
        275                 280                 285

Leu Val Glu Asp Lys Phe Pro Ser Ser Ser Lys Ala Gln Lys Ala Leu
    290                 295                 300

Asn Glu Leu Val Gly Pro Asp Thr Gly Pro Gln Thr Glu Val Leu Asn
305                 310                 315                 320

Leu Phe Phe Arg Ala Leu Asn Gly Cys Ser Pro Arg Ile Phe Ser Gly
                325                 330                 335

Ala Glu Lys Lys Gln Gln Leu Ala Ser Val Ile Thr Asn Thr Leu Asp
            340                 345                 350

Ala Ile Asn Ala Asp Asn Glu Asp Tyr Pro Lys Pro Gly Asp Phe Pro
        355                 360                 365

Arg Ser Ser Phe Ser Ser Thr Pro Pro His Ala Pro Val Pro Gln Ser
    370                 375                 380

Glu Ile Pro Thr Ser Pro Thr Ser Thr Gln Pro Pro Ser Pro
385                 390                 395

<210> SEQ ID NO 89
<211> LENGTH: 591
<212> TYPE: DNA
<213> ORGANISM: Chlamydia trachomatis

<400> SEQUENCE: 89

tgttgcgcca actcttatgg atcgactctt gcaaaaaata cagccgagat aaaagaagaa      60

tctgttacac ttcgcgagaa gccggatgcc ggctgtaaaa agaaatcttc ttgttacttg     120

agaaaatttt tctcgcgcaa gaaacctaaa gagaagacag agcctgtgtt gccgaacttt     180

aagtcttacg cagatccaat gacagattcc gaaagaaaag acctttcttt cgtagtatct     240

gctgctgctg ataagtcttc tattgctttg gctatggctc agggggaaat taaaggcgca     300

ttatcgcgta ttagagagat ccatcctctt gcattgttac aagctcttgc agaagatcct     360

gctttaattg ctggaatgaa aaagatgcaa ggacgggatt gggtctggaa tatctttatc     420

acagaattaa gcaaagtttt ttctcaagca gcatctttag gggctttcag cgttgcagac     480
```

gttgccgcgt tcgcgtcgac cttaggatta gactcgggga ccgttacctc aattgttgat 540
ggggaaaggt gggctgagct gatcgatgtc gtgattcaga accctgctat a 591

<210> SEQ ID NO 90
<211> LENGTH: 197
<212> TYPE: PRT
<213> ORGANISM: Chlamydia trachomatis

<400> SEQUENCE: 90

Cys Cys Ala Asn Ser Tyr Gly Ser Thr Leu Ala Lys Asn Thr Ala Glu
1 5 10 15

Ile Lys Glu Glu Ser Val Thr Leu Arg Glu Lys Pro Asp Ala Gly Cys
20 25 30

Lys Lys Lys Ser Ser Cys Tyr Leu Arg Lys Phe Phe Ser Arg Lys Lys
35 40 45

Pro Lys Glu Lys Thr Glu Pro Val Leu Pro Asn Phe Lys Ser Tyr Ala
50 55 60

Asp Pro Met Thr Asp Ser Glu Arg Lys Asp Leu Ser Phe Val Val Ser
65 70 75 80

Ala Ala Ala Asp Lys Ser Ser Ile Ala Leu Ala Met Ala Gln Gly Glu
85 90 95

Ile Lys Gly Ala Leu Ser Arg Ile Arg Glu Ile His Pro Leu Ala Leu
100 105 110

Leu Gln Ala Leu Ala Glu Asp Pro Ala Leu Ile Ala Gly Met Lys Lys
115 120 125

Met Gln Gly Arg Asp Trp Val Trp Asn Ile Phe Ile Thr Glu Leu Ser
130 135 140

Lys Val Phe Ser Gln Ala Ala Ser Leu Gly Ala Phe Ser Val Ala Asp
145 150 155 160

Val Ala Ala Phe Ala Ser Thr Leu Gly Leu Asp Ser Gly Thr Val Thr
165 170 175

Ser Ile Val Asp Gly Glu Arg Trp Ala Glu Leu Ile Asp Val Val Ile
180 185 190

Gln Asn Pro Ala Ile
195

<210> SEQ ID NO 91
<211> LENGTH: 723
<212> TYPE: DNA
<213> ORGANISM: Chlamydia trachomatis

<400> SEQUENCE: 91
aaagttaaaa ttaatgatca gttcatttgt atttccccat acatttctgc tcgatggaat 60
cagatagctt tcatagagtc ttgtgatgga gggacggaag gggtattac tttgaaactc 120 catttaattg atggagagac agtctctata cctaatctag gacaagcgat tgttgatgag 180
gtgttccaag agcacttgct atatttagag tccacagctc ctcagaaaaa caaggaagag 240
gaaaaaatta gctctttgtt aggagctgtt caacaaatgg ctaaaggatg cgaagtacag 300
gttttttctc aaaagggctt ggtttctatg ttactaggag gagctggttc gattaatgtg 360
ttgttgcaac attctccaga acataaggat catcctgatc ttcctaccga tttactggag 420
aggatagcgc aaatgatgcg ttcattatct ataggaccaa cttctatttt agctaagcca 480
gagcctcatt gcaactgttt gcattgtcaa attggacgag ctacagtgga agaagaggat 540
gccggagtat cggatgagga tcttactttt cgttcatggg atatctctca aagtggagaa 600
aagatgtaca ctgttacaga tcctttgaat ccagaagagc agtttaatgt gtatttagga 660
acgccgattg gatgcacatg tgggcagcca tactgtgaac acgtgaaagc tgttctttat 720
act 723

<210> SEQ ID NO 92
<211> LENGTH: 241
<212> TYPE: PRT
<213> ORGANISM: Chlamydia trachomatis

<400> SEQUENCE: 92

Lys Val Lys Ile Asn Asp Gln Phe Ile Cys Ile Ser Pro Tyr Ile Ser
1 5 10 15

Ala Arg Trp Asn Gln Ile Ala Phe Ile Glu Ser Cys Asp Gly Gly Thr
20 25 30

Glu Gly Gly Ile Thr Leu Lys Leu His Leu Ile Asp Gly Glu Thr Val
35 40 45

Ser Ile Pro Asn Leu Gly Gln Ala Ile Val Asp Glu Val Phe Gln Glu
50 55 60

His Leu Leu Tyr Leu Glu Ser Thr Ala Pro Gln Lys Asn Lys Glu Glu
65 70 75 80

Glu Lys Ile Ser Ser Leu Leu Gly Ala Val Gln Gln Met Ala Lys Gly
85 90 95

Cys Glu Val Gln Val Phe Ser Gln Lys Gly Leu Val Ser Met Leu Leu
100 105 110

Gly Gly Ala Gly Ser Ile Asn Val Leu Leu Gln His Ser Pro Glu His
115 120 125

Lys Asp His Pro Asp Leu Pro Thr Asp Leu Leu Glu Arg Ile Ala Gln
130 135 140

Met Met Arg Ser Leu Ser Ile Gly Pro Thr Ser Ile Leu Ala Lys Pro
145 150 155 160

Glu Pro His Cys Asn Cys Leu His Cys Gln Ile Gly Arg Ala Thr Val
165 170 175

Glu Glu Glu Asp Ala Gly Val Ser Asp Glu Asp Leu Thr Phe Arg Ser
180 185 190

Trp Asp Ile Ser Gln Ser Gly Glu Lys Met Tyr Thr Val Thr Asp Pro
195 200 205

Leu Asn Pro Glu Glu Gln Phe Asn Val Tyr Leu Gly Thr Pro Ile Gly
210 215 220

Cys Thr Cys Gly Gln Pro Tyr Cys Glu His Val Lys Ala Val Leu Tyr
225 230 235 240

Thr

<210> SEQ ID NO 93
<211> LENGTH: 951
<212> TYPE: DNA
<213> ORGANISM: Chlamydia muridarum

<400> SEQUENCE: 93
gcatccaagt ctcgtcatta tcttaaccag ccttggtaca ttatcttatt catctttgtt 60
cttagtctgg ttgctggtac cccttctttct tcagtttcct atgttctatc tccaatccaa 120
aaacaagctg cagaatttga tcgtaatcag caaatgttga tggccgcaca aattatttcc 180
tatgacaata aattccaaat atatgctgaa ggggattggc aacctgctgt ctataataca 240
aaaaaacaga tactagaaaa aagctcttcc actccaccac aagtgactgt ggcgactcta 300

```
tgctcttatt ttcaaaattt tgttagagtt ttgcttacag actcccaagg gaatctttct    360

tcttttgaag atcacaatct taacctagaa gagttcttat cccaccccac atcttcagta    420

caagatcact ctctgcatgt aatttatgct attctagcaa acgatgaatc ctctaaaaag    480

ttatcatcct cccaagtagc aaaaaatccg gtatccatag agtctattat tcttcctata    540

aaaggatttg gtttatgggg accaatctat ggatttcttg ctttagaaaa ggacggtaat    600

acggttctag ggacatgctg gtatcaacat ggtgagactc caggattagg agcaaatata    660

actaatcccc aatggcaaca aaatttcaga ggaaaaaaag tatttctcgc ttcctcttcc    720

ggagaaaccg attttgctaa aacaactcta ggactagaag ttataaaagg atctgtttct    780

gcattattag ggactctcc caaagctaat tccgctgttg atggaatttc aggagctaca    840

ctgacctgta atggagttac tgaagctttt gctaattcgc tagctcctta ccgcccctta    900

ttgactttct tcgccaatct taactctagt ggagaatctc atgacaacca a             951
```

<210> SEQ ID NO 94
<211> LENGTH: 317
<212> TYPE: PRT
<213> ORGANISM: Chlamydia muridarum

<400> SEQUENCE: 94

```
Ala Ser Lys Ser Arg His Tyr Leu Asn Gln Pro Trp Tyr Ile Ile Leu
1               5                   10                  15

Phe Ile Phe Val Leu Ser Leu Val Ala Gly Thr Leu Leu Ser Ser Val
            20                  25                  30

Ser Tyr Val Leu Ser Pro Ile Gln Lys Gln Ala Ala Glu Phe Asp Arg
        35                  40                  45

Asn Gln Gln Met Leu Met Ala Ala Gln Ile Ile Ser Tyr Asp Asn Lys
    50                  55                  60

Phe Gln Ile Tyr Ala Glu Gly Asp Trp Gln Pro Ala Val Tyr Asn Thr
65                  70                  75                  80

Lys Lys Gln Ile Leu Glu Lys Ser Ser Ser Thr Pro Pro Gln Val Thr
                85                  90                  95

Val Ala Thr Leu Cys Ser Tyr Phe Gln Asn Phe Val Arg Val Leu Leu
            100                 105                 110

Thr Asp Ser Gln Gly Asn Leu Ser Ser Phe Glu Asp His Asn Leu Asn
        115                 120                 125

Leu Glu Glu Phe Leu Ser His Pro Thr Ser Ser Val Gln Asp His Ser
    130                 135                 140

Leu His Val Ile Tyr Ala Ile Leu Ala Asn Asp Glu Ser Ser Lys Lys
145                 150                 155                 160

Leu Ser Ser Ser Gln Val Ala Lys Asn Pro Val Ser Ile Glu Ser Ile
                165                 170                 175

Ile Leu Pro Ile Lys Gly Phe Gly Leu Trp Gly Pro Ile Tyr Gly Phe
            180                 185                 190

Leu Ala Leu Glu Lys Asp Gly Asn Thr Val Leu Gly Thr Cys Trp Tyr
        195                 200                 205

Gln His Gly Glu Thr Pro Gly Leu Gly Ala Asn Ile Thr Asn Pro Gln
    210                 215                 220

Trp Gln Gln Asn Phe Arg Gly Lys Lys Val Phe Leu Ala Ser Ser Ser
225                 230                 235                 240

Gly Glu Thr Asp Phe Ala Lys Thr Thr Leu Gly Leu Glu Val Ile Lys
                245                 250                 255
```

```
Gly Ser Val Ser Ala Leu Leu Gly Asp Ser Pro Lys Ala Asn Ser Ala
            260                 265                 270

Val Asp Gly Ile Ser Gly Ala Thr Leu Thr Cys Asn Gly Val Thr Glu
        275                 280                 285

Ala Phe Ala Asn Ser Leu Ala Pro Tyr Arg Pro Leu Leu Thr Phe Phe
    290                 295                 300

Ala Asn Leu Asn Ser Ser Gly Glu Ser His Asp Asn Gln
305                 310                 315


<210> SEQ ID NO 95
<211> LENGTH: 1410
<212> TYPE: DNA
<213> ORGANISM: Chlamydia muridarum

<400> SEQUENCE: 95

aatggaaaag ttctgtgtga ggtttctgtg tccttccgtt cgattctgct gacggctctg      60

ctttcacttt cttttacaaa cactatgcag gctgcacacc atcattatca ccgttatgat     120

gataaactac gcagacaata ccataaaaag gacttgccca ctcaagagaa tgttcggaaa     180

gagttttgta atccctactc tcatagtagt gatcctatcc ctttgtcaca acaacgagga     240

gtcctatctc ctatctgtga tttagtctca gagtgctcgt tttgaacgg gatttccgtt     300

aggagtctta aacaaacact gaaaaattct gctgggactc aagttgcttt agactggtct     360

atccttcctc aatggttcaa tcctagatcc tcttgggctc ctaagctctc tattcgagat     420

cttggatatg gtaaacccca gtcccttatt gaagcagatt ccccttgttg tcaaacctgc     480

ttcaacccat ctgctgctat tacgatttac gattcttcat gtgggaaggg tgttgtccaa     540

gtgtcataca cccttgttcg ttattggaga gaaacggctg cacttgcagg gcaaactatg     600

atgcttgcag gaagtattaa tgattatcct gctcgccaaa acatattctc tcaacttaca     660

ttttcccaaa ctttccctaa tgagagagta aatctaactg ttggtcaata ctctctttac     720

tcgatagacg gaacgctgta caacaatgat cagcagctag gatttattag ttatgcgttg     780

tcgcaaaatc caacagcgac ttattcctct ggaagccttg gcgcctatct acaagtcgct     840

ccaacagaaa gcacctgtct tcaagttggg ttccaagatg cctataatat ttcaggttcc     900

tcgatcaaat ggaataatct tacaaaaaat aagtataact tccatggcta tgcatcttgg     960

gctccacact gttgcttagg acctggacaa tactctgttc ttctttatgt aaccagaaag    1020

gttcctgagc aaatgatgca gacaatgggc tggtctgtga atgcaagtca atacatctct    1080

tctaaacttt atgtatttgg aagatacagc ggagtcacag gccaattgtc tcctattaac    1140

cgaacctatt catttggctt agtctctcct aatttattga accgtaaccc acaagactta    1200

tttggagtag cttgcgcatt caataatata cacgcctccg cctttcaaaa tgctcaaaga    1260

aaatatgaaa ctgtgatcga gggatttgca actattggtt gcggacctta catctccttt    1320

gctccagatt tccaacttta cctctatcct gctctgcgtc caaataaaca aagcgcccga    1380

gtctatagcg ttcgcgcaaa cctagctatt                                     1410


<210> SEQ ID NO 96
<211> LENGTH: 470
<212> TYPE: PRT
<213> ORGANISM: Chlamydia muridarum

<400> SEQUENCE: 96

Asn Gly Lys Val Leu Cys Glu Val Ser Val Ser Phe Arg Ser Ile Leu
1               5                   10                  15
```

```
Leu Thr Ala Leu Leu Ser Leu Ser Phe Thr Asn Thr Met Gln Ala Ala
            20                  25                  30

His His His Tyr His Arg Tyr Asp Asp Lys Leu Arg Arg Gln Tyr His
        35                  40                  45

Lys Lys Asp Leu Pro Thr Gln Glu Asn Val Arg Lys Glu Phe Cys Asn
    50                  55                  60

Pro Tyr Ser His Ser Ser Asp Pro Ile Pro Leu Ser Gln Gln Arg Gly
65                  70                  75                  80

Val Leu Ser Pro Ile Cys Asp Leu Val Ser Glu Cys Ser Phe Leu Asn
                85                  90                  95

Gly Ile Ser Val Arg Ser Leu Lys Gln Thr Leu Lys Asn Ser Ala Gly
            100                 105                 110

Thr Gln Val Ala Leu Asp Trp Ser Ile Leu Pro Gln Trp Phe Asn Pro
        115                 120                 125

Arg Ser Ser Trp Ala Pro Lys Leu Ser Ile Arg Asp Leu Gly Tyr Gly
    130                 135                 140

Lys Pro Gln Ser Leu Ile Glu Ala Asp Ser Pro Cys Cys Gln Thr Cys
145                 150                 155                 160

Phe Asn Pro Ser Ala Ala Ile Thr Ile Tyr Asp Ser Ser Cys Gly Lys
                165                 170                 175

Gly Val Val Gln Val Ser Tyr Thr Leu Val Arg Tyr Trp Arg Glu Thr
            180                 185                 190

Ala Ala Leu Ala Gly Gln Thr Met Met Leu Ala Gly Ser Ile Asn Asp
        195                 200                 205

Tyr Pro Ala Arg Gln Asn Ile Phe Ser Gln Leu Thr Phe Ser Gln Thr
    210                 215                 220

Phe Pro Asn Glu Arg Val Asn Leu Thr Val Gly Gln Tyr Ser Leu Tyr
225                 230                 235                 240

Ser Ile Asp Gly Thr Leu Tyr Asn Asn Asp Gln Gln Leu Gly Phe Ile
                245                 250                 255

Ser Tyr Ala Leu Ser Gln Asn Pro Thr Ala Thr Tyr Ser Ser Gly Ser
            260                 265                 270

Leu Gly Ala Tyr Leu Gln Val Ala Pro Thr Glu Ser Thr Cys Leu Gln
        275                 280                 285

Val Gly Phe Gln Asp Ala Tyr Asn Ile Ser Gly Ser Ser Ile Lys Trp
    290                 295                 300

Asn Asn Leu Thr Lys Asn Lys Tyr Asn Phe His Gly Tyr Ala Ser Trp
305                 310                 315                 320

Ala Pro His Cys Cys Leu Gly Pro Gly Gln Tyr Ser Val Leu Leu Tyr
                325                 330                 335

Val Thr Arg Lys Val Pro Glu Gln Met Met Gln Thr Met Gly Trp Ser
            340                 345                 350

Val Asn Ala Ser Gln Tyr Ile Ser Ser Lys Leu Tyr Val Phe Gly Arg
        355                 360                 365

Tyr Ser Gly Val Thr Gly Gln Leu Ser Pro Ile Asn Arg Thr Tyr Ser
    370                 375                 380

Phe Gly Leu Val Ser Pro Asn Leu Leu Asn Arg Asn Pro Gln Asp Leu
385                 390                 395                 400

Phe Gly Val Ala Cys Ala Phe Asn Asn Ile His Ala Ser Ala Phe Gln
                405                 410                 415

Asn Ala Gln Arg Lys Tyr Glu Thr Val Ile Glu Gly Phe Ala Thr Ile
            420                 425                 430

Gly Cys Gly Pro Tyr Ile Ser Phe Ala Pro Asp Phe Gln Leu Tyr Leu
```

-continued

```
        435                 440                 445

Tyr Pro Ala Leu Arg Pro Asn Lys Gln Ser Ala Arg Val Tyr Ser Val
    450                 455                 460

Arg Ala Asn Leu Ala Ile
465                 470


<210> SEQ ID NO 97
<211> LENGTH: 1578
<212> TYPE: DNA
<213> ORGANISM: Chlamydia muridarum

<400> SEQUENCE: 97

agcggggtgt tagagacctc tatggcagag tctctctcta ccaacgttat tagcttagct     60

gacaccaaag cgaaagagac cacttctcat caaaaagaca gaaaagcaag aaaaaatcat    120

caaaatagga cttccgtagt ccgtaaagag gttactgcag ttcgtgatac taaagctgta    180

gagcctagac aggattcttg ctttggcaaa atgtatacag tcaaagttaa tgatgatcgt    240

aatgtagaaa tcgtgcagtc cgttcctgaa tatgctacgg taggatctcc atatcctatt    300

gagattactg ctatagggaa aagagactgt gttgatgtaa tcattacaca gcaattacca    360

tgcgaagcag agtttgttag cagtgatcca gctactactc ctactgctga tggtaagcta    420

gtttggaaaa ttgatcggtt aggacagggc gaaaagagta aaattactgt atgggtaaaa    480

cctcttaaag aaggttgctg ctttacagct gcaacggttt gtgcttgtcc agagatccgt    540

tcggttacga aatgtggcca gcctgctatc tgtgttaaac aggaaggtcc agaaagcgca    600

tgtttgcgtt gcccagtaac ttatagaatt aatgtagtca accaaggaac agcaacagca    660

cgtaatgttg ttgtggaaaa tcctgttcca gatggctatg ctcatgcatc cggacagcgt    720

gtattgacat atactcttgg ggatatgcaa cctggagaac agagaacaat caccgtggag    780

ttttgtccgc ttaaacgtgg tcgagtcaca aatattgcta cagtttctta ctgtggtgga    840

cacaaaaata ctgctagcgt aacaacagtg atcaatgagc cttgcgtgca agttaacatc    900

gagggagcag attggtctta tgtttgtaag cctgtagaat atgttatctc tgtttctaac    960

cctggtgact tagttttacg agacgttgta attgaagata cgctttctcc tggaataact   1020

gttgttgaag cagctggagc tcagatttct tgtaataaat tggtttggac tttgaaggaa   1080

ctcaatcctg gagagtcttt acaatataag gttctagtaa gagctcaaac tccagggcaa   1140

ttcacaaaca acgttgttgt gaaaagttgc tctgattgcg gtatttgtac ttcttgcgca   1200

gaagcaacaa cttactggaa aggagttgct gctactcata tgtgcgtagt agatacttgt   1260

gatcctattt gcgtaggaga gaacactgtt tatcgtatct gtgtgacaaa cagaggttct   1320

gctgaagata caaatgtgtc cttaattttg aaattctcta aagaattaca acctatatct   1380

ttctctggac caactaaagg aaccattaca ggaaacacgg tagtgtttga ttcgttacct   1440

agattaggtt ctaaagaaac tgtagagttt tctgtaacgt tgaaagcagt atccgctgga   1500

gatgctcgtg gggaagctat tctttcttcc gatacattga cagttcctgt atctgatacg   1560

gagaatacac atatctat                                                 1578


<210> SEQ ID NO 98
<211> LENGTH: 526
<212> TYPE: PRT
<213> ORGANISM: Chlamydia muridarum

<400> SEQUENCE: 98

Ser Gly Val Leu Glu Thr Ser Met Ala Glu Ser Leu Ser Thr Asn Val
```

-continued

```
1               5                   10                  15

Ile Ser Leu Ala Asp Thr Lys Ala Lys Glu Thr Thr Ser His Gln Lys
            20                  25                  30

Asp Arg Lys Ala Arg Lys Asn His Gln Asn Arg Thr Ser Val Val Arg
        35                  40                  45

Lys Glu Val Thr Ala Val Arg Asp Thr Lys Ala Val Glu Pro Arg Gln
    50                  55                  60

Asp Ser Cys Phe Gly Lys Met Tyr Thr Val Lys Val Asn Asp Asp Arg
65                  70                  75                  80

Asn Val Glu Ile Val Gln Ser Val Pro Glu Tyr Ala Thr Val Gly Ser
                85                  90                  95

Pro Tyr Pro Ile Glu Ile Thr Ala Ile Gly Lys Arg Asp Cys Val Asp
            100                 105                 110

Val Ile Ile Thr Gln Gln Leu Pro Cys Glu Ala Glu Phe Val Ser Ser
        115                 120                 125

Asp Pro Ala Thr Thr Pro Thr Ala Asp Gly Lys Leu Val Trp Lys Ile
    130                 135                 140

Asp Arg Leu Gly Gln Gly Glu Lys Ser Lys Ile Thr Val Trp Val Lys
145                 150                 155                 160

Pro Leu Lys Glu Gly Cys Cys Phe Thr Ala Ala Thr Val Cys Ala Cys
                165                 170                 175

Pro Glu Ile Arg Ser Val Thr Lys Cys Gly Gln Pro Ala Ile Cys Val
            180                 185                 190

Lys Gln Glu Gly Pro Glu Ser Ala Cys Leu Arg Cys Pro Val Thr Tyr
        195                 200                 205

Arg Ile Asn Val Val Asn Gln Gly Thr Ala Thr Ala Arg Asn Val Val
    210                 215                 220

Val Glu Asn Pro Val Pro Asp Gly Tyr Ala His Ala Ser Gly Gln Arg
225                 230                 235                 240

Val Leu Thr Tyr Thr Leu Gly Asp Met Gln Pro Gly Glu Gln Arg Thr
                245                 250                 255

Ile Thr Val Glu Phe Cys Pro Leu Lys Arg Gly Arg Val Thr Asn Ile
            260                 265                 270

Ala Thr Val Ser Tyr Cys Gly Gly His Lys Asn Thr Ala Ser Val Thr
        275                 280                 285

Thr Val Ile Asn Glu Pro Cys Val Gln Val Asn Ile Glu Gly Ala Asp
    290                 295                 300

Trp Ser Tyr Val Cys Lys Pro Val Glu Tyr Val Ile Ser Val Ser Asn
305                 310                 315                 320

Pro Gly Asp Leu Val Leu Arg Asp Val Val Ile Glu Asp Thr Leu Ser
                325                 330                 335

Pro Gly Ile Thr Val Val Glu Ala Ala Gly Ala Gln Ile Ser Cys Asn
            340                 345                 350

Lys Leu Val Trp Thr Leu Lys Glu Leu Asn Pro Gly Glu Ser Leu Gln
        355                 360                 365

Tyr Lys Val Leu Val Arg Ala Gln Thr Pro Gly Gln Phe Thr Asn Asn
    370                 375                 380

Val Val Val Lys Ser Cys Ser Asp Cys Gly Ile Cys Thr Ser Cys Ala
385                 390                 395                 400

Glu Ala Thr Thr Tyr Trp Lys Gly Val Ala Ala Thr His Met Cys Val
                405                 410                 415

Val Asp Thr Cys Asp Pro Ile Cys Val Gly Glu Asn Thr Val Tyr Arg
            420                 425                 430
```

```
Ile Cys Val Thr Asn Arg Gly Ser Ala Glu Asp Thr Asn Val Ser Leu
        435                 440                 445

Ile Leu Lys Phe Ser Lys Glu Leu Gln Pro Ile Ser Phe Ser Gly Pro
    450                 455                 460

Thr Lys Gly Thr Ile Thr Gly Asn Thr Val Val Phe Asp Ser Leu Pro
465                 470                 475                 480

Arg Leu Gly Ser Lys Glu Thr Val Glu Phe Ser Val Thr Leu Lys Ala
                485                 490                 495

Val Ser Ala Gly Asp Ala Arg Gly Glu Ala Ile Leu Ser Ser Asp Thr
            500                 505                 510

Leu Thr Val Pro Val Ser Asp Thr Glu Asn Thr His Ile Tyr
        515                 520                 525
```

<210> SEQ ID NO 99
<211> LENGTH: 498
<212> TYPE: DNA
<213> ORGANISM: Chlamydia muridarum

<400> SEQUENCE: 99

```
tccagacaga atgctgagga aaatctaaaa aattttgcta aagagctcaa gctccccgac      60

gtggccttcg atcagaataa tacgtgcatt ttgtttgttg atggagagtt ttctcttcac     120

ctgacctacg aagagcactc tgatcgcctt tatgtttacg cacctctcct tgacggactc     180

ccagataatc cgcaaagaaa gttggctctg tatgagaaat tgttggaagg ctctatgctc     240

ggaggccaaa tggctggtgg aggagtagga gttgctacta aagaacagtt gatcctaatg     300

cattgcgtgt tagatatgaa atatgcagag actaatctat tgaaagcttt tgcacagctt     360

ttcattgaaa ctgttgtgaa atggcgaacg gtctgttctg atatcagcgc tggacgagaa     420

ccttccgttg acactatgcc tcaaatgcct caaggaggca gcggaggaat tcaacctcct     480

ccaacaggaa ttcgtgcg                                                   498
```

<210> SEQ ID NO 100
<211> LENGTH: 166
<212> TYPE: PRT
<213> ORGANISM: Chlamydia muridarum

<400> SEQUENCE: 100

```
Ser Arg Gln Asn Ala Glu Glu Asn Leu Lys Asn Phe Ala Lys Glu Leu
1               5                   10                  15

Lys Leu Pro Asp Val Ala Phe Asp Gln Asn Asn Thr Cys Ile Leu Phe
            20                  25                  30

Val Asp Gly Glu Phe Ser Leu His Leu Thr Tyr Glu Glu His Ser Asp
        35                  40                  45

Arg Leu Tyr Val Tyr Ala Pro Leu Leu Asp Gly Leu Pro Asp Asn Pro
    50                  55                  60

Gln Arg Lys Leu Ala Leu Tyr Glu Lys Leu Leu Glu Gly Ser Met Leu
65                  70                  75                  80

Gly Gly Gln Met Ala Gly Gly Gly Val Gly Val Ala Thr Lys Glu Gln
                85                  90                  95

Leu Ile Leu Met His Cys Val Leu Asp Met Lys Tyr Ala Glu Thr Asn
            100                 105                 110

Leu Leu Lys Ala Phe Ala Gln Leu Phe Ile Glu Thr Val Val Lys Trp
        115                 120                 125

Arg Thr Val Cys Ser Asp Ile Ser Ala Gly Arg Glu Pro Ser Val Asp
    130                 135                 140
```

```
Thr Met Pro Gln Met Pro Gln Gly Gly Ser Gly Gly Ile Gln Pro Pro
145                 150                 155                 160

Pro Thr Gly Ile Arg Ala
                165


<210> SEQ ID NO 101
<211> LENGTH: 603
<212> TYPE: DNA
<213> ORGANISM: Chlamydia muridarum

<400> SEQUENCE: 101

ctcgctaatc ggttatttct aatcaccctt ataggttttg gctattctgc ttacggtgcc      60

agcacaggga aatcaccttc tttacaggtt attttagctg aagtcgagga tacatcttcg     120

cgcttacaag ctcatcagaa tgagcttgtt atgctctcgg aacgtttaga tgagcaagac     180

acaaaacttc aacaactctc gtcaactcag gcccgtaatc ttcctcaaca agttcaacgg     240

cttgagattg atctgagagc tctggctaaa acagctgctg tgctctcgca atctgttcag     300

gatatccgat catccgtgca aaataaatta caagaaatcc aacaagaaca aaaaaattta     360

gctcaaaatt tacgagcgct tcgcaactcc ttacaagcac tagttgatgg ctcttcccca     420

gaaaattata ttgatttttt ggccggggag acacctgaac atattcacgt tgttaaacaa     480

ggagaaaccc tgagtaaaat cgctagtaag tacaatatcc ctgtcgcaga attgaaaaaa     540

cttaataaat taaattccga tactattttt actgatcaaa gaatccgact tccaaaaaag     600

aaa                                                                   603


<210> SEQ ID NO 102
<211> LENGTH: 201
<212> TYPE: PRT
<213> ORGANISM: Chlamydia muridarum

<400> SEQUENCE: 102

Leu Ala Asn Arg Leu Phe Leu Ile Thr Leu Ile Gly Phe Gly Tyr Ser
1               5                   10                  15

Ala Tyr Gly Ala Ser Thr Gly Lys Ser Pro Ser Leu Gln Val Ile Leu
            20                  25                  30

Ala Glu Val Glu Asp Thr Ser Ser Arg Leu Gln Ala His Gln Asn Glu
        35                  40                  45

Leu Val Met Leu Ser Glu Arg Leu Asp Glu Gln Asp Thr Lys Leu Gln
    50                  55                  60

Gln Leu Ser Ser Thr Gln Ala Arg Asn Leu Pro Gln Gln Val Gln Arg
65                  70                  75                  80

Leu Glu Ile Asp Leu Arg Ala Leu Ala Lys Thr Ala Ala Val Leu Ser
                85                  90                  95

Gln Ser Val Gln Asp Ile Arg Ser Ser Val Gln Asn Lys Leu Gln Glu
            100                 105                 110

Ile Gln Gln Glu Gln Lys Asn Leu Ala Gln Asn Leu Arg Ala Leu Arg
        115                 120                 125

Asn Ser Leu Gln Ala Leu Val Asp Gly Ser Ser Pro Glu Asn Tyr Ile
    130                 135                 140

Asp Phe Leu Ala Gly Glu Thr Pro Glu His Ile His Val Val Lys Gln
145                 150                 155                 160

Gly Glu Thr Leu Ser Lys Ile Ala Ser Lys Tyr Asn Ile Pro Val Ala
                165                 170                 175

Glu Leu Lys Lys Leu Asn Lys Leu Asn Ser Asp Thr Ile Phe Thr Asp
```

180 185 190

Gln Arg Ile Arg Leu Pro Lys Lys Lys
195 200

<210> SEQ ID NO 103
<211> LENGTH: 3018
<212> TYPE: DNA
<213> ORGANISM: Chlamydia muridarum

<400> SEQUENCE: 103
acgactccaa taagtaattc tccatcttct attccaactg ttacagtatc aactactaca 60
gcatcttctg gatctctcgg aacttctact gtatcatcaa cgactacaag tacttcagtc 120
gcacaaacag caacaacaac atcttctgct tctacatcta taattcagtc tagtggagaa 180
aacatccaat ccactacagg taccccttct cctattacgt ctagtgtttc aacatccgct 240
ccatctccta aagcctccgc cactgcaaac aaaacttcaa gcgctgtttc tgggaaaatt 300
acctcacaag aaacttctga ggaatccgaa acccaagcca ctacatctga tggagaagtt 360
agtagtaatt acgatgatgt tgataccccg accaattcgt ccgattcgac agttgatagt 420
gattaccaag atgttgagac tcagtacaaa acaattagca acaatggtga aaacacttat 480
gaaacaatcg gaagtcatgg tgagaaaaac acacacgtcc aggaaagcca tgcatccgga 540
acaggaaatc ccataaataa tcagcaagaa gctattagac agctccgatc atctacctat 600
acaaccagcc ctcgtaatga gaatatattt agtccaggac cggaaggtct acctaatatg 660
tctcttccta gttacagccc tacagataaa agttctctac tagctttcct atctaatccc 720
aatacaaaag caaaaatgct cgaacactcc gggcatttag tctttataga cacaactaga 780
agtagcttta tctttgttcc gaatggaaat tgggatcaag tctgttccat gaaggttcag 840
aatgggaaaa ctaaagaaga ccttggctta aaggacttag aagatatgtg tgcaaagttt 900
tgcacaggat acaataaatt ctcctctgat tggggaaatc gagttgaccc cttggtctct 960
tctaaggccg ggatagaaag tgggggcac ctcccaagct cagttatcat caacaacaaa 1020
tttagaacct gtgttgccta tggccgtgg aaccccaaag aaaacggccc caattatact 1080
ccttcagcct ggagacgtgg gcatcgagta gattttggaa agatctttga tggaacagcg 1140
ccgtttaata aaatcaactg gggctcttcc cctacccctg gtgatgacgg catctccttc 1200
tctaatgaaa ctattgggtc tgaaccattc gcgacacctc cctcatcccc atcgcaaacc 1260
cccgttatca acgtcaatgt taatgtcggt ggaaccaatg ttaatattgg ggatacaaac 1320
gtatctaaag gatccggcac accaacatct tctcaatctg tggacatgtc tacagatact 1380
agcgatttag ataccagtga tattgataca aacaaccaaa ctaacggcga tatcaacacg 1440
aatgacaact ccaataatgt cgatggaagt ttatctgacg ttgattcaag ggtggaagac 1500
gatgacggtg tatcggatac agagtccact aatggcaatg actctggtaa aactacttcc 1560
acagaagaaa atggtgaccc aagcggacca gacatcctgg ctgctgtacg taaacaccta 1620
gacactgtct atccaggaga aaatggcgga tctacagaag gacctctccc tgctaatcaa 1680
aatctgggga acgttatcca tgatgtggag cagaatggat ctgctaaaga aactattatc 1740
actccaggag atacagggcc tacagactca agctcctctg tagatgctga tgcagacgtt 1800
gaagatactt ctgatactga ctctggaatc ggagacgacg acggtgtatc ggatacagag 1860
tccactaatg gtaataactc tggtaaaact acttccacag aagaaaatgg tgacccaagc 1920
ggaccagaca tcctggctgc tgtacgtaaa cacctagaca ctgtctatcc aggagaaaat 1980

```
ggcggatcta cagaaggacc tctccctgct aatcaaaatc tggggaacgt tatccatgat   2040

gtagaacaaa acggagccgc tcaagaaact attatcactc caggagatac ggaatctaca   2100

gacacaagct ctagtgtaaa tgctaatgca gacttagaag atgtttctga tgctgattca   2160

ggattcgggg atgatgacgg tatatcggat acagagtcca ctaatggtaa cgactctgga   2220

aaaaatactc ctgtagggga tggtggtaca ccaagcggac cagatatcct agctgctgta   2280

cgcaaacatc tagacactgt ctatccagga gaaaatggtg gatctacaga gagaccttta   2340

cccgctaatc aaaatttagg agatatcatt catgatgtag aacaaaacgg aagcgctaaa   2400

gaaactgtag tatcgcctta tcgaggagga ggaggaaata catcttcccc aattggatta   2460

gcctccctgc ttccagcaac accatccaca cctttgatga caacacctag aacaaatggg   2520

aaagctgcag cttcttcttt gatgataaaa ggaggagaaa ctcaagccaa gctagttaag   2580

aatggcggca atatccctgg agaaaccaca ttagcagaat tactccctcg tttaagagga   2640

caccttgaca aagtctttac ttcagacggg aagtttacaa atcttaatgg acctcaactt   2700

ggagccatca tagaccaatt ccgcaaagaa acgggttccg gaggaatcat agctcataca   2760

gatagtgttc caggagagaa cggaacagcc tctcctctca caggaagttc aggggaaaaa   2820

gtctctctct atgatgcagc gaaaaacgtc actcaagctt taacaagtgt tacgaacaaa   2880

gtaaccctag caatgcaagg acaaaaactg gaaggaatta taaacaacaa caataccccc   2940

tcttctattg gacaaaatct tttcgcagca gcgagggcaa cgacacaatc cctcagttca   3000

ttaattggaa ccgtacaa                                                 3018
```

```
<210> SEQ ID NO 104
<211> LENGTH: 1006
<212> TYPE: PRT
<213> ORGANISM: Chlamydia muridarum

<400> SEQUENCE: 104

Thr Thr Pro Ile Ser Asn Ser Pro Ser Ser Ile Pro Thr Val Thr Val
1               5                   10                  15

Ser Thr Thr Thr Ala Ser Ser Gly Ser Leu Gly Thr Ser Thr Val Ser
            20                  25                  30

Ser Thr Thr Thr Ser Thr Ser Val Ala Gln Thr Ala Thr Thr Thr Ser
        35                  40                  45

Ser Ala Ser Thr Ser Ile Ile Gln Ser Ser Gly Glu Asn Ile Gln Ser
    50                  55                  60

Thr Thr Gly Thr Pro Ser Pro Ile Thr Ser Ser Val Ser Thr Ser Ala
65                  70                  75                  80

Pro Ser Pro Lys Ala Ser Ala Thr Ala Asn Lys Thr Ser Ser Ala Val
                85                  90                  95

Ser Gly Lys Ile Thr Ser Gln Glu Thr Ser Glu Glu Ser Glu Thr Gln
            100                 105                 110

Ala Thr Thr Ser Asp Gly Glu Val Ser Ser Asn Tyr Asp Asp Val Asp
        115                 120                 125

Thr Pro Thr Asn Ser Ser Asp Ser Thr Val Asp Ser Asp Tyr Gln Asp
    130                 135                 140

Val Glu Thr Gln Tyr Lys Thr Ile Ser Asn Asn Gly Glu Asn Thr Tyr
145                 150                 155                 160

Glu Thr Ile Gly Ser His Gly Glu Lys Asn Thr His Val Gln Glu Ser
                165                 170                 175

His Ala Ser Gly Thr Gly Asn Pro Ile Asn Asn Gln Gln Glu Ala Ile
            180                 185                 190
```

```
Arg Gln Leu Arg Ser Ser Thr Tyr Thr Thr Ser Pro Arg Asn Glu Asn
        195                 200                 205

Ile Phe Ser Pro Gly Pro Glu Gly Leu Pro Asn Met Ser Leu Pro Ser
    210                 215                 220

Tyr Ser Pro Thr Asp Lys Ser Ser Leu Leu Ala Phe Leu Ser Asn Pro
225                 230                 235                 240

Asn Thr Lys Ala Lys Met Leu Glu His Ser Gly His Leu Val Phe Ile
                245                 250                 255

Asp Thr Thr Arg Ser Ser Phe Ile Phe Val Pro Asn Gly Asn Trp Asp
            260                 265                 270

Gln Val Cys Ser Met Lys Val Gln Asn Gly Lys Thr Lys Glu Asp Leu
        275                 280                 285

Gly Leu Lys Asp Leu Glu Asp Met Cys Ala Lys Phe Cys Thr Gly Tyr
    290                 295                 300

Asn Lys Phe Ser Ser Asp Trp Gly Asn Arg Val Asp Pro Leu Val Ser
305                 310                 315                 320

Ser Lys Ala Gly Ile Glu Ser Gly Gly His Leu Pro Ser Ser Val Ile
                325                 330                 335

Ile Asn Asn Lys Phe Arg Thr Cys Val Ala Tyr Gly Pro Trp Asn Pro
            340                 345                 350

Lys Glu Asn Gly Pro Asn Tyr Thr Pro Ser Ala Trp Arg Arg Gly His
        355                 360                 365

Arg Val Asp Phe Gly Lys Ile Phe Asp Gly Thr Ala Pro Phe Asn Lys
    370                 375                 380

Ile Asn Trp Gly Ser Ser Pro Thr Pro Gly Asp Asp Gly Ile Ser Phe
385                 390                 395                 400

Ser Asn Glu Thr Ile Gly Ser Glu Pro Phe Ala Thr Pro Pro Ser Ser
                405                 410                 415

Pro Ser Gln Thr Pro Val Ile Asn Val Asn Val Asn Val Gly Gly Thr
            420                 425                 430

Asn Val Asn Ile Gly Asp Thr Asn Val Ser Lys Gly Ser Gly Thr Pro
        435                 440                 445

Thr Ser Ser Gln Ser Val Asp Met Ser Thr Asp Thr Ser Asp Leu Asp
    450                 455                 460

Thr Ser Asp Ile Asp Thr Asn Asn Gln Thr Asn Gly Asp Ile Asn Thr
465                 470                 475                 480

Asn Asp Asn Ser Asn Asn Val Asp Gly Ser Leu Ser Asp Val Asp Ser
                485                 490                 495

Arg Val Glu Asp Asp Asp Gly Val Ser Asp Thr Glu Ser Thr Asn Gly
            500                 505                 510

Asn Asp Ser Gly Lys Thr Thr Ser Thr Glu Glu Asn Gly Asp Pro Ser
        515                 520                 525

Gly Pro Asp Ile Leu Ala Ala Val Arg Lys His Leu Asp Thr Val Tyr
    530                 535                 540

Pro Gly Glu Asn Gly Gly Ser Thr Glu Gly Pro Leu Pro Ala Asn Gln
545                 550                 555                 560

Asn Leu Gly Asn Val Ile His Asp Val Glu Gln Asn Gly Ser Ala Lys
                565                 570                 575

Glu Thr Ile Ile Thr Pro Gly Asp Thr Gly Pro Thr Asp Ser Ser Ser
            580                 585                 590

Ser Val Asp Ala Asp Ala Asp Val Glu Asp Thr Ser Asp Thr Asp Ser
        595                 600                 605
```

```
Gly Ile Gly Asp Asp Asp Gly Val Ser Asp Thr Glu Ser Thr Asn Gly
    610                 615                 620

Asn Asn Ser Gly Lys Thr Thr Ser Thr Glu Glu Asn Gly Asp Pro Ser
625                 630                 635                 640

Gly Pro Asp Ile Leu Ala Ala Val Arg Lys His Leu Asp Thr Val Tyr
                645                 650                 655

Pro Gly Glu Asn Gly Gly Ser Thr Glu Gly Pro Leu Pro Ala Asn Gln
            660                 665                 670

Asn Leu Gly Asn Val Ile His Asp Val Glu Gln Asn Gly Ala Ala Gln
        675                 680                 685

Glu Thr Ile Ile Thr Pro Gly Asp Thr Glu Ser Thr Asp Thr Ser Ser
    690                 695                 700

Ser Val Asn Ala Asn Ala Asp Leu Glu Asp Val Ser Asp Ala Asp Ser
705                 710                 715                 720

Gly Phe Gly Asp Asp Asp Gly Ile Ser Asp Thr Glu Ser Thr Asn Gly
                725                 730                 735

Asn Asp Ser Gly Lys Asn Thr Pro Val Gly Asp Gly Gly Thr Pro Ser
            740                 745                 750

Gly Pro Asp Ile Leu Ala Ala Val Arg Lys His Leu Asp Thr Val Tyr
        755                 760                 765

Pro Gly Glu Asn Gly Gly Ser Thr Glu Arg Pro Leu Pro Ala Asn Gln
    770                 775                 780

Asn Leu Gly Asp Ile Ile His Asp Val Glu Gln Asn Gly Ser Ala Lys
785                 790                 795                 800

Glu Thr Val Val Ser Pro Tyr Arg Gly Gly Gly Gly Asn Thr Ser Ser
                805                 810                 815

Pro Ile Gly Leu Ala Ser Leu Leu Pro Ala Thr Pro Ser Thr Pro Leu
            820                 825                 830

Met Thr Thr Pro Arg Thr Asn Gly Lys Ala Ala Ala Ser Ser Leu Met
        835                 840                 845

Ile Lys Gly Gly Glu Thr Gln Ala Lys Leu Val Lys Asn Gly Gly Asn
    850                 855                 860

Ile Pro Gly Glu Thr Thr Leu Ala Glu Leu Leu Pro Arg Leu Arg Gly
865                 870                 875                 880

His Leu Asp Lys Val Phe Thr Ser Asp Gly Lys Phe Thr Asn Leu Asn
                885                 890                 895

Gly Pro Gln Leu Gly Ala Ile Ile Asp Gln Phe Arg Lys Glu Thr Gly
            900                 905                 910

Ser Gly Gly Ile Ile Ala His Thr Asp Ser Val Pro Gly Glu Asn Gly
        915                 920                 925

Thr Ala Ser Pro Leu Thr Gly Ser Ser Gly Glu Lys Val Ser Leu Tyr
    930                 935                 940

Asp Ala Ala Lys Asn Val Thr Gln Ala Leu Thr Ser Val Thr Asn Lys
945                 950                 955                 960

Val Thr Leu Ala Met Gln Gly Gln Lys Leu Glu Gly Ile Ile Asn Asn
                965                 970                 975

Asn Asn Thr Pro Ser Ser Ile Gly Gln Asn Leu Phe Ala Ala Ala Arg
            980                 985                 990

Ala Thr Thr Gln Ser Leu Ser Ser  Leu Ile Gly Thr Val  Gln
        995                 1000                1005
```

<210> SEQ ID NO 105
<211> LENGTH: 702
<212> TYPE: DNA

<213> ORGANISM: Chlamydia muridarum

<400> SEQUENCE: 105

```
tgttcaaaag agagcaaaga ctctgttagt gaaaaattta ttgtaggaac taacgcaacg      60
tatcctcctt ttgagtttgt tgatgaaaga ggtgagacgg ttggctttga tattgattta     120
gctagggaga ttagtaaaaa gctagggaaa aaattagaag tccgagaatt tgcttttgat     180
gcactcgttc tcaatttaaa acagcatcgt attgatgcaa ttatggcagg ggtgtccatt     240
acgtcttctc gattgaaaga aattttgatg attccctact atggcgaaga aataaagagt     300
ttggttttag tgtttaagga tggagactca aagtctttac cactagatca gtataattct     360
gttgctgttc aaactggcac gtaccaagag gaatatttac agtctcttcc aggggtgcgt     420
attcgctctt ttgatagtac tttagaagtg cttatggaag ttttgcatag caagtctcct     480
atagctgttt tagaaccgtc tattgcgcag gtcgttttaa aagattttcc gacgctcact     540
actgaaacga tagatcttcc tgaagataaa tgggttttag ggtatggaat tggagttgct     600
tctgatcgac catctctagc ttctgatata gaagctgctg tacaagagat caagaaagaa     660
ggagtgttag cagagttaga gcaaaaatgg ggtttgaacg gc                        702
```

<210> SEQ ID NO 106
<211> LENGTH: 234
<212> TYPE: PRT
<213> ORGANISM: Chlamydia muridarum

<400> SEQUENCE: 106

```
Cys Ser Lys Glu Ser Lys Asp Ser Val Ser Glu Lys Phe Ile Val Gly
1               5                   10                  15

Thr Asn Ala Thr Tyr Pro Pro Phe Glu Phe Val Asp Glu Arg Gly Glu
            20                  25                  30

Thr Val Gly Phe Asp Ile Asp Leu Ala Arg Glu Ile Ser Lys Lys Leu
        35                  40                  45

Gly Lys Lys Leu Glu Val Arg Glu Phe Ala Phe Asp Ala Leu Val Leu
    50                  55                  60

Asn Leu Lys Gln His Arg Ile Asp Ala Ile Met Ala Gly Val Ser Ile
65                  70                  75                  80

Thr Ser Ser Arg Leu Lys Glu Ile Leu Met Ile Pro Tyr Tyr Gly Glu
                85                  90                  95

Glu Ile Lys Ser Leu Val Leu Val Phe Lys Asp Gly Asp Ser Lys Ser
            100                 105                 110

Leu Pro Leu Asp Gln Tyr Asn Ser Val Ala Val Gln Thr Gly Thr Tyr
        115                 120                 125

Gln Glu Glu Tyr Leu Gln Ser Leu Pro Gly Val Arg Ile Arg Ser Phe
    130                 135                 140

Asp Ser Thr Leu Glu Val Leu Met Glu Val Leu His Ser Lys Ser Pro
145                 150                 155                 160

Ile Ala Val Leu Glu Pro Ser Ile Ala Gln Val Val Leu Lys Asp Phe
                165                 170                 175

Pro Thr Leu Thr Thr Glu Thr Ile Asp Leu Pro Glu Asp Lys Trp Val
            180                 185                 190

Leu Gly Tyr Gly Ile Gly Val Ala Ser Asp Arg Pro Ser Leu Ala Ser
        195                 200                 205

Asp Ile Glu Ala Ala Val Gln Glu Ile Lys Lys Glu Gly Val Leu Ala
    210                 215                 220

Glu Leu Glu Gln Lys Trp Gly Leu Asn Gly
```

225 230

<210> SEQ ID NO 107
<211> LENGTH: 378
<212> TYPE: DNA
<213> ORGANISM: Chlamydia trachomatis

<400> SEQUENCE: 107
gaagaaaaag gcatcttaca attggttgaa atttcgcgag caatggcttt acagggagtt 60
tgtccttgga ctaatttaca gagtgtggag tctatgttgc agtatatagc aggggagtgt 120
caggagttgg ctgatgctgt acaagaaaat aaagcttcgt tggaaatcgc ttcggaagcc 180
ggagacgtac ttactttagt attgaccttg tgtttcttgc tagaaagaga aggaaagctt 240
aaagctgaag aagtatttgt agaagctttg gctaagttgc gtcgtcgatc tcctcatgtt 300
tttgatcctc ataatcaaat ttctttagaa caggctgaag aatactgggc tcgtatgaaa 360
cagcaagaaa aaatttct 378

<210> SEQ ID NO 108
<211> LENGTH: 126
<212> TYPE: PRT
<213> ORGANISM: Chlamydia trachomatis

<400> SEQUENCE: 108

Glu Glu Lys Gly Ile Leu Gln Leu Val Glu Ile Ser Arg Ala Met Ala
1 5 10 15

Leu Gln Gly Val Cys Pro Trp Thr Asn Leu Gln Ser Val Glu Ser Met
20 25 30

Leu Gln Tyr Ile Ala Gly Glu Cys Gln Glu Leu Ala Asp Ala Val Gln
35 40 45

Glu Asn Lys Ala Ser Leu Glu Ile Ala Ser Glu Ala Gly Asp Val Leu
50 55 60

Thr Leu Val Leu Thr Leu Cys Phe Leu Leu Glu Arg Glu Gly Lys Leu
65 70 75 80

Lys Ala Glu Glu Val Phe Val Glu Ala Leu Ala Lys Leu Arg Arg Arg
85 90 95

Ser Pro His Val Phe Asp Pro His Asn Gln Ile Ser Leu Glu Gln Ala
100 105 110

Glu Glu Tyr Trp Ala Arg Met Lys Gln Gln Glu Lys Ile Ser
115 120 125

<210> SEQ ID NO 109
<211> LENGTH: 1173
<212> TYPE: DNA
<213> ORGANISM: Chlamydia trachomatis

<400> SEQUENCE: 109
gattactaca cgatattggg tgtagcgaag actgctactc ctgaagaaat aaagaaagct 60
taccgtaagc tcgctgtaaa gtaccatcca gataagaatc ctggggatgc tgaagcggag 120
cgacgcttta aagaagtttc tgaagcctat gaagtattag gtgatgcgca gaagcgggag 180
tcatatgatc gttacggcaa agacggtcca tttgctggtg ctggaggatt cggtggcgct 240
ggcatgggga atatggaaga cgctttgcga acatttatgg gagcttttgg cggcgatttc 300
ggtggtaatg gaggcggttt ctttgaaggg ctttttggag gacttggaga agctttcgga 360
atgcgtggag gctcagaaag ttctcgacaa ggagctagta agaaggtgca tattacgctg 420
tccttcgagg aggcggcaaa aggtgttgaa aaagaacttc ttgtttcagg ctataaatct 480

```
tgtgatgctt gttctggtag tggagccaat actgctaaag gtgtaaaagt ttgtgatcga    540

tgcaagggct ctggtcaggt agtgcaaagc cgaggctttt tctccatggc ttctacttgc    600

cctgattgta gtggtgaagg tcgggttatc acagatcctt gttcagtttg tcgtgggcag    660

ggacgtatca aggataaacg tagcgtccat gttaatatcc cagctggagt cgattctggg    720

atgagattaa agatggaagg ctatggagat gctggccaaa atggagcgcc tgcaggggat    780

ctgtatgttt ttattgatgt agagcctcat cctgttttcg agcgccatgg ggatgattta    840

gttttagagc ttcctattgg atttgttgat gcggctttag ggatcaagaa ggaaatccct    900

acactcttaa aagaaggtac ttgccgtttg agtatcccag aagggattca gagcggaaca    960

gttcttaaag ttagagggca gggattccct aatgtgcatg ggaaatccag aggagatctt   1020

ttagtaagag tatctgtgga gactccccag cacctatcta atgaacaaaa agatttattg   1080

agacagtttg ctgctacgga gaaggctgaa aatttcccta agaaacggag tttcttagac   1140

aaaatcaaag gttttttttc tgactttgct gta                                1173


<210> SEQ ID NO 110
<211> LENGTH: 391
<212> TYPE: PRT
<213> ORGANISM: Chlamydia trachomatis

<400> SEQUENCE: 110

Asp Tyr Tyr Thr Ile Leu Gly Val Ala Lys Thr Ala Thr Pro Glu Glu
1               5                   10                  15

Ile Lys Lys Ala Tyr Arg Lys Leu Ala Val Lys Tyr His Pro Asp Lys
            20                  25                  30

Asn Pro Gly Asp Ala Glu Ala Glu Arg Arg Phe Lys Glu Val Ser Glu
        35                  40                  45

Ala Tyr Glu Val Leu Gly Asp Ala Gln Lys Arg Glu Ser Tyr Asp Arg
    50                  55                  60

Tyr Gly Lys Asp Gly Pro Phe Ala Gly Ala Gly Gly Phe Gly Gly Ala
65                  70                  75                  80

Gly Met Gly Asn Met Glu Asp Ala Leu Arg Thr Phe Met Gly Ala Phe
                85                  90                  95

Gly Gly Asp Phe Gly Gly Asn Gly Gly Gly Phe Phe Glu Gly Leu Phe
            100                 105                 110

Gly Gly Leu Gly Glu Ala Phe Gly Met Arg Gly Gly Ser Glu Ser Ser
        115                 120                 125

Arg Gln Gly Ala Ser Lys Lys Val His Ile Thr Leu Ser Phe Glu Glu
    130                 135                 140

Ala Ala Lys Gly Val Glu Lys Glu Leu Leu Val Ser Gly Tyr Lys Ser
145                 150                 155                 160

Cys Asp Ala Cys Ser Gly Ser Gly Ala Asn Thr Ala Lys Gly Val Lys
                165                 170                 175

Val Cys Asp Arg Cys Lys Gly Ser Gly Gln Val Val Gln Ser Arg Gly
            180                 185                 190

Phe Phe Ser Met Ala Ser Thr Cys Pro Asp Cys Ser Gly Glu Gly Arg
        195                 200                 205

Val Ile Thr Asp Pro Cys Ser Val Cys Arg Gly Gln Gly Arg Ile Lys
    210                 215                 220

Asp Lys Arg Ser Val His Val Asn Ile Pro Ala Gly Val Asp Ser Gly
225                 230                 235                 240

Met Arg Leu Lys Met Glu Gly Tyr Gly Asp Ala Gly Gln Asn Gly Ala
```

-continued

```
                245                 250                 255

Pro Ala Gly Asp Leu Tyr Val Phe Ile Asp Val Glu Pro His Pro Val
            260                 265                 270

Phe Glu Arg His Gly Asp Asp Leu Val Leu Glu Leu Pro Ile Gly Phe
        275                 280                 285

Val Asp Ala Ala Leu Gly Ile Lys Lys Glu Ile Pro Thr Leu Leu Lys
    290                 295                 300

Glu Gly Thr Cys Arg Leu Ser Ile Pro Glu Gly Ile Gln Ser Gly Thr
305                 310                 315                 320

Val Leu Lys Val Arg Gly Gln Gly Phe Pro Asn Val His Gly Lys Ser
                325                 330                 335

Arg Gly Asp Leu Leu Val Arg Val Ser Val Glu Thr Pro Gln His Leu
            340                 345                 350

Ser Asn Glu Gln Lys Asp Leu Leu Arg Gln Phe Ala Ala Thr Glu Lys
        355                 360                 365

Ala Glu Asn Phe Pro Lys Lys Arg Ser Phe Leu Asp Lys Ile Lys Gly
    370                 375                 380

Phe Phe Ser Asp Phe Ala Val
385                 390


<210> SEQ ID NO 111
<211> LENGTH: 360
<212> TYPE: DNA
<213> ORGANISM: Chlamydia trachomatis

<400> SEQUENCE: 111

aataaaaaac tccaagatct gtctaaactg ctcactattg agcttttcaa gaaacgtaca      60

cggttggaaa cagtaaaaaa agcgctctcc acaatagaac atcgcttaca acaaatacag     120

gagcacatcg cgaaaatttc cttaacaagg cacaaacaat tcctatgtcg gtcatatacc     180

catgaatatg accaacattt agaacattta caaagagagc aaacttctct atataaacag     240

catcagaccc tgaaaacgtc tttgaaagat gcttatggcg acatacaaaa acaactagac     300

caaagaaaaa ttatcgaaaa gatccatgac agtaaatatc ctataaagag cgcgaataac     360


<210> SEQ ID NO 112
<211> LENGTH: 120
<212> TYPE: PRT
<213> ORGANISM: Chlamydia trachomatis

<400> SEQUENCE: 112

Asn Lys Lys Leu Gln Asp Leu Ser Lys Leu Leu Thr Ile Glu Leu Phe
1               5                   10                  15

Lys Lys Arg Thr Arg Leu Glu Thr Val Lys Lys Ala Leu Ser Thr Ile
            20                  25                  30

Glu His Arg Leu Gln Gln Ile Gln Glu His Ile Ala Lys Ile Ser Leu
        35                  40                  45

Thr Arg His Lys Gln Phe Leu Cys Arg Ser Tyr Thr His Glu Tyr Asp
    50                  55                  60

Gln His Leu Glu His Leu Gln Arg Glu Gln Thr Ser Leu Tyr Lys Gln
65                  70                  75                  80

His Gln Thr Leu Lys Thr Ser Leu Lys Asp Ala Tyr Gly Asp Ile Gln
                85                  90                  95

Lys Gln Leu Asp Gln Arg Lys Ile Ile Glu Lys Ile His Asp Ser Lys
            100                 105                 110

Tyr Pro Ile Lys Ser Ala Asn Asn
```

115 120

<210> SEQ ID NO 113
<211> LENGTH: 1224
<212> TYPE: DNA
<213> ORGANISM: Chlamydia trachomatis

<400> SEQUENCE: 113
gcgtggtggc tacacaaacg attccctcat gtgcagctgt ctattctaga aaaagagtct 60
cgatctggag ggctaattgt cacagagaaa caacaagggt tttccctcaa tatgggccct 120
aaaggttttg ttttagctca tgatgggcaa cacacccttc acctcattca gtctttaggc 180
ctagcagacg agctattata tagctctcca gaggctaaaa accgctttat ccactataat 240
aataaaaccc gaaaagtctc gccttggact attttcaaac aaaatctccc tctctctttt 300
gctaaggatt tctttgcgcg tccttacaaa caagacagct ccgtggaagc cttctttaaa 360
agacacagtt cttccaagct tagaagaaat cttttaaatc ccattagcat tgctattcgt 420
gcaggacata gtcatatatt gtctgcacag atggcttacc cagaattaac acgaagagaa 480
gctcaaacag gatcgttgtt acgtagttat ctcaaagatt ttcctaaaga gaaacgcaca 540
ggcccttatt tagctacctt gcggtctggg atgggaatgc taacccaggc tttgcatgat 600
aaattgcctg ctacctggta tttttctgca cccgtcagca aaatccgtca gttggcgaat 660
gggaaaattt ctctttcatc tcctcaagga gaaataacgg gagatatgct catttatgct 720
gggtccgtgc acgatctccc ttcctgtcta gaagggatcc ctgaaaccaa gcttatcaag 780
caaacgactt catcttggga tctctcttgt gtatctttag gatggcatgc atccttccct 840
atccctcatg gatatggcat gcttttcgct gatacgcctc ccttattagg gatcgtgttt 900
aatacggaag tgttccctca acccgagcgg cctaatacaa tagtctctct tcttttagaa 960
ggtcgatggc accaagaaga agcgtatgct ttctcactag cagctatttc tgagtacctg 1020
caaatttaca ctcctcccca agctttctca ctattctctc ctcgagaggg acttccccaa 1080
caccatgttg gatttatcca atcccgccaa cgccttctat ctaaacttcc tcacaatata 1140
aaaattgtag ggcagaattt tgcaggtcca ggtctcaacc gcgctacagc gtctgcttat 1200
aaagctatag cttctttact atca 1224

<210> SEQ ID NO 114
<211> LENGTH: 408
<212> TYPE: PRT
<213> ORGANISM: Chlamydia trachomatis

<400> SEQUENCE: 114

Ala Trp Trp Leu His Lys Arg Phe Pro His Val Gln Leu Ser Ile Leu
1 5 10 15

Glu Lys Glu Ser Arg Ser Gly Gly Leu Ile Val Thr Glu Lys Gln Gln
20 25 30

Gly Phe Ser Leu Asn Met Gly Pro Lys Gly Phe Val Leu Ala His Asp
35 40 45

Gly Gln His Thr Leu His Leu Ile Gln Ser Leu Gly Leu Ala Asp Glu
50 55 60

Leu Leu Tyr Ser Ser Pro Glu Ala Lys Asn Arg Phe Ile His Tyr Asn
65 70 75 80

Asn Lys Thr Arg Lys Val Ser Pro Trp Thr Ile Phe Lys Gln Asn Leu
85 90 95

Pro Leu Ser Phe Ala Lys Asp Phe Phe Ala Arg Pro Tyr Lys Gln Asp

```
            100                 105                 110

Ser Ser Val Glu Ala Phe Phe Lys Arg His Ser Ser Ser Lys Leu Arg
        115                 120                 125

Arg Asn Leu Leu Asn Pro Ile Ser Ile Ala Ile Arg Ala Gly His Ser
    130                 135                 140

His Ile Leu Ser Ala Gln Met Ala Tyr Pro Glu Leu Thr Arg Arg Glu
145                 150                 155                 160

Ala Gln Thr Gly Ser Leu Leu Arg Ser Tyr Leu Lys Asp Phe Pro Lys
                165                 170                 175

Glu Lys Arg Thr Gly Pro Tyr Leu Ala Thr Leu Arg Ser Gly Met Gly
            180                 185                 190

Met Leu Thr Gln Ala Leu His Asp Lys Leu Pro Ala Thr Trp Tyr Phe
        195                 200                 205

Ser Ala Pro Val Ser Lys Ile Arg Gln Leu Ala Asn Gly Lys Ile Ser
    210                 215                 220

Leu Ser Ser Pro Gln Gly Glu Ile Thr Gly Asp Met Leu Ile Tyr Ala
225                 230                 235                 240

Gly Ser Val His Asp Leu Pro Ser Cys Leu Glu Gly Ile Pro Glu Thr
                245                 250                 255

Lys Leu Ile Lys Gln Thr Thr Ser Ser Trp Asp Leu Ser Cys Val Ser
            260                 265                 270

Leu Gly Trp His Ala Ser Phe Pro Ile Pro His Gly Tyr Gly Met Leu
        275                 280                 285

Phe Ala Asp Thr Pro Pro Leu Leu Gly Ile Val Phe Asn Thr Glu Val
    290                 295                 300

Phe Pro Gln Pro Glu Arg Pro Asn Thr Ile Val Ser Leu Leu Leu Glu
305                 310                 315                 320

Gly Arg Trp His Gln Glu Glu Ala Tyr Ala Phe Ser Leu Ala Ala Ile
                325                 330                 335

Ser Glu Tyr Leu Gln Ile Tyr Thr Pro Pro Gln Ala Phe Ser Leu Phe
            340                 345                 350

Ser Pro Arg Glu Gly Leu Pro Gln His His Val Gly Phe Ile Gln Ser
        355                 360                 365

Arg Gln Arg Leu Leu Ser Lys Leu Pro His Asn Ile Lys Ile Val Gly
    370                 375                 380

Gln Asn Phe Ala Gly Pro Gly Leu Asn Arg Ala Thr Ala Ser Ala Tyr
385                 390                 395                 400

Lys Ala Ile Ala Ser Leu Leu Ser
                405


<210> SEQ ID NO 115
<211> LENGTH: 2070
<212> TYPE: DNA
<213> ORGANISM: Chlamydia trachomatis

<400> SEQUENCE: 115

acgctctttc attctcatca tgatgccgtc tctccagaca gctacctatg ttcttccctt      60

cagttagttg gtactggcgt atacgaagga gaaatcgaga ttcaaaatat cccctcttat     120

ttccttggat tccaattacc ctctcattgc atacacctta atttaaagag ctctctagct     180

caattaggaa tagatgcctc ccttcttcac tgcgaattga gcaaaaatca acatcgagca     240

catatacatg ctcaatttac cggtcatggc cccattgctg aatctatgct agcccttctc     300

caaccaggag atcgtgtagc aaaactattt gctgcagacg atcgcagact ggtccgatct     360
```

-continued

```
ccagattacc tcgaaagcat gctgaaaaat acagataaag ctggccatcc tttgctctgt    420
tttgggaaaa aattagaaca cttgatttct tttgatgtgg tagatgatcg ccttgtcgtc    480
tcccttccta ccctgccggg agttgttcgt tatgattcgg atatttatgg actccttcct    540
cttattcaaa aatcactcag taatcccaaa ctcagcattc gtcacttttt agctctgtac    600
caacagattg tggaagggca acatgtctct tgcggaaacc atattcttct gatcaaaaca    660
gaaccgctgc acatccgcac tgtatttgct cgcgtggtaa atcaactcct ccctcaaggt    720
ctctcccaca cttctgccaa tattttggaa ccaaccactc gagaatccgg ggatatcttt    780
gaattttttg ggaacccttc tgcacagata gaaagaattc ctttagaatt tttcactatc    840
gaaccctata aagaacattc ttacttctgt aatcgggatt tattacaaac catcttacaa    900
tcagaaagcg aaatcaaaaa aatattcgaa acagcgccca aagaacctgt caaagctgcc    960
acctatttat caaaaggcag tgaaatctct tccctgcaca cagactcttg gctcacagga   1020
tccgcagctg cctatcaata tagtgagcaa gcagataaaa acgagtacac tcatgctcaa   1080
ccttgctatc ctttcttaga agcaatggaa atgggcctga tcaatagcga aggagcctta   1140
ctcactcgtt atttcccttc agctagctta aaaggaatgt tgatttccta ccatgtgcgc   1200
cactatctca aacaaatcta ctttcaagtt ccctcttata cacatggaaa ctatttctct   1260
cataatgaca gaggtttgct attagatctg cagcaagcag atattgatgt tttctgggca   1320
gatgaagaaa gcggccgtgt gttgcaatat acaaaacgac gcgataagaa tagcggtatg   1380
ttcgtgatca aaaatcgtgt tgaagagttt cgatcagctt attttattgc tatttatggc   1440
tctcgtctcc ttgagaataa tttctctgct cagctccata ccctcctagc gggcttacag   1500
caagcagcac atactctcgg cattcctgga ttctcaaagc ctaccccact tgcagtcatc   1560
accggaggcg gcactggagt tatggccaca ggaaatcgtg tagctaaaga actaggaatc   1620
ctatcttgtg gaaccgttct tgatttagaa gcttctccag cacaaatcga ccaacctacc   1680
aatgaattct tagatgctaa aatgacatac cgcctacctc aacttataga aaggcaagaa   1740
cacttttatg cagaccttcc tatccttgta gttggcggtg taggaaccga tttcgaactc   1800
tacctagaac ttgtctatct caaaacagga gctaaaccac cgactcccat tttcctaatt   1860
ggacctattg aatactggaa agaaaaagtg gcccacgcct acgagatcaa cctcaaagca   1920
ggaaccatcc gtggatccga atggatcagc aactgcctat attgtatcac ttctccggaa   1980
gctggaattg ccgtattcga acaattccta gctggagaac tccctatagg atacgactat   2040
cctccagctc cagatggatt agtgatcgtc                                    2070
```

<210> SEQ ID NO 116
<211> LENGTH: 690
<212> TYPE: PRT
<213> ORGANISM: Chlamydia trachomatis

<400> SEQUENCE: 116

```
Thr Leu Phe His Ser His His Asp Ala Val Ser Pro Asp Ser Tyr Leu
1               5                   10                  15

Cys Ser Ser Leu Gln Leu Val Gly Thr Gly Val Tyr Glu Gly Glu Ile
            20                  25                  30

Glu Ile Gln Asn Ile Pro Ser Tyr Phe Leu Gly Phe Gln Leu Pro Ser
        35                  40                  45

His Cys Ile His Leu Asn Leu Lys Ser Ser Leu Ala Gln Leu Gly Ile
    50                  55                  60

Asp Ala Ser Leu Leu His Cys Glu Leu Ser Lys Asn Gln His Arg Ala
```

-continued

```
65                  70                  75                  80

His Ile His Ala Gln Phe Thr Gly His Gly Pro Ile Ala Glu Ser Met
                85                  90                  95

Leu Ala Leu Leu Gln Pro Gly Asp Arg Val Ala Lys Leu Phe Ala Ala
            100                 105                 110

Asp Asp Arg Arg Leu Val Arg Ser Pro Asp Tyr Leu Glu Ser Met Leu
        115                 120                 125

Lys Asn Thr Asp Lys Ala Gly His Pro Leu Leu Cys Phe Gly Lys Lys
    130                 135                 140

Leu Glu His Leu Ile Ser Phe Asp Val Val Asp Asp Arg Leu Val Val
145                 150                 155                 160

Ser Leu Pro Thr Leu Pro Gly Val Val Arg Tyr Asp Ser Asp Ile Tyr
                165                 170                 175

Gly Leu Leu Pro Leu Ile Gln Lys Ser Leu Ser Asn Pro Lys Leu Ser
            180                 185                 190

Ile Arg His Phe Leu Ala Leu Tyr Gln Gln Ile Val Glu Gly Gln His
        195                 200                 205

Val Ser Cys Gly Asn His Ile Leu Leu Ile Lys Thr Glu Pro Leu His
    210                 215                 220

Ile Arg Thr Val Phe Ala Arg Val Val Asn Gln Leu Leu Pro Gln Gly
225                 230                 235                 240

Leu Ser His Thr Ser Ala Asn Ile Leu Glu Pro Thr Thr Arg Glu Ser
                245                 250                 255

Gly Asp Ile Phe Glu Phe Phe Gly Asn Pro Ser Ala Gln Ile Glu Arg
            260                 265                 270

Ile Pro Leu Glu Phe Phe Thr Ile Glu Pro Tyr Lys Glu His Ser Tyr
        275                 280                 285

Phe Cys Asn Arg Asp Leu Leu Gln Thr Ile Leu Gln Ser Glu Ser Glu
    290                 295                 300

Ile Lys Lys Ile Phe Glu Thr Ala Pro Lys Glu Pro Val Lys Ala Ala
305                 310                 315                 320

Thr Tyr Leu Ser Lys Gly Ser Glu Ile Ser Ser Leu His Thr Asp Ser
                325                 330                 335

Trp Leu Thr Gly Ser Ala Ala Ala Tyr Gln Tyr Ser Glu Gln Ala Asp
            340                 345                 350

Lys Asn Glu Tyr Thr His Ala Gln Pro Cys Tyr Pro Phe Leu Glu Ala
        355                 360                 365

Met Glu Met Gly Leu Ile Asn Ser Glu Gly Ala Leu Leu Thr Arg Tyr
    370                 375                 380

Phe Pro Ser Ala Ser Leu Lys Gly Met Leu Ile Ser Tyr His Val Arg
385                 390                 395                 400

His Tyr Leu Lys Gln Ile Tyr Phe Gln Val Pro Ser Tyr Thr His Gly
                405                 410                 415

Asn Tyr Phe Ser His Asn Asp Arg Gly Leu Leu Leu Asp Leu Gln Gln
            420                 425                 430

Ala Asp Ile Asp Val Phe Trp Ala Asp Glu Glu Ser Gly Arg Val Leu
        435                 440                 445

Gln Tyr Thr Lys Arg Arg Asp Lys Asn Ser Gly Met Phe Val Ile Lys
    450                 455                 460

Asn Arg Val Glu Glu Phe Arg Ser Ala Tyr Phe Ile Ala Ile Tyr Gly
465                 470                 475                 480

Ser Arg Leu Leu Glu Asn Asn Phe Ser Ala Gln Leu His Thr Leu Leu
                485                 490                 495
```

```
Ala Gly Leu Gln Gln Ala Ala His Thr Leu Gly Ile Pro Gly Phe Ser
            500                 505                 510

Lys Pro Thr Pro Leu Ala Val Ile Thr Gly Gly Gly Thr Gly Val Met
        515                 520                 525

Ala Thr Gly Asn Arg Val Ala Lys Glu Leu Gly Ile Leu Ser Cys Gly
    530                 535                 540

Thr Val Leu Asp Leu Glu Ala Ser Pro Ala Gln Ile Asp Gln Pro Thr
545                 550                 555                 560

Asn Glu Phe Leu Asp Ala Lys Met Thr Tyr Arg Leu Pro Gln Leu Ile
                565                 570                 575

Glu Arg Gln Glu His Phe Tyr Ala Asp Leu Pro Ile Leu Val Val Gly
            580                 585                 590

Gly Val Gly Thr Asp Phe Glu Leu Tyr Leu Glu Leu Val Tyr Leu Lys
        595                 600                 605

Thr Gly Ala Lys Pro Pro Thr Pro Ile Phe Leu Ile Gly Pro Ile Glu
    610                 615                 620

Tyr Trp Lys Glu Lys Val Ala His Ala Tyr Glu Ile Asn Leu Lys Ala
625                 630                 635                 640

Gly Thr Ile Arg Gly Ser Glu Trp Ile Ser Asn Cys Leu Tyr Cys Ile
                645                 650                 655

Thr Ser Pro Glu Ala Gly Ile Ala Val Phe Glu Gln Phe Leu Ala Gly
            660                 665                 670

Glu Leu Pro Ile Gly Tyr Asp Tyr Pro Pro Ala Pro Asp Gly Leu Val
        675                 680                 685

Ile Val
    690
```

<210> SEQ ID NO 117
<211> LENGTH: 4500
<212> TYPE: DNA
<213> ORGANISM: Chlamydia trachomatis

<400> SEQUENCE: 117

```
tgcgtagatc ttcatgctgg aggacagtct gtaaatgagc tggtatatgt aggccctcaa     60

gcggttttat tgttagacca aattcgagat ctattcgttg ggtctaaaga tagtcaggct    120

gaaggacagt ataggttaat tgtaggagat ccaagttctt tccaagagaa agatgcggat    180

actcttcccg ggaaggtaga gcaaagtact ttgttctcag taaccaatcc cgtggttttc    240

caaggtgtgg accaacagga tcaagtctct tcccaagggt taatttgtag ttttacgagc    300

agcaaccttg attctcctcg tgacggagaa tctttttttag gtattgcttt tgttggggat    360

agtagtaagg ctggaatcac attaactgac gtgaaagctt ctttgtctgg agcggcttta    420

tattctacag aagatcttat ctttgaaaag attaagggtg gattggaatt tgcatcatgt    480

tcttctctag aacagggggg agcttgtgca gctcaaagta ttttgattca tgattgtcaa    540

ggattgcagg ttaaacactg tactacagcc gtgaatgctg aggggtctag tgcgaatgat    600

catcttggat ttggaggagg cgctttcttt gttacgggtt ctctttctgg agagaaaagt    660

ctctatatgc ctgcaggaga tatggtagtt gcgaattgtg atggggctat atcttttgaa    720

ggaaacagcg cgaactttgc taatggagga gcgattgctg cctctgggaa agtgcttttt    780

gtcgctaatg ataaaaagac ttcttttata gagaaccgag ctttgtctgg aggagcgatt    840

gcagcctctt ctgatattgc ctttcaaaac tgcgcagaac tagttttcaa aggcaattgt    900

gcaattggaa cagaggataa aggttcttta ggtggagggg ctatatcttc tctaggcacc    960
```

-continued

```
gttcttttgc aagggaatca cgggataact tgtgataaga atgagtctgc ttcgcaagga   1020
ggcgccattt ttggcaaaaa ttgtcagatt tctgacaacg aggggccagt ggttttcaga   1080
gatagtacag cttgcttagg aggaggcgct attgcagctc aagaaattgt ttctattcag   1140
aacaatcagg ctgggatttc cttcgaggga ggtaaggcta gtttcggagg aggtattgcg   1200
tgtggatctt tttcttccgc aggtggtgct tctgttttag ggaccattga tatttcgaag   1260
aatttaggcg cgatttcgtt ctctcgtact ttatgtacga cctcagattt aggacaaatg   1320
gagtaccagg gaggaggagc tctatttggt gaaaatattt ctctttctga gaatgctggt   1380
gtgctcacct ttaaagacaa cattgtgaag actttttgctt cgaatgggaa aattctggga   1440
ggaggagcga ttttagctac tggtaaggtg gaaattacta ataattccga aggaatttct   1500
tttacaggaa atgcgagagc tccacaagct cttccaactc aagaggagtt tcctttattc   1560
agcaaaaaag aagggcgacc actctcttca ggatattctg gggaggagc gattttagga   1620
agagaagtag ctattctcca caacgctgca gtagtatttg agcaaaatcg tttgcagtgc   1680
agcgaagaag aagcgacatt attaggttgt tgtggaggag gcgctgttca tgggatggat   1740
agcacttcga ttgttggcaa ctcttcagta agatttggta ataattacgc aatgggacaa   1800
ggagtctcag gaggagctct tttatctaaa acagtgcagt tagctgggaa tggaagcgtc   1860
gatttttctc gaaatattgc tagtttggga ggaggagctc ttcaagcttc tgaaggaaat   1920
tgtgagctag ttgataacgg ctatgtgcta ttcagagata atcgagggag ggtttatggg   1980
ggtgctattt cttgcttacg tggagatgta gtcatttctg gaaacaaggg tagagttgaa   2040
tttaaagaca acatagcaac acgtctttat gtggaagaaa ctgtagaaaa ggttgaagag   2100
gtagagccag ctcctgagca aaaagacaat aatgagcttt ctttcttagg gagagcagaa   2160
cagagtttta ttactgcagc taatcaagct cttttcgcat ctgaagatgg ggatttatca   2220
cctgagtcat ccatttcttc tgaagaactt gcgaaaagaa gagagtgtgc tggaggagct   2280
atttttgcaa aacgggttcg tattgtagat aaccaagagg ccgttgtatt ctcgaataac   2340
ttctctgata tttatggcgg cgccattttt acaggttctc ttcgagaaga ggataagtta   2400
gatgggcaaa tccctgaagt cttgatctca ggcaatgcag gggatgttgt tttttccgga   2460
aattcctcga agcgtgatga gcatcttcct catacaggtg gggagccat ttgtactcaa   2520
aatttgacga tttctcagaa tacagggaat gttctgtttt ataacaacgt ggcctgttcg   2580
ggaggagctg ttcgtataga ggatcatggt aatgttcttt tagaagcttt tggaggagat   2640
attgttttta aggaaattc ttctttcaga gcacaaggat ccgatgctat ctattttgca   2700
ggtaaagaat cgcatattac agccctgaat gctacggaag gacatgctat tgttttccac   2760
gacgcattag tttttgaaaa tctagaagaa aggaaatctg ctgaagtatt gttaatcaat   2820
agtcgagaaa atccaggtta cactggatct attcgatttt tagaagcaga aagtaaagtt   2880
cctcaatgta ttcatgtaca acaaggaagc cttgagttgc taaatggagc cacattatgt   2940
agttatggtt ttaaacaaga tgctggagct aagttggtat tggctgctgg agctaaactg   3000
aagattttag attcaggaac tcctgtacaa caagggcatg ctatcagtaa acctgaagca   3060
gaaatcgagt catcttctga accagagggt gcacattctc tttggattgc gaagaatgct   3120
caaacaacag ttcctatggt tgatatccat actatttctg tagatttagc ctccttctct   3180
tctagtcaac aggaggggac agtagaagct cctcaggtta ttgttcctgg aggaagttat   3240
gttcgatctg gagagcttaa tttggagtta gttaacacaa caggtactgg ttatgaaaat   3300
```

-continued

```
catgctttat tgaagaatga ggctaaagtt ccattgatgt ctttcgttgc ttctggtgat   3360

gaagcttcag ccgaaatcag taacttgtcg gtttctgatt tacagattca tgtagtaact   3420

ccagagattg aagaagacac atacggccat atgggagatt ggtctgaggc taaaattcaa   3480

gatggaactc ttgtcattag ttggaatcct actggatatc gattagatcc tcaaaaagca   3540

ggggctttag tatttaatgc attatgggaa gaaggggctg tcttgtctgc tctgaaaaat   3600

gcacgctttg ctcataatct cactgctcag cgtatggaat tcgattattc tacaaatgtg   3660

tggggattcg cctttggtgg tttccgaact ctatctgcag agaatctggt tgctattgat   3720

ggatacaaag gagcttatgg tggtgcttct gctggagtcg atattcaatt gatggaagat   3780

tttgttctag gagttagtgg agctgctttc ctaggtaaaa tggatagtca gaagtttgat   3840

gcggaggttt ctcggaaggg agttgttggt tctgtatata caggattttt agctggatcc   3900

tggttcttca aaggacaata tagccttgga gaaacacaga acgatatgaa aacgcgttat   3960

ggagtactag gagagtcgag tgcttcttgg acatctcgag gagtactggc agatgcttta   4020

gttgaatacc gaagtttagt tggtcctgtg agacctactt tttatgcttt gcatttcaat   4080

ccttatgtcg aagtatctta tgcttctatg aaattccctg gctttacaga acaaggaaga   4140

gaagcgcgtt cttttgaaga cgcttccctt accaatatca ccattccttt agggatgaag   4200

tttgaattgg cgttcataaa aggacagttt tcagaggtga actctttggg aataagttat   4260

gcatgggaag cttatcgaaa agtagaagga ggcgcggtgc agcttttaga agctgggttt   4320

gattgggagg gagctccaat ggatcttcct agacaggagc tgcgtgtcgc tctggaaaat   4380

aatacggaat ggagttctta cttcagcaca gtcttaggat taacagcttt ttgtggagga   4440

tttacttcta cagatagtaa actaggatat gaggcgaata ctggattgcg attgatcttt   4500
```

<210> SEQ ID NO 118
<211> LENGTH: 1500
<212> TYPE: PRT
<213> ORGANISM: Chlamydia trachomatis

<400> SEQUENCE: 118

```
Cys Val Asp Leu His Ala Gly Gly Gln Ser Val Asn Glu Leu Val Tyr
1               5                   10                  15

Val Gly Pro Gln Ala Val Leu Leu Leu Asp Gln Ile Arg Asp Leu Phe
            20                  25                  30

Val Gly Ser Lys Asp Ser Gln Ala Glu Gly Gln Tyr Arg Leu Ile Val
        35                  40                  45

Gly Asp Pro Ser Ser Phe Gln Glu Lys Asp Ala Asp Thr Leu Pro Gly
    50                  55                  60

Lys Val Glu Gln Ser Thr Leu Phe Ser Val Thr Asn Pro Val Val Phe
65                  70                  75                  80

Gln Gly Val Asp Gln Gln Asp Gln Val Ser Ser Gln Gly Leu Ile Cys
                85                  90                  95

Ser Phe Thr Ser Ser Asn Leu Asp Ser Pro Arg Asp Gly Glu Ser Phe
            100                 105                 110

Leu Gly Ile Ala Phe Val Gly Asp Ser Ser Lys Ala Gly Ile Thr Leu
        115                 120                 125

Thr Asp Val Lys Ala Ser Leu Ser Gly Ala Ala Leu Tyr Ser Thr Glu
    130                 135                 140

Asp Leu Ile Phe Glu Lys Ile Lys Gly Gly Leu Glu Phe Ala Ser Cys
145                 150                 155                 160

Ser Ser Leu Glu Gln Gly Gly Ala Cys Ala Ala Gln Ser Ile Leu Ile
```

-continued

```
                165                 170                 175

His Asp Cys Gln Gly Leu Gln Val Lys His Cys Thr Thr Ala Val Asn
            180                 185                 190

Ala Glu Gly Ser Ser Ala Asn Asp His Leu Gly Phe Gly Gly Gly Ala
        195                 200                 205

Phe Phe Val Thr Gly Ser Leu Ser Gly Glu Lys Ser Leu Tyr Met Pro
    210                 215                 220

Ala Gly Asp Met Val Val Ala Asn Cys Asp Gly Ala Ile Ser Phe Glu
225                 230                 235                 240

Gly Asn Ser Ala Asn Phe Ala Asn Gly Gly Ala Ile Ala Ala Ser Gly
                245                 250                 255

Lys Val Leu Phe Val Ala Asn Asp Lys Lys Thr Ser Phe Ile Glu Asn
            260                 265                 270

Arg Ala Leu Ser Gly Gly Ala Ile Ala Ala Ser Ser Asp Ile Ala Phe
        275                 280                 285

Gln Asn Cys Ala Glu Leu Val Phe Lys Gly Asn Cys Ala Ile Gly Thr
    290                 295                 300

Glu Asp Lys Gly Ser Leu Gly Gly Gly Ala Ile Ser Ser Leu Gly Thr
305                 310                 315                 320

Val Leu Leu Gln Gly Asn His Gly Ile Thr Cys Asp Lys Asn Glu Ser
                325                 330                 335

Ala Ser Gln Gly Gly Ala Ile Phe Gly Lys Asn Cys Gln Ile Ser Asp
            340                 345                 350

Asn Glu Gly Pro Val Val Phe Arg Asp Ser Thr Ala Cys Leu Gly Gly
        355                 360                 365

Gly Ala Ile Ala Ala Gln Glu Ile Val Ser Ile Gln Asn Asn Gln Ala
    370                 375                 380

Gly Ile Ser Phe Glu Gly Gly Lys Ala Ser Phe Gly Gly Gly Ile Ala
385                 390                 395                 400

Cys Gly Ser Phe Ser Ser Ala Gly Gly Ala Ser Val Leu Gly Thr Ile
                405                 410                 415

Asp Ile Ser Lys Asn Leu Gly Ala Ile Ser Phe Ser Arg Thr Leu Cys
            420                 425                 430

Thr Thr Ser Asp Leu Gly Gln Met Glu Tyr Gln Gly Gly Gly Ala Leu
        435                 440                 445

Phe Gly Glu Asn Ile Ser Leu Ser Glu Asn Ala Gly Val Leu Thr Phe
    450                 455                 460

Lys Asp Asn Ile Val Lys Thr Phe Ala Ser Asn Gly Lys Ile Leu Gly
465                 470                 475                 480

Gly Gly Ala Ile Leu Ala Thr Gly Lys Val Glu Ile Thr Asn Asn Ser
                485                 490                 495

Glu Gly Ile Ser Phe Thr Gly Asn Ala Arg Ala Pro Gln Ala Leu Pro
            500                 505                 510

Thr Gln Glu Glu Phe Pro Leu Phe Ser Lys Lys Glu Gly Arg Pro Leu
        515                 520                 525

Ser Ser Gly Tyr Ser Gly Gly Gly Ala Ile Leu Gly Arg Glu Val Ala
    530                 535                 540

Ile Leu His Asn Ala Ala Val Val Phe Glu Gln Asn Arg Leu Gln Cys
545                 550                 555                 560

Ser Glu Glu Glu Ala Thr Leu Leu Gly Cys Cys Gly Gly Gly Ala Val
                565                 570                 575

His Gly Met Asp Ser Thr Ser Ile Val Gly Asn Ser Ser Val Arg Phe
            580                 585                 590
```

```
Gly Asn Asn Tyr Ala Met Gly Gln Gly Val Ser Gly Gly Ala Leu Leu
        595                 600                 605

Ser Lys Thr Val Gln Leu Ala Gly Asn Gly Ser Val Asp Phe Ser Arg
    610                 615                 620

Asn Ile Ala Ser Leu Gly Gly Gly Ala Leu Gln Ala Ser Glu Gly Asn
625                 630                 635                 640

Cys Glu Leu Val Asp Asn Gly Tyr Val Leu Phe Arg Asp Asn Arg Gly
                645                 650                 655

Arg Val Tyr Gly Gly Ala Ile Ser Cys Leu Arg Gly Asp Val Val Ile
            660                 665                 670

Ser Gly Asn Lys Gly Arg Val Glu Phe Lys Asp Asn Ile Ala Thr Arg
        675                 680                 685

Leu Tyr Val Glu Glu Thr Val Glu Lys Val Glu Glu Val Glu Pro Ala
    690                 695                 700

Pro Glu Gln Lys Asp Asn Asn Glu Leu Ser Phe Leu Gly Arg Ala Glu
705                 710                 715                 720

Gln Ser Phe Ile Thr Ala Ala Asn Gln Ala Leu Phe Ala Ser Glu Asp
                725                 730                 735

Gly Asp Leu Ser Pro Glu Ser Ser Ile Ser Ser Glu Glu Leu Ala Lys
            740                 745                 750

Arg Arg Glu Cys Ala Gly Gly Ala Ile Phe Ala Lys Arg Val Arg Ile
        755                 760                 765

Val Asp Asn Gln Glu Ala Val Val Phe Ser Asn Asn Phe Ser Asp Ile
    770                 775                 780

Tyr Gly Gly Ala Ile Phe Thr Gly Ser Leu Arg Glu Glu Asp Lys Leu
785                 790                 795                 800

Asp Gly Gln Ile Pro Glu Val Leu Ile Ser Gly Asn Ala Gly Asp Val
                805                 810                 815

Val Phe Ser Gly Asn Ser Ser Lys Arg Asp Glu His Leu Pro His Thr
            820                 825                 830

Gly Gly Gly Ala Ile Cys Thr Gln Asn Leu Thr Ile Ser Gln Asn Thr
        835                 840                 845

Gly Asn Val Leu Phe Tyr Asn Asn Val Ala Cys Ser Gly Gly Ala Val
    850                 855                 860

Arg Ile Glu Asp His Gly Asn Val Leu Leu Glu Ala Phe Gly Gly Asp
865                 870                 875                 880

Ile Val Phe Lys Gly Asn Ser Ser Phe Arg Ala Gln Gly Ser Asp Ala
                885                 890                 895

Ile Tyr Phe Ala Gly Lys Glu Ser His Ile Thr Ala Leu Asn Ala Thr
            900                 905                 910

Glu Gly His Ala Ile Val Phe His Asp Ala Leu Val Phe Glu Asn Leu
        915                 920                 925

Glu Glu Arg Lys Ser Ala Glu Val Leu Leu Ile Asn Ser Arg Glu Asn
    930                 935                 940

Pro Gly Tyr Thr Gly Ser Ile Arg Phe Leu Glu Ala Glu Ser Lys Val
945                 950                 955                 960

Pro Gln Cys Ile His Val Gln Gln Gly Ser Leu Glu Leu Leu Asn Gly
                965                 970                 975

Ala Thr Leu Cys Ser Tyr Gly Phe Lys Gln Asp Ala Gly Ala Lys Leu
            980                 985                 990

Val Leu Ala Ala Gly Ala Lys Leu  Lys Ile Leu Asp Ser  Gly Thr Pro
        995                 1000                1005
```

-continued

Val Gln Gln Gly His Ala Ile Ser Lys Pro Glu Ala Glu Ile Glu
1010 1015 1020

Ser Ser Ser Glu Pro Glu Gly Ala His Ser Leu Trp Ile Ala Lys
1025 1030 1035

Asn Ala Gln Thr Thr Val Pro Met Val Asp Ile His Thr Ile Ser
1040 1045 1050

Val Asp Leu Ala Ser Phe Ser Ser Ser Gln Gln Glu Gly Thr Val
1055 1060 1065

Glu Ala Pro Gln Val Ile Val Pro Gly Gly Ser Tyr Val Arg Ser
1070 1075 1080

Gly Glu Leu Asn Leu Glu Leu Val Asn Thr Thr Gly Thr Gly Tyr
1085 1090 1095

Glu Asn His Ala Leu Leu Lys Asn Glu Ala Lys Val Pro Leu Met
1100 1105 1110

Ser Phe Val Ala Ser Gly Asp Glu Ala Ser Ala Glu Ile Ser Asn
1115 1120 1125

Leu Ser Val Ser Asp Leu Gln Ile His Val Val Thr Pro Glu Ile
1130 1135 1140

Glu Glu Asp Thr Tyr Gly His Met Gly Asp Trp Ser Glu Ala Lys
1145 1150 1155

Ile Gln Asp Gly Thr Leu Val Ile Ser Trp Asn Pro Thr Gly Tyr
1160 1165 1170

Arg Leu Asp Pro Gln Lys Ala Gly Ala Leu Val Phe Asn Ala Leu
1175 1180 1185

Trp Glu Glu Gly Ala Val Leu Ser Ala Leu Lys Asn Ala Arg Phe
1190 1195 1200

Ala His Asn Leu Thr Ala Gln Arg Met Glu Phe Asp Tyr Ser Thr
1205 1210 1215

Asn Val Trp Gly Phe Ala Phe Gly Gly Phe Arg Thr Leu Ser Ala
1220 1225 1230

Glu Asn Leu Val Ala Ile Asp Gly Tyr Lys Gly Ala Tyr Gly Gly
1235 1240 1245

Ala Ser Ala Gly Val Asp Ile Gln Leu Met Glu Asp Phe Val Leu
1250 1255 1260

Gly Val Ser Gly Ala Ala Phe Leu Gly Lys Met Asp Ser Gln Lys
1265 1270 1275

Phe Asp Ala Glu Val Ser Arg Lys Gly Val Val Gly Ser Val Tyr
1280 1285 1290

Thr Gly Phe Leu Ala Gly Ser Trp Phe Phe Lys Gly Gln Tyr Ser
1295 1300 1305

Leu Gly Glu Thr Gln Asn Asp Met Lys Thr Arg Tyr Gly Val Leu
1310 1315 1320

Gly Glu Ser Ser Ala Ser Trp Thr Ser Arg Gly Val Leu Ala Asp
1325 1330 1335

Ala Leu Val Glu Tyr Arg Ser Leu Val Gly Pro Val Arg Pro Thr
1340 1345 1350

Phe Tyr Ala Leu His Phe Asn Pro Tyr Val Glu Val Ser Tyr Ala
1355 1360 1365

Ser Met Lys Phe Pro Gly Phe Thr Glu Gln Gly Arg Glu Ala Arg
1370 1375 1380

Ser Phe Glu Asp Ala Ser Leu Thr Asn Ile Thr Ile Pro Leu Gly
1385 1390 1395

Met Lys Phe Glu Leu Ala Phe Ile Lys Gly Gln Phe Ser Glu Val 1400 1405 1410

Asn Ser Leu Gly Ile Ser Tyr Ala Trp Glu Ala Tyr Arg Lys Val
1415 1420 1425

Glu Gly Gly Ala Val Gln Leu Leu Glu Ala Gly Phe Asp Trp Glu
1430 1435 1440

Gly Ala Pro Met Asp Leu Pro Arg Gln Glu Leu Arg Val Ala Leu
1445 1450 1455

Glu Asn Asn Thr Glu Trp Ser Ser Tyr Phe Ser Thr Val Leu Gly
1460 1465 1470

Leu Thr Ala Phe Cys Gly Gly Phe Thr Ser Thr Asp Ser Lys Leu
1475 1480 1485

Gly Tyr Glu Ala Asn Thr Gly Leu Arg Leu Ile Phe
1490 1495 1500

<210> SEQ ID NO 119
<211> LENGTH: 2247
<212> TYPE: DNA
<213> ORGANISM: Chlamydia trachomatis

<400> SEQUENCE: 119
tgcgtagatc ttcatgctgg aggacagtct gtaaatgagc tggtatatgt aggccctcaa 60
gcggttttat tgttagacca aattcgagat ctattcgttg ggtctaaaga tagtcaggct 120
gaaggacagt ataggttaat tgtaggagat ccaagttctt tccaagagaa agatgcggat 180
actcttcccg ggaaggtaga gcaaagtact ttgttctcag taaccaatcc cgtggttttc 240
caaggtgtgg accaacagga tcaagtctct tcccaagggt taatttgtag ttttacgagc 300
agcaaccttg attctcctcg tgacggagaa tctttttag gtattgcttt tgttggggat 360
agtagtaagg ctggaatcac attaactgac gtgaaagctt ctttgtctgg agcggcttta 420
tattctacag aagatcttat ctttgaaaag attaagggtg gattggaatt tgcatcatgt 480
tcttctctag aacagggggg agcttgtgca gctcaaagta ttttgattca tgattgtcaa 540
ggattgcagg ttaaacactg tactacagcc gtgaatgctg aggggtctag tgcgaatgat 600
catcttggat ttggaggagg cgctttcttt gttacgggtt ctctttctgg agagaaaagt 660
ctctatatgc ctgcaggaga tatggtagtt gcgaattgtg atggggctat atcttttgaa 720
ggaaacagcg cgaactttgc taatggagga gcgattgctg cctctgggaa agtgcttttt 780
gtcgctaatg ataaaaagac ttcttttata gagaaccgag ctttgtctgg aggagcgatt 840
gcagcctctt ctgatattgc ctttcaaaac tgcgcagaac tagttttcaa aggcaattgt 900
gcaattggaa cagaggataa aggttcttta ggtggagggg ctatatcttc tctaggcacc 960
gttcttttgc aagggaatca cgggataact tgtgataaga atgagtctgc ttcgcaagga 1020
ggcgccattt ttggcaaaaa ttgtcagatt tctgacaacg aggggccagt ggttttcaga 1080
gatagtacag cttgcttagg aggaggcgct attgcagctc aagaaattgt ttctattcag 1140
aacaatcagg ctgggatttc cttcgaggga ggtaaggcta gtttcggagg aggtattgcg 1200
tgtggatctt tttcttccgc aggtggtgct tctgttttag ggaccattga tatttcgaag 1260
aatttaggcg cgatttcgtt ctctcgtact ttatgtacga cctcagattt aggacaaatg 1320
gagtaccagg gaggaggagc tctatttggt gaaaatattt ctctttctga gaatgctggt 1380
gtgctcacct ttaaagacaa cattgtgaag acttttgctt cgaatgggaa aattctggga 1440
ggaggagcga ttttagctac tggtaaggtg gaaattacta ataattccga aggaatttct 1500
tttacaggaa atgcgagagc tccacaagct cttccaactc aagaggagtt tcctttattc 1560

```
agcaaaaaag aagggcgacc actctcttca ggatattctg ggggaggagc gattttagga   1620

agagaagtag ctattctcca caacgctgca gtagtatttg agcaaaatcg tttgcagtgc   1680

agcgaagaag aagcgacatt attaggttgt tgtggaggag gcgctgttca tgggatggat   1740

agcacttcga ttgttggcaa ctcttcagta agatttggta ataattacgc aatgggacaa   1800

ggagtctcag gaggagctct tttatctaaa acagtgcagt tagctgggaa tggaagcgtc   1860

gatttttctc gaaatattgc tagtttggga ggaggagctc ttcaagcttc tgaaggaaat   1920

tgtgagctag ttgataacgg ctatgtgcta ttcagagata atcgagggag ggtttatggg   1980

ggtgctattt cttgcttacg tggagatgta gtcatttctg gaaacaaggg tagagttgaa   2040

tttaaagaca acatagcaac acgtctttat gtggaagaaa ctgtagaaaa ggttgaagag   2100

gtagagccag ctcctgagca aaaagacaat aatgagcttt ctttcttagg gagagcagaa   2160

cagagtttta ttactgcagc taatcaagct cttttcgcat ctgaagatgg ggatttatca   2220

cctgagtcat ccatttcttc tgaagaa                                       2247


<210> SEQ ID NO 120
<211> LENGTH: 749
<212> TYPE: PRT
<213> ORGANISM: Chlamydia trachomatis

<400> SEQUENCE: 120

Cys Val Asp Leu His Ala Gly Gly Gln Ser Val Asn Glu Leu Val Tyr
1               5                   10                  15

Val Gly Pro Gln Ala Val Leu Leu Leu Asp Gln Ile Arg Asp Leu Phe
            20                  25                  30

Val Gly Ser Lys Asp Ser Gln Ala Glu Gly Gln Tyr Arg Leu Ile Val
        35                  40                  45

Gly Asp Pro Ser Ser Phe Gln Glu Lys Asp Ala Asp Thr Leu Pro Gly
    50                  55                  60

Lys Val Glu Gln Ser Thr Leu Phe Ser Val Thr Asn Pro Val Val Phe
65                  70                  75                  80

Gln Gly Val Asp Gln Gln Asp Gln Val Ser Ser Gln Gly Leu Ile Cys
                85                  90                  95

Ser Phe Thr Ser Ser Asn Leu Asp Ser Pro Arg Asp Gly Glu Ser Phe
            100                 105                 110

Leu Gly Ile Ala Phe Val Gly Asp Ser Ser Lys Ala Gly Ile Thr Leu
        115                 120                 125

Thr Asp Val Lys Ala Ser Leu Ser Gly Ala Ala Leu Tyr Ser Thr Glu
    130                 135                 140

Asp Leu Ile Phe Glu Lys Ile Lys Gly Gly Leu Glu Phe Ala Ser Cys
145                 150                 155                 160

Ser Ser Leu Glu Gln Gly Gly Ala Cys Ala Ala Gln Ser Ile Leu Ile
                165                 170                 175

His Asp Cys Gln Gly Leu Gln Val Lys His Cys Thr Thr Ala Val Asn
            180                 185                 190

Ala Glu Gly Ser Ser Ala Asn Asp His Leu Gly Phe Gly Gly Gly Ala
        195                 200                 205

Phe Phe Val Thr Gly Ser Leu Ser Gly Glu Lys Ser Leu Tyr Met Pro
    210                 215                 220

Ala Gly Asp Met Val Val Ala Asn Cys Asp Gly Ala Ile Ser Phe Glu
225                 230                 235                 240

Gly Asn Ser Ala Asn Phe Ala Asn Gly Gly Ala Ile Ala Ala Ser Gly
```

-continued

```
                245                 250                 255

Lys Val Leu Phe Val Ala Asn Asp Lys Lys Thr Ser Phe Ile Glu Asn
            260                 265                 270

Arg Ala Leu Ser Gly Gly Ala Ile Ala Ala Ser Ser Asp Ile Ala Phe
        275                 280                 285

Gln Asn Cys Ala Glu Leu Val Phe Lys Gly Asn Cys Ala Ile Gly Thr
    290                 295                 300

Glu Asp Lys Gly Ser Leu Gly Gly Gly Ala Ile Ser Ser Leu Gly Thr
305                 310                 315                 320

Val Leu Leu Gln Gly Asn His Gly Ile Thr Cys Asp Lys Asn Glu Ser
                325                 330                 335

Ala Ser Gln Gly Gly Ala Ile Phe Gly Lys Asn Cys Gln Ile Ser Asp
            340                 345                 350

Asn Glu Gly Pro Val Val Phe Arg Asp Ser Thr Ala Cys Leu Gly Gly
        355                 360                 365

Gly Ala Ile Ala Ala Gln Glu Ile Val Ser Ile Gln Asn Asn Gln Ala
    370                 375                 380

Gly Ile Ser Phe Glu Gly Gly Lys Ala Ser Phe Gly Gly Gly Ile Ala
385                 390                 395                 400

Cys Gly Ser Phe Ser Ser Ala Gly Gly Ala Ser Val Leu Gly Thr Ile
                405                 410                 415

Asp Ile Ser Lys Asn Leu Gly Ala Ile Ser Phe Ser Arg Thr Leu Cys
            420                 425                 430

Thr Thr Ser Asp Leu Gly Gln Met Glu Tyr Gln Gly Gly Gly Ala Leu
        435                 440                 445

Phe Gly Glu Asn Ile Ser Leu Ser Glu Asn Ala Gly Val Leu Thr Phe
    450                 455                 460

Lys Asp Asn Ile Val Lys Thr Phe Ala Ser Asn Gly Lys Ile Leu Gly
465                 470                 475                 480

Gly Gly Ala Ile Leu Ala Thr Gly Lys Val Glu Ile Thr Asn Asn Ser
                485                 490                 495

Glu Gly Ile Ser Phe Thr Gly Asn Ala Arg Ala Pro Gln Ala Leu Pro
            500                 505                 510

Thr Gln Glu Glu Phe Pro Leu Phe Ser Lys Lys Glu Gly Arg Pro Leu
        515                 520                 525

Ser Ser Gly Tyr Ser Gly Gly Gly Ala Ile Leu Gly Arg Glu Val Ala
    530                 535                 540

Ile Leu His Asn Ala Ala Val Val Phe Glu Gln Asn Arg Leu Gln Cys
545                 550                 555                 560

Ser Glu Glu Glu Ala Thr Leu Leu Gly Cys Cys Gly Gly Gly Ala Val
                565                 570                 575

His Gly Met Asp Ser Thr Ser Ile Val Gly Asn Ser Ser Val Arg Phe
            580                 585                 590

Gly Asn Asn Tyr Ala Met Gly Gln Gly Val Ser Gly Gly Ala Leu Leu
        595                 600                 605

Ser Lys Thr Val Gln Leu Ala Gly Asn Gly Ser Val Asp Phe Ser Arg
    610                 615                 620

Asn Ile Ala Ser Leu Gly Gly Gly Ala Leu Gln Ala Ser Glu Gly Asn
625                 630                 635                 640

Cys Glu Leu Val Asp Asn Gly Tyr Val Leu Phe Arg Asp Asn Arg Gly
                645                 650                 655

Arg Val Tyr Gly Gly Ala Ile Ser Cys Leu Arg Gly Asp Val Val Ile
            660                 665                 670
```

Ser Gly Asn Lys Gly Arg Val Glu Phe Lys Asp Asn Ile Ala Thr Arg
675 680 685

Leu Tyr Val Glu Glu Thr Val Glu Lys Val Glu Glu Val Glu Pro Ala
690 695 700

Pro Glu Gln Lys Asp Asn Asn Glu Leu Ser Phe Leu Gly Arg Ala Glu
705 710 715 720

Gln Ser Phe Ile Thr Ala Ala Asn Gln Ala Leu Phe Ala Ser Glu Asp
725 730 735

Gly Asp Leu Ser Pro Glu Ser Ser Ile Ser Ser Glu Glu
740 745

<210> SEQ ID NO 121
<211> LENGTH: 2259
<212> TYPE: DNA
<213> ORGANISM: Chlamydia trachomatis

<400> SEQUENCE: 121
gaagaacttg cgaaaagaag agagtgtgct ggaggagcta tttttgcaaa acgggttcgt 60
attgtagata accaagaggc cgttgtattc tcgaataact tctctgatat ttatggcggc 120
gccattttta caggttctct tcgagaagag gataagttag atgggcaaat ccctgaagtc 180
ttgatctcag gcaatgcagg ggatgttgtt ttttccggaa attcctcgaa gcgtgatgag 240
catcttcctc atacaggtgg gggagccatt tgtactcaaa atttgacgat ttctcagaat 300
acagggaatg ttctgtttta taacaacgtg gcctgttcgg gaggagctgt tcgtatagag 360
gatcatggta atgttctttt agaagctttt ggaggagata ttgtttttaa aggaaattct 420
tctttcagag cacaaggatc cgatgctatc tattttgcag gtaaagaatc gcatattaca 480
gccctgaatg ctacggaagg acatgctatt gttttccacg acgcattagt ttttgaaaat 540
ctagaagaaa ggaaatctgc tgaagtattg ttaatcaata gtcgagaaaa tccaggttac 600
actggatcta ttcgattttt agaagcagaa agtaaagttc ctcaatgtat tcatgtacaa 660
caaggaagcc ttgagttgct aaatggagcc acattatgta gttatggttt taaacaagat 720
gctggagcta agttggtatt ggctgctgga gctaaactga agattttaga ttcaggaact 780
cctgtacaac aagggcatgc tatcagtaaa cctgaagcag aaatcgagtc atcttctgaa 840
ccagagggtg cacattctct ttggattgcg aagaatgctc aaacaacagt tcctatggtt 900
gatatccata ctatttctgt agatttagcc tccttctctt ctagtcaaca ggaggggaca 960
gtagaagctc ctcaggttat tgttcctgga ggaagttatg ttcgatctgg agagcttaat 1020
ttggagttag ttaacacaac aggtactggt tatgaaaatc atgctttatt gaagaatgag 1080
gctaaagttc cattgatgtc tttcgttgct tctggtgatg aagcttcagc cgaaatcagt 1140
aacttgtcgg tttctgattt acagattcat gtagtaactc cagagattga agaagacaca 1200
tacggccata tgggagattg gtctgaggct aaaattcaag atggaactct tgtcattagt 1260
tggaatccta ctggatatcg attagatcct caaaaagcag gggctttagt atttaatgca 1320
ttatgggaag aaggggctgt cttgtctgct ctgaaaaatg cacgctttgc tcataatctc 1380
actgctcagc gtatggaatt cgattattct acaaatgtgt ggggattcgc ctttggtggt 1440
ttccgaactc tatctgcaga gaatctggtt gctattgatg gatacaaagg agcttatggt 1500
ggtgcttctg ctggagtcga tattcaattg atggaagatt ttgttctagg agttagtgga 1560
gctgctttcc taggtaaaat ggatagtcag aagtttgatg cggaggtttc tcggaaggga 1620
gttgttggtt ctgtatatac aggattttta gctggatcct ggttcttcaa aggacaatat 1680

```
agccttggag aaacacagaa cgatatgaaa acgcgttatg gagtactagg agagtcgagt   1740

gcttcttgga catctcgagg agtactggca gatgctttag ttgaataccg aagtttagtt   1800

ggtcctgtga gacctacttt ttatgctttg catttcaatc cttatgtcga agtatcttat   1860

gcttctatga aattccctgg ctttacagaa caaggaagag aagcgcgttc ttttgaagac   1920

gcttccctta ccaatatcac cattccttta gggatgaagt ttgaattggc gttcataaaa   1980

ggacagtttt cagaggtgaa ctctttggga ataagttatg catgggaagc ttatcgaaaa   2040

gtagaaggag gcgcggtgca gcttttagaa gctgggtttg attgggaggg agctccaatg   2100

gatcttccta gacaggagct gcgtgtcgct ctggaaaata atacggaatg gagttcttac   2160

ttcagcacag tcttaggatt aacagctttt tgtggaggat ttacttctac agatagtaaa   2220

ctaggatatg aggcgaatac tggattgcga ttgatcttt                          2259
```

<210> SEQ ID NO 122
<211> LENGTH: 753
<212> TYPE: PRT
<213> ORGANISM: Chlamydia trachomatis

<400> SEQUENCE: 122

```
Glu Glu Leu Ala Lys Arg Arg Glu Cys Ala Gly Gly Ala Ile Phe Ala
1               5                   10                  15

Lys Arg Val Arg Ile Val Asp Asn Gln Glu Ala Val Val Phe Ser Asn
            20                  25                  30

Asn Phe Ser Asp Ile Tyr Gly Gly Ala Ile Phe Thr Gly Ser Leu Arg
        35                  40                  45

Glu Glu Asp Lys Leu Asp Gly Gln Ile Pro Glu Val Leu Ile Ser Gly
    50                  55                  60

Asn Ala Gly Asp Val Val Phe Ser Gly Asn Ser Ser Lys Arg Asp Glu
65                  70                  75                  80

His Leu Pro His Thr Gly Gly Gly Ala Ile Cys Thr Gln Asn Leu Thr
                85                  90                  95

Ile Ser Gln Asn Thr Gly Asn Val Leu Phe Tyr Asn Asn Val Ala Cys
            100                 105                 110

Ser Gly Gly Ala Val Arg Ile Glu Asp His Gly Asn Val Leu Leu Glu
        115                 120                 125

Ala Phe Gly Gly Asp Ile Val Phe Lys Gly Asn Ser Ser Phe Arg Ala
    130                 135                 140

Gln Gly Ser Asp Ala Ile Tyr Phe Ala Gly Lys Glu Ser His Ile Thr
145                 150                 155                 160

Ala Leu Asn Ala Thr Glu Gly His Ala Ile Val Phe His Asp Ala Leu
                165                 170                 175

Val Phe Glu Asn Leu Glu Glu Arg Lys Ser Ala Glu Val Leu Leu Ile
            180                 185                 190

Asn Ser Arg Glu Asn Pro Gly Tyr Thr Gly Ser Ile Arg Phe Leu Glu
        195                 200                 205

Ala Glu Ser Lys Val Pro Gln Cys Ile His Val Gln Gln Gly Ser Leu
    210                 215                 220

Glu Leu Leu Asn Gly Ala Thr Leu Cys Ser Tyr Gly Phe Lys Gln Asp
225                 230                 235                 240

Ala Gly Ala Lys Leu Val Leu Ala Ala Gly Ala Lys Leu Lys Ile Leu
                245                 250                 255

Asp Ser Gly Thr Pro Val Gln Gln Gly His Ala Ile Ser Lys Pro Glu
            260                 265                 270
```

```
Ala Glu Ile Glu Ser Ser Ser Glu Pro Glu Gly Ala His Ser Leu Trp
        275                 280                 285

Ile Ala Lys Asn Ala Gln Thr Thr Val Pro Met Val Asp Ile His Thr
    290                 295                 300

Ile Ser Val Asp Leu Ala Ser Phe Ser Ser Ser Gln Gln Glu Gly Thr
305                 310                 315                 320

Val Glu Ala Pro Gln Val Ile Val Pro Gly Gly Ser Tyr Val Arg Ser
                325                 330                 335

Gly Glu Leu Asn Leu Glu Leu Val Asn Thr Thr Gly Thr Gly Tyr Glu
            340                 345                 350

Asn His Ala Leu Leu Lys Asn Glu Ala Lys Val Pro Leu Met Ser Phe
        355                 360                 365

Val Ala Ser Gly Asp Glu Ala Ser Ala Glu Ile Ser Asn Leu Ser Val
    370                 375                 380

Ser Asp Leu Gln Ile His Val Val Thr Pro Glu Ile Glu Glu Asp Thr
385                 390                 395                 400

Tyr Gly His Met Gly Asp Trp Ser Glu Ala Lys Ile Gln Asp Gly Thr
                405                 410                 415

Leu Val Ile Ser Trp Asn Pro Thr Gly Tyr Arg Leu Asp Pro Gln Lys
            420                 425                 430

Ala Gly Ala Leu Val Phe Asn Ala Leu Trp Glu Glu Gly Ala Val Leu
        435                 440                 445

Ser Ala Leu Lys Asn Ala Arg Phe Ala His Asn Leu Thr Ala Gln Arg
    450                 455                 460

Met Glu Phe Asp Tyr Ser Thr Asn Val Trp Gly Phe Ala Phe Gly Gly
465                 470                 475                 480

Phe Arg Thr Leu Ser Ala Glu Asn Leu Val Ala Ile Asp Gly Tyr Lys
                485                 490                 495

Gly Ala Tyr Gly Gly Ala Ser Ala Gly Val Asp Ile Gln Leu Met Glu
            500                 505                 510

Asp Phe Val Leu Gly Val Ser Gly Ala Ala Phe Leu Gly Lys Met Asp
        515                 520                 525

Ser Gln Lys Phe Asp Ala Glu Val Ser Arg Lys Gly Val Val Gly Ser
    530                 535                 540

Val Tyr Thr Gly Phe Leu Ala Gly Ser Trp Phe Phe Lys Gly Gln Tyr
545                 550                 555                 560

Ser Leu Gly Glu Thr Gln Asn Asp Met Lys Thr Arg Tyr Gly Val Leu
                565                 570                 575

Gly Glu Ser Ser Ala Ser Trp Thr Ser Arg Gly Val Leu Ala Asp Ala
            580                 585                 590

Leu Val Glu Tyr Arg Ser Leu Val Gly Pro Val Arg Pro Thr Phe Tyr
        595                 600                 605

Ala Leu His Phe Asn Pro Tyr Val Glu Val Ser Tyr Ala Ser Met Lys
    610                 615                 620

Phe Pro Gly Phe Thr Glu Gln Gly Arg Glu Ala Arg Ser Phe Glu Asp
625                 630                 635                 640

Ala Ser Leu Thr Asn Ile Thr Ile Pro Leu Gly Met Lys Phe Glu Leu
                645                 650                 655

Ala Phe Ile Lys Gly Gln Phe Ser Glu Val Asn Ser Leu Gly Ile Ser
            660                 665                 670

Tyr Ala Trp Glu Ala Tyr Arg Lys Val Glu Gly Gly Ala Val Gln Leu
        675                 680                 685
```

-continued

```
Leu Glu Ala Gly Phe Asp Trp Glu Gly Ala Pro Met Asp Leu Pro Arg
    690                 695                 700

Gln Glu Leu Arg Val Ala Leu Glu Asn Asn Thr Glu Trp Ser Ser Tyr
705                 710                 715                 720

Phe Ser Thr Val Leu Gly Leu Thr Ala Phe Cys Gly Gly Phe Thr Ser
                725                 730                 735

Thr Asp Ser Lys Leu Gly Tyr Glu Ala Asn Thr Gly Leu Arg Leu Ile
            740                 745                 750

Phe


<210> SEQ ID NO 123
<211> LENGTH: 2838
<212> TYPE: DNA
<213> ORGANISM: Chlamydia trachomatis

<400> SEQUENCE: 123

agagaggttc cttctagaat ctttcttatg cccaactcag ttccagatcc tacgaaagag      60

tcgctatcaa ataaaattag tttgacagga gacactcaca atctcactaa ctgctatctc     120

gataacctac gctacatact ggctattcta caaaaaactc ccaatgaagg agctgctgtc     180

acaataacag attacctaag ctttttttgat acacaaaaag aaggtattta ttttgcaaaa     240

aatctcaccc ctgaaagtgg tggtgcgatt ggttatgcga gtcccaattc tcctaccgtg     300

gagattcgtg atacaatagg tcctgtaatc tttgaaaata atacttgttg cagactattt     360

acatggagaa atccttatgc tgctgataaa ataagagaag gcggagccat tcatgctcaa     420

aatctttaca taaatcataa tcatgatgtg gtcggattta tgaagaactt ttcttatgtc     480

caaggaggag ccattagtac cgctaatacc tttgttgtga gcgagaatca gtcttgtttt     540

ctctttatgg acaacatctg tattcaaact aatacagcag gaaaaggtgg cgctatctat     600

gctggaacga gcaattcttt tgagagtaat aactgcgatc tcttcttcat caataacgcc     660

tgttgtgcag gaggagcgat cttctcccct atctgttctc taacaggaaa tcgtggtaac     720

atcgttttct ataacaatcg ctgctttaaa aatgtagaaa cagcttcttc agaagcttct     780

gatggaggag caattaaagt aactactcgc ctagatgtta caggcaatcg tggtaggatc     840

ttttttagtg acaatatcac aaaaaattat ggcggagcta tttacgctcc tgtagttacc     900

ctagtggata atggccctac ctactttata aacaatatcg ccaataataa ggggggcgct     960

atctatatag acggaaccag taactccaaa atttctgccg accgccatgc tattattttt    1020

aatgaaaata ttgtgactaa tgtaactaat gcaaatggta ccagtacgtc agctaatcct    1080

cctagaagaa atgcaataac agtagcaagc tcctctggtg aaattctatt aggagcaggg    1140

agtagccaaa atttaatttt ttatgatcct attgaagtta gcaatgcagg ggtctctgtg    1200

tccttcaata aggaagctga tcaaacaggc tctgtagtat tttcaggagc tactgttaat    1260

tctgcagatt ttcatcaacg caatttacaa acaaaaacac ctgcacccct tactctcagt    1320

aatggttttc tatgtatcga agatcatgct cagcttacag tgaatcgatt cacacaaact    1380

gggggtgttg tttctcttgg gaatggagca gttctgagtt gctataaaaa tggtacagga    1440

gattctgcta gcaatgcctc tataacactg aagcatattg gattgaatct ttcttccatt    1500

ctgaaaagtg gtgctgagat tcctttattg tgggtagagc ctacaaataa cagcaataac    1560

tatacagcag atactgcagc taccttttca ttaagtgatg taaaactctc actcattgat    1620

gactacggga actctcctta tgaatccaca gatctgaccc atgctctgtc atcacagcct    1680

atgctatcta tttctgaagc tagcgataac cagctacaat cagaaaatat agatttttcg    1740
```

```
ggactaaatg tccctcatta tggatggcaa ggactttgga cttggggctg ggcaaaaact   1800

caagatccag aaccagcatc ttcagcaaca atcactgatc cacaaaaagc caatagattt   1860

catagaacct tactactaac atggcttcct gccgggtatg ttcctagccc aaaacacaga   1920

agtcccctca tagctaacac cttatggggg aatatgctgc ttgcaacaga aagcttaaaa   1980

aatagtgcag agctgacacc tagtggtcat cctttctggg gaattacagg aggaggacta   2040

ggcatgatgg tttaccaaga tcctcgagaa aatcatcctg gattccatat gcgctcttcc   2100

ggatactctg cggggatgat agcagggcag acacacacct tctcattgaa attcagtcag   2160

acctacacca aactcaatga gcgttacgca aaaaacaacg tatcttctaa aaattactca   2220

tgccaaggag aaatgctctt ctcattgcaa gaaggtttct tgctgactaa attagttggg   2280

ctttacagct atggagacca taactgtcac catttctata ctcaaggaga aaatctaaca   2340

tctcaaggga cgttccgcag tcaaacgatg ggaggtgctg tctttttttga tctccctatg   2400

aaaccctttg gatcaacgca tatactgaca gctccctttt taggtgctct tggtatttat   2460

tctagcctgt ctcactttac tgaggtggga gcctatccgc gaagcttttc tacaaagact   2520

cctttgatca atgtcctagt ccctattgga gttaaaggta gctttatgaa tgctacccac   2580

agacctcaag cctggactgt agaattggca taccaacccg ttctgtatag acaagaacca   2640

gggatcgcag cccagctcct agccagtaag ggtatttggt tcggtagtgg aagcccctca   2700

tcgcgtcatg ccatgtccta taaaatctca cagcaaacac aacctttgag ttggttaact   2760

ctccatttcc agtatcatgg attctactcc tcttcaacct tctgtaatta tctcaatggg   2820

gaaattgctc tgcgattc                                                 2838
```

```
<210> SEQ ID NO 124
<211> LENGTH: 946
<212> TYPE: PRT
<213> ORGANISM: Chlamydia trachomatis

<400> SEQUENCE: 124

Arg Glu Val Pro Ser Arg Ile Phe Leu Met Pro Asn Ser Val Pro Asp
1               5                   10                  15

Pro Thr Lys Glu Ser Leu Ser Asn Lys Ile Ser Leu Thr Gly Asp Thr
            20                  25                  30

His Asn Leu Thr Asn Cys Tyr Leu Asp Asn Leu Arg Tyr Ile Leu Ala
        35                  40                  45

Ile Leu Gln Lys Thr Pro Asn Glu Gly Ala Ala Val Thr Ile Thr Asp
    50                  55                  60

Tyr Leu Ser Phe Phe Asp Thr Gln Lys Glu Gly Ile Tyr Phe Ala Lys
65                  70                  75                  80

Asn Leu Thr Pro Glu Ser Gly Gly Ala Ile Gly Tyr Ala Ser Pro Asn
                85                  90                  95

Ser Pro Thr Val Glu Ile Arg Asp Thr Ile Gly Pro Val Ile Phe Glu
            100                 105                 110

Asn Asn Thr Cys Cys Arg Leu Phe Thr Trp Arg Asn Pro Tyr Ala Ala
        115                 120                 125

Asp Lys Ile Arg Glu Gly Gly Ala Ile His Ala Gln Asn Leu Tyr Ile
    130                 135                 140

Asn His Asn His Asp Val Val Gly Phe Met Lys Asn Phe Ser Tyr Val
145                 150                 155                 160

Gln Gly Gly Ala Ile Ser Thr Ala Asn Thr Phe Val Val Ser Glu Asn
                165                 170                 175
```

```
Gln Ser Cys Phe Leu Phe Met Asp Asn Ile Cys Ile Gln Thr Asn Thr
            180                 185                 190

Ala Gly Lys Gly Gly Ala Ile Tyr Ala Gly Thr Ser Asn Ser Phe Glu
        195                 200                 205

Ser Asn Asn Cys Asp Leu Phe Phe Ile Asn Asn Ala Cys Cys Ala Gly
    210                 215                 220

Gly Ala Ile Phe Ser Pro Ile Cys Ser Leu Thr Gly Asn Arg Gly Asn
225                 230                 235                 240

Ile Val Phe Tyr Asn Asn Arg Cys Phe Lys Asn Val Glu Thr Ala Ser
                245                 250                 255

Ser Glu Ala Ser Asp Gly Gly Ala Ile Lys Val Thr Thr Arg Leu Asp
            260                 265                 270

Val Thr Gly Asn Arg Gly Arg Ile Phe Phe Ser Asp Asn Ile Thr Lys
        275                 280                 285

Asn Tyr Gly Gly Ala Ile Tyr Ala Pro Val Val Thr Leu Val Asp Asn
    290                 295                 300

Gly Pro Thr Tyr Phe Ile Asn Asn Ile Ala Asn Asn Lys Gly Gly Ala
305                 310                 315                 320

Ile Tyr Ile Asp Gly Thr Ser Asn Ser Lys Ile Ser Ala Asp Arg His
                325                 330                 335

Ala Ile Ile Phe Asn Glu Asn Ile Val Thr Asn Val Thr Asn Ala Asn
            340                 345                 350

Gly Thr Ser Thr Ser Ala Asn Pro Pro Arg Arg Asn Ala Ile Thr Val
        355                 360                 365

Ala Ser Ser Ser Gly Glu Ile Leu Leu Gly Ala Gly Ser Ser Gln Asn
    370                 375                 380

Leu Ile Phe Tyr Asp Pro Ile Glu Val Ser Asn Ala Gly Val Ser Val
385                 390                 395                 400

Ser Phe Asn Lys Glu Ala Asp Gln Thr Gly Ser Val Val Phe Ser Gly
                405                 410                 415

Ala Thr Val Asn Ser Ala Asp Phe His Gln Arg Asn Leu Gln Thr Lys
            420                 425                 430

Thr Pro Ala Pro Leu Thr Leu Ser Asn Gly Phe Leu Cys Ile Glu Asp
        435                 440                 445

His Ala Gln Leu Thr Val Asn Arg Phe Thr Gln Thr Gly Gly Val Val
    450                 455                 460

Ser Leu Gly Asn Gly Ala Val Leu Ser Cys Tyr Lys Asn Gly Thr Gly
465                 470                 475                 480

Asp Ser Ala Ser Asn Ala Ser Ile Thr Leu Lys His Ile Gly Leu Asn
                485                 490                 495

Leu Ser Ser Ile Leu Lys Ser Gly Ala Glu Ile Pro Leu Leu Trp Val
            500                 505                 510

Glu Pro Thr Asn Asn Ser Asn Asn Tyr Thr Ala Asp Thr Ala Ala Thr
        515                 520                 525

Phe Ser Leu Ser Asp Val Lys Leu Ser Leu Ile Asp Asp Tyr Gly Asn
    530                 535                 540

Ser Pro Tyr Glu Ser Thr Asp Leu Thr His Ala Leu Ser Ser Gln Pro
545                 550                 555                 560

Met Leu Ser Ile Ser Glu Ala Ser Asp Asn Gln Leu Gln Ser Glu Asn
                565                 570                 575

Ile Asp Phe Ser Gly Leu Asn Val Pro His Tyr Gly Trp Gln Gly Leu
            580                 585                 590
```

-continued

```
Trp Thr Trp Gly Trp Ala Lys Thr Gln Asp Pro Glu Pro Ala Ser Ser
        595                 600                 605

Ala Thr Ile Thr Asp Pro Gln Lys Ala Asn Arg Phe His Arg Thr Leu
    610                 615                 620

Leu Leu Thr Trp Leu Pro Ala Gly Tyr Val Pro Ser Pro Lys His Arg
625                 630                 635                 640

Ser Pro Leu Ile Ala Asn Thr Leu Trp Gly Asn Met Leu Leu Ala Thr
                645                 650                 655

Glu Ser Leu Lys Asn Ser Ala Glu Leu Thr Pro Ser Gly His Pro Phe
            660                 665                 670

Trp Gly Ile Thr Gly Gly Gly Leu Gly Met Met Val Tyr Gln Asp Pro
        675                 680                 685

Arg Glu Asn His Pro Gly Phe His Met Arg Ser Ser Gly Tyr Ser Ala
    690                 695                 700

Gly Met Ile Ala Gly Gln Thr His Thr Phe Ser Leu Lys Phe Ser Gln
705                 710                 715                 720

Thr Tyr Thr Lys Leu Asn Glu Arg Tyr Ala Lys Asn Asn Val Ser Ser
                725                 730                 735

Lys Asn Tyr Ser Cys Gln Gly Glu Met Leu Phe Ser Leu Gln Glu Gly
            740                 745                 750

Phe Leu Leu Thr Lys Leu Val Gly Leu Tyr Ser Tyr Gly Asp His Asn
        755                 760                 765

Cys His His Phe Tyr Thr Gln Gly Glu Asn Leu Thr Ser Gln Gly Thr
    770                 775                 780

Phe Arg Ser Gln Thr Met Gly Gly Ala Val Phe Phe Asp Leu Pro Met
785                 790                 795                 800

Lys Pro Phe Gly Ser Thr His Ile Leu Thr Ala Pro Phe Leu Gly Ala
                805                 810                 815

Leu Gly Ile Tyr Ser Ser Leu Ser His Phe Thr Glu Val Gly Ala Tyr
            820                 825                 830

Pro Arg Ser Phe Ser Thr Lys Thr Pro Leu Ile Asn Val Leu Val Pro
        835                 840                 845

Ile Gly Val Lys Gly Ser Phe Met Asn Ala Thr His Arg Pro Gln Ala
    850                 855                 860

Trp Thr Val Glu Leu Ala Tyr Gln Pro Val Leu Tyr Arg Gln Glu Pro
865                 870                 875                 880

Gly Ile Ala Ala Gln Leu Leu Ala Ser Lys Gly Ile Trp Phe Gly Ser
                885                 890                 895

Gly Ser Pro Ser Ser Arg His Ala Met Ser Tyr Lys Ile Ser Gln Gln
            900                 905                 910

Thr Gln Pro Leu Ser Trp Leu Thr Leu His Phe Gln Tyr His Gly Phe
        915                 920                 925

Tyr Ser Ser Ser Thr Phe Cys Asn Tyr Leu Asn Gly Glu Ile Ala Leu
    930                 935                 940

Arg Phe
945


<210> SEQ ID NO 125
<211> LENGTH: 1914
<212> TYPE: DNA
<213> ORGANISM: Chlamydia trachomatis

<400> SEQUENCE: 125

aacgttcgta cgtactctgt tcagaggggg ggggtaaaaa cgatttctgc tagtgcagtt      60
```

-continued

```
cctcctacag cagctgtttt atcgagaaaa aagcgtgcta tagaagagaa gaaggaggaa    120
gcttcttctg gaaagataga aaatcttgat gctagcaaat acgatcttac tcccaagaac    180
atagaagaaa aactaggaat tactcctgaa cagaaatcta ctgttaaaga cctattaaat    240
aaactgaaaa aggtcattag tgcttacaac tctatgccag ataaaaattc ggaagcggga    300
cagaattcct tgattcaaca aggaaaatac gtcgatgcca ttcagaagaa gcttccagca    360
tcatcgcagg ctcagcctaa acaggcaaaa gctaaggaac agaaagccga agaaaaacct    420
aagacgactc cgattgaagg tgttcttgaa accatcaaaa cagaatttaa aggccatcgt    480
gtacctgttg agaaaatcat ccatggaata tggatcgcag gagcgcctcc ggatggtatc    540
gaagattata tgcgagtctt tttagatact tatgaaggtt ttgacttcta cttctgggta    600
gatgagaatg cttatgcagc agctaaattt tctagcattt tgaagaaggt cgctttcgat    660
gcggctattc aagatctacg atctgccaca gatgagtcta cgaaggcctt tgttaaagac    720
tacgatgaat taaaacagaa atatgaaaag aaagttgcgg agacgacttc tcaagcagaa    780
aaagaccaat atctcaaaga tctaaaggat cttttagaga aatttacaaa aatcagtgat    840
gagattcgtg gaaaatttga tcggctgttt cttaagaatg tgattgttgc tcagaacgga    900
ttctttaatt tctgcttgct gaaaggcctc ggcaatatca atgacgaaac gcgtgcagag    960
tatttagaga aagaactcaa acttcctact gaggagatcg aacagtataa aaagcttaaa   1020
gagacgaaca aagagaagat agccgctatt gtaaaacaac taaacgagaa acttggatcg   1080
gatcgggtaa aaatcaaaga cattaaagag ctgcaatcta tgaagcaagc tcgaaatgtc   1140
tacaattatg aacaggaaat gtttctgcgc tggaactatg cagccgcaac agatcagatt   1200
cgtatgtata tgttggagga acttggaggt ctttatactg atctggatat gatgccttca   1260
tactctcagg aagtattgga gcttatcaaa aagcacagtg atggaaaccg aatgtttgag   1320
gatatgagct ctagacgggc gatttctgat gcggttttaa agatggctgt aggtaaggcg   1380
acaacagttt ccatggaaga ggtagcaaag gatatcgatg tttctcgctt aacagaagag   1440
gataagacaa aattaaatgc tctatttaag gatctagagc catttgcaaa accggattct   1500
aaaggagctg aagcagaagg gggtgaagga gcaaaaggta tgaaaaagag ctttttccag   1560
cccatagatc tgaatattgt cagaaatacc atgcctatct tgagacgcta tcatcactat   1620
cctgagttag gatggtttat tcgaggattg aacggattga tggtctctca taagggaagc   1680
actgcggttt ctgctgtcat tgtagggcaa caggctgcct accaggaact agcagcactt   1740
agacaagatg tcctttcagg ggagtttttc cattctttag aaaatttgac acatagaaac   1800
cataaggagc gtattggaaa tcatctcgtc gctaattatt tggctaaaag tctctttttt   1860
gattactgcc aagattcagt gatgccggag gctgtaagta ccttaggtat taga         1914
```

<210> SEQ ID NO 126
<211> LENGTH: 638
<212> TYPE: PRT
<213> ORGANISM: Chlamydia trachomatis

<400> SEQUENCE: 126

```
Asn Val Arg Thr Tyr Ser Val Gln Arg Gly Gly Val Lys Thr Ile Ser
1               5                   10                  15

Ala Ser Ala Val Pro Pro Thr Ala Ala Val Leu Ser Arg Lys Lys Arg
            20                  25                  30

Ala Ile Glu Glu Lys Lys Glu Glu Ala Ser Ser Gly Lys Ile Glu Asn
        35                  40                  45
```

```
Leu Asp Ala Ser Lys Tyr Asp Leu Thr Pro Lys Asn Ile Glu Glu Lys
    50                  55                  60

Leu Gly Ile Thr Pro Glu Gln Lys Ser Thr Val Lys Asp Leu Leu Asn
65                  70                  75                  80

Lys Leu Lys Lys Val Ile Ser Ala Tyr Asn Ser Met Pro Asp Lys Asn
                85                  90                  95

Ser Glu Ala Gly Gln Asn Ser Leu Ile Gln Gln Gly Lys Tyr Val Asp
            100                 105                 110

Ala Ile Gln Lys Lys Leu Pro Ala Ser Ser Gln Ala Gln Pro Lys Gln
        115                 120                 125

Ala Lys Ala Lys Glu Gln Lys Ala Glu Glu Lys Pro Lys Thr Thr Pro
    130                 135                 140

Ile Glu Gly Val Leu Glu Thr Ile Lys Thr Glu Phe Lys Gly His Arg
145                 150                 155                 160

Val Pro Val Glu Lys Ile Ile His Gly Ile Trp Ile Ala Gly Ala Pro
                165                 170                 175

Pro Asp Gly Ile Glu Asp Tyr Met Arg Val Phe Leu Asp Thr Tyr Glu
            180                 185                 190

Gly Phe Asp Phe Tyr Phe Trp Val Asp Glu Asn Ala Tyr Ala Ala Ala
        195                 200                 205

Lys Phe Ser Ser Ile Leu Lys Lys Val Ala Phe Asp Ala Ala Ile Gln
    210                 215                 220

Asp Leu Arg Ser Ala Thr Asp Glu Ser Thr Lys Ala Phe Val Lys Asp
225                 230                 235                 240

Tyr Asp Glu Leu Lys Gln Lys Tyr Glu Lys Lys Val Ala Glu Thr Thr
                245                 250                 255

Ser Gln Ala Glu Lys Asp Gln Tyr Leu Lys Asp Leu Lys Asp Leu Leu
            260                 265                 270

Glu Lys Phe Thr Lys Ile Ser Asp Glu Ile Arg Gly Lys Phe Asp Arg
        275                 280                 285

Leu Phe Leu Lys Asn Val Ile Val Ala Gln Asn Gly Phe Phe Asn Phe
    290                 295                 300

Cys Leu Leu Lys Gly Leu Gly Asn Ile Asn Asp Glu Thr Arg Ala Glu
305                 310                 315                 320

Tyr Leu Glu Lys Glu Leu Lys Leu Pro Thr Glu Glu Ile Glu Gln Tyr
                325                 330                 335

Lys Lys Leu Lys Glu Thr Asn Lys Glu Lys Ile Ala Ala Ile Val Lys
            340                 345                 350

Gln Leu Asn Glu Lys Leu Gly Ser Asp Arg Val Lys Ile Lys Asp Ile
        355                 360                 365

Lys Glu Leu Gln Ser Met Lys Gln Ala Arg Asn Val Tyr Asn Tyr Glu
    370                 375                 380

Gln Glu Met Phe Leu Arg Trp Asn Tyr Ala Ala Ala Thr Asp Gln Ile
385                 390                 395                 400

Arg Met Tyr Met Leu Glu Glu Leu Gly Gly Leu Tyr Thr Asp Leu Asp
                405                 410                 415

Met Met Pro Ser Tyr Ser Gln Glu Val Leu Glu Leu Ile Lys Lys His
            420                 425                 430

Ser Asp Gly Asn Arg Met Phe Glu Asp Met Ser Ser Arg Arg Ala Ile
        435                 440                 445

Ser Asp Ala Val Leu Lys Met Ala Val Gly Lys Ala Thr Thr Val Ser
    450                 455                 460

Met Glu Glu Val Ala Lys Asp Ile Asp Val Ser Arg Leu Thr Glu Glu
```

-continued 465 470 475 480

Asp Lys Thr Lys Leu Asn Ala Leu Phe Lys Asp Leu Glu Pro Phe Ala
485 490 495

Lys Pro Asp Ser Lys Gly Ala Glu Ala Glu Gly Gly Glu Gly Ala Lys
500 505 510

Gly Met Lys Lys Ser Phe Phe Gln Pro Ile Asp Leu Asn Ile Val Arg
515 520 525

Asn Thr Met Pro Ile Leu Arg Arg Tyr His His Tyr Pro Glu Leu Gly
530 535 540

Trp Phe Ile Arg Gly Leu Asn Gly Leu Met Val Ser His Lys Gly Ser
545 550 555 560

Thr Ala Val Ser Ala Val Ile Val Gly Gln Gln Ala Ala Tyr Gln Glu
565 570 575

Leu Ala Ala Leu Arg Gln Asp Val Leu Ser Gly Glu Phe Phe His Ser
580 585 590

Leu Glu Asn Leu Thr His Arg Asn His Lys Glu Arg Ile Gly Asn His
595 600 605

Leu Val Ala Asn Tyr Leu Ala Lys Ser Leu Phe Phe Asp Tyr Cys Gln
610 615 620

Asp Ser Val Met Pro Glu Ala Val Ser Thr Leu Gly Ile Arg
625 630 635

<210> SEQ ID NO 127
<211> LENGTH: 1523
<212> TYPE: DNA
<213> ORGANISM: Chlamydia trachomatis

<400> SEQUENCE: 127
gttatcataa aaaagaagaa ccaaaagatg ttttgcggat tgcgatctgt catgatccaa 60
tgtctttaga tccgcgtcag gttttttaa gcaaagatgt ttctattgta aaagctctct 120
atgaagggtt agtccgggaa aaagaagctg cgttccagct agctttggca gaaagatatc 180
atcaatctga tgatggttgt gtttatactt tttttctaaa aatacattc tggagcaacg 240 gagatgttgt aacagcatat gattttgaag agtctattaa acaaatttat ttccgagaaa 300
ttgataaccc ttcgttacgc tctcttgcat taattaaaaa ttctcatgct gttttaacag 360
gagctctccc tgttgaagat ttaggtgtta gagctttgaa tgcgaaaact ctagaaattg 420
ttttagaaaa cccgtttcct tattttctag agatattggc gcacccggtt ttttatccgg 480
tgcacacctc tttacgagaa tattacaaag ataagcgtaa caaacgcgtt ttcccgataa 540
tttctaatgg tccttttgcg attcaatgtt atgagccgca aagatattta ctaatcaaca 600
aaaaccctct gtatcatgcc aagcacgatg ttctgttaaa ttcggtatgt ttgcagatag 660
ttcctgatat ccatacagct atgcagttat tccaaaaaaa tcatatcgat ttagttgggt 720
taccctggag ctcctccttt tctttagaag aacaaagaaa tctccctaga gaaaaattat 780
ttgattatcc tgtattgagt tgctctgttt tattctgtaa cattcatcaa acacctttaa 840
ataatccctc gctgagaaca gccctctctt tagcaatcaa tcgagaaact ttattaaaac 900
tagcaggtaa aggctgtagc gctacgagct ttgttcaccc acaattatct cagatacctg 960
ctactacttt gtctcaagat gagcggattg ctttagcaaa aggctacttg accgaagctt 1020
taaagacttt atctcaagaa gatttagaaa aaattacatt aatttatcct atagaatctg 1080
tttgcttacg agccgttgtt caagaaattc gccaacaatt atttgatgta ctgggattta 1140
aaatttctac attaggatta gaatatcatt gtttttaga caaacgttcc agaggagaat 1200

```
tctccttagc aactggtaat tggattgcag actatcatca agctagtgct ttcctgtctg   1260

tcctaggtaa tgggacaaga tataaagact ttcaattgat taactggcag aaccaaaagt   1320

acacaaatat agttgctcaa cttctgattc aagaatcaag cgacctacag cttatggcag   1380

agcagttgtt gcttaaagaa agtcctctta ttcctctata ccacctcgat tatgtgtatg   1440

cgaaacagcc tcgggtgtct gatctccaaa cctcttctcg tggagaaatt gatttaaaaa   1500

gagtttcatt agctgaagga tag                                           1523


<210> SEQ ID NO 128
<211> LENGTH: 507
<212> TYPE: PRT
<213> ORGANISM: Chlamydia trachomatis

<400> SEQUENCE: 128

Cys Tyr His Lys Lys Glu Glu Pro Lys Asp Val Leu Arg Ile Ala Ile
1               5                   10                  15

Cys His Asp Pro Met Ser Leu Asp Pro Arg Gln Val Phe Leu Ser Lys
            20                  25                  30

Asp Val Ser Ile Val Lys Ala Leu Tyr Glu Gly Leu Val Arg Glu Lys
        35                  40                  45

Glu Ala Ala Phe Gln Leu Ala Leu Ala Glu Arg Tyr His Gln Ser Asp
    50                  55                  60

Asp Gly Cys Val Tyr Thr Phe Phe Leu Lys Asn Thr Phe Trp Ser Asn
65                  70                  75                  80

Gly Asp Val Val Thr Ala Tyr Asp Phe Glu Glu Ser Ile Lys Gln Ile
                85                  90                  95

Tyr Phe Arg Glu Ile Asp Asn Pro Ser Leu Arg Ser Leu Ala Leu Ile
            100                 105                 110

Lys Asn Ser His Ala Val Leu Thr Gly Ala Leu Pro Val Glu Asp Leu
        115                 120                 125

Gly Val Arg Ala Leu Asn Ala Lys Thr Leu Glu Ile Val Leu Glu Asn
    130                 135                 140

Pro Phe Pro Tyr Phe Leu Glu Ile Leu Ala His Pro Val Phe Tyr Pro
145                 150                 155                 160

Val His Thr Ser Leu Arg Glu Tyr Tyr Lys Asp Lys Arg Asn Lys Arg
                165                 170                 175

Val Phe Pro Ile Ile Ser Asn Gly Pro Phe Ala Ile Gln Cys Tyr Glu
            180                 185                 190

Pro Gln Arg Tyr Leu Leu Ile Asn Lys Asn Pro Leu Tyr His Ala Lys
        195                 200                 205

His Asp Val Leu Leu Asn Ser Val Cys Leu Gln Ile Val Pro Asp Ile
    210                 215                 220

His Thr Ala Met Gln Leu Phe Gln Lys Asn His Ile Asp Leu Val Gly
225                 230                 235                 240

Leu Pro Trp Ser Ser Ser Phe Ser Leu Glu Glu Gln Arg Asn Leu Pro
                245                 250                 255

Arg Glu Lys Leu Phe Asp Tyr Pro Val Leu Ser Cys Ser Val Leu Phe
            260                 265                 270

Cys Asn Ile His Gln Thr Pro Leu Asn Asn Pro Ser Leu Arg Thr Ala
        275                 280                 285

Leu Ser Leu Ala Ile Asn Arg Glu Thr Leu Leu Lys Leu Ala Gly Lys
    290                 295                 300

Gly Cys Ser Ala Thr Ser Phe Val His Pro Gln Leu Ser Gln Ile Pro
```

305 310 315 320

Ala Thr Thr Leu Ser Gln Asp Glu Arg Ile Ala Leu Ala Lys Gly Tyr
325 330 335

Leu Thr Glu Ala Leu Lys Thr Leu Ser Gln Glu Asp Leu Glu Lys Ile
340 345 350

Thr Leu Ile Tyr Pro Ile Glu Ser Val Cys Leu Arg Ala Val Val Gln
355 360 365

Glu Ile Arg Gln Gln Leu Phe Asp Val Leu Gly Phe Lys Ile Ser Thr
370 375 380

Leu Gly Leu Glu Tyr His Cys Phe Leu Asp Lys Arg Ser Arg Gly Glu
385 390 395 400

Phe Ser Leu Ala Thr Gly Asn Trp Ile Ala Asp Tyr His Gln Ala Ser
405 410 415

Ala Phe Leu Ser Val Leu Gly Asn Gly Thr Arg Tyr Lys Asp Phe Gln
420 425 430

Leu Ile Asn Trp Gln Asn Gln Lys Tyr Thr Asn Ile Val Ala Gln Leu
435 440 445

Leu Ile Gln Glu Ser Ser Asp Leu Gln Leu Met Ala Glu Gln Leu Leu
450 455 460

Leu Lys Glu Ser Pro Leu Ile Pro Leu Tyr His Leu Asp Tyr Val Tyr
465 470 475 480

Ala Lys Gln Pro Arg Val Ser Asp Leu Gln Thr Ser Ser Arg Gly Glu
485 490 495

Ile Asp Leu Lys Arg Val Ser Leu Ala Glu Gly
500 505

<210> SEQ ID NO 129
<211> LENGTH: 2076
<212> TYPE: DNA
<213> ORGANISM: Chlamydia muridarum

<400> SEQUENCE: 129
atgacactct ttcacactca tcacgatgcc gtctctccgg acggctactt atgttcttcc 60
cttcagttag ttggctctgg cacatatgaa ggagaaatcg aaatccaaaa tattccttct 120
tatttccttg gattccgatt acccacccat tgcgttcatc ttaatttgaa gagttctcta 180
gcccagttag gagtagatgc atctcttctt cactgcgaac taagcaaaaa tcaacaacgt 240
gcacatatgc acgtgcagtt caccggctat ggccctatcg ctgagtccat gctatctctt 300
ctcaaacccg gagatcgagt agccaaactg tttgctgcag atgatcgtag actagtccgc 360
tcccctgatt atcttgaaag catgctaaaa aatactgata agacaggaca tcctctgctc 420
cgatttggaa aaaaactcga gcatcttatc tcttttgatg tggtggacga tcgcctcgtt 480
gtatcactcc ccaccttgcc aggcatagtc aattatgacc cagacatcta tggacttctt 540
cccttaattc aaaaatcact aagcaatcct aaattgagta ttcgccactt cttgtctctc 600
tatcagaaga tcgtagaagg accacacatc ccttatgaag gaaacatttt gttaatcaaa 660
acagagcctc ttcatatccg cacagtattt gctcgcgtgg tcgatcaaat gctccctcaa 720
ggtctatttc acacttctgc caacatttta gaacccacaa cgcgagagtc tggagatatt 780
tttgaatttt ttggaaatcc ctccactctt gtagaaagaa tccctctaga attcttcact 840
atcgaaccct acaaagaaca ctcttacttc tgtaatcgag atctattgca aactaccttg 900
caatcggaaa gtgaaatcaa aaaaatattc gatacagctc ctcaagagcc tgtaaaagcc 960
gccacttatt tatcaaaagg aagtgaaatt tcttctcttg atgcagattc ttggcttacg 1020

```
ggatccgcag ctgcatacca atgtagcgaa aaacaggcag ctaaagacga atacatccac   1080

gctcaaccct gttatccatt tttggaagca atggaaacgg gactcatcaa tagcgaagga   1140

gctttactca ctcggttttt cccctcttcc agcttaaaag ggatgttgat ctcctatcat   1200

gtacgccact atcttaagca aatttacttt caagttcctt cttatacata tggagactac   1260

ttctctcata atgaccgagg attactgtta gatctatatc aggcgaacat tgatgtgttc   1320

tgggctgatg aagagagcgg ccgtgtattg caatatacaa aacggcgcga caaaaatagt   1380

ggaatgttcg tcgttaaaaa tcgagtagaa gagttccaat cagcatattt cgtagcgatt   1440

tatggatcac gtctcctgga aaataatttc tcggcccaac taaacacgct tcttgcaggg   1500

ttacaaaaag ctgcacacac tctaggcatt ccaggcttct caaaacccac tcctcttgcc   1560

gtaatcacag gaggagggac tggcgttatg gctacaggaa atcgtgttgc aaaagagttg   1620

ggaattcttt cttgcgggac cgttctcgat ttggaagctt cacctgcaca aatagatcag   1680

cctgcaaacg aatttttaga tgccaaaatg acataccgtc taccgcaact tatagaaaga   1740

caagaacatt tttattcaga ccttgccatt ttagttgttg gtggtgttgg aacagatttc   1800

gaactttacc tagaactcgt ctacttgaaa acaggcgcca aacctcctac tccaattttc   1860

cttattgggc ctgttgaata ctggaaagag aaagttgctc atgcctatga gattaatctt   1920

aaagcaggaa ctattcgtgg ttctgagtgg atcagcaact gcttattctg cattacatct   1980

cctgaagcag gaattgctgt attcgaacag ttcctcgctg gagaacttcc cataggatat   2040

gattatcctc cagctccaga cggattagtt atcgtc                             2076
```

<210> SEQ ID NO 130
<211> LENGTH: 692
<212> TYPE: PRT
<213> ORGANISM: Chlamydia muridarum

<400> SEQUENCE: 130

```
Met Thr Leu Phe His Thr His His Asp Ala Val Ser Pro Asp Gly Tyr
1               5                   10                  15

Leu Cys Ser Ser Leu Gln Leu Val Gly Ser Gly Thr Tyr Glu Gly Glu
            20                  25                  30

Ile Glu Ile Gln Asn Ile Pro Ser Tyr Phe Leu Gly Phe Arg Leu Pro
        35                  40                  45

Thr His Cys Val His Leu Asn Leu Lys Ser Ser Leu Ala Gln Leu Gly
    50                  55                  60

Val Asp Ala Ser Leu Leu His Cys Glu Leu Ser Lys Asn Gln Gln Arg
65                  70                  75                  80

Ala His Met His Val Gln Phe Thr Gly Tyr Gly Pro Ile Ala Glu Ser
                85                  90                  95

Met Leu Ser Leu Leu Lys Pro Gly Asp Arg Val Ala Lys Leu Phe Ala
            100                 105                 110

Ala Asp Asp Arg Arg Leu Val Arg Ser Pro Asp Tyr Leu Glu Ser Met
        115                 120                 125

Leu Lys Asn Thr Asp Lys Thr Gly His Pro Leu Leu Arg Phe Gly Lys
    130                 135                 140

Lys Leu Glu His Leu Ile Ser Phe Asp Val Val Asp Asp Arg Leu Val
145                 150                 155                 160

Val Ser Leu Pro Thr Leu Pro Gly Ile Val Asn Tyr Asp Pro Asp Ile
                165                 170                 175

Tyr Gly Leu Leu Pro Leu Ile Gln Lys Ser Leu Ser Asn Pro Lys Leu
```

```
            180                 185                 190

Ser Ile Arg His Phe Leu Ser Leu Tyr Gln Lys Ile Val Glu Gly Pro
        195                 200                 205

His Ile Pro Tyr Glu Gly Asn Ile Leu Leu Ile Lys Thr Glu Pro Leu
    210                 215                 220

His Ile Arg Thr Val Phe Ala Arg Val Val Asp Gln Met Leu Pro Gln
225                 230                 235                 240

Gly Leu Phe His Thr Ser Ala Asn Ile Leu Glu Pro Thr Thr Arg Glu
                245                 250                 255

Ser Gly Asp Ile Phe Glu Phe Phe Gly Asn Pro Ser Thr Leu Val Glu
            260                 265                 270

Arg Ile Pro Leu Glu Phe Phe Thr Ile Glu Pro Tyr Lys Glu His Ser
        275                 280                 285

Tyr Phe Cys Asn Arg Asp Leu Leu Gln Thr Thr Leu Gln Ser Glu Ser
    290                 295                 300

Glu Ile Lys Lys Ile Phe Asp Thr Ala Pro Gln Glu Pro Val Lys Ala
305                 310                 315                 320

Ala Thr Tyr Leu Ser Lys Gly Ser Glu Ile Ser Ser Leu Asp Ala Asp
                325                 330                 335

Ser Trp Leu Thr Gly Ser Ala Ala Ala Tyr Gln Cys Ser Glu Lys Gln
            340                 345                 350

Ala Ala Lys Asp Glu Tyr Ile His Ala Gln Pro Cys Tyr Pro Phe Leu
        355                 360                 365

Glu Ala Met Glu Thr Gly Leu Ile Asn Ser Glu Gly Ala Leu Leu Thr
    370                 375                 380

Arg Phe Phe Pro Ser Ser Ser Leu Lys Gly Met Leu Ile Ser Tyr His
385                 390                 395                 400

Val Arg His Tyr Leu Lys Gln Ile Tyr Phe Gln Val Pro Ser Tyr Thr
                405                 410                 415

Tyr Gly Asp Tyr Phe Ser His Asn Asp Arg Gly Leu Leu Leu Asp Leu
            420                 425                 430

Tyr Gln Ala Asn Ile Asp Val Phe Trp Ala Asp Glu Glu Ser Gly Arg
        435                 440                 445

Val Leu Gln Tyr Thr Lys Arg Arg Asp Lys Asn Ser Gly Met Phe Val
    450                 455                 460

Val Lys Asn Arg Val Glu Glu Phe Gln Ser Ala Tyr Phe Val Ala Ile
465                 470                 475                 480

Tyr Gly Ser Arg Leu Leu Glu Asn Asn Phe Ser Ala Gln Leu Asn Thr
                485                 490                 495

Leu Leu Ala Gly Leu Gln Lys Ala Ala His Thr Leu Gly Ile Pro Gly
            500                 505                 510

Phe Ser Lys Pro Thr Pro Leu Ala Val Ile Thr Gly Gly Gly Thr Gly
        515                 520                 525

Val Met Ala Thr Gly Asn Arg Val Ala Lys Glu Leu Gly Ile Leu Ser
    530                 535                 540

Cys Gly Thr Val Leu Asp Leu Glu Ala Ser Pro Ala Gln Ile Asp Gln
545                 550                 555                 560

Pro Ala Asn Glu Phe Leu Asp Ala Lys Met Thr Tyr Arg Leu Pro Gln
                565                 570                 575

Leu Ile Glu Arg Gln Glu His Phe Tyr Ser Asp Leu Ala Ile Leu Val
            580                 585                 590

Val Gly Gly Val Gly Thr Asp Phe Glu Leu Tyr Leu Glu Leu Val Tyr
        595                 600                 605
```

-continued

```
Leu Lys Thr Gly Ala Lys Pro Pro Thr Pro Ile Phe Leu Ile Gly Pro
    610                 615                 620

Val Glu Tyr Trp Lys Glu Lys Val Ala His Ala Tyr Glu Ile Asn Leu
625                 630                 635                 640

Lys Ala Gly Thr Ile Arg Gly Ser Glu Trp Ile Ser Asn Cys Leu Phe
                645                 650                 655

Cys Ile Thr Ser Pro Glu Ala Gly Ile Ala Val Phe Glu Gln Phe Leu
            660                 665                 670

Ala Gly Glu Leu Pro Ile Gly Tyr Asp Tyr Pro Pro Ala Pro Asp Gly
        675                 680                 685

Leu Val Ile Val
    690
```

<210> SEQ ID NO 131
<211> LENGTH: 4473
<212> TYPE: DNA
<213> ORGANISM: Chlamydia muridarum

<400> SEQUENCE: 131

```
aattgttccg atctttatgc cgtaggaagt tctgcagacc atcctgccta cttgattcct     60

caagcggggt tattattgga tcatattaag gatatattca ttggccctaa agatagtcag    120

gataaggggc agtataagtt gattattggt gaggctggct ctttccaaga tagtaatgca    180

gagactcttc ctcaaaaggt agagcacagc actttgtttt cagttacaac acctataatt    240

gtgcaaggaa tagatcaaca agatcaggtc tcttcgcagg gattggtctg taatttttca    300

ggagatcatt cagaggagat ttttgagaga gaatcctttt tagggatcgc tttcctaggg    360

aatggtagca aggatggaat cacgttaaca gatataaaat cttcgttatc tggtgctgcc    420

ttgtattctt cagatgatct tatttttgaa agaattaagg gagatataga gctttcttct    480

tgttcatctt tagaaagagg aggagcttgt tcagctcaaa gtattttaat tcatgattgt    540

caaggattaa cggtaaaaca ttgtgccgca ggggtgaatg ttgaaggagt tagtgctagc    600

gaccatctcg gatttggggg cggggccttc tctactacaa gttctctttc tggagagaag    660

agtttgtata tgcctgcagg cgatattgtg gtggctacct gcgatggtcc tgtgtgtttc    720

gaaggaaata gtgctcagtt agcaaatggt ggcgctattg ccgcttctgg taaagttctt    780

tttgtagcta acgaaaaaaa gatttccttt acagacaacc aagctttgtc tggaggagct    840

atttctgcat cttctagtat ttctttccaa aattgtgctg agcttgtgtt caagagtaat    900

cttgcaaaag gagttaaaga taaatgttct ttgggaggag gtgctttagc ctctttagaa    960

tccgtagttt tgaaagataa tctcggtatt acttatgaaa aaaatcagtc ctattcggaa   1020

ggaggggcta tttttgggaa ggattgtgag atttttgaaa acaggggggcc tgttgtattc   1080

agagataata cagctgcttt aggaggcgga gctattttgg cgcaacaaac tgtggcgatt   1140

tgtggtaata agtctggaat atcttttgaa ggaagtaagt ctagttttgg aggggccatt   1200

gcttgtggaa atttctcttc tgagaataat tcttcagctt tgggatcaat tgatatctct   1260

aacaatctag gagatatctc ttttcttcgg actctgtgta ctacttcgga tttagggcaa   1320

acggattacc aagggggagg ggccttattc gctgaaaata tttctctttc tgagaatgct   1380

ggtgcaatta ctttcaaaga caatattgtg aagacatttg cctcaaatgg aaaaatgttg   1440

ggtggagggg caattttagc ttcaggaaat gttttgatta gcaaaaactc tggagagatt   1500

tcttttgtag ggaatgctcg agctcctcag gctattccga ctcgttcatc tgacgaattg   1560
```

-continued

```
tcttttggcg cacaattaac tcaaactact tcaggatgtt ctggaggagg agctcttttt   1620
ggtaaagagg ttgccattgt tcaaaatgcc actgttgtat tcgagcaaaa tcgcttacag   1680
tgtggcgagc aggaaacaca tggtggaggc ggtgctgttt atggtatgga gagtgcctct   1740
attattggaa actcttttgt gagattcgga aataattacg ctgtagggaa tcagatttct   1800
ggaggagctc ttttatccaa gaaggtccgt ttagctgaaa atacaagggt agatttttct   1860
cgaaatatcg ctactttctg cggcggggct gttcaagttt ctgatggaag ttgcgaattg   1920
atcaacaatg ggtatgtgct attcagagat aaccgagggc agacatttgg tggggctatt   1980
tcttgcttga aaggagatgt gatcatttcc ggaaataaag atagggttga gtttagagat   2040
aacattgtga cgcggcctta ttttgaagaa aatgaagaaa aagttgagac agcagatatt   2100
aattcagata agcaagaagc agaagagcgc tctttattag agaacattga gcagagcttt   2160
attactgcaa ctaatcagac ctttttctta gaggaagaga aactcccatc agaagctttt   2220
atctctgctg aagaactttc aaagagaaga gaatgtgctg gtggggcgat tttgcaaaa    2280
cgggtctaca ttacggataa taaagaacct atcttgtttt cgcataattt ttctgatgtt   2340
tatgggggag ctatttttac gggttctcta caggaaactg ataaacaaga tgttgtaact   2400
cctgaagttg tgatatcagg caacgatggg gatgtcattt tttctggaaa tgcagctaaa   2460
catgataagc atttacctga tacaggtggt ggagccattt gtacacagaa tttgacgatt   2520
tcccaaaaca atgggaatgt cttgttcttg aacaattttg cttgttctgg tggagcagtt   2580
cgcatagagg atcatggaga agttctttta gaggcttttg gggagatat tattttcaat    2640
ggaaactctt ctttcagagc tcaaggatcg gatgcgatct attttgctgg taaggactct   2700
agaattaaag ctttaaatgc tactgaagga catgcgattg tgttccaaga tgcattggtg   2760
tttgaaaata tagaagaaag aaagtcttcg ggactattgg tgattaactc tcaggaaaat   2820
gagggttata cgggatccgt ccgattttta ggatctgaaa gtaaggttcc tcaatggatt   2880
catgtgcaac agggaggtct tgagttgcta catggagcta ttttatgtag ttatggggtt   2940
aaacaagatc ctagagctaa aatagtatta tctgctggat ctaaattgaa gattctagat   3000
tcagagcaag aaaataacgc agaaattgga gatcttgaag attctgttaa ttcagaaaaa   3060
acaccatctc tttggattgg gaagaacgct caagcaaaag tccctctggt tgatatccat   3120
actatttcta ttgatttagc atcattttct tctaaagctc aggaaacccc tgaggaagct   3180
ccacaagtca tcgtccctaa gggaagttgt gtccactcgg gagagttaag tttggagttg   3240
gttaatacaa caggaaaagg ttatgagaat catgcgttgt taaaaaatga tactcaggtt   3300
tctctcatgt ctttcaaaga ggaaaatgat ggatctttag aagatttgag taagttgtct   3360
gtttcggatt tacgcattaa agtttctact ccagatattg tagaagaaac ttatggccat   3420
atgggggatt ggtctgaagc tacaattcaa gatggggctc ttgtcattaa ttggcatcct   3480
actggatata aattagatcc gcaaaaagct ggttctttgg tattcaatgc attatgggag   3540
gaagaggctg tattgtctac tctaaaaaat gctcggattg cccataacct taccattcag   3600
agaatggaat ttgattattc tacaaatgct tggggattag cttttagtag ctttagagag   3660
ctatcttcag agaagcttgt ttctgttgat ggatatagag gctcttatat aggggcttct   3720
gcaggcattg atactcagtt gatggaagat tttgttttgg gaatcagcac ggcttccttc   3780
ttcgggaaaa tgcatagtca gaattttgat gcagagattt ctcgacatgg ttttgttggt   3840
tcggtctata caggcttcct agctggggcc tggttcttca aggggcagta cagtcttggc   3900
gaaacacata acgatatgac aactcgttac ggggttttgg gagaatctaa tgctacttgg   3960
```

```
aagtctcgag gagtactagc agatgcttta gttgaatatc gtagtttagt cggtccagca   4020

cgacctaaat tttatgcttt gcattttaat ccttatgtcg aggtatctta tgcatctgcg   4080

aagttcccta gttttgtaga acaaggagga gaagctcgtg cttttgaaga aacctcttta   4140

acaaacatta ccgttccctt tggtatgaaa tttgaactat cttttacaaa aggacagttt   4200

tcagagacta attctcttgg aataggttgt gcatgggaaa tgtatcggaa agtcgaagga   4260

agatctgtag agctactaga agctggtttt gattgggaag gatctcctat agatctccct   4320

aaacaagagc tgagagtggc tttagaaaac aatacggaat ggagttcgta ttttagtaca   4380

gctctaggag taacagcatt ttgtggagga ttttcttcta tggataataa actaggatac   4440

gaagcgaatg ctggaatgcg tttgattttc tag                                4473
```

```
<210> SEQ ID NO 132
<211> LENGTH: 1490
<212> TYPE: PRT
<213> ORGANISM: Chlamydia muridarum

<400> SEQUENCE: 132

Asn Cys Ser Asp Leu Tyr Ala Val Gly Ser Ser Ala Asp His Pro Ala
1               5                   10                  15

Tyr Leu Ile Pro Gln Ala Gly Leu Leu Leu Asp His Ile Lys Asp Ile
            20                  25                  30

Phe Ile Gly Pro Lys Asp Ser Gln Asp Lys Gly Gln Tyr Lys Leu Ile
        35                  40                  45

Ile Gly Glu Ala Gly Ser Phe Gln Asp Ser Asn Ala Glu Thr Leu Pro
    50                  55                  60

Gln Lys Val Glu His Ser Thr Leu Phe Ser Val Thr Thr Pro Ile Ile
65                  70                  75                  80

Val Gln Gly Ile Asp Gln Gln Asp Gln Val Ser Ser Gln Gly Leu Val
                85                  90                  95

Cys Asn Phe Ser Gly Asp His Ser Glu Glu Ile Phe Glu Arg Glu Ser
            100                 105                 110

Phe Leu Gly Ile Ala Phe Leu Gly Asn Gly Ser Lys Asp Gly Ile Thr
        115                 120                 125

Leu Thr Asp Ile Lys Ser Ser Leu Ser Gly Ala Ala Leu Tyr Ser Ser
    130                 135                 140

Asp Asp Leu Ile Phe Glu Arg Ile Lys Gly Asp Ile Glu Leu Ser Ser
145                 150                 155                 160

Cys Ser Ser Leu Glu Arg Gly Gly Ala Cys Ser Ala Gln Ser Ile Leu
                165                 170                 175

Ile His Asp Cys Gln Gly Leu Thr Val Lys His Cys Ala Ala Gly Val
            180                 185                 190

Asn Val Glu Gly Val Ser Ala Ser Asp His Leu Gly Phe Gly Gly Gly
        195                 200                 205

Ala Phe Ser Thr Thr Ser Ser Leu Ser Gly Glu Lys Ser Leu Tyr Met
    210                 215                 220

Pro Ala Gly Asp Ile Val Val Ala Thr Cys Asp Gly Pro Val Cys Phe
225                 230                 235                 240

Glu Gly Asn Ser Ala Gln Leu Ala Asn Gly Gly Ala Ile Ala Ala Ser
                245                 250                 255

Gly Lys Val Leu Phe Val Ala Asn Glu Lys Lys Ile Ser Phe Thr Asp
            260                 265                 270

Asn Gln Ala Leu Ser Gly Gly Ala Ile Ser Ala Ser Ser Ser Ile Ser
```

```
        275                 280                 285

Phe Gln Asn Cys Ala Glu Leu Val Phe Lys Ser Asn Leu Ala Lys Gly
    290                 295                 300

Val Lys Asp Lys Cys Ser Leu Gly Gly Gly Ala Leu Ala Ser Leu Glu
305                 310                 315                 320

Ser Val Val Leu Lys Asp Asn Leu Gly Ile Thr Tyr Glu Lys Asn Gln
                325                 330                 335

Ser Tyr Ser Glu Gly Gly Ala Ile Phe Gly Lys Asp Cys Glu Ile Phe
            340                 345                 350

Glu Asn Arg Gly Pro Val Val Phe Arg Asp Asn Thr Ala Ala Leu Gly
        355                 360                 365

Gly Gly Ala Ile Leu Ala Gln Gln Thr Val Ala Ile Cys Gly Asn Lys
    370                 375                 380

Ser Gly Ile Ser Phe Glu Gly Ser Lys Ser Ser Phe Gly Gly Ala Ile
385                 390                 395                 400

Ala Cys Gly Asn Phe Ser Ser Glu Asn Asn Ser Ser Ala Leu Gly Ser
                405                 410                 415

Ile Asp Ile Ser Asn Asn Leu Gly Asp Ile Ser Phe Leu Arg Thr Leu
            420                 425                 430

Cys Thr Thr Ser Asp Leu Gly Gln Thr Asp Tyr Gln Gly Gly Gly Ala
        435                 440                 445

Leu Phe Ala Glu Asn Ile Ser Leu Ser Glu Asn Ala Gly Ala Ile Thr
    450                 455                 460

Phe Lys Asp Asn Ile Val Lys Thr Phe Ala Ser Asn Gly Lys Met Leu
465                 470                 475                 480

Gly Gly Gly Ala Ile Leu Ala Ser Gly Asn Val Leu Ile Ser Lys Asn
                485                 490                 495

Ser Gly Glu Ile Ser Phe Val Gly Asn Ala Arg Ala Pro Gln Ala Ile
            500                 505                 510

Pro Thr Arg Ser Ser Asp Glu Leu Ser Phe Gly Ala Gln Leu Thr Gln
        515                 520                 525

Thr Thr Ser Gly Cys Ser Gly Gly Gly Ala Leu Phe Gly Lys Glu Val
    530                 535                 540

Ala Ile Val Gln Asn Ala Thr Val Val Phe Glu Gln Asn Arg Leu Gln
545                 550                 555                 560

Cys Gly Glu Gln Glu Thr His Gly Gly Gly Gly Ala Val Tyr Gly Met
                565                 570                 575

Glu Ser Ala Ser Ile Ile Gly Asn Ser Phe Val Arg Phe Gly Asn Asn
            580                 585                 590

Tyr Ala Val Gly Asn Gln Ile Ser Gly Gly Ala Leu Leu Ser Lys Lys
        595                 600                 605

Val Arg Leu Ala Glu Asn Thr Arg Val Asp Phe Ser Arg Asn Ile Ala
    610                 615                 620

Thr Phe Cys Gly Gly Ala Val Gln Val Ser Asp Gly Ser Cys Glu Leu
625                 630                 635                 640

Ile Asn Asn Gly Tyr Val Leu Phe Arg Asp Asn Arg Gly Gln Thr Phe
                645                 650                 655

Gly Gly Ala Ile Ser Cys Leu Lys Gly Asp Val Ile Ile Ser Gly Asn
            660                 665                 670

Lys Asp Arg Val Glu Phe Arg Asp Asn Ile Val Thr Arg Pro Tyr Phe
        675                 680                 685

Glu Glu Asn Glu Glu Lys Val Glu Thr Ala Asp Ile Asn Ser Asp Lys
    690                 695                 700
```

-continued

```
Gln Glu Ala Glu Glu Arg Ser Leu Leu Glu Asn Ile Glu Gln Ser Phe
705                 710                 715                 720

Ile Thr Ala Thr Asn Gln Thr Phe Phe Leu Glu Glu Glu Lys Leu Pro
                725                 730                 735

Ser Glu Ala Phe Ile Ser Ala Glu Glu Leu Ser Lys Arg Arg Glu Cys
            740                 745                 750

Ala Gly Gly Ala Ile Phe Ala Lys Arg Val Tyr Ile Thr Asp Asn Lys
        755                 760                 765

Glu Pro Ile Leu Phe Ser His Asn Phe Ser Asp Val Tyr Gly Gly Ala
    770                 775                 780

Ile Phe Thr Gly Ser Leu Gln Glu Thr Asp Lys Gln Asp Val Val Thr
785                 790                 795                 800

Pro Glu Val Val Ile Ser Gly Asn Asp Gly Asp Val Ile Phe Ser Gly
                805                 810                 815

Asn Ala Ala Lys His Asp Lys His Leu Pro Asp Thr Gly Gly Gly Ala
            820                 825                 830

Ile Cys Thr Gln Asn Leu Thr Ile Ser Gln Asn Asn Gly Asn Val Leu
        835                 840                 845

Phe Leu Asn Asn Phe Ala Cys Ser Gly Gly Ala Val Arg Ile Glu Asp
    850                 855                 860

His Gly Glu Val Leu Leu Glu Ala Phe Gly Gly Asp Ile Ile Phe Asn
865                 870                 875                 880

Gly Asn Ser Ser Phe Arg Ala Gln Gly Ser Asp Ala Ile Tyr Phe Ala
                885                 890                 895

Gly Lys Asp Ser Arg Ile Lys Ala Leu Asn Ala Thr Glu Gly His Ala
            900                 905                 910

Ile Val Phe Gln Asp Ala Leu Val Phe Glu Asn Ile Glu Glu Arg Lys
        915                 920                 925

Ser Ser Gly Leu Leu Val Ile Asn Ser Gln Glu Asn Glu Gly Tyr Thr
    930                 935                 940

Gly Ser Val Arg Phe Leu Gly Ser Glu Ser Lys Val Pro Gln Trp Ile
945                 950                 955                 960

His Val Gln Gln Gly Gly Leu Glu Leu Leu His Gly Ala Ile Leu Cys
                965                 970                 975

Ser Tyr Gly Val Lys Gln Asp Pro Arg Ala Lys Ile Val Leu Ser Ala
            980                 985                 990

Gly Ser Lys Leu Lys Ile Leu Asp  Ser Glu Gln Glu Asn  Asn Ala Glu
        995                 1000                 1005

Ile Gly  Asp Leu Glu Asp Ser  Val Asn Ser Glu Lys  Thr Pro Ser
    1010                 1015                 1020

Leu Trp  Ile Gly Lys Asn Ala  Gln Ala Lys Val Pro  Leu Val Asp
    1025                 1030                 1035

Ile His  Thr Ile Ser Ile Asp  Leu Ala Ser Phe Ser  Ser Lys Ala
    1040                 1045                 1050

Gln Glu  Thr Pro Glu Glu Ala  Pro Gln Val Ile Val  Pro Lys Gly
    1055                 1060                 1065

Ser Cys  Val His Ser Gly Glu  Leu Ser Leu Glu Leu  Val Asn Thr
    1070                 1075                 1080

Thr Gly  Lys Gly Tyr Glu Asn  His Ala Leu Leu Lys  Asn Asp Thr
    1085                 1090                 1095

Gln Val  Ser Leu Met Ser Phe  Lys Glu Glu Asn Asp  Gly Ser Leu
    1100                 1105                 1110
```

-continued

```
Glu Asp  Leu Ser Lys Leu Ser  Val Ser Asp Leu Arg  Ile Lys Val
    1115                1120                1125

Ser Thr  Pro Asp Ile Val Glu  Glu Thr Tyr Gly His  Met Gly Asp
    1130                1135                1140

Trp Ser  Glu Ala Thr Ile Gln  Asp Gly Ala Leu Val  Ile Asn Trp
    1145                1150                1155

His Pro  Thr Gly Tyr Lys Leu  Asp Pro Gln Lys Ala  Gly Ser Leu
    1160                1165                1170

Val Phe  Asn Ala Leu Trp Glu  Glu Glu Ala Val Leu  Ser Thr Leu
    1175                1180                1185

Lys Asn  Ala Arg Ile Ala His  Asn Leu Thr Ile Gln  Arg Met Glu
    1190                1195                1200

Phe Asp  Tyr Ser Thr Asn Ala  Trp Gly Leu Ala Phe  Ser Ser Phe
    1205                1210                1215

Arg Glu  Leu Ser Ser Glu Lys  Leu Val Ser Val Asp  Gly Tyr Arg
    1220                1225                1230

Gly Ser  Tyr Ile Gly Ala Ser  Ala Gly Ile Asp Thr  Gln Leu Met
    1235                1240                1245

Glu Asp  Phe Val Leu Gly Ile  Ser Thr Ala Ser Phe  Phe Gly Lys
    1250                1255                1260

Met His  Ser Gln Asn Phe Asp  Ala Glu Ile Ser Arg  His Gly Phe
    1265                1270                1275

Val Gly  Ser Val Tyr Thr Gly  Phe Leu Ala Gly Ala  Trp Phe Phe
    1280                1285                1290

Lys Gly  Gln Tyr Ser Leu Gly  Glu Thr His Asn Asp  Met Thr Thr
    1295                1300                1305

Arg Tyr  Gly Val Leu Gly Glu  Ser Asn Ala Thr Trp  Lys Ser Arg
    1310                1315                1320

Gly Val  Leu Ala Asp Ala Leu  Val Glu Tyr Arg Ser  Leu Val Gly
    1325                1330                1335

Pro Ala  Arg Pro Lys Phe Tyr  Ala Leu His Phe Asn  Pro Tyr Val
    1340                1345                1350

Glu Val  Ser Tyr Ala Ser Ala  Lys Phe Pro Ser Phe  Val Glu Gln
    1355                1360                1365

Gly Gly  Glu Ala Arg Ala Phe  Glu Glu Thr Ser Leu  Thr Asn Ile
    1370                1375                1380

Thr Val  Pro Phe Gly Met Lys  Phe Glu Leu Ser Phe  Thr Lys Gly
    1385                1390                1395

Gln Phe  Ser Glu Thr Asn Ser  Leu Gly Ile Gly Cys  Ala Trp Glu
    1400                1405                1410

Met Tyr  Arg Lys Val Glu Gly  Arg Ser Val Glu Leu  Leu Glu Ala
    1415                1420                1425

Gly Phe  Asp Trp Glu Gly Ser  Pro Ile Asp Leu Pro  Lys Gln Glu
    1430                1435                1440

Leu Arg  Val Ala Leu Glu Asn  Asn Thr Glu Trp Ser  Ser Tyr Phe
    1445                1450                1455

Ser Thr  Ala Leu Gly Val Thr  Ala Phe Cys Gly Gly  Phe Ser Ser
    1460                1465                1470

Met Asp  Asn Lys Leu Gly Tyr  Glu Ala Asn Ala Gly  Met Arg Leu
    1475                1480                1485

Ile Phe
    1490
```

<210> SEQ ID NO 133
<211> LENGTH: 2877
<212> TYPE: DNA
<213> ORGANISM: Chlamydia muridarum

<400> SEQUENCE: 133

```
actcgagaag tccctccttc gattctttta aagcctatac taaatccata ccatatgacc     60
gggttatttt ttcccaaggt taatttgctt ggagacacac ataatctcac tgattaccat    120
ttggataatc taaaatgcat tctggcttgc ctacaaagaa ctccttatga aggagctgct    180
ttcacagtaa ccgattactt aggtttttca gatacacaaa aggatggtat tttttgtttt    240
aaaaatctta ctccagagag tggaggggtt attggttccc caactcaaaa cactcctact    300
ataaaaattc ataatacaat cggccccgtt cttttcgaaa ataatacctg tcatagactg    360
tggacacaga ccgatcccga aaatgaagga aacaaagcac gcgaaggcgg ggcaattcat    420
gctggggacg tttacataag caataaccag aaccttgtcg gattcataaa gaactttgct    480
tatgttcaag gtggagctat tagtgctaat acttttgcct ataaagaaaa taaatcgagc    540
tttctttgcc taaataactc ttgtatacaa actaagacgg gagggaaagg tggtgctatt    600
tacgttagta cgagctgctc tttcgagaac aataacaagg atctgctttt catccaaaac    660
tccggctgtg caggaggagc tatcttctct ccaacctgtt ctctaatagg aaaccaagga    720
gatattgttt tttacagcaa ccacggtttt aaaaatgttg ataatgcaac taacgaatct    780
ggggatggag gagctattaa agtaactacc cgcttggaca tcaccaataa tggtagtcaa    840
atcttttttt ctgataatat ctcaagaaat tttggaggag ctattcatgc tccttgtctt    900
catcttgttg gtaatgggcc aacctatttt acaaacaata tagctaatca cacaggtggg    960
gctatttata taacaggaac agaaacctca aagatttctg cagatcacca tgctattatt   1020
tttgataata acatttctgc aaacgccacc aatgcggacg gatctagcag caacactaat   1080
cctcctcaca gaaatgcgat cactatggac aattccgctg gaggaataga acttggtgca   1140
gggaagagcc agaatcttat tttctatgat cctattcaag tgacgaatgc tggagttacc   1200
gtagacttca ataaggatgc ctcccaaacc ggatgtgtag ttttctctgg agcgactgtc   1260
ctttctgcag atatttctca ggctaatttg caaactaaaa cacctgcaac gcttactctc   1320
agtcacggtc ttctgtgtat cgaagatcgt gctcagctca cagtgaacaa ttttacacaa   1380
acaggaggga ttgtagcctt aggaaatgga gcagttttaa gcagctacca acacagcact   1440
acagacgcca ctcaaactcc ccctacaacc accactacag atgcttccgt aactcttaat   1500
cacattggat taaatctccc ctctattctt aaggatggag cagagatgcc tctattatgg   1560
gtagaaccta taagcacaac tcaaggtaac actacaacat atacgtcaga taccgcggct   1620
tccttctcat taaatggagc cacactctct ctcattgatg aagatggaaa ttctccctat   1680
gaaaacacgg acctctctcg tgcattgtac gctcaaccta tgctagcaat ttctgaggcc   1740
agtgataacc aattgcaatc cgaaagcatg gacttttcta aagttaatgt tcctcactat   1800
ggatggcaag gactttggac ctgggggtgg gcaaaaactg aaaatccaac aacaactcct   1860
ccagcaacaa ttactgatcc gaaaaaagct aatcagtttc atagaacttt attattaacg   1920
tggctccctg ctggttatat ccccagccct aaacataaaa gccctttaat agctaatacc   1980
ttgtggggga atatactttt tgcaacggaa aacttaaaaa atagctcagg gcaagaactt   2040
cttgatcgtc ctttctgggg aattacagga gggggcttgg ggatgatggt ctatcaagaa   2100
cctagaaaag accatcctgg attccacatg catacctccg gatattcagc aggaatgatt   2160
```

acaggaaaca cacatacctt ctcattacga ttcagccagt cctatacaaa actcaatgaa 2220
cgttatgcca agaactatgt gtcttctaaa aattactctt gccaagggga aatgcttttg 2280
tccttacaag aaggactcat gctgactaaa ctaattggtc tctatagtta tgggaatcac 2340
aacagccacc atttctatac ccaaggagaa gacctatcgt ctcaagggga gttccatagt 2400
cagacttttg gaggggctgt ctttttgat ctacctctga aaccttttgg aagaacacac 2460
atacttacag ctcctttctt aggtgccatt ggtatgtatt ctaagctgtc tagctttaca 2520
gaagtaggag cctatccaag aacctttatt acagaaacgc ctttaatcaa tgtcctgatt 2580
cctatcggag taaaaggtag cttcatgaat gccacccata gacctcaggc ctggactgta 2640
gagcttgctt accaacctgt tctttacaga caagaaccta gtatctctac ccaattactc 2700
gctggtaaag gtatgtggtt tggcatggaa agtcctgcat ctcgccacgc tctagcttat 2760
aaaatttcac agaaaacaca gcttttgcga tttgcaacac ttcaactcca gtatcacgga 2820
tactattcgt cttccacttt ctgtaattat ctgaatggag aggtatcttt acgtttc 2877

<210> SEQ ID NO 134
<211> LENGTH: 959
<212> TYPE: PRT
<213> ORGANISM: Chlamydia muridarum

<400> SEQUENCE: 134

Thr Arg Glu Val Pro Pro Ser Ile Leu Leu Lys Pro Ile Leu Asn Pro
1               5                   10                  15

Tyr His Met Thr Gly Leu Phe Phe Pro Lys Val Asn Leu Leu Gly Asp
            20                  25                  30

Thr His Asn Leu Thr Asp Tyr His Leu Asp Asn Leu Lys Cys Ile Leu
        35                  40                  45

Ala Cys Leu Gln Arg Thr Pro Tyr Glu Gly Ala Ala Phe Thr Val Thr
    50                  55                  60

Asp Tyr Leu Gly Phe Ser Asp Thr Gln Lys Asp Gly Ile Phe Cys Phe
65                  70                  75                  80

Lys Asn Leu Thr Pro Glu Ser Gly Gly Val Ile Gly Ser Pro Thr Gln
                85                  90                  95

Asn Thr Pro Thr Ile Lys Ile His Asn Thr Ile Gly Pro Val Leu Phe
            100                 105                 110

Glu Asn Asn Thr Cys His Arg Leu Trp Thr Gln Thr Asp Pro Glu Asn
        115                 120                 125

Glu Gly Asn Lys Ala Arg Glu Gly Gly Ala Ile His Ala Gly Asp Val
    130                 135                 140

Tyr Ile Ser Asn Asn Gln Asn Leu Val Gly Phe Ile Lys Asn Phe Ala
145                 150                 155                 160

Tyr Val Gln Gly Gly Ala Ile Ser Ala Asn Thr Phe Ala Tyr Lys Glu
                165                 170                 175

Asn Lys Ser Ser Phe Leu Cys Leu Asn Asn Ser Cys Ile Gln Thr Lys
            180                 185                 190

Thr Gly Gly Lys Gly Gly Ala Ile Tyr Val Ser Thr Ser Cys Ser Phe
        195                 200                 205

Glu Asn Asn Asn Lys Asp Leu Leu Phe Ile Gln Asn Ser Gly Cys Ala
    210                 215                 220

Gly Gly Ala Ile Phe Ser Pro Thr Cys Ser Leu Ile Gly Asn Gln Gly
225                 230                 235                 240

Asp Ile Val Phe Tyr Ser Asn His Gly Phe Lys Asn Val Asp Asn Ala
                245                 250                 255

```
Thr Asn Glu Ser Gly Asp Gly Gly Ala Ile Lys Val Thr Thr Arg Leu
            260                 265                 270

Asp Ile Thr Asn Asn Gly Ser Gln Ile Phe Phe Ser Asp Asn Ile Ser
        275                 280                 285

Arg Asn Phe Gly Gly Ala Ile His Ala Pro Cys Leu His Leu Val Gly
    290                 295                 300

Asn Gly Pro Thr Tyr Phe Thr Asn Asn Ile Ala Asn His Thr Gly Gly
305                 310                 315                 320

Ala Ile Tyr Ile Thr Gly Thr Glu Thr Ser Lys Ile Ser Ala Asp His
                325                 330                 335

His Ala Ile Ile Phe Asp Asn Asn Ile Ser Ala Asn Ala Thr Asn Ala
            340                 345                 350

Asp Gly Ser Ser Ser Asn Thr Asn Pro Pro His Arg Asn Ala Ile Thr
        355                 360                 365

Met Asp Asn Ser Ala Gly Gly Ile Glu Leu Gly Ala Gly Lys Ser Gln
    370                 375                 380

Asn Leu Ile Phe Tyr Asp Pro Ile Gln Val Thr Asn Ala Gly Val Thr
385                 390                 395                 400

Val Asp Phe Asn Lys Asp Ala Ser Gln Thr Gly Cys Val Val Phe Ser
                405                 410                 415

Gly Ala Thr Val Leu Ser Ala Asp Ile Ser Gln Ala Asn Leu Gln Thr
            420                 425                 430

Lys Thr Pro Ala Thr Leu Thr Leu Ser His Gly Leu Leu Cys Ile Glu
        435                 440                 445

Asp Arg Ala Gln Leu Thr Val Asn Asn Phe Thr Gln Thr Gly Gly Ile
    450                 455                 460

Val Ala Leu Gly Asn Gly Ala Val Leu Ser Ser Tyr Gln His Ser Thr
465                 470                 475                 480

Thr Asp Ala Thr Gln Thr Pro Pro Thr Thr Thr Thr Thr Asp Ala Ser
                485                 490                 495

Val Thr Leu Asn His Ile Gly Leu Asn Leu Pro Ser Ile Leu Lys Asp
            500                 505                 510

Gly Ala Glu Met Pro Leu Leu Trp Val Glu Pro Ile Ser Thr Thr Gln
        515                 520                 525

Gly Asn Thr Thr Thr Tyr Thr Ser Asp Thr Ala Ala Ser Phe Ser Leu
    530                 535                 540

Asn Gly Ala Thr Leu Ser Leu Ile Asp Glu Asp Gly Asn Ser Pro Tyr
545                 550                 555                 560

Glu Asn Thr Asp Leu Ser Arg Ala Leu Tyr Ala Gln Pro Met Leu Ala
                565                 570                 575

Ile Ser Glu Ala Ser Asp Asn Gln Leu Gln Ser Glu Ser Met Asp Phe
            580                 585                 590

Ser Lys Val Asn Val Pro His Tyr Gly Trp Gln Gly Leu Trp Thr Trp
        595                 600                 605

Gly Trp Ala Lys Thr Glu Asn Pro Thr Thr Thr Pro Pro Ala Thr Ile
    610                 615                 620

Thr Asp Pro Lys Lys Ala Asn Gln Phe His Arg Thr Leu Leu Leu Thr
625                 630                 635                 640

Trp Leu Pro Ala Gly Tyr Ile Pro Ser Pro Lys His Lys Ser Pro Leu
                645                 650                 655

Ile Ala Asn Thr Leu Trp Gly Asn Ile Leu Phe Ala Thr Glu Asn Leu
            660                 665                 670
```

-continued

```
Lys Asn Ser Ser Gly Gln Glu Leu Leu Asp Arg Pro Phe Trp Gly Ile
        675                 680                 685

Thr Gly Gly Gly Leu Gly Met Met Val Tyr Gln Glu Pro Arg Lys Asp
    690                 695                 700

His Pro Gly Phe His Met His Thr Ser Gly Tyr Ser Ala Gly Met Ile
705                 710                 715                 720

Thr Gly Asn Thr His Thr Phe Ser Leu Arg Phe Ser Gln Ser Tyr Thr
                725                 730                 735

Lys Leu Asn Glu Arg Tyr Ala Lys Asn Tyr Val Ser Ser Lys Asn Tyr
            740                 745                 750

Ser Cys Gln Gly Glu Met Leu Leu Ser Leu Gln Glu Gly Leu Met Leu
        755                 760                 765

Thr Lys Leu Ile Gly Leu Tyr Ser Tyr Gly Asn His Asn Ser His His
    770                 775                 780

Phe Tyr Thr Gln Gly Glu Asp Leu Ser Ser Gln Gly Glu Phe His Ser
785                 790                 795                 800

Gln Thr Phe Gly Gly Ala Val Phe Phe Asp Leu Pro Leu Lys Pro Phe
                805                 810                 815

Gly Arg Thr His Ile Leu Thr Ala Pro Phe Leu Gly Ala Ile Gly Met
            820                 825                 830

Tyr Ser Lys Leu Ser Ser Phe Thr Glu Val Gly Ala Tyr Pro Arg Thr
        835                 840                 845

Phe Ile Thr Glu Thr Pro Leu Ile Asn Val Leu Ile Pro Ile Gly Val
    850                 855                 860

Lys Gly Ser Phe Met Asn Ala Thr His Arg Pro Gln Ala Trp Thr Val
865                 870                 875                 880

Glu Leu Ala Tyr Gln Pro Val Leu Tyr Arg Gln Glu Pro Ser Ile Ser
                885                 890                 895

Thr Gln Leu Leu Ala Gly Lys Gly Met Trp Phe Gly His Gly Ser Pro
            900                 905                 910

Ala Ser Arg His Ala Leu Ala Tyr Lys Ile Ser Gln Lys Thr Gln Leu
        915                 920                 925

Leu Arg Phe Ala Thr Leu Gln Leu Gln Tyr His Gly Tyr Tyr Ser Ser
    930                 935                 940

Ser Thr Phe Cys Asn Tyr Leu Asn Gly Glu Val Ser Leu Arg Phe
945                 950                 955
```

<210> SEQ ID NO 135
<211> LENGTH: 567
<212> TYPE: DNA
<213> ORGANISM: Chlamydia trachomatis

<400> SEQUENCE: 135

```
atgagaaaga ctatttttaa agcgtttaat ttattattct cccttctttt tctttcttca      60

tgctcttatc cttgcagaga ttgggaatgc catggttgcg actccgcaag acctcgtaaa     120

tcctcttttg gattcgtacc tttctactcc gatgaagaaa ttcaacaagc ttttgttgaa     180

gattttgatt ccaaagaaga gcagctgtac aaaacgagcg cacagagtac ctctttccga     240

aatatcactt tcgctacaga tagttattct attaaaggag aggataacct cacgattctt     300

gcaagcttag ttcgtcattt gcataaatct cctaaagcta cgctatatat agagggccat     360

acagatgaac gtggagctgc agcttataac ctagctttag gagctcgtcg tgcgaatgct     420

gtaaaacaat acctcatcaa acagggaatc gctgcagacc gcttattcac tatttcttac     480

ggaaaagaac atcctgttca tccaggccat aatgaattag cttggcaaca aaatcgtcgt     540
```

actgaattta agatccatgc tcgctaa 567

<210> SEQ ID NO 136
<211> LENGTH: 188
<212> TYPE: PRT
<213> ORGANISM: Chlamydia trachomatis

<400> SEQUENCE: 136

Met Arg Lys Thr Ile Phe Lys Ala Phe Asn Leu Leu Phe Ser Leu Leu
1 5 10 15

Phe Leu Ser Ser Cys Ser Tyr Pro Cys Arg Asp Trp Glu Cys His Gly
20 25 30

Cys Asp Ser Ala Arg Pro Arg Lys Ser Ser Phe Gly Phe Val Pro Phe
35 40 45

Tyr Ser Asp Glu Glu Ile Gln Gln Ala Phe Val Glu Asp Phe Asp Ser
50 55 60

Lys Glu Glu Gln Leu Tyr Lys Thr Ser Ala Gln Ser Thr Ser Phe Arg
65 70 75 80

Asn Ile Thr Phe Ala Thr Asp Ser Tyr Ser Ile Lys Gly Glu Asp Asn
85 90 95

Leu Thr Ile Leu Ala Ser Leu Val Arg His Leu His Lys Ser Pro Lys
100 105 110

Ala Thr Leu Tyr Ile Glu Gly His Thr Asp Glu Arg Gly Ala Ala Ala
115 120 125

Tyr Asn Leu Ala Leu Gly Ala Arg Arg Ala Asn Ala Val Lys Gln Tyr
130 135 140

Leu Ile Lys Gln Gly Ile Ala Ala Asp Arg Leu Phe Thr Ile Ser Tyr
145 150 155 160

Gly Lys Glu His Pro Val His Pro Gly His Asn Glu Leu Ala Trp Gln
165 170 175

Gln Asn Arg Arg Thr Glu Phe Lys Ile His Ala Arg
180 185

<210> SEQ ID NO 137
<211> LENGTH: 504
<212> TYPE: DNA
<213> ORGANISM: Chlamydia trachomatis

<400> SEQUENCE: 137
tgctcttatc cttgcagaga ttgggaatgc catggttgcg actccgcaag acctcgtaaa 60
tcctcttttg gattcgtacc tttctactcc gatgaagaaa ttcaacaagc ttttgttgaa 120
gattttgatt ccaaagaaga gcagctgtac aaaacgagcg cacagagtac ctctttccga 180
aatatcactt tcgctacaga tagttattct attaaaggag aggataacct cacgattctt 240
gcaagcttag ttcgtcattt gcataaatct cctaaagcta cgctatatat agagggccat 300
acagatgaac gtggagctgc agcttataac ctagctttag gagctcgtcg tgcgaatgct 360
gtaaaacaat acctcatcaa acagggaatc gctgcagacc gcttattcac tatttcttac 420
ggaaaagaac atcctgttca tccaggccat aatgaattag cttggcaaca aaatcgtcgt 480
actgaattta agatccatgc tcgc 504

<210> SEQ ID NO 138
<211> LENGTH: 168
<212> TYPE: PRT
<213> ORGANISM: Chlamydia trachomatis

<400> SEQUENCE: 138

```
Cys Ser Tyr Pro Cys Arg Asp Trp Glu Cys His Gly Cys Asp Ser Ala
1               5                   10                  15

Arg Pro Arg Lys Ser Ser Phe Gly Phe Val Pro Phe Tyr Ser Asp Glu
            20                  25                  30

Glu Ile Gln Gln Ala Phe Val Glu Asp Phe Asp Ser Lys Glu Glu Gln
        35                  40                  45

Leu Tyr Lys Thr Ser Ala Gln Ser Thr Ser Phe Arg Asn Ile Thr Phe
    50                  55                  60

Ala Thr Asp Ser Tyr Ser Ile Lys Gly Glu Asp Asn Leu Thr Ile Leu
65                  70                  75                  80

Ala Ser Leu Val Arg His Leu His Lys Ser Pro Lys Ala Thr Leu Tyr
                85                  90                  95

Ile Glu Gly His Thr Asp Glu Arg Gly Ala Ala Ala Tyr Asn Leu Ala
            100                 105                 110

Leu Gly Ala Arg Arg Ala Asn Ala Val Lys Gln Tyr Leu Ile Lys Gln
        115                 120                 125

Gly Ile Ala Ala Asp Arg Leu Phe Thr Ile Ser Tyr Gly Lys Glu His
    130                 135                 140

Pro Val His Pro Gly His Asn Glu Leu Ala Trp Gln Gln Asn Arg Arg
145                 150                 155                 160

Thr Glu Phe Lys Ile His Ala Arg
                165
```

<210> SEQ ID NO 139
<211> LENGTH: 1494
<212> TYPE: DNA
<213> ORGANISM: Chlamydia trachomatis

<400> SEQUENCE: 139

```
atgatgaaaa gattattatg tgtgttgcta tcgacatcag ttttctcttc gccaatgcta     60

ggctatagtg cgtcaaagaa agattctaag gctgatattt gtcttgcagt atcctcagga    120

gatcaagagg tttcacaaga agatctgctc aaagaagtat cccgaggatt ttctcgggtc    180

gctgctaagg caacgcctgg agttgtatat atagaaaatt ttcctaaaac agggaaccag    240

gctattgctt ctccaggaaa caaaagaggc tttcaagaga accctttttga ttattttaat    300

gacgaatttt ttaatcgatt ttttggattg ccttcgcata gagagcagca gcgtccgcag    360

cagcgtgatg ctgtaagagg aactgggttc attgtttctg aagatggtta tgttgttact    420

aaccatcatg tagtcgagga tgcaggaaaa attcatgtta ctctccacga cggacaaaaa    480

tacacagcta agatcgtggg gttagatcca aaaacagatc ttgctgtgat caaaattcaa    540

gcggagaaat taccattttt gacttttggg aattctgatc agctgcagat aggtgactgg    600

gctattgcta ttggaaatcc ttttggattg caagcaacgg tcactgtcgg ggtcattagt    660

gctaaaggaa gaaatcagct acatattgta gatttcgaag actttattca aacagatgct    720

gccattaatc ctgggaattc aggcggtcca ttgttaaaca tcaatggtca agttatcggg    780

gttaatactg ccattgtcag tggtagcggg ggatatattg gaatagggtt tgctattcct    840

agcttgatgg ctaaacgagt cattgatcaa ttgattagtg atgggcaggt aacaagaggc    900

tttttgggag ttaccttgca accgatagat tctgaattgg ctacttgtta caaattggaa    960

aaagtgtacg gagctttggt gacggatgtt gttaaaggtt ctccagcaga aaaagcaggg   1020

ctgcgccaag aagatgtcat tgtggcttac aatggaaaag aagtagagtc tttgagtgcg   1080
```

```
ttgcgtaatg ccatttccct aatgatgcca gggactcgtg ttgttttaaa aatcgttcgt   1140

gaagggaaaa caatcgagat acctgtgacg gttacacaga tcccaacaga ggatggcgtt   1200

tcagcgttgc agaagatggg agtccgtgtt cagaacatta ctccagaaat ttgtaagaaa   1260

ctcggattgg cagcagatac ccgagggatt ctggtagttg ctgtggaggc aggctcgcct   1320

gcagcttctg caggcgtcgc tcctggacag cttatcttag cggtgaatag gcagcgagtc   1380

gcttccgttg aagagttaaa tcaggttttg aaaaactcga aaggagagaa tgttctcctt   1440

atggtttctc aaggagatgt ggtgcgattc atcgtcttga aatcagacga gtag         1494
```

<210> SEQ ID NO 140
<211> LENGTH: 497
<212> TYPE: PRT
<213> ORGANISM: Chlamydia trachomatis

<400> SEQUENCE: 140

```
Met Met Lys Arg Leu Leu Cys Val Leu Leu Ser Thr Ser Val Phe Ser
1               5                   10                  15

Ser Pro Met Leu Gly Tyr Ser Ala Ser Lys Lys Asp Ser Lys Ala Asp
            20                  25                  30

Ile Cys Leu Ala Val Ser Ser Gly Asp Gln Glu Val Ser Gln Glu Asp
        35                  40                  45

Leu Leu Lys Glu Val Ser Arg Gly Phe Ser Arg Val Ala Ala Lys Ala
    50                  55                  60

Thr Pro Gly Val Val Tyr Ile Glu Asn Phe Pro Lys Thr Gly Asn Gln
65                  70                  75                  80

Ala Ile Ala Ser Pro Gly Asn Lys Arg Gly Phe Gln Glu Asn Pro Phe
                85                  90                  95

Asp Tyr Phe Asn Asp Glu Phe Phe Asn Arg Phe Phe Gly Leu Pro Ser
            100                 105                 110

His Arg Glu Gln Gln Arg Pro Gln Gln Arg Asp Ala Val Arg Gly Thr
        115                 120                 125

Gly Phe Ile Val Ser Glu Asp Gly Tyr Val Val Thr Asn His His Val
    130                 135                 140

Val Glu Asp Ala Gly Lys Ile His Val Thr Leu His Asp Gly Gln Lys
145                 150                 155                 160

Tyr Thr Ala Lys Ile Val Gly Leu Asp Pro Lys Thr Asp Leu Ala Val
                165                 170                 175

Ile Lys Ile Gln Ala Glu Lys Leu Pro Phe Leu Thr Phe Gly Asn Ser
            180                 185                 190

Asp Gln Leu Gln Ile Gly Asp Trp Ala Ile Ala Ile Gly Asn Pro Phe
        195                 200                 205

Gly Leu Gln Ala Thr Val Thr Val Gly Val Ile Ser Ala Lys Gly Arg
    210                 215                 220

Asn Gln Leu His Ile Val Asp Phe Glu Asp Phe Ile Gln Thr Asp Ala
225                 230                 235                 240

Ala Ile Asn Pro Gly Asn Ser Gly Gly Pro Leu Leu Asn Ile Asn Gly
                245                 250                 255

Gln Val Ile Gly Val Asn Thr Ala Ile Val Ser Gly Ser Gly Gly Tyr
            260                 265                 270

Ile Gly Ile Gly Phe Ala Ile Pro Ser Leu Met Ala Lys Arg Val Ile
        275                 280                 285

Asp Gln Leu Ile Ser Asp Gly Gln Val Thr Arg Gly Phe Leu Gly Val
    290                 295                 300
```

-continued

```
Thr Leu Gln Pro Ile Asp Ser Glu Leu Ala Thr Cys Tyr Lys Leu Glu
305                 310                 315                 320

Lys Val Tyr Gly Ala Leu Val Thr Asp Val Val Lys Gly Ser Pro Ala
                325                 330                 335

Glu Lys Ala Gly Leu Arg Gln Glu Asp Val Ile Val Ala Tyr Asn Gly
            340                 345                 350

Lys Glu Val Glu Ser Leu Ser Ala Leu Arg Asn Ala Ile Ser Leu Met
        355                 360                 365

Met Pro Gly Thr Arg Val Val Leu Lys Ile Val Arg Glu Gly Lys Thr
    370                 375                 380

Ile Glu Ile Pro Val Thr Val Thr Gln Ile Pro Thr Glu Asp Gly Val
385                 390                 395                 400

Ser Ala Leu Gln Lys Met Gly Val Arg Val Gln Asn Ile Thr Pro Glu
                405                 410                 415

Ile Cys Lys Lys Leu Gly Leu Ala Ala Asp Thr Arg Gly Ile Leu Val
            420                 425                 430

Val Ala Val Glu Ala Gly Ser Pro Ala Ala Ser Ala Gly Val Ala Pro
        435                 440                 445

Gly Gln Leu Ile Leu Ala Val Asn Arg Gln Arg Val Ala Ser Val Glu
    450                 455                 460

Glu Leu Asn Gln Val Leu Lys Asn Ser Lys Gly Glu Asn Val Leu Leu
465                 470                 475                 480

Met Val Ser Gln Gly Asp Val Val Arg Phe Ile Val Leu Lys Ser Asp
                485                 490                 495

Glu
```

<210> SEQ ID NO 141
<211> LENGTH: 1443
<212> TYPE: DNA
<213> ORGANISM: Chlamydia trachomatis

<400> SEQUENCE: 141

```
tcgccaatgc taggctatag tgcgtcaaag aaagattcta aggctgatat ttgtcttgca      60

gtatcctcag gagatcaaga ggtttcacaa gaagatctgc tcaaagaagt atcccgagga     120

ttttctcggg tcgctgctaa ggcaacgcct ggagttgtat atatagaaaa ttttcctaaa     180

acagggaacc aggctattgc ttctccagga aacaaaagag gctttcaaga gaaccctttt     240

gattatttta atgacgaatt ttttaatcga ttttttggat tgccttcgca tagagagcag     300

cagcgtccgc agcagcgtga tgctgtaaga ggaactgggt tcattgtttc tgaagatggt     360

tatgttgtta ctaaccatca tgtagtcgag gatgcaggaa aaattcatgt tactctccac     420

gacggacaaa aatacacagc taagatcgtg gggttagatc caaaaacaga tcttgctgtg     480

atcaaaattc aagcggagaa attaccattt ttgacttttg ggaattctga tcagctgcag     540

ataggtgact gggctattgc tattggaaat ccttttggat tgcaagcaac ggtcactgtc     600

ggggtcatta gtgctaaagg aagaaatcag ctacatattg tagatttcga agactttatt     660

caaacagatg ctgccattaa tcctgggaat tcaggcggtc cattgttaaa catcaatggt     720

caagttatcg gggttaatac tgccattgtc agtggtagcg ggggatatat tggaataggg     780

tttgctattc ctagcttgat ggctaaacga gtcattgatc aattgattag tgatgggcag     840

gtaacaagag gctttttggg agttaccttg caaccgatag attctgaatt ggctacttgt     900

tacaaattgg aaaaagtgta cggagctttg gtgacggatg ttgttaaagg ttctccagca     960

gaaaaagcag ggctgcgcca agaagatgtc attgtggctt acaatggaaa agaagtagag    1020
```

tctttgagtg cgttgcgtaa tgccatttcc ctaatgatgc cagggactcg tgttgtttta 1080
aaaatcgttc gtgaagggaa aacaatcgag atacctgtga cggttacaca gatcccaaca 1140
gaggatggcg tttcagcgtt gcagaagatg ggagtccgtg ttcagaacat tactccagaa 1200
atttgtaaga aactcggatt ggcagcagat acccgaggga ttctggtagt tgctgtggag 1260
gcaggctcgc ctgcagcttc tgcaggcgtc gctcctggac agcttatctt agcggtgaat 1320
aggcagcgag tcgcttccgt tgaagagtta aatcaggttt tgaaaaactc gaaaggagag 1380
aatgttctcc ttatggtttc tcaaggagat gtggtgcgat tcatcgtctt gaaatcagac 1440
gag 1443

<210> SEQ ID NO 142
<211> LENGTH: 481
<212> TYPE: PRT
<213> ORGANISM: Chlamydia trachomatis

<400> SEQUENCE: 142

Ser Pro Met Leu Gly Tyr Ser Ala Ser Lys Lys Asp Ser Lys Ala Asp
1 5 10 15

Ile Cys Leu Ala Val Ser Ser Gly Asp Gln Glu Val Ser Gln Glu Asp
20 25 30

Leu Leu Lys Glu Val Ser Arg Gly Phe Ser Arg Val Ala Ala Lys Ala
35 40 45

Thr Pro Gly Val Val Tyr Ile Glu Asn Phe Pro Lys Thr Gly Asn Gln
50 55 60

Ala Ile Ala Ser Pro Gly Asn Lys Arg Gly Phe Gln Glu Asn Pro Phe
65 70 75 80

Asp Tyr Phe Asn Asp Glu Phe Phe Asn Arg Phe Phe Gly Leu Pro Ser
85 90 95

His Arg Glu Gln Gln Arg Pro Gln Gln Arg Asp Ala Val Arg Gly Thr
100 105 110

Gly Phe Ile Val Ser Glu Asp Gly Tyr Val Val Thr Asn His His Val
115 120 125

Val Glu Asp Ala Gly Lys Ile His Val Thr Leu His Asp Gly Gln Lys
130 135 140

Tyr Thr Ala Lys Ile Val Gly Leu Asp Pro Lys Thr Asp Leu Ala Val
145 150 155 160

Ile Lys Ile Gln Ala Glu Lys Leu Pro Phe Leu Thr Phe Gly Asn Ser
165 170 175

Asp Gln Leu Gln Ile Gly Asp Trp Ala Ile Ala Ile Gly Asn Pro Phe
180 185 190

Gly Leu Gln Ala Thr Val Thr Val Gly Val Ile Ser Ala Lys Gly Arg
195 200 205

Asn Gln Leu His Ile Val Asp Phe Glu Asp Phe Ile Gln Thr Asp Ala
210 215 220

Ala Ile Asn Pro Gly Asn Ser Gly Gly Pro Leu Leu Asn Ile Asn Gly
225 230 235 240

Gln Val Ile Gly Val Asn Thr Ala Ile Val Ser Gly Ser Gly Gly Tyr
245 250 255

Ile Gly Ile Gly Phe Ala Ile Pro Ser Leu Met Ala Lys Arg Val Ile
260 265 270

Asp Gln Leu Ile Ser Asp Gly Gln Val Thr Arg Gly Phe Leu Gly Val
275 280 285

```
Thr Leu Gln Pro Ile Asp Ser Glu Leu Ala Thr Cys Tyr Lys Leu Glu
    290                 295                 300

Lys Val Tyr Gly Ala Leu Val Thr Asp Val Val Lys Gly Ser Pro Ala
305                 310                 315                 320

Glu Lys Ala Gly Leu Arg Gln Glu Asp Val Ile Val Ala Tyr Asn Gly
                325                 330                 335

Lys Glu Val Glu Ser Leu Ser Ala Leu Arg Asn Ala Ile Ser Leu Met
            340                 345                 350

Met Pro Gly Thr Arg Val Val Leu Lys Ile Val Arg Glu Gly Lys Thr
        355                 360                 365

Ile Glu Ile Pro Val Thr Val Thr Gln Ile Pro Thr Glu Asp Gly Val
    370                 375                 380

Ser Ala Leu Gln Lys Met Gly Val Arg Val Gln Asn Ile Thr Pro Glu
385                 390                 395                 400

Ile Cys Lys Lys Leu Gly Leu Ala Ala Asp Thr Arg Gly Ile Leu Val
                405                 410                 415

Val Ala Val Glu Ala Gly Ser Pro Ala Ala Ser Ala Gly Val Ala Pro
            420                 425                 430

Gly Gln Leu Ile Leu Ala Val Asn Arg Gln Arg Val Ala Ser Val Glu
        435                 440                 445

Glu Leu Asn Gln Val Leu Lys Asn Ser Lys Gly Glu Asn Val Leu Leu
    450                 455                 460

Met Val Ser Gln Gly Asp Val Val Arg Phe Ile Val Leu Lys Ser Asp
465                 470                 475                 480

Glu
```

<210> SEQ ID NO 143
<211> LENGTH: 1347
<212> TYPE: DNA
<213> ORGANISM: Chlamydia muridarum

<400> SEQUENCE: 143

```
atgctaacta actttacctt tcgcaactgt cttttgtttt tcgtcacatt gtccagtgtc      60

cctgttttct cggcacccca acctcgcgta acgcttccta gtggagccaa taaaatcgga     120

tcagaagctt ggatagagca aaaagtccgt caatatccag aacttttgtg gttagttgaa     180

ccttctcctg caggaacttc tttaaacgct ccttcgggga tgatcttttc tcccctattg     240

ttccaaaaga aagtccctgc ttttgatatc gcagtacgca gtctgattca cctacacctg     300

cttatccagg gctcccgcca agcttatgct cagcttgtcc agctgcaggc taatgaatcc     360

cctatgacat ttaaacagtt ccttacccta cataagcagc tctccttatt cctaaattct     420

cctaaagagt tttatgattc cgtcaaaatt ttagaaactg ctatcatcct acgccactta     480

ggatgttcaa caaaagctgt tgccacattt aagccttatt tttcagaaac gcaaaaagag     540

gtcttctata caaaagcttt gcatgttctg catactttcc cagaattgag cccttcgttt     600

gctagactct ctccagaaca aaaaacgctc ttcttctcat tgagaaagct cgctaattat     660

gatgagttac tttccctgac aaatgcccct agtttacaac tactatctgc tgtacgctcg     720

cgacgcgcgc ttttggctct agacttgtat ctctatgctt tagatttttg tggagaacag     780

gggatatcct ctcagtttca tatggacttt tctcctttac agtccatgtt gcaacaatat     840

gctacggttg aagaagcctt ctcccgctac tttacttacc gagctaatcg cctaggattt     900

gcgggttctt ctcgaactga aatggcctta gttagaatag ctactttaat gaacctatcc     960

ccttcagaag ctgctatttt aacaacaagc tttaagtctc tttccttgga agatgctgaa    1020
```

```
agcttagtga atagctttta tacaaataag ggagactctt tagctctttc tttacgagga   1080

ctaccaactc ttatatctga actaacacgc gctgcgcatg gaaatacgaa tgcggaagct   1140

cgagctcagc aaatttacgc cacaacgtta tcattggtag caaaaagctt gaaagctcac   1200

aaagagatgc aaaacaaaca aattcttccc gaagaagtcg ttttagattt ctctgaaact   1260

gcttcttcct gtcaaggatt ggacatcttc tctgagaacg ttgctgttca aatccacttg   1320

aatggatctg tcagcatcca tctataa                                       1347
```

<210> SEQ ID NO 144
<211> LENGTH: 448
<212> TYPE: PRT
<213> ORGANISM: Chlamydia muridarum

<400> SEQUENCE: 144

```
Met Leu Thr Asn Phe Thr Phe Arg Asn Cys Leu Leu Phe Phe Val Thr
1               5                   10                  15

Leu Ser Ser Val Pro Val Phe Ser Ala Pro Gln Pro Arg Val Thr Leu
            20                  25                  30

Pro Ser Gly Ala Asn Lys Ile Gly Ser Glu Ala Trp Ile Glu Gln Lys
        35                  40                  45

Val Arg Gln Tyr Pro Glu Leu Leu Trp Leu Val Glu Pro Ser Pro Ala
    50                  55                  60

Gly Thr Ser Leu Asn Ala Pro Ser Gly Met Ile Phe Ser Pro Leu Leu
65                  70                  75                  80

Phe Gln Lys Lys Val Pro Ala Phe Asp Ile Ala Val Arg Ser Leu Ile
                85                  90                  95

His Leu His Leu Leu Ile Gln Gly Ser Arg Gln Ala Tyr Ala Gln Leu
            100                 105                 110

Val Gln Leu Gln Ala Asn Glu Ser Pro Met Thr Phe Lys Gln Phe Leu
        115                 120                 125

Thr Leu His Lys Gln Leu Ser Leu Phe Leu Asn Ser Pro Lys Glu Phe
    130                 135                 140

Tyr Asp Ser Val Lys Ile Leu Glu Thr Ala Ile Ile Leu Arg His Leu
145                 150                 155                 160

Gly Cys Ser Thr Lys Ala Val Ala Thr Phe Lys Pro Tyr Phe Ser Glu
                165                 170                 175

Thr Gln Lys Glu Val Phe Tyr Thr Lys Ala Leu His Val Leu His Thr
            180                 185                 190

Phe Pro Glu Leu Ser Pro Ser Phe Ala Arg Leu Ser Pro Glu Gln Lys
        195                 200                 205

Thr Leu Phe Phe Ser Leu Arg Lys Leu Ala Asn Tyr Asp Glu Leu Leu
    210                 215                 220

Ser Leu Thr Asn Ala Pro Ser Leu Gln Leu Leu Ser Ala Val Arg Ser
225                 230                 235                 240

Arg Arg Ala Leu Leu Ala Leu Asp Leu Tyr Leu Tyr Ala Leu Asp Phe
                245                 250                 255

Cys Gly Glu Gln Gly Ile Ser Ser Gln Phe His Met Asp Phe Ser Pro
            260                 265                 270

Leu Gln Ser Met Leu Gln Gln Tyr Ala Thr Val Glu Glu Ala Phe Ser
        275                 280                 285

Arg Tyr Phe Thr Tyr Arg Ala Asn Arg Leu Gly Phe Ala Gly Ser Ser
    290                 295                 300

Arg Thr Glu Met Ala Leu Val Arg Ile Ala Thr Leu Met Asn Leu Ser
```

```
305                 310                 315                 320

Pro Ser Glu Ala Ala Ile Leu Thr Thr Ser Phe Lys Ser Leu Ser Leu
                325                 330                 335

Glu Asp Ala Glu Ser Leu Val Asn Ser Phe Tyr Thr Asn Lys Gly Asp
            340                 345                 350

Ser Leu Ala Leu Ser Leu Arg Gly Leu Pro Thr Leu Ile Ser Glu Leu
        355                 360                 365

Thr Arg Ala Ala His Gly Asn Thr Asn Ala Glu Ala Arg Ala Gln Gln
    370                 375                 380

Ile Tyr Ala Thr Thr Leu Ser Leu Val Ala Lys Ser Leu Lys Ala His
385                 390                 395                 400

Lys Glu Met Gln Asn Lys Gln Ile Leu Pro Glu Glu Val Val Leu Asp
                405                 410                 415

Phe Ser Glu Thr Ala Ser Ser Cys Gln Gly Leu Asp Ile Phe Ser Glu
            420                 425                 430

Asn Val Ala Val Gln Ile His Leu Asn Gly Ser Val Ser Ile His Leu
        435                 440                 445


<210> SEQ ID NO 145
<211> LENGTH: 1224
<212> TYPE: DNA
<213> ORGANISM: Chlamydia muridarum

<400> SEQUENCE: 145

tcagaagctt ggatagagca aaaagtccgt caatatccag aacttttgtg gttagttgaa      60

ccttctcctg caggaacttc tttaaacgct ccttcgggga tgatcttttc tcccctattg     120

ttccaaaaga aagtccctgc ttttgatatc gcagtacgca gtctgattca cctacacctg     180

cttatccagg gctcccgcca agcttatgct cagcttgtcc agctgcaggc taatgaatcc     240

cctatgacat ttaaacagtt ccttacccta cataagcagc tctccttatt cctaaattct     300

cctaaagagt tttatgattc cgtcaaaatt ttagaaactg ctatcatcct acgccactta     360

ggatgttcaa caaaagctgt tgccacattt aagccttatt tttcagaaac gcaaaaagag     420

gtcttctata caaaagcttt gcatgttctg catactttcc cagaattgag cccttcgttt     480

gctagactct ctccagaaca aaaaacgctc ttcttctcat tgagaaagct cgctaattat     540

gatgagttac tttccctgac aaatgcccct agtttacaac tactatctgc tgtacgctcg     600

cgacgcgcgc ttttggctct agacttgtat ctctatgctt tagatttttg tggagaacag     660

gggatatcct ctcagtttca tatggacttt tctcctttac agtccatgtt gcaacaatat     720

gctacggttg aagaagcctt ctcccgctac tttacttacc gagctaatcg cctaggattt     780

gcgggttctt ctcgaactga aatggcctta gttagaatag ctactttaat gaacctatcc     840

ccttcagaag ctgctatttt aacaacaagc tttaagtctc tttccttgga agatgctgaa     900

agcttagtga atagctttta tacaaataag ggagactctt tagctctttc tttacgagga     960

ctaccaactc ttatatctga actaacacgc gctgcgcatg gaaatacgaa tgcggaagct    1020

cgagctcagc aaatttacgc cacaacgtta tcattggtag caaaaagctt gaaagctcac    1080

aaagagatgc aaaacaaaca aattcttccc gaagaagtcg ttttagattt ctctgaaact    1140

gcttcttcct gtcaaggatt ggacatcttc tctgagaacg ttgctgttca aatccacttg    1200

aatggatctg tcagcatcca tcta                                           1224


<210> SEQ ID NO 146
<211> LENGTH: 408
```

<212> TYPE: PRT
<213> ORGANISM: Chlamydia muridarum

<400> SEQUENCE: 146

```
Ser Glu Ala Trp Ile Glu Gln Lys Val Arg Gln Tyr Pro Glu Leu Leu
1               5                   10                  15

Trp Leu Val Glu Pro Ser Pro Ala Gly Thr Ser Leu Asn Ala Pro Ser
            20                  25                  30

Gly Met Ile Phe Ser Pro Leu Leu Phe Gln Lys Lys Val Pro Ala Phe
        35                  40                  45

Asp Ile Ala Val Arg Ser Leu Ile His Leu His Leu Leu Ile Gln Gly
    50                  55                  60

Ser Arg Gln Ala Tyr Ala Gln Leu Val Gln Leu Gln Ala Asn Glu Ser
65                  70                  75                  80

Pro Met Thr Phe Lys Gln Phe Leu Thr Leu His Lys Gln Leu Ser Leu
                85                  90                  95

Phe Leu Asn Ser Pro Lys Glu Phe Tyr Asp Ser Val Lys Ile Leu Glu
            100                 105                 110

Thr Ala Ile Ile Leu Arg His Leu Gly Cys Ser Thr Lys Ala Val Ala
        115                 120                 125

Thr Phe Lys Pro Tyr Phe Ser Glu Thr Gln Lys Glu Val Phe Tyr Thr
    130                 135                 140

Lys Ala Leu His Val Leu His Thr Phe Pro Glu Leu Ser Pro Ser Phe
145                 150                 155                 160

Ala Arg Leu Ser Pro Glu Gln Lys Thr Leu Phe Phe Ser Leu Arg Lys
                165                 170                 175

Leu Ala Asn Tyr Asp Glu Leu Leu Ser Leu Thr Asn Ala Pro Ser Leu
            180                 185                 190

Gln Leu Leu Ser Ala Val Arg Ser Arg Arg Ala Leu Leu Ala Leu Asp
        195                 200                 205

Leu Tyr Leu Tyr Ala Leu Asp Phe Cys Gly Glu Gln Gly Ile Ser Ser
    210                 215                 220

Gln Phe His Met Asp Phe Ser Pro Leu Gln Ser Met Leu Gln Gln Tyr
225                 230                 235                 240

Ala Thr Val Glu Glu Ala Phe Ser Arg Tyr Phe Thr Tyr Arg Ala Asn
                245                 250                 255

Arg Leu Gly Phe Ala Gly Ser Ser Arg Thr Glu Met Ala Leu Val Arg
            260                 265                 270

Ile Ala Thr Leu Met Asn Leu Ser Pro Ser Glu Ala Ala Ile Leu Thr
        275                 280                 285

Thr Ser Phe Lys Ser Leu Ser Leu Glu Asp Ala Glu Ser Leu Val Asn
    290                 295                 300

Ser Phe Tyr Thr Asn Lys Gly Asp Ser Leu Ala Leu Ser Leu Arg Gly
305                 310                 315                 320

Leu Pro Thr Leu Ile Ser Glu Leu Thr Arg Ala Ala His Gly Asn Thr
                325                 330                 335

Asn Ala Glu Ala Arg Ala Gln Gln Ile Tyr Ala Thr Thr Leu Ser Leu
            340                 345                 350

Val Ala Lys Ser Leu Lys Ala His Lys Glu Met Gln Asn Lys Gln Ile
        355                 360                 365

Leu Pro Glu Glu Val Val Leu Asp Phe Ser Glu Thr Ala Ser Ser Cys
    370                 375                 380

Gln Gly Leu Asp Ile Phe Ser Glu Asn Val Ala Val Gln Ile His Leu
385                 390                 395                 400
```

Asn Gly Ser Val Ser Ile His Leu
405

<210> SEQ ID NO 147
<211> LENGTH: 2430
<212> TYPE: DNA
<213> ORGANISM: Chlamydia muridarum

<400> SEQUENCE: 147
atgccccact ctcctttttt atatgttgtt caaccgcatt ctgtttttaa tcctagattg 60
ggagagcggc accctattac tttagatttc atcaaagaaa agaatcgatt agctgatttt 120
attgaaaacc tacctttaga aatttttgga gccccttctt tcttggaaaa tgcttcttta 180
gaagcctctt atgtcttgtc tagggaatcc acaaaagatg gcactctttt taccgttcta 240
gaacccaaac tatctgcctg cgtagctact tgccttgtgg attcttctat tcctatggag 300
cccgataacg agctcttaga agaaattaaa cacactttgt tgaaaagctc ttgtgatggc 360
gtacaatatc gtgtaacccg agagactctc caaaacaaag atgaagcccc cagagtctct 420
ttagttgctg atgatatcga acttatccgc aatgtagatt ttttaggacg ttccgttgat 480
attgtaaaat tggatccctt gaatattcct aataccgtaa gcgaggagaa tgctctcgat 540
tactctttca caagggaaac cgccaaactt agccctgacg gacgagttgg catccctcaa 600
gggacaaaaa ttttgccagc tccctctctt gaagttgaaa ttagcacctc tatttttgag 660
gaaacctctt cttttgaaca aaacttttct tcctctatta ctttttgtgt accacctctt 720
acctcttttt ctcctttgca agaacctcct ctagtgggag ctggacagca ggaaattctt 780
gtgactaaaa agcacttatt ccctagctat accccctaaac ttattgatat tgtcaaacga 840
cacaaaagag acgcaaagat tctagtaaac aagatccagt tcgagaaact atggagaagt 900
catgccaaaa gtcaaatctt aaaagaaggc tctgttcgct tggatttaca aggatttaca 960
ggggagctgt ttaactacca acttcaagta ggatctcata caattgcagc cgtgttaatt 1020
gatccggaaa ttgctaacgt caaatccctc cccgaacaaa cttacgctgt aagaaaaatt 1080
aaatcagggt tccaatgtag tttggatgac caacacattt atcaagtcgc agtaaaaaaa 1140
catctttctc tgtcttcaca acctccgaag atatctccgt tatctcaatc cgaaagctcc 1200
gatttaagtc tctttgaagc agcagcgttt tcagcaagcc taacttacga gttcgtaaag 1260
aaaaatacat atcatgctaa gaatactgta acttgctcca cggtatcgca ctctctgtat 1320
attctcaaag aagatgacgg ggctaatgct gcagaaaaac gcttagacaa cagtttccga 1380
aactgggtcg aaaataagtt gaacgcaaat tctccagatt cttgtactgc atttattcaa 1440
aaattcggca cacattacat cacatcggca acttttggag gatctgggtt ccaagttctt 1500
aaattatcct ttgaacaggt agaaggcctc cgtagtaaga agatctccct agaagcagca 1560
gcagcaaatt ccttattaaa aagctctgtg tcaaacagca cggaatctgg ctactctact 1620
tacgattcct cttcttcttc tcatacagta ttcctagggg gcactgtatt accctctgtt 1680
catgatggac agttagattt taaagattgg tctgaaagtg tctgtttaga acctgttccc 1740
attcacattt ctttactccc cttaacagac ttgctcaccc ctctttattt tcctgaaacg 1800
gatacaaccg aactatctaa taaacgtaat gctctccaac aagcggttcg agtttacctt 1860
aaagaccatc gttcagctaa acaaagcgaa cgctccgtat tcacagcggg gatcaatagt 1920
ccttcttcct ggttcacatt agaatctgct aattcacctc ttgttgtgag ttctccttac 1980
atgacgtatt ggtctactct cccctatctc ttccccacat taaaagagcg ttcttcagca 2040

```
gctcccatcg ttttttattt ttgtgtggat aataatgaac acgcctccca aaaaatttta   2100

aaccaaacat attgcttcat aggttcttta cctattcgac aaaagatttt tggcagagaa   2160

tttgctgaga atccttattt atctttctat ggaaggtttg gagaagctta ttttgatggc   2220

ggttatccag aacgttgtgg atggattgtt gaaaagttaa atactactaa agatcaaatt   2280

ctccgcgatg aggatgaagt gcaactaaag catgtttata gcggagagta tctgtctaca   2340

attcctatta aggattccca ttgcacactc tcgcgtacat gcaccgaatc gaatgctgtt   2400

tttattatca aaaaaccttc gagctattga                                    2430
```

<210> SEQ ID NO 148
<211> LENGTH: 809
<212> TYPE: PRT
<213> ORGANISM: Chlamydia muridarum

<400> SEQUENCE: 148

```
Met Pro His Ser Pro Phe Leu Tyr Val Val Gln Pro His Ser Val Phe
1               5                   10                  15

Asn Pro Arg Leu Gly Glu Arg His Pro Ile Thr Leu Asp Phe Ile Lys
            20                  25                  30

Glu Lys Asn Arg Leu Ala Asp Phe Ile Glu Asn Leu Pro Leu Glu Ile
        35                  40                  45

Phe Gly Ala Pro Ser Phe Leu Glu Asn Ala Ser Leu Glu Ala Ser Tyr
    50                  55                  60

Val Leu Ser Arg Glu Ser Thr Lys Asp Gly Thr Leu Phe Thr Val Leu
65                  70                  75                  80

Glu Pro Lys Leu Ser Ala Cys Val Ala Thr Cys Leu Val Asp Ser Ser
                85                  90                  95

Ile Pro Met Glu Pro Asp Asn Glu Leu Leu Glu Glu Ile Lys His Thr
            100                 105                 110

Leu Leu Lys Ser Ser Cys Asp Gly Val Gln Tyr Arg Val Thr Arg Glu
        115                 120                 125

Thr Leu Gln Asn Lys Asp Glu Ala Pro Arg Val Ser Leu Val Ala Asp
    130                 135                 140

Asp Ile Glu Leu Ile Arg Asn Val Asp Phe Leu Gly Arg Ser Val Asp
145                 150                 155                 160

Ile Val Lys Leu Asp Pro Leu Asn Ile Pro Asn Thr Val Ser Glu Glu
                165                 170                 175

Asn Ala Leu Asp Tyr Ser Phe Thr Arg Glu Thr Ala Lys Leu Ser Pro
            180                 185                 190

Asp Gly Arg Val Gly Ile Pro Gln Gly Thr Lys Ile Leu Pro Ala Pro
        195                 200                 205

Ser Leu Glu Val Glu Ile Ser Thr Ser Ile Phe Glu Glu Thr Ser Ser
    210                 215                 220

Phe Glu Gln Asn Phe Ser Ser Ser Ile Thr Phe Cys Val Pro Pro Leu
225                 230                 235                 240

Thr Ser Phe Ser Pro Leu Gln Glu Pro Pro Leu Val Gly Ala Gly Gln
                245                 250                 255

Gln Glu Ile Leu Val Thr Lys Lys His Leu Phe Pro Ser Tyr Thr Pro
            260                 265                 270

Lys Leu Ile Asp Ile Val Lys Arg His Lys Arg Asp Ala Lys Ile Leu
        275                 280                 285

Val Asn Lys Ile Gln Phe Glu Lys Leu Trp Arg Ser His Ala Lys Ser
    290                 295                 300
```

```
Gln Ile Leu Lys Glu Gly Ser Val Arg Leu Asp Leu Gln Gly Phe Thr
305                 310                 315                 320

Gly Glu Leu Phe Asn Tyr Gln Leu Gln Val Gly Ser His Thr Ile Ala
                325                 330                 335

Ala Val Leu Ile Asp Pro Glu Ile Ala Asn Val Lys Ser Leu Pro Glu
            340                 345                 350

Gln Thr Tyr Ala Val Arg Lys Ile Lys Ser Gly Phe Gln Cys Ser Leu
        355                 360                 365

Asp Asp Gln His Ile Tyr Gln Val Ala Val Lys Lys His Leu Ser Leu
    370                 375                 380

Ser Ser Gln Pro Pro Lys Ile Ser Pro Leu Ser Gln Ser Glu Ser Ser
385                 390                 395                 400

Asp Leu Ser Leu Phe Glu Ala Ala Ala Phe Ser Ala Ser Leu Thr Tyr
                405                 410                 415

Glu Phe Val Lys Lys Asn Thr Tyr His Ala Lys Asn Thr Val Thr Cys
            420                 425                 430

Ser Thr Val Ser His Ser Leu Tyr Ile Leu Lys Glu Asp Asp Gly Ala
        435                 440                 445

Asn Ala Ala Glu Lys Arg Leu Asp Asn Ser Phe Arg Asn Trp Val Glu
    450                 455                 460

Asn Lys Leu Asn Ala Asn Ser Pro Asp Ser Cys Thr Ala Phe Ile Gln
465                 470                 475                 480

Lys Phe Gly Thr His Tyr Ile Thr Ser Ala Thr Phe Gly Gly Ser Gly
                485                 490                 495

Phe Gln Val Leu Lys Leu Ser Phe Glu Gln Val Glu Gly Leu Arg Ser
            500                 505                 510

Lys Lys Ile Ser Leu Glu Ala Ala Ala Ala Asn Ser Leu Leu Lys Ser
        515                 520                 525

Ser Val Ser Asn Ser Thr Glu Ser Gly Tyr Ser Thr Tyr Asp Ser Ser
    530                 535                 540

Ser Ser Ser His Thr Val Phe Leu Gly Gly Thr Val Leu Pro Ser Val
545                 550                 555                 560

His Asp Gly Gln Leu Asp Phe Lys Asp Trp Ser Glu Ser Val Cys Leu
                565                 570                 575

Glu Pro Val Pro Ile His Ile Ser Leu Leu Pro Leu Thr Asp Leu Leu
            580                 585                 590

Thr Pro Leu Tyr Phe Pro Glu Thr Asp Thr Thr Glu Leu Ser Asn Lys
        595                 600                 605

Arg Asn Ala Leu Gln Gln Ala Val Arg Val Tyr Leu Lys Asp His Arg
    610                 615                 620

Ser Ala Lys Gln Ser Glu Arg Ser Val Phe Thr Ala Gly Ile Asn Ser
625                 630                 635                 640

Pro Ser Ser Trp Phe Thr Leu Glu Ser Ala Asn Ser Pro Leu Val Val
                645                 650                 655

Ser Ser Pro Tyr Met Thr Tyr Trp Ser Thr Leu Pro Tyr Leu Phe Pro
            660                 665                 670

Thr Leu Lys Glu Arg Ser Ser Ala Ala Pro Ile Val Phe Tyr Phe Cys
        675                 680                 685

Val Asp Asn Asn Glu His Ala Ser Gln Lys Ile Leu Asn Gln Thr Tyr
    690                 695                 700

Cys Phe Ile Gly Ser Leu Pro Ile Arg Gln Lys Ile Phe Gly Arg Glu
705                 710                 715                 720
```

-continued

```
Phe Ala Glu Asn Pro Tyr Leu Ser Phe Tyr Gly Arg Phe Gly Glu Ala
                725                 730                 735

Tyr Phe Asp Gly Gly Tyr Pro Glu Arg Cys Gly Trp Ile Val Glu Lys
            740                 745                 750

Leu Asn Thr Thr Lys Asp Gln Ile Leu Arg Asp Glu Asp Glu Val Gln
        755                 760                 765

Leu Lys His Val Tyr Ser Gly Glu Tyr Leu Ser Thr Ile Pro Ile Lys
    770                 775                 780

Asp Ser His Cys Thr Leu Ser Arg Thr Cys Thr Glu Ser Asn Ala Val
785                 790                 795                 800

Phe Ile Ile Lys Lys Pro Ser Ser Tyr
                805

<210> SEQ ID NO 149
<211> LENGTH: 2424
<212> TYPE: DNA
<213> ORGANISM: Chlamydia muridarum

<400> SEQUENCE: 149
ccccactctc ctttttata tgttgttcaa ccgcattctg tttttaatcc tagattggga      60
gagcggcacc ctattacttt agatttcatc aaagaaaaga atcgattagc tgattttatt    120
gaaaacctac ctttagaaat ttttggagcc ccttctttct tggaaaatgc ttctttagaa    180
gcctcttatg tcttgtctag ggaatccaca aaagatggca ctctttttac cgttctagaa    240
cccaaactat ctgcctgcgt agctacttgc cttgtggatt cttctattcc tatggagccc    300
gataacgagc tcttagaaga aattaaacac actttgttga aaagctcttg tgatggcgta    360
caatatcgtg taacccgaga gactctccaa aacaaagatg aagcccccag agtctcttta    420
gttgctgatg atatcgaact tatccgcaat gtagattttt taggacgttc cgttgatatt    480
gtaaaattgg atcccttgaa tattcctaat accgtaagcg aggagaatgc tctcgattac    540
tctttcacaa gggaaaccgc caaacttagc cctgacggac gagttggcat ccctcaaggg    600
acaaaaattt tgccagctcc ctctcttgaa gttgaaatta gcacctctat tttgaggaa     660 acctcttctt ttgaacaaaa cttttcttcc tctattactt tttgtgtacc acctcttacc    720
tctttttctc ctttgcaaga acctcctcta gtgggagctg gacagcagga aattcttgtg    780
actaaaaagc acttattccc tagctatacc cctaaactta ttgatattgt caaacgacac    840
aaaagagacg caaagattct agtaaacaag atccagttcg agaaactatg gagaagtcat    900
gccaaaagtc aaatcttaaa agaaggctct gttcgcttgg atttacaagg atttacaggg    960
gagctgttta actaccaact tcaagtagga tctcatacaa ttgcagccgt gttaattgat   1020
ccggaaattg ctaacgtcaa atccctcccc gaacaaactt acgctgtaag aaaaattaaa   1080
tcagggttcc aatgtagttt ggatgaccaa cacatttatc aagtcgcagt aaaaaaacat   1140
ctttctctgt cttcacaacc tccgaagata tctccgttat ctcaatccga aagctccgat   1200
ttaagtctct ttgaagcagc agcgttttca gcaagcctaa cttacgagtt cgtaaagaaa   1260
aatacatatc atgctaagaa tactgtaact tgctccacgg tatcgcactc tctgtatatt   1320
ctcaaagaag atgacggggc taatgctgca gaaaaacgct tagacaacag tttccgaaac   1380
tgggtcgaaa ataagttgaa cgcaaattct ccagattctt gtactgcatt tattcaaaaa   1440
ttcggcacac attacatcac atcggcaact tttggaggat ctgggttcca agttcttaaa   1500
ttatcctttg aacaggtaga aggcctccgt agtaagaaga tctccctaga agcagcagca   1560
gcaaattcct tattaaaaag ctctgtgtca aacagcacgg aatctggcta ctctacttac   1620
```

```
gattcctctt cttcttctca tacagtattc ctagggggca ctgtattacc ctctgttcat   1680

gatggacagt tagattttaa agattggtct gaaagtgtct gtttagaacc tgttcccatt   1740

cacatttctt tactcccctt aacagacttg ctcacccctc tttattttcc tgaaacggat   1800

acaaccgaac tatctaataa acgtaatgct ctccaacaag cggttcgagt ttaccttaaa   1860

gaccatcgtt cagctaaaca aagcgaacgc tccgtattca cagcggggat caatagtcct   1920

tcttcctggt tcacattaga atctgctaat tcacctcttg ttgtgagttc tccttacatg   1980

acgtattggt ctactctccc ctatctcttc cccacattaa aagagcgttc ttcagcagct   2040

cccatcgttt tttattttg tgtggataat aatgaacacg cctcccaaaa aattttaaac   2100

caaacatatt gcttcatagg ttctttacct attcgacaaa agatttttgg cagagaattt   2160

gctgagaatc cttatttatc tttctatgga aggtttggag aagcttattt tgatggcggt   2220

tatccagaac gttgtggatg gattgttgaa aagttaaata ctactaaaga tcaaattctc   2280

cgcgatgagg atgaagtgca actaaagcat gtttatagcg gagagtatct gtctacaatt   2340

cctattaagg attcccattg cacactctcg cgtacatgca ccgaatcgaa tgctgttttt   2400

attatcaaaa aaccttcgag ctat                                          2424
```

<210> SEQ ID NO 150
<211> LENGTH: 808
<212> TYPE: PRT
<213> ORGANISM: Chlamydia muridarum

<400> SEQUENCE: 150

```
Pro His Ser Pro Phe Leu Tyr Val Val Gln Pro His Ser Val Phe Asn
1               5                   10                  15

Pro Arg Leu Gly Glu Arg His Pro Ile Thr Leu Asp Phe Ile Lys Glu
            20                  25                  30

Lys Asn Arg Leu Ala Asp Phe Ile Glu Asn Leu Pro Leu Glu Ile Phe
        35                  40                  45

Gly Ala Pro Ser Phe Leu Glu Asn Ala Ser Leu Glu Ala Ser Tyr Val
    50                  55                  60

Leu Ser Arg Glu Ser Thr Lys Asp Gly Thr Leu Phe Thr Val Leu Glu
65                  70                  75                  80

Pro Lys Leu Ser Ala Cys Val Ala Thr Cys Leu Val Asp Ser Ser Ile
                85                  90                  95

Pro Met Glu Pro Asp Asn Glu Leu Leu Glu Glu Ile Lys His Thr Leu
            100                 105                 110

Leu Lys Ser Ser Cys Asp Gly Val Gln Tyr Arg Val Thr Arg Glu Thr
        115                 120                 125

Leu Gln Asn Lys Asp Glu Ala Pro Arg Val Ser Leu Val Ala Asp Asp
    130                 135                 140

Ile Glu Leu Ile Arg Asn Val Asp Phe Leu Gly Arg Ser Val Asp Ile
145                 150                 155                 160

Val Lys Leu Asp Pro Leu Asn Ile Pro Asn Thr Val Ser Glu Glu Asn
                165                 170                 175

Ala Leu Asp Tyr Ser Phe Thr Arg Glu Thr Ala Lys Leu Ser Pro Asp
            180                 185                 190

Gly Arg Val Gly Ile Pro Gln Gly Thr Lys Ile Leu Pro Ala Pro Ser
        195                 200                 205

Leu Glu Val Glu Ile Ser Thr Ser Ile Phe Glu Glu Thr Ser Ser Phe
    210                 215                 220
```

Glu Gln Asn Phe Ser Ser Ser Ile Thr Phe Cys Val Pro Pro Leu Thr
225 230 235 240

Ser Phe Ser Pro Leu Gln Glu Pro Pro Leu Val Gly Ala Gly Gln Gln
245 250 255

Glu Ile Leu Val Thr Lys Lys His Leu Phe Pro Ser Tyr Thr Pro Lys
260 265 270

Leu Ile Asp Ile Val Lys Arg His Lys Arg Asp Ala Lys Ile Leu Val
275 280 285

Asn Lys Ile Gln Phe Glu Lys Leu Trp Arg Ser His Ala Lys Ser Gln
290 295 300

Ile Leu Lys Glu Gly Ser Val Arg Leu Asp Leu Gln Gly Phe Thr Gly
305 310 315 320

Glu Leu Phe Asn Tyr Gln Leu Gln Val Gly Ser His Thr Ile Ala Ala
325 330 335

Val Leu Ile Asp Pro Glu Ile Ala Asn Val Lys Ser Leu Pro Glu Gln
340 345 350

Thr Tyr Ala Val Arg Lys Ile Lys Ser Gly Phe Gln Cys Ser Leu Asp
355 360 365

Asp Gln His Ile Tyr Gln Val Ala Val Lys Lys His Leu Ser Leu Ser
370 375 380

Ser Gln Pro Pro Lys Ile Ser Pro Leu Ser Gln Ser Glu Ser Ser Asp
385 390 395 400

Leu Ser Leu Phe Glu Ala Ala Ala Phe Ser Ala Ser Leu Thr Tyr Glu
405 410 415

Phe Val Lys Lys Asn Thr Tyr His Ala Lys Asn Thr Val Thr Cys Ser
420 425 430

Thr Val Ser His Ser Leu Tyr Ile Leu Lys Glu Asp Asp Gly Ala Asn
435 440 445

Ala Ala Glu Lys Arg Leu Asp Asn Ser Phe Arg Asn Trp Val Glu Asn
450 455 460

Lys Leu Asn Ala Asn Ser Pro Asp Ser Cys Thr Ala Phe Ile Gln Lys
465 470 475 480

Phe Gly Thr His Tyr Ile Thr Ser Ala Thr Phe Gly Gly Ser Gly Phe
485 490 495

Gln Val Leu Lys Leu Ser Phe Glu Gln Val Glu Gly Leu Arg Ser Lys
500 505 510

Lys Ile Ser Leu Glu Ala Ala Ala Ala Asn Ser Leu Leu Lys Ser Ser
515 520 525

Val Ser Asn Ser Thr Glu Ser Gly Tyr Ser Thr Tyr Asp Ser Ser Ser
530 535 540

Ser Ser His Thr Val Phe Leu Gly Gly Thr Val Leu Pro Ser Val His
545 550 555 560

Asp Gly Gln Leu Asp Phe Lys Asp Trp Ser Glu Ser Val Cys Leu Glu
565 570 575

Pro Val Pro Ile His Ile Ser Leu Leu Pro Leu Thr Asp Leu Leu Thr
580 585 590

Pro Leu Tyr Phe Pro Glu Thr Asp Thr Thr Glu Leu Ser Asn Lys Arg
595 600 605

Asn Ala Leu Gln Gln Ala Val Arg Val Tyr Leu Lys Asp His Arg Ser
610 615 620

Ala Lys Gln Ser Glu Arg Ser Val Phe Thr Ala Gly Ile Asn Ser Pro
625 630 635 640

Ser Ser Trp Phe Thr Leu Glu Ser Ala Asn Ser Pro Leu Val Val Ser

```
                645                 650                 655

Ser Pro Tyr Met Thr Tyr Trp Ser Thr Leu Pro Tyr Leu Phe Pro Thr
            660                 665                 670

Leu Lys Glu Arg Ser Ser Ala Ala Pro Ile Val Phe Tyr Phe Cys Val
        675                 680                 685

Asp Asn Asn Glu His Ala Ser Gln Lys Ile Leu Asn Gln Thr Tyr Cys
    690                 695                 700

Phe Ile Gly Ser Leu Pro Ile Arg Gln Lys Ile Phe Gly Arg Glu Phe
705                 710                 715                 720

Ala Glu Asn Pro Tyr Leu Ser Phe Tyr Gly Arg Phe Gly Glu Ala Tyr
                725                 730                 735

Phe Asp Gly Gly Tyr Pro Glu Arg Cys Gly Trp Ile Val Glu Lys Leu
            740                 745                 750

Asn Thr Thr Lys Asp Gln Ile Leu Arg Asp Glu Asp Glu Val Gln Leu
        755                 760                 765

Lys His Val Tyr Ser Gly Glu Tyr Leu Ser Thr Ile Pro Ile Lys Asp
    770                 775                 780

Ser His Cys Thr Leu Ser Arg Thr Cys Thr Glu Ser Asn Ala Val Phe
785                 790                 795                 800

Ile Ile Lys Lys Pro Ser Ser Tyr
                805
```

<210> SEQ ID NO 151
<211> LENGTH: 1494
<212> TYPE: DNA
<213> ORGANISM: Chlamydia muridarum

<400> SEQUENCE: 151

```
atgatgaaaa gattattatg tgtgttgcta tcgacatcag ttttctcttc gcccatgttg     60

ggctatagtg cgccaaagaa agattccagt actggcattt gtcttgcagc atctcaaagt    120

gatcgggaac tttcccaaga agatttgcta aaagaagtgt ctagaggatt ttccaaagtc    180

gctgctcagg caactccagg agttgtgtat atagaaaatt ttcctaaaac tgggagtcaa    240

gctattgctt ctcctgggaa taaaaggggt tttcaagaga atccctttga ttatttcaat    300

gatgagtttt tcaatcgatt ttttggttta ccctcgcata gagagcagcc tcgtccccaa    360

cagcgtgatg ctgtaagagg aacaggtttt attgtgtcag aagatgggta cgttgtgacc    420

aaccatcacg tagtggaaga tgcggggaaa attcatgtta ctttacacga tggacaaaaa    480

tacaccgcaa aaatcatagg attagatcct aaaacggatc tcgctgtgat taagatccaa    540

gcaaaaaatc tccctttttt aacttttgga aactctgatc agcttcagat aggggattgg    600

tcaatagcca ttggaaatcc tttcggatta caagccacag taaccgttgg cgtgattagt    660

gctaagggaa gaaaccaatt acatattgtt gattttgaag attttattca gacggatgca    720

gcaattaatc ccgggaattc aggtggtcca ttattgaaca ttgatggaca ggttattgga    780

gtgaatacag caatcgttag cggtagcggg ggatacattg gaataggatt tgccattcct    840

agcttaatgg ctaaacgagt tattgaccaa ctcattagcg atggacaggt gacgagagga    900

tttttaggag taaccttaca gcctattgat tcggagcttg ccgcttgtta caaattagaa    960

aaggtgtacg gagccttgat tacggatgtt gttaagggat ctcctgcaga aaaagcaggt   1020

ttgcgccagg aagatgtcat tgttgcttac aatgggaaag aagtggagtc tttgagtgct   1080

ttacgtaatg cgatttcttt gatgatgcca gggactcgtg ttgtcttaaa agttgtgcgt   1140

gaagggaaat tcattgaaat acctgtcact gttacacaaa ttcctgcgga ggatggggta   1200
```

-continued tctgctcttc aaaaaatggg agttcgggta cagaatctta ctccagagat atgcaagaaa 1260
ctaggattag cgtctgatac tcgagggatt tttgtagtgt ccgtagaagc tggttctcct 1320
gcagcttctg caggagtggt tccaggacaa cttattctgg ctgtaaacag acagagagtt 1380
tcttctgttg aagaattgaa tcaggtcttg aagaatgcaa aaggagagaa tgttctcctt 1440
atggtttctc aaggagaagt cattcgattc gttgttttaa agtctgatga atag 1494

<210> SEQ ID NO 152
<211> LENGTH: 497
<212> TYPE: PRT
<213> ORGANISM: Chlamydia muridarum

<400> SEQUENCE: 152

Met Met Lys Arg Leu Leu Cys Val Leu Leu Ser Thr Ser Val Phe Ser
1 5 10 15

Ser Pro Met Leu Gly Tyr Ser Ala Pro Lys Lys Asp Ser Ser Thr Gly
20 25 30

Ile Cys Leu Ala Ala Ser Gln Ser Asp Arg Glu Leu Ser Gln Glu Asp
35 40 45

Leu Leu Lys Glu Val Ser Arg Gly Phe Ser Lys Val Ala Ala Gln Ala
50 55 60

Thr Pro Gly Val Val Tyr Ile Glu Asn Phe Pro Lys Thr Gly Ser Gln
65 70 75 80

Ala Ile Ala Ser Pro Gly Asn Lys Arg Gly Phe Gln Glu Asn Pro Phe
85 90 95

Asp Tyr Phe Asn Asp Glu Phe Phe Asn Arg Phe Phe Gly Leu Pro Ser
100 105 110

His Arg Glu Gln Pro Arg Pro Gln Gln Arg Asp Ala Val Arg Gly Thr
115 120 125

Gly Phe Ile Val Ser Glu Asp Gly Tyr Val Val Thr Asn His His Val
130 135 140

Val Glu Asp Ala Gly Lys Ile His Val Thr Leu His Asp Gly Gln Lys
145 150 155 160

Tyr Thr Ala Lys Ile Ile Gly Leu Asp Pro Lys Thr Asp Leu Ala Val
165 170 175

Ile Lys Ile Gln Ala Lys Asn Leu Pro Phe Leu Thr Phe Gly Asn Ser
180 185 190

Asp Gln Leu Gln Ile Gly Asp Trp Ser Ile Ala Ile Gly Asn Pro Phe
195 200 205

Gly Leu Gln Ala Thr Val Thr Val Gly Val Ile Ser Ala Lys Gly Arg
210 215 220

Asn Gln Leu His Ile Val Asp Phe Glu Asp Phe Ile Gln Thr Asp Ala
225 230 235 240

Ala Ile Asn Pro Gly Asn Ser Gly Gly Pro Leu Leu Asn Ile Asp Gly
245 250 255

Gln Val Ile Gly Val Asn Thr Ala Ile Val Ser Gly Ser Gly Gly Tyr
260 265 270

Ile Gly Ile Gly Phe Ala Ile Pro Ser Leu Met Ala Lys Arg Val Ile
275 280 285

Asp Gln Leu Ile Ser Asp Gly Gln Val Thr Arg Gly Phe Leu Gly Val
290 295 300

Thr Leu Gln Pro Ile Asp Ser Glu Leu Ala Ala Cys Tyr Lys Leu Glu
305 310 315 320

-continued

```
Lys Val Tyr Gly Ala Leu Ile Thr Asp Val Val Lys Gly Ser Pro Ala
                325                 330                 335

Glu Lys Ala Gly Leu Arg Gln Glu Asp Val Ile Val Ala Tyr Asn Gly
            340                 345                 350

Lys Glu Val Glu Ser Leu Ser Ala Leu Arg Asn Ala Ile Ser Leu Met
        355                 360                 365

Met Pro Gly Thr Arg Val Val Leu Lys Val Val Arg Glu Gly Lys Phe
    370                 375                 380

Ile Glu Ile Pro Val Thr Val Thr Gln Ile Pro Ala Glu Asp Gly Val
385                 390                 395                 400

Ser Ala Leu Gln Lys Met Gly Val Arg Val Gln Asn Leu Thr Pro Glu
                405                 410                 415

Ile Cys Lys Lys Leu Gly Leu Ala Ser Asp Thr Arg Gly Ile Phe Val
            420                 425                 430

Val Ser Val Glu Ala Gly Ser Pro Ala Ala Ser Ala Gly Val Val Pro
        435                 440                 445

Gly Gln Leu Ile Leu Ala Val Asn Arg Gln Arg Val Ser Ser Val Glu
    450                 455                 460

Glu Leu Asn Gln Val Leu Lys Asn Ala Lys Gly Glu Asn Val Leu Leu
465                 470                 475                 480

Met Val Ser Gln Gly Glu Val Ile Arg Phe Val Val Leu Lys Ser Asp
                485                 490                 495

Glu


<210> SEQ ID NO 153
<211> LENGTH: 1443
<212> TYPE: DNA
<213> ORGANISM: Chlamydia muridarum

<400> SEQUENCE: 153

tcgcccatgt tgggctatag tgcgccaaag aaagattcca gtactggcat ttgtcttgca      60

gcatctcaaa gtgatcggga actttcccaa gaagatttgc taaaagaagt gtctagagga     120

ttttccaaag tcgctgctca ggcaactcca ggagttgtgt atatagaaaa ttttcctaaa     180

actgggagtc aagctattgc ttctcctggg aataaaaggg gttttcaaga gaatcccttt     240

gattatttca atgatgagtt tttcaatcga ttttttggtt taccctcgca tagagagcag     300

cctcgtcccc aacagcgtga tgctgtaaga ggaacaggtt ttattgtgtc agaagatggg     360

tacgttgtga ccaaccatca cgtagtggaa gatgcgggga aaattcatgt tactttacac     420

gatggacaaa aatacaccgc aaaaatcata ggattagatc ctaaaacgga tctcgctgtg     480

attaagatcc aagcaaaaaa tctccctttt ttaacttttg gaaactctga tcagcttcag     540

ataggggatt ggtcaatagc cattggaaat cctttcggat tacaagccac agtaaccgtt     600

ggcgtgatta gtgctaaggg aagaaaccaa ttacatattg ttgattttga agattttatt     660

cagacggatg cagcaattaa tcccgggaat tcaggtggtc cattattgaa cattgatgga     720

caggttattg gagtgaatac agcaatcgtt agcggtagcg gggatacat tggaatagga      780

tttgccattc ctagcttaat ggctaaacga gttattgacc aactcattag cgatggacag     840

gtgacgagag gatttttagg agtaacctta cagcctattg attcggagct tgccgcttgt     900

tacaaattag aaaaggtgta cggagccttg attacggatg ttgttaaggg atctcctgca     960

gaaaaagcag gtttgcgcca ggaagatgtc attgttgctt acaatgggaa agaagtggag    1020

tctttgagtg ctttacgtaa tgcgatttct ttgatgatgc cagggactcg tgttgtctta    1080
```

```
aaagttgtgc gtgaagggaa attcattgaa atacctgtca ctgttacaca aattcctgcg   1140

gaggatgggg tatctgctct tcaaaaaatg ggagttcggg tacagaatct tactccagag   1200

atatgcaaga aactaggatt agcgtctgat actcgaggga tttttgtagt gtccgtagaa   1260

gctggttctc ctgcagcttc tgcaggagtg gttccaggac aacttattct ggctgtaaac   1320

agacagagag tttcttctgt tgaagaattg aatcaggtct tgaagaatgc aaaaggagag   1380

aatgttctcc ttatggtttc tcaaggagaa gtcattcgat tcgttgtttt aaagtctgat   1440

gaa                                                                 1443


<210> SEQ ID NO 154
<211> LENGTH: 481
<212> TYPE: PRT
<213> ORGANISM: Chlamydia muridarum

<400> SEQUENCE: 154

Ser Pro Met Leu Gly Tyr Ser Ala Pro Lys Lys Asp Ser Ser Thr Gly
1               5                   10                  15

Ile Cys Leu Ala Ala Ser Gln Ser Asp Arg Glu Leu Ser Gln Glu Asp
            20                  25                  30

Leu Leu Lys Glu Val Ser Arg Gly Phe Ser Lys Val Ala Ala Gln Ala
        35                  40                  45

Thr Pro Gly Val Val Tyr Ile Glu Asn Phe Pro Lys Thr Gly Ser Gln
    50                  55                  60

Ala Ile Ala Ser Pro Gly Asn Lys Arg Gly Phe Gln Glu Asn Pro Phe
65                  70                  75                  80

Asp Tyr Phe Asn Asp Glu Phe Phe Asn Arg Phe Phe Gly Leu Pro Ser
                85                  90                  95

His Arg Glu Gln Pro Arg Pro Gln Gln Arg Asp Ala Val Arg Gly Thr
            100                 105                 110

Gly Phe Ile Val Ser Glu Asp Gly Tyr Val Val Thr Asn His His Val
        115                 120                 125

Val Glu Asp Ala Gly Lys Ile His Val Thr Leu His Asp Gly Gln Lys
    130                 135                 140

Tyr Thr Ala Lys Ile Ile Gly Leu Asp Pro Lys Thr Asp Leu Ala Val
145                 150                 155                 160

Ile Lys Ile Gln Ala Lys Asn Leu Pro Phe Leu Thr Phe Gly Asn Ser
                165                 170                 175

Asp Gln Leu Gln Ile Gly Asp Trp Ser Ile Ala Ile Gly Asn Pro Phe
            180                 185                 190

Gly Leu Gln Ala Thr Val Thr Val Gly Val Ile Ser Ala Lys Gly Arg
        195                 200                 205

Asn Gln Leu His Ile Val Asp Phe Glu Asp Phe Ile Gln Thr Asp Ala
    210                 215                 220

Ala Ile Asn Pro Gly Asn Ser Gly Gly Pro Leu Leu Asn Ile Asp Gly
225                 230                 235                 240

Gln Val Ile Gly Val Asn Thr Ala Ile Val Ser Gly Ser Gly Gly Tyr
                245                 250                 255

Ile Gly Ile Gly Phe Ala Ile Pro Ser Leu Met Ala Lys Arg Val Ile
            260                 265                 270

Asp Gln Leu Ile Ser Asp Gly Gln Val Thr Arg Gly Phe Leu Gly Val
        275                 280                 285

Thr Leu Gln Pro Ile Asp Ser Glu Leu Ala Ala Cys Tyr Lys Leu Glu
    290                 295                 300
```

-continued

```
Lys Val Tyr Gly Ala Leu Ile Thr Asp Val Val Lys Gly Ser Pro Ala
305                 310                 315                 320

Glu Lys Ala Gly Leu Arg Gln Glu Asp Val Ile Val Ala Tyr Asn Gly
                325                 330                 335

Lys Glu Val Glu Ser Leu Ser Ala Leu Arg Asn Ala Ile Ser Leu Met
            340                 345                 350

Met Pro Gly Thr Arg Val Val Leu Lys Val Val Arg Glu Gly Lys Phe
        355                 360                 365

Ile Glu Ile Pro Val Thr Val Thr Gln Ile Pro Ala Glu Asp Gly Val
    370                 375                 380

Ser Ala Leu Gln Lys Met Gly Val Arg Val Gln Asn Leu Thr Pro Glu
385                 390                 395                 400

Ile Cys Lys Lys Leu Gly Leu Ala Ser Asp Thr Arg Gly Ile Phe Val
                405                 410                 415

Val Ser Val Glu Ala Gly Ser Pro Ala Ala Ser Ala Gly Val Val Pro
            420                 425                 430

Gly Gln Leu Ile Leu Ala Val Asn Arg Gln Arg Val Ser Ser Val Glu
        435                 440                 445

Glu Leu Asn Gln Val Leu Lys Asn Ala Lys Gly Glu Asn Val Leu Leu
    450                 455                 460

Met Val Ser Gln Gly Glu Val Ile Arg Phe Val Val Leu Lys Ser Asp
465                 470                 475                 480

Glu
```

<210> SEQ ID NO 155
<211> LENGTH: 1647
<212> TYPE: DNA
<213> ORGANISM: Chlamydia trachomatis

<400> SEQUENCE: 155

```
atgtttgtgt cgttcgataa atcccgttgc agagcggatg tccccgattt ttttgaaagg      60

acaggaaact ttcttctcca ttgtgtggca agagggatca atgttttata tcgtgtgaaa     120

caaatctcta actatccttc atgctatttc tcacataaag agatttcgtg ttgtcgtcgt     180

attgcaaaca ttgtgatctg tattctcaca gggcctctga tgttattggc cactgtgtta     240

ggattattag cgtataggtt ttcttctact taccagactt ctttacaaga acgctttcgt     300

tataaatatg aacaaaagca agctttagat gaataccgtg atagggaaga aaaagtcatt     360

acgcttcaga agttttgtag aggatttcta gttagaaatc atttgctcaa ccaagaaact     420

ttaacaacgt gtaagcaatg gggcaaaaa ctattagaag gagaaaaatt cccaagggtc      480

ccagaaggac ggtctcttgt atatatttca aaacagtttc cttctttagt agcaaaacac     540

gttggggctc aagatgccag gtctcgttgg catcatattt tttctatgcg caaagcgctt     600

gcttatttag atattaagcg catacgagca ccacgcgcta gagtttatca aaactttata     660

ttcgaagaaa aacttcctgt ttcacgaatt tctgtagatt caatgtgtct ctataaagaa     720

aatccacaag ctttcgatga ggcgatcaaa gaactcttat ttctatttaa agaagtgcat     780

ttcagggatt ttgttgtaga aacagagtct ccaacagacg atttcccctt agccgtgaaa     840

gtacacaact attgggtatg cccacgatac gataatttac ctttatttat tcaagaagga     900

aaagatggct ctccagaagg gcgtatagga ctggtcgatc tagaaacttt ttcttggtct     960

ccacatccat accccgtaga agaactagct gtgatgtttc ctatgcataa agagcttctt    1020

atgacagagg cgaaaaaact acaaatccct ttctctacaa aggaggtcga gcgctctgta    1080
```

-continued

```
gagaaagggc ttgctttttt tgaacatatg ctagggcatc aagatttttg ttcccaaaaa   1140

agcgtaacgc cattgcgtaa ttgtgcccct tatattcatc tagaagtatg gagattctca   1200

ctgaaaattt ttgatatttt aaaagctgct attcaactaa atggagcact caatgttctg   1260

ttatctccag atattcgaga gcggttgagt gctatttcgg ataagcaatg gttggctatt   1320

agctcccagg ttacgtcatc gttactcgag caagtttcta caaacatcta tcagtctcat   1380

actgaagagg ctaaacgagt aaattcttca gggactttta tcatgtgtcg atctcctatc   1440

ttccggaaaa gcatcttcat taaaaatctc ccacaattct taaacaagaa attgcagttg   1500

cttccagagg agaaagcaat cagcgaggcg cttgcttctc tatgtttacg tgcagtaatg   1560

gaagagctag tagcaacagg aaatatttat tcttatgatt ctatggatga ttttttgaa   1620

gggcagtatt gtcgcattcg ttattag                                       1647
```

<210> SEQ ID NO 156
<211> LENGTH: 548
<212> TYPE: PRT
<213> ORGANISM: Chlamydia trachomatis

<400> SEQUENCE: 156

```
Met Phe Val Ser Phe Asp Lys Ser Arg Cys Arg Ala Asp Val Pro Asp
1               5                   10                  15

Phe Phe Glu Arg Thr Gly Asn Phe Leu Leu His Cys Val Ala Arg Gly
            20                  25                  30

Ile Asn Val Leu Tyr Arg Val Lys Gln Ile Ser Asn Tyr Pro Ser Cys
        35                  40                  45

Tyr Phe Ser His Lys Glu Ile Ser Cys Cys Arg Arg Ile Ala Asn Ile
    50                  55                  60

Val Ile Cys Ile Leu Thr Gly Pro Leu Met Leu Leu Ala Thr Val Leu
65                  70                  75                  80

Gly Leu Leu Ala Tyr Arg Phe Ser Ser Thr Tyr Gln Thr Ser Leu Gln
                85                  90                  95

Glu Arg Phe Arg Tyr Lys Tyr Glu Gln Lys Gln Ala Leu Asp Glu Tyr
            100                 105                 110

Arg Asp Arg Glu Glu Lys Val Ile Thr Leu Gln Lys Phe Cys Arg Gly
        115                 120                 125

Phe Leu Val Arg Asn His Leu Leu Asn Gln Glu Thr Leu Thr Thr Cys
    130                 135                 140

Lys Gln Trp Gly Gln Lys Leu Leu Glu Gly Glu Lys Phe Pro Arg Val
145                 150                 155                 160

Pro Glu Gly Arg Ser Leu Val Tyr Ile Ser Lys Gln Phe Pro Ser Leu
                165                 170                 175

Val Ala Lys His Val Gly Ala Gln Asp Ala Arg Ser Arg Trp His His
            180                 185                 190

Ile Phe Ser Met Arg Lys Ala Leu Ala Tyr Leu Asp Ile Lys Arg Ile
        195                 200                 205

Arg Ala Pro Arg Ala Arg Val Tyr Gln Asn Phe Ile Phe Glu Glu Lys
    210                 215                 220

Leu Pro Val Ser Arg Ile Ser Val Asp Ser Met Cys Leu Tyr Lys Glu
225                 230                 235                 240

Asn Pro Gln Ala Phe Asp Glu Ala Ile Lys Glu Leu Leu Phe Leu Phe
                245                 250                 255

Lys Glu Val His Phe Arg Asp Phe Val Val Glu Thr Glu Ser Pro Thr
            260                 265                 270
```

-continued

```
Asp Asp Phe Pro Leu Ala Val Lys Val His Asn Tyr Trp Val Cys Pro
        275                 280                 285

Arg Tyr Asp Asn Leu Pro Leu Phe Ile Gln Glu Gly Lys Asp Gly Ser
    290                 295                 300

Pro Glu Gly Arg Ile Gly Leu Val Asp Leu Glu Thr Phe Ser Trp Ser
305                 310                 315                 320

Pro His Pro Tyr Pro Val Glu Glu Leu Ala Val Met Phe Pro Met His
                325                 330                 335

Lys Glu Leu Leu Met Thr Glu Ala Lys Lys Leu Gln Ile Pro Phe Ser
            340                 345                 350

Thr Lys Glu Val Glu Arg Ser Val Glu Lys Gly Leu Ala Phe Phe Glu
        355                 360                 365

His Met Leu Gly His Gln Asp Phe Cys Ser Gln Lys Ser Val Thr Pro
    370                 375                 380

Leu Arg Asn Cys Ala Pro Tyr Ile His Leu Glu Val Trp Arg Phe Ser
385                 390                 395                 400

Leu Lys Ile Phe Asp Ile Leu Lys Ala Ala Ile Gln Leu Asn Gly Ala
                405                 410                 415

Leu Asn Val Leu Leu Ser Pro Asp Ile Arg Glu Arg Leu Ser Ala Ile
            420                 425                 430

Ser Asp Lys Gln Trp Leu Ala Ile Ser Ser Gln Val Thr Ser Ser Leu
        435                 440                 445

Leu Glu Gln Val Ser Thr Asn Ile Tyr Gln Ser His Thr Glu Glu Ala
    450                 455                 460

Lys Arg Val Asn Ser Ser Gly Thr Phe Ile Met Cys Arg Ser Pro Ile
465                 470                 475                 480

Phe Arg Lys Ser Ile Phe Ile Lys Asn Leu Pro Gln Phe Leu Asn Lys
                485                 490                 495

Lys Leu Gln Leu Leu Pro Glu Glu Lys Ala Ile Ser Glu Ala Leu Ala
            500                 505                 510

Ser Leu Cys Leu Arg Ala Val Met Glu Glu Leu Val Ala Thr Gly Asn
        515                 520                 525

Ile Tyr Ser Tyr Asp Ser Met Asp Asp Phe Phe Glu Gly Gln Tyr Cys
    530                 535                 540

Arg Ile Arg Tyr
545


<210> SEQ ID NO 157
<211> LENGTH: 1641
<212> TYPE: DNA
<213> ORGANISM: Chlamydia trachomatis

<400> SEQUENCE: 157

tttgtgtcgt tcgataaatc ccgttgcaga gcggatgtcc ccgatttttt tgaaaggaca      60

ggaaactttc ttctccattg tgtggcaaga gggatcaatg ttttatatcg tgtgaaacaa     120

atctctaact atccttcatg ctatttctca cataaagaga tttcgtgttg tcgtcgtatt     180

gcaaacattg tgatctgtat tctcacaggg cctctgatgt tattggccac tgtgttagga     240

ttattagcgt ataggttttc ttctacttac cagacttctt tacaagaacg ctttcgttat     300

aaatatgaac aaaagcaagc tttagatgaa taccgtgata gggaagaaaa agtcattacg     360

cttcagaagt tttgtagagg atttctagtt agaaatcatt tgctcaacca agaaacttta     420

acaacgtgta agcaatgggg gcaaaaacta ttagaaggag aaaaattccc aagggtccca     480

gaaggacggt ctcttgtata tatttcaaaa cagtttcctt ctttagtagc aaaacacgtt     540
```

```
ggggctcaag atgccaggtc tcgttggcat catatttttt ctatgcgcaa agcgcttgct    600

tatttagata ttaagcgcat acgagcacca cgcgctagag tttatcaaaa ctttatattc    660

gaagaaaaac ttcctgtttc acgaatttct gtagattcaa tgtgtctcta taaagaaaat    720

ccacaagctt tcgatgaggc gatcaaagaa ctcttatttc tatttaaaga agtgcatttc    780

agggattttg ttgtagaaac agagtctcca acagacgatt tccccttagc cgtgaaagta    840

cacaactatt gggtatgccc acgatacgat aatttacctt tatttattca agaaggaaaa    900

gatggctctc cagaagggcg tataggactg gtcgatctag aaactttttc ttggtctcca    960

catccatacc ccgtagaaga actagctgtg atgtttccta tgcataaaga gcttcttatg   1020

acagaggcga aaaaactaca aatccctttc tctacaaagg aggtcgagcg ctctgtagag   1080

aaagggcttg ctttttttga acatatgcta gggcatcaag atttttgttc ccaaaaaagc   1140

gtaacgccat tgcgtaattg tgccccttat attcatctag aagtatggag attctcactg   1200

aaaatttttg atattttaaa agctgctatt caactaaatg gagcactcaa tgttctgtta   1260

tctccagata ttcgagagcg gttgagtgct atttcggata agcaatggtt ggctattagc   1320

tcccaggtta cgtcatcgtt actcgagcaa gtttctacaa acatctatca gtctcatact   1380

gaagaggcta aacgagtaaa ttcttcaggg actttttatca tgtgtcgatc tcctatcttc   1440

cggaaaagca tcttcattaa aaatctccca caattcttaa acaagaaatt gcagttgctt   1500

ccagaggaga aagcaatcag cgaggcgctt gcttctctat gtttacgtgc agtaatggaa   1560

gagctagtag caacaggaaa tatttattct tatgattcta tggatgattt ttttgaaggg   1620

cagtattgtc gcattcgtta t                                             1641
```

```
<210> SEQ ID NO 158
<211> LENGTH: 547
<212> TYPE: PRT
<213> ORGANISM: Chlamydia trachomatis

<400> SEQUENCE: 158

Phe Val Ser Phe Asp Lys Ser Arg Cys Arg Ala Asp Val Pro Asp Phe
1               5                   10                  15

Phe Glu Arg Thr Gly Asn Phe Leu Leu His Cys Val Ala Arg Gly Ile
            20                  25                  30

Asn Val Leu Tyr Arg Val Lys Gln Ile Ser Asn Tyr Pro Ser Cys Tyr
        35                  40                  45

Phe Ser His Lys Glu Ile Ser Cys Cys Arg Arg Ile Ala Asn Ile Val
    50                  55                  60

Ile Cys Ile Leu Thr Gly Pro Leu Met Leu Leu Ala Thr Val Leu Gly
65                  70                  75                  80

Leu Leu Ala Tyr Arg Phe Ser Ser Thr Tyr Gln Thr Ser Leu Gln Glu
                85                  90                  95

Arg Phe Arg Tyr Lys Tyr Glu Gln Lys Gln Ala Leu Asp Glu Tyr Arg
            100                 105                 110

Asp Arg Glu Glu Lys Val Ile Thr Leu Gln Lys Phe Cys Arg Gly Phe
        115                 120                 125

Leu Val Arg Asn His Leu Leu Asn Gln Glu Thr Leu Thr Thr Cys Lys
    130                 135                 140

Gln Trp Gly Gln Lys Leu Leu Glu Gly Glu Lys Phe Pro Arg Val Pro
145                 150                 155                 160

Glu Gly Arg Ser Leu Val Tyr Ile Ser Lys Gln Phe Pro Ser Leu Val
                165                 170                 175
```

```
Ala Lys His Val Gly Ala Gln Asp Ala Arg Ser Arg Trp His His Ile
            180                 185                 190

Phe Ser Met Arg Lys Ala Leu Ala Tyr Leu Asp Ile Lys Arg Ile Arg
        195                 200                 205

Ala Pro Arg Ala Arg Val Tyr Gln Asn Phe Ile Phe Glu Glu Lys Leu
    210                 215                 220

Pro Val Ser Arg Ile Ser Val Asp Ser Met Cys Leu Tyr Lys Glu Asn
225                 230                 235                 240

Pro Gln Ala Phe Asp Glu Ala Ile Lys Glu Leu Leu Phe Leu Phe Lys
                245                 250                 255

Glu Val His Phe Arg Asp Phe Val Val Glu Thr Glu Ser Pro Thr Asp
            260                 265                 270

Asp Phe Pro Leu Ala Val Lys Val His Asn Tyr Trp Val Cys Pro Arg
        275                 280                 285

Tyr Asp Asn Leu Pro Leu Phe Ile Gln Glu Gly Lys Asp Gly Ser Pro
    290                 295                 300

Glu Gly Arg Ile Gly Leu Val Asp Leu Glu Thr Phe Ser Trp Ser Pro
305                 310                 315                 320

His Pro Tyr Pro Val Glu Glu Leu Ala Val Met Phe Pro Met His Lys
                325                 330                 335

Glu Leu Leu Met Thr Glu Ala Lys Lys Leu Gln Ile Pro Phe Ser Thr
            340                 345                 350

Lys Glu Val Glu Arg Ser Val Glu Lys Gly Leu Ala Phe Phe Glu His
        355                 360                 365

Met Leu Gly His Gln Asp Phe Cys Ser Gln Lys Ser Val Thr Pro Leu
    370                 375                 380

Arg Asn Cys Ala Pro Tyr Ile His Leu Glu Val Trp Arg Phe Ser Leu
385                 390                 395                 400

Lys Ile Phe Asp Ile Leu Lys Ala Ala Ile Gln Leu Asn Gly Ala Leu
                405                 410                 415

Asn Val Leu Leu Ser Pro Asp Ile Arg Glu Arg Leu Ser Ala Ile Ser
            420                 425                 430

Asp Lys Gln Trp Leu Ala Ile Ser Ser Gln Val Thr Ser Ser Leu Leu
        435                 440                 445

Glu Gln Val Ser Thr Asn Ile Tyr Gln Ser His Thr Glu Glu Ala Lys
    450                 455                 460

Arg Val Asn Ser Ser Gly Thr Phe Ile Met Cys Arg Ser Pro Ile Phe
465                 470                 475                 480

Arg Lys Ser Ile Phe Ile Lys Asn Leu Pro Gln Phe Leu Asn Lys Lys
                485                 490                 495

Leu Gln Leu Leu Pro Glu Glu Lys Ala Ile Ser Glu Ala Leu Ala Ser
            500                 505                 510

Leu Cys Leu Arg Ala Val Met Glu Glu Leu Val Ala Thr Gly Asn Ile
        515                 520                 525

Tyr Ser Tyr Asp Ser Met Asp Asp Phe Phe Glu Gly Gln Tyr Cys Arg
    530                 535                 540

Ile Arg Tyr
545
```

<210> SEQ ID NO 159
<211> LENGTH: 1644
<212> TYPE: DNA
<213> ORGANISM: Chlamydia trachomatis

<400> SEQUENCE: 159
atgcgaacag actctctttt caatcctccc gactctacta gaggagtttt tcagttttta 60
gagactcagt gtgatcgagc cgtggctcgg tccagacaaa gccaatttat agggttagtc 120
tctgctgtag cagctgcagc attattattg ttgcttgtgg tcgctctatc tgttccagga 180
ttcccagttg cagcttcaat tgttgtaggg gttctctttg ctttatcgat cgtagcatta 240
acagcttcgt ttttggtata tatagctaat gctaagcttg ttgcaataag aattaaattc 300
ttgagtagtg gtctgcaaga tcacttttcg gagtcatcta ttttagggac tctccgtaaa 360
ggacgtggtg ctagtattcc gcttatttcc ggacaagcag atgatcctct ccctaatcgg 420
attgggatca aaaaaagcac tgaaatgcgt gttcttcaaa aaggaattgg gacagattat 480
aaaaaatata agcagcatct tgatagagtg aataatgatt tcacttttgt ctgtgagggg 540
attagcgctt taattcctac agaaaaagat gctccattcc ctatagaacc ttctcattta 600
gcaggtgttt ttttagtatc attttcacca gacaagaatc cgattctaaa gattacgcgt 660
catgctgaga agatgttaca gcctcctcaa ggcggattcc ctaacgggct ggtttggttg 720
tgtggagctc tttctgatcc taagaaattt gcagctccct ttctatcttt gattgagaag 780
actcaccaag ggattttggt gagtaaagac ttgaaagaca ataaggaaag aaagctagct 840
ttagaggctt ccccttcttc attgaatatt ttcttttccg gttggtgttt ggggaatccg 900
gagtacaatc agtatatcac aactgctgta gctgagaaat atagggatgt ctctgtaaga 960
aattgtattt atgatttcct ggatacaggg aatgtgattt cagctcttgc tttagcaagt 1020
agttattcac aagattccgc ttgggctgca gggttgcaga aagttttacg tgaagaagat 1080
aaaaagacta agaaaaagtc acgtgaagaa gtctcttgtt tgtatcgtga tatagatcca 1140
ggctgttgtt taagagccct tcctaagcga tttgaatcca agtcttcagg tagtcaaggt 1200
agtcctaaag agcagttaag ctctttgttg aaagctttag accagaaaat tccttcaggg 1260
attttaggat tgattgcaaa agcttcttct gcagatctca aggctgattt tgcaggtatg 1320
cttgaagtta ttaagcaatt acaagcttta ttcgattctt acccaccttt atgcgaagac 1380
aatattctct tgtggttaag cgcttcttta gaacaagtag gcttgcagaa gaaattgaga 1440
acctttttac cttcatcaga aaaaaaactc ttagaaagag ttctctctac atttttatta 1500
ggtttgtata ctcgaggagt cttttctgta gggcaagtga atcagctagc tactatttgt 1560
aatactcagg actctacaga attctgccag agagtaagtg acctttcgtt aattaaacga 1620
gctctacctg cattatttgg ttaa 1644

<210> SEQ ID NO 160
<211> LENGTH: 547
<212> TYPE: PRT
<213> ORGANISM: Chlamydia trachomatis

<400> SEQUENCE: 160

Met Arg Thr Asp Ser Leu Phe Asn Pro Pro Asp Ser Thr Arg Gly Val
1 5 10 15

Phe Gln Phe Leu Glu Thr Gln Cys Asp Arg Ala Val Ala Arg Ser Arg
20 25 30

Gln Ser Gln Phe Ile Gly Leu Val Ser Ala Val Ala Ala Ala Ala Leu
35 40 45

Leu Leu Leu Leu Val Val Ala Leu Ser Val Pro Gly Phe Pro Val Ala
50 55 60

Ala Ser Ile Val Val Gly Val Leu Phe Ala Leu Ser Ile Val Ala Leu

```
65                  70                  75                  80

Thr Ala Ser Phe Leu Val Tyr Ile Ala Asn Ala Lys Leu Val Ala Ile
                85                  90                  95

Arg Ile Lys Phe Leu Ser Ser Gly Leu Gln Asp His Phe Ser Glu Ser
            100                 105                 110

Ser Ile Leu Gly Thr Leu Arg Lys Gly Arg Gly Ala Ser Ile Pro Leu
        115                 120                 125

Ile Ser Gly Gln Ala Asp Asp Pro Leu Pro Asn Arg Ile Gly Ile Lys
    130                 135                 140

Lys Ser Thr Glu Met Arg Val Leu Gln Lys Gly Ile Gly Thr Asp Tyr
145                 150                 155                 160

Lys Lys Tyr Lys Gln His Leu Asp Arg Val Asn Asn Asp Phe Thr Phe
                165                 170                 175

Val Cys Glu Gly Ile Ser Ala Leu Ile Pro Thr Glu Lys Asp Ala Pro
            180                 185                 190

Phe Pro Ile Glu Pro Ser His Leu Ala Gly Val Phe Leu Val Ser Phe
        195                 200                 205

Ser Pro Asp Lys Asn Pro Ile Leu Lys Ile Thr Arg His Ala Glu Lys
    210                 215                 220

Met Leu Gln Pro Pro Gln Gly Gly Phe Pro Asn Gly Leu Val Trp Leu
225                 230                 235                 240

Cys Gly Ala Leu Ser Asp Pro Lys Lys Phe Ala Ala Pro Phe Leu Ser
                245                 250                 255

Leu Ile Glu Lys Thr His Gln Gly Ile Leu Val Ser Lys Asp Leu Lys
            260                 265                 270

Asp Asn Lys Glu Arg Lys Leu Ala Leu Glu Ala Ser Leu Leu Ser Leu
        275                 280                 285

Asn Ile Phe Phe Ser Gly Trp Cys Leu Gly Asn Pro Glu Tyr Asn Gln
    290                 295                 300

Tyr Ile Thr Thr Ala Val Ala Glu Lys Tyr Arg Asp Val Ser Val Arg
305                 310                 315                 320

Asn Cys Ile Tyr Asp Phe Leu Asp Thr Gly Asn Val Ile Ser Ala Leu
                325                 330                 335

Ala Leu Ala Ser Ser Tyr Ser Gln Asp Ser Ala Trp Ala Ala Gly Leu
            340                 345                 350

Gln Lys Val Leu Arg Glu Glu Asp Lys Lys Thr Lys Lys Lys Ser Arg
        355                 360                 365

Glu Glu Val Ser Cys Leu Tyr Arg Asp Ile Asp Pro Gly Cys Cys Leu
    370                 375                 380

Arg Ala Leu Pro Lys Arg Phe Glu Ser Lys Ser Ser Gly Ser Gln Gly
385                 390                 395                 400

Ser Pro Lys Glu Gln Leu Ser Ser Leu Leu Lys Ala Leu Asp Gln Lys
                405                 410                 415

Ile Pro Ser Gly Ile Leu Gly Leu Ile Ala Lys Ala Ser Ser Ala Asp
            420                 425                 430

Leu Lys Ala Asp Phe Ala Gly Met Leu Glu Val Ile Lys Gln Leu Gln
        435                 440                 445

Ala Leu Phe Asp Ser Tyr Pro Pro Leu Cys Glu Asp Asn Ile Leu Leu
    450                 455                 460

Trp Leu Ser Ala Ser Leu Glu Gln Val Gly Leu Gln Lys Lys Leu Arg
465                 470                 475                 480

Thr Phe Leu Pro Ser Ser Glu Lys Lys Leu Leu Glu Arg Val Leu Ser
                485                 490                 495
```

```
Thr Phe Leu Leu Gly Leu Tyr Thr Arg Gly Val Phe Ser Val Gly Gln
            500                 505                 510

Val Asn Gln Leu Ala Thr Ile Cys Asn Thr Gln Asp Ser Thr Glu Phe
        515                 520                 525

Cys Gln Arg Val Ser Asp Leu Ser Leu Ile Lys Arg Ala Leu Pro Ala
    530                 535                 540

Leu Phe Gly
545


<210> SEQ ID NO 161
<211> LENGTH: 1638
<212> TYPE: DNA
<213> ORGANISM: Chlamydia trachomatis

<400> SEQUENCE: 161

cgaacagact ctcttttcaa tcctcccgac tctactagag gagtttttca gtttttagag     60

actcagtgtg atcgagccgt ggctcggtcc agacaaagcc aatttatagg gttagtctct    120

gctgtagcag ctgcagcatt attattgttg cttgtggtcg ctctatctgt tccaggattc    180

ccagttgcag cttcaattgt tgtaggggtt ctctttgctt tatcgatcgt agcattaaca    240

gcttcgtttt tggtatatat agctaatgct aagcttgttg caataagaat taaattcttg    300

agtagtggtc tgcaagatca cttttcggag tcatctattt tagggactct ccgtaaagga    360

cgtggtgcta gtattccgct tatttccgga caagcagatg atcctctccc taatcggatt    420

gggatcaaaa aaagcactga aatgcgtgtt cttcaaaaag gaattgggac agattataaa    480

aaatataagc agcatcttga tagagtgaat aatgatttca cttttgtctg tgaggggatt    540

agcgctttaa ttcctacaga aaaagatgct ccattcccta tagaaccttc tcatttagca    600

ggtgtttttt tagtatcatt ttcaccagac aagaatccga ttctaaagat tacgcgtcat    660

gctgagaaga tgttacagcc tcctcaaggc ggattcccta acgggctggt ttggttgtgt    720

ggagctcttt ctgatcctaa gaaatttgca gctccctttc tatctttgat tgagaagact    780

caccaaggga ttttggtgag taaagacttg aaagacaata aggaaagaaa gctagcttta    840

gaggcttccc ttctttcatt gaatattttc ttttccggtt ggtgtttggg gaatccggag    900

tacaatcagt atatcacaac tgctgtagct gagaaatata gggatgtctc tgtaagaaat    960

tgtatttatg atttcctgga tacagggaat gtgatttcag ctcttgcttt agcaagtagt   1020

tattcacaag attccgcttg ggctgcaggg ttgcagaaag ttttacgtga agaagataaa   1080

aagactaaga aaaagtcacg tgaagaagtc tcttgtttgt atcgtgatat agatccaggc   1140

tgttgtttaa gagcccttcc taagcgattt gaatccaagt cttcaggtag tcaaggtagt   1200

cctaaagagc agttaagctc tttgttgaaa gctttagacc agaaaattcc ttcagggatt   1260

ttaggattga ttgcaaaagc ttcttctgca gatctcaagg ctgattttgc aggtatgctt   1320

gaagttatta agcaattaca agctttattc gattcttacc cacctttatg cgaagacaat   1380

attctcttgt ggttaagcgc ttctttagaa caagtaggct tgcagaagaa attgagaacc   1440

tttttacctt catcagaaaa aaaactctta gaaagagttc tctctacatt tttattaggt   1500

ttgtatactc gaggagtctt ttctgtaggg caagtgaatc agctagctac tatttgtaat   1560

actcaggact ctacagaatt ctgccagaga gtaagtgacc tttcgttaat taaacgagct   1620

ctacctgcat tatttggt                                                 1638


<210> SEQ ID NO 162
```

<211> LENGTH: 546
<212> TYPE: PRT
<213> ORGANISM: Chlamydia trachomatis

<400> SEQUENCE: 162

Arg Thr Asp Ser Leu Phe Asn Pro Pro Asp Ser Thr Arg Gly Val Phe
1 5 10 15

Gln Phe Leu Glu Thr Gln Cys Asp Arg Ala Val Ala Arg Ser Arg Gln
20 25 30

Ser Gln Phe Ile Gly Leu Val Ser Ala Val Ala Ala Ala Ala Leu Leu
35 40 45

Leu Leu Leu Val Val Ala Leu Ser Val Pro Gly Phe Pro Val Ala Ala
50 55 60

Ser Ile Val Val Gly Val Leu Phe Ala Leu Ser Ile Val Ala Leu Thr
65 70 75 80

Ala Ser Phe Leu Val Tyr Ile Ala Asn Ala Lys Leu Val Ala Ile Arg
85 90 95

Ile Lys Phe Leu Ser Ser Gly Leu Gln Asp His Phe Ser Glu Ser Ser
100 105 110

Ile Leu Gly Thr Leu Arg Lys Gly Arg Gly Ala Ser Ile Pro Leu Ile
115 120 125

Ser Gly Gln Ala Asp Asp Pro Leu Pro Asn Arg Ile Gly Ile Lys Lys
130 135 140

Ser Thr Glu Met Arg Val Leu Gln Lys Gly Ile Gly Thr Asp Tyr Lys
145 150 155 160

Lys Tyr Lys Gln His Leu Asp Arg Val Asn Asn Asp Phe Thr Phe Val
165 170 175

Cys Glu Gly Ile Ser Ala Leu Ile Pro Thr Glu Lys Asp Ala Pro Phe
180 185 190

Pro Ile Glu Pro Ser His Leu Ala Gly Val Phe Leu Val Ser Phe Ser
195 200 205

Pro Asp Lys Asn Pro Ile Leu Lys Ile Thr Arg His Ala Glu Lys Met
210 215 220

Leu Gln Pro Pro Gln Gly Gly Phe Pro Asn Gly Leu Val Trp Leu Cys
225 230 235 240

Gly Ala Leu Ser Asp Pro Lys Lys Phe Ala Ala Pro Phe Leu Ser Leu
245 250 255

Ile Glu Lys Thr His Gln Gly Ile Leu Val Ser Lys Asp Leu Lys Asp
260 265 270

Asn Lys Glu Arg Lys Leu Ala Leu Glu Ala Ser Leu Leu Ser Leu Asn
275 280 285

Ile Phe Phe Ser Gly Trp Cys Leu Gly Asn Pro Glu Tyr Asn Gln Tyr
290 295 300

Ile Thr Thr Ala Val Ala Glu Lys Tyr Arg Asp Val Ser Val Arg Asn
305 310 315 320

Cys Ile Tyr Asp Phe Leu Asp Thr Gly Asn Val Ile Ser Ala Leu Ala
325 330 335

Leu Ala Ser Ser Tyr Ser Gln Asp Ser Ala Trp Ala Ala Gly Leu Gln
340 345 350

Lys Val Leu Arg Glu Glu Asp Lys Lys Thr Lys Lys Lys Ser Arg Glu
355 360 365

Glu Val Ser Cys Leu Tyr Arg Asp Ile Asp Pro Gly Cys Cys Leu Arg
370 375 380

Ala Leu Pro Lys Arg Phe Glu Ser Lys Ser Ser Gly Ser Gln Gly Ser

-continued

```
385                 390                 395                 400

Pro Lys Glu Gln Leu Ser Ser Leu Leu Lys Ala Leu Asp Gln Lys Ile
                405                 410                 415

Pro Ser Gly Ile Leu Gly Leu Ile Ala Lys Ala Ser Ser Ala Asp Leu
            420                 425                 430

Lys Ala Asp Phe Ala Gly Met Leu Glu Val Ile Lys Gln Leu Gln Ala
        435                 440                 445

Leu Phe Asp Ser Tyr Pro Pro Leu Cys Glu Asp Asn Ile Leu Leu Trp
    450                 455                 460

Leu Ser Ala Ser Leu Glu Gln Val Gly Leu Gln Lys Lys Leu Arg Thr
465                 470                 475                 480

Phe Leu Pro Ser Ser Glu Lys Lys Leu Leu Glu Arg Val Leu Ser Thr
                485                 490                 495

Phe Leu Leu Gly Leu Tyr Thr Arg Gly Val Phe Ser Val Gly Gln Val
            500                 505                 510

Asn Gln Leu Ala Thr Ile Cys Asn Thr Gln Asp Ser Thr Glu Phe Cys
        515                 520                 525

Gln Arg Val Ser Asp Leu Ser Leu Ile Lys Arg Ala Leu Pro Ala Leu
    530                 535                 540

Phe Gly
545
```

<210> SEQ ID NO 163
<211> LENGTH: 1155
<212> TYPE: DNA
<213> ORGANISM: Chlamydia trachomatis

<400> SEQUENCE: 163

```
atggacggga caaaaattca cgaaacacgc tccttctctt ggttaaacaa ccaacaagcc     60

atccctcctt ccgaaatggt gaaggaggct tttcaacgtt acgcagacgt attttcgtac    120

agcgcaaata cctccattct gactttacaa gcagaagctg aagcttctgc ccgcaaactc    180

acagggtgtc aggagaaggc ttttaccttt cattttattc ttcattaccc gaatgtcacg    240

gccattatcg tggccgctct tctggaaaac caaaatgcct tccaggggcg taatcacctt    300

cttgttcctt cttgcgagca acaatttatc attaatgctc tctgccgtcg gcaaaactta    360

gggacaacct atgattgggt aaccagcaaa aacggccgcg taaaagaatc cgatctagca    420

gaagctcttt ccccgcggac cttgctgttt tccatatctg ctgcgaatgg tatgacagga    480

tttctggaag cgatccctga gcttgctgcg ttatgtaaag aacgcggggt aattttccac    540

atagacctga gtgatatctt aggaagatgc gcgctacccg cagaactcta tcaagcagat    600

atccttactt tttcttcaca gtctcttggt gggattggtc cctcaggagc gatgtttatt    660

tctcccgctt taacaaaata tttttcctta tggcttccta gtaatccaca agtccctacc    720

tgcctgagtt ctcttgcagc tttttctctt gcctgtcagg aacgtacaac cgctttctcc    780

tctcttgtgc tttctgctat ttcttctcga gcagctctta aacaggctct ttccgctatt    840

cctcaagtcg aattcctttt ggaagacagt gcccctcgtc tccctaatgt cgctgtcttt    900

gctattcctg gtatccctgc agagtcctta ggatttttcc tttcccagaa aaatattttt    960

gtagggttag gctatgaacg cttccagcct ctatcgcaga ttttacaaag ttcgggcatc   1020

tctcccttct tatgccacag cgctttacac gtatctttta ctgaacgtac tcctactaca   1080

cacttctctg cattagcaac cgccttacaa gaagggatct ctcacctaca accactggtt   1140

actcaatcct tatga                                                    1155
```

<210> SEQ ID NO 164
<211> LENGTH: 384
<212> TYPE: PRT
<213> ORGANISM: Chlamydia trachomatis

<400> SEQUENCE: 164

```
Met Asp Gly Thr Lys Ile His Glu Thr Arg Ser Phe Ser Trp Leu Asn
1               5                   10                  15

Asn Gln Gln Ala Ile Pro Pro Ser Glu Met Val Lys Glu Ala Phe Gln
            20                  25                  30

Arg Tyr Ala Asp Val Phe Ser Tyr Ser Ala Asn Thr Ser Ile Leu Thr
        35                  40                  45

Leu Gln Ala Glu Ala Glu Ala Ser Ala Arg Lys Leu Thr Gly Cys Gln
    50                  55                  60

Glu Lys Ala Phe Thr Phe His Phe Ile Leu His Tyr Pro Asn Val Thr
65                  70                  75                  80

Ala Ile Ile Val Ala Ala Leu Leu Glu Asn Gln Asn Ala Phe Gln Gly
                85                  90                  95

Arg Asn His Leu Leu Val Pro Ser Cys Glu Gln Gln Phe Ile Ile Asn
            100                 105                 110

Ala Leu Cys Arg Arg Gln Asn Leu Gly Thr Thr Tyr Asp Trp Val Thr
        115                 120                 125

Ser Lys Asn Gly Arg Val Lys Glu Ser Asp Leu Ala Glu Ala Leu Ser
    130                 135                 140

Pro Arg Thr Leu Leu Phe Ser Ile Ser Ala Ala Asn Gly Met Thr Gly
145                 150                 155                 160

Phe Leu Glu Ala Ile Pro Glu Leu Ala Ala Leu Cys Lys Glu Arg Gly
                165                 170                 175

Val Ile Phe His Ile Asp Leu Ser Asp Ile Leu Gly Arg Cys Ala Leu
            180                 185                 190

Pro Ala Glu Leu Tyr Gln Ala Asp Ile Leu Thr Phe Ser Ser Gln Ser
        195                 200                 205

Leu Gly Gly Ile Gly Pro Ser Gly Ala Met Phe Ile Ser Pro Ala Leu
    210                 215                 220

Thr Lys Tyr Phe Ser Leu Trp Leu Pro Ser Asn Pro Gln Val Pro Thr
225                 230                 235                 240

Cys Leu Ser Ser Leu Ala Ala Phe Ser Leu Ala Cys Gln Glu Arg Thr
                245                 250                 255

Thr Ala Phe Ser Ser Leu Val Leu Ser Ala Ile Ser Ser Arg Ala Ala
            260                 265                 270

Leu Lys Gln Ala Leu Ser Ala Ile Pro Gln Val Glu Phe Leu Leu Glu
        275                 280                 285

Asp Ser Ala Pro Arg Leu Pro Asn Val Ala Val Phe Ala Ile Pro Gly
    290                 295                 300

Ile Pro Ala Glu Ser Leu Gly Phe Phe Leu Ser Gln Lys Asn Ile Phe
305                 310                 315                 320

Val Gly Leu Gly Tyr Glu Arg Phe Gln Pro Leu Ser Gln Ile Leu Gln
                325                 330                 335

Ser Ser Gly Ile Ser Pro Phe Leu Cys His Ser Ala Leu His Val Ser
            340                 345                 350

Phe Thr Glu Arg Thr Pro Thr Thr His Phe Ser Ala Leu Ala Thr Ala
        355                 360                 365

Leu Gln Glu Gly Ile Ser His Leu Gln Pro Leu Val Thr Gln Ser Leu
```

370 375 380

<210> SEQ ID NO 165
<211> LENGTH: 1149
<212> TYPE: DNA
<213> ORGANISM: Chlamydia trachomatis

<400> SEQUENCE: 165
gacgggacaa aaattcacga aacacgctcc ttctcttggt taaacaacca acaagccatc 60
cctccttccg aaatggtgaa ggaggctttt caacgttacg cagacgtatt ttcgtacagc 120
gcaaatacct ccattctgac tttacaagca gaagctgaag cttctgcccg caaactcaca 180
gggtgtcagg agaaggcttt tacctttcat tttattcttc attacccgaa tgtcacggcc 240
attatcgtgg ccgctcttct ggaaaaccaa aatgccttcc aggggcgtaa tcaccttctt 300
gttccttctt gcgagcaaca atttatcatt aatgctctct gccgtcggca aaacttaggg 360
acaacctatg attgggtaac cagcaaaaac ggccgcgtaa aagaatccga tctagcagaa 420
gctctttccc cgcggacctt gctgttttcc atatctgctg cgaatggtat gacaggattt 480
ctggaagcga tccctgagct tgctgcgtta tgtaaagaac gcggggtaat tttccacata 540
gacctgagtg atatcttagg aagatgcgcg ctacccgcag aactctatca agcagatatc 600
cttacttttt cttcacagtc tcttggtggg attggtccct caggagcgat gtttatttct 660
cccgctttaa caaaatattt ttccttatgg cttcctagta atccacaagt ccctacctgc 720
ctgagttctc ttgcagcttt ttctcttgcc tgtcaggaac gtacaaccgc tttctcctct 780
cttgtgcttt ctgctatttc ttctcgagca gctcttaaac aggctctttc cgctattcct 840
caagtcgaat tccttttgga agacagtgcc cctcgtctcc ctaatgtcgc tgtctttgct 900
attcctggta tccctgcaga gtccttagga tttttccttt cccagaaaaa tatttttgta 960
gggttaggct atgaacgctt ccagcctcta tcgcagattt tacaaagttc gggcatctct 1020
cccttcttat gccacagcgc tttacacgta tcttttactg aacgtactcc tactacacac 1080
ttctctgcat tagcaaccgc cttacaagaa gggatctctc acctacaacc actggttact 1140
caatcctta 1149

<210> SEQ ID NO 166
<211> LENGTH: 383
<212> TYPE: PRT
<213> ORGANISM: Chlamydia trachomatis

<400> SEQUENCE: 166

Asp Gly Thr Lys Ile His Glu Thr Arg Ser Phe Ser Trp Leu Asn Asn
1 5 10 15

Gln Gln Ala Ile Pro Pro Ser Glu Met Val Lys Glu Ala Phe Gln Arg
20 25 30

Tyr Ala Asp Val Phe Ser Tyr Ser Ala Asn Thr Ser Ile Leu Thr Leu
35 40 45

Gln Ala Glu Ala Glu Ala Ser Ala Arg Lys Leu Thr Gly Cys Gln Glu
50 55 60

Lys Ala Phe Thr Phe His Phe Ile Leu His Tyr Pro Asn Val Thr Ala
65 70 75 80

Ile Ile Val Ala Ala Leu Leu Glu Asn Gln Asn Ala Phe Gln Gly Arg
85 90 95

Asn His Leu Leu Val Pro Ser Cys Glu Gln Gln Phe Ile Ile Asn Ala
100 105 110

```
Leu Cys Arg Arg Gln Asn Leu Gly Thr Thr Tyr Asp Trp Val Thr Ser
        115                 120                 125

Lys Asn Gly Arg Val Lys Glu Ser Asp Leu Ala Glu Ala Leu Ser Pro
    130                 135                 140

Arg Thr Leu Leu Phe Ser Ile Ser Ala Ala Asn Gly Met Thr Gly Phe
145                 150                 155                 160

Leu Glu Ala Ile Pro Glu Leu Ala Ala Leu Cys Lys Glu Arg Gly Val
                165                 170                 175

Ile Phe His Ile Asp Leu Ser Asp Ile Leu Gly Arg Cys Ala Leu Pro
            180                 185                 190

Ala Glu Leu Tyr Gln Ala Asp Ile Leu Thr Phe Ser Ser Gln Ser Leu
        195                 200                 205

Gly Gly Ile Gly Pro Ser Gly Ala Met Phe Ile Ser Pro Ala Leu Thr
    210                 215                 220

Lys Tyr Phe Ser Leu Trp Leu Pro Ser Asn Pro Gln Val Pro Thr Cys
225                 230                 235                 240

Leu Ser Ser Leu Ala Ala Phe Ser Leu Ala Cys Gln Glu Arg Thr Thr
                245                 250                 255

Ala Phe Ser Ser Leu Val Leu Ser Ala Ile Ser Ser Arg Ala Ala Leu
            260                 265                 270

Lys Gln Ala Leu Ser Ala Ile Pro Gln Val Glu Phe Leu Leu Glu Asp
        275                 280                 285

Ser Ala Pro Arg Leu Pro Asn Val Ala Val Phe Ala Ile Pro Gly Ile
    290                 295                 300

Pro Ala Glu Ser Leu Gly Phe Phe Leu Ser Gln Lys Asn Ile Phe Val
305                 310                 315                 320

Gly Leu Gly Tyr Glu Arg Phe Gln Pro Leu Ser Gln Ile Leu Gln Ser
                325                 330                 335

Ser Gly Ile Ser Pro Phe Leu Cys His Ser Ala Leu His Val Ser Phe
            340                 345                 350

Thr Glu Arg Thr Pro Thr Thr His Phe Ser Ala Leu Ala Thr Ala Leu
        355                 360                 365

Gln Glu Gly Ile Ser His Leu Gln Pro Leu Val Thr Gln Ser Leu
    370                 375                 380
```

<210> SEQ ID NO 167
<211> LENGTH: 852
<212> TYPE: DNA
<213> ORGANISM: Chlamydia trachomatis

<400> SEQUENCE: 167

```
atgccgcacc aagtcttatt gtctcctgtt tgcgatcttt tatcgaatgc tgaaggtata     60

gagacgcaag tactgtttgg agaaaggata tgcaaccata accatcgaca ctatgcctat    120

tctcaactag tcttttcttc tatatggaag ccataccctg gcgactctct acagaatatt    180

cctctattct cttcccaact gcagcctcct aatgctgttg tctgctctca agaagctttt    240

ttagatcctt ggcatatccc cttacctttt gccgctccgc tccacataga taaccaaaat    300

caagtgtccc tatctcctgc tagcatagca ttattaaatt ccaattccag aagtaactat    360

gcaaaagctt tctgctctac caaagagatt cgttttttaa attcttcatt ctctccaaga    420

gatttagttt ctttcgcaga acaattgata gatactccgt acgtttgggg tggccggtgc    480

attcataaac agcttcctcg taatggtgta gattgttcgg ggtatattca actactttac    540

caagtcacag gaagaaatat ccctcgcaat gctagagatc aatacagaga ctgttctcca    600
```

```
gtaaaagatt tctcgtctct acctatagga ggacttatct tcctcaagaa agcaagcacg    660

ggacaaatca accatgttat gatgaaaatc tcggagcatg aattcattca tgctgcggaa    720

aaaataggga aagtagaaaa agtaatccta ggaaataggg ctttctttaa agggaatcta    780

ttctgctcat taggtgaacc gcctatagaa gctgtttttg gcgttcctaa aaatagaaaa    840

gccttctttt ga                                                        852
```

<210> SEQ ID NO 168
<211> LENGTH: 283
<212> TYPE: PRT
<213> ORGANISM: Chlamydia trachomatis

<400> SEQUENCE: 168

```
Met Pro His Gln Val Leu Leu Ser Pro Val Cys Asp Leu Leu Ser Asn
1               5                   10                  15

Ala Glu Gly Ile Glu Thr Gln Val Leu Phe Gly Glu Arg Ile Cys Asn
            20                  25                  30

His Asn His Arg His Tyr Ala Tyr Ser Gln Leu Val Phe Ser Ser Ile
        35                  40                  45

Trp Lys Pro Tyr Pro Gly Asp Ser Leu Gln Asn Ile Pro Leu Phe Ser
    50                  55                  60

Ser Gln Leu Gln Pro Pro Asn Ala Val Val Cys Ser Gln Glu Ala Phe
65                  70                  75                  80

Leu Asp Pro Trp His Ile Pro Leu Pro Phe Ala Ala Pro Leu His Ile
                85                  90                  95

Asp Asn Gln Asn Gln Val Ser Leu Ser Pro Ala Ser Ile Ala Leu Leu
            100                 105                 110

Asn Ser Asn Ser Arg Ser Asn Tyr Ala Lys Ala Phe Cys Ser Thr Lys
        115                 120                 125

Glu Ile Arg Phe Leu Asn Ser Ser Phe Ser Pro Arg Asp Leu Val Ser
    130                 135                 140

Phe Ala Glu Gln Leu Ile Asp Thr Pro Tyr Val Trp Gly Gly Arg Cys
145                 150                 155                 160

Ile His Lys Gln Leu Pro Arg Asn Gly Val Asp Cys Ser Gly Tyr Ile
                165                 170                 175

Gln Leu Leu Tyr Gln Val Thr Gly Arg Asn Ile Pro Arg Asn Ala Arg
            180                 185                 190

Asp Gln Tyr Arg Asp Cys Ser Pro Val Lys Asp Phe Ser Ser Leu Pro
        195                 200                 205

Ile Gly Gly Leu Ile Phe Leu Lys Lys Ala Ser Thr Gly Gln Ile Asn
    210                 215                 220

His Val Met Met Lys Ile Ser Glu His Glu Phe Ile His Ala Ala Glu
225                 230                 235                 240

Lys Ile Gly Lys Val Glu Lys Val Ile Leu Gly Asn Arg Ala Phe Phe
                245                 250                 255

Lys Gly Asn Leu Phe Cys Ser Leu Gly Glu Pro Pro Ile Glu Ala Val
            260                 265                 270

Phe Gly Val Pro Lys Asn Arg Lys Ala Phe Phe
        275                 280
```

<210> SEQ ID NO 169
<211> LENGTH: 846
<212> TYPE: DNA
<213> ORGANISM: Chlamydia trachomatis

<400> SEQUENCE: 169

```
ccgcaccaag tcttattgtc tcctgtttgc gatcttttat cgaatgctga aggtatagag     60

acgcaagtac tgtttggaga aaggatatgc aaccataacc atcgacacta tgcctattct    120

caactagtct tttcttctat atggaagcca taccctggcg actctctaca gaatattcct    180

ctattctctt cccaactgca gcctcctaat gctgttgtct gctctcaaga agctttttta    240

gatccttggc atatcccctt accttttgcc gctccgctcc acatagataa ccaaaatcaa    300

gtgtccctat ctcctgctag catagcatta ttaaattcca attccagaag taactatgca    360

aaagcttctt gctctaccaa agagattcgt tttttaaatt cttcattctc tccaagagat    420

ttagtttctt tcgcagaaca attgatagat actccgtacg tttggggtgg ccggtgcatt    480

cataaacagc ttcctcgtaa tggtgtagat tgttcggggt atattcaact actttaccaa    540

gtcacaggaa gaaatatccc tcgcaatgct agagatcaat acagagactg ttctccagta    600

aaagatttct cgtctctacc tataggagga cttatcttcc tcaagaaagc aagcacggga    660

caaatcaacc atgttatgat gaaaatctcg gagcatgaat tcattcatgc tgcggaaaaa    720

atagggaaag tagaaaaagt aatcctagga aatagggctt tctttaaagg gaatctattc    780

tgctcattag gtgaaccgcc tatagaagct gtttttggcg ttcctaaaaa tagaaaagcc    840

ttcttt                                                               846
```

<210> SEQ ID NO 170
<211> LENGTH: 282
<212> TYPE: PRT
<213> ORGANISM: Chlamydia trachomatis

<400> SEQUENCE: 170

```
Pro His Gln Val Leu Leu Ser Pro Val Cys Asp Leu Leu Ser Asn Ala
1               5                   10                  15

Glu Gly Ile Glu Thr Gln Val Leu Phe Gly Glu Arg Ile Cys Asn His
            20                  25                  30

Asn His Arg His Tyr Ala Tyr Ser Gln Leu Val Phe Ser Ser Ile Trp
        35                  40                  45

Lys Pro Tyr Pro Gly Asp Ser Leu Gln Asn Ile Pro Leu Phe Ser Ser
    50                  55                  60

Gln Leu Gln Pro Pro Asn Ala Val Val Cys Ser Gln Glu Ala Phe Leu
65                  70                  75                  80

Asp Pro Trp His Ile Pro Leu Pro Phe Ala Ala Pro Leu His Ile Asp
                85                  90                  95

Asn Gln Asn Gln Val Ser Leu Ser Pro Ala Ser Ile Ala Leu Leu Asn
            100                 105                 110

Ser Asn Ser Arg Ser Asn Tyr Ala Lys Ala Phe Cys Ser Thr Lys Glu
        115                 120                 125

Ile Arg Phe Leu Asn Ser Ser Phe Ser Pro Arg Asp Leu Val Ser Phe
    130                 135                 140

Ala Glu Gln Leu Ile Asp Thr Pro Tyr Val Trp Gly Gly Arg Cys Ile
145                 150                 155                 160

His Lys Gln Leu Pro Arg Asn Gly Val Asp Cys Ser Gly Tyr Ile Gln
                165                 170                 175

Leu Leu Tyr Gln Val Thr Gly Arg Asn Ile Pro Arg Asn Ala Arg Asp
            180                 185                 190

Gln Tyr Arg Asp Cys Ser Pro Val Lys Asp Phe Ser Ser Leu Pro Ile
        195                 200                 205

Gly Gly Leu Ile Phe Leu Lys Lys Ala Ser Thr Gly Gln Ile Asn His
```

-continued

```
    210                 215                 220

Val Met Met Lys Ile Ser Glu His Glu Phe Ile His Ala Ala Glu Lys
225                 230                 235                 240

Ile Gly Lys Val Glu Lys Val Ile Leu Gly Asn Arg Ala Phe Phe Lys
                245                 250                 255

Gly Asn Leu Phe Cys Ser Leu Gly Glu Pro Pro Ile Glu Ala Val Phe
            260                 265                 270

Gly Val Pro Lys Asn Arg Lys Ala Phe Phe
        275                 280


<210> SEQ ID NO 171
<211> LENGTH: 11
<212> TYPE: PRT
<213> ORGANISM: Artificial Sequence
<220> FEATURE:
<223> OTHER INFORMATION: Synthetic peptide

<400> SEQUENCE: 171

Lys Leu Lys Leu Leu Leu Leu Leu Lys Leu Lys
1               5                   10
```

CHLAMYDIA ANTIGENS

This application is continuation of U.S. application Ser. No. 13/255,002, now U.S. Pat. No. 8,568,732, which is a §371 filing of PCT/IB2010/050988, filed Mar. 8, 2010, and claims the benefit of U.S. provisional application 61/157,921 filed on Mar. 6, 2009, from which applications priority is claimed pursuant to 35 U.S.C. §§119/120, and which applications are incorporated herein by reference in their entireties.

TECHNICAL FIELD

This invention is in the field of *Chlamydia trahomatis* proteins and their uses.

BACKGROUND ART

Vaccine development has been identified as essential to controlling infection with *C. trachomatis*. Vaccines against *C. trachomatis* appear to elicit protective T-cell and/or B-cell immunity in the genital tract mucosa.

Protective immunity to *C. trachomatis* seems to depend on a Th1-polarized cell-mediated immune response, in particular on CD4+ lymphocytes secreting IFNγ. For example, depletion of CD4+ T cells in mice results in loss of protective immunity, and adoptive transfer of *Chlamydia*-specific CD4+ T cells confers protection against challenge with *C. trachomatis*. Furthermore, recent studies report that *C. trachomatis* infection in mice induces a CD4-Th1 protective immune response, indicating that critical *Chlamydia* antigens are processed and presented via the MHC class II pathway (Brunham R C and Rey-Ladino J (2005), Nat Rev Immunol 5: 149-1611; Su H and Caldwell H D (1995), Infect Immun 63: 3302-3308).

Although B-cells and antibodies do not have a decisive role in resolution of primary infection, they are likely to be important for enhancing the protective effector T-cell response and to be required to control re-infection with various mechanisms such as antibody-mediated neutralization and opsonization.

Because immune protection against infection with *C. trachomatis* is likely to be mediated by immunization with *C. trachomatis* proteins that are targets of CD4+ T cells and that are capable of inducing B-cell responses, identification of such proteins is particularly important. It is therefore an object of the invention to provide further antigens for use in *Chlamydia* vaccines.

DISCLOSURE OF THE INVENTION

The invention provides identifies *Chlamydia* antigens for use in the treatment, prevention and/or diagnosis of *Chlamydia* infection. In particular, the invention provides one or more of the following antigens (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) from *C. trachomatis* for the treatment, prevention or diagnosis of *Chlamydia* infection (and, in particular, *C. trachomatis* infection): CT733, CT153, CT601, CT279, CT443, CT372, CT456, CT381, CT255, CT341, CT716, CT745, CT812, CT869, CT387, CT166, CT175, CT163, CT214, CT721, CT127, CT043, CT823, CT600, CT711, CT114, CT480, CT089, CT734 and CT016 for example, one or more of CT733, CT153, CT601, CT279, CT443, CT372, CT456, CT381, CT255, CT341, CT716 and CT745.

In particular, the invention provides proteins for use in the treatment, prevention and/or diagnosis of *Chlamydia* infection (and, in particular, *C. trachomatis* infection). Immunisation with the proteins is preferably able to induce a specific CD4+ Th1 cell mediated response against *Chlamydia*.

In one embodiment, the nucleic acid sequence and/or amino acid sequence of the protein comprises the sequence presented in SEQ ID NO:1 and SEQ ID NO:2 respectively. This protein is also known as "CT733" and is annotated as a hypothetical protein from *C. trachomatis*. In another embodiment, the nucleic acid sequence and/or amino acid sequence of the protein comprises the sequence presented in SEQ ID NO:3 and SEQ ID NO:4 respectively. This protein is also known as "CT153" and is annotated as MACPF/membrane-attack complex (MAC)/perforin from *C. trachomatis*. In another embodiment, the nucleic acid sequence and/or amino acid sequence of the protein comprises the sequence presented in SEQ ID NO:5 and SEQ ID NO:6 respectively. This protein is also known as "CT601" from *C. trachomatis*. In another embodiment, the nucleic acid sequence and/or amino acid sequence of the protein comprises the sequence presented in SEQ ID NO:7 and SEQ ID NO:8 respectively. This protein is also known as "CT279" from *C. trachomatis*. In another embodiment, the nucleic acid sequence and/or amino acid sequence of the protein comprises the sequence presented in SEQ ID NO:9 and SEQ ID NO:10 respectively. This protein is also known as "CT443" from *C. trachomatis*. In another embodiment, the nucleic acid sequence and/or amino acid sequence of the protein comprises the sequence presented in SEQ ID NO:11 and SEQ ID NO:12 respectively. This protein is also known as "CT372" from *C. trachomatis*. In another embodiment, the nucleic acid sequence and/or amino acid sequence of the protein comprises the sequence presented in SEQ ID NO:13 and SEQ ID NO:14 respectively. This protein is also known as "CT456" from *C. trachomatis*. In another embodiment, the nucleic acid sequence and/or amino acid sequence of the protein comprises the sequence presented in SEQ ID NO:15 and SEQ ID NO:16 respectively. This protein is also known as "CT381" from *C. trachomatis*. In another embodiment, the nucleic acid sequence and/or amino acid sequence of the protein comprises the sequence presented in SEQ ID NO:39 and SEQ ID NO:40 respectively. This protein is also known as "CT255" from *C. trachomatis*. In another embodiment, the nucleic acid sequence and/or amino acid sequence of the protein comprises the sequence presented in SEQ ID NO:41 and SEQ ID NO:42 respectively. This protein is also known as "CT341" from *C. trachomatis*. In another embodiment, the nucleic acid sequence and/or amino acid sequence of the protein comprises the sequence presented in SEQ ID NO:43 and SEQ ID NO:44 respectively. This protein is also known as "CT716" from *C. trachomatis*. In another embodiment, the nucleic acid sequence and/or amino acid sequence of the protein comprises the sequence presented in SEQ ID NO:45 and SEQ ID NO:46 respectively. This protein is also known as "CT745" from *C. trachomatis*. In another embodiment, the nucleic acid sequence and/or amino acid sequence of the protein comprises the sequence presented in SEQ ID NO:47 and SEQ ID NO:48, respectively. This protein is also known as "CT387" from *C. trachomatis* and is annotated as a hypothetical protein. In another embodiment, the nucleic acid and/or amino acid sequence of the protein comprises the sequence presented in SEQ ID NO:49 and SEQ ID NO:50, respectively. This protein is also known as "CT812" from *C. trachomatis* and is annotated as a polymorphic outer membrane protein. In another embodiment, the nucleic acid and/or amino acid sequence of the protein comprises the sequence presented in SEQ ID NO:51 and SEQ ID NO:52, respectively. This protein is also known as "CT869" from *C. trachomatis* and is annotated as a polymorphic outer membrane protein. In another embodiment, the nucleic acid and/or amino acid sequence of the protein comprises the sequence presented in SEQ ID NO:53 and SEQ ID NO:54, respectively. This protein is also known as "CT166" from *C. trachomatis*. In another embodiment, the nucleic acid and/or amino acid sequence of the protein comprises the sequence presented in SEQ ID NO:55 and SEQ ID NO:56, respectively. This protein is also known as "CT175" from *C. trachomatis*. In another embodiment, the nucleic acid and/or amino acid sequence of the protein comprises the sequence presented in SEQ ID NO:155 and SEQ ID NO:156, respectively. This protein is also known as "CT163" from *C. trachomatis*. In another embodiment, the nucleic acid and/or amino acid sequence of the protein comprises the sequence presented in SEQ ID NO:159 and SEQ ID NO:160, respectively. This protein is also known as "CT214" from *C. trachomatis*. In another embodiment, the nucleic acid and/or amino acid sequence of the protein comprises the sequence presented in SEQ ID NO:163 and SEQ ID NO:164, respectively. This protein is also known as "CT721" from *C. trachomatis*. In another embodiment, the nucleic acid and/or amino acid sequence of the protein comprises the sequence presented in SEQ ID NO:167 and SEQ ID NO:168, respectively. This protein is also known as "CT127" from *C. trachomatis*.

In some embodiments, the protein is a variant of a protein as described above. For example, the protein may comprise one or more mutations (for example, 1, 2, 3, 4, 5, 6, 7, 8, 9, 10 or more mutations) in the sequence of SEQ ID NO: 2, 4, 6, 8, 10, 12, 14, 16, 18, 19, 20, 21, 22, 23, 24, 40, 42, 44, 46, 48, 50, 52, 54, 56, 136, 140, 156, 160, 164 or 168, for example, in the sequence of SEQ ID NO: 2, 4, 6, 8, 10, 12, 14, 16, 40, 42, 44, or 46. Preferred mutations are those which do not cause a significant conformational change in the protein such that the protein of the invention retains the ability to elicit an immune response against the wild-type *Chlamydia* protein. The proteins having the sequences presented in SEQ ID NO: 2, 4, 6, 8, 10, 12, 14, 16, 40, 42, 44, 46, 48, 50, 52, 54 and 56 are the wild-type proteins.

In some embodiments, the one or more mutations are present in the N-terminal portion of the protein, for example, between residues 1 and 20 of the protein, between residues 21 and 40, between residues 41 and 60, between residues 1 and 60 or between residues 1 and 40 of the protein. In some embodiments, the one or more mutations are present in the C-terminal portion of the protein, for example, between the C-terminal 20 residues of the protein, between residues 21 and 40 from the C-terminus, between residues 41 and 60 from the C-terminus; between residues 1 and 60 from the C-terminus or between residues 1 and 40 from the C-terminus of the protein.

Preferably, the amino acid sequences contain fewer than twenty mutations (e.g. 19, 18, 17, 16, 15, 14, 13, 12, 11, 10, 9, 8, 7, 6, 5, 4, 3, 2 or 1). Each mutation preferably involves a single amino acid and is preferably a point mutation. The mutations may each independently be a substitution, an insertion or a deletion. Preferred mutations are single amino acid substitutions. The proteins may also include one or more (e.g. 1, 2, 3, 4, 5, 6, 7, 8, 9, etc.) single amino acid deletions relative to the *Chlamydia* sequences. The proteins may also include one or more (e.g. 1, 2, 3, 4, 5, 6, 7, 8, 9, etc.) insertions (e.g. each of 1, 2, 3, 4 or 5 or more amino acids) relative to the *Chlamydia* sequences. Deletions, substitutions or insertions may be at the N-terminus and/or C-terminus, or may be between the two termini. Thus a truncation is an example of a deletion. Truncations may involve deletion of up to 40 (or more) amino acids at the N-terminus and/or C-terminus (for example, 1-10, 11-40, 41-70, 71-100 or more amino acids).

Amino acid substitutions may be to any one of the other nineteen naturally occurring amino acids. Preferably, a substitution mutation is a conservative substitution. Alternatively, a substitution mutation is a non-conservative substitution. A conservative substitution is commonly defined as a substitution introducing an amino acid having sufficiently similar chemical properties, e.g. having a related side chain (e.g. a basic, positively charged amino acid should be replaced by another basic, positively charged amino acid), in order to preserve the structure and the biological function of the molecule. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Further examples of conversative substitutions that may be used in the invention are presented in Table 1.

TABLE 1

| Amino Acid | Synonymous Groups | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

Examples of non-conservative substitutions that may be used in the invention include the substitution of an uncharged polar amino acid with a nonpolar amino acid, the substitution of a nonpolar amino acid with an uncharged polar amino acid, the substitution of an acidic amino acid with a basic amino acid and the substitution of a basic amino acid with an acidic amino acid.

Mutations may also be introduced to improve stability, e.g., the insertion of disulphide bonds (van den Akker et al. Protein Sci., 1997, 6:2644-2649). For example, the protein may comprise an amino acid sequence having sequence identity to the amino acid sequence of any one of SEQ ID NOs: 2, 4, 6, 8, 10, 12, 14, 16, 18, 19, 20, 21, 22, 23, 24, 40, 42, 44, 46, 48, 50, 52, 54, 56, 136, 140, 156, 160, 164 and 168, for example, of any one of SEQ ID NOs: 2, 4, 6, 8, 10, 12, 14, 16, 40, 42, 44 and 46. The degree of sequence identity is preferably greater than 50% (e.g. 60%, 70%, 80%, 90%, 95%, 97%, 98%, 99% or more). These proteins include homologs, orthologs, allelic variants and functional mutants. Identity between proteins is preferably determined by the Smith-Waterman homology search algorithm as implemented in the MPSRCH program (Oxford Molecular), using an affine gap search with parameters gap open penalty=12 and gap extension penalty=1.

The *Chlamydia* protein of the invention may comprise one or more amino acid derivatives. By "amino acid derivative" is intended an amino acid or amino acid-like chemical entity other than one of the 20 genetically encoded naturally occurring amino acids. In particular, the amino acid derivative may contain substituted or non-substituted, linear, branched, or cyclic alkyl moieties, and may include one or more heteroatoms. The amino acid derivatives can be made de novo or obtained from commercial sources (Calbiochem-Novabiochem AG; Sachem).

In some embodiments, the variant protein is a homologous protein from *C. pneumoniae, C. psittaci, C. pecorum, C. muridarum* or *C. suis.*

The invention further provides a protein comprising or consisting of a fragment of a protein comprising or consisting of the amino acid sequence of any of SEQ ID NOs: 2, 4, 6, 8, 10, 12, 14, 16, 18, 19, 20, 21, 22, 23, 24, 40, 42, 44, 46, 48, 50, 52, 54, 56, 136, 140, 156, 160, 164 or 168, for example, of any one of SEQ ID NO: 2, 4, 6, 8, 10, 12, 14, 16, 40, 42, 44 or 46, or a fragment of a variant thereof. The fragment should comprise at least n consecutive amino acids from the protein and, depending on the particular sequence, n is 6 or more (e.g. 8, 11, 16, 31, 51, 76, 121, 181, 231, 281, 331, 381, 431, 440, 445, 446, 481, 531, 581, 631, 681, 731, 781, 801, 806, 808 or more). The fragment is n-1 amino acids or less in length, wherein n=the number of amino acids in the full length protein (e.g. n-5, n-20, n-50, n-110, n-180, n-240, n-310, n-380, n-445, n-515, n-595, n-675, n-745, n-785, n-800 amino acids or less in length). Preferably the fragment comprises one or more epitopes from the protein. Preferably, one or more of the epitopes is an MHC class II epitope, for example, a CD4+ T cell epitope. In some embodiments, the fragment comprises or consists of the amino acid sequence of any of SEQ ID NOs 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 142, 146, 150, 154, 158, 162, 166 and 170. In some embodiments, the invention provides a protein comprising or consisting of a fragment of a protein comprising or consisting of the amino acid sequence recited in SEQ ID NO: 122. Table 3 below shows which fragments correspond to which full length sequences.

TABLE 3

| Annotation | SEQ ID NO. for full length sequence | SEQ ID NO. for fragment |
|---|---|---|
| CT733 | 1 | 63 |
| CT733 | 2 | 64 |
| CT153 | 3 | 65 |
| CT153 | 4 | 66 |
| CT601 | 5 | 67 |
| CT601 | 6 | 68 |
| CT279 | 7 | 69 |
| CT279 | 8 | 70 |
| CT443 | 9 | 71 |
| CT443 | 10 | 72 |
| CT372 | 11 | 73 |
| CT372 | 12 | 74 |
| CT456 | 13 | 75 |
| CT456 | 14 | 76 |
| CT381 | 15 | 77 |
| CT381 | 16 | 78 |
| CT043 | 17 | 79 |
| CT043 | 18 | 80 |
| CT711 | 19 | 81 (nucleotide); 82 (protein) |
| CT114 | 20 | 83 (nucleotide); 84 (protein) |
| CT480 | 21 | 85 (nucleotide); 86 (protein) |

TABLE 3-continued

| Annotation | SEQ ID NO. for full length sequence | SEQ ID NO. for fragment |
|---|---|---|
| CT089 | 22 | 87 (nucleotide); 88 (protein) |
| CT734 | 23 | 89 (nucleotide); 90 (protein) |
| CT016 | 24 | 91 (nucleotide); 92 (protein) |
| TC0551 (CT279) | 25 | 93 |
| TC0551 (CT279) | 26 | 94 |
| TC0651 (CT372) | 27 | 95 |
| TC0651 (CT372) | 28 | 96 |
| TC0727 (CT443) | 29 | 97 |
| TC0727 (CT443) | 30 | 98 |
| TC0313 (CT043) | 31 | 99 |
| TC0313 (CT043) | 32 | 100 |
| TC0890 (CT601) | 33 | 101 |
| TC0890 (CT601) | 34 | 102 |
| TC0741 (CT456) | 35 | 103 |
| TC0741 (CT456) | 36 | 104 |
| TC0660 (CT381) | 37 | 105 |
| TC0660 (CT381) | 38 | 106 |
| CT255 | 39 | 107 |
| CT255 | 40 | 108 |
| CT341 | 41 | 109 |
| CT341 | 42 | 110 |
| CT716 | 43 | 111 |
| CT716 | 44 | 112 |
| CT745 | 45 | 113 |
| CT745 | 46 | 114 |
| CT387 | 47 | 115 |
| CT387 | 48 | 116 |
| CT812 | 49 | 117 (mature full length); 119 (N-terminal fragment); 121 (C-terminal fragment) |
| CT812 | 50 | 118 (mature full length) 120 (N-terminal fragment) 122 (C-terminal fragment) |
| CT869 | 51 | 123 |
| CT869 | 52 | 124 |
| CT166 | 53 | 125 |
| CT166 | 54 | 126 |
| CT175 | 55 | 127 |
| CT175 | 56 | 128 |
| TC0666 (CT387) | 57 | 129 |
| TC0666 (CT387) | 58 | 130 |
| TC0197 | 59 | 131 |
| TC0197 | 60 | 132 |
| TC0261 | 61 | 133 |
| TC0261 | 62 | 134 |
| CT600 | 135 | 137 |
| CT600 | 136 | 138 |
| CT823 | 139 | 141 |
| CT823 | 140 | 142 |
| TC0106 | 143 | 145 |
| TC0106 | 144 | 146 |
| TC0431 | 147 | 149 |
| TC0431 | 148 | 150 |
| TC0210 | 151 | 153 |
| TC0210 | 152 | 154 |
| CT163 | 155 | 157 |
| CT163 | 156 | 158 |
| CT214 | 159 | 161 |
| CT214 | 160 | 162 |
| CT721 | 163 | 165 |
| CT721 | 164 | 166 |
| CT127 | 167 | 169 |
| CT127 | 168 | 170 |

The protein of the invention, for example the variant protein or the fragment, is preferably immunogenic.

The term "immunogenic" in the context of "an immunogenic variant" and "immunogenic fragment", is used to mean that the protein is capable of eliciting an immune response, such as a cell-mediated and/or an antibody response, against the wild-type *Chlamydia* protein from which it is derived, for example, when used to immunise a subject (preferably a mammal, more preferably a human or a mouse). For example, the protein of the invention (for example, the variant or fragment) is preferably capable of stimulating in vitro CD4+

IFNγ+ cells in splenocytes purified from mice infected with live *C. trachomatis* to a level comparable with the wild-type *Chlamydia* protein. The protein of the invention preferably retains the ability to elicit antibodies that recognise the wild-type protein. For example, the protein of the invention preferably elicits antibodies that can bind to, and preferably neutralise the activity of, the wild-type protein. In a further embodiment, the protein of the invention is capable of eliciting antibodies that are capable of neutralising *Chlamydia* infectivity and/or virulence. In some embodiments, the antibodies are able to cross-react with the protein of the invention and the wild-type protein, but with no other homologous protein (e.g. from another *Chlamydia* species). In other embodiments, the antibodies are cross-reactive with the wild-type protein and with homologous proteins from other *Chlamydia* species. In some embodiments, the antibodies are cross-reactive with the wild-type protein and with homologous protein from other organisms (for example from *E. coli* or *H. influenzae*). Mice immunized with the protein of the invention and the wild-type *Chlamydia* protein preferably show similar antigen-specific antibody titers. Antibody titres and specificities can be measured using standard methods available in the art. Other methods of testing the immunogenicity of proteins are also well known in the art.

For example, the variant or fragment is preferably capable of eliciting an immune response, such as a cell-mediated and/or an antibody response, against the wild-type *Chlamydia* protein. In one embodiment the fragment is capable of stimulating in vitro CD4+ IFNγ+ cells in splenocytes purified from mice infected with live *C. trachomatis* to a level comparable with the wild-type *Chlamydia* protein and/or retains the ability to elicit antibodies that recognise the wild-type protein.

Preferably, the variant or the fragment is capable of inducing a specific CD4-Th1 cell mediated response against the wild type *Chlamydia* protein.

The proteins of the invention can, of course, be prepared by various means (e.g. recombinant expression, purification from native host, purification from cell culture, chemical synthesis etc.) and in various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). Generally, the recombinant fusion proteins of the present invention are prepared as a GST-fusion protein and/or a His-tagged fusion protein.

The proteins of the invention are preferably prepared in purified or substantially pure form (i.e. substantially free from host cell proteins and/or other *Chlamydia* proteins), and are generally at least about 50% pure (by weight), and usually at least about 90% pure, i.e. less than about 50%, and more preferably less than about 10% (e.g. 5%) of a composition is made up of other expressed polypeptides. Thus the antigens in the compositions are separated from the whole organism with which the molecule is expressed.

Whilst expression of the proteins of the invention may take place in *Chlamydia*, the invention preferably utilises a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

The term "polypeptide" or "protein" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence —P-Q- or -Q-P—, wherein: —P— is an amino acid sequence as defined above and -Q- is not a sequence as defined above i.e. the invention provides fusion proteins. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more), maltose-binding protein, or glutathione-S-transferase (GST).

Proteins of the invention may be attached to a solid support. They may comprise a detectable label (e.g. a radioactive or fluorescent label, or a biotin label).

Antibodies

The proteins of the invention induce antibodies that may be used as a vaccine capable of neutralising the activity of infectious EB. The antibodies may alternatively be used for the diagnosis of *Chlamydia* infection. Thus, the invention provides antibodies for use in the treatment, prevention or diagnosis of *Chlamydia* infection. Preferably, the infection is by *C. trachomatis*, but may alternatively be by *C. psittaci, C. pecorum, C. muridarum* or *C. suis*.

The term "antibody" includes intact immunoglobulin molecules, as well as fragments thereof which are capable of binding an antigen. These include hybrid (chimeric) antibody molecules (Winter et al., (1991) *Nature* 349:293-99; U.S. Pat. No. 4,816,567); F(ab')2 and F(ab) fragments and Fv molecules; non-covalent heterodimers (Inbar et al., (1972) *Proc. Natl. Acad. Sci. U.S.A.* 69:2659-62; Ehrlich et al., (1980) *Biochem* 19:4091-96); single-chain Fv molecules (sFv) (Huston et al., (1988) Proc. Natl. Acad. Sci. U.S.A. 85:5897-83); dimeric and trimeric antibody fragment constructs; minibodies Pack et al., (1992) *Biochem* 31, 1579-84; Cumber et al., (1992) *J. Immunology* 149B, 120-26); humanized antibody molecules (Riechmann et al., (1988) *Nature* 332, 323-27; Verhoeyan et al., (1988) *Science* 239, 1534-36; and GB 2,276, 169); and any functional fragments obtained from such molecules, as well as antibodies obtained through non-conventional processes such as phage display. Preferably, the antibodies are monoclonal antibodies. Methods of obtaining monoclonal antibodies are well known in the art. Humanised or fully-human antibodies are preferred.

The antibodies may be polyclonal or monoclonal and may be produced by any suitable means. The antibody may include a detectable label.

Also provided is a method for preparing antibodies comprising immunising a mammal (such as a mouse or a rabbit) with a protein of the invention and obtaining polyclonal antibodies or monoclonal antibodies by conventional techniques. For example, polyclonal antisera may be obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). Monoclonal antibodies may be prepared using the standard method of Kohler & Milstein [*Nature* (1975) 256:495-96], or a modification thereof, or by any other suitable method.

Nucleic Acids

According to a further aspect, the invention provides a nucleic acid encoding a protein or antibody of the invention. In some embodiments, the nucleic acid sequence encoding a protein of the invention preferably comprises or consists of any one of SEQ ID NOs:1, 3, 5, 7, 9, 11, 13, 15, 17, 39, 41, 43, 45, 47, 49, 51, 53, 55, 135, 139, 155, 159, 163 or 167, for example, of any one of SEQ ID NOs:1, 3, 5, 7, 9, 11, 13, 15, 39, 41, 43 or 45. In some embodiments, the nucleic acid sequence encoding a protein of the invention comprises or consists of any one of SEQ ID NOs: 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131 and 133.

The invention also provides nucleic acid comprising nucleotide sequences having sequence identity to such nucleotide sequences. Identity between sequences is preferably determined by the Smith-Waterman homology search algorithm as described above. Such nucleic acids include those using alternative codons to encode the same amino acid.

The invention also provides nucleic acid which can hybridize to these nucleic acids. Hybridization reactions can be performed under conditions of different "stringency". Conditions that increase stringency of a hybridization reaction of widely known and published in the art (e.g. page 7.52 of Kaplitt, *Nature Genetics* (1994) 6:148). Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art (e.g. see U.S. Pat. No. 5,707,829, *Current Protocols in Molecular Biology* (F. M. Ausubel et al. eds., 1987) Supplement 30, Kaplitt, *Nature Genetics* (1994) 6:148, and WO 94/03622, etc.).

The nucleic acid may be used in hybridisation reactions (e.g. Northern or Southern blots, or in nucleic acid microarrays or 'gene chips') or in amplification reactions (e.g. PCR, SDA, SSSR, LCR, NASBA, TMA) etc.

The invention also provides a nucleic acid comprising sequences complementary to those described above (e.g. for antisense or probing, or for use as primers). In one embodiment, the nucleic acid is complementary to the full length of the nucleic acid described above.

Nucleic acid according to the invention may be labelled e.g. with a radioactive or fluorescent label. This is particularly useful where the nucleic acid is to be used as a primer or probe e.g. in PCR, LCR or TMA.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention can take various forms (e.g. single stranded, double stranded, vectors, primers, probes etc.). Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably prepared in substantially pure form (i.e. substantially free from naturally-occurring nucleic acids, particularly from chlamydial or other host cell nucleic acids), generally being at least about 50% pure (by weight), and usually at least about 90% pure.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The invention provides vectors comprising nucleotide sequences of the invention (e.g. cloning or expression vectors) and host cells transformed with such vectors. Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which are designed to result in the production of a recombinant virus or virus-like particle, or "shuttle vectors", which comprise the attributes of more than one type of vector. Preferred vectors are plasmids.

Also provided is a host cell comprising a nucleic acid of the invention. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention, for example, with a vector of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

For certain embodiments of the invention, nucleic acids are preferably at least 24 nucleotides in length (e.g. 60, 120, 240, 390, 540, 720, 900, 1200, 1320, 1500, 1800, 2100, 2400, 2415 nucleotides or longer).

For certain embodiments of the invention, nucleic acids are preferably at most 2430 nucleotides in length (e.g. 2427, 2394, 2250, 2034, 1450, 1300, 1150, 1000, 850, 700, 500 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

Immunogenic Compositions and Medicaments

The protein, antibody, and/or nucleic acid or medicament may be in the form of a composition. These compositions may be suitable as immunogenic compositions (e.g. vaccines), or as diagnostic reagents.

Preferably, the composition is an immunogenic composition. It is particularly advantageous to use a protein of the invention in an immunogenic composition such as a vaccine. It is also envisaged that the immunogenic composition may comprise a nucleic acid which encodes a protein of the invention such that the protein is generated in vivo.

An immunogenic composition of the invention comprises a protein, antibody, nucleic acid, vector and/or host cell according to the invention. Immunogenic compositions according to the invention may either be prophylactic (i.e. to prevent infection) or therapeutic (i.e. to treat infection), but will typically be prophylactic. Where the immunogenic composition is for prophylactic use, the human is preferably a child (e.g. a toddler or infant) or a teenager; where the immunogenic composition is for therapeutic use, the human is preferably a teenager or an adult. An immunogenic composition intended for children may also be administered to adults e.g. to assess safety, dosage, immunogenicity, etc.

In some embodiments, the immunogenic composition is for treatment or prevention of *Chlamydia* infection or an associated condition (e.g. trachoma, blindness, cervicitis, pelvic inflammatory disease, infertility, ectopic pregnancy, chronic pelvic pain, salpingitis, urethritis, epididymitis, infant pneumonia, patients infected with cervical squamous cell carcinoma, and/or HIV infection, etc.), preferably, *C. trachomatis* infection. The immunogenic composition may be effective against *C. pneumoniae.*

Immunogenic compositions used as vaccines comprise an immunologically effective amount of the protein of the invention, as well as any other components, as needed. By ‘immunologically effective amount’, it is meant that the administration of that amount to an individual, either in a single dose or as part of a series, is effective for treatment or prevention. This amount varies depending upon the health and physical condition of the individual to be treated, age, the taxonomic group of the individual to be treated (e.g. non-human primate, primate, etc.), the capacity of the individual’s immune system to synthesise antibodies, the degree of protection desired, the formulation of the vaccine, the treating doctor’s assessment of the medical situation, and other relevant factors. It is expected that the amount will fall in a relatively broad range that can be determined through routine trials.

Antigens in the composition will typically be present at a concentration of at least 1 μg/ml each.

In general, the concentration of any given antigen will be sufficient to elicit an immune response against that antigen.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In some embodiments, three or more doses are provided (for example, three, four or five) doses. In some embodiments, three doses are given intramuscularly at 2 week-intervals, for example, three doses of 10-20 μg of each protein, at 2 week-intervals, given intramuscularly.

The pH of an immunogenic composition is preferably between 6 and 8, preferably about 7. pH may be maintained by the use of a buffer. The composition may be sterile and/or pyrogen-free. The composition may be isotonic with respect to humans.

Immunogenic compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration.

*Chlamydia* infections affect various areas of the body and so the immunogenic compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The invention also provides a delivery device pre-filled with an immunogenic composition of the invention.

The invention also provides a kit comprising a first component and a second component wherein neither the first component nor the second component is a composition of the invention as described herein, but wherein the first component and the second component can be combined to provide a composition of the invention as described herein. The kit may further include a third component comprising one or more of the following: instructions, syringe or other delivery device, adjuvant, or pharmaceutically acceptable formulating solution.

A composition as described above may alternatively and/or additionally be used for diagnosis of chlamydia infection.

Combinations with Other Antigens

The therapeutic or diagnostic efficiency of a *Chlamydia* antigen may be improved by combination with a different *Chlamydia* antigen. For example, the immunogenicity of a protein of the invention may be improved by comaintion with another protein of the invention or with another known *Chlamydia* antigen. The invention thus includes an immunogenic composition comprising a combination of *Chlamydia* antigens, said combination comprising a protein of the invention in combination with one or more additional *Chlamydia* antigens. The one or more additional *Chlamydia* antigens that are present in the composition may be in the form of a protein or nucleic acid or any other suitable form. A protein of the invention may be combined with one or more (e.g. 2, 3, 4, 5, 6, 7, 8, 9, 10, 15, 20 or more) different proteins of the invention and/or with one or more (e.g. 2, 3, 4, 5, 6, 7, 8, 9, 10, 15, 20 or more) other known *Chlamydia* antigens. For example, an immunogenic composition is provided comprising two or more (e.g. 3, 4, 5, 6, 7, 8, 9, 10, 15, 20 or more) proteins of the invention. The proteins of the invention may alternatively and/or additionally be provided in the composition in the form of their corresponding nucleic acids, vectors, host cells, etc. Also provided is a protein or nucleic acid of the invention for a use as described above, wherein the protein or nucleic acid is for use in combination with one or more additional *Chlamydia* antigens (or their encoding nucleic acids). The one or more additional antigens (e.g. 2, 3, 4, 5, 6, 7 or more additional antigens) may be administered simultaneously, separately or sequentially with the protein or nucleic acid of the invention, for example as a combined preparation.

Likewise, the antibodies of the invention may be used in combination with one or more antibodies specific for one or more additional *Chlamydia* antigens for use in diagnosis of *Chlamydia* infections.

In one embodiment, one or more of the additional *Chlamydia* antigens is selected from the antigens presented in Table 2, or their variants. For example, one or more (for example, all) of the additional antigens are selected from the *Chlamydia trachomatis* antigens listed in Table 2, but may alternatively or additionally be selected from the *Chlamydia pneumoniae* antigens listed in Table 2. In some embodiments, the one or more (for example, all) of the additional antigens are selected from the *Chlamydia trachomatis* antigens and/or *Chlamydia pneumoniae* antigens listed in Table 2 and CT387, CT812, CT869, CT166, CT175, CT163, CT214, CT721 and CT127. In one embodiment, one or more of the one or more additional antigens are selected from CT372, CT443, CT043, CT153, CT279, CT601, CT711, CT114, CT480, CT456, CT381, CT089, CT734, CT016, CT600, CT823, CT387, CT812, CT869, CT166, CT175, CT163, CT214, CT721 and CT127 (or their variants), for example, from CT372, CT443, CT043, CT153, CT279, CT601, CT711, CT114, CT480, CT456, CT381, CT089, CT734, CT016, CT600 and CT823. These additional antigens are listed in Table 2 and their sequences are set out in the "Sequences" section that follows Table 2. In one embodiment, one or more proteins of the invention is combined with CT089. In another embodiment, one or more proteins of the invention is combined with CT089 and CT381 (or their variants). In some embodiments, the C-terminal fragment of CT812 "CT812C" (for example, a protein comprising or consisting of the amino acid sequence set out in SEQ ID NO:122 or a fragment or variant thereof) is used instead of full length CT812.

In some embodiments, the following combinations of antigens (or their variants) are used: CT733+CT601, CT733+CT279, CT733+CT443, CT733+CT372, CT733+CT456, CT733+CT381, CT153+CT601, CT153+CT279, CT153+CT443, CT153+CT372, CT153+CT456, CT153+CT381, CT601+CT443, CT601+CT372, CT601+CT456, CT601+CT381, CT279+CT443, CT279+CT372, CT279+CT456, CT279+CT381, CT443+CT372, CT443+CT456, CT443+CT381, CT372+CT456, CT372+CT381, CT387+CT812+CT869, CT387+CT812C+CT869. These combinations may be used in the absence of any other chlamydia antigens or in the presence of one or more additional chlamydia antigens. Particularly preferred combinations are: (i) CT279+CT601; (ii) CT372+CT443; (iii) CT733+CT153; (iv) CT456+CT381; (v) CT279+CT601+CT733+CT153; (vi) CT279+CT601+CT372+CT443; (vii) CT823+CT733+CT043+CT456; (viii) CT387+CT812+CT869; and (ix) CT387+CT812C+CT869 (or their variants).

The human serovariants ("serovars") of *C. trachomatis* are divided into two biovariants ("biovars"). Serovars A-K elicit epithelial infections primarily in the ocular tissue (A-C) or urogenital tract (D-K). Serovars L1, L2 and L3 are the agents of invasive lymphogranuloma venereum (LGV). In some embodiments, one or more of the additional Chlamydial antigens may, for example, be of any of Serovars A-K or L1, L2 or L3. One or more of the additional *Chlamydia* antigens is preferably from *C. trachomatis* serovar D, or from another epidemiologically prevalent serotype.

In some embodiments, one or more of the additional *Chlamydia* antigens is a homologous antigen from *C. pneumoniae, C. psittaci, C. pecorum, C. muridarum* or *C. suis.*

In some embodiments, TC0551 (the *C. muridarum* homologue of CT279) is used in place of the *C. trachomatis* protein. *C. muridarum* is the mouse adapted strain of *Chlamydia trachomatis*. Although *C. muridarum* is not a human pathogen, infection of mice with *C. muridarum* phenotypically mimics many aspects of *C. trachomatis* infection in humans and is frequently used to measure immunoprotective responses against *C. trachomatis*. In some embodiments, TC0890 (the *C. muridarum* homologue of CT601) is used in place of the *C. trachomatis* protein. In some embodiments, TC0651 (the *C. muridarum* homologue of CT372) is used in place of the *C. trachomatis* protein. In some embodiments, TC0727 (the *C. muridarum* homologue of CT443) is used in place of the *C. trachomatis* protein. In some embodiments, TC0106 (the *C. muridarum* homologue of CT733) is used in place of the *C. trachomatis* protein. In some embodiments, TC0431 (the *C. muridarum* homologue of CT153) is used in place of the *C. trachomatis* protein. In some embodiments, TC0660 (the *C. muridarum* homologue of CT381) is used in place of the *C. trachomatis* protein. In some embodiments, TC0741 (the *C. muridarum* homologue of CT456) is used in place of the *C. trachomatis* protein. In some embodiments, TC0210 (the *C. muridarum* homologue of CT823) is used in place of the *C. trachomatis* protein. In some embodiments, TC0666 (the *C. muridarum* homologue of CT387) is used in place of the *C. trachomatis* protein. TC0666 is annotated as a hypothetical protein. In some embodiments, TC0197 (the *C. muridarum* homologue of CT812) is used in place of the *C. trachomatis* protein. TC0197 is annotated as polymorphic membrane protein D family protein. In some embodiments, TC0261 (the *C. muridarum* homologue of CT869) is used in place of the *C. trachomatis* protein. TC0261 is annotated as polymorphic membrane protein E/F family protein. In some embodiments, TC0313 (the *C. muridarum* homologue of CT043) is used in place of the *C. trachomatis* protein. In some embodiments, TC0889 (the *C. muridarum* homologue of CT600) is used in place of the *C. trachomatis* protein. In some embodiments, TC0210 (the *C. muridarum* homologue of CT823) is used in place of the *C. trachomatis* protein. In some embodiments in which the composition comprises a single *Chlamydia* antigen, the *C. muridarum* homologue is used in place of the single *C. trachomatis* antigen. In some embodiments in which the composition comprises a combination of *Chlamydia* antigens, the *C. muridarum* homologue is used in place of one or more (for example, 1, 2, 3, 4, 5, 6, 7, 8, 9, 10) or all *C. trachomatis* antigens.

Advantageous combinations of the invention are those in which two or more antigens (for example, two, three or four antigens) act synergistically. Thus, the protection against *Chlamydia* achieved by their combined administration exceeds that expected by mere addition of their individual protective efficacy.

In some embodiments, the one or more additional *Chlamydia* antigens may comprise an amino acid sequence: (a) which is a variant of a Table 2 antigen (i.e. has 50% or more identity (e.g. 60%, 65%, 70%, 75%, 80%, 85%, 90%, 91%, 92%, 93%, 94%, 95%, 96%, 97%, 98%, 99%, 99.5% or more) to a sequence presented in Table 2); and/or (b) comprising a fragment of at least 'n' consecutive amino acids of a sequence presented in Table 2 or of a variant of a Table 2 antigen, wherein 'n' is 7 or more (e.g. 8, 10, 12, 14, 16, 18, 20, 25, 30, 35, 40, 50, 60, 70, 80, 90, 100, 150, 200, 250, 350, 450, 550, 650, 750, 780, 800 or more). Preferred fragments of (b) comprise an epitope from a sequence presented in Table 2. Preferably, the epitope is a MHC class II epitope, for example, a CD4+ T cell epitope. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of a sequence presented in Table 2, while retaining at least one epitope of a sequence presented in Table 2. Other fragments omit one or more protein domains. When an additional *Chlamydia* antigen comprises a sequence that is not identical to a complete sequence from Table 2 (e.g. when it comprises a sequence with less than 100% sequence identity thereto, or when it comprises a fragment thereof), it is preferred in each individual instance that the additional *Chlamydia* antigen can elicit an antibody that recognises a protein having the complete sequence from the Table 2 antigen from which it is derived.

In some embodiments, the combination of two or more chlamydia antigens is provided as a combined preparation for simultaneous, separate or sequential administration. The invention also provides a kit comprising a protein of the invention and one or more additional antigens for simultaneous, separate or sequential administration.

The *Chlamydia* antigens used in the invention may be present in the composition as individual separate polypeptides. Alternatively, the combination may be present as a hybrid polypeptide in which two or more (i.e. 2, 3, 4, 5, 6, 7, 8, 9, 10, 11, 12, 13, 14, 15, 16, 17, 18, 19 or 20 or more) of the antigens are expressed as a single polypeptide chain. Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful. Different hybrid polypeptides may be mixed together in a single formulation. Within such combinations, a *Chlamydia trachomatis* antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-{—X-L-}$_n$-B—COOH, wherein: at least one X is an amino acid sequence of a *Chlamydia* protein according to the invention as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, thus aiding cloning and manipulation, and the $(Gly)_4$ tetrapeptide being a typical poly-glycine linker.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

The invention also provides a nucleic acid encoding a hybrid polypeptide of the invention. Furthermore, the invention provides a nucleic acid which can hybridise to this nucleic acid, preferably under "high stringency" conditions (e.g. 65° C. in a 0.1×SSC, 0.5% SDS solution).

Further Components of the Composition

Compositions may thus be pharmaceutically acceptable. They will usually include components in addition to the antigens e.g. they typically include one or more pharmaceutical carrier(s) and/or excipient(s). A thorough discussion of such components is available in *Remington The Science and Practice of Pharmacy.*

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in U.S. Pat. No. 6,355,271). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [WO00/23105].

The adjuvants known as aluminum hydroxide and aluminum phosphate may be used. These names are conventional, but are used for convenience only, as neither is a precise description of the actual chemical compound which is present (e.g. see chapter 9 of *Vaccine Design* . . . (1995) eds. Powell & Newman. ISBN: 030644867X. Plenum). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4$/Al molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of *Vaccine Design* . . . (1995) eds. Powell & Newman. ISBN: 030644867X. Plenum; see also WO90/14837] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsion adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' (WO90/14837, Podda & Del Giudice (2003) *Expert Rev Vaccines* 2:197-203, Podda (2001) *Vaccine* 19: 2673-2680; as described in more detail in Chapter 10 of *Vaccine Design: The Subunit and Adjuvant Approach* (eds. Powell & Newman) Plenum Press 1995 (ISBN 0-306-44867-X) and chapter 12 of *Vaccine Adjuvants: Preparation Methods and Research Protocols* (Volume 42 of *Methods in Molecular Medicine series*). ISBN: 1-59259-083-7. Ed. O'Hagan). The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 m/ml polysorbate 80, 110 m/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (Allison & Byars (1992) *Res Immunol* 143: 519-25) (0.05-1% Thr-MDP, 5% squalane, 2.5% Pluronic L121 and 0.2% polysorbate 80). It can also be used without the Thr-MDP, as in the "AF" adjuvant (Hariharan et al. (1995) *Cancer Res* 55:3486-9) (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm (US-2007/014805.). The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion o US-2007/014805.f squalene, poloxamer 105 and Abil-Care (Suli et al. (2004) *Vaccine* 22(25-26): 3464-9). The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in WO95/11700, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in U.S. Pat. No. 6,080,725, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles (WO2005/097181).

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) (WO2006/113373).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) (Wu et al. (2004) *Antiviral Res.* 64(2):79-83).

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease. Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group (Han et al. (2005) *Impact of Vitamin E on Immune Function and Infectious Diseases in the Aged* at *Nutrition, Immune functions and Health* EuroConference, Paris, 9-10 Jun. 2005). They also have antioxidant properties that may help to stabilize the emulsions (U.S. Pat. No. 6,630,161). A preferred α-tocopherol is DL-α-tocopherol, and the preferred salt of this tocopherol is the succinate. The succinate salt has been found to cooperate with TNF-related ligands in vivo.

C. Saponin Formulations (Chapter 22 of *Vaccine Design* . . . (1995) Eds. Powell & Newman. ISBN: 030644867X. Plenum)

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officinalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (WO96/33739).

Combinations of saponins and cholesterols can be used to form unique particles called immunostimulating complexes (ISCOMs) (chapter 23 of *Vaccine Design* . . . (1995) eds. Powell & Newman. ISBN: 030644867X. Plenum). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in Podda & Del Giudice (2003) *Expert Rev Vaccines* 2:197-203; Podda (2001) *Vaccine* 19: 2673-2680; *Vaccine Design: The Subunit and Adjuvant Approach* (eds. Powell & Newman) Plenum Press 1995 (ISBN 0-306-44867-X); *Vaccine Adjuvants: Preparation Methods and Research Protocols* (Volume 42 of *Methods in Molecular Medicine* series). ISBN: 1-59259-083-7. Ed. O'Hagan; Allison & Byars (1992) *Res Immunol* 143:519-25; Hariharan et al. (1995) *Cancer Res* 55:3486-9; US-2007/014805; Suli et al. (2004) *Vaccine* 22(25-26):3464-9; WO95/11700; U.S. Pat. No. 6,080,725; WO2005/097181; WO2006/113373; Han et al. (2005) *Impact of Vitamin E on Immune Function and Infectious Diseases in the Aged* at *Nutrition, Immune functions and Health* EuroConference, Paris, 9-10 Jun. 2005; U.S. Pat. No. 6,630,161; U.S. Pat. No. 5,057,540; WO96/33739; EP-A-0109942; and WO96/11711. Optionally, the ISCOMS may be devoid of additional detergent (WO00/07621).

A review of the development of saponin based adjuvants can be found in Barr et al. (1998) *Advanced Drug Delivery Reviews* 32:247-271 and Sjolanderet et al. (1998) *Advanced Drug Delivery Reviews* 32:321-338.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in Niikura et al. (2002) *Virology* 293:273-280; Lenz et al. (2001) *J Immunol* 166:5346-5355; Pinto et al. (2003) *J Infect Dis* 188:327-338; Gerber et al. (2001) *J Virol* 75:4752-4760; WO03/024480 and WO03/024481. Virosomes are discussed further in, for example, Gluck et al. (2002) *Vaccine* 20:B10-B16.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in EP-A-0689454. Such "small particles" of 3dMPL are small enough to be sterile filtered through a 0.22 μm membrane (U.S. Pat. No. 6,630,161). Other non-toxic LPS derivatives include monophosphoryl lipid A mimics, such as aminoalkyl glucosaminide phosphate derivatives e.g. RC-529 (Johnson et al. (1999) *Bioorg Med Chem Lett* 9:2273-2278; and Evans et al. (2003) *Expert Rev Vaccines* 2:219-229).

Lipid A derivatives include derivatives of lipid A from *Escherichia coli* such as OM-174. OM-174 is described for example in Meraldi et al. (2003) *Vaccine* 21:2485-2491 and Pajak et al. (2003) *Vaccine* 21:836-842.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. Kandimalla et al. (2003) *Nucleic Acids Research* 31:2393-2400, WO02/26757 and WO99/62923 disclose possible analog substitutions e.g. replacement of guanosine with 2'-deoxy-7-deazaguanosine. The adjuvant effect of CpG oligonucleotides is further discussed in Krieg (2003) *Nature Medicine* 9:831-835; McCluskie et al. (2002) *FEMS Immunology and Medical Microbiology* 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT (Kandimalla et al. (2003) *Biochemical Society Transactions* 31 (part 3):654-658). The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) *J Immunol* 170:4061-4068; Krieg (2002) *Trends Immunol* 23:64-65; and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Gluck et al. (2002) *Vaccine* 20:B10-B16; Kandimalla et al. (2003) *BBRC* 306:948-953; Bhagat et al. (2003) *BBRC* 300:853-861; and WO03/035836.

A useful CpG adjuvant is CpG7909, also known as ProMune™ (Coley Pharmaceutical Group, Inc.). Another is CpG1826. As an alternative, or in addition, to using CpG sequences, TpG sequences can be used (WO01/22972), and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in Pajak et al. (2003) *Vaccine* 21:836-842), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in Pajak et al. (2003) *Vaccine* 21:836-842), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC-31™ (Schellack et al. (2006) *Vaccine* 24:5461-72). Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC) 13-3'. The polycationic polymer may be a peptide comprising 11-mer amino acid sequence KLKLLLLLKLK (SEQ ID NO:171).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in Beignon et al. (2002) *Infect Immun* 70:3012-3019; Pizza et al. (2001) *Vaccine* 19:2534-2541; Pizza et al. (2000) *Int J Med Microbiol* 290:455-461; Scharton-Kersten et al. (2000) *Infect Immun* 68:5306-5313; Ryan et al. (1999) *Infect Immun* 67:6270-6280; Partidos et al. (1999) *Immunol Lett* 67:209-216; Peppoloni et al. (2003) *Expert Rev Vaccines* 2:285-293; and Pine et al. (2002) *J Control Release* 85:263-270.

A useful CT mutant is or CT-E29H (Tebbey et al. (2000) *Vaccine* 18:2723-34). Numerical reference for amino acid substitutions is preferably based on the alignments of the A and B subunits of ADP-ribosylating toxins set forth in Domenighini et al. (1995) *Mol Microbiol* 15:1165-1167, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 (WO99/40936), etc.) (WO99/44636), interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres (Singh et al. (2001) *J Cont Release* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO99/27960).

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of *Vaccine Design* . . . (1995) eds. Powell & Newman. ISBN: 030644867X. Plenum.)

Examples of liposome formulations suitable for use as adjuvants are described in U.S. Pat. No. 6,090,406; U.S. Pat. No. 5,916,588; and EP-A-0626169.

J. Polyoxyethylene Ether and Polyoxyethylene Ester Formulations

Adjuvants suitable for use in the invention include polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes

A phosphazene, such as poly[di(carboxylatophenoxy) phosphazene] ("PCPP") as described, for example, in Andrianov et al. (1998) *Biomaterials* 19:109-115 and Payne et al. (1998) *Adv Drug Delivery Review* 31:185-196, may be used.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquimod ("R-837") (U.S. Pat. No. 4,680,338; U.S. Pat. No. 4,988,815), Resiquimod ("R-848") (WO92/15582), and their analogs; and salts thereof (e.g. the hydrochloride salts). Further details about immunostimulatory imidazoquinolines can be found in Stanley (2002) *Clin Exp Dermatol* 27:571-577; Wu et al. (2004) *Antiviral Res.* 64(2):79-83; Vasilakos et al. (2000) *Cell Immunol.* 204(1):64-74; U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293; and Jones (2003) *Curr Opin Investig Drugs* 4:214-218.

N. Substituted Ureas

Substituted ureas useful as adjuvants include compounds of formula I, II or III, or salts thereof:

I

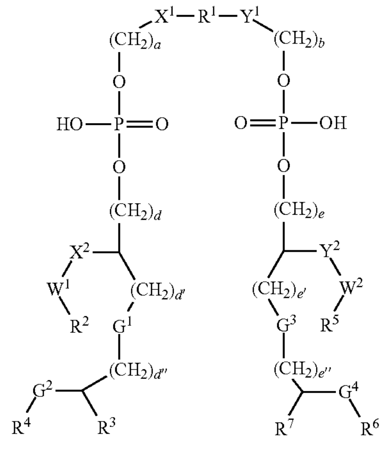

-continued
II
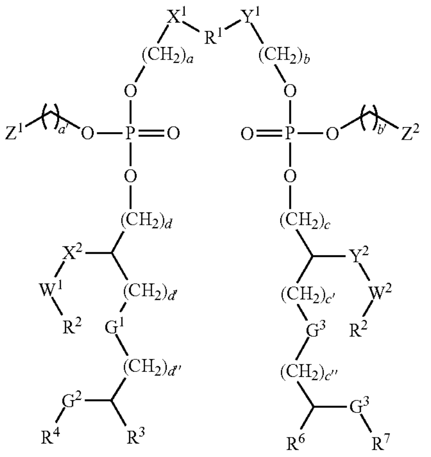
-continued
III
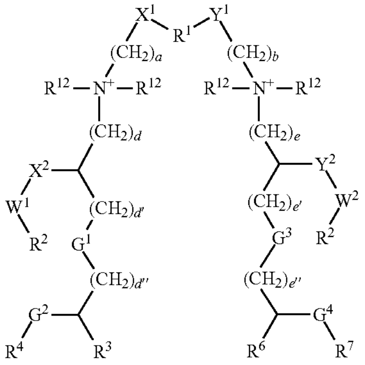
as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:
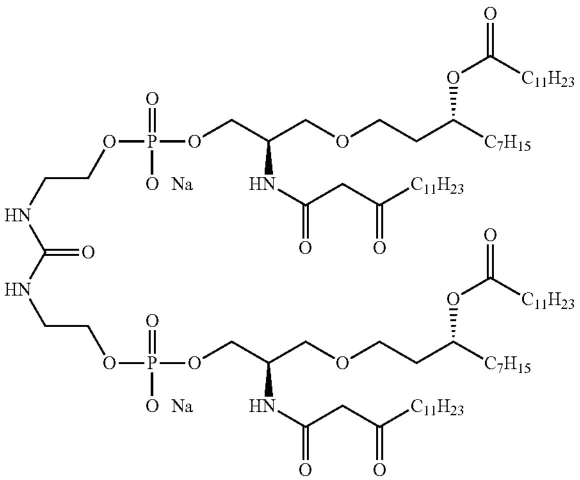
ER804057
ER-803022:
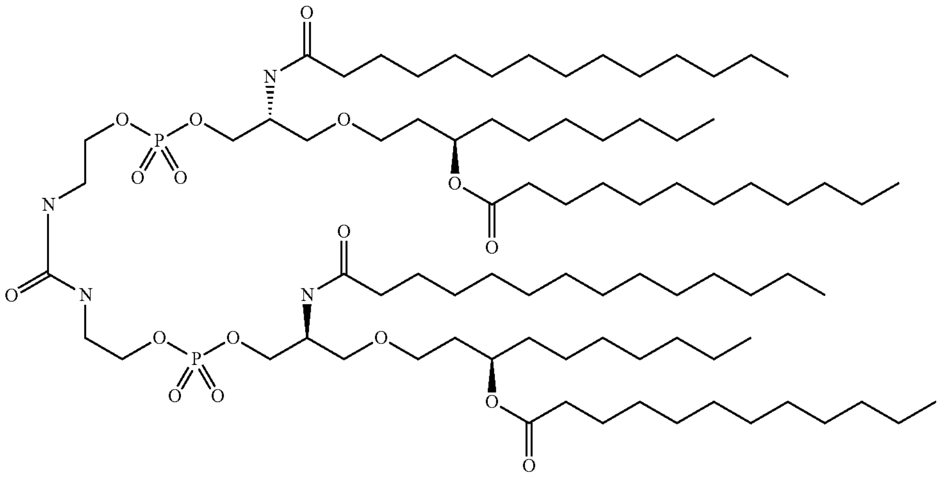

O. Further Adjuvants

Further adjuvants that may be used with the invention include:

An aminoalkyl glucosaminide phosphate derivative, such as RC-529 (Johnson et al. (1999) *Bioorg Med Chem Lett* 9:2273-2278; Evans et al. (2003) *Expert Rev Vaccines* 2:219-229)

A thiosemicarbazone compound, such as those disclosed in WO2004/060308. Methods of formulating, manufacturing, and screening for active compounds are also described in Bhagat et al. (2003) *BBRC* 300:853-861. The thiosemicarbazones are particularly effective in the stimulation of human peripheral blood mononuclear cells for the production of cytokines, such as TNF-α.

A tryptanthrin compound, such as those disclosed in WO2004/064759. Methods of formulating, manufacturing, and screening for active compounds are also described in WO03/035836. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

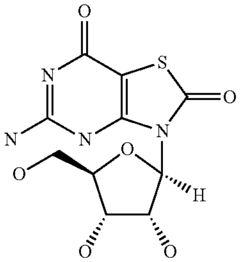 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in U.S. Pat. No. 6,924,271, US2005/0070556 and U.S. Pat. No. 5,658,731, oxoribine (7-allyl-8-oxoguanosine) (U.S. Pat. No. 5,011,828).

Compounds disclosed in WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,605,617, WO02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Compounds containing lipids linked to a phosphate-containing acyclic backbone, such as the TLR4 antagonist E5564 (Wong et al. (2003) *J Clin Pharmacol* 43(7):735-42; US2005/0215517).

A polyoxidonium polymer (Dyakonova et al. (2004) Int Immunopharmacol 4(13):1615-23; FR-2859633) or other N-oxidized polyethylene-piperazine derivative.

Methyl inosine 5'-monophosphate ("MIMP") (Signorelli & Hadden (2003) *Int Immunopharmacol* 3(8):1177-86).

A polyhydroxlated pyrrolizidine compound (WO2004/064715), such as one having formula:

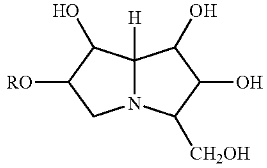

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide (De Libero et al, *Nature Reviews Immunology,* 2005, 5: 485-496; U.S. Pat. No. 5,936,076; Oki et al. *J. Clin. Investig.,* 113: 1631-1640; US2005/0192248; Yang et al, *Angew. Chem. Int. Ed.,* 2004, 43: 3818-3822; WO2005/102049; Goff et al, *J. Am. Chem., Soc.,* 2004, 126: 13602-13603; WO03/105769) e.g. α-galactosylceramide), phytosphingosine-containing α-glycosylceramides, OCH, KRN7000 [(2S, 3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin (Cooper (1995) *Pharm Biotechnol* 6:559-80) or derivative thereof, such as algammulin.

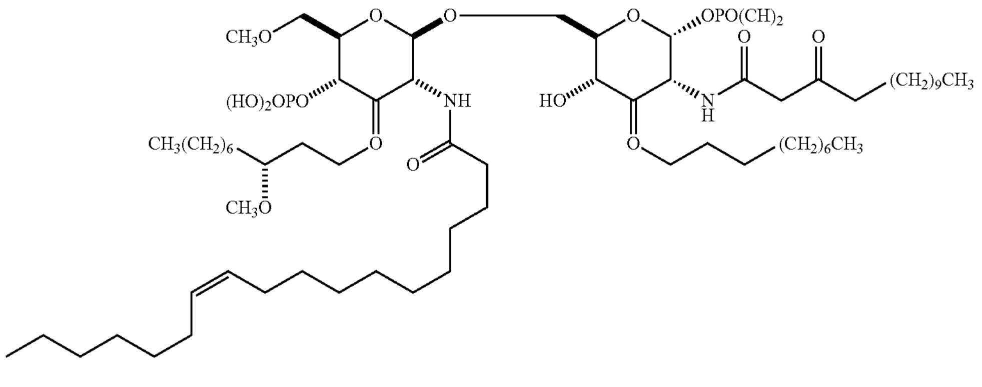

Adjuvant Combinations

The invention may also comprise combinations of one or more of the adjuvants identified above. For example, the following adjuvant compositions may be used in the invention: (1) a saponin and an oil-in-water emulsion (WO99/11241); (2) a saponin (e.g. QS21)+a non-toxic LPS derivative (e.g. 3dMPL) (WO94/00153); (3) a saponin (e.g. QS21)+a non-toxic LPS derivative (e.g. 3dMPL)+a cholesterol; (4) a saponin (e.g. QS21)+3dMPL+IL-12 (optionally+a sterol) (WO98/57659); (5) combinations of 3dMPL with, for example, QS21 and/or oil-in-water emulsions (European patent applications 0835318, 0735898 and 0761231); (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL). In some embodiments a combination of a toxin (e.g. LTK63) and an immunostimulatory oligonucleotide (e.g. CpG) is used. In some embodiments, a combination of an emulsion (e.g. montanide) and an immunostimulatory oligonucleotide (e.g. CpG) is used.

Other substances that act as immunostimulating agents are disclosed in chapter 7 of *Vaccine Design*, (1995) eds. Powell & Newman. ISBN: 030644867X. Plenum.

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminium phosphate and 3dMPL may be used.

To improve thermal stability, a composition may include a temperature protective agent. This component may be particularly useful in adjuvanted compositions (particularly those containing a mineral adjuvant, such as an aluminium salt). As described in WO2006/110603, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

The invention provides an immunogenic composition comprising: (i) one or more proteins of the invention; and (ii) a temperature protective agent. This composition may be formed by mixing (i) an aqueous composition comprising one or more proteins of the invention, with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising one or more proteins of the invention, with (ii) a liquid composition comprising the temperature protective agent. Thus component (ii) can be used to reconstitute component (i).

The compositions of the invention may elicit either or both of a cell mediated immune response and a humoral immune response. This immune response will preferably induce long lasting (e.g. neutralising) antibodies and a cell mediated immunity that can quickly respond upon exposure to chlamydia.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFNγ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFNγ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune resonse will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response. Preferably, the immune response includes an increase in the production of IgG1 and/or IgG2 and/or IgGA.

The invention is preferably used to elicit systemic and/or mucosal immunity. The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Methods of Treatment, and Administration of the Vaccine

The invention also provides a method for raising an immune response in a mammal comprising the step of administering an effective amount of a protein, antibody, nucleic acid, vector, host cell or composition of the invention. The immune response is preferably protective and preferably involves antibodies and/or cell-mediated immunity. The method may raise a booster response.

The invention also provides a protein or combination, as defined above, for use as a medicament e.g. for use in raising an immune response in a mammal.

The invention also provides the use of a protein or combination of the invention in the manufacture of a medicament for raising an immune response in a mammal. By raising an immune response in the mammal by these uses and methods, the mammal can be protected against *Chlamydia* infection. More particularly, the mammal may be protected against *Chlamydia trachomatis*. The invention is effective against *Chlamydia* of various different serotypes, but can be particularly useful in protecting against disease resulting from *Chlamydia* infection by strains in serovar D.

Thus, according to a further aspect, the invention also provides a nucleic acid, protein, antibody, vector or host cell according to the invention for use as a medicament (e.g. a vaccine) or a diagnostic reagent. In one embodiment, the protein, nucleic acid or antibody is used for treatment, prevention or diagnosis of *Chlamydia* infection (preferably *C. trachomatis*) in a mammal. The invention also provides a method of treating, preventing of diagnosing *Chlamydia* infection (preferably, *C. trachomatis* infection) in a patient (preferably a mammal), comprising administering a therapeutically effective amount of a nucleic acid, protein or antibody of the invention.

Preferably, the nucleic acid, protein or antibody according to the invention is for treatment or prevention of *Chlamydia* infection or an associated condition (e.g. trachoma, blindness, cervicitis, pelvic inflammatory disease, infertility, ectopic pregnancy, chronic pelvic pain, salpingitis, urethritis, epididymitis, infant pneumonia, cervical squamous cell carcinoma, etc.), preferably, *C. trachomatis* infection. The immunogenic composition may additionally or alternatively be effective against *C. pneumoniae.*

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Thus a human patient may be less than 1 year old, 1-5 years old, 5-15 years old, 15-55 years old, or at least 55 years old. Preferred patients for receiving the vaccines are people going through puberty, teenagers, sexually active people, the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a human papillomavirus vaccine such as Cervarix™ or Gardasil™; a tetanus, diphtheria and acellular pertussis vaccine such as TDaP, DTaP or Boostrix™; a rubella vaccine such as MMR; or a tubercolosis vaccine such as the BCG. Examples of other vaccines that the vaccine produced by the invention may be administered at substantially the same time as are a measles vaccine, a mumps vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

In a preferred embodiment, the protein of the invention is used to elicit antibodies that are capable of neutralising the activity of the wild type *Chlamydia* protein, for example, of one or more of wild-type *Chlamydia* CT733, CT153, CT601, CT279, CT443, CT372, CT456, CT381, CT255, CT341, CT716, CT745, CT387, CT812, CT869, CT166, CT175, CT163, CT214, CT721, CT127, CT043, CT600 and/or CT823 for example, of one or more of wild-type *Chlamydia* CT733, CT153, CT601, CT279, CT443, CT372, CT456 and/or CT381. Neutralizing antibodies may be used as a vaccine capable of neutralising the activity of a native *Chlamydia* protein expressed by infectious EB. In one embodiment, the protein of the invention is used to elicit antibodies that are capable of neutralising *Chlamydia* infectivity and/or virulence. Thus, the invention also provides the antibodies of the invention for neutralising wild-type *Chlamydia* proteins and/or *Chlamydia* infectivity and/or virulence.

The invention also provides the use of a nucleic acid, protein, or antibody of the invention in the manufacture of: (i) a medicament for treating or preventing bacterial infection; (ii) a diagnostic reagent for detecting the presence of bacteria or of antibodies raised against bacteria; and/or (iii) a reagent which can raise antibodies against bacteria. Said bacteria is preferably a *Chlamydia*, e.g. *Chlamydia trachomatis* or *Chlamydia pneumoniae*, but is preferably *Chlamydia trachomatis*.

Also provided is a method for diagnosing *Chlamydia* infection, comprising:

(a) raising an antibody against a protein of the invention;
(b) contacting the antibody of step (a) with a biological sample suspected of being infected with *Chlamydia* under conditions suitable for the formation of antibody-antigen complexes; and
(c) detecting said complexes, wherein detection of said complex is indicative of *Chlamydia* infection.

Also provided is a method for diagnosing *Chlamydia* infection, comprising: (a) contacting an antibody which was raised against a protein of the invention with a biological sample suspected of being infected with *Chlamydia* under conditions suitable for the formation of antibody-antigen complexes; and (b) detecting said complexes, wherein detection of said complex is indicative of *Chlamydia* infection.

Proteins of the invention can be used in immunoassays to detect antibody levels (or, conversely, antibodies of the invention can be used to detect protein levels). Immunoassays based on well defined, recombinant antigens can be developed to replace invasive diagnostics methods. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Testing Efficacy of Compositions

The efficacy of the immunogenic compositions of the present invention can be evaluated in in vitro and in vivo animal models prior to host, e.g., human, administration. For example, in vitro neutralization by Peterson et al (1988) is suitable for testing vaccine compositions directed toward *Chlamydia trachomatis*.

One way of checking efficacy of therapeutic treatment involves monitoring *C. trachomatis* infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the *Chlamydia trachomatis* antigens in the compositions of the invention after administration of the composition. Typically, serum *Chlamydia* specific antibody responses are determined post-immunisation but pre-challenge whereas mucosal *Chlamydia* specific antibody body responses are determined post-immunisation and post-challenge.

One example of such an in vitro test is described as follows. Hyper-immune antisera is diluted in PBS containing 5% guinea pig serum, as a complement source. *Chlamydia trachomatis* ($10^4$ IFU; inclusion forming units) are added to the antisera dilutions. The antigen-antibody mixtures are incubated at 37° C. for 45 minutes and inoculated into duplicate confluent Hep-2 or HeLa cell monolayers contained in glass vials (e.g., 15 by 45 mm), which have been washed twice with PBS prior to inoculation. The monolayer cells are infected by centrifugation at 1000×g for 1 hour followed by stationary incubation at 37° C. for 1 hour. Infected monolayers are incubated for 48 or 72 hours, fixed and stained with *Chlamydia* specific antibody, such as anti-MOMP. Inclusion-bearing cells are counted in ten fields at a magnification of 200×. Neutralization titer is assigned on the dilution that gives 50% inhibition as compared to control monolayers/IFU.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of vaccine compositions can also be determined in vivo by challenging animal models of *Chlamydia trachomatis* infection, e.g., guinea pigs or mice, with the vaccine compositions. For example, in vivo vaccine composition challenge studies in the guinea pig model of *Chlamydia trachomatis* infection can be performed. A description of one example of this type of approach follows. Female guinea pigs weighing 450-500 g are housed in an environmentally controlled room with a 12 hour light-dark cycle and immunized with vaccine compositions via a variety of immunization routes. Post-vaccination, guinea pigs are infected in the genital tract with the agent of guinea pig inclusion conjunctivitis (GPIC), which has been grown in HeLa or McCoy cells (Rank et al. (1988)). Each animal receives approximately $1.4\times10^7$ inclusion forming units (IFU) contained in 0.05 ml of sucrose-phosphate-glutamate buffer, pH 7.4 (Schacter, 1980). The course of infection monitored by determining the percentage of inclusion-bearing cells by indirect immunofluorescence with GPIC specific antisera, or by Giemsa-stained smear from a scraping from the genital tract (Rank et al 1988). Antibody titers in the serum is determined by an enzyme-linked immunosorbent assay.

Alternatively, in vivo vaccine compositions challenge studies can be performed in the murine model of *Chlamydia trachomatis* (Morrison et al 1995). A description of one example of this type of approach is as follows. Female mice 7 to 12 weeks of age receive 2.5 mg of depo-provera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH 7.4. The course of infection is monitored by determining the percentage of inclusion-bearing cells by indirect immunofluorescence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay.

Nucleic Acid Immunisation

The immunogenic compositions described above include *Chlamydia* antigens. In all cases, however, the polypeptide antigens can be replaced by nucleic acids (typically DNA) encoding those polypeptides, to give compositions, methods and uses based on nucleic acid immunisation. Nucleic acid immunisation is now a developed field (e.g. see Donnelly et al. (1997) *Annu Rev Immunol* 15:617-648; Strugnell et al. (1997) *Immunol Cell Biol* 75(4):364-369; Cui (2005) *Adv Genet* 54:257-89; Robinson & Torres (1997) *Seminars in Immunol* 9:271-283; Brunham et al. (2000) *J Infect Dis* 181 Suppl 3:S538-43; Svanholm et al. (2000) *Scand J Immunol* 51(4):345-53; *DNA Vaccination—Genetic Vaccination* (1998) eds. Koprowski et al. (ISBN 3540633928); *Gene Vaccination: Theory and Practice* (1998) ed. Raz (ISBN 3540644288), etc.).

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site.

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA delivery techniques are described in, for example, Findeis et al., *Trends Biotechnol*. (1993) 11:202; Chiou et al. (1994) *Gene Therapeutics: Methods And Applications Of Direct Gene Transfer*. ed. Wolff; Wu et al., *J. Biol. Chem*. (1988) 263:621; Wu et al., *J. Biol. Chem*. (1994) 269: 542; Zenke et al., *Proc. Natl. Acad. Sci*. (*USA*) (1990) 87:3655; and Wu et al., *J. Biol. Chem*. (1991) 266:338.

Therapeutic compositions containing a nucleic acid are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148).

Viral-based vectors for delivery of a desired nucleic acid and expression in a desired cell are well known in the art. Exemplary viral-based vehicles include, but are not limited to, recombinant retroviruses (e.g. WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP-A-0345242; and WO 91/02805), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP-A-0345242; WO 91/02805; WO 94/12649; WO 93/03769; WO 93/19191; WO 94/28938; WO 95/11984; and WO 95/00655). Administration of DNA linked to killed adenovirus (Curiel, *Hum. Gene Ther*. (1992) 3:147) can also be employed.

Non-viral delivery vehicles and methods can also be employed, including, but not limited to, polycationic condensed DNA linked or unlinked to killed adenovirus alone (e.g. De Libero et al, *Nature Reviews Immunology,* 2005, 5: 485-496), ligand-linked DNA (Wu, *J. Biol. Chem*. (1989)

264:16985), eukaryotic cell delivery vehicles cells (U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes (e.g. immunoliposomes) that can act as gene delivery vehicles are described in U.S. Pat. No. 5,422,120; WO 95/13796; WO 94/23697; WO 91/14445; and EP-0524968. Additional approaches are described in Philip, *Mol. Cell Biol.* (1994) 14:2411 and Woffendin, *Proc. Natl. Acad. Sci.* (1994) 91:11581.

Further non-viral delivery suitable for use includes mechanical delivery systems such as the approach described in Donnelly et al. (1997) *Annu Rev Immunol* 15:617-648. Moreover, the coding sequence and the product of expression of such can be delivered through deposition of photopolymerized hydrogel materials or use of ionizing radiation (e.g. U.S. Pat. No. 5,206,152 and WO 92/11033). Other conventional methods for gene delivery that can be used for delivery of the coding sequence include, for example, use of hand-held gene transfer particle gun (U.S. Pat. No. 5,149,655) or use of ionizing radiation for activating transferred genes (Strugnell et al. (1997) *Immunol Cell Biol* 75(4):364-369 and Cui (2005) *Adv Genet* 54:257-89).

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Antibody Immunisation

The antibodies of the invention may be used, for example, for neutralising the activity of the wild-type *Chlamydia* protein. Antibodies against *Chlamydia* antigens can be used for passive immunisation (Brandt et al. (2006) *J Antimicrob Chemother.* 58(6):1291-4. Epub 2006 Oct. 26). Thus the invention provides the use of antibodies of the invention in therapy. The invention also provides the use of such antibodies in the manufacture of a medicament. The invention also provides a method for treating a mammal comprising the step of administering an effective amount of an antibody of the invention. As described above for immunogenic compositions, these methods and uses allow a mammal to be protected against *Chlamydia* infection.

Processes

According to further aspects, the invention provides various processes.

A process for producing a protein of the invention is provided, comprising the step of culturing a host cell of the invention under conditions which induce protein expression.

A process for producing protein or nucleic acid of the invention is provided, wherein the protein or nucleic acid is synthesised in part or in whole using chemical means.

A process for detecting *Chlamydia* (preferably *C. trachomatis*) in a biological sample is also provided, comprising the step of contacting a nucleic acid according to the invention with the biological sample under hybridising conditions. The process may involve nucleic acid amplification (e.g. PCR, SDA, SSSR, LCR, TMA etc.) or hybridisation (e.g. microarrays, blots, hybridisation with probe in solution etc.).

A process for detecting wild-type *Chlamydia* (preferably, *C. trachomatis*) is provided, comprising the steps of: (a) contacting an antibody of the invention with a biological sample under conditions suitable for the formation of an antibody-antigen complex(es); and (b) detecting said complex(es). This process may advantageously be used to diagnose *Chlamydia* infection.

General

The practice of the present invention will employ, unless otherwise indicated, conventional methods of chemistry, biochemistry, molecular biology, immunology and pharmacology, within the skill of the art. Such techniques are explained fully in the literature. See, e.g., Gennaro (2000) *Remington: The Science and Practice of Pharmacy.* 20th edition, ISBN: 0683306472*; Methods In Enzymology* (S. Colowick and N. Kaplan, eds., Academic Press, Inc.); *Handbook of Experimental Immunology*, Vols. I-IV (D. M. Weir and C. C. Blackwell, eds, 1986, Blackwell Scientific Publications); Sambrook et al. (2001) *Molecular Cloning: A Laboratory Manual,* 3rd edition (Cold Spring Harbor Laboratory Press); *Handbook of Surface and Colloidal Chemistry* (Birdi, K. S. ed., CRC Press, 1997); Ausubel et al. (eds) (2002) *Short protocols in molecular biology,* 5th edition (Current Protocols); *Molecular Biology Techniques An Intensive Laboratory Course*, (Ream et al., eds., 1998, Academic Press); and *PCR* (*Introduction to Biotechniques Series*), 2nd ed. (Newton & Graham eds., 1997, Springer Verlag) etc.

"GI" numbering is used herein. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN (Geysen et al. (1984) *PNAS USA* 81:3998-4002; Carter (1994) *Methods Mol Biol* 36:207-23) or similar methods), or they can be predicted (e.g. using the Jameson-Wolf antigenic index (Jameson, B A et al. 1988, *CABIOS* 4(1):181-186), matrix-based approaches (Raddrizzani & Hammer (2000) *Brief Bioinform* 1(2):179-89). MAPITOPE (Bublil et al. (2007) *Proteins* 68(1):294-304), TEPITOPE (De Lalla et al. (1999) *J. Immunol.* 163:1725-29; Kwok et al. (2001) *Trends Immunol* 22:583-88), neural networks (Brusic et al. (1998) *Bioinformatics* 14(2):121-30), OptiMer & EpiMer (Meister et al. (1995) *Vaccine* 13(6):581-91; Roberts et al. (1996) *AIDS Res Hum Retroviruses* 12(7):593-610), ADEPT (Maksyutov & Zagrebelnaya (1993) *Comput Appl Biosci* 9(3):291-7), Tsites (Feller & de la Cruz (1991) *Nature* 349(6311):720-1), hydrophilicity (Hopp (1993) *Peptide Research* 6:183-190), antigenic index (Welling et al. (1985) *FEBS Lett.* 188:215-218) or the methods disclosed in Davenport et al. (1995) *Immunogenetics* 42:392-297; Tsurui Sr. Takahashi (2007) *J Pharmacol Sci.* 105(4):299-316; Tong et al. (2007) *Brief Bioinform.* 8(2): 96-108; Schirle et al. (2001) *J Immunol Methods.* 257(1-2): 1-16; and Chen et al. (2007) *Amino Acids* 33(3):423-8, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489.

BRIEF DESCRIPTION OF DRAWINGS

FIG. 1 is a graph which shows the ability of 20 selected *C. trachomatis* antigens to induce IFNγ production by CD4+ T cells.

FIG. 2*a* shows the bacterial shedding (IFUs recovered from lungs) after *Chlamydia* challenge in mice to whom EB-CM CD4+ T cells had been adoptively transferred.

FIG. 10A shows the protection results achieved with various antigens combinations in the mouse model of *C. muridarum* intranasal challenge. FIG. 10B shows the frequency of IFNg-producing CD4+ T cells induced by vaccination with the antigen combination TC0890+TC0551. From left to right, the bars represent stimutaion with 1) TC0551, TC0890, TC0551+TC0890 (for adjuvant-immunized mice) and 2) TC0551, TC0890, TC0551+TC0890 (for MIX TC0890+TC0551-immunized mice).

FIG. 12 shows protective activity of antigens TC0313, TC0741, TC0106 and TC0210 given singly or in combination. In 12A to 12D the bars show mean IFU/lung (Log 10), with the left-hand bar being adjuvant alone (LTK61+CpG) and the right-hand bar being the TC antigen. FIG. 12E shows the IFU reduction over time (Mean IFU/lung against days post-challenge) using the combination (squares) or adjuvant alone (diamonds).

MODES FOR CARRYING OUT THE INVENTION

Example 1

Figure 2B:
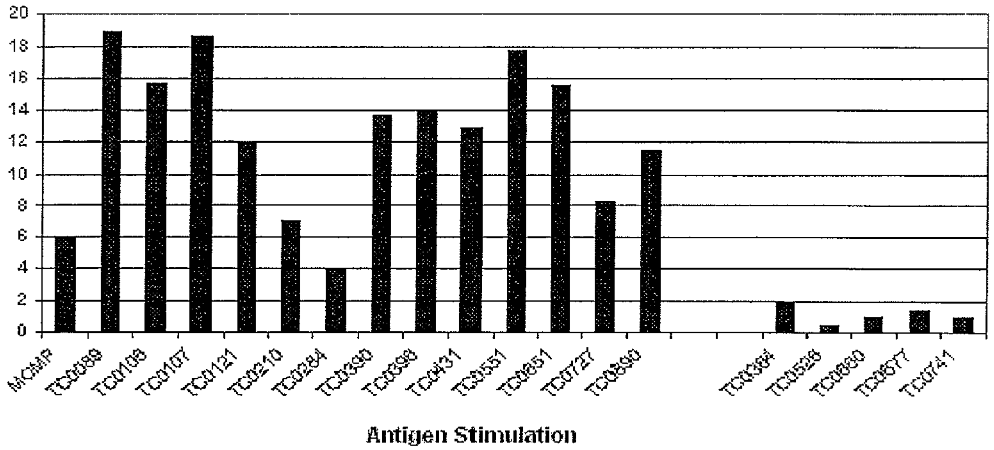
FIG. 2*b* shows the ability of various *C. muridarum* antigens to stimulate the protective EB-CD4+ T cell line to produce IFNγ.

Induction of Population of CD4+ T Cells to Produce IFNγ

20 antigens have been found which induce a population of CD4+ T cells to produce IFNγ (see FIG. 1). 17 of these are newly discovered (CT016, CT043, CT114, CT153, CT255, CT279, CT341, CT372, CT480, CT600, CT601, CT711, CT716, CT733, CT734. CT745, CT823), while three antigens (CT681-MOMP, CT396-Hsp60 and CT587-Enolase) have already been described as targets of CD4+ T cells (Goodall J C et al. 2001; Hassell A B et al. 1993). Significantly, some antigens were able to induce a frequency of antigen-specific CD4+ responding T cells at least comparable to what observed with the positive control antigen MOMP.

The 17 new antigens are as follows:

| Antigen | Annotation | Gene name |
|---|---|---|
| CT016 | Hypothetical protein | |
| CT043 | Hypothetical protein | |
| CT114 | Hypothetical protein | |
| CT153 | Hypothetical protein | |
| CT255 | Hypothetical protein | |
| CT279 | Na(+)-translocating NADH-quinone reductase subunit C | nqr3 |
| CT341 | Heat shock protein J (Hsp-J) | dnaJ |
| CT372 | Hypothetical protein | |
| CT480 | Oligopeptide Binding Lipoprotein | oppA_4 |
| CT600 | | |
| CT601 | Invasin repeat family phosphatase | papQ |
| CT711 | Hypothetical protein | |
| CT716 | Hypothetical protein | |
| CT733 | Hypothetical protein | |
| CT734 | Hypothetical protein | |
| CT745 | protoporphyrinogen oxidase | hemG |
| CT823 | DO serine protease | htrA |

Of these 17 new antigens, CT341 may be the least suitable for use in immunization because it is a heat shock protein.

Example 2

Characterization of the Antigen-Specificity of Protective *Chlamydia* Specific CD4+ Th1 Cell Lines The relevance of the newly discovered antigens for protective immunity to *Chlamydia* was further corroborated by showing that they were recognized by T cells belonging to a *Chlamydia*-specific CD4+/IFNγ+ cell line, conferring protection when adoptively transferred to naïve recipient mice. To this aim we have derived a short-term CD4+ T cell line, produced against the extracellular EB form of *C. muridarum* that showed a high capacity to protect adoptively transferred naïve mice from *C. muridarum* challenge. The protective CD4+ cell line, which had undergone only a few cycles of expansion, maintained a polyclonal cell population with broad specificity that should correlate more closely to the in vivo protective response than long-term lines or clones. The polyclonal cell line was analysed for its antigen recognition profile versus the *C. muridarum* antigens, homologous to the *C. trachomatis* CD4-Th1 inducing proteins. The dissection of the antigen specificity of the protective CD4+ T cell polyclonal population demonstrated that the *Chlamydia* CD4+/IFNγ+ inducing-antigens identified during an infection are also targets of CD4+ T cells that play a part in the rapid clearance of the bacterium in a protective response to the infection, in the absence of antibodies.

*Chlamydia* T cell lines were derived from Balb/c infected mice and their protective activity was verified in naïve mice against *C. muridarum* challenge. Subsequently, the antigen recognition profile of the *C. muridarum* CD4+ T cell line was characterized to define the possible contribution of each *C. muridarum* antigen in inducing protective CD4+ T cells. For the preparation of *Chlamydia*-specific CD4+ T cells, splenic CD4+ T lymphocytes were purified from donor Balb/c mice that had previously been infected intranasally with $10^3$ viable Elementary Bodies (EBs) of *C. muridarum*. An EB-responding CD4+ T cell line was derived (referred as EB-CD4+ cell line) and expanded in vitro with a short term stimulation with heat inactivated EBs. The line showed the capacity to respond to *C. muridarum* EBs by producing IFNγ with a high frequency (data not shown). To determine the efficacy of the EB-CD4+ cell line in resolving an infection, $10^7$ CD4+ T cells were adoptively transferred into 4 Balb/c recipient naïve mice. Mice were challenged intranasally 24 hours after i.v. infusion of CD4+ T cells with $10^3$ IFUs of *C. muridarum*. The protective effect of adoptive immunization was evaluated by quantitating the number of IFUs recovered from lungs taken 10 days after *Chlamydia* challenge. As shown in FIG. 2*a*, naïve mice adoptively transferred with EB-CM CD4+ T cells shed 3 $Log_{10}$ fewer IFUs in the lungs 10 days after intranasal challenge with $10^3$ IFUs of *C. muridarum*, as compared to either non treated mice (p value: 0.008) or mice receiving an unrelated CD4+ T cell line. Similarly, splenic CD4+ T cells isolated from mice that resolved an intravaginal primary infection with $10^5$ IFUs of *C. trachomatis* conferred significant IFU reduction in adoptively transferred mice (data not shown).

To characterize the antigen recognition profile of the *C. muridarum* CD4+ T cells, most of the *C. muridarum* proteins, homolog of the proteins identified as CD4+ Th1 inducers during *C. trachomatis* infection (FIG. 1), were obtained in recombinant form and tested for their ability to stimulate the protective EB-CD4+ T cell line to produce IFNγ. In this analysis we excluded both the proteins which after purification did not reach the purity/endoxin level required for the cytokine stimulation assay, or those which, due to their homology with human bacterial proteins were not suitable for developing a vaccine (e.g. heat shock proteins, enolase). The protective EB-CD4+ T cell line was stimulated in vitro with a panel of 19 *C. muridarum* recombinant proteins, including MOMP. Fourteen of them were homologs of *C. trachomatis* CD4+ Th1 inducing antigens identified in the primary screening in infected mice, and 5 were negative controls. As shown in FIG. 2*b*, all the 14 CD4+-inducing antigens tested were found also to be targets of the protective EB-CM CD4+ T cell line, and able to induce IFNγ production in a percentage of CD4+ T cells at least 3 times higher than the frequency of negative control antigens. Therefore the pattern of T cell antigens recognized by the protective *Chlamydia* EB-CM T cell line is comparable to the recognition profile of T cells identified in the *C. trachomatis* infected mice.

Example 3

CT733 and CT153 Specific CD4+ Th1 Response in BALB/c Mice after a Primary *C. trachomatis* Infection Splenocytes of primary infected BALB/c mice and non infected controls were collected 10 days after infection and stimulated with LPS-free recombinant antigens CT733 and CT153 (20 mg/ml). After 4 hours of stimulation, 5 mg/ml of Brefeldin A were added to the cells for the following 12 hrs to block cytokine secretion. Afterwards, cells were fixed, permeabilized and stained. Intracellular IFNγ and IL-5 expression were analyzed versus CD4 surface expression of the gated viable cells and assessed by flow cytometry.

Figure 3:
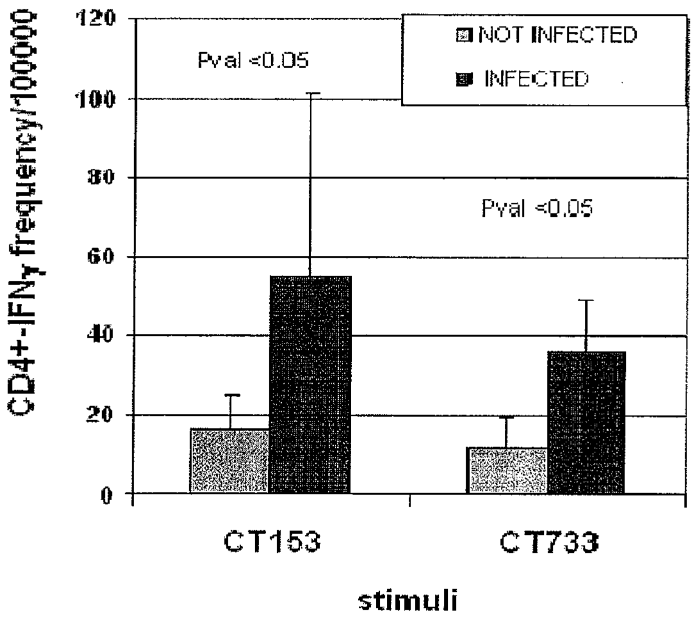
FIG. 3 is a histogram which shows the number of CD4+ T cells that produce IFNγ, upon specific stimulation with *C. trachomatis* recombinant antigens CT153 and CT733.

The histogram in FIG. 3 shows the number of CD4+ T cells per $10^5$ CD4+ T splenocytes of primary infected (dark grey bars) and non-infected (light grey bars) mice that produce IFNγ upon specific stimulation with the *C. trachomatis* recombinant antigens CT153 and CT733. The data were confirmed in several further experiments using the same protocol.

The results indicate that CT733 and CT153 are able to induce significant frequencies of specific CD4+/IFNγ+ cells in splenocytes from Balb/c mice that were infected intravaginally with *C. trachomatis*, suggesting a potential role as antigen candidates for these proteins.

Example 4

Protective Activity of Single Antigens TC0106 and TC0431 Against *C. muridarum* Challenge CT733 and CT153 were tested in a mouse model of chlamydial infection to evaluate their protective properties. This was done by adopting the mouse model of lung infection with the species *Chlamydia muridarum.*

The *C. muridarum* proteins TC0106 and TC0431, homologous to CT733 and CT153, respectively, were cloned and purified, and used for the mouse model.

Groups of BALB/c mice were immunized with either TC0106 or TC0431 recombinant antigens formulated with LTK63+CpG adjuvant (3 doses of 15 ug protein, at 2 week interval, given intramuscularly). As negative control, mice were immunized with the adjuvant only. Four weeks after the last immunization animals were infected intranasally with $10^3$ IFU of infectious *C. muridarum*. After 10 days, the protective activity conferred by the two antigens was measured by counting the infectious IFU in the lung of challenge animals.

Figure 4:
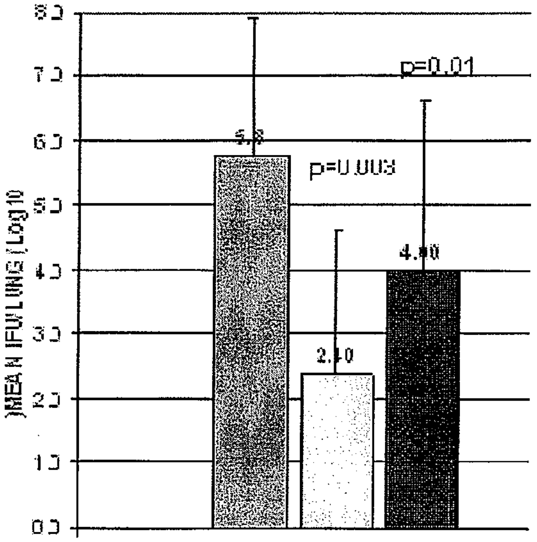
FIG. 4 shows the protective activity of TC0106 (*C. muridarum* homologue of CT733) and TC0431 (*C. muridarum* homologue of CT153) as single antigens. The graph shows mean IFU/ml in BALB/C mice immunised with the two antigens and then challenged with *C. muridarum*. The three bars are, from left to right: adjuvant alone; TC0106 as immunogen; and TC0431 as immunogen.

As shown in FIG. 4, each of the two antigens (middle and right hand columns of the histogram) was able to reduce significantly the number of IFU/lung in challenged mice as compared to adjuvant immunized mice (left hand column of the histogram), indicating that both TC0106 and TC0431 (and therefore CT733 and CT153) confer protective immunity to *Chlamydia* infection Example 5

Protective Activity of the Combination of TC0106+TC0431 Against *C. muridarum* Challenge Groups of BALB/c mice (10 to 15 mice) were immunized with the combination of TC0106+TC0431 recombinant antigens formulated with LTK63+CpG adjuvant (3 doses of 10 ug of each protein at 2 week-interval, given intramuscularly). As negative control, mice were immunized with the adjuvant only. Four weeks after the last immunization, animals were infected intranasally with $10^3$ IFU of infectious *C. muridarum*. After 10 days, the protective activity conferred by the two antigens was measured by counting the infectious IFU in the lung of challenge animals. As positive control, a group of mice receiving a primary and a secondary *C. muridarum* infection was also included (left column in the histogram of FIG. 5).

Figure 5:
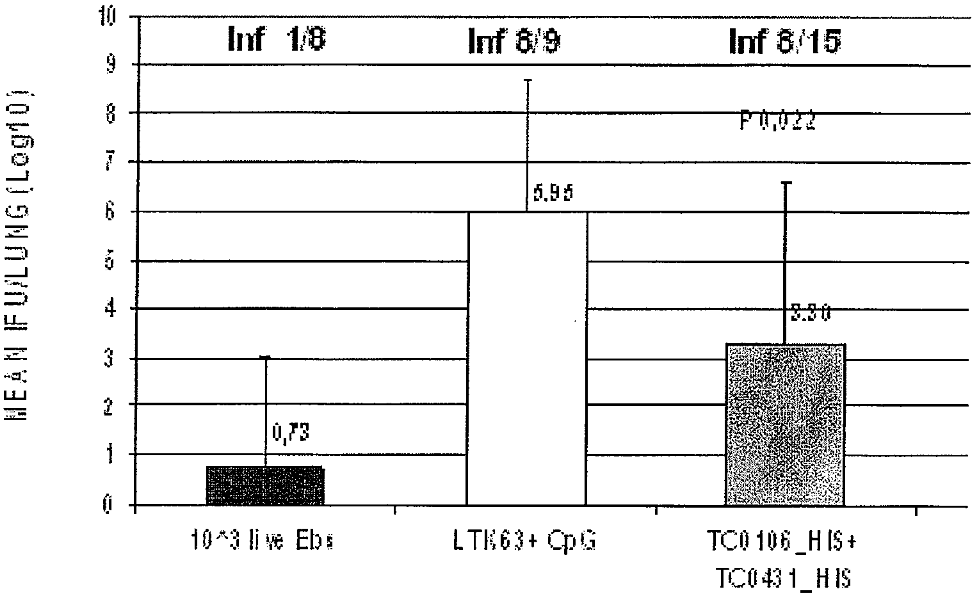
FIG. 5 shows the protective activity of the combination TC0106+TC0431. The graph shows mean IFU per lung (Log 10) recovered from infected lungs of mice immunised with the combination. The three bars are, from left to right: $10^3$ live Ebs; adjuvant alone; antigen combination.

As shown in FIG. 5, the antigen combination (right hand column of histogram) was able to significantly reduce the number of IFU/lung in challenged mice as compared to adjuvant immunized mice (middle column of histogram).

Thus, immunization with the CT733 and CT153, either alone or in combination, was able to significantly reduce the bacterial load in the lungs of challenged mice (see FIGS. 4 and 5).

Example 6

Figure 6:
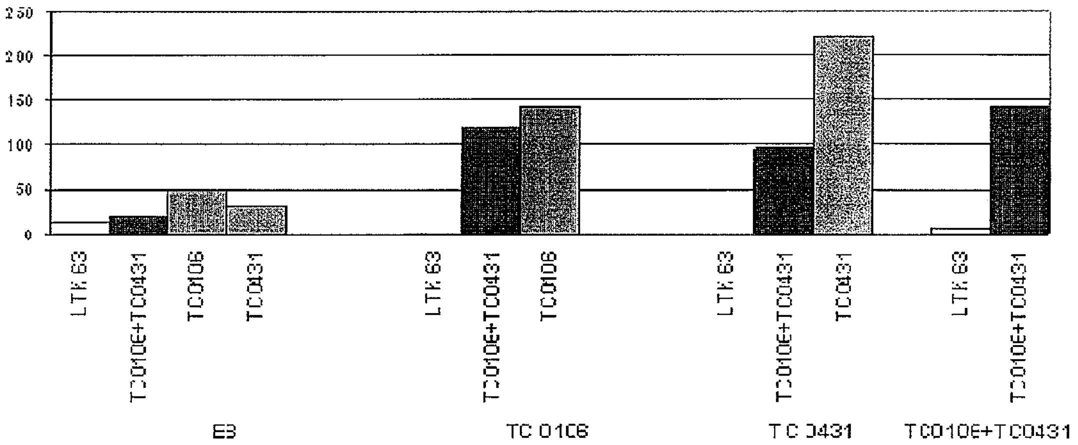
FIG. 6 shows CD4 T cells producing IFNγ in PBMC of mice immunized with TC0106+TC0431, TC0106, TC0431 and LTK 63+CpG. From left to right, the bars represent stimulation with 1) LTK 63, TC0106+TC0431, TC0106, TC0431 (all EB-immunized mice); 2) LTK 63, TC0106+TC0431, TC0106 (all TC 0106-immunized mice); 3) LTK63, TC0106+TC0431. TC0431 (all TC0431-immunized mice); and 4) LTK63 and TC0106+TC0431 (both TC0106+TC043'-immunized mice). It shows that immunization with TC0106 (*C. muridarum* homologue of CT733) and TC0431 (*C. muridarum* homologue of CT153) elicits a significant frequency of specific CD4+/IFNγ+ cells. The Y axis shows frequency on $10^6$ CD4.

Elicitation of CD4+ Th1 Cells in BALB/c Mice after Immunization with TC0431 and TC0106 Recombinant Antigens, Alone or in Combination Groups of BALB/c mice (10 to 15 mice) were immunized with the recombinant antigens TC0431 and TC0106 as single antigens or in combination (i.m., 10-15 micrograms/dose, 3 doses at 2 week-intervals) using LTK63+CpG adjuvant. Ten days after the third immunization dose, splenocytes were collected and stimulated with LPS-free recombinant antigens (20 mg/ml). As negative control, splenocytes of adjuvant immunized mice were included. After 4 hours of stimulation, 5 mg/ml of Brefeldin A was added to the cells for the following 12 hrs to block cytokine secretion. Afterwards, cells were fixed, permeabilized and stained. The intracellular IFNγ was analyzed versus CD4 surface expression of the gated viable cells and assessed by flow cytometry. The histogram in FIG. 6 shows the number of CD4+ T cells per $10^5$ CD4+ T splenocytes that produce IFNγ upon specific stimulation with the recombinant antigens in mice immunized with TC0106, TC0431, the combination of TC0106+TC0431 and adjuvant immunized mice.

The results indicate that immunization with these antigens elicits a high frequency of CD4+ Th1 cells.

Example 7

Evaluation of the Protective Effect of the Chlamydial Antigen(s) Against *C. muridarum* Challenge The protective effect of combinations of two antigens selected from *C. trachomatis* CT279, CT601, CT372, CT443, CT733, CT153, CT456 and CT381 was tested in the *C. muridarum* mouse model using their *C. muridarum* homologues TC0551 (CT279), TC0651 (CT372), TC0727 (CT443), TC0890 (CT601), TC0106 (CT733), TC0431 (CT153), TC0660 (CT381) and TC0741 (CT456). The protective effect of CT733 and CT153 individually was also tested.

Figure 7:
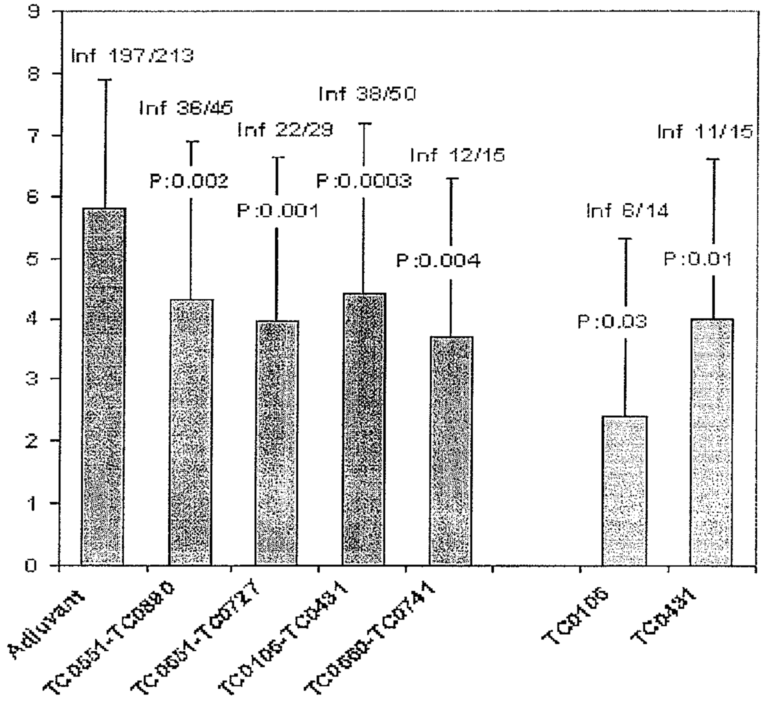
FIG. 7 is a summary of protection results for various combinations and single antigens in the mouse model of *C. muridarum* intransal challenge. It shows the mean IFU/lung of mice immunised imtramuscularly with single antigens, or antigen combinations, adjuvanted with LTK63 and CpG, then challenged intranasally with $10^3$ *C. muridarum* IFU.

BALB/c mice were immunized three times intramuscularly with a combination of two antigens or single antigens with LTK63+CpG as adjuvant. Twenty-four days post last immunization mice were challenged intranasally with $10^3$ IFU *C. muridarum*. After 10 days, lungs were collected, homogenized and the number of viable chlamydiae (IFU/lung) was measured. The data in FIG. 7 shows the mean IFU/lung counts in antigen-immunized mice and adjuvant-immunized control. From left to right, the lanes relate to (a) adjuvant only; (b) TC0551+TC0890 (CT279+CT601); (c) TC0651+TC0727 (CT372+CT443); (d) TC0106+TC0431 (CT733+CT153); (e) TC0660+TC0741 (CT456+CT381); (f) TC0106 (CT733); (g) TC0431 (CT153). For each antigen formulation, the numbers of infected mice out of the total immunized are reported in the form "Inf X/Y", wherein X is the number of infected mice and Y is the total number of mice challenged. The statistical significance of immunizing antigen/s (P), was determined by Student t-test.

Four combinations of two antigens have been identified as capable of conferring protection against *C. muridarum* intranasal challenge. For three of them (TC0431+TC0106; TC0727+TC0651; TC0551+TC0890; homologs of CT733+CT153; CT443+CT372; CT279+CT601) protection has been confirmed in a high number of mice using LTK63+CpG adjuvant (FIG. 7). Immunization experiments with TC0431 and TC0106 (CT153 and CT733) as single antigens indicate that the two antigens are both immunogenic individually and that either of the two antigens contributes to protection of the CT153+CT733 combination (FIG. 7). A fourth antigen combination has been recently identified (TC660+TC0741; homologs of CT456 and CT381) showing protection in an immunization experiment (15 mice) (FIG. 7).

Figure 8:
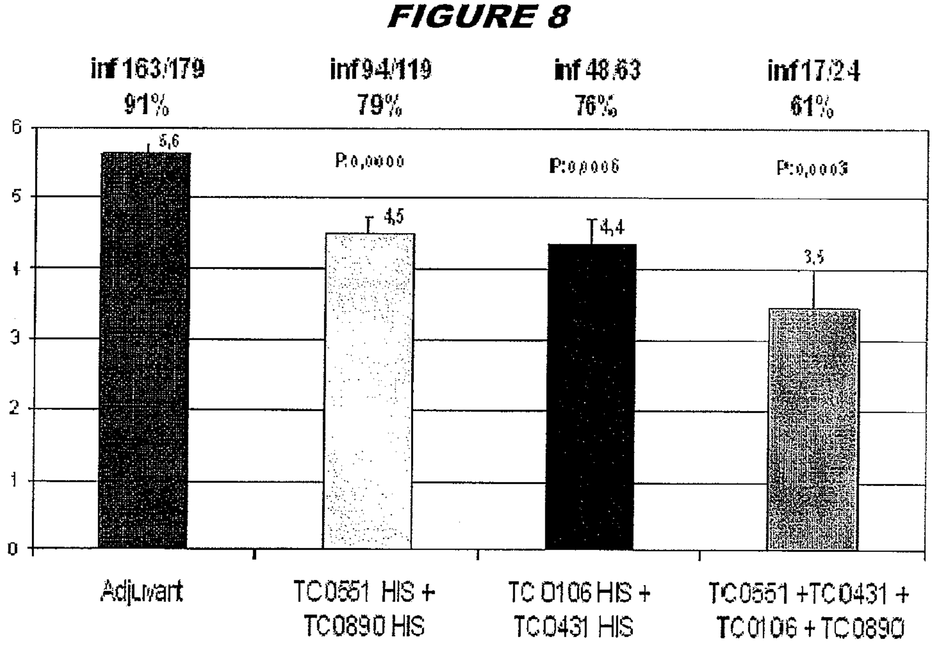
FIG. 8 is a summary of protection results for various combinations of antigens in the mouse model of *C. muridarum* intransal challenge. It shows mean IFU/lung (log 10) of *C. muridarum* recovered from infected lungs of immunised mice.

The experiments were repeated where the protocol differed from that described above in that the mice were challenged intranasally with $10^3$ IFUs of *C. muridarum* three weeks after the last immunization. Since differences in the duration of infections in the animals may occur, the presence of infectious Chlamydiae in the lungs was determined in each mouse at days 10 and 12 after challenge. Immunization experiments were repeated at least three times so as to generate data from a statistically significant number of mice. FIG. 8 reports the mean number of infectious chlamydiae recovered from lungs of mice immunized with each antigen formulation, in which data obtained at days 10 and 12 were averaged. As shown in FIG. 8, two of the four combinations tested in the mouse model, namely TC0551 (CT279 homolog, 82.6% identity)+TC0890 (CT0601 homolog, 87.6% identity) and TC0106 (CT733 homolog, 84.8% identity)+TC0431 (CT153 homolog, 64.6% identity), showed a statistically significant protective effect in the immunized groups with an IFU reduction of more than 1 Log as compared to the adjuvant-injected mice (P:<0.001). Moreover, 20-25% of the animals immunized with either of the two combinations resolved completely the infection by days 10-12, as compared to 9% of the adjuvant group.

Example 8

Evaluation of the Protective Activity of the Combination TC0551+TC0890+TC0106+TC0431 Against Challenge with *C. muridarum*

On the basis of the result discussed in the preceeding Example, groups of mice were immunized with a combination of four antigens TC0551+TC0890+TC0106+TC0431 using the same immunization regimen as in the Example above. As shown in FIG. 8, the 4-antigen combination appeared to have an additive protective effect over the 2-antigen combinations, showing 2.2 Logs reduction of bacterial shedding in the lung (P:0.0003). Moreover, 39% of animals totally resolved the infection, indicating a higher efficacy of this antigen combination in accelerating the bacterial clearance.

The remarkable reduction observed in the number of viable Chlamydiae recovered from the lungs of immunized mice is the first demonstration of a high level of protection induced by systemic immunization with recombinant *Chlamydia* proteins. It has also to be pointed out that, since denatured forms of the recombinant antigens were used, further optimization of antigen conformation could maximize their protective activity.

Preliminary data aimed at defining whether any of the 4 recombinant antigens were protective when given as single antigens, indicated that a lower level of IFU reduction was observed (less than 1 log) was obtained with any of them (data not shown). This is in agreement with the notion that, in general, combinatorial vaccination approaches are more effective in conferring protective immunity against a given pathogen than single vaccine approaches, since elicited immune responses target different aspects of the bacterial developmental cycle.

Example 9

Evaluation of the Protective Activity of the Combination TC0551+TC0651+TC0727+TC0890 Against Intraovarian Bursa Challenge with *C. muridarum*

The protective effect of the combination TC0551+TC0651+TC0727+TC0890 (homologs of *C. trachomatis* CT279+CT372+CT443+CT601) was tested in the mouse model of ovarian bursa challenge with *C. muridarum* using the Montanide+CpG adjuvant. This model has previously been described to assess the protective activity of native MOMP (nMOMP), the chlamydial major outer membrane protein (Pal S et al, Infect Immun., 73:8153, 2005). In this model, the protective activity of the antigens is assessed against progression of infection by counting the chlamydia shedding in vaginals swabs.

BALB/c mice were immunized three times intranasally with a combination of the four antigens or with MOMP, with LTK63+CpG as adjuvant. As negative control, a group of mice immunized with ovalbumin was also included. Four weeks after the last immunization, mice received a *C. muridarum* challenge in the ovarian bursa and chlamydial shedding was measured by counting the IFU in the vaginal swabs of infected animals.

Figure 9:
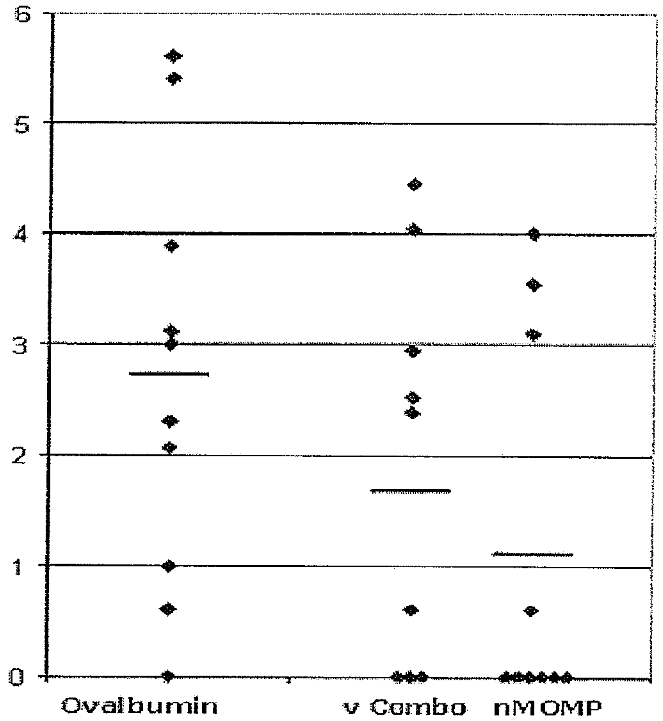
FIG. 9 shows the results of the combination TC0551+TC0651+TC0727+TC0890 in the mouse model of ovarian bursa challenge with *C. muridarum*. The Y axis shows IFU/swab (log 10). The three groups, from left to right, are for different immunizing antigens: ovalbiumin; the combination; and nMOMP.

The results shown in FIG. 9 represent the number of IFU/vaginal swab at two weeks post challenge. As shown in FIG. 9, mice receiving the combination of all four antigens show a reduced bacterial shedding as compared to the negative control group (Ovalbumin). Thus, the combination reduced the progression of infection. Interestingly, the protection level obtained with the combination does not differ significantly from that obtained with nMOMP, which is the most protective antigen that has been identified so far. Thus, this combination of four antigens is a particularly immunogenic combination.

Example 10

Antigen-Specific Cytokine Profiles of Protective CD4+ T Cells

Figure 10C:
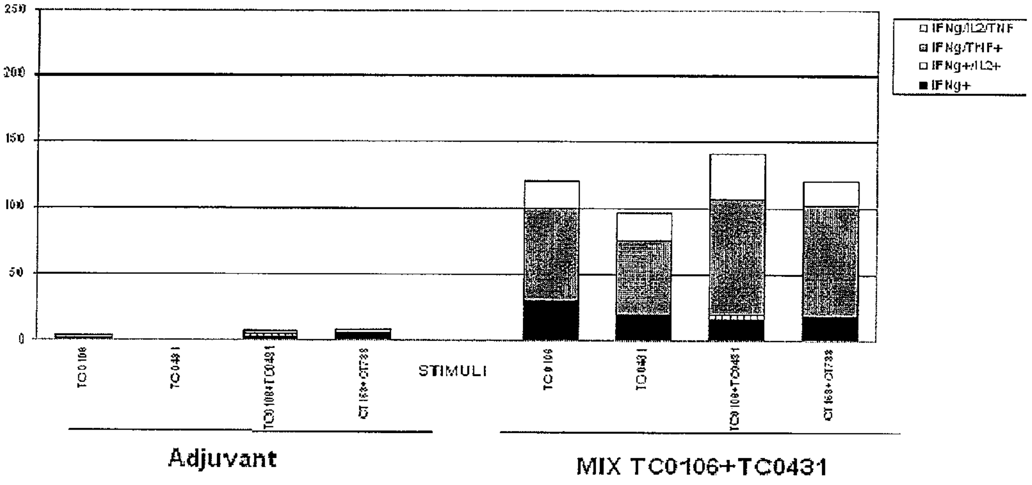
FIG. 10C shows CD4 T cells producing TFNg and IL2/TNF in PBMC of mice immunized with TC0106+TC0431 with Ltk63+CpG. From left to right, the bars represent stimulation with a) TC0106. TC0431, TC0106+TC0431, CT153+CT733 (all adjuvant-immunized mice); 2) TC0106, TC0431, TC0106+TC0431, CT153+CT733 (all MIX TC0106+TC0431-immunized mice).

Given the importance of the CD4-Th1 response in mediating protection from *Chlamydia* infection, the type of immune response induced by vaccination with two antigen combinations that elicited protection in mice was analysed (TC0551+TC0890 and TC0106+TC0431). In particular, we measured the simultaneous production from antigen-specific CD4+ T cells of IFNγ, TNF-α and IL-2, considering this as an indication of optimal effector functions of CD4+ T cells, possibly improving protection for vaccines aimed at targeting T-cell responses. The assessment of the cytokine profile induced in a single antigen specific CD4+ T cell by vaccination was performed by multiparametric flow cytometric analysis (Perfetto S P et al., Nat. Rev. Immunol. 4, 648-655, 2004) in immunized mice. Peripheral blood was collected 12 days after the last immunization with antigen combinations TC0551+TC0890 and TC0106+TC0431. PBMC were prepared and the frequency of CD3+, CD4+ antigen-specific IFNγ, IL-2 and TNF-producing cells was assessed by intracellular cytokine staining and flow cytometric determination. As shown in FIG. 10B, vaccination with the antigen combination TC0551-TC0890 induced a high frequency of TC0551-responding CD4+ T cells producing IFNγ (93 TC0551 specific CD4+ T cells on $10^5$ CD4+ cells), while the response to TC0890 was very low, with a frequency of 16 IFNγ+ responding T cells on $10^5$ CD4+ cells. The response to the antigen combination used for immunization showed an increased response compared to single antigens, with 132 IFNγ producing T cells on $10^5$ CD4+ cells. Furthermore, there was a predominant frequency of multifunctional CD4+ T cells, producing either IFNγ and TNF-α or IFNγ/TNF-α/IL-2 simultaneously. In the control group of mock immunized mice there was no cytokine secretion in response to any recombinant antigen used for stimulation, indicating the specificity of the response observed in the vaccinated mice. As far as the CD4+ response to the antigen combination TC0106-TC0431 is concerned (FIG. 10C) both antigens, TC0106 and TC0431 induced a similar response with a frequency respectively of 120 and 98 IFNγ antigen-specific T cells on 10' CD4+, while the antigen combination showed a frequency of 145 IFNγ+ responding T cells on $10^5$ CD4+ cells. The further analysis of cytokines produced simultaneously with IFNγ showed that about 50% of IFNγ+ cells produced also TNF-α and IL-2, while about 30% of them produced TNF-α. Overall these data underline that the Th1 cytokines produced by antigen-specific CD4+ T cells induced by vaccination showed a functional difference that could reflect differences in the capacity to clear the infection.

Example: 11

Expression Analysis of CD4+ Inducing *Chlamydia* Antigens

Figure 11:
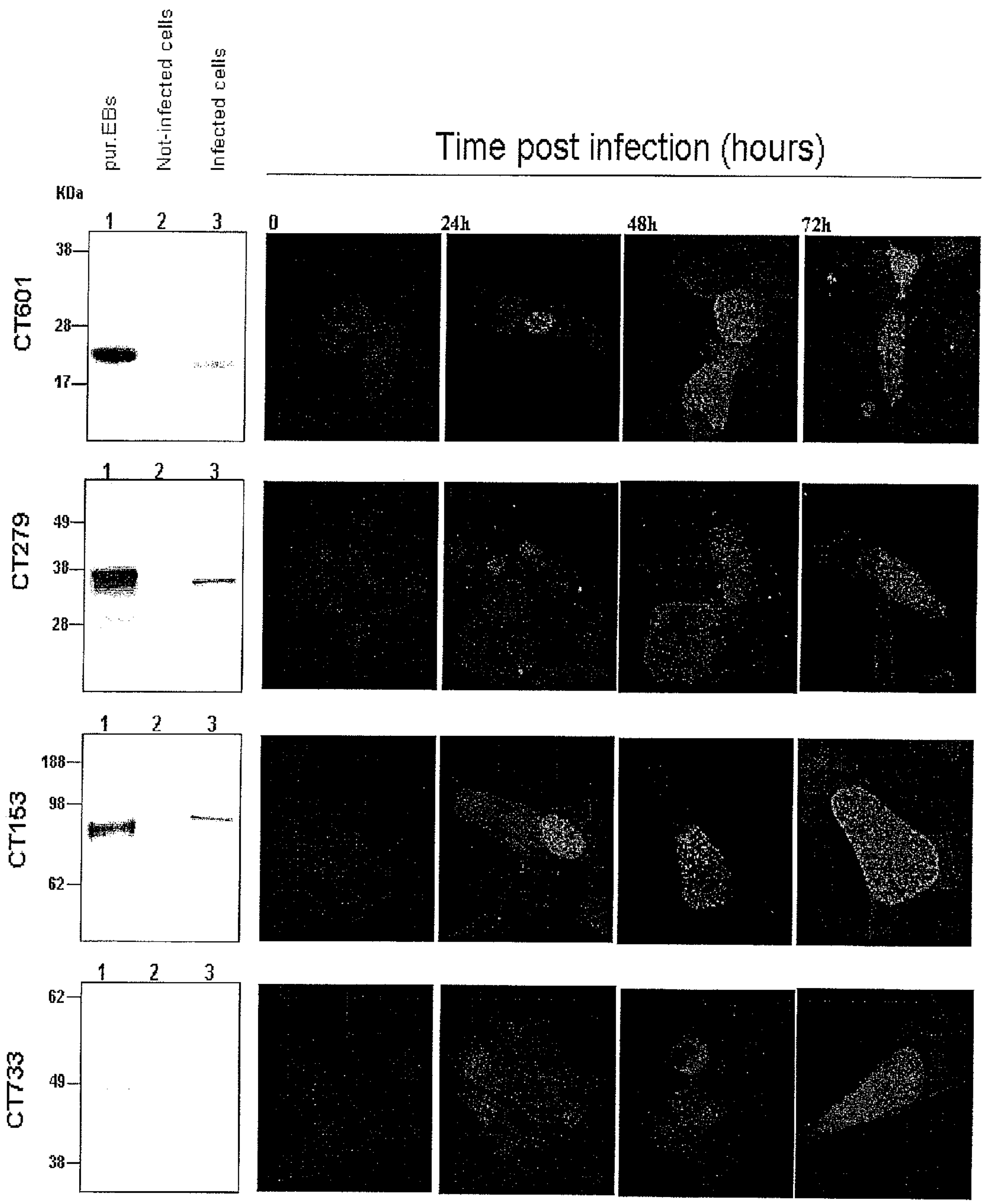
FIG. 11 shows an immunoblot analysis of CT601, CT279, CT153 and CT733 in Ct-EBs and *C. trachomatis*-infected HeLa cells using their specific mouse immune antisera.

We then investigated the expression of CT279 (subunit C of Na(+)-translocating NADH-quinone reductase), CT601 (Invasin repeat family phosphatase), CT733 (-Hypothetical protein) and CT153 (MAC-Perforin Protein) by immunoblot analysis both in Ct-EBs and within *C. trachomatis* infected HeLa cells, using their specific mouse immune antisera (FIG. 11A). Total protein lysates of renografin-purified EBs (corresponding to approximately $10^7$ EBs per lane) showed that each tested antiserum was able to react with a protein band of the expected molecular weight in both EB samples, showing in general a higher reactivity against CM EBs. For analysis of antigen expression in *Chlamydia*-infected cells, total protein extracts were prepared from Hela 229 cells at different time points after infection (24-48-72 h) and tested by immunoblot.

The amount of Chlamydial proteins loaded on the gel was normalized on the basis of MOMP expression as described. As shown in FIG. 11B, the four antigens appeared to be expressed at different phases of the *Chlamydia* development.

Finally, we also investigated antigen cellular localization within infected HeLa cells by confocal microscopy in infected Hela cells at 6, 24, 48 and 72 h post infection. As shown in FIG. 11B, expression of all antigens was clearly detected within the inclusions at 24 h post infection and was still visible at 72 h. Interestingly, CT153 staining appeared to accumulate at the inclusion membrane while the other proteins were homogeneously distributed. Since CT153 encodes a MAC-Perforin protein, belonging to a protein family capable of disrupting the cell membrane, the amassing of this protein at the inclusion membrane might anticipate its involvement in the *Chlamydia* exit from infected cells.

The analysis of the immune response after vaccination with the combinations has shown that all the recombinant antigens induced a robust humoral response, with the production of IgG2a antibody titers higher than IgG1, as expected for a Th1 driven immune response. Since the resolution of a *Chlamydia* infection requires a Th1 type of cellular immune response, the regulation of CD4+ Th1 effector and memory cells after vaccination has also been investigated. Differences in the type of cytokines produced by individual cells have important implications for their capacity to mediate effector functions, be sustained as memory T cells or both. CD4+ T cells that secrete only IFNγ have limited capacity to develop into memory T cells as compared with IL-2-IFNγ double positive cells (Hayashi N. et al. 2002). Therefore vaccines eliciting high frequency of single-positive IFNγ producing cells may be limited in their ability to provide long-lasting protection. Furthermore the majority of CD4+ T cells that produce IL-2, IFNγ and TNF are classified as effector memory cells, playing an essential role for mediating protection against intracellular pathogens (Darrah P A et al. 2007). We demonstrated that antigen-specific CD4+ T cells induced by immunization with the protective combinations were predominantly multifunctional, being differentiated to ensure a population of Th1 cells that included either effectors and memory cells. An appropriate balance of Th1 lineage cells that can be maintained and those with immediate protective functions might be the successful formula for an effective vaccine.

Example 12

Combination of CT823+CT733+CT043+CT456

To evaluate the protective activity of antigens TC0106, TC0313, TC0210, TC0741 and their combination, groups of mice were immunized with the 4 antigens either as single or in a 4 antigen-combination, using the same immunization regimen described in Example 7. The protective activity of the single antigens was assessed by measuring the IFU/Lung at day 12 post infection. The protective activity of the 4-ag combination was measured at days 10, 12, 14 post infection, to evaluate the kinetics of the infection clearance. As shown in FIG. 12, the single antigens conferred approximately 0.5-1 log IFU reduction in the lung of infected animals.

The four antigens combination showed a highest protective property, indicating a synergic activity of the four antigens in conferring protection, eliciting approximately 4 logs reduction of bacterial shedding in the lung ($P<0.0001$) at day 12 and showing the tendency to resolve the infection at day 12. Moreover a high number of mice (42%) totally resolved the infection, indicating the efficacy of the antigen combination in accelerating the bacterial clearance.

Example 13

Evaluation of Antigenicity of CT812, CT387, CT869, CT166 and CT175

Figure 13A:
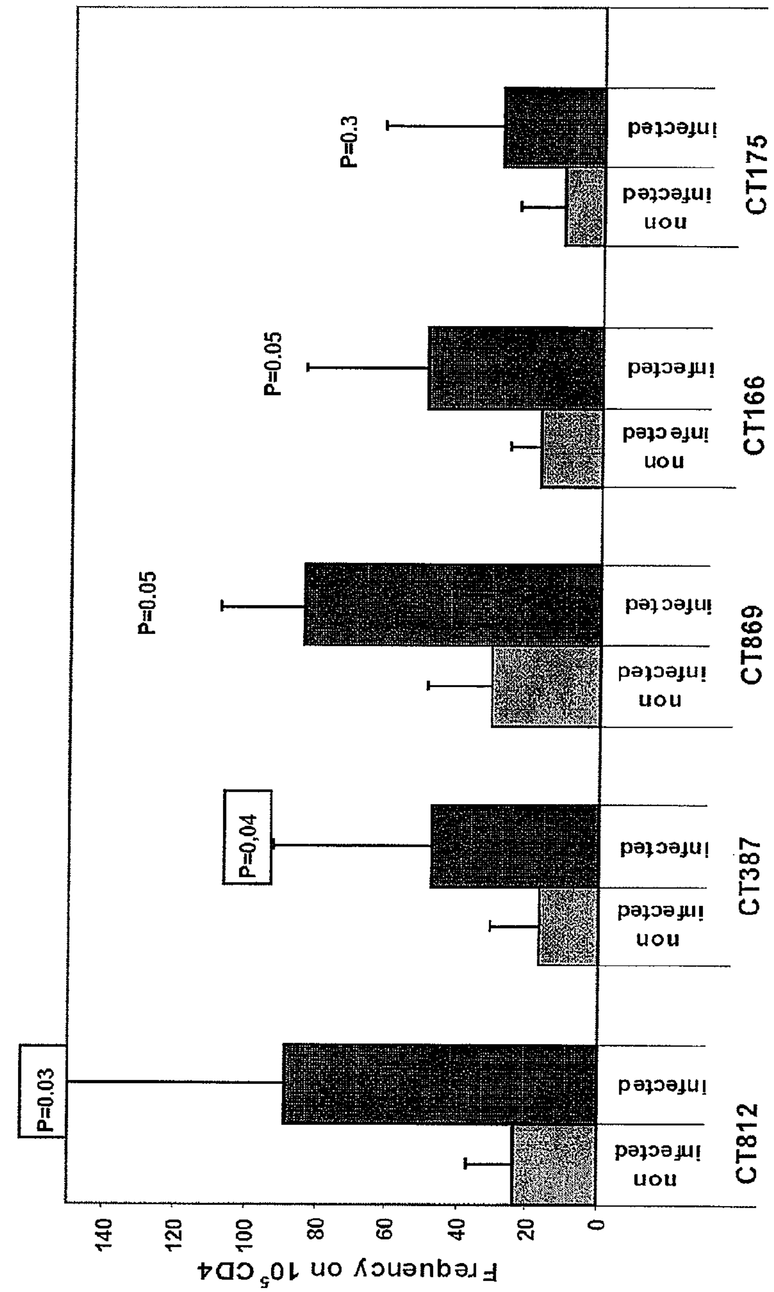
FIGS. 13A and 13B are histograms showing the antigen specific CD4 Th1 response in BALB/c mice after a primary *C. trachomatis* (CT) infection. Results are the mean of 4 independent experiments. Two results are shown for each experiment: non-infected mice (left hand bar) and primary infected mice (right hand bar). From left to right in FIG. 13A, the results relate to stimulation with CT812C, CT387, CT869, CT166 and CT175. From left to right in FIG. 13B, the results relate to stimulation with MOMP, CT163, CT812, CT812C, CT166, CT869, CT163, CT812, CT214, CT387, CT721, CT127 and CT175. The frequency on $10^5$ CD4 T cells is shown on the Y axis.
Figure 13B:
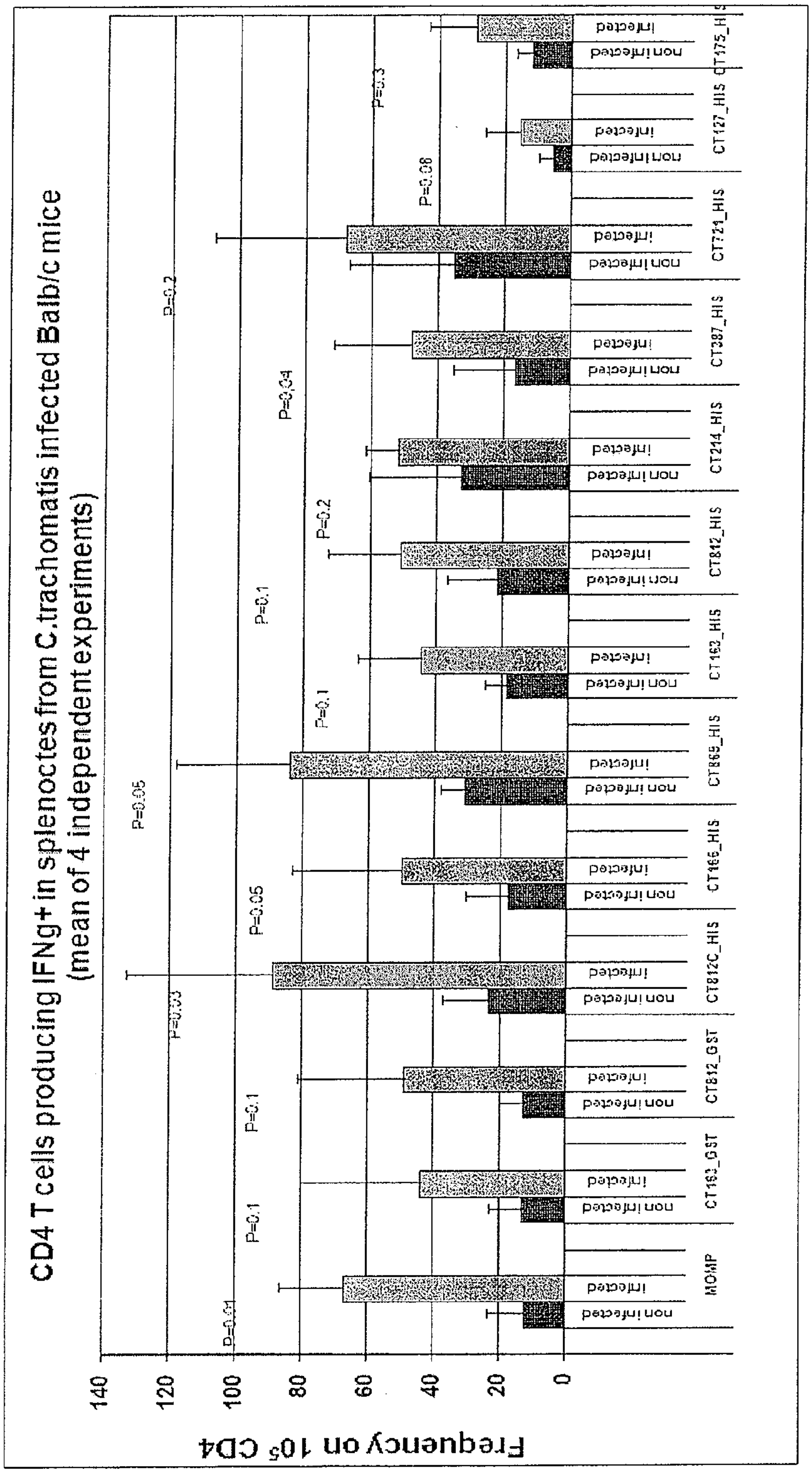

Antigen Specific CD4 Tg1 Response in BALB/c Mice after a Primary *C. Trachomatis* (CT Infection The antigen specific CD4 Th1 response in BALB/c mice after a primary *C. trachomatis* (CT) infection was evaluated. *C. trachomatis* antigens identified by the proteomic characterization of the membrane fraction of CT infected HeLa cells were tested for their capability to induce specific CD4+ Th1 response in mice that received an experimental CT infection. Splenocytes of primary infected BALB/c mice and non infected controls were collected 10 days after infection and stimulated with LPS-free recombinant antigens (20 μg/ml). After 4 hours of stimulation, 5 μg/ml of Brefeldin A was added to the cells for the following 12 hrs, to block cytokine secretion. Afterwards, cells were fixed, permeabilized and stained. The intracellular IFN-γ expression was analyzed versus CD4 surface expression of the gated viable cells, and assessed by flow cytometry. The histogram in FIG. 13A and FIG. 13B show the number of CD4+ T cells that produce IFNγ, upon specific stimulation with CT recombinant antigens per $10^5$ CD4+ T splenocytes of primary infected (right hand bars) and not-infected (left hand bars) mice. Data are representative of 4 different experiments. As shown in FIG. 13A, CT812C, CT387, CT869 and CT166 induced a significant frequency of $CD4^+$-IFNγ+ cells in splenocytes of infected animals (Pval<0.05). As shown in FIG. 13B, CT812C (a C-terminal fragment of CT812) surprisingly induced a higher frequency of $CD4^+$-IFNγ+ cells in splenocytes of infected animals than did the full length CT812 sequence.

Figure 14:
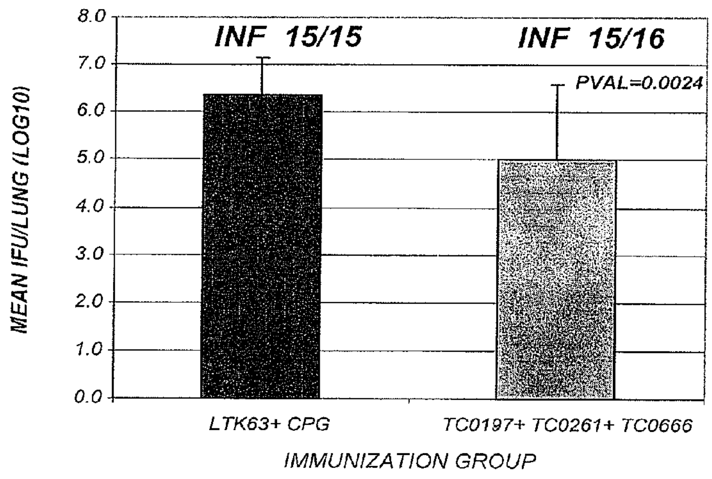
FIG. 14 is a histogram showing *C. muridarum* IFUs recovered from infected lungs of immunised mice (Day 12 post I.N. challenge with $10^3$ IFUs). The immunisation group is shown on the X axis: the left hand bar relates to mice immuised with LTK63+CpG; the right hand bar relates to mice immunised with TC0197+TC0261+TC0666+LTK63+CpG. Mean IFU/lung (Log 10) is shown on the Y axis.

Protective Activity of the Combination of TC0197+TC0261+TC0666 Against *C. muridarum* Challenge The protective effect of the combination of the three *C. trachomatis* antigens CT387+CT812+CT869 was tested in the *C. muridarum* mouse model using their *C. muridarum* orthologues TC0666, TC0197 and TC0261, respectively. TC0197, TC0261 and TC0666 were cloned and purified for protection studies in the mouse model of intranasal infection with *C. muridarum*. Groups of BALB/c mice (16 mice per group) were immunized with the combination of the three recombinant antigens TC0197+TC0261+TC0666 formulated with LTK63+CpG adjuvant (3 doses of 10 μg of each protein, at 2 week-interval, given intramuscularly). As a negative control, mice were immunized with the adjuvant only. Four weeks after the last immunization, animals were infected intranasally with $10^3$ IFU of infectious *C. muridarum*. After 12 days, the protective activity conferred by the two antigens was measured by counting the infectious IFU in the lung of challenge animals. As shown in FIG. 14, the antigen combination TC0197+TC0261+TC0666 was able to reduce significantly the number of IFU/lung in challenged mice as compared to adjuvant immunized mice (1.4 log IFU reduction with Pval<0.05). The finding that the combination of TC0197+TC0261+TC0666 is able to protect mice against *C. muridarum* challenge (FIG. 14) provides evidence that the combinations CT812+CT869+CT387 and CT812C+CT869+CT387 from *C. trachomatis* are protective against infection by *C. trachomatis*.

Figure 15:
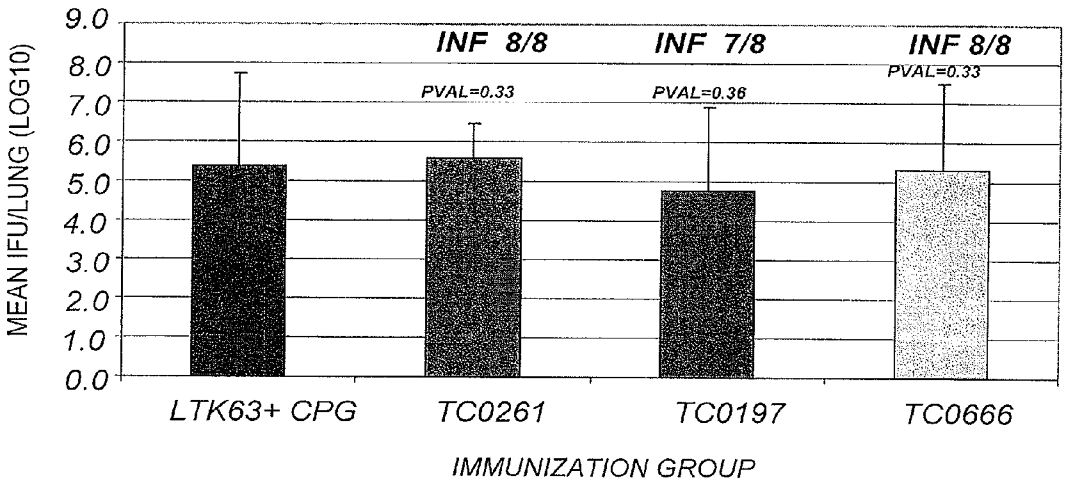
FIG. 15 is a histogram showing *C. muridarum* IFUs recovered from infected lungs of immunised mice (Day 12 post I.N. challenge with $10^3$ IFUs). The immunisation group is shown on the X axis: from left to right, the results relate to mice immunised with i) LTK63+CpG, ii) TC0261+LTK63+CpG, iii) TC0197+LTK63+CpG, and iv) TC0666+LTK63+CpG. Mean IFU/lung (Log 10) is shown on the Y axis.

Protective Activity of TC0197, TC0261 and TC0666 as Single Antigens Against *C. Muridarum* Challenge The protective activity of TC0197, TC0261 and TC0666 as single antigens against *C. muridarum* challenge was assessed. 3 Groups of BALB/c mice (16 mice per group) were immunized with the three recombinant antigens individually formulated with LTK63+CpG adjuvant (3 doses of 20 ug of each protein, at 2 week-interval, given intramuscularly). As a negative control, mice were immunized with the adjuvant only. Four weeks after the last immunization, animals were infected intranasally (I.N.) with $10^3$ IFU of infectious *C. muridarum*. After 12 days, the protective activity conferred by the three single antigens was measured by counting the infectious IFU in the lung of challenge animals. As shown in FIG. 15, none of the 3 antigens individually were able to reduce significantly the number of IFU/lung in challenged mice as compared to adjuvant immunized mice.

Thus, the combination of TC0197+TC0261+TC0666 is able to protect mice against *C. muridarum* challenge (FIG. 14). In particular, FIG. 14 shows protection in terms of reduction in the mean number of IFUs recovered from lungs of immunized mice versus adjuvant immunized controls [p=0.0024]. In contrast, the three antigens are not protective when administered individually (FIG. 15).

Example 14

Materials and Methods

The experimental protocols used in Examples 1, 2, 7 (repeated experiments), 8, 10 and 11 are described in further detail in this Example.

Bacterial Strains, Cultures and Reagents

*Chlamydia muridarum* Nigg and *Chlamydia trachomatis* serovar D strain D/UW-3/CX were grown on confluent monolayers of LLCMK2 (ATCC CCL7) or HeLa 229 cells (ATCC CCL 2.1) in Earle minimal essential medium (EMEM) as described (Caldwell et al. (1981) *Infect Immun* 31: 1161-1176). Purification of *C. trachomatis* and *C. muridarum* EBs was carried out by Renografin density gradient centrifugation as described (Montigiani et al. (2002) *Infect Immun* 70: 368-379.). Bacteria were aliquoted and stored at −70° C. in sucrose-phosphate-glutamine buffer (SPG) until use. When indicated, EBs were heat inactivated at 56° C. for 3 hours.

*E. coli* DH5α or BL21 (DE3) was grown aerobically in Luria Broth (LB) medium (Difco) at 37° C. When appropriate, ampicillin (100 μg/ml) and isopropyl-beta-D-galactopyranoside (IPTG, 0.5 mM) were added to the medium.

Unless specified, all chemicals were purchased from Sigma. Restriction enzymes and DNA modification enzymes were from New England Biolabs. Unless differently stated, all reagents and antibody for intracellular cytokine staining were from BD Biosciences Pharmingen. Confocal microscopy reagents were from Molecular Probes.

Gene Cloning, Protein Expression and Preparation of Antisera

To produce *C. trachomatis* recombinant proteins and their *C. muridarum* homologs, genes were PCR-amplified from *C. trachomatis* and *C. muridarum* chromosomal DNA using specific primers annealing at the 5' and 3' ends of either gene. The genes were cloned into plasmid pET21b$^+$ (Invitrogen) or pGEXKG (Amersham) in order to express them both as a C-terminal His-tag fusion and as a double fusion protein with an N-terminal Glutathione transferase-encoding sequence and a C-terminal His-tag.

Cloning and purification of His- and GST fusions were performed as already described (Montigiani et al., 2002). CT0681 and TC0052, encoding for *C. trachomatis* and *C. muridarum* MOMP respectively (Ct MOMP and Cm MOMP, respectively) were expressed as His fusions and purified from the insoluble protein fraction. With the exception of TC0313 and TC0210, all the *C. muridarum* proteins used in this work were purified only from the insoluble protein fraction in a denatured form.

For T cell in vitro stimulation assays, LPS-free proteins were prepared by washing of column-immobilized proteins with buffer Tris-HCl 10 mM, pH 8, containing 1% Triton X114 (35 ml) at 4° C. The amount of residual endotoxin was determined using a *Limulus* Amebocyte Lysate Analysis Kit (QCL-100, BioWhittaker, Walkerville, Md.).

Mouse antisera were generated and treated as described (Montigiani et al., 2002). Where specified, sera from mice immunized with 20 mg of *E. coli* contaminant proteins (IMAC-purified proteins from *E. coli* bacteria containing pET21b+ empty vector) were used as negative control. Western blot, ELISA and Flow cytometry of *C. trachomatis* EBs were performed as described (Finco et al. (2005) *Vaccine* 23: 1178-1188.).

Screening of Antigen Specific CD4-Th1 Response in Splenocytes from Infected Mice Groups of 6 week-old female BALB/c mice purchased from Charles River Laboratories (3 mice/group) received a subcutaneous hormonal treatment with 2.5 mg of Depo-provera (Medroxyprogesterone acetate) and after five days mice were inoculated intravaginally with 15 μl of SPG buffer containing $10^6$ of *C. trachomatis* IFU. The level of infection was analyzed 7 days post-challenge, by collecting vaginal swabs and counting chlamydial inclusions 48 h later stained with FITC-conjugated anti *Chlamydia* antibody (Merifluor) using a UV microscope.

The swabs were collected in 400 μl of SPG and were inoculated on LLCMK2 cell monolayers seeded on 96 w flat bottom plates. After 48 hours incubation the number of infectious chlamydiae was determined by counting chlamydial inclusions.

Ten days post challenge mice were sacrificed and their spleens were taken. Splenocytes were prepared by homogenization through a nylon filter (BD) and the erythrocytes were removed by hypotonic lysis in Ack lysis buffer ($NH_4Cl$ 0.155 M, $KHCO_3$ 10 mM, $Na_2EDTA$ 0.1 mM) for 3 minutes at RT, then the cells were plated in 96 wells plates at $2\times10^6$ cells per well and stimulated with 20 μg/ml of endotoxin-free specific antigen or with 4 μg/ml of purified EBS in presence of 1 μg/ml anti-CD28 antibody (BD Biosciences Pharmingen) for 4 h at 37° C. Brefeldin A (BFA; Sigma-Aldrich) was then added at a final concentration of 2.5 μg/ml and cells were incubated for an additional 16 h before intracellular cytokine staining. Cells were stained for viability with LIVE/DEAD® (Molecular Probes) dye according to the manufacturer's instructions. Cells were then fixed and permeabilized using the Cytofix/Cytoperm kit (BD Biosciences Pharmingen) and stained with fluorochrome-labelled monoclonal antibodies for the detection of cells expressing CD3, CD4 on the surface and intracellular IFNγ and IL-4. Finally, cells were resuspended in PBS 1% BSA. All antibodies for intracellular cytokine staining were purchased from BD Pharmingen. Acquisition of the samples was performed using a BD Canto flow cytometer and data were analyzed using FlowJo software (Tree Star Inc., Ashland, USA). The intracellular expression of IFNγ and IL-4 was analysed in CD4 expressing singlet cells, previously gated for, morphology, CD3 expression and viability. Cells were then harvested and stained for CD4 surface expression and IFNγ, or IL-4 intracellular production, to investigate whether the observed responses were of the Th1 (IFNγ) or Th2 (IL-4) type. As negative control, spleens from not infected mice were harvested and analyzed in parallel.

Preparation of CD4+ Th1 Cell Lines and of Antigen Presenting Cells (APCs)

Splenocytes were prepared by homogenization from spleens from donor Balb/c mice that had previously been infected intranasally with $10^3$ viable Elementary Bodies (EBs) of *Chlamydia muridarum* (*C. muridarum*) as described above. Following centrifugation at 1200 rpm and suspension in Macs Buffer (PBS PH 7.2 0.5% BSA and 2 mM EDTA), the cells were incubated with CD4 (L3T4) microbeads (Milteny Biotec) for 15 minutes and then loaded on a LS columns. The CD4 cells bound to the magnet were recovered, washed and suspended in RPMI 1640 supplemented with 2.5% fetal bovine serum (Hyclone), antibiotics, L-Glutammine 2 mM, Sodium Piruvate 1 mM, MEM Not essential amino Acids, MEM Vitamins (Gibco) and Beta-mercaptoethanol 0.5 μM. Then the cells were plated in 6 multiwell plates, $10^7$ cells/wells. After the first stimulation, the purified CD4 were washed twice and then plated with APCs as described below.

Also a CD4+ cell line with *C. trachomatis* was obtained by spleens from donor Balb/c mice that had previously been infected intravaginally with $10^6$ viable Elementary Bodies (EBs) of *Chlamydia trachomatis* and it was performed as described above for *Chlamydia muridarum.*

The CD4 cells were plated ($6\times10^6$/well) with APCs ($2\times10^7$/well) prepared by naive mice spleens. Splenocytes were prepared as described above, then were washed twice with the medium, gamma irradiated for 7 minutes washed again and suspended in medium.

Cultures were then incubated at 37° C. in a humidified atmosphere containing 5% $CO_2$. After 24 h, Aldesleukin Proleukin (IL2) was added at a concentration of 20 U/ml.

*C. Muridarum* and *C. Trachomatis*-Mouse Model of Adoptive Transfer

Groups of 6 week-old female BALB/c mice purchased from Charles River Laboratories (4 mice/group), were adoptively transferred by intravenous administration of $10^7$ CD4+ T cells in 100 μl of RPMI-1640 medium (Sigma). Mice were challenged intranasally 24 hours after with $10^3$ IFUs of *C. muridarum* or $10^5$ IFUs of *C. trachomatis*. The effect of adoptive immunization was evaluated by quantitating the number of IFUs recovered from lungs taken 10 days after *C. muridarum* challenge or 6 days after *C. trachomatis* challenge, as described above.

Characterization of the *C. Muridarum* CD4+ T Cell Line

The same day of the adoptive transfer, an aliquot of purified CD4+ T cells were taken to assess the capability of *C. muridarum* antigens identified in the previous CD4+ Th1+ screening to stimulate them in vitro. 250000 cells/w were plated in 96 multiwell plates with $10^6$ mouse splenocytes CD4 depleted as APC and stimulated with 20 μg/ml of *C. muridarum* proteins, homologous to the *C. trachomatis* proteins identified as CD4+ Th1 inducers, in presence of 1 μg/ml anti-CD28 antibody (BD Biosciences Pharmingen) for 3 h at 37° C. Then BFA was added and intracellular staining was carried out as described for the splenocytes.

Mouse Protection Model

Groups of 6 week-old female BALB/c mice (10-15 mice/group), were immunized intramuscularly (i.m.) with 3 doses of the antigen combinations TC0551-TC890 (15 μg/dose) and TC0106-TC0431 (containing 10 μg of each protein/dose) at days 1, 15, and 28 formulated with 5 μg of LTK63 (Ryan et al., 2000)+10 μg of CpG (ODN 1826) adjuvant dissolved in 50 μl PBS. As negative control, groups of mice that received the adjuvant alone were included and treated in parallel.

Three weeks after the last immunization mice were inoculated intranasally (i.n.) with 40 μl of SPG buffer containing $10^3$ IFU of *C. muridarum*. The *Chlamydia* challenge dose given to each mouse was confirmed by culturing in triplicate serial dilutions of the inoculating dose on LLCMK2 cell monolayers seeded on 96 wells flat bottom plates. After 24 hours incubation the number of infectious chlamydiae was determined by counting chlamydial inclusions. In the time period between 10- and 12 days post challenge mice were sacrificed, lungs were isolated and their homogenates were used to assess chlamydia growth.

Analysis of Antigen Specific CD4-Th1 Response in PBMC of Mice

PBMC from mouse were isolated from up to 2 ml of heparinized blood, diluted ⅕ in HBSS (Hanks' Balanced Salt Solution) and separated by density gradient centrifugation over Lympholite-M (Cedarlane). $10^6$ PBMC were plated in duplicate in 96 multiwell plates with $10^6$ mouse splenocytes CD4 depleted as APC and stimulated and stained as described above for mouse splenocytes for 16 h. In this staining was analyzed the expression of IFNγ, TNFα and IL-2.

Confocal Microscopy

To examine cellular localization of *C. trachomatis* proteins after infection, HeLa cells (20000) were plated on onto glass coverslides (Ø 13 mm) and after 24 hours were infected with CT EBs in 1:1 ratio as described above. At 6, 24, 48 and 72 hours post infection the cells were fixed in 2% paraformaldehyde in PBS buffer for 20 minutes at room temperature. After 2 washes with PBS the cells were permeabilized with a solution of 1%/saponin-0.1% Triton in PBS for 20 minutes.

After washing twice and blocking with PBS containing 1% BSA (PBS-BSA), the cell samples were subjected to antibody and chemical staining. The samples were incubated for 1 h at RT (standard dilution 1:5000 in PBS-BSA) with polyclonal antisera obtained from mice immunized with TC601, TC279, TC733 and TC153, previously pre-adsorbed overnight at 4° C. onto nitrocellulose strips containing *E. coli* BL21 cell total proteins. Goat anti-mouse Alexa Fluor (Molecular Probes) conjugated antibodies (excitation at 488) were used to visualize the localization of each antigen. Propidium Iodide and Phalloidin conjugated with Alexa Fluor dye A620 (Molecular Probes) were used to visualize respectively DNA and actin.

After extensive washes in PBS, cells were mounted with Anti-Fade reagent (Molecular Probes) and observed under a laser scanning confocal microscope (Bio-Rad) with 100× oil immersion objective lens.

It will be understood that the invention has been described by way of example only and modifications may be made whilst remaining within the scope and spirit of the invention.

TABLE 2

| *C. pneumoniae* accession number & annotation | *C. trachomatis* accession number & annotation | CT No. |
|---|---|---|
| | Hypothetical protein (AAC67968) | CT372 |
| | omcB (AAC68042) | CT443 |
| | Hypothetical protein (AAC67634) | CT043 |
| | Hypothetical protein (AAC67744) | CT153 |
| | Nqr3 (AAC67872) | CT279 |
| | papQ (AAC68203) | CT601 |
| | Hypothetical protein (AAC68306) | CT711 |
| | Hypothetical protein (AAC67705) | CT114 |
| | oppA_4 (AAC68080) | CT480 |
| | Hypothetical protein (AAC68056) | CT456 |
| | ArtJ (AAC67977) | CT381 |
| | IcrE (AAC67680) | CT089 |
| | Hypothetical protein (AAC68329) | CT734 |
| | Hypothetical protein (AAC67606) | CT016 |
| gi\|4376729\|gb\|AAD18590.1\| Polymorphic Outer Membrane Protein G Family | gi\|3329346\|gb\|AAC68469.1\| Putative Outer Membrane Protein G | |
| gi\|4376729\|gb\|AAD18590.1\| Polymorphic Outer Membrane Protein G Family | gi\|3329346\|gb\|AAC68469.1\| Putative Outer Membrane Protein G | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376731\|gb\|AAD18591.1\| Polymorphic Outer Membrane Protein G/I Family | gi\|3329350\|gb\|AAC68472.1\| Putative Outer Membrane Protein I | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376733\|gb\|AAD18593.1\| Polymorphic Outer Membrane Protein G Family | gi\|3328840\|gb\|AAC68009.1\| Putative outer membrane protein A | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376754\|gb\|AAD18611.1\| Polymorphic Outer Membrane Protein (Frame-shift with C | gi\|3329344\|gb\|AAC68467.1\| Putative Outer Membrane Protein E | |
| gi\|4376260\|gb\|AAD18163.1\| Polymorphic Outer Membrane Protein G Family | gi\|3329346\|gb\|AAC68469.1\| Putative Outer Membrane Protein G | |
| gi\|4376262\|gb\|AAD18165.1\| hypothetical protein | gi\|3328765\|gb\|AAC67940.1\| hypothetical protein | |
| gi\|4376269\|gb\|AAD18171.1\| hypothetical protein | gi\|3328825\|gb\|AAC67995.1\| hypothetical protein | |
| gi\|4376270\|gb\|AAD18172.1\| Polymorphic Outer Membrane Protein G Family | gi\|3329350\|gb\|AAC68472.1\| Putative Outer Membrane Protein I | |
| gi\|4376272\|gb\|AAD18173.1\| Predicted OMP {leader peptide: outer membrane} | gi\|3328772\|gb\|AAC67946.1\| hypothetical protein | CT351 |
| gi\|4376273\|gb\|AAD18174.1\| Predicted OMP {leader peptide} | gi\|3328771\|gb\|AAC67945.1\| hypothetical protein | CT350 |
| gi\|4376296\|gb\|AAD18195.1\| hypothetical protein | gi\|3328520\|gb\|AAC67712.1\| Ribulose-P Epimerase | |
| gi\|4376362\|gb\|AAD18254.1\| YbbP family hypothetical protein | gi\|3328401\|gb\|AAC67602.1\| hypothetical protein | |
| gi\|4376372\|gb\|AAD18263.1\| Signal Peptidase I | gi\|3328410\|gb\|AAC67610.1\| Signal Peptidase I | |
| gi\|4376397\|gb\|AAD18286.1\| CHLPS hypothetical protein | gi\|3328506\|gb\|AAC67700.1\| CHLPS hypothetical protein | |
| gi\|4376402\|gb\|AAD18290.1\| ACR family | gi\|3328505\|gb\|AAC67699.1\| ACR family | |
| gi\|4376419\|gb\|AAD18305.1\| CT149 hypothetical protein | gi\|3328551\|gb\|AAC67740.1\| possible hydrolase | |
| gi\|4376446\|gb\|AAD18330.1\| hypothetical protein | gi\|3329261\|gb\|AAC68390.1\| hypothetical protein | |
| gi\|4376466\|gb\|AAD18348.1\| Oligopeptide Binding Protein | gi\|3328604\|gb\|AAC67790.1\| Oligopeptide Binding Protein | CT198 |
| gi\|4376467\|gb\|AAD18349.1\| Oligopeptide Binding Protein | gi\|3328604\|gb\|AAC67790.1\| Oligopeptide Binding Protein | |
| gi\|4376468\|gb\|AAD18350.1\| Oligopeptide Binding Protein | gi\|3328539\|gb\|AAC67730.1\| Oligopeptide Binding Protein | |
| gi\|4376469\|gb\|AAD18351.1\| Oligopeptide Binding Protein | gi\|3328579\|gb\|AAC67766.1\| Oligopeptide binding protein permease | |
| gi\|4376520\|gb\|AAD18398.1\| Polysaccharide Hydrolase-Invasin Repeat Family | gi\|3328526\|gb\|AAC67718.1\| predicted polysaccharide hydrolase-invasin repeat family | |
| gi\|4376567\|gb\|AAD18441.1\| Inclusion Membrane Protein C | gi\|3328642\|gb\|AAC67825.1\| Inclusion Membrane Protein C | |
| gi\|4376576\|gb\|AAD18449.1\| Omp85 Analog | gi\|3328651\|gb\|AAC67834.1\| Omp85 Analog | CT241 |
| gi\|4376577\|gb\|AAD18450.1\| (OmpH-Like Outer Membrane Protein) | gi\|3328652\|gb\|AAC67835.1\| (OmpH-Like Outer Membrane Protein) | CT242 |
| gi\|4376601\|gb\|AAD18472.1\| Low Calcium Response D | gi\|3328486\|gb\|AAC67681.1\| Low Calcium Response D | |
| gi\|4376602\|gb\|AAD18473.1\| Low Calcium Response E | gi\|3328485\|gb\|AAC67680.1\| Low Calcium Response E | CT089 |
| gi\|4376607\|gb\|AAD18478.1\| Phopholipase D Superfamily | gi\|3328479\|gb\|AAC67675.1\| Phopholipase D Superfamily {leader (33) peptide} | |
| gi\|4376615\|gb\|AAD18485.1\| YojL hypothetical protein | gi\|3328472\|gb\|AAC67668.1\| hypothetical protein | CT077 |
| gi\|4376624\|gb\|AAD18493.1\| Solute Protein Binding Family | gi\|3328461\|gb\|AAC67658.1\| Solute Protein Binding Family | |
| gi\|4376639\|gb\|AAD18507.1\| Flagellar Secretion Protein | gi\|3328453\|gb\|AAC67651.1\| Flagellar Secretion Protein | |

TABLE 2-continued

| *C. pneumoniae* accession number & annotation | *C. trachomatis* accession number & annotation | CT No. |
|---|---|---|
| gi\|4376664\|gb\|AAD18529.1\| Leucyl Aminopeptidase A | gi\|3328437\|gb\|AAC67636.1\| Leucyl Aminopeptidase A | CT045 |
| gi\|4376672\|gb\|AAD18537.1\| CBS Domain protein (Hemolysin Homolog) | gi\|3328667\|gb\|AAC67849.1\| Hypothetical protein containing CBS domains | |
| gi\|4376679\|gb\|AAD18543.1\| CT253 hypothetical protein | gi\|3328664\|gb\|AAC67846.1\| hypothetical protein | |
| gi\|4376696\|gb\|AAD18559.1\| CT266 hypothetical protein | gi\|3328678\|gb\|AAC67859.1\| hypothetical protein | CT266 |
| gi\|4376717\|gb\|AAD18579.1\| Phospholipase D superfamily | gi\|3328698\|gb\|AAC67877.1\| Phospholipase D superfamily | |
| gi\|4376727\|gb\|AAD18588.1\| Polymorphic Outer Membrane Protein G/I Family | gi\|3329346\|gb\|AAC68469.1\| Putative Outer Membrane Protein G | |
| gi\|4376728\|gb\|AAD18589.1\| Polymorphic Outer Membrane Protein G Family | gi\|3329346\|gb\|AAC68469.1\| Putative Outer Membrane Protein G | |
| gi\|4376729\|gb\|AAD18590.1\| Polymorphic Outer Membrane Protein G Family | gi\|3329350\|gb\|AAC68472.1\| Putative Outer Membrane Protein I | |
| gi\|4376731\|gb\|AAD18591.1\| Polymorphic Outer Membrane Protein G/I Family | gi\|3329350\|gb\|AAC68472.1\| Putative Outer Membrane Protein I | |
| gi\|4376733\|gb\|AAD18593.1\| Polymorphic Outer Membrane Protein G Family | gi\|3328840\|gb\|AAC68009.1\| Putative outer membrane protein A | |
| gi\|4376735\|gb\|AAD18594.1\| Polymorphic Outer Membrane Protein (truncated) A/I Fam | gi\|3328840\|gb\|AAC68009.1\| Putative outer membrane protein A | |
| gi\|4376736\|gb\|AAD18595.1\| Polymorphic Outer Membrane Protein G Family | gi\|3329346\|gb\|AAC68469.1\| Putative Outer Membrane Protein G | |
| gi\|4376737\|gb\|AAD18596.1\| Polymorphic Outer Membrane Protein H Family | gi\|3329347\|gb\|AAC68470.1\| Putative Outer Membrane Protein H | |
| gi\|4376751\|gb\|AAD18608.1\| Polymorphic Outer Membrane Protein E Family | gi\|3329344\|gb\|AAC68467.1\| Putative Outer Membrane Protein E | |
| gi\|4376752\|gb\|AAD18609.1\| Polymorphic Outer Membrane Protein E Family | gi\|3329344\|gb\|AAC68467.1\| Putative Outer Membrane Protein E | |
| gi\|4376753\|gb\|AAD18610.1\| Polymorphic Outer Membrane Protein E/F Family | gi\|3329344\|gb\|AAC68467.1\| Putative Outer Membrane Protein E | |
| gi\|4376757\|gb\|AAD18613.1\| hypothetical protein | gi\|3328701\|gb\|AAC67880.1\| PP-loop superfamily ATPase | |
| gi\|4376767\|gb\|AAD18622.1\| Arginine Periplasmic Binding Protein | gi\|3328806\|gb\|AAC67977.1\| Arginine Binding Protein | CT381 |
| gi\|4376790\|gb\|AAD18643.1\| Heat Shock Protein-70 | gi\|3328822\|gb\|AAC67993.1\| HSP-70 | CT396 |
| gi\|4376802\|gb\|AAD18654.1\| CT427 hypothetical protein | gi\|3328857\|gb\|AAC68024.1\| hypothetical protein | |
| gi\|4376814\|gb\|AAD18665.1\| CT398 hypothetical protein | gi\|3328825\|gb\|AAC67995.1\| hypothetical protein | CT398 |
| gi\|4376829\|gb\|AAD18679.1\| polymorphic membrane protein A Family | gi\|3328840\|gb\|AAC68009.1\| Putative outer membrane protein A | |
| gi\|4376830\|gb\|AAD18680.1\| polymorphic membrane protein B Family | gi\|3328841\|gb\|AAC68010.1\| Putative outer membrane protein B | |
| gi\|4376832\|gb\|AAD18681.1\| Solute binding protein | gi\|3328844\|gb\|AAC68012.1\| Solute-binding protein | CT415 |
| gi\|4376834\|gb\|AAD18683.1\| (Metal Transport Protein) | gi\|3328846\|gb\|AAC68014.1\| (Metal Transport Protein) | |
| gi\|4376847\|gb\|AAD18695.1\| Tail-Specific Protease | gi\|3328872\|gb\|AAC68040.1\| Tail-Specific Protease | |
| gi\|4376848\|gb\|AAD18696.1\| 15 kDa Cysteine-Rich Protein | gi\|3328873\|gb\|AAC68041.1\| 15 kDa Cysteine-Rich Protein | |
| gi\|4376849\|gb\|AAD18697.1\| 60 kDa Cysteine-Rich OMP | gi\|3328874\|gb\|AAC68042.1\| 60 kDa Cysteine-Rich OMP | CT443 |
| gi\|4376850\|gb\|AAD18698.1\| 9 kDa-Cysteine-Rich Lipoprotein | gi\|3328876\|gb\|AAC68043.1\| 9 kDa-Cysteine-Rich Lipoprotein | CT444 |
| gi\|4376878\|gb\|AAD18723.1\| 2-Component Sensor | gi\|3328901\|gb\|AAC68067.1\| 2-component regulatory system-sensor histidine kinase | CT467 |
| gi\|4376879\|gb\|AAD18724.1\| similarity to CHLPS IncA | gi\|3328451\|gb\|AAC67649.1\| hypothetical protein | |
| gi\|4376884\|gb\|AAD18729.1\| CT471 hypothetical protein | gi\|3328905\|gb\|AAC68071.1\| hypothetical protein | |
| gi\|4376886\|gb\|AAD18731.1\| YidD family | gi\|3328908\|gb\|AAC68073.1\| hypothetical protein | |
| gi\|4376890\|gb\|AAD18734.1\| CT476 hypothetical protein | gi\|3328911\|gb\|AAC68076.1\| hypothetical protein | |
| gi\|4376892\|gb\|AAD18736.1\| Oligopeptide Permease | gi\|3328913\|gb\|AAC68078.1\| Oligopeptide Permease | |
| gi\|4376894\|gb\|AAD18738.1\| Oligopeptide Binding Lipoprotein | gi\|3328915\|gb\|AAC68080.1\| oligopeptide Binding Lipoprotein | |
| gi\|4376900\|gb\|AAD18743.1\| Glutamine Binding Protein | gi\|3328922\|gb\|AAC68086.1\| Glutamine Binding Protein | |
| gi\|4376909\|gb\|AAD18752.1\| Protease | gi\|6578107\|gb\|AAC68094.2\| Protease | |
| gi\|4376952\|gb\|AAD18792.1\| Apolipoprotein N-Acetyltransferase | gi\|3328972\|gb\|AAC68136.1\| Apolipoprotein N-Acetyltransferase | |
| gi\|4376960\|gb\|AAD18800.1\| FKBP-type peptidyl-prolyl cis-trans isomerise | gi\|3328979\|gb\|AAC68143.1\| FKBP-type peptidyl-prolyl cis-trans isomerise | CT541 |
| gi\|4376968\|gb\|AAD18807.1\| CT547 hypothetical protein | gi\|3328986\|gb\|AAC68149.1\| hypothetical protein | CT547 |
| gi\|4376969\|gb\|AAD18808.1\| CT548 hypothetical protein | gi\|3328987\|gb\|AAC68150.1\| hypothetical protein | |
| gi\|4376998\|gb\|AAD18834.1\| Major Outer Membrane Protein | gi\|3329133\|gb\|AAC68276.1\| Major Outer Membrane Protein | CT681 |
| gi\|4377005\|gb\|AAD18841.1\| YopC/Gen Secretion Protein D | gi\|3329125\|gb\|AAC68269.1\| probable Yop proteins translocation protein | |
| gi\|4377015\|gb\|AAD18851.1\| FHA domain; (homology to adenylate cyclase) | gi\|3329115\|gb\|AAC68259.1\| (FHA domain; homology to adenylate cyclase) | |
| gi\|4377033\|gb\|AAD18867.1\| CHLPN 76 kDa Homolog_1 (CT622) | gi\|3329069\|gb\|AAC68226.1\| CHLPN 76 kDa Homolog | CT622 |
| gi\|4377034\|gb\|AAD18868.1\| CHLPN 76 kDa Homolog_2 (CT623) | gi\|6578109\|gb\|AAC68227.2\| CHLPN 76 kDa Homolog | CT623 |
| gi\|4377035\|gb\|AAD18869.1\| Integral Membrane Protein | gi\|3329071\|gb\|AAC68228.1\| Integral Membrane Protein | |
| gi\|4377072\|gb\|AAD18902.1\| CT648 hypothetical protein | gi\|3329097\|gb\|AAC68825.1\| hypothetical protein | |
| gi\|4377073\|gb\|AAD18903.1\| CT647 hypothetical protein | gi\|3329096\|gb\|AAC68824.1\| hypothetical protein | CT647 |
| gi\|4377085\|gb\|AAD18914.1\| CT605 hypothetical protein | gi\|3329050\|gb\|AAC68208.1\| hypothetical protein | |
| gi\|4377090\|gb\|AAD18919.1\| Peptidoglycan-Associated Lipoprotein | gi\|3329044\|gb\|AAC68202.1\| Peptidoglycan-Associated Lipoprotein | CT600 |
| gi\|4377091\|gb\|AAD18920.1\| macromolecule transporter | gi\|3329043\|gb\|AAC68201.1\| component of a macromolecule transport system | |
| gi\|4377092\|gb\|AAD18921.1\| CT598 hypothetical protein | gi\|3329042\|gb\|AAC68200.1\| hypothetical protein | |

TABLE 2-continued

| *C. pneumoniae* accession number & annotation | *C. trachomatis* accession number & annotation | CT No. |
|---|---|---|
| gi\|4377093\|gb\|AAD18922.1\| Biopolymer Transport Protein | gi\|3329041\|gb\|AAC68199.1\| Biopolymer Transport Protein | CT597 |
| gi\|4377094\|gb\|AAD18923.1\| Macromolecule transporter | gi\|3329040\|gb\|AAC68198.1\| polysaccharide transporter | |
| gi\|4377101\|gb\|AAD18929.1\| CT590 hypothetical protein | gi\|3329033\|gb\|AAC68192.1\| hypothetical protein | |
| gi\|4377102\|gb\|AAD18930.1\| CT589 hypothetical protein | gi\|3329032\|gb\|AAC68191.1\| hypothetical protein | CT589 |
| gi\|4377106\|gb\|AAD18933.1\| hypothetical protein | gi\|3328796\|gb\|AAC67968.1\| hypothetical protein | |
| gi\|4377111\|gb\|AAD18938.1\| Enolase | gi\|3329030\|gb\|AAC68189.1\| Enolase | CT587 |
| gi\|4377127\|gb\|AAD18953.1\| General Secretion Protein D | gi\|3329013\|gb\|AAC68174.1\| Gen. Secretion Protein D | |
| gi\|4377130\|gb\|AAD18956.1\| predicted OMP {leader peptide} | gi\|3329010\|gb\|AAC68171.1\| predicted OMP | CT569 |
| gi\|4377132\|gb\|AAD18958.1\| CT567 hypothetical protein | gi\|3329008\|gb\|AAC68169.1\| hypothetical protein | CT567 |
| gi\|4377133\|gb\|AAD18959.1\| CT566 hypothetical protein | gi\|3329007\|gb\|AAC68168.1\| hypothetical protein | |
| gi\|4377140\|gb\|AAD18965.1\| Yop Translocation J | gi\|3329000\|gb\|AAC68161.1\| Yop proteins translocation lipoprotein J | CT559 |
| gi\|4377170\|gb\|AAD18992.1\| Outer Membrane Protein B | gi\|3329169\|gb\|AAC68308.1\| Outer Membrane Protein Analog | CT713 |
| gi\|4377177\|gb\|AAD18998.1\| Flagellar M-Ring Protein | gi\|3329175\|gb\|AAC68314.1\| Flagellar M-Ring Protein | |
| gi\|4377182\|gb\|AAD19003.1\| CT724 hypothetical protein | gi\|3329181\|gb\|AAC68319.1\| hypothetical protein | |
| gi\|4377184\|gb\|AAD19005.1\| Rod Shape Protein | gi\|3329183\|gb\|AAC68321.1\| Rod Shape Protein | |
| gi\|4377193\|gb\|AAD19013.1\| CT734 hypothetical protein | gi\|3329192\|gb\|AAC68329.1\| hypothetical protein | |
| gi\|4377206\|gb\|AAD19025.1\| CHLTR possible phosphoprotein | gi\|3329204\|gb\|AAC68339.1\| CHLTR possible phosphoprotein | |
| gi\|4377222\|gb\|AAD19040.1\| Muramidase (invasin repeat family) | gi\|3329221\|gb\|AAC68354.1\| Muramidase (invasin repeat family) | CT759 |
| gi\|4377223\|gb\|AAD19041.1\| Cell Division Protein FtsW | gi\|3329222\|gb\|AAC68355.1\| Cell Division Protein FtsW | |
| gi\|4377224\|gb\|AAD19042.1\| Peptidoglycan Transferase | gi\|3329223\|gb\|AAC68356.1\| Peptidoglycan Transferase | CT761 |
| gi\|4377225\|gb\|AAD19043.1\| Muramate-Ala Ligase & D-Ala-D-Ala Ligase | gi\|3329224\|gb\|AAC68357.1\| UDP-N-acetylmuramate-alanine ligase | |
| gi\|4377248\|gb\|AAD19064.1\| Thioredoxin Disulfide Isomerase | gi\|3329244\|gb\|AAC68375.1\| Thioredoxin Disulfide Isomerase | |
| gi\|4377261\|gb\|AAD19076.1\| CT788 hypothetical protein - {leader peptide-periplasmi | gi\|3329253\|gb\|AAC68383.1\| {leader (60) peptide-periplasmic} | |
| gi\|4377280\|gb\|AAD19093.1\| Insulinase family/Protease III | gi\|3329273\|gb\|AAC68402.1\| Insulinase family/Protease III | |
| gi\|4377287\|gb\|AAD19099.1\| Putative Outer Membrane Protein D Family | gi\|3329279\|gb\|AAC68408.1\| Putative Outer Membrane Protein D | |
| gi\|4377306\|gb\|AAD19116.1\| DO Serine Protease | gi\|3329293\|gb\|AAC68420.1\| DO Serine Protease | CT823 |
| gi\|4377342\|gb\|AAD19149.1\| ABC transporter permease | gi\|3329327\|gb\|AAC68451.1\| ABC transporter permease - pyrimidine biosynthesis protein | |
| gi\|4377347\|gb\|AAD19153.1\| CT858 hypothetical protein | gi\|6578118\|gb\|AAC68456.2\| predicted Protease containing IRBP and DHR domains | |
| gi\|4377353\|gb\|AAD19159.1\| CT863 hypothetical protein | gi\|3329337\|gb\|AAC68461.1\| hypothetical protein | |
| gi\|4377367\|gb\|AAD19171.1\| Predicted OMP | gi\|3328795\|gb\|AAC67967.1\| hypothetical protein | |
| gi\|4377408\|gb\|AAD19209.1\| hypothetical protein | gi\|3328795\|gb\|AAC67967.1\| hypothetical protein | |
| gi\|4377409\|gb\|AAD19210.1\| Predicted Outer Membrane Protein (CT371) | gi\|3328795\|gb\|AAC67967.1\| hypothetical protein | |
| gi\|4376411\|gb\| | gi\|3328512\|gb\|AAC67705.1\| hypothetical protein | CT114 |
| gi\|4376508\|gb\| | gi\|3328585\|gb\|AAC67772.1\| hypothetical protein | CT181 |
| gi\|4376710\|gb\| | gi\|3328692\|gb\|AAC67872.1\| NADH (Ubiquinone) Oxidoreductase, Gamma | CT279 |
| gi\|4376777\|gb\| | gi\|3328815\|gb\|AAC67986.1\| hypothetical protein | CT389 |
| gi\|4376782\|gb\| | gi\|3328817\|gb\|AAC67988.1\| hypothetical protein | CT391 |
| gi\|4376863\|gb\| | gi\|3328887\|gb\|AAC68054.1\| Arginyl tRNA transferase | CT454 |
| gi\|4376866\|gb\| | gi\|3328889\|gb\|AAC68056.1\| hypothetical protein | CT456 |
| gi\|4376972\|gb\| | gi\|3328991\|gb\|AAC68153.1\| D-Ala-D-Ala Carboxypeptidase | CT551 |
| gi\|4377139\|gb\| | gi\|3329001\|gb\|AAC68162.1\| hypothetical protein | CT560 |
| gi\|4377154\|gb\| | gi\|3329154\|gb\|AAC68295.1\| hypothetical protein | CT700 |

SEQUENCE LISTING

SEQ ID NO: 1 - CT733 nucleotide sequence

```
ATGTTAATAAACTTTACCTTTCGCAACTGTCTTTTGTTCCTTGTCACACTGTCTAGTGTCCCTGTTTTCTCAGCACC
TCAACCTCGCGGAACGCTTCCTAGCTCGACCACAAAAATTGGATCAGAAGTTTGGATTGAACAAAAAGTCCGCCAAT
ATCCAGAGCTTTTATGGTTAGTAGAGCCGTCCTCTACGGGAGCCTCTTTAAAATCTCCTTCAGGAGCCATCTTTTCT
CCAACATTATTCCAAAAAAAGGTCCCTGCTTTCGATATCGCAGTGCGCAGTTTGATTCACTTACATTTATTAATCCA
GGGTTCCCGCCAAGCCTATGCTCAACTGATCCAACTACAGACCAGCGAATCCCCTCTAACATTTAAGCAATTCCTTG
CATTGCATAAGCAATTAACTCTATTTTTAAATTCCCCTAAGGAATTTTATGACTCTGTTAAAGTGTTAGAGACAGCT
ATCGTCTTACGTCACTTAGGCTGTTCAACTAAGGCTGTTGCTGCGTTTAAACCTTATTTCTCAGAAATGCAAAGAGA
GGCTTTTTACACTAAGGCTCTGCATGTACTACACACCTTCCCAGAGCTAAGCCCATCATTTGCTCGCCTCTCTCCGG
AGCAGAAAACTCTCTTCTTCTCCTTGAGAAAATTGGCGAATTACGATGAGTTACTCTCGCTGACGAACACCCCAAGT
TTTCAGCTTCTGTCTGCTGGGCGCTCGCAACGAGCTCTTTTAGCTCTGGACTTGTACCTCTATGCTTTGGATTCCTG
TGGAGAACAGGGGATGTCCTCTCAATTCCACACAAACTTCGCACCTCTACAGTCCATGTTGCAACAATACGCTACTG
TAGAAGAGGCCTTTTCTCGTTATTTTACTTACCGAGCTAATCGATTAGGATTTGATGGCTCTTCTCGATCCGAGATG
GCTTTAGTAAGAATGGCCACCTTGATGAACTTGTCTCCTTCCGAAGCTGCGATTTTAACCACAAGCTTCAAAACCCT
TCCTACAGAAGAAGCGGATACTTTGATCAATAGTTTCTATACCAATAAGGGCGATTCGTTGGCTCTTTCTCTGCGAG
GGTTGCCTACACTTGTATCCGAACTGACGCGAACTGCCCATGGCAATACCAATGCAGAAGCTCGATCTCAGCAAATT
TATGCAACTACCCTATCGCTAGTAGTAAAGAGTCTGAAAGCGCACAAAGAAATGCTAAACAAGCAAATTCTTTCTAA
GGAAATTGTTTTAGATTTCTCAGAAACTGCAGCTTCTTGCCAAGGATTGGATATCTTTTCCGAGAATGTCGCTGTTC
AAATTCACTTAAATGGAACCGTTAGTATCCATTTATAA
```

-continued

SEQUENCE LISTING

SEQ ID NO: 2 - CT733 protein sequence
MLINFTFRNCLLFLVTLSSVPVFSAPQPRGTLPSSTTKIGSEVWIEQKVRQYPELLWLVEPSSTGASLKSPSGAIFS
PTLFQKKVPAFDIAVRSLIHLHLLIQGSRQAYAQLIQLQTSESPLTFKQFLALHKQLTLFLNSPKEFYDSVKVLETA
IVLRHLGCSTKAVAAFKPYFSEMQREAFYTKALHVLHTFPELSPSFARLSPEQKTLFFSLRKLANYDELLSLTNTPS
FQLLSAGRSQRALLALDLYLYALDSCGEQGMSSQFHTNFAPLQSMLQQYATVEEAFSRYFTYRANRLGFDGSSRSEM
ALVRMATLMNLSPSEAAILTTSFKTLPTEEADTLINSFYTNKGDSLALSLRGLPTLVSELTRTAHGNTNAEARSQQI
YATTLSLVVKSLKAHKEMLNKQILSKEIVLDFSETAASCQGLDIFSENVAVQIHLNGTVSIHL SEQ ID NO: 3 - CT153 nucleotide sequence
ATGACTAAGCCTTCTTTCTTATACGTTATTCAACCTTTTTCCGTATTTAATCCACGATTAGGACGTTTCTCTACAGA
CTCAGATACTTATATCGAAGAAGAAAACCGCCTAGCATCGTTCATTGAGAGTTTGCCACTGGAGATCTTCGATATAC
CTTCTTTCATGGAAACCGCGATTTCCAATAGCCCCTATATTTTATCTTGGGAGACAACTAAAGACGGCGCTCTGTTC
ACTATTCTTGAACCCAAACTCTCAGCTTGCGCAGCCACTTGCCTGGTAGCCCCTTCTATACAAATGAAATCCGATGC
GGAGCTCCTAGAAGAAATTAAGCAAGCGTTATTACGCAGCTCTCATGACGGTGTGAAATATCGCATCACCAGAGAAT
CCTTCTCTCCAGAAAAGAAAACTCCTAAGGTTGCTCTAGTCGATGACGATATTGAATTGATTCGCAATGTCGACTTT
TTGGGTAGAGCTGTTGACATTGTCAAATTAGACCCTATTAATATTCTGAATACCGTAAGCGAAGAGAATATTCTAGA
TTACTCTTTTACAAGAGAAACGGCTCAGCTGAGCGCGGATGGTCGTTTTGGTATTCCTCCAGGGACTAAGCTATTCC
CTAAACCTTCTTTTGATGTAGAAATCAGTACCTCCATTTTCGAAGAAACAACTTCATTTACTCGAAGTTTTTCTGCA
TCGGTTACTTTTAGTGTACCAGACCTCGCGGCGACTATGCCTCTTCAAAGCCCTCCCATGGTAGAAAATGGTCAAAA
AGAAATTTGTGTCATTCAAAAACACTTATTCCCAAGCTACTCTCCTAAACTAGTCGATATTGTTAAACGATACAAAA
GAGAGGCTAAGATCTTGATTAACAAGCTTGCCTTTGGAATGTTATGGCGACATCGGGCTAAAAGCCAAATCCTCACC
GAGGGAAGCGTACGTCTAGACTTACAAGGATTCACAGAATCGAAGTACAATTACCAGATTCAAGTAGGATCCCATAC
GATTGCAGCTGTATTAATCGATATGGATATTTCCAAGATTCAATCCAAATCAGAACAAGCTTATGCAATTAGGAAAA
TCAAATCAGGCTTTCAACGTAGCTTGGATGACTATCATATTTATCAAATTGAAAGAAAACAAACCTTTTCTTTTTCT
CCGAAGCATCGCAGCCTCTCATCCACATCCCATTCCGAAGATTCTGATTTGGATCTTTCTGAAGCAGCCGCCTTTTC
AGGAAGTCTTACCTGCGAGTTTGTAAAAAAAAGCACTCAACATGCCAAGAATACCGTCACATGTTCCACAGCCGCTC
ATTCCCTATACACACTCAAAGAAGATGACAGCTCGAACCCCTCTGAAAAACGATTAGATAGTTGTTTCCGCAATTGG
ATTGAAAACAAACTAAGCGCCAATTCTCCAGATTCCTGGTCAGCGTTTATTCAAAAATTCGGAACACACTATATTGC
ATCAGCAACTTTTGGAGGGATAGGTTTCCAAGTGCTCAAACTATCTTTTGAACAGGTGGAGGATCTACATAGCAAAA
AGATCTCCTTAGAAACCGCAGCAGCCAACTCTCTATTAAAAGGTTCTGTATCCAGCAGCACAGAATCTGGATACTCC
AGCTATAGCTCCACGTCTTCTTCTCATACGGTATTTTTAGGAGGAACGGTCTTACCTTCGGTTCATGATGAACGTTT
AGACTTTAAAGATTGGTCGGAAAGTGTGCACCTGGAACCTGTTCCTATCCAGGTTTCTTTACAACCTATAACGAATT
TACTAGTTCCTCTCCATTTTCCTAATATCGGTGCTGCAGAGCTCTCTAATAAACGAGAATCTCTTCAACAAGCGATT
CGAGTCTATCTCAAAGAACATAAAGTAGATGAGCAAGGAGAACGTACTACATTTACATCAGGAATCGATAATCCTTC
TTCCTGGTTTACCTTAGAAGCTGCCCACTCTCCTCTTATAGTCAGTACTCCTTACATTGCTTCGTGGTCTACGCTTC
CTTATTTGTTCCCAACATTAAGAGAACGTTCTTCGGCAACCCCTATCGTTTTCTATTTTTGTGTAGATAATAATGAA
CATGCTTCGCAAAAAATATTAAACCAATCGTATTGCTTCCTCGGGTCCTTGCCTATTCGACAAAAAATTTTTGGTAG
CGAATTTGCTAGTTTCCCCTATCTATCTTTCTATGGAAATGCAAAAGAGGCGTACTTTGATAACACGTACTACCCAA
CGCGTTGTGGGTGGATTGTTGAAAAGTTAAATACTACACAAGATCAATTCCTCCGGGATGGAGACGAGGTGCGACTA
AAACATGTTTCCAGCGGAAAGTATCTAGCAACAACTCCTCTTAAGGATACCCATGGTACACTCACGCGTACAACGAA
CTGTGAAGATGCTATCTTTATTATTAAAAAATCTTCAGGTTATTGA SEQ ID NO: 4 - CT153 protein sequence
MTKPSFLYVIQPFSVFNPRLGRFSTDSDTYIEEENRLASFIESLPLEIFDIPSFMETAISNSPYILSWETTKDGALF
TILEPKLSACAATCLVAPSIQMKSDAELLEEIKQALLRSSHDGVKYRITRESFSPEKKTPKVALVDDDIELIRNVDF
LGRAVDIVKLDPINILNTVSEENILDYSFTRETAQLSADGRFGIPPGTKLFPKPSFDVEISTSIFEETTSFTRSFSA
SVTFSVPDLAATMPLQSPPMVENGQKEICVIQKHLFPSYSPKLVDIVKRYKREAKILINKLAFGMLWRHRAKSQILT
EGSVRLDLQGFTESKYNYQIQVGSHTIAAVLIDMDISKIQSKSEQAYAIRKIKSGFQRSLDDYHIYQIERKQTFSFS
PKHRSLSSTSHSEDSDLDLSEAAAFSGSLTCEFVKKSTQHAKNTVTCSTAAHSLYTLKEDDSSNPSEKRLDSCFRNW
IENKLSANSPDSWSAFIQKFGTHYIASATFGGIGFQVLKLSFEQVEDLHSKKISLETAAANSLLKGSVSSSTESGYS
SYSSTSSSHTVFLGGTVLPSVHDERLDFKDWSESVHLEPVPIQVSLQPITNLLVPLHFPNIGAAELSNKRESLQQAI
RVYLKEHKVDEQGERTTFTSGIDNPSSWFTLEAAHSPLIVSTPYIASWSTLPYLFPTLRERSSATPIVFYFCVDNNE
HASQKILNQSYCFLGSLPIRQKIFGSEFASFPYLSFYGNAKEAYFDNTYYPTRCGWIVEKLNTTQDQFLRDGDEVRL
KHVSSGKYLATTPLKDTHGTLTRTTNCEDAIFIIKKSSGY SEQ ID NO: 5 - CT601 nucleotide sequence
ATGCTCGCTAATCGCTTATTCTTAATAACCCTTTTAGGGTTAAGTTCGTCTGTTTACGGCGCAGGTAAAGCACCGTC
TTTGCAGGCTATTCTAGCCGAAGTCGAAGACACCTCCTCTCGTCTACACGCTCATCACAATGAGCTTGCTATGATCT
CTGAACGCCTCGATGAGCAAGACACGAAACTACAGCAACTTTCGTCAACACAAGATCATAACCTACCTCGACAAGTT
CAGCGACTAGAAACGGACCAAAAAGCTTTGGCAAAAACACTGGCGATTCTTTCGCAATCCGTCCAAGATATTCGGTC
TTCTGTACAAAATAAATTACAAGAAATCCAACAAGAACAAAAAAAATTAGCACAAAATTTGCGAGCGCTTCGTAACT
CTTTACAAGCTCTCGTTGATGGCTCTTCTCCAGAAAATTATATTGATTTCCTAACTGGTGAAACCCCGGAACATATT
CATATTGTTAAACAAGGAGAGACCCTGAGCAAGATCGCGAGTAAATATAACATCCCCGTCGTAGAATTAAAAAAACT
TAATAAACTAAATTCGGATACTATTTTTACAGATCAAAGAATTCGCCTTCCGAAAAAGAAATAG SEQ ID NO: 6 - CT601 protein sequence
MLANRLFLITLLGLSSSVYGAGKAPSLQAILAEVEDTSSRLHAHHNELAMISERLDEQDTKLQQLSSTQDHNLPRQV
QRLETDQKALAKTLAILSQSVQDIRSSVQNKLQEIQQEQKKLAQNLRALRNSLQALVDGSSPENYIDFLTGETPEHI
HIVKQGETLSKIASKYNIPVVELKKLNKLNSDTIFTDQRIRLPKKK SEQ ID NO: 7 - CT279 nucleotide sequence
ATGGCATCCAAGTCTCGCCATTATCTTAATCAGCCTTGGTACATTATCTTATTCATCTTTGTTCTTAGTTTAATTGC
TGGTACCCTCCTGTCTTCTGTGTATTATGTCCTTGCACCTATCCAACAGCAAGCTGCGGAATTCGATCGCAATCAAC
AAATGCTAATGGCTGCACAAGTAATTTCTTCCGATAACACATTCCAAGTCTATGAAAAGGGAGATTGGCACCCAGCC
CTATATAATACTAAAAAGCAGTTGCTAGAGATCTCCTCTACTCCTCCTAAAGTAACCGTGACAACTTTAAGCTCATA
TTTTCAAAACTTTGTTAGAGTCTTGCTTACAGATACACAAGGAAATCTTTCTTCATTCGAAGACCATAATCTCAATC
TAGAAGAATTTTTATCTCAACCAACTCCTGTAATACATGGTCTTGCCCTTTATGTGGTCTACGCTATCCTACACAAC -continued

SEQUENCE LISTING

GATGCAGCTTCCTCTAAATTATCTGCTTCCCAAGTAGCGAAAAATCCAACAGCTATAGAATCTATAGTTCTTCCTAT
AGAAGGTTTTGGTTTGTGGGGACCTATCTATGGATTCCTTGCTCTAGAAAAAGACGGGAATACTGTTCTTGGTACTT
CTTGGTATCAACATGGCGAGACTCCTGGATTAGGAGCAAATATCGCTAACCCTCAATGGCAAAAAAATTTCAGAGGC
AAAAAAGTATTTCTAGTCTCAGCTTCTGGAGAAACAGATTTTGCTAAGACAACCCTAGGACTGGAAGTTATAAAAGG
ATCTGTATCTGCAGCATTAGGAGACTCACCTAAAGCTGCTTCTTCCATCGACGGAATTTCAGGAGCTACTTTGACTT
GTAATGGTGTTACCGAATCCTTCTCTCATTCTCTAGCTCCCTACCGCGCTTTGTTGACTTTCTTCGCCAACTCTAAA
CCTAGTGGAGAGTCTCATGACCACTAA

SEQ ID NO: 8 - CT279 protein sequence
MASKSRHYLNQPWYIILFIFVLSLIAGTLLSSVYYVLAPIQQQAAEFDRNQQMLMAAQVISSDNTFQVYEKGDWHPA
LYNTKKQLLEISSTPPKVTVTTLSSYFQNFVRVLLTDTQGNLSSFEDHNLNLEEFLSQPTPVIHGLALYVVYAILHN
DAASSKLSASQVAKNPTAIESIVLPIEGFGLWGPIYGFLALEKDGNTVLGTSWYQHGETPGLGANIANPQWQKNFRG
KKVFLVSASGETDFAKTTLGLEVIKGSVSAALGDSPKAASSIDGISGATLTCNGVTESFSHSLAPYRALLTFFANSK
PSGESHDH SEQ ID NO: 9 - CT443 nucleotide sequence
ATGCGAATAGGAGATCCTATGAACAAACTCATCAGACGAGCAGTGACGATCTTCGCGGTGACTAGTGTGGCGAGTTT
ATTTGCTAGCGGGGTGTTAGAGACCTCTATGGCAGAGTCTCTCTCTACAAACGTTATTAGCTTAGCTGACACCAAAG
CGAAAGACAACACTTCTCATAAAAGCAAAAAAGCAAGAAAAAACCACAGCAAAGAGACTCCCGTAGACCGTAAAGAG
GTTGCTCCGGTTCATGAGTCTAAAGCTACAGGACCTAAACAGGATTCTTGCTTTGGCAGAATGTATACAGTCAAAGT
TAATGATGATCGCAATGTTGAAATCACACAAGCTGTTCCTGAATATGCTACGGTAGGATCTCCCTATCCTATTGAAA
TTACTGCTACAGGTAAAGGGATTGTGTTGATGTTATCATTACTCAGCAATTACCATGTGAAGCAGAGTTCGTACGC
AGTGATCCAGCGACAACTCCTACTGCTGATGGTAAGCTAGTTTGGAAAATTGACCGCTTAGGACAAGGCGAAAAGAG
TAAAATTACTGTATGGGTAAAACCTCTTAAAGAAGGTTGCTGCTTTACAGCTGCAACAGTATGCGCTTGTCCAGAGA
TCCGTTCGGTTACAAAATGTGGACAACCTGCTATCTGTGTTAAACAAGAAGGCCCAGAGAATGCTTGTTTGCGTTGC
CCAGTAGTTTACAAAATTAATATAGTGAACCAAGGAACAGCAACAGCTCGTAACGTTGTTGTTGAAAATCCTGTTCC
AGATGGTTACGCTCATTCTTCTGGACAGCGTGTACTGACGTTTACTCTTGGAGATATGCAACCTGGAGAGCACAGAA
CAATTACTGTAGAGTTTTGTCCGCTTAAACGTGGTCGTGCTACCAATATAGCAACGGTTTCTTACTGTGGAGGACAT
AAAAATACAGCAAGCGTAACAACTGTGATCAACGAGCCTTGCGTACAAGTAAGTATTGCAGGAGCAGATTGGTCTTA
TGTTTGTAAGCCTGTAGAATATGTGATCTCCGTTTCCAATCCTGGAGATCTTGTGTTGCGAGATGTCGTCGTTGAAG
ACACTCTTTCTCCCGGAGTCACAGTTCTTGAAGCTGCAGGAGCTCAAATTTCTTGTAATAAAGTAGTTTGGACTGTG
AAAGAACTGAATCCTGGAGAGTCTCTACAGTATAAAGTTCTAGTAAGAGCACAAACTCCTGGACAATTCACAAATAA
TGTTGTTGTGAAGAGCTGCTCTGACTGTGGTACTTGTACTTCTTGCGCAGAAGCGACAACTTACTGGAAAGGAGTTG
CTGCTACTCATATGTGCGTAGTAGATACTTGTGACCCTGTTTGTGTAGGAGAAAATACTGTTTACCGTATTTGTGTC
ACCAACAGAGGTTCTGCAGAAGATACAAATGTTTCTTTAATGCTTAAATTCTCTAAAGAACTGCAACCTGTATCCTT
CTCTGGACCAACTAAAGGAACGATTACAGGCAATACAGTAGTATTCGATTCGTTACCTAGATTAGGTTCTAAAGAAA
CTGTAGAGTTTTCTGTAACATTGAAAGCAGTATCAGCTGGAGATGCTCGTGGGGAAGCGATTCTTTCTTCCGATACA
TTGACTGTTCCAGTTTCTGATACAGAGAATACACACATCTATTAA SEQ ID NO: 10 - CT443 protein sequence
MRIGDPMNKLIRRAVTIFAVTSVASLFASGVLETSMAESLSTNVISLADTKAKDNTSHKSKKARKNHSKETPVDRKE
VAPVHESKATGPKQDSCFGRMYTVKVNDDRNVEITQAVPEYATVGSPYPIEITATGKRDCVDVIITQQLPCEAEFVR
SDPATTPTADGKLVWKIDRLGQGEKSKITVWVKPLKEGCCFTAATVCACPEIRSVTKCGQPAICVKQEGPENACLRC
PVVYKINIVNQGTATARNVVVENPVPDGYAHSSGQRVLIFTLGDMQPGEHRTITVEFCPLKRGRATNIATVSYCGGH
KNTASVTTVINEPCVQVSIAGADWSYVCKPVEYVISVSNPGDLVLRDVVVEDTLSPGVTVLEAAGAQISCNKVVWTV
KELNPGESLQYKVLVRAQTPGQFTNNVVVKSCSDCGTCTSCAEATTYWKGVAATHMCVVDTCDPVCVGENTVYRICV
TNRGSAEDTNVSLMLKFSKELQPVSFSGPTKGTITGNTVVFDSLPRLGSKETVEFSVTLKAVSAGDARGEAILSSDT
LTVPVSDTENTHIY SEQ ID NO: 11 - CT372 nucleotide sequence
ATGCAGGCTGCACACCATCACTATCACCGCTACACAGATAAACTGCACAGACAAAACCATAAAAAAGATCTCATCTC
TCCCAAACCTACCGAACAAGAGGCGTGCAATACTTCTTCCCTTAGTAAGGAATTAATCCCTCTATCAGAACAAAGAG
GCCTTTTATCCCCCATCTGTGACTTTATTTCGGAACGCCCTTGCTTACACGGAGTTTCTGTTAGAAATCTCAAGCAA
GCGCTAAAAAATTCTGCAGGAACCCAAATTGCACTGGATTGGTCTATTCTCCCTCAATGGTTCAATCCTCGGGTCTC
TCATGCCCCTAAGCTTTCTATCCGAGACTTTGGGTATAGCGCACACCAAACTGTTACCGAAGCCACTCCTCCTTGCT
GGCAAAACTGCTTTAATCCATCTGCGGCCGTTACTATCTATGATTCCTCATATGGGAAAGGGGTCTTTCAAATATCC
TATACCCTTGTCCGCTATTGGAGAGAGAATGCTGCGACTGCTGGCGATGCTATGATGCTCGCAGGGAGTATCAATGA
TTATCCCTCTCGTCAGAACATTTTCTCTCAGTTTACTTTCTCCCAAAACTTCCCAAATGAACGGGTGAGTCTGACAA
TTGGTCAGTACTCACTCTATGCAATAGACGGAACATTATACAATAACGATCAACAACTTGGATTCATTAGTTACGCA
TTATCACAAAATCCAACAGCAACTTATTCCTCTGGAAGTCTTGGAGCTTACCTACAAGTCGCTCCTACCGCAAGCAC
AAGTCTTCAAATAGGATTTCAAGACGCTTATAATATCTCCGGATCCTCTATCAAATGGAGTAACCTTACAAAAAATA
GATACAATTTTCACGGTTTTGCTTCCTGGGCTCCCCGCTGTTGCTTAGGATCTGGCCAGTACTCCGTGCTTCTTTAT
GTGACTAGACAAGTTCCAGAACAGATGGAACAAACAATGGGATGGTCAGTCAATGCGAGTCAACACATATCTTCTAA
ACTGTATGTGTTTGGAAGATACAGCGGTGTTACAGGACATGTGTTCCCGATTAACCGCACGTATTCATTCGGTATGG
CCTCTGCAAATTTATTTAACCGTAACCCACAAGATTTATTTGGAATTGCTTGCGCATTCAATAATGTACACCTCTCT
GCTTCTCCAAATACTAAAAGAAAATACGAAACTGTAATCGAAGGGTTTGCAACTATCGGTTGCGGCCCCTATCTTTC
TTTCGCTCCAGACTTCCAACTCTACCTCTACCCAGCTCTTCGTCCAAACAAACAATCTGCCCGTGTTTATAGCGTGC
GAGCTAATTTAGCTATCTAA SEQ ID NO: 12 - CT372 protein sequence
MQAAHHHYHRYTDKLHRQNHKKDLISPKPTEQEACNTSSLSKELIPLSEQRGLLSPICDFISERPCLHGVSVRNLKQ
ALKNSAGTQIALDWSILPQWFNPRVSHAPKLSIRDFGYSAHQTVTEATPPCWQNCFNPSAAVTIYDSSYGKGVFQIS
YTLVRYWRENAATAGDAMMLAGSINDYPSRQNIFSQFTFSQNFPNERVSLTIGQYSLYAIDGTLYNNDQQLGFISYA
LSQNPTATYSSGSLGAYLQVAPTASTSLQIGFQDAYNISGSSIKWSNLTKNRYNFHGFASWAPRCCLGSGQYSVLLY
VTRQVPEQMEQTMGWSVNASQHISSKLYVFGRYSGVTGHVFPINRTYSFGMASANLFNRNPQDLFGIACAFNNVHLS
ASPNTKRKYETVIEGFATIGCGPYLSFAPDFQLYLYPALRPNKQSARVYSVRANLAI -continued

SEQUENCE LISTING

SEQ ID NO: 13 - CT456 nucleotide sequence
ATGACGAATTCTATATCAGGTTATCAACCTACTGTTACAACTTCTACATCATCAACCACTTCGGCATCAGGTGCTTC
CGGATCTCTGGGAGCTTCTTCTGTATCTACTACCGCAAACGCTACAGTTACACAAACAGCAAACGCAACAAATTCAG
CGGCTACATCTTCTATCCAAACGACTGGAGAGACTGTAGTAAACTATACGAATTCAGCCTCCGCCCCCAATGTAACT
GTATCGACCTCCTCTTCTTCCACACAAGCCACAGCCACTTCGAATAAAACTTCCCAAGCCGTTGCTGGAAAAATCAC
TTCTCCAGATACTTCAGAAAGCTCAGAAACTAGCTCTACCTCATCAAGCGATCATATCCCTAGCGATTACGATGACG
TTGGTAGCAATAGTGGAGATATTAGCAACAACTACGATGACGTAGGTAGTAACAACGGAGATATCAGTAGCAATTAT
GACGATGCTGCTGCTGATTACGAGCCGATAAGAACTACTGAAAATATTTATGAGAGTATTGGTGGCTCTAGAACAAG
TGGCCCAGAAAATACAAGTGGTGGTGCAGCAGCAGCACTCAATTCTCTAAGAGGCTCCTCCTACAGCAATTATGACG
ATGCTGCTGCTGATTACGAGCCGATAAGAACTACTGAAAATATTTATGAGAGTATTGGTGGCTCTAGAACAAGTGGC
CCAGAAAATACGAGTGGTGGTGCAGCAGCAGCACTCAATTCTCTAAGAGGCTCCTCCTACAGCAATTATGACGATGC
TGCTGCTGATTACGAGCCGATAAGAACTACTGAAAATATTTATGAGAGTATTGGTGGCTCTAGAACAAGTGGCCCAG
AAAATACGAGTGATGGTGCAGCAGCAGCAGCACTCAATTCTCTAAGAGGCTCCTCCTACACAACAGGGCCTCGTAAC
GAGGGTGTATTCGGCCCTGGACCGGAAGGACTACCAGACATGTCTCTTCCTTCATACGATCCTACAAATAAAACCTC
GTTATTGACTTTCCTCTCCAACCCTCATGTAAAGTCGAAAATGCTTGAAAACTCGGGGCATTTCGTCTTCATTGATA
CAGATAGAAGTAGTTTCATTCTTGTTCCTAACGGAAATTGGGACCAAGTCTGTTCAATTAAAGTTCAAAATGGAAAG
ACCAAAGAAGATCTCGACATCAAAGACTTGGAAAACATGTGTGCAAAATTCTGTACAGGGTTTAGCAAATTCTCTGG
TGACTGGGACAGTCTTGTAGAACCTATGGTGTCAGCCAAAGCTGGAGTGGCCAGCGGAGGCAATCTTCCCAATACAG
TGATTATCAATAATAAATTCAAAACTTGCGTTGCTTATGGTCCTTGGAATAGCCAGGAAGCAAGTTCTGGTTATACA
CCTTCTGCTTGGAGACGTGGTCATCGAGTAGATTTTGGAGGAATTTTTGAGAAAGCCAACGACTTTAATAAAATCAA
CTGGGGAACTCAAGCCGGGCCTAGTAGCGAAGACGATGGCATTTCCTTCTCCAATGAAACTCCTGGAGCTGGTCCTG
CAGCTGCTCCATCACCAACGCCATCCTCTATTCCTATCATCAATGTCAATGTCAATGTTGGCGGAACTAATGTGAAT
ATTGGAGATACGAATGTCAACACGACTAACACCACACCAACAACTCAATCTACAGACGCCTCTACAGATACAAGCGA
TATCGATGACATAAATACCAACAACCAAACTGATGATATCAATACGACAGACAAAGACTCTGACGGAGCTGGTGGAG
TCAATGGCGATATATCCGAAACAGAATCCTCTTCTGGAGATGATTCAGGAAGTGTCTCTTCCTCAGAATCAGACAAG
AATGCCTCTGTCGGAAATGACGGACCTGCTATGAAAGATATCCTTTCTGCCGTGCGTAAACACCTAGACGTCGTTTA
CCCTGGCGAAAATGGCGGTTCTACAGAAGGGCCTCTCCCAGCTAACCAAACTCTCGGAGACGTAATCTCTGATGTAG
AGAATAAAGGCTCCGCTCAGGATACAAAATTGTCAGGAAATACAGGAGCTGGGGATGACGATCCAACAACCACAGCT
GCTGTAGGTAATGGAGCGGAAGAGATCACTCTTTCCGACACAGATTCTGGTATCGGAGATGATGTATCCGATACAGC
GTCTTCATCTGGGGATGAATCCGGAGGAGTCTCCTCTCCCTCTTCAGAATCCAATAAAAATACTGCCGTTGGAAATG
ACGGACCTTCTGGACTAGATATCCTCGCTGCCGTACGTAAACATTTAGATAAGGTTTACCCTGGCGACAATGGTGGT
TCTACAGAAGGGCCTCTCCAAGCTAACCAAACTCTTGGAGATATCGTCCAGGATATGGAAACAACAGGGACATCCCA
AGAAACCGTTGTATCCCCATGGAAAGGAAGCACTTCTTCAACGGAATCAGCAGGAGGAAGTGGTAGCGTACAAACAC
TACTGCCTTCACCACCTCCAACCCCGTCAACTACAACATTAAGAACGGGCACAGGAGCTACCACCACATCCTTGATG
ATGGGAGGACCAATCAAAGCTGACATAATAACAACTGGTGGCGGAGGACGAATTCCTGGAGGAGGAACGTTAGAAAA
GCTGCTCCCTCGTATACGTGCGCACTTAGACATATCCTTTGATGCGCAAGGCGATCTCGTAAGTACTGAAGAGCCTC
AGCTTGGCTCGATTGTAAACAAATTCCGCCAAGAAACTGGTTCAAGAGGAATCTTAGCTTTCGTTGAGAGTGCTCCA
GGCAAGCCGGGATCTGCACAGGTCTTAACGGGTACAGGGGGAGATAAAGGCAACCTATTCCAAGCAGCTGCCGCAGT
CACCCAAGCCTTAGGAAATGTTGCAGGGAAAGTCAACCTTGCGATACAAGGCCAAAAACTATCATCCCTAGTCAATG
ACGACGGGAAGGGGTCTGTTGGAAGAGATTTATTCCAAGCAGCAGCCCAAACAACTCAAGTGCTAAGCGCACTGATT
GATACCGTAGGATAA SEQ ID NO: 14 - CT456 protein sequence
MTNSISGYQPTVTTSTSSTTSASGASGSLGASSVSTTANATVTQTANATNSAATSSIQTTGETVVNYTNSASAPNVT
VSTSSSSTQATATSNKTSQAVAGKITSPDTSESSETSSTSSSDHIPSDYDDVGSNSGDISNNYDDVGSNNGDISSNY
DDAAADYEPIRTTENIYESIGGSRTSGPENTSGGAAAALNSLRGSSYSNYDDAAADYEPIRTTENIYESIGGSRTSG
PENTSGGAAAALNSLRGSSYSNYDDAAADYEPIRTTENIYESIGGSRTSGPENTSDGAAAAALNSLRGSSYTTGPRN
EGVFGPGPEGLPDMSLPSYDPTNKTSLLTFLSNPHVKSKMLENSGHFVFIDTDRSSFILVPNGNWDQVCSIKVQNGK
TKEDLDIKDLENMCAKFCTGFSKFSGDWDSLVEPMVSAKAGVASGGNLPNTVIINNKFKTCVAYGPWNSQEASSGYT
PSAWRRGHRVDFGGIFEKANDFNKINWGTQAGPSSEDDGISFSNETPGAGPAAAPSPTPSSIPIINVNVNVGGTNVN
IGDTNVNTTNTTPTTQSTDASTDTSDIDDINTNNQTDDINTTDKDSDGAGGVNGDISETESSSGDDSGSVSSSESDK
NASVGNDGPAMKDILSAVRKHLDVVYPGENGGSTEGPLPANQTLGDVISDVENKGSAQDTKLSGNTGAGDDDPTTTA
AVGNGAEEITLSDTDSGIGDDVSDTASSSGDESGGVSSPSSESNKNTAVGNDGPSGLDILAAVRKHLDKVYPGDNGG
STEGPLQANQTLGDIVQDMETTGTSQETVVSPWKGSTSSTESAGGSGSVQTLLPSPPPTPSTTTLRTGTGATTTSLM
MGGPIKADIITTGGGGRIPGGGTLEKLLPRIRAHLDISFDAQGDLVSTEEPQLGSIVNKFRQETGSRGILAFVESAP
GKPGSAQVLTGTGGDKGNLFQAAAAVTQALGNVAGKVNLAIQGQKLSSLVNDDGKGSVGRDLFQAAAQTTQVLSALI
DTVG SEQ ID NO: 15: CT381 nucleotide sequence
ATGTGCATAAAAAGAAAAAAAACATGGATAGCTTTTTTAGCAGTTGTCTGTAGTTTTTGTTTGACGGGTTGTTTAAA
AGAAGGGGGAGACTCCAATAGTGAAAAATTTATTGTAGGGACTAATGCAACCTACCCTCCTTTTGAGTTTGTTGATA
AGCGAGGAGAGGTTGTAGGCTTCGATATAGACTTGGCTAGAGAGATTAGTAACAAGCTGGGGAAAACGCTGGACGTT
CGGGAGTTTTCCTTTGATGCACTCATTCTAAACCTAAAACAGCATCGGATTGATGCGGTTATAACAGGGATGTCCAT
TACTCCTTCTAGATTGAAGGAAATTCTTATGATTCCCTATTATGGGGAGGAAATAAAACACTTGGTTTTAGTGTTTA
AAGGAGAGAATAAGCATCCATTGCCACTCACTCAATATCGTTCTGTAGCTGTTCAAACAGGAACCTATCAAGAGGCC
TATTTACAGTCTCTTTCTGAAGTTCATATTCGCTCTTTTGATAGCACTCTAGAAGTACTCATGGAAGTCATGCATGG
TAAATCTCCCGTCGCTGTTTTAGAGCCATCTATCGCTCAAGTTGTCTTGAAAGATTTCCCGGCTCTTTCTACAGCAA
CCATAGATCTCCCTGAAGATCAGTGGGTTTTAGGATACGGGATTGGCGTTGCTTCAGATCGCCCAGCTTTAGCCTTG
AAAATCGAGGCAGCTGTGCAAGAGATCCGAAAAGAAGGAGTGCTAGCAGAGTTGGAACAGAAGTGGGGTTTGAACAA
CTAA SEQ ID NO: 16: CT381 protein sequence
MCIKRKKTWIAFLAVVCSFCLTGCLKEGGDSNSEKFIVGTNATYPPFEFVDKRGEVVGFDIDLAREISNKLGKTLDV
REFSFDALILNLKQHRIDAVITGMSITPSRLKEILMIPYYGEEIKHLVLVFKGENKHPLPLTQYRSVAVQTGTYQEA
YLQSLSEVHIRSFDSTLEVLMEVMHGKSPVAVLEPSIAQVVLKDFPALSTATIDLPEDQWVLGYGIGVASDRPALAL
KIEAAVQEIRKEGVLAELEQKWGLNN -continued

SEQUENCE LISTING

SEQ ID NO: 17: CT043 nucleotide sequence
ATGTCCAGGCAGAATGCTGAGGAAAATCTAAAAAATTTTGCTAAAGAGCTTAAACTCCCCGACGTGGCCTTCGATCA
GAATAATACGTGCATTTTGTTTGTTGATGGAGAGTTTTCTCTTCACCTGACCTACGAAGAACACTCTGATCGCCTTT
ATGTTTACGCACCTCTTCTTGACGGACTGCCAGACAATCCGCAAAGAAGGTTAGCTCTATATGAGAAGTTGTTAGAA
GGCTCTATGCTCGGAGGCCAAATGGCTGGTGGAGGGGTAGGAGTCGCTACTAAGGAACAGTTGATCTTAATGCACTG
CGTGTTAGACATGAAGTATGCAGAGACCAACCTACTCAAAGCTTTTGCACAGCTTTTTATTGAAACCGTTGTGAAAT
GGCGAACTGTTTGTTCTGATATCAGCGCTGGACGAGAACCCACTGTTGATACCATGCCACAAATGCCTCAAGGGGGT
GGCGGAGGAATTCAACCTCCTCCAGCAGGAATCCGTGCATAA SEQ ID NO: 18: CT043 protein sequence
MSRQNAEENLKNFAKELKLPDVAFDQNNTCILFVDGEFSLHLTYEEHSDRLYVYAPLLDGLPDNPQRRLALYEKLLE
GSMLGGQMAGGGVGVATKEQLILMHCVLDMKYAETNLLKAFAQLFIETVVKWRTVCSDISAGREPTVDTMPQMPQGG
GGGIQPPPAGIRA SEQ ID NO: 19: CT711/hypothetical protein (AAC68306)
MSIQPTSISLTKNITAALAGEQVDAAAVYMPQAVFFFQQLDEKSKGLKQALGLLEEVDLEKFIPSLEKSPTPITTGT
TSKISADGIEIVGELSSETILADPNKAAAQVFGEGLADSFDDWLRLSENGGIQDPTAIEEEIVTKYQTELNTLRNKL
KQQSLTDDEYTKLYAIPQNFVKEIESLKNENNVRLIPKSKVTNFWQNIMLTYNSVTSLSEPVTDAMNTTMAEYSLYI
ERATEAAKLIREITNTIKDIFNPVWDVREQTGIFGLKGAEYNALEGNMIQSLLSFAGLFRQLMSRTATVDEIGALYP
KNDKNEDVIHTAIDDYVNSLADLKANEQVKLNGLLSLVYAYYASTLGFAKKDVFNNAQASFTDYTNFLNQEIQYWTP
RETSSFNISNQALQTFKNKPSADYNGVYLFDNKGLETNLFNPTFFFDVVSLMTADPTKTMSRQDYNKVITASESSIQ
KINQAITAWELAIAECGTKKAKLEPSSLNYFNAMVEAKKTFVETSPIQMVYSSLMLDKYLPNQQYILETLGSQMTFS
NKAARYLNDIIAYAVSFQTADVYYSLGMYLRQMNQQEFPEVISRANDTVKKEIDRSRADLFHCKKAIEKIKELVTSV
NADTELTSSQRAELLETLASYAFEFENLYHNLSNVYVMVSKVQISGVSKPDEVDEAFTAKIGSKEFDTWIQQLTTFE
SAVIEGGRNGVMPGGEQQVLQSLESKQQDYTSFNQNQQLALQMESAAIQQEWTMVAAALALMNQIFAKLIRRFK SEQ ID NO: 20: CT114/hypothetical protein (AAC67705)
MCFIGIGSLLLPTALRATERMRKEPIPLLDKQQSFWNVDPYCLESICACFVAHRDPLSAKQLMYLFPQLSEEDVSVF
ARCILSSKRPEYLFSKSEEELFAKLILPRVSLGVHRDDDLARVLVLAEPSAEEQKARYYSLYLDVLALRAYVERERL
ASAAHGDPERIDLATIEAINTILFQEEGWRYPSKQEMFENRFSELAAVTDSKFGVCLGTVVLYQAVAQRLDLSLDPV
TPPGHIYLRYKDKVNIETTSGGRHLPTERYCECIKESQLKVRSQMELIGLTFMNRGAFFLQKGEFLQASLAYEQAQS
YLSDEQISDLLGITYVLLGKKAAGEALLKKSAEKTRRGSSIYDYFQGYISPEILGVLFADSGVTYQETLEYRKKLVM
LSKKYPKSGSLRLRLATTALELGLVKEGVQLLEESVKDAPEDLSLRLQFCKILCNRHDYVRAKYHFDQAQALLIKEG
LFSEKTSYTLLKTIGKKLSLFAPS SEQ ID NO: 21: CT480/oppA_4 (AAC68080)
MIDKIIRTILVLSLFLLYWSSDLLEKDVKSIKRELKALHEDVLELVRISHQQKNWVQSTDFSVSPEISVLKDCGDPA
FPNLLCEDPYVEKVVPSLLKEGFVPKGILRTAQVGRPDNLSPFNGFVNIVRFYELCVPNLAVEHVGKYEEFAPSLAL
KIEEHYVEDGSGDKEFHIYLRPNMFWEPIDPTLFPKNITLADSFLRPHPVTAHDVKFYYDVVMNPYVAEMRAVAMRS
YFEDMVSVRVENDLKLIVRWRAHTVRNEQGEEEKKVLYSAFANTLALQPLPCFVYQHFANGEKIVPEDSDPDTYRKD
SVWAQNFSSHWAYNYIVSCGAFRFAGMDDEKITLVRNPNYHNPFAALVEKRYIYMKDSTDSLFQDFKAGKVDIAYFP
PNHVDNLASFMQTSAYKEQAARGEAILEKNSSDRSYSYIGWNCLSLFFNNRSVRQAMNMLIDRDRIIEQCLDGRGVS
VSGPFSLCSPSYNRDVEGWQYSPEEAARKLEEEGWIDADGDGIREKVIDGVVVPFRFRLCYYVKSVTARTIAEYVAT
VCKEVGIECCLLGLDMADYSQALEEKNFDAILSGWCLGTPPEDPRALWHSEGALEKGSANAVGFCNEEADRIIEQLS
YEYDSNKRQALYHRFHEVIHEESPYAFLYSRQYSLVYKEFVKNIFVPTEHQDLIPGAQDETVNLSMLWVDKEEGRCS
AIS SEQ ID NO: 22: CT089/lcrE (AAC67680)
MTASGGAGGLGSTQTVDVARAQAAAATQDAQEVIGSQEASEASMLKGCEDLINPAAATRIKKKGEKFESLEARRKPT
ADKAEKKSESTEEKGDTPLEDRFTEDLSEVSGEDFRGLKNSFDDDSSPDEILDALTSKFSDPTIKDLALDYLIQTAP
SDGKLKSTLIQAKHQLMSQNPQAIVGGRNVLLASETFASRANTSPSSLRSLYFQVTSSPSNCANLHQMLASYLPSEK
TAVMEFLVNGMVADLKSEGPSIPPAKLQVYMTELSNLQALHSVNSFFDRNIGNLENSLKHEGHAPIPSLTTGNLTKT
FLQLVEDKFPSSSKAQKALNELVGPDTGPQTEVLNLFFRALNGCSPRIFSGAEKKQQLASVITNTLDAINADNEDYP
KPGDFPRSSFSSTPPHAPVPQSEIPTSPTSTQPPSP SEQ ID NO: 23: CT734/hypothetical protein (AAC68329)
MKKFIYKYSFGALLLLSGLSGLSSCCANSYGSTLAKNTAEIKEESVTLREKPDAGCKKKSSCYLRKFFSRKKPKEKT
EPVLPNFKSYADPMTDSERKDLSFVVSAAADKSSIALAMAQGEIKGALSRIREIHPLALLQALAEDPALIAGMKKMQ
GRDWVWNIFITELSKVFSQAASLGAFSVADVAAFASTLGLDSGTVTSIVDGERWAELIDVVIQNPAI SEQ ID NO: 24: CT016/hypothetical protein (AAC67606)
MKVKINDQFICISPYISARWNQIAFIESCDGGTEGGITLKLHLIDGETVSIPNLGQAIVDEVFQEHLLYLESTAPQK
NKEEEKISSLLGAVQQMAKGCEVQVFSQKGLVSMLLGGAGSINVLLQHSPEHKDHPDLPTDLLERIAQMMRSLSIGP
TSILAKPEPHCNCLHCQIGRATVEEEDAGVSDEDLTFRSWDISQSGEKMYTVTDPLNPEEQFNVYLGTPIGCTCGQP
YCEHVKAVLYT SEQ ID NO: 25: CM homolog of CT279 = TC_0551
ATGGCATCCAAGTCTCGTCATTATCTTAACCAGCCTTGGTACATTATCTTATTCATCTTTGTTCTTAGTCTGGTTGC
TGGTACCCTTCTTTCTTCAGTTTCCTATGTTCTATCTCCAATCCAAAAACAAGCTGCAGAATTTGATCGTAATCAGC
AAATGTTGATGGCCGCACAAATTATTTCCTATGACAATAAATTCCAAATATATGCTGAAGGGGATTGGCAACCTGCT
GTCTATAATACAAAAAAACAGATACTAGAAAAAAGCTCTTCCACTCCACCACAAGTGACTGTGGCGACTCTATGCTC
TTATTTTCAAAATTTTGTTAGAGTTTTGCTTACAGACTCCCAAGGGAATCTTTCTTCTTTTGAAGATCACAATCTTA
ACCTAGAAGAGTTCTTATCCCACCCCACATCTTCAGTACAAGATCACTCTCTGCATGTAATTTATGCTATTCTAGCA
AACGATGAATCCTCTAAAAAGTTATCATCCTCCCAAGTAGCAAAAAATCCGGTATCCATAGAGTCTATTATTCTTCC
TATAAAAGGATTTGGTTTATGGGGACCAATCTATGGATTTCTTGCTTTAGAAAAGGACGGTAATACGGTTCTAGGGA
CATGCTGGTATCAACATGGTGAGACTCCAGGATTAGGAGCAAATATAACTAATCCCCAATGGCAACAAAATTTCAGA
GGAAAAAAAGTATTTCTCGCTTCCTCTTCCGGAGAAACCGATTTTGCTAAAACAACTCTAGGACTAGAAGTTATAAA -continued

SEQUENCE LISTING

AGGATCTGTTTCTGCATTATTAGGGGACTCTCCCAAAGCTAATTCCGCTGTTGATGGAATTTCAGGAGCTACACTGA
CCTGTAATGGAGTTACTGAAGCTTTTGCTAATTCGCTAGCTCCTTACCGCCCCTTATTGACTTTCTTCGCCAATCTT
AACTCTAGTGGAGAATCTCATGACAACCAATAA

SEQ ID NO: 26: CM homologue of CT279 protein sequence = TC_0551 protein sequence
MASKSRHYLNQPWYIILFIFVLSLVAGTLLSSVSYVLSPIQKQAAEFDRNQQMLMAAQIISYDNKFQIYAEGDWQPA
VYNTKKQILEKSSSTPPQVTVATLCSYFQNFVRVLLTDSQGNLSSFEDHNLNLEEFLSHPTSSVQDHSLHVIYAILA
NDESSKKLSSSQVAKNPVSIESIILPIKGFGLWGPIYGFLALEKDGNTVLGTCWYQHGETPGLGANITNPQWQQNFR
GKKVFLASSSGETDFAKTTLGLEVIKGSVSALLGDSPKANSAVDGISGATLTCNGVTEAFANSLAPYRPLLTFFANL
NSSGESHDNQ SEQ ID NO: 27: CM homologue of CT372 = TC_0651 nucleotide sequence
ATGAATGGAAAAGTTCTGTGTGAGGTTTCTGTGTCCTTCCGTTCGATTCTGCTGACGGCTCTGCTTTCACTTTCTTT
TACAAACACTATGCAGGCTGCACACCATCATTATCACCGTTATGATGATAAACTACGCAGACAATACCATAAAAAGG
ACTTGCCCACTCAAGAGAATGTTCGGAAAGAGTTTTGTAATCCCTACTCTAGTAGTGATCCTATCCCTTTGTCA
CAACAACGAGGAGTCCTATCTCCTATCTGTGATTTAGTCTCAGAGTGCTCGTTTTTGAACGGGATTTCCGTTAGGAG
TCTTAAACAAACACTGAAAAATTCTGCTGGGACTCAAGTTGCTTTAGACTGGTCTATCCTTCCTCAATGGTTCAATC
CTAGATCCTCTTGGGCTCCTAAGCTCTCTATTCGAGATCTTGGATATGGTAAACCCCAGTCCCTTATTGAAGCAGAT
TCCCCTTGTTGTCAAACCTGCTTCAACCCATCTGCTGCTATTACGATTTACGATTCTTCATGTGGGAAGGGTGTTGT
CCAAGTGTCATACACCCTTGTTCGTTATTGGAGAGAAACGGCTGCACTTGCAGGGCAAACTATGATGCTTGCAGGAA
GTATTAATGATTATCCTGCTCGCCAAAACATATTCTCTCAACTTACATTTTCCCAAACTTTCCCTAATGAGAGAGTA
AATCTAACTGTTGGTCAATACTCTCTTTACTCGATAGACGGAACGCTGTACAACAATGATCAGCAGCTAGGATTTAT
TAGTTATGCGTTGTCGCAAAATCCAACAGCGACTTATTCCTCTGGAAGCCTTGGCGCCTATCTACAAGTCGCTCCAA
CAGAAAGCACCTGTCTTCAAGTTGGGTTCCAAGATGCCTATAATATTTCAGGTTCCTCGATCAAATGGAATAATCTT
ACAAAAAATAAGTATAACTTCCATGGCTATGCATCTTGGGCTCCACACTGTTGCTTAGGACCTGGACAATACTCTGT
TCTTCTTTATGTAACCAGAAAGGTTCCTGAGCAAATGATGCAGACAATGGGCTGGTCTGTGAATGCAAGTCAATACA
TCTCTTCTAAACTTTATGTATTTGGAAGATACAGCGGAGTCACAGGCCAATTGTCTCCTATTAACCGAACCTATTCA
TTTGGCTTAGTCTCTCCTAATTTATTGAACCGTAACCCACAAGACTTATTTGGAGTAGCTTGCGCATTCAATAATAT
ACACGCCTCCGCCTTTCAAAATGCTCAAAGAAAATATGAAACTGTGATCGAGGGATTTGCAACTATTGGTTGCGGAC
CTTACATCTCCTTTGCTCCAGATTTCCAACTTTACCTCTATCCTGCTCTGCGTCCAAATAAACAAAGCGCCCGAGTC
TATAGCGTTCGCGCAAACCTAGCTATTTAG SEQ ID NO: 28: CM homologue of CT372 = TC_0651 protein sequence
MNGKVLCEVSVSFRSILLTALLSLSFTNTMQAAHHHYHRYDDKLRRQYHKKDLPTQENVRKEFCNPYSHSSDPIPLS
QQRGVLSPICDLVSECSFLNGISVRSLKQTLKNSAGTQVALDWSILPQWFNPRSSWAPKLSIRDLGYGKPQSLIEAD
SPCCQTCFNPSAAITIYDSSCGKGVVQVSYTLVRYWRETAALAGQTMMLAGSINDYPARQNIFSQLTFSQTFPNERV
NLTVGQYSLYSIDGTLYNNDQQLGFISYALSQNPTATYSSGSLGAYLQVAPTESTCLQVGFQDAYNISGSSIKWNNL
TKNKYNFHGYASWAPHCCLGPGQYSVLLYVTRKVPEQMMQTMGWSVNASQYISSKLYVFGRYSGVTGQLSPINRTYS
FGLVSPNLLNRNPQDLFGVACAFNNIHASAFQNAQRKYETVIEGFATIGCGPYISFAPDFQLYLYPALRPNKQSARV
YSVRANLAI SEQ ID NO: 29: CM homologue of CT443 = TC_0727
ATGCGAATAGGAGATCCTATGAACAAACTCATCAGACGAGCTGTGACGATCTTCGCGGTGACTAGTGTGGCGAGTTT
ATTTGCTAGCGGGGTGTTAGAGACCTCTATGGCAGAGTCTCTCTCTACCAACGTTATTAGCTTAGCTGACACCAAAG
CGAAAGAGACCACTTCTCATCAAAAAGACAGAAAAGCAAGAAAAAATCATCAAAATAGGACTTCCGTAGTCCGTAAA
GAGGTTACTGCAGTTCGTGATACTAAAGCTGTAGAGCCTAGACAGGATTCTTGCTTTGGCAAAATGTATACAGTCAA
AGTTAATGATGATCGTAATGTAGAAATCGTGCAGTCCGTTCCTGAATATGCTACGGTAGGATCTCCATATCCTATTG
AGATTACTGCTATAGGGAAAAGAGACTGTGTTGATGTAATCATTACACAGCAATTACCATGCGAAGCAGAGTTTGTT
AGCAGTGATCCAGCTACTACTCCTACTGCTGATGGTAAGCTAGTTTGGAAAATTGATCGGTTAGGACAGGGCGAAAA
GAGTAAAATTACTGTATGGGTAAAACCTCTTAAAGAAGGTTGCTGCTTTACAGCTGCAACGGTTTGTGCTTGTCCAG
AGATCCGTTCGGTTACGAAATGTGGCCAGCCTGCTATCTGTGTTAAACAGGAAGGTCCAGAAAGCGCATGTTTGCGT
TGCCCAGTAACTTATAGAATTAATGTAGTCAACCAAGGAACAGCAACAGCACGTAATGTTGTTGTGGAAAATCCTGT
TCCAGATGGCTATGCTCATGCATCCGGACAGCGTGTATTGACATATACTCTTGGGGATATGCAACCTGGAGAACAGA
GAACAATCACCGTGGAGTTTTGTCCGCTTAAACGTGGTCGAGTCACAAATATTGCTACAGTTTCTTACTGTGGTGGA
CACAAAAATACTGCTAGCGTAACAACAGTGATCAATGAGCCTTGCGTGCAAGTTAACATCGAGGGAGCAGATTGGTC
TTATGTTTGTAAGCCTGTAGAATATGTTATCTCTGTTTCTAACCCTGGTGACTTAGTTTTACGAGACGTTGTAATTG
AAGATACGCTTTCTCCTGGAATAACTGTTGTTGAAGCAGCTGGAGCTCAGATTTCTTGTAATAAATTGGTTTGGACT
TTGAAGGAACTCAATCCTGGAGAGTCTTTACAATATAAGGTTCTAGTAAGAGCTCAAACTCCAGGGCAATTCACAAA
CAACGTTGTTGTGAAAAGTTGCTCTGATTGCGGTATTTGTACTTCTTGCGCAGAAGCAACAACTTACTGGAAAGGAG
TTGCTGCTACTCATATGTGCGTAGTAGATACTTGTGATCCTATTTGCGTAGGAGAGAACACTGTTTATCGTATCTGT
GTGACAAACAGAGGTTCTGCTGAAGATACAAATGTGTCCTTAATTTTGAAATTCTCTAAAGAATTACAACCTATATC
TTTCTCTGGACCAACTAAAGGAACCATTACAGGAAACACGGTAGTGTTTGATTCGTTACCTAGATTAGGTTCTAAAG
AAACTGTAGAGTTTTCTGTAACGTTGAAAGCAGTATCCGCTGGAGATGCTCGTGGGGAAGCTATTCTTTCTTCCGAT
ACATTGACAGTTCCTGTATCTGATACGGAGAATACACATATCTATTAA SEQ ID NO: 30: CM homologue of CT443 = TC_0727
MRIGDPMNKLIRRAVTIFAVTSVASLFASGVLETSMAESLSTNVISLADTKAKETTSHQKDRKARKNHQNRTSVVRK
EVTAVRDTKAVEPRQDSCFGKMYTVKVNDDRNVEIVQSVPEYATVGSPYPIEITAIGKRDCVDVIITQQLPCEAEFV
SSDPATTPTADGKLVWKIDRLGQGEKSKITVWVKPLKEGCCFTAATVCACPEIRSVTKCGQPAICVKQEGPESACLR
CPVTYRINVVNQGTATARNVVVENPVPDGYAHASGQRVLTYTLGDMQPGEQRTITVEFCPLKRGRVTNIATVSYCGG
HKNTASVTTVINEPCVQVNIEGADWSYVCKPVEYVISVSNPGDLVLRDVVIEDTLSPGITVVEAAGAQISCNKLVWT
LKELNPGESLQYKVLVRAQTPGQFTNNVVVKSCSDCGICTSCAEATTYWKGVAATHMCVVDTCDPICVGENTVYRIC
VTNRGSAEDTNVSLILKFSKELQPISFSGPTKGTITGNTVVFDSLPRLGSKETVEFSVTLKAVSAGDARGEAILSSD
TLTVPVSDTENTHIY SEQ ID NO: 31: CM homologue of CT043 = TC_0313 nucleotide sequence
ATGTCCAGACAGAATGCTGAGGAAAATCTAAAAAATTTGCTAAAGAGCTCAAGCTCCCCGACGTGGCCTTCGATCA

SEQUENCE LISTING

GAATAATACGTGCATTTTGTTTGTTGATGGAGAGTTTTCTCTTCACCTGACCTACGAAGAGCACTCTGATCGCCTTT
ATGTTTACGCACCTCTCCTTGACGGACTCCCAGATAATCCGCAAAGAAAGTTGGCTCTGTATGAGAAATTGTTGGAA
GGCTCTATGCTCGGAGGCCAAATGGCTGGTGGAGGAGTAGGAGTTGCTACTAAAGAACAGTTGATCCTAATGCATTG
CGTGTTAGATATGAAATATGCAGAGACTAATCTATTGAAAGCTTTTGCACAGCTTTTCATTGAAACTGTTGTGAAAT
GGCGAACGGTCTGTTCTGATATCAGCGCTGGACGAGAACCTTCCGTTGACACTATGCCTCAAATGCCTCAAGGAGGC
AGCGGAGGAATTCAACCTCCTCCAACAGGAATTCGTGCGTAG

SEQ ID NO: 32: CM homologue of CT043 = TC_0313 protein sequence
MSRQNAEENLKNFAKELKLPDVAFDQNNTCILFVDGEFSLHLTYEEHSDRLYVYAPLLDGLPDNPQRKLALYEKLLE
GSMLGGQMAGGGVGVATKEQLILMHCVLDMKYAETNLLKAFAQLFIETVVKWRTVCSDISAGREPSVDTMPQMPQGG
SGGIQPPPTGIRA SEQ ID NO: 33: CM homologue of CT601 = TC_0890 nucleotide sequence
ATGCTCGCTAATCGGTTATTTCTAATCACCCTTATAGGTTTTGGCTATTCTGCTTACGGTGCCAGCACAGGGAAATC
ACCTTCTTTACAGGTTATTTTAGCTGAAGTCGAGGATACATCTTCGCGCTTACAAGCTCATCAGAATGAGCTTGTTA
TGCTCTCGGAACGTTTAGATGAGCAAGACACAAAACTTCAACAACTCTCGTCAACTCAGGCCCGTAATCTTCCTCAA
CAAGTTCAACGGCTTGAGATTGATCTGAGAGCTCTGGCTAAAACAGCTGCTGTGCTCTCGCAATCTGTTCAGGATAT
CCGATCATCCGTGCAAAATAAATTACAAGAAATCCAACAAGAACAAAAAAATTTAGCTCAAAATTTACGAGCGCTTC
GCAACTCCTTACAAGCACTAGTTGATGGCTCTTCCCCAGAAAATTATATTGATTTTTTGGCCGGGGAGACACCTGAA
CATATTCACGTTGTTAAACAAGGAGAAACCCTGAGTAAAATCGCTAGTAAGTACAATATCCCTGTCGCAGAATTGAA
AAAACTTAATAAATTAAATTCCGATACTATTTTTACTGATCAAAGAATCCGACTTCCAAAAAAGAAATAA SEQ ID NO: 34: CM homologue of CT601 = TC_0890 protein sequence
MLANRLFLITLIGFGYSAYGASTGKSPSLQVILAEVEDTSSRLQAHQNELVMLSERLDEQDTKLQQLSSTQARNLPQ
QVQRLEIDLRALAKTAAVLSQSVQDIRSSVQNKLQEIQQEQKNLAQNLRALRNSLQALVDGSSPENYIDFLAGETPE
HIHVVKQGETLSKIASKYNIPVAELKKLNKLNSDTIFTDQRIRLPKKK SEQ ID NO: 35: CM homologue of CT456 = TC_0741
ATGACGACTCCAATAAGTAATTCTCCATCTTCTATTCCAACTGTTACAGTATCAACTACTACAGCATCTTCTGGATC
TCTCGGAACTTCTACTGTATCATCAACGACTACAAGTACTTCAGTCGCACAAACAGCAACAACAACATCTTCTGCTT
CTACATCTATAATTCAGTCTAGTGGAGAAAACATCCAATCCACTACAGGTACCCCTTCTCCTATTACGTCTAGTGTT
TCAACATCCGCTCCATCTCCTAAAGCCTCCGCCACTGCAAACAAAACTTCAAGCGCTGTTTCTGGGAAAATTACCTC
ACAAGAAACTTCTGAGGAATCCGAAACCCAAGCCACTACATCTGATGGAGAAGTTAGTAGTAATTACGATGATGTTG
ATACCCCGACCAATTCGTCCGATTCGACAGTTGATAGTGATTACCAAGATGTTGAGACTCAGTACAAAACAATTAGC
AACAATGGTGAAAACACTTATGAAACAATCGGAAGTCATGGTGAGAAAAACACACACGTCCAGGAAAGCCATGCATC
CGGAACAGGAAATCCCATAAATAATCAGCAAGAAGCTATTAGACAGCTCCGATCATCTACCTATACAACCAGCCCTC
GTAATGAGAATATATTTAGTCCAGGACCGGAAGGTCTACCTAATATGTCTCTTCCTAGTTACAGCCCTACAGATAAA
AGTTCTCTACTAGCTTTCCTATCTAATCCCAATACAAAAGCAAAAATGCTCGAACACTCCGGGCATTTAGTCTTTAT
AGACACAACTAGAAGTAGCTTTATCTTTGTTCCGAATGGAAATTGGGATCAAGTCTGTTCCATGAAGGTTCAGAATG
GGAAAACTAAAGAAGACCTTGGCTTAAAGGACTTAGAAGATATGTGTGCAAAGTTTTGCACAGGATACAATAAATTC
TCCTCTGATTGGGGAAATCGAGTTGACCCCTTGGTCTCTTCTAAGGCCGGGATAGAAAGTGGGGGGCACCTCCCAAG
CTCAGTTATCATCAACAACAAATTTAGAACCTGTGTTGCCTATGGGCCGTGGAACCCCAAAGAAAACGGCCCCAATT
ATACTCCTTCAGCCTGGAGACGTGGGCATCGAGTAGATTTTGGAAAGATCTTTGATGGAACAGCGCCGTTTAATAAA
ATCAACTGGGGCTCTTCCCCTACCCCTGGTGATGACGGCATCTCCTTCTCTAATGAAACTATTGGGTCTGAACCATT
CGCGACACCTCCCTCATCCCCATCGCAAACCCCCGTTATCAACGTCAATGTTAATGTCGGTGGAACCAATGTTAATA
TTGGGGATACAAACGTATCTAAAGGATCCGGCACACCAACATCTTCTCAATCTGTGGACATGTCTACAGATACTAGC
GATTTAGATACCAGTGATATTGATACAAACAACCAAACTAACGGCGATATCAACACGAATGACAACTCCAATAATGT
CGATGGAAGTTTATCTGACGTTGATTCAAGGGTGGAAGACGATGACGGTGTATCGGATACAGAGTCCACTAATGGCA
ATGACTCTGGTAAAACTACTTCCACAGAAGAAAATGGTGACCCAAGCGGACCAGACATCCTGGCTGCTGTACGTAAA
CACCTAGACACTGTCTATCCAGGAGAAAATGGCGGATCTACAGAAGGACCTCTCCCTGCTAATCAAAATCTGGGGAA
CGTTATCCATGATGTGGAGCAGAATGGATCTGCTAAAGAAACTATTATCACTCCAGGAGATACAGGGCCTACAGACT
CAAGCTCCTCTGTAGATGCTGATGCAGACGTTGAAGATACTTCTGATACTGACTCTGGAATCGGAGACGACGACGGT
GTATCGGATACAGAGTCCACTAATGGTAATAACTCTGGTAAAACTACTTCCACAGAAGAAAATGGTGACCCAAGCGG
ACCAGACATCCTGGCTGCTGTACGTAAACACCTAGACACTGTCTATCCAGGAGAAAATGGCGGATCTACAGAAGGAC
CTCTCCCTGCTAATCAAAATCTGGGGAACGTTATCCATGATGTAGAACAAAACGGAGCCGCTCAAGAAACTATTATC
ACTCCAGGAGATACGGAATCTACAGACACAAGCTCTAGTGTAAATGCTAATGCAGACTTAGAAGATGTTTCTGATGC
TGATTCAGGATTCGGGGATGATGACGGTATATCGGATACAGAGTCCACTAATGGTAACGACTCTGGAAAAAATACTC
CTGTAGGGGATGGTGGTACACCAAGCGGACCAGATATCCTAGCTGCTGTACGCAAACATCTAGACACTGTCTATCCA
GGAGAAAATGGTGGATCTACAGAGAGACCTTTACCCGCTAATCAAAATTTAGGAGATATCATTCATGATGTAGAACA
AAACGGAAGCGCTAAAGAAACTGTAGTATCGCCTTATCGAGGAGGAGGAGGAAATACATCTTCCCCAATTGGATTAG
CCTCCCTGCTTCCAGCAACACCATCCACACCTTTGATGACAACACCTAGAACAAATGGGAAAGCTGCAGCTTCTTCT
TTGATGATAAAAGGAGGAGAAACTCAAGCCAAGCTAGTTAAGAATGGCGGCAATATCCCTGGAGAAACCACATTAGC
AGAATTACTCCCTCGTTTAAGAGGACACCTTGACAAAGTCTTTACTTCAGACGGGAAGTTTACAAATCTTAATGGAC
CTCAACTTGGAGCCATCATAGACCAATTCCGCAAAGAAACGGGTTCCGGAGGAATCATAGCTCATACAGATAGTGTT
CCAGGAGAGAACGGAACAGCCTCTCCTCTCACAGGAAGTTCAGGGGAAAAAGTCTCTCTCTATGATGCAGCGAAAAA
CGTCACTCAAGCTTTAACAAGTGTTACGAACAAAGTAACCCTAGCAATGCAAGGACAAAAACTGGAAGGAATTATAA
ACAACAACAATACCCCCTCTTCTATTGGACAAAATCTTTTCGCAGCAGCGAGGGCAACGACACAATCCCTCAGTTCA
TTAATTGGAACCGTACAATAA SEQ ID NO: 36: CM homologue of CT456 = TC_0741 protein sequence
MTTPISNSPSSIPTVIVSTTTASSGSLGTSTVSSTTTSTSVAQTATTTSSASTSSIIQSSGENIQSTTGTPSPITSSV
STSAPSPKASATANKTSSAVSGKITSQETSEESETQATTSDGEVSSNYDDVDTPTNSSDSTVDSDYQDVETQYKTIS
NNGENTYETIGSHGEKNTHVQESHASGTGNPINNQQEAIRQLRSSTYTTSPRNENIFSPGPEGLPNMSLPSYSPTDK
SSLLAFLSNPNTKAKMLEHSGHLVFIDTTRSSFIFVPNGNWDQVCSMKVQNGKTKEDLGLKDLEDMCAKFCTGYNKF
SSDWGNRVDPLVSSKAGIESGGHLPSSVIINNKFRTCVAYGPWNPKENGPNYTPSAWRRGHRVDFGKIFDGTAPFNK
INWGSSPTPGDDGISFSNETIGSEPFATPPSSPSQTPVINVNVNVGGTNVNIGDTNVSKGSGTPTSSQSVDMSTDTS
DLDTSDIDTNNQTNGDINTNDNSNNVDGSLSDVDSRVEDDDGVSDTESTNGNDSGKTTSTEENGDPSGPDILAAVRK -continued

SEQUENCE LISTING

HLDTVYPGENGGSTEGPLPANQNLGNVIHDVEQNGSAKETIITPGDTGPTDSSSSVDADADVEDTSDTDSGIGDDDG
VSDTESTNGNNSGKTTSTEENGDPSGPDILAAVRKHLDTVYPGENGGSTEGPLPANQNLGNVIHDVEQNGAAQETII
TPGDTESTDTSSSVNANADLEDVSDADSGFGDDDGISDTESTNGNDSGKNTPVGDGGTPSGPDILAAVRKHLDTVYP
GENGGSTERPLPANQNLGDIIHDVEQNGSAKETVVSPYRGGGGNTSSPIGLASLLPATPSTPLMTTPRTNGKAAASS
LMIKGGETQAKLVKNGGNIPGETTLAELLPRLRGHLDKVFTSDGKFTNLNGPQLGAIIDQFRKETGSGGIIAHTDSV
PGENGTASPLTGSSGEKVSLYDAAKNVTQALTSVTNKVTLAMQGQKLEGIINNNNTPSSIGQNLFAAARATTQSLSS
LIGTVQ

SEQ ID NO: 37: CM homologue of CT381 = TC_0660
GTGAGTATGTATATAAAAAGAAAGAAAGCTTGGATGACTTTCTTAGCAATTGTCTGTAGTTTCTGTTTGGCGGGCTG
TTCAAAAGAGAGCAAAGACTCTGTTAGTGAAAAATTTATTGTAGGAACTAACGCAACGTATCCTCCTTTTGAGTTTG
TTGATGAAAGAGGTGAGACGGTTGGCTTTGATATTGATTTAGCTAGGGAGATTAGTAAAAAGCTAGGGAAAAAATTA
GAAGTCCGAGAATTTGCTTTTGATGCACTCGTTCTCAATTTAAAACAGCATCGTATTGATGCAATTATGGCAGGGGT
GTCCATTACGTCTTCTCGATTGAAAGAAATTTTGATGATTCCCTACTATGGCGAAGAAATAAAGAGTTTGGTTTTAG
TGTTTAAGGATGGAGACTCAAAGTCTTTACCACTAGATCAGTATAATTCTGTTGCTGTTCAAACTGGCACGTACCAA
GAGGAATATTTACAGTCTCTTCCAGGGGTGCGTATTCGCTCTTTTGATAGTACTTTAGAAGTGCTTATGGAAGTTTT
GCATAGCAAGTCTCCTATAGCTGTTTTAGAACCGTCTATTGCGCAGGTCGTTTTAAAAGATTTTCCGACGCTCACTA
CTGAAACGATAGATCTTCCTGAAGATAAATGGGTTTTAGGGTATGGAATTGGAGTTGCTTCTGATCGACCATCTCTA
GCTTCTGATATAGAAGCTGCTGTACAAGAGATCAAGAAAGAAGGAGTGTTAGCAGAGTTAGAGCAAAAATGGGGTTT
GAACGGCTAA SEQ ID NO: 38: CM homologue of CT381 = TC_0660
MSMYIKRKKAWMTFLAIVCSFCLAGCSKESKDSVSEKFIVGTNATYPPFEFVDERGETVGFDIDLAREISKKLGKKL
EVREFAFDALVLNLKQHRIDAIMAGVSITSSRLKEILMIPYYGEEIKSLVLVFKDGDSKSLPLDQYNSVAVQTGTYQ
EEYLQSLPGVRIRSFDSTLEVLMEVLHSKSPIAVLEPSIAQVVLKDFPTLTTETIDLPEDKWVLGYGIGVASDRPSL
ASDIEAAVQEIKKEGVLAELEQKWGLNG SEQ ID NO: 39 - CT255 nucleotide sequence
ATGGAAGAAAAAGGCATCTTACAATTGGTTGAAATTTCGCGAGCAATGGCTTTACAGGGAGTTTGTCCTTGGACTAA
TTTACAGAGTGTGGAGTCTATGTTGCAGTATATAGCAGGGGAGTGTCAGGAGTTGGCTGATGCTGTACAAGAAAATA
AAGCTTCGTTGGAAATCGCTTCGGAAGCCGGAGACGTACTTACTTTAGTATTGACCTTGTGTTTCTTGCTAGAAAGA
GAAGGAAAGCTTAAAGCTGAAGAAGTATTTGTAGAAGCTTTGGCTAAGTTGCGTCGTCGATCTCCTCATGTTTTTGA
TCCTCATAATCAAATTTCTTTAGAACAGGCTGAAGAATACTGGGCTCGTATGAAACAGCAAGAAAAAATTTCTTAA SEQ ID NO: 40 - CT255 protein sequence
MEEKGILQLVEISRAMALQGVCPWTNLQSVESMLQYIAGECQELADAVQENKASLEIASEAGDVLTLVLTLCFLLER
EGKLKAEEVFVEALAKLRRRSPHVFDPHNQISLEQAEEYWARMKQQEKIS SEQ ID NO: 41 - CT341 nucleotide sequence
ATGGATTACTACACGATATTGGGTGTAGCGAAGACTGCTACTCCTGAAGAAATAAAGAAAGCTTACCGTAAGCTCGC
TGTAAAGTACCATCCAGATAAGAATCCTGGGGATGCTGAAGCGGAGCGACGCTTTAAAGAAGTTTCTGAAGCCTATG
AAGTATTAGGTGATGCGCAGAAGCGGGAGTCATATGATCGTTACGGCAAAGACGGTCCATTTGCTGGTGCTGGAGGA
TTCGGTGGCGCTGGCATGGGGAATATGGAAGACGCTTTGCGAACATTTATGGGAGCTTTTGGCGGCGATTTCGGTGG
TAATGGAGGCGGTTTCTTTGAAGGGCTTTTTGGAGGACTTGGAGAAGCTTTCGGAATGCGTGGAGGCTCAGAAAGTT
CTCGACAAGGAGCTAGTAAGAAGGTGCATATTACGCTGTCCTTCGAGGAGGCGGCAAAAGGTGTTGAAAAAGAACTT
CTTGTTTCAGGCTATAAATCTTGTGATGCTTGTTCTGGTAGTGGAGCCAATACTGCTAAAGGTGTAAAAGTTTGTGA
TCGATGCAAGGGCTCTGGTCAGGTAGTGCAAAGCCGAGGCTTTTTCTCCATGGCTTCTACTTGCCCTGATTGTAGTG
GTGAAGGTCGGGTTATCACAGATCCTTGTTCAGTTTGTCGTGGGCAGGGACGTATCAAGGATAAACGTAGCGTCCAT
GTTAATATCCCAGCTGGAGTCGATTCTGGGATGAGATTAAAGATGGAAGGCTATGGAGATGCTGGCCAAAATGGAGC
GCCTGCAGGGGATCTGTATGTTTTTATTGATGTAGAGCCTCATCCTGTTTTCGAGCGCCATGGGGATGATTTAGTTT
TAGAGCTTCCTATTGGATTTGTTGATGCGGCTTTAGGGATCAAGAAGGAAATCCCTACACTCTTAAAAGAAGGTACT
TGCCGTTTGAGTATCCCAGAAGGGATTCAGAGCGGAACAGTTCTTAAAGTTAGAGGGCAGGGATTCCCTAATGTGCA
TGGGAAATCCAGAGGAGATCTTTTAGTAAGAGTATCTGTGGAGACTCCCCAGCACCTATCTAATGAACAAAAAGATT
TATTGAGACAGTTTGCTGCTACGGAGAAGGCTGAAAATTTCCCTAAGAAACGGAGTTTCTTAGACAAAATCAAAGGT
TTTTTTTCTGACTTTGCTGTATAG SEQ ID NO: 42 - CT341 protein sequence
MDYYTILGVAKTATPEEIKKAYRKLAVKYHPDKNPGDAEAERRFKEVSEAYEVLGDAQKRESYDRYGKDGPFAGAGG
FGGAGMGNMEDALRTFMGAFGGDFGGNGGFFEGLFGGLGEAFGMRGGSESSRQGASKKVHITLSFEEAAKGVEKEL
LVSGYKSCDACSGSGANTAKGVKVCDRCKGSGQVVQSRGFFSMASTCPDCSGEGRVITDPCSVCRGQGRIKDKRSVH
VNIPAGVDSGMRLKMEGYGDAGQNGAPAGDLYVFIDVEPHPVFERHGDDLVLELPIGFVDAALGIKKEIPTLLKEGT
CRLSIPEGIQSGTVLKVRGQGFPNVHGKSRGDLLVRVSVETPQHLSNEQKDLLRQFAATEKAENFPKKRSFLDKIKG
FFSDFAV SEQ ID NO: 43 - CT716 nucleotide sequence
ATGAATAAAAAACTCCAAGATCTGTCTAAACTGCTCACTATTGAGCTTTTCAAGAAACGTACACGGTTGGAAACAGT
AAAAAAAGCGCTCTCCACAATAGAACATCGCTTACAACAAATACAGGAGCACATCGCGAAAATTTCCTTAACAAGGC
ACAAACAATTCCTATGTCGGTCATATACCCATGAATATGACCAACATTTAGAACATTTACAAAGAGAGCAAACTTCT
CTATATAAACAGCATCAGACCCTGAAAACGTCTTTGAAAGATGCTTATGGCGACATACAAAAACAACTAGACCAAAG
AAAAATTATCGAAAAGATCCATGACAGTAAATATCCTATAAAGAGCGCGAATAACTAA SEQ ID NO: 44 - CT716 protein sequence
MNKKLQDLSKLLTIELFKKRTRLETVKKALSTIEHRLQQIQEHIAKISLTRHKQFLCRSYTHEYDQHLEHLQREQTS
LYKQHQTLKTSLKDAYGDIQKQLDQRKIIEKIHDSKYPIKSANN SEQ ID NO: 45 - CT745 nucleotide sequence
ATGAAACATGCTCTCATTGTTGGCTCAGGTATTGCCGGCCTTTCTGCCGCGTGGTGGCTACACAAACGATTCCCTCA -continued

SEQUENCE LISTING

TGTGCAGCTGTCTATTCTAGAAAAAGAGTCTCGATCTGGAGGGCTAATTGTCACAGAGAAACAACAAGGGTTTTCCC
TCAATATGGGCCCTAAAGGTTTTGTTTTAGCTCATGATGGGCAACACACCCTTCACCTCATTCAGTCTTTAGGCCTA
GCAGACGAGCTATTATATAGCTCTCCAGAGGCTAAAAACCGCTTTATCCACTATAATAATAAAACCCGAAAAGTCTC
GCCTTGGACTATTTTCAAACAAAATCTCCCTCTCTCTTTTGCTAAGGATTTCTTTGCGCGTCCTTACAAACAAGACA
GCTCCGTGGAAGCCTTCTTTAAAAGACACAGTTCTTCCAAGCTTAGAAGAAATCTTTTAAATCCCATTAGCATTGCT
ATTCGTGCAGGACATAGTCATATATTGTCTGCACAGATGGCTTACCCAGAATTAACACGAAGAGAAGCTCAAACAGG
ATCGTTGTTACGTAGTTATCTCAAAGATTTTCCTAAAGAGAAACGCACAGGCCCTTATTTAGCTACCTTGCGGTCTG
GGATGGGAATGCTAACCCAGGCTTTGCATGATAAATTGCCTGCTACCTGGTATTTTTCTGCACCCGTCAGCAAAATC
CGTCAGTTGGCGAATGGGAAAATTTCTCTTTCATCTCCTCAAGGAGAAATAACGGGAGATATGCTCATTTATGCTGG
GTCCGTGCACGATCTCCCTTCCTGTCTAGAAGGGATCCCTGAAACCAAGCTTATCAAGCAAACGACTTCATCTTGGG
ATCTCTCTTGTGTATCTTTAGGATGGCATGCATCCTTCCCTATCCCTCATGGATATGGCATGCTTTTCGCTGATACG
CCTCCCTTATTAGGGATCGTGTTTAATACGGAAGTGTTCCCTCAACCCGAGCGGCCTAATACAATAGTCTCTCTTCT
TTTAGAAGGTCGATGGCACCAAGAAGAAGCGTATGCTTTCTCACTAGCAGCTATTTCTGAGTACCTGCAAATTTACA
CTCCTCCCCAAGCTTTCTCACTATTCTCTCCTCGAGAGGGACTTCCCCAACACCATGTTGGATTTATCCAATCCCGC
CAACGCCTTCTATCTAAACTTCCTCACAATATAAAAATTGTAGGGCAGAATTTTGCAGGTCCAGGTCTCAACCGCGC
TACAGCGTCTGCTTATAAAGCTATAGCTTCTTTACTATCATGA

SEQ ID NO: 46 - CT745 protein sequence
MKHALIVGSGIAGLSAAWWLHKRFPHVQLSILEKESRSGGLIVTEKQQGFSLNMGPKGFVLAHDGQHTLHLIQSLGL
ADELLYSSPEAKNRFIHYNNKTRKVSPWTIFKQNLPLSFAKDFFARPYKQDSSVEAFFKRHSSSKLRRNLLNPISIA
IRAGHSHILSAQMAYPELTRREAQTGSLLRSYLKDFPKEKRTGPYLATLRSGMGMLTQALHDKLPATWYFSAPVSKI
RQLANGKISLSSPQGEITGDMLIYAGSVHDLPSCLEGIPETKLIKQTTSSWDLSCVSLGWHASFPIPHGYGMLFADT
PPLLGIVFNTEVFPQPERPNTIVSLLLEGRWHQEEAYAFSLAAISEYLQIYTPPQAFSLFSPREGLPQHHVGFIQSR
QRLLSKLPHNIKIVGQNFAGPGLNRATASAYKAIASLLS SEQ ID NO: 47 - CT387 nucleotide sequence
ATGACGCTCTTTCATTCTCATCATGATGCCGTCTCTCCAGACAGCTACCTATGTTCTTCCCTTCAGTTAGTTGGTAC
TGGCGTATACGAAGGAGAAATCGAGATTCAAAATATCCCCTCTTATTTCCTTGGATTCCAATTACCCTCTCATTGCA
TACACCTTAATTTAAAGAGCTCTCTAGCTCAATTAGGAATAGATGCCTCCCTTCTTCACTGCGAATTGAGCAAAAAT
CAACATCGAGCACATATACATGCTCAATTTACCGGTCATGGCCCCATTGCTGAATCTATGCTAGCCCTTCTCCAACC
AGGAGATCGTGTAGCAAAACTATTTGCTGCAGACGATCGCAGACTGGTCCGATCTCCAGATTACCTCGAAAGCATGC
TGAAAAATACAGATAAAGCTGGCCATCCTTTGCTCTGTTTTGGGAAAAAATTAGAACACTTGATTTCTTTTGATGTG
GTAGATGATCGCCTTGTCGTCTCCCTTCCTACCCTGCCGGGAGTTGTTCGTTATGATTCGGATATTTATGGACTCCT
TCCTCTTATTCAAAAATCACTCAGTAATCCCAAACTCAGCATTCGTCACTTTTTAGCTCTGTACCAACAGATTGTGG
AAGGGCAACATGTCTCTTGCGGAAACCATATTCTTCTGATCAAAACAGAACCGCTGCACATCCGCACTGTATTTGCT
CGCGTGGTAAATCAACTCCTCCCTCAAGGTCTCTCCCACACTTCTGCCAATATTTTGGAACCAACCACTCGAGAATC
CGGGGATATCTTTGAATTTTTTGGGAACCCTTCTGCACAGATAGAAAGAATTCCTTTAGAATTTTTCACTATCGAAC
CCTATAAAGAACATTCTTACTTCTGTAATCGGGATTTATTACAAACCATCTTACAATCAGAAAGCGAAATCAAAAAA
ATATTCGAAACAGCGCCCAAAGAACCTGTCAAAGCTGCCACCTATTTATCAAAAGGCAGTGAAATCTCTTCCCTGCA
CACAGACTCTTGGCTCACAGGATCCGCAGCTGCCTATCAATATAGTGAGCAAGCAGATAAAAACGAGTACACTCATG
CTCAACCTTGCTATCCTTTCTTAGAAGCAATGGAAATGGGCCTGATCAATAGCGAAGGAGCCTTACTCACTCGTTAT
TTCCCTTCAGCTAGCTTAAAAGGAATGTTGATTTCCTACCATGTGCGCCACTATCTCAAACAAATCTACTTTCAAGT
TCCCTCTTATACACATGGAAACTATTTCTCTCATAATGACAGAGGTTTGCTATTAGATCTGCAGCAAGCAGATATTG
ATGTTTTCTGGGCAGATGAAGAAAGCGGCCGTGTGTTGCAATATACAAAACGACGCGATAAGAATAGCGGTATGTTC
GTGATCAAAAATCGTGTTGAAGAGTTTCGATCAGCTTATTTTATTGCTATTTATGGCTCTCGTCTCCTTGAGAATAA
TTTCTCTGCTCAGCTCCATACCCTCCTAGCGGGCTTACAGCAAGCAGCACATACTCTCGGCATTCCTGGATTCTCAA
AGCCTACCCCACTTGCAGTCATCACCGGAGGCGGCACTGGAGTTATGGCCACAGGAAATCGTGTAGCTAAAGAACTA
GGAATCCTATCTTGTGGAACCGTTCTTGATTTAGAAGCTTCTCCAGCACAAATCGACCAACCTACCAATGAATTCTT
AGATGCTAAAATGACATACCGCCTACCTCAACTTATAGAAAGGCAAGAACACTTTTATGCAGACCTTCCTATCCTTG
TAGTTGGCGGTGTAGGAACCGATTTCGAACTCTACCTAGAACTTGTCTATCTCAAAACAGGAGCTAAACCACCGACT
CCCATTTTCCTAATTGGACCTATTGAATACTGGAAAGAAAAAGTGGCCCACGCCTACGAGATCAACCTCAAAGCAGG
AACCATCCGTGGATCCGAATGGATCAGCAACTGCCTATATTGTATCACTTCTCCGGAAGCTGGAATTGCCGTATTCG
AACAATTCCTAGCTGGAGAACTCCCTATAGGATACGACTATCCTCCAGCTCCAGATGGATTAGTGATCGTCTAA SEQ ID NO: 48 - CT387 protein sequence
MTLFHSHHDAVSPDSYLCSSLQLVGTGVYEGEIEIQNIPSYFLGFQLPSHCIHLNLKSSLAQLGIDASLLHCELSKN
QHRAHIHAQFTGHGPIAESMLALLQPGDRVAKLFAADDRRLVRSPDYLESMLKNTDKAGHPLLCFGKKLEHLISFDV
VDDRLVVSLPTLPGVVRYDSDIYGLLPLIQKSLSNPKLSIRHFLALYQQIVEGQHVSCGNHILLIKTEPLHIRTVFA
RVVNQLLPQGLSHTSANILEPTTRESGDIFEFFGNPSAQIERIPLEFFTIEPYKEHSYFCNRDLLQTILQSESEIKK
IFETAPKEPVKAATYLSKGSEISSLHTDSWLIGSAAAYQYSEQADKNEYTHAQPCYPFLEAMEMGLINSEGALLTRY
FPSASLKGMLISYHVRHYLKQIYFQVPSYTHGNYFSHNDRGLLLDLQQADIDVFWADEESGRVLQYTKRRDKNSGMF
VIKNRVEEFRSAYFIAIYGSRLLENNFSAQLHTLLAGLQQAAHTLGIPGFSKPTPLAVITGGGTGVMATGNRVAKEL
GILSCGTVLDLEASPAQIDQPTNEFLDAKMTYRLPQLIERQEHFYADLPILVVGGVGTDFELYLELVYLKTGAKPPT
PIFLIGPIEYWKEKVAHAYEINLKAGTIRGSEWISNCLYCITSPEAGIAVFEQFLAGELPIGYDYPPAPDGLVIV SEQ ID NO: 49 - CT812 nucleotide sequence
ATGAGTTCCGAGAAAGATATAAAAAGCACCTGTTCTAAGTTTTCTTTGTCTGTAGTAGCAGCTATCCTTGCCTCTGT
TAGCGGGTTAGCTAGTTGCGTAGATCTTCATGCTGGAGGACAGTCTGTAAATGAGCTGGTATATGTAGGCCCTCAAG
CGGTTTTATTGTTAGACCAAATTCGAGATCTATTCGTTGGGTCTAAAGATAGTCAGGCTGAAGGACAGTATAGGTTA
ATTGTAGGAGATCCAAGTTCTTTCCAAGAGAAAGATGCGGATACTCTTCCCGGGAAGGTAGAGCAAAGTACTTTGTT
CTCAGTAACCAATCCCGTGGTTTTCCAAGGTGTGGACCAACAGGATCAAGTCTCTTCCCAAGGGTTAATTTGTAGTT
TTACGAGCAGCAACCTTGATTCTCCTCGTGACGGAGAATCTTTTTTAGGTATTGCTTTTGTTGGGGATAGTAGTAAG
GCTGGAATCACATTAACTGACGTGAAAGCTTCTTTGTCTGGAGCGGCTTTATATTCTACAGAAGATCTTATCTTTGA
AAAGATTAAGGGTGGATTGGAATTTGCATCATGTTCTTCTCTAGAACAGGGGGGAGCTTGTGCAGCTCAAAGTATTT
TGATTCATGATTGTCAAGGATTGCAGGTTAAACACTGTACTACAGCCGTGAATGCTGAGGGGTCTAGTGCGAATGAT
CATCTTGGATTTGGAGGAGGCGCTTTCTTTGTTACGGGTTCTCTTTCTGGAGAGAAAAGTCTCTATATGCCTGCAGG
AGATATGGTAGTTGCGAATTGTGATGGGGCTATATCTTTTGAAGGAAACAGCGCGAACTTTGCTAATGGAGGAGCGA -continued

SEQUENCE LISTING

TTGCTGCCTCTGGGAAAGTGCTTTTTGTCGCTAATGATAAAAAGACTTCTTTTATAGAGAACCGAGCTTTGTCTGGA
GGAGCGATTGCAGCCTCTTCTGATATTGCCTTTCAAAACTGCGCAGAACTAGTTTTCAAAGGCAATTGTGCAATTGG
AACAGAGGATAAAGGTTCTTTAGGTGGAGGGGCTATATCTTCTCTAGGCACCGTTCTTTTGCAAGGGAATCACGGGA
TAACTTGTGATAAGAATGAGTCTGCTTCGCAAGGAGGCGCCATTTTTGGCAAAAATTGTCAGATTTCTGACAACGAG
GGGCCAGTGGTTTTCAGAGATAGTACAGCTTGCTTAGGAGGAGGCGCTATTGCAGCTCAAGAAATTGTTTCTATTCA
GAACAATCAGGCTGGGATTTCCTTCGAGGGAGGTAAGGCTAGTTTCGGAGGAGGTATTGCGTGTGGATCTTTTTCTT
CCGCAGGTGGTGCTTCTGTTTTAGGGACCATTGATATTTCGAAGAATTTAGGCGCGATTTCGTTCTCTCGTACTTTA
TGTACGACCTCAGATTTAGGACAAATGGAGTACCAGGGAGGAGGAGCTCTATTTGGTGAAAATATTTCTCTTTCTGA
GAATGCTGGTGTGCTCACCTTTAAAGACAACATTGTGAAGACTTTTGCTTCGAATGGGAAAATTCTGGGAGGAGGAG
CGATTTTAGCTACTGGTAAGGTGGAAATTACTAATAATTCCGAAGGAATTTCTTTTACAGGAAATGCGAGAGCTCCA
CAAGCTCTTCCAACTCAAGAGGAGTTTCCTTTATTCAGCAAAAAAGAAGGGCGACCACTCTCTTCAGGATATTCTGG
GGGAGGAGCGATTTTAGGAAGAGAAGTAGCTATTCTCCACAACGCTGCAGTAGTATTTGAGCAAAATCGTTTGCAGT
GCAGCGAAGAAGAAGCGACATTATTAGGTTGTTGTGGAGGAGGCGCTGTTCATGGGATGGATAGCACTTCGATTGTT
GGCAACTCTTCAGTAAGATTTGGTAATAATTACGCAATGGGACAAGGAGTCTCAGGAGGAGCTCTTTTATCTAAAAC
AGTGCAGTTAGCTGGGAATGGAAGCGTCGATTTTTCTCGAAATATTGCTAGTTTGGGAGGAGGAGCTCTTCAAGCTT
CTGAAGGAAATTGTGAGCTAGTTGATAACGGCTATGTGCTATTCAGAGATAATCGAGGGAGGGTTTATGGGGGTGCT
ATTTCTTGCTTACGTGGAGATGTAGTCATTTCTGGAAACAAGGGTAGAGTTGAATTTAAAGACAACATAGCAACACG
TCTTTATGTGGAAGAAACTGTAGAAAAGGTTGAAGAGGTAGAGCCAGCTCCTGAGCAAAAAGACAATAATGAGCTTT
CTTTCTTAGGGAGAGCAGAACAGAGTTTTATTACTGCAGCTAATCAAGCTCTTTTCGCATCTGAAGATGGGGATTTA
TCACCTGAGTCATCCATTTCTTCTGAAGAACTTGCGAAAAGAAGAGAGTGTGCTGGAGGAGCTATTTTTGCAAAACG
GGTTCGTATTGTAGATAACCAAGAGGCCGTTGTATTCTCGAATAACTTCTCTGATATTTATGGCGGCGCCATTTTTA
CAGGTTCTCTTCGAGAAGAGGATAAGTTAGATGGGCAAATCCCTGAAGTCTTGATCTCAGGCAATGCAGGGGATGTT
GTTTTTTCCGGAAATTCCTCGAAGCGTGATGAGCATCTTCCTCATACAGGTGGGGGAGCCATTTGTACTCAAAATTT
GACGATTTCTCAGAATACAGGGAATGTTCTGTTTTATAACAACGTGGCCTGTTCGGGAGGAGCTGTTCGTATAGAGG
ATCATGGTAATGTTCTTTTAGAAGCTTTTGGAGGAGATATTGTTTTTAAAGGAAATTCTTCTTTCAGAGCACAAGGA
TCCGATGCTATCTATTTTGCAGGTAAAGAATCGCATATTACAGCCCTGAATGCTACGGAAGGACATGCTATTGTTTT
CCACGACGCATTAGTTTTTGAAAATCTAGAAGAAAGGAAATCTGCTGAAGTATTGTTAATCAATAGTCGAGAAAATC
CAGGTTACACTGGATCTATTCGATTTTTAGAAGCAGAAAGTAAAGTTCCTCAATGTATTCATGTACAACAAGGAAGC
CTTGAGTTGCTAAATGGAGCCACATTATGTAGTTATGGTTTTAAACAAGATGCTGGAGCTAAGTTGGTATTGGCTGC
TGGAGCTAAACTGAAGATTTTAGATTCAGGAACTCCTGTACAACAAGGGCATGCTATCAGTAAACCTGAAGCAGAAA
TCGAGTCATCTTCTGAACCAGAGGGTGCACATTCTCTTTGGATTGCGAAGAATGCTCAAACAACAGTTCCTATGGTT
GATATCCATACTATTTCTGTAGATTTAGCCTCCTTCTCTTCTAGTCAACAGGAGGGGACAGTAGAAGCTCCTCAGGT
TATTGTTCCTGGAGGAAGTTATGTTCGATCTGGAGAGCTTAATTTGGAGTTAGTTAACACAACAGGTACTGGTTATG
AAAATCATGCTTTATTGAAGAATGAGGCTAAAGTTCCATTGATGTCTTTCGTTGCTTCTGGTGATGAAGCTTCAGCC
GAAATCAGTAACTTGTCGGTTTCTGATTTACAGATTCATGTAGTAACTCCAGAGATTGAAGAAGACACATACGGCCA
TATGGGAGATTGGTCTGAGGCTAAAATTCAAGATGGAACTCTTGTCATTAGTTGGAATCCTACTGGATATCGATTAG
ATCCTCAAAAAGCAGGGGCTTTAGTATTTAATGCATTATGGGAAGAAGGGGCTGTCTTGTCTGCTCTGAAAAATGCA
CGCTTTGCTCATAATCTCACTGCTCAGCGTATGGAATTCGATTATTCTACAAATGTGTGGGGATTCGCCTTTGGTGG
TTTCCGAACTCTATCTGCAGAGAATCTGGTTGCTATTGATGGATACAAAGGAGCTTATGGTGGTGCTTCTGCTGGAG
TCGATATTCAATTGATGGAAGATTTTGTTCTAGGAGTTAGTGGAGCTGCTTTCCTAGGTAAAATGGATAGTCAGAAG
TTTGATGCGGAGGTTTCTCGGAAGGGAGTTGTTGGTTCTGTATATACAGGATTTTTAGCTGGATCCTGGTTCTTCAA
AGGACAATATAGCCTTGGAGAAACACAGAACGATATGAAAACGCGTTATGGAGTACTAGGAGAGTCGAGTGCTTCTT
GGACATCTCGAGGAGTACTGGCAGATGCTTTAGTTGAATACCGAAGTTTAGTTGGTCCTGTGAGACCTACTTTTTAT
GCTTTGCATTTCAATCCTTATGTCGAAGTATCTTATGCTTCTATGAAATTCCCTGGCTTTACAGAACAAGGAAGAGA
AGCGCGTTCTTTTGAAGACGCTTCCCTTACCAATATCACCATTCCTTTAGGGATGAAGTTTGAATTGGCGTTCATAA
AAGGACAGTTTTCAGAGGTGAACTCTTTGGGAATAAGTTATGCATGGGAAGCTTATCGAAAAGTAGAAGGAGGCGCG
GTGCAGCTTTTAGAAGCTGGGTTTGATTGGGAGGGAGCTCCAATGGATCTTCCTAGACAGGAGCTGCGTGTCGCTCT
GGAAAATAATACGGAATGGAGTTCTTACTTCAGCACAGTCTTAGGATTAACAGCTTTTTGTGGAGGATTTACTTCTA
CAGATAGTAAACTAGGATATGAGGCGAATACTGGATTGCGATTGATCTTTTAA

SEQ ID NO: 50 - CT812 protein sequence
MSSEKDIKSTCSKFSLSVVAAILASVSGLASCVDLHAGGQSVNELVYVGPQAVLLLDQIRDLFVGSKDSQAEGQYRL
IVGDPSSFQEKDADTLPGKVEQSTLFSVTNPVVFQGVDQQDQVSSQGLICSFTSSNLDSPRDGESFLGIAFVGDSSK
AGITLTDVKASLSGAALYSTEDLIFEKIKGGLEFASCSSLEQGGACAAQSILIHDCQGLQVKHCTTAVNAEGSSAND
HLGFGGGAFFVTGSLSGEKSLYMPAGDMVVANCDGAISFEGNSANFANGGAIAASGKVLFVANDKKTSFIENRALSG
GAIAASSDIAFQNCAELVFKGNCAIGTEDKGSLGGGAISSLGTVLLQGNHGITCDKNESASQGGAIFGKNCQISDNE
GPVVFRDSTACLGGGAIAAQEIVSIQNNQAGISFEGGKASFGGGIACGSFSSAGGASVLGTIDISKNLGAISFSRTL
CTTSDLGQMEYQGGGALFGENISLSENAGVLTFKDNIVKTFASNGKILGGGAILATGKVEITNNSEGISFTGNARAP
QALPTQEEFPLFSKKEGRPLSSGYSGGGAILGREVAILHNAAVVFEQNRLQCSEEEATLLGCCGGGAVHGMDSTSIV
GNSSVRFGNNYAMGQGVSGGALLSKTVQLAGNGSVDFSRNIASLGGGALQASEGNCELVDNGYVLFRDNRGRVYGGA
ISCLRGDVVISGNKGRVEFKDNIATRLYVEETVEKVEEVEPAPEQKDNNELSFLGRAEQSFITAANQALFASEDGDL
SPESSISSEELAKRRECAGGAIFAKRVRIVDNQEAVVFSNNFSDIYGGAIFTGSLREEDKLDGQIPEVLISGNAGDV
VFSGNSSKRDEHLPHTGGGAICTQNLTISQNTGNVLFYNNVACSGGAVRIEDHGNVLLEAFGGDIVFKGNSSFRAQG
SDAIYFAGKESHITALNATEGHAIVFHDALVFENLEERKSAEVLLINSRENPGYTGSIRFLEAESKVPQCIHVQQGS
LELLNGATLCSYGFKQDAGAKLVLAAGAKLKILDSGTPVQQGHAISKPEAEIESSSEPEGAHSLWIAKNAQTTVPMV
DIHTISVDLASFSSSQQEGTVEAPQVIVPGGSYVRSGELNLELVNTTGTGYENHALLKNEAKVPLMSFVASGDEASA
EISNLSVSDLQIHVVTPEIEEDTYGHMGDWSEAKIQDGTLVISWNPTGYRLDPQKAGALVFNALWEEGAVLSALKNA
RFAHNLTAQRMEFDYSTNVWGFAFGGFRTLSAENLVAIDGYKGAYGGASAGVDIQLMEDFVLGVSGAAFLGKMDSQK
FDAEVSRKGVVGSVYTGFLAGSWFFKGQYSLGETQNDMKTRYGVLGESSASWTSRGVLADALVEYRSLVGPVRPTFY
ALHFNPYVEVSYASMKFPGFTEQGREARSFEDASLTNITIPLGMKFELAFIKGQFSEVNSLGISYAWEAYRKVEGGA
VQLLEAGFDWEGAPMDLPRQELRVALENNTEWSSYFSTVLGLTAFCGGFTSTDSKLGYEANTGLRLIF SEQ ID NO: 51 - CT869 nucleotide sequence
ATGAAAAAAGCGTTTTTCTTTTTCCTTATCGGAAACTCCCTATCAGGACTAGCTAGAGAGGTTCCTTCTAGAATCTT
TCTTATGCCCAACTCAGTTCCAGATCCTACGAAAGAGTCGCTATCAAATAAAATTAGTTTGACAGGAGACACTCACA
ATCTCACTAACTGCTATCTCGATAACCTACGCTACATACTGGCTATTCTACAAAAACTCCCAATGAAGGAGCTGCT
GTCACAATAACAGATTACCTAAGCTTTTTTGATACACAAAAAGAAGGTATTTATTTTGCAAAAAATCTCACCCCTGA -continued

SEQUENCE LISTING

AAGTGGTGGTGCGATTGGTTATGCGAGTCCCAATTCTCCTACCGTGGAGATTCGTGATACAATAGGTCCTGTAATCT
TTGAAAATAATACTTGTTGCAGACTATTTACATGGAGAAATCCTTATGCTGCTGATAAAATAAGAGAAGGCGGAGCC
ATTCATGCTCAAAATCTTTACATAAATCATAATCATGATGTGGTCGGATTTATGAAGAACTTTTCTTATGTCCAAGG
AGGAGCCATTAGTACCGCTAATACCTTTGTTGTGAGCGAGAATCAGTCTTGTTTTCTCTTTATGGACAACATCTGTA
TTCAAACTAATACAGCAGGAAAAGGTGGCGCTATCTATGCTGGAACGAGCAATTCTTTTGAGAGTAATAACTGCGAT
CTCTTCTTCATCAATAACGCCTGTTGTGCAGGAGGAGCGATCTTCTCCCCTATCTGTTCTCTAACAGGAAATCGTGG
TAACATCGTTTTCTATAACAATCGCTGCTTTAAAAATGTAGAAACAGCTTCTTCAGAAGCTTCTGATGGAGGAGCAA
TTAAAGTAACTACTCGCCTAGATGTTACAGGCAATCGTGGTAGGATCTTTTTTAGTGACAATATCACAAAAAATTAT
GGCGGAGCTATTTACGCTCCTGTAGTTACCCTAGTGGATAATGGCCCTACCTACTTTATAAACAATATCGCCAATAA
TAAGGGGGGCGCTATCTATATAGACGGAACCAGTAACTCCAAAATTTCTGCCGACCGCCATGCTATTATTTTTAATG
AAAATATTGTGACTAATGTAACTAATGCAAATGGTACCAGTACGTCAGCTAATCCTCCTAGAAGAAATGCAATAACA
GTAGCAAGCTCCTCTGGTGAAATTCTATTAGGAGCAGGGAGTAGCCAAAATTTAATTTTTTATGATCCTATTGAAGT
TAGCAATGCAGGGGTCTCTGTGTCCTTCAATAAGGAAGCTGATCAAACAGGCTCTGTAGTATTTTCAGGAGCTACTG
TTAATTCTGCAGATTTTCATCAACGCAATTTACAAACAAAAACACCTGCACCCCTTACTCTCAGTAATGGTTTTCTA
TGTATCGAAGATCATGCTCAGCTTACAGTGAATCGATTCACACAAACTGGGGGTGTTGTTTCTCTTGGGAATGGAGC
AGTTCTGAGTTGCTATAAAAATGGTACAGGAGATTCTGCTAGCAATGCCTCTATAACACTGAAGCATATTGGATTGA
ATCTTTCTTCCATTCTGAAAAGTGGTGCTGAGATTCCTTTATTGTGGGTAGAGCCTACAAATAACAGCAATAACTAT
ACAGCAGATACTGCAGCTACCTTTTCATTAAGTGATGTAAAACTCTCACTCATTGATGACTACGGGAACTCTCCTTA
TGAATCCACAGATCTGACCCATGCTCTGTCATCACAGCCTATGCTATCTATTTCTGAAGCTAGCGATAACCAGCTAC
AATCAGAAAATATAGATTTTTCGGGACTAAATGTCCCTCATTATGGATGGCAAGGACTTTGGACTTGGGGCTGGGCA
AAAACTCAAGATCCAGAACCAGCATCTTCAGCAACAATCACTGATCCACAAAAAGCCAATAGATTTCATAGAACCTT
ACTACTAACATGGCTTCCTGCCGGGTATGTTCCTAGCCCAAAACACAGAAGTCCCCTCATAGCTAACACCTTATGGG
GGAATATGCTGCTTGCAACAGAAAGCTTAAAAAATAGTGCAGAGCTGACACCTAGTGGTCATCCTTTCTGGGGAATT
ACAGGAGGAGGACTAGGCATGATGGTTTACCAAGATCCTCGAGAAAATCATCCTGGATTCCATATGCGCTCTTCCGG
ATACTCTGCGGGGATGATAGCAGGGCAGACACACACCTTCTCATTGAAATTCAGTCAGACCTACACCAAACTCAATG
AGCGTTACGCAAAAAACAACGTATCTTCTAAAAATTACTCATGCCAAGGAGAAATGCTCTTCTCATTGCAAGAAGGT
TTCTTGCTGACTAAATTAGTTGGGCTTTACAGCTATGGAGACCATAACTGTCACCATTTCTATACTCAAGGAGAAAA
TCTAACATCTCAAGGGACGTTCCGCAGTCAAACGATGGGAGGTGCTGTCTTTTTTGATCTCCCTATGAAACCCTTTG
GATCAACGCATATACTGACAGCTCCCTTTTTAGGTGCTCTTGGTATTTATTCTAGCCTGTCTCACTTTACTGAGGTG
GGAGCCTATCCGCGAAGCTTTTCTACAAAGACTCCTTTGATCAATGTCCTAGTCCCTATTGGAGTTAAAGGTAGCTT
TATGAATGCTACCCACAGACCTCAAGCCTGGACTGTAGAATTGGCATACCAACCCGTTCTGTATAGACAAGAACCAG
GGATCGCAGCCCAGCTCCTAGCCAGTAAGGGTATTTGGTTCGGTAGTGGAAGCCCCTCATCGCGTCATGCCATGTCC
TATAAAATCTCACAGCAAACACAACCTTTGAGTTGGTTAACTCTCCATTTCCAGTATCATGGATTCTACTCCTCTTC
AACCTTCTGTAATTATCTCAATGGGGAAATTGCTCTGCGATTCTAG

SEQ ID NO: 52 - CT869 protein sequence
MKKAFFFFLIGNSLSGLAREVPSRIFLMPNSVPDPTKESLSNKISLTGDTHNLTNCYLDNLRYILAILQKTPNEGAA
VTITDYLSFFDTQKEGIYFAKNLTPESGGAIGYASPNSPTVEIRDTIGPVIFENNTCCRLFTWRNPYAADKIREGGA
IHAQNLYINHNHDVVGFMKNFSYVQGGAISTANTFVVSENQSCFLFMDNICIQTNTAGKGGAIYAGTSNSFESNNCD
LFFINNACCAGGAIFSPICSLTGNRGNIVFYNNRCFKNVETASSEASDGGAIKVTTRLDVTGNRGRIFFSDNITKNY
GGAIYAPVVTLVDNGPTYFINNIANNKGGAIYIDGTSNSKISADRHAIIFNENIVTNVTNANGTSTSANPPRRNAIT
VASSSGEILLGAGSSQNLIFYDPIEVSNAGVSVSFNKEADQTGSVVFSGATVNSADFHQRNLQTKTPAPLTLSNGFL
CIEDHAQLTVNRFTQTGGVVSLGNGAVLSCYKNGTGDSASNASITLKHIGLNLSSILKSGAEIPLLWVEPTNNSNNY
TADTAATFSLSDVKLSLIDDYGNSPYESTDLTHALSSQPMLSISEASDNQLQSENIDFSGLNVPHYGWQGLWTWGWA
KTQDPEPASSATITDPQKANRFHRTLLLTWLPAGYVPSPKHRSPLIANTLWGNMLLATESLKNSAELTPSGHPFWGI
TGGGLGMMVYQDPRENHPGFHMRSSGYSAGMIAGQTHTFSLKFSQTYTKLNERYAKNNVSSKNYSCQGEMLFSLQEG
FLLTKLVGLYSYGDHNCHHFYTQGENLTSQGTFRSQTMGGAVFFDLPMKPFGSTHILTAPFLGALGIYSSLSHFTEV
GAYPRSFSTKTPLINVLVPIGVKGSFMNATHRPQAWTVELAYQPVLYRQEPGIAAQLLASKGIWFGSGSPSSRHAMS
YKISQQTQPLSWLTLHFQYHGFYSSSTFCNYLNGEIALRF SEQ ID NO: 53 - CT166 nucleotide sequence
GTGAACGTTCGTACGTACTCTGTTCAGAGGGGGGGGGTAAAAACGATTTCTGCTAGTGCAGTTCCTCCTACAGCAGC
TGTTTTATCGAGAAAAAAGCGTGCTATAGAAGAGAAGAAGGAGGAGGAAGCTTCTTCTGGAAAGATAGAAAATCTTGATG
CTAGCAAATACGATCTTACTCCCAAGAACATAGAAGAAAAACTAGGAATTACTCCTGAACAGAAATCTACTGTTAAA
GACCTATTAAATAAACTGAAAAAGGTCATTAGTGCTTACAACTCTATGCCAGATAAAAATTCGGAAGCGGGACAGAA
TTCCTTGATTCAACAAGGAAAATACGTCGATGCCATTCAGAAGAAGCTTCCAGCATCATCGCAGGCTCAGCCTAAAC
AGGCAAAAGCTAAGGAACAGAAAGCCGAAGAAAAACCTAAGACGACTCCGATTGAAGGTGTTCTTGAAACCATCAAA
ACAGAATTTAAAGGCCATCGTGTACCTGTTGAGAAAATCATCCATGGAATATGGATCGCAGGAGCGCCTCCGGATGG
TATCGAAGATTATATGCGAGTCTTTTTAGATACTTATGAAGGTTTTGACTTCTACTTCTGGGTAGATGAGAATGCTT
ATGCAGCAGCTAAATTTTCTAGCATTTTGAAGAAGGTCGCTTTCGATGCGGCTATTCAAGATCTACGATCTGCCACA
GATGAGTCTACGAAGGCCTTTGTTAAAGACTACGATGAATTAAAACAGAAATATGAAAAGAAAGTTGCGGAGACGAC
TTCTCAAGCAGAAAAAGACCAATATCTCAAAGATCTAAAGGATCTTTTAGAGAAATTTACAAAAAATCAGTGATGAGA
TTCGTGGAAAATTTGATCGGCTGTTTCTTAAGAATGTGATTGTTGCTCAGAACGGATTCTTTAATTTCTGCTTGCTG
AAAGGCCTCGGCAATATCAATGACGAAACGCGTGCAGAGTATTTAGAGAAAGAACTCAAACTTCCTACTGAGGAGAT
CGAACAGTATAAAAAGCTTAAAGAGACGAACAAAGAGAAGATAGCCGCTATTGTAAAACAACTAAACGAGAAACTTG
GATCGGATCGGGTAAAAATCAAAGACATTAAAGAGCTGCAATCTATGAAGCAAGCTCGAAATGTCTACAATTATGAA
CAGGAAATGTTTCTGCGCTGGAACTATGCAGCCGCAACAGATCAGATTCGTATGTATATGTTGGAGGAACTTGGAGG
TCTTTATACTGATCTGGATATGATGCCTTCATACTCTCAGGAAGTATTGGAGCTTATCAAAAAGCACAGTGATGGAA
ACCGAATGTTTGAGGATATGAGCTCTAGACGGGCGATTTCTGATGCGGTTTTAAAGATGGCTGTAGGTAAGGCGACA
ACAGTTTCCATGGAAGAGGTAGCAAAGGATATCGATGTTTCTCGCTTAACAGAAGAGGATAAGACAAAATTAAATGC
TCTATTTAAGGATCTAGAGCCATTTGCAAAACCGGATTCTAAAGGAGCTGAAGCAGAAGGGGGTGAAGGAGCAAAAG
GTATGAAAAAGAGCTTTTTCCAGCCCATAGATCTGAATATTGTCAGAAATACCATGCCTATCTTGAGACGCTATCAT
CACTATCCTGAGTTAGGATGGTTTATTCGAGGATTGAACGGATTGATGGTCTCTCATAAGGGAAGCACTGCGGTTTC
TGCTGTCATTGTAGGGCAACAGGCTGCCTACCAGGAACTAGCAGCACTTAGACAAGATGTCCTTTCAGGGGAGTTTT
TCCATTCTTTAGAAAATTTGACACATAGAAACCATAAGGAGCGTATTGGAAATCATCTCGTCGCTAATTATTTGGCT
AAAAGTCTCTTTTTTGATTACTGCCAAGATTCAGTGATGCCGGAGGCTGTAAGTACCTTAGGTATTAGATGA -continued

SEQUENCE LISTING

SEQ ID NO: 54 - CT166 protein sequence
MNVRTYSVQRGGVKTISASAVPPTAAVLSRKKRAIEEKKEEASSGKIENLDASKYDLTPKNIEEKLGITPEQKSTVK
DLLNKLKKVISAYNSMPDKNSEAGQNSLIQQGKYVDAIQKKLPASSQAQPKQAKAKEQKAEEKPKTTPIEGVLETIK
TEFKGHRVPVEKIIHGIWIAGAPPDGIEDYMRVFLDTYEGFDFYFWVDENAYAAAKFSSILKKVAFDAAIQDLRSAT
DESTKAFVKDYDELKQKYEKKVAETTSQAEKDQYLKDLKDLLEKFTKISDEIRGKFDRLFLKNVIVAQNGFFNFCLL
KGLGNINDETRAEYLEKELKLPTEEIEQYKKLKETNKEKIAAIVKQLNEKLGSDRVKIKDIKELQSMKQARNVYNYE
QEMFLRWNYAAATDQIRMYMLEELGGLYTDLDMMPSYSQEVLELIKKHSDGNRMFEDMSSRRAISDAVLKMAVGKAT
TVSMEEVAKDIDVSRLTEEDKTKLNALFKDLEPFAKPDSKGAEAEGGEGAKGMKKSFFQPIDLNIVRNTMPILRRYH
HYPELGWFIRGLNGLMVSHKGSTAVSAVIVGQQAAYQELAALRQDVLSGEFFHSLENLTHRNHKERIGNHLVANYLA
KSLFFDYCQDSVMPEAVSTLGIR SEQ ID NO: 55 - CT175 nucleotide sequence
ATGCATCACAGGAAGTTTTTAGCAGTTTCCATTGCTTTCGTAAGTTTAGCTTTTGGGCTAACATCTTGTTATCATAA
AAAAGAAGAACCAAAAGATGTTTTGCGGATTGCGATCTGTCATGATCCAATGTCTTTAGATCCGCGTCAGGTTTTTT
TAAGCAAAGATGTTTCTATTGTAAAAGCTCTCTATGAAGGGTTAGTCCGGGAAAAAGAAGCTGCGTTCCAGCTAGCT
TTGGCAGAAAGATATCATCAATCTGATGATGGTTGTGTTTATACTTTTTTTCTAAAAAATACATTCTGGAGCAACGG
AGATGTTGTAACAGCATATGATTTTGAAGAGTCTATTAAACAAATTTATTTCCGAGAAATTGATAACCCTTCGTTAC
GCTCTCTTGCATTAATTAAAAATTCTCATGCTGTTTTAACAGGAGCTCTCCCTGTTGAAGATTTAGGTGTTAGAGCT
TTGAATGCGAAAACTCTAGAAATTGTTTTAGAAAACCCGTTTCCTTATTTTCTAGAGATATTGGCGCACCCGGTTTT
TTATCCGGTGCACACCTCTTTACGAGAATATTACAAAGATAAGCGTAACAAACGCGTTTTCCCGATAATTTCTAATG
GTCCTTTTGCGATTCAATGTTATGAGCCGCAAAGATATTTACTAATCAACAAAAACCCTCTGTATCATGCCAAGCAC
GATGTTCTGTTAAATTCGGTATGTTTGCAGATAGTTCCTGATATCCATACAGCTATGCAGTTATTCCAAAAAAATCA
TATCGATTTAGTTGGGTTACCCTGGAGCTCCTCCTTTTCTTTAGAAGAACAAAGAAATCTCCCTAGAGAAAAATTAT
TTGATTATCCTGTATTGAGTTGCTCTGTTTTATTCTGTAACATTCATCAAACACCTTTAAATAATCCCTCGCTGAGA
ACAGCCCTCTCTTTAGCAATCAATCGAGAAACTTTATTAAAACTAGCAGGTAAAGGCTGTAGCGCTACGAGCTTTGT
TCACCCACAATTATCTCAGATACCTGCTACTACTTTGTCTCAAGATGAGCGGATTGCTTTAGCAAAAGGCTACTTGA
CCGAAGCTTTAAAGACTTTATCTCAAGAAGATTTAGAAAAAATTACATTAATTTATCCTATAGAATCTGTTTGCTTA
CGAGCCGTTGTTCAAGAAATTCGCCAACAATTATTTGATGTACTGGGATTTAAAATTTCTACATTAGGATTAGAATA
TCATTGTTTTTTAGACAAACGTTCCAGAGGAGAATTCTCCTTAGCAACTGGTAATTGGATTGCAGACTATCATCAAG
CTAGTGCTTTCCTGTCTGTCCTAGGTAATGGGACAAGATATAAAGACTTTCAATTGATTAACTGGCAGAACCAAAAG
TACACAAATATAGTTGCTCAACTTCTGATTCAAGAATCAAGCGACCTACAGCTTATGGCAGAGCAGTTGTTGCTTAA
AGAAAGTCCTCTTATTCCTCTATACCACCTCGATTATGTGTATGCGAAACAGCCTCGGGTGTCTGATCTCCAAACCT
CTTCTCGTGGAGAAATTGATTTAAAAAGAGTTTCATTAGCTGAAGGATAG SEQ ID NO: 56 - CT175 protein sequence
MHHRKFLAVSIAFVSLAFGLTSCYHKKEEPKDVLRIAICHDPMSLDPRQVFLSKDVSIVKALYEGLVREKEAAFQLA
LAERYHQSDDGCVYTFFLKNTFWSNGDVVTAYDFEESIKQIYFREIDNPSLRSLALIKNSHAVLTGALPVEDLGVRA
LNAKTLEIVLENPFPYFLEILAHPVFYPVHTSLREYYKDKRNKRVFPIISNGPFAIQCYEPQRYLLINKNPLYHAKH
DVLLNSVCLQIVPDIHTAMQLFQKNHIDLVGLPWSSSFSLEEQRNLPREKLFDYPVLSCSVLFCNIHQTPLNNPSLR
TALSLAINRETLLKLAGKGCSATSFVHPQLSQIPATTLSQDERIALAKGYLTEALKTLSQEDLEKITLIYPIESVCL
RAVVQEIRQQLFDVLGFKISTLGLEYHCFLDKRSRGEFSLATGNWIADYHQASAFLSVLGNGTRYKDFQLINWQNQK
YTNIVAQLLIQESSDLQLMAEQLLLKESPLIPLYHLDYVYAKQPRVSDLQTSSRGEIDLKRVSLAEG SEQ ID NO: 57 - TC0666 nucleotide sequence (homologue of CT387)
ATGAGGATTCCAATGACACTCTTTCACACTCATCACGATGCCGTCTCTCCGGACGGCTACTTATGTTCTTCCCTTCA
GTTAGTTGGCTCTGGCACATATGAAGGAGAAATCGAAATCCAAAATATTCCTTCTTATTTCCTTGGATTCCGATTAC
CCACCCATTGCGTTCATCTTAATTTGAAGAGTTCTCTAGCCCAGTTAGGAGTAGATGCATCTCTTCTTCACTGCGAA
CTAAGCAAAAATCAACAACGTGCACATATGCACGTGCAGTTCACCGGCTATGGCCCTATCGCTGAGTCCATGCTATC
TCTTCTCAAACCCGGAGATCGAGTAGCCAAACTGTTTGCTGCAGATGATCGTAGACTAGTCCGCTCCCCTGATTATC
TTGAAAGCATGCTAAAAAATACTGATAAGACAGGACATCCTCTGCTCCGATTTGGAAAAAAACTCGAGCATCTTATC
TCTTTTGATGTGGTGGACGATCGCCTCGTTGTATCACTCCCCACCTTGCCAGGCATAGTCAATTATGACCCAGACAT
CTATGGACTTCTTCCCTTAATTCAAAAATCACTAAGCAATCCTAAATTGAGTATTCGCCACTTCTTGTCTCTCTATC
AGAAGATCGTAGAAGGACCACACATCCCTTATGAAGGAAACATTTTGTTAATCAAAACAGAGCCTCTTCATATCCGC
ACAGTATTTGCTCGCGTGGTCGATCAAATGCTCCCTCAAGGTCTATTTCACACTTCTGCCAACATTTTAGAACCCAC
AACGCGAGAGTCTGGAGATATTTTTGAATTTTTTGGAAATCCTCCACTCTTGTAGAAAGAATCCCTCTAGAATTCT
TCACTATCGAACCCTACAAAGAACACTCTTACTTCTGTAATCGAGATCTATTGCAAACTACCTTGCAATCGGAAAGT
GAAATCAAAAAAATATTCGATACAGCTCCTCAAGAGCCTGTAAAAGCCGCCACTTATTTATCAAAAGGAAGTGAAAT
TTCTTCTCTTGATGCAGATTCTTGGCTTACGGGATCCGCAGCTGCATACCAATGTAGCGAAAAACAGGCAGCTAAAG
ACGAATACATCCACGCTCAACCCTGTTATCCATTTTTGGAAGCAATGGAAACGGGACTCATCAATAGCGAAGGAGCT
TTACTCACTCGGTTTTTCCCCTCTTCCAGCTTAAAAGGGATGTTGATCTCCTATCATGTACGCCACTATCTTAAGCA
AATTTACTTTCAAGTTCCTTCTTATACATATGGAGACTACTTCTCTCATAATGACCGAGGATTACTGTTAGATCTAT
ATCAGGCGAACATTGATGTGTTCTGGGCTGATGAAGAGAGCGGCCGTGTATTGCAATATACAAAACGGCGCGACAAA
AATAGTGGAATGTTCGTCGTTAAAAATCGAGTAGAAGAGTTCCAATCAGCATATTTCGTAGCGATTTATGGATCACG
TCTCCTGGAAAATAATTTCTCGGCCCAACTAAACACGCTTCTTGCAGGGTTACAAAAAGCTGCACACACTCTAGGCA
TTCCAGGCTTCTCAAAACCCACTCCTCTTGCCGTAATCACAGGAGGAGGGACTGGCGTTATGGCTACAGGAAATCGT
GTTGCAAAAGAGTTGGGAATTCTTTCTTGCGGGACCGTTCTCGATTTGGAAGCTTCACCTGCACAAATAGATCAGCC
TGCAAACGAATTTTTAGATGCCAAAATGACATACCGTCTACCGCAACTTATAGAAAGACAAGAACATTTTTATTCAG
ACCTTGCCATTTTAGTTGTTGGTGGTGTTGGAACAGATTTCGAACTTTACCTAGAACTCGTCTACTTGAAAACAGGC
GCCAAACCTCCTACTCCAATTTTCCTTATTGGGCCTGTTGAATACTGGAAAGAGAAAGTTGCTCATGCCTATGAGAT
TAATCTTAAAGCAGGAACTATTCGTGGTTCTGAGTGGATCAGCAACTGCTTATTCTGCATTACATCTCCTGAAGCAG
GAATTGCTGTATTCGAACAGTTCCTCGCTGGAGAACTTCCCATAGGATATGATTATCCTCCAGCTCCAGACGGATTA
GTTATCGTCTAA SEQ ID NO: 58 - TC0666 protein sequence (homologue of CT387)
MRIPMTLFHTHHDAVSPDGYLCSSLQLVGSGTYEGEIEIQNIPSYFLGFRLPTHCVHLNLKSSLAQLGVDASLLHCE
LSKNQQRAHMHVQFTGYGPIAESMLSLLKPGDRVAKLFAADDRRLVRSPDYLESMLKNTDKTGHPLLRFGKKLEHLI
SFDVVDDRLVVSLPTLPGIVNYDPDIYGLLPLIQKSLSNPKLSIRHFLSLYQKIVEGPHIPYEGNILLIKTEPLHIR -continued

SEQUENCE LISTING

TVFARVVDQMLPQGLFHTSANILEPTTRESGDIFEFFGNPSTLVERIPLEFFTIEPYKEHSYFCNRDLLQTTLQSES
EIKKIFDTAPQEPVKAATYLSKGSEISSLDADSWLTGSAAAYQCSEKQAAKDEYIHAQPCYPFLEAMETGLINSEGA
LLTRFFPSSSLKGMLISYHVRHYLKQIYFQVPSYTYGDYFSHNDRGLLLDLYQANIDVFWADEESGRVLQYTKRRDK
NSGMFVVKNRVEEFQSAYFVAIYGSRLLENNFSAQLNTLLAGLQKAAHTLGIPGFSKPTPLAVITGGGTGVMATGNR
VAKELGILSCGTVLDLEASPAQIDQPANEFLDAKMTYRLPQLIERQEHFYSDLAILVVGGVGTDFELYLELVYLKTG
AKPPTPIFLIGPVEYWKEKVAHAYEINLKAGTIRGSEWISNCLFCITSPEAGIAVFEQFLAGELPIGYDYPPAPDGL
VIV

SEQ ID NO: 59 - TC0197 nucleotide sequence
ATGAGTTCCGAGAAAGATAAAAAAAACTCCTGTTCTAAGTTTTCCTTATCGGTAGTAGCAGCTATTCTCGCTTCTAT
GAGTGGTTTATCGAATTGTTCCGATCTTTATGCCGTAGGAAGTTCTGCAGACCATCCTGCCTACTTGATTCCTCAAG
CGGGGTTATTATTGGATCATATTAAGGATATATTCATTGGCCCTAAAGATAGTCAGGATAAGGGGCAGTATAAGTTG
ATTATTGGTGAGGCTGGCTCTTTCCAAGATAGTAATGCAGAGACTCTTCCTCAAAAGGTAGAGCACAGCACTTTGTT
TTCAGTTACAACACCTATAATTGTGCAAGGAATAGATCAACAAGATCAGGTCTCTTCGCAGGGATTGGTCTGTAATT
TTTCAGGAGATCATTCAGAGGAGATTTTTGAGAGAGAATCCTTTTTAGGGATCGCTTTCCTAGGGAATGGTAGCAAG
GATGGAATCACGTTAACAGATATAAAATCTTCGTTATCTGGTGCTGCCTTGTATTCTTCAGATGATCTTATTTTTGA
AAGAATTAAGGGAGATATAGAGCTTTCTTCTTGTTCATCTTTAGAAAGAGGAGGAGCTTGTTCAGCTCAAAGTATTT
TAATTCATGATTGTCAAGGATTAACGGTAAAACATTGTGCCGCAGGGGTGAATGTTGAAGGAGTTAGTGCTAGCGAC
CATCTCGGATTTGGGGGCGGGGCCTTCTCTACTACAAGTTCTCTTTCTGGAGAGAAGAGTTTGTATATGCCTGCAGG
CGATATTGTGGTGGCTACCTGCGATGGTCCTGTGTGTTTCGAAGGAAATAGTGCTCAGTTAGCAAATGGTGGCGCTA
TTGCCGCTTCTGGTAAAGTTCTTTTTGTAGCTAACGAAAAAAAGATTTCCTTTACAGACAACCAAGCTTTGTCTGGA
GGAGCTATTTCTGCATCTTCTAGTATTTCTTTCCAAAATTGTGCTGAGCTTGTGTTCAAGAGTAATCTTGCAAAAGG
AGTTAAAGATAAATGTTCTTTGGGAGGAGGTGCTTTAGCCTCTTTAGAATCCGTAGTTTTGAAAGATAATCTCGGTA
TTACTTATGAAAAAAATCAGTCCTATTCGGAAGGAGGGGCTATTTTTGGGAAGGATTGTGAGATTTTTGAAAACAGG
GGGCCTGTTGTATTCAGAGATAATACAGCTGCTTTAGGAGGCGGAGCTATTTTGGCGCAACAAACTGTGGCGATTTG
TGGTAATAAGTCTGGAATATCTTTTGAAGGAAGTAAGTCTAGTTTTGGAGGGGCCATTGCTTGTGGAAATTTCTCTT
CTGAGAATAATTCTTCAGCTTTGGGATCAATTGATATCTCTAACAATCTAGGAGATATCTCTTTTCTTCGGACTCTG
TGTACTACTTCGGATTTAGGGCAAACGGATTACCAAGGGGGAGGGGCCTTATTCGCTGAAAATATTTCTCTTTCTGA
GAATGCTGGTGCAATTACTTTCAAAGACAATATTGTGAAGACATTTGCCTCAAATGGAAAAATGTTGGGTGGAGGGG
CAATTTTAGCTTCAGGAAATGTTTTGATTAGCAAAAACTCTGGAGAGATTTCTTTTGTAGGGAATGCTCGAGCTCCT
CAGGCTATTCCGACTCGTTCATCTGACGAATTGTCTTTTGGCGCACAATTAACTCAAACTACTTCAGGATGTTCTGG
AGGAGGAGCTCTTTTTGGTAAAGAGGTTGCCATTGTTCAAAATGCCACTGTTGTATTCGAGCAAAATCGCTTACAGT
GTGGCGAGCAGGAAACACATGGTGGAGGCGGTGCTGTTTATGGTATGGAGAGTGCCTCTATTATTGGAAACTCTTTT
GTGAGATTCGGAAATAATTACGCTGTAGGGAATCAGATTTCTGGAGGAGCTCTTTTATCCAAGAAGGTCCGTTTAGC
TGAAAATACAAGGGTAGATTTTTCTCGAAATATCGCTACTTTCTGCGGCGGGGCTGTTCAAGTTTCTGATGGAAGTT
GCGAATTGATCAACAATGGGTATGTGCTATTCAGAGATAACCGAGGGCAGACATTTGGTGGGGCTATTTCTTGCTTG
AAAGGAGATGTGATCATTTCCGGAAATAAAGATAGGGTTGAGTTTAGAGATAACATTGTGACGCGGCCTTATTTTGA
AGAAAATGAAGAAAAAGTTGAGACAGCAGATATTAATTCAGATAAGCAAGAAGCAGAAGAGCGCTCTTTATTAGAGA
ACATTGAGCAGAGCTTTATTACTGCAACTAATCAGACCTTTTTCTTAGAGGAAGAGAAACTCCCATCAGAAGCTTTT
ATCTCTGCTGAAGAACTTTCAAAGAGAAGAGAATGTGCTGGTGGGGCGATTTTTGCAAAACGGGTCTACATTACGGA
TAATAAAGAACCTATCTTGTTTTCGCATAATTTTTCTGATGTTTATGGGGGAGCTATTTTTACGGGTTCTCTACAGG
AAACTGATAAACAAGATGTTGTAACTCCTGAAGTTGTGATATCAGGCAACGATGGGGATGTCATTTTTTCTGGAAAT
GCAGCTAAACATGATAAGCATTTACCTGATACAGGTGGTGGAGCCATTTGTACACAGAATTTGACGATTTCCCAAAA
CAATGGGAATGTCTTGTTCTTGAACAATTTTGCTTGTTCTGGTGGAGCAGTTCGCATAGAGGATCATGGAGAAGTTC
TTTTAGAGGCTTTTGGGGGAGATATTATTTTCAATGGAAACTCTTCTTTCAGAGCTCAAGGATCGGATGCGATCTAT
TTTGCTGGTAAGGACTCTAGAATTAAAGCTTTAAATGCTACTGAAGGACATGCGATTGTGTTCCAAGATGCATTGGT
GTTTGAAAATATAGAAGAAAGAAAGTCTTCGGGACTATTGGTGATTAACTCTCAGGAAAATGAGGGTTATACGGGAT
CCGTCCGATTTTTAGGATCTGAAAGTAAGGTTCCTCAATGGATTCATGTGCAACAGGGAGGTCTTGAGTTGCTACAT
GGAGCTATTTTATGTAGTTATGGGGTTAAACAAGATCCTAGAGCTAAAATAGTATTATCTGCTGGATCTAAATTGAA
GATTCTAGATTCAGAGCAAGAAAATAACGCAGAAATTGGAGATCTTGAAGATTCTGTTAATTCAGAAAAAACACCAT
CTCTTTGGATTGGGAAGAACGCTCAAGCAAAAGTCCCTCTGGTTGATATCCATACTATTTCTATTGATTTAGCATCA
TTTTCTTCTAAAGCTCAGGAAACCCCTGAGGAAGCTCCACAAGTCATCGTCCCTAAGGGAAGTTGTGTCCACTCGGG
AGAGTTAAGTTTGGAGTTGGTTAATACAACAGGAAAAGGTTATGAGAATCATGCGTTGTTAAAAAATGATACTCAGG
TTTCTCTCATGTCTTTCAAAGAGGAAAATGATGGATCTTTAGAAGATTTGAGTAAGTTGTCTGTTTCGGATTTACGC
ATTAAAGTTTCTACTCCAGATATTGTAGAAGAAACTTATGGCCATATGGGGGATTGGTCTGAAGCTACAATTCAAGA
TGGGGCTCTTGTCATTAATTGGCATCCTACTGGATATAAATTAGATCCGCAAAAAGCTGGTTCTTTGGTATTCAATG
CATTATGGGAGGAAGAGGCTGTATTGTCTACTCTAAAAAATGCTCGGATTGCCCATAACCTTACCATTCAGAGAATG
GAATTTGATTATTCTACAAATGCTTGGGGATTAGCTTTTAGTAGCTTTAGAGAGCTATCTTCAGAGAAGCTTGTTTC
TGTTGATGGATATAGAGGCTCTTATATAGGGGCTTCTGCAGGCATTGATACTCAGTTGATGGAAGATTTTGTTTTGG
GAATCAGCACGGCTTCCTTCTTCGGGAAAATGCATAGTCAGAATTTTGATGCAGAGATTTCTCGACATGGTTTTGTT
GGTTCGGTCTATACAGGCTTCCTAGCTGGGGCCTGGTTCTTCAAGGGGCAGTACAGTCTTGGCGAAACACATAACGA
TATGACAACTCGTTACGGGGTTTTGGGAGAATCTAATGCTACTTGGAAGTCTCGAGGAGTACTAGCAGATGCTTTAG
TTGAATATCGTAGTTTAGTCGGTCCAGCACGACCTAAATTTTATGCTTTGCATTTTAATCCTTATGTCGAGGTATCT
TATGCATCTGCGAAGTTCCCTAGTTTTGTAGAACAAGGAGGAGAAGCTCGTGCTTTTGAAGAAACCTCTTTAACAAA
CATTACCGTTCCCTTTGGTATGAAATTTGAACTATCTTTTACAAAAGGACAGTTTTCAGAGACTAATTCTCTTGGAA
TAGGTTGTGCATGGGAAATGTATCGGAAAGTCGAAGGAAGATCTGTAGAGCTACTAGAAGCTGGTTTTGATTGGGAA
GGATCTCCTATAGATCTCCCTAAACAAGAGCTGAGAGTGGCTTTAGAAAACAATACGGAATGGAGTTCGTATTTTAG
TACAGCTCTAGGAGTAACAGCATTTTGTGGAGGATTTTCTTCTATGGATAATAAACTAGGATACGAAGCGAATGCTG
GAATGCGTTTGATTTTCTAG SEQ ID NO: 60 - TC0197 protein sequence
MSSEKDKKNSCSKFSLSVVAAILASMSGLSNCSDLYAVGSSADHPAYLIPQAGLLLDHIKDIFIGPKDSQDKGQYKL
IIGEAGSFQDSNAETLPQKVEHSTLFSVTTPIIVQGIDQQDQVSSQGLVCNFSGDHSEEIFERESFLGIAFLGNGSK
DGITLTDIKSSLSGAALYSSDDLIFERIKGDIELSSCSSLERGGACSAQSILIHDCQGLTVKHCAAGVNVEGVSASD
HLGFGGGAFSTTSSLSGEKSLYMPAGDIVVATCDGPVCFEGNSAQLANGGAIAASGKVLFVANEKKISFTDNQALSG
GAISASSSISFQNCAELVFKSNLAKGVKDKCSLGGGALASLESVVLKDNLGITYEKNQSYSEGGAIFGKDCEIFENR
GPVVFRDNTAALGGGAILAQQTVAICGNKSGISFEGSKSSFGGAIACGNFSSENNSSALGSIDISNNLGDISFLRTL -continued

SEQUENCE LISTING

CTTSDLGQTDYQGGGALFAENISLSENAGAITFKDNIVKTFASNGKMLGGGAILASGNVLISKNSGEISFVGNARAP
QAIPTRSSDELSFGAQLTQTTSGCSGGGALFGKEVAIVQNATVVFEQNRLQCGEQETHGGGGAVYGMESASIIGNSF
VRFGNNYAVGNQISGGALLSKKVRLAENTRVDFSRNIATFCGGAVQVSDGSCELINNGYVLFRDNRGQTFGGAISCL
KGDVIISGNKDRVEFRDNIVTRPYFEENEEKVETADINSDKQEAEERSLLENIEQSFITATNQTFFLEEEKLPSEAF
ISAEELSKRRECAGGAIFAKRVYITDNKEPILFSHNFSDVYGGAIFTGSLQETDKQDVVTPEVVISGNDGDVIFSGN
AAKHDKHLPDTGGGAICTQNLTISQNNGNVLFLNNFACSGGAVRIEDHGEVLLEAFGGDIIFNGNSSFRAQGSDAIY
FACKDSRIKALNATEGHAIVFQDALVFENIEERKSSGLLVINSQENEGYTGSVRFLGSESKVPQWIHVQQGGLELLH
GAILCSYGVKQDPRAKIVLSAGSKLKILDSEQENNAEIGDLEDSVNSEKTPSLWIGKNAQAKVPLVDIHTISIDLAS
FSSKAQETPEEAPQVIVPKGSCVHSGELSLELVNTTGKGYENHALLKNDTQVSLMSFKEENDGSLEDLSKLSVSDLR
IKVSTPDIVEETYGHMGDWSEATIQDGALVINWHPTGYKLDPQKAGSLVFNALWEEEAVLSTLKNARIAHNLTIQRM
EFDYSTNAWGLAFSSFRELSSEKLVSVDGYRGSYIGASAGIDTQLMEDFVLGISTASFFGKMHSQNFDAEISRHGFV
GSVYTGFLAGAWFFKGQYSLGETHNDMTTRYGVLGESNATWKSRGVLADALVEYRSLVGPARPKFYALHFNPYVEVS
YASAKFPSFVEQGGEARAFEETSLTNITVPFGMKFELSFTKGQFSETNSLGIGCAWEMYRKVEGRSVELLEAGFDWE
GSPIDLPKQELRVALENNTEWSSYFSTALGVTAFCGGFSSMDNKLGYEANAGMRLIF

SEQ ID NO: 61 - TC0261 nucleotide sequence
ATGAAAAAACTGTTCTTTTTTGTCCTTATTGGAAGCTCTATACTGGGATTTACTCGAGAAGTCCCTCCTTCGATTCT
TTTAAAGCCTATACTAAATCCATACCATATGACCGGGTTATTTTTTCCCAAGGTTAATTTGCTTGGAGACACACATA
ATCTCACTGATTACCATTTGGATAATCTAAAATGCATTCTGGCTTGCCTACAAAGAACTCCTTATGAAGGAGCTGCT
TTCACAGTAACCGATTACTTAGGTTTTTCAGATACACAAAAGGATGGTATTTTTTGTTTTAAAAATCTTACTCCAGA
GAGTGGAGGGGTTATTGGTTCCCCAACTCAAAACACTCCTACTATAAAAATTCATAATACAATCGGCCCCGTTCTTT
TCGAAAATAATACCTGTCATAGACTGTGGACACAGACCGATCCCGAAAATGAAGGAAACAAAGCACGCGAAGGCGGG
GCAATTCATGCTGGGGACGTTTACATAAGCAATAACCAGAACCTTGTCGGATTCATAAAGAACTTTGCTTATGTTCA
AGGTGGAGCTATTAGTGCTAATACTTTTGCCTATAAAGAAAATAAATCGAGCTTTCTTTGCCTAAATAACTCTTGTA
TACAAACTAAGACGGGAGGGAAAGGTGGTGCTATTTACGTTAGTACGAGCTGCTCTTTCGAGAACAATAACAAGGAT
CTGCTTTTCATCCAAAACTCCGGCTGTGCAGGAGGAGCTATCTTCTCTCCAACCTGTTCTCTAATAGGAAACCAAGG
AGATATTGTTTTTTACAGCAACCACGGTTTTAAAAATGTTGATAATGCAACTAACGAATCTGGGGATGGAGGAGCTA
TTAAAGTAACTACCCGCTTGGACATCACCAATAATGGTAGTCAAATCTTTTTTTCTGATAATATCTCAAGAAATTTT
GGAGGAGCTATTCATGCTCCTTGTCTTCATCTTGTTGGTAATGGGCCAACCTATTTTACAAACAATATAGCTAATCA
CACAGGTGGGGCTATTTATATAACAGGAACAGAAACCTCAAAGATTTCTGCAGATCACCATGCTATTATTTTTGATA
ATAACATTTCTGCAAACGCCACCAATGCGGACGGATCTAGCAGCAACACTAATCCTCCTCACAGAAATGCGATCACT
ATGGACAATTCCGCTGGAGGAATAGAACTTGGTGCAGGGAAGAGCCAGAATCTTATTTTCTATGATCCTATTCAAGT
GACGAATGCTGGAGTTACCGTAGACTTCAATAAGGATGCCTCCCAAACCGGATGTGTAGTTTTCTCTGGAGCGACTG
TCCTTTCTGCAGATATTTCTCAGGCTAATTTGCAAACTAAAACACCTGCAACGCTTACTCTCAGTCACGGTCTTCTG
TGTATCGAAGATCGTGCTCAGCTCACAGTGAACAATTTTACACAAACAGGAGGGATTGTAGCCTTAGGAAATGGAGC
AGTTTTAAGCAGCTACCAACACAGCACTACAGACGCCACTCAAACTCCCCCTACAACCACCACTACAGATGCTTCCG
TAACTCTTAATCACATTGGATTAAATCTCCCCTCTATTCTTAAGGATGGAGCAGAGATGCCTCTATTATGGGTAGAA
CCTATAAGCACAACTCAAGGTAACACTACAACATATACGTCAGATACCGCGGCTTCCTTCTCATTAAATGGAGCCAC
ACTCTCTCTCATTGATGAAGATGGAAATTCTCCCTATGAAAACACGGACCTCTCTCGTGCATTGTACGCTCAACCTA
TGCTAGCAATTTCTGAGGCCAGTGATAACCAATTGCAATCCGAAAGCATGGACTTTTCTAAAGTTAATGTTCCTCAC
TATGGATGGCAAGGACTTTGGACCTGGGGGTGGGCAAAAACTGAAAATCCAACAACAACTCCTCCAGCAACAATTAC
TGATCCGAAAAAAGCTAATCAGTTTCATAGAACTTTATTATTAACGTGGCTCCCTGCTGGTTATATCCCCAGCCCTA
AACATAAAAGCCCTTTAATAGCTAATACCTTGTGGGGGAATATACTTTTTGCAACGGAAAACTTAAAAAATAGCTCA
GGGCAAGAACTTCTTGATCGTCCTTTCTGGGGAATTACAGGAGGGGGCTTGGGGATGATGGTCTATCAAGAACCTAG
AAAAGACCATCCTGGATTCCACATGCATACCTCCGGATATTCAGCAGGAATGATTACAGGAAACACACATACCTTCT
CATTACGATTCAGCCAGTCCTATACAAAACTCAATGAACGTTATGCCAAGAACTATGTGTCTTCTAAAAATTACTCT
TGCCAAGGGGAAATGCTTTTGTCCTTACAAGAAGGACTCATGCTGACTAAACTAATTGGTCTCTATAGTTATGGGAA
TCACAACAGCCACCATTTCTATACCCAAGGAGAAGACCTATCGTCTCAAGGGGAGTTCCATAGTCAGACTTTTGGAG
GGGCTGTCTTTTTTGATCTACCTCTGAAACCTTTTGGAAGAACACACATACTTACAGCTCCTTTCTTAGGTGCCATT
GGTATGTATTCTAAGCTGTCTAGCTTTACAGAAGTAGGAGCCTATCCAAGAACCTTTATTACAGAAACGCCTTTAAT
CAATGTCCTGATTCCTATCGGAGTAAAAGGTAGCTTCATGAATGCCACCCATAGACCTCAGGCCTGGACTGTAGAGC
TTGCTTACCAACCTGTTCTTTACAGACAAGAACCTAGTATCTCTACCCAATTACTCGCTGGTAAAGGTATGTGGTTT
GGGCATGGAAGTCCTGCATCTCGCCACGCTCTAGCTTATAAAATTTCACAGAAAACACAGCTTTTGCGATTTGCAAC
ACTTCAACTCCAGTATCACGGATACTATTCGTCTTCCACTTTCTGTAATTATCTGAATGGAGAGGTATCTTTACGTT
TCTAA SEQ ID NO: 62 - TC0261 protein sequence
MKKLFFFVLIGSSILGFTREVPPSILLKPILNPYHMTGLFFPKVNLLGDTHNLTDYHLDNLKCILACLQRTPYEGAA
FTVTDYLGFSDTQKDGIFCFKNLTPESGGVIGSPTQNTPTIKIHNTIGPVLFENNTCHRLWTQTDPENEGNKAREGG
AIHAGDVYISNNQNLVGFIKNFAYVQGGAISANTFAYKENKSSFLCLNNSCIQTKTGGKGGAIYVSTSCSFENNNKD
LLFIQNSGCAGGAIFSPTCSLIGNQGDIVFYSNHGFKNVDNATNESGDGGAIKVTTRLDITNNGSQIFFSDNISRNF
GGAIHAPCLHLVGNGPTYFTNNIANHTGGAIYITGTETSKISADHHAIIFDNNISANATNADGSSSNTNPPHRNAIT
MDNSAGGIELGAGKSQNLIFYDPIQVTNAGVTVDFNKDASQTGCVVFSGATVLSADISQANLQTKTPATLTLSHGLL
CIEDRAQLTVNNFTQTGGIVALGNGAVLSSYQHSTTDATQTPPTTTTDASVTLNHIGLNLPSILKDGAEMPLLWVE
PISTTQGNTTTYTSDTAASFSLNGATLSLIDEDGNSPYENTDLSRALYAQPMLAISEASDNQLQSESMDFSKVNVPH
YGWQGLWTWGWAKTENPTTTPPATITDPKKANQFHRTLLLTWLPAGYIPSPKHKSPLIANTLWGNILFATENLKNSS
GQELLDRPFWGITGGGLGMMVYQEPRKDHPGFHMHTSGYSAGMITGNTHTFSLRFSQSYTKLNERYAKNYVSSKNYS
CQGEMLLSLQEGLMLTKLIGLYSYGNHNSHHFYTQGEDLSSQGEFHSQTFGGAVFFDLPLKPFGRTHILTAPFLGAI
GMYSKLSSFTEVGAYPRTFITETPLINVLIPIGVKGSFMNATHRPQAWTVELAYQPVLYRQEPSISTQLLAGKGMWF
GHGSPASRHALAYKISQKTQLLRFATLQLQYHGYYSSSTFCNYLNGEVSLRF SEQ ID NO: 63 - CT733 fragment nucleotide sequence
GCACCTCAACCTCGCGGAACGCTTCCTAGCTCGACCACAAAAATTGGATCAGAAGTTTGGATTGAACAAAAAGTCCG
CCAATATCCAGAGCTTTTATGGTTAGTAGAGCCGTCCTCTACGGGAGCCTCTTTAAAATCTCCTTCAGGAGCCATCT
TTTCTCCAACATTATTCCAAAAAAAGGTCCCTGCTTTCGATATCGCAGTGCGCAGTTTGATTCACTTACATTTATTA
ATCCAGGGTTCCCGCCAAGCCTATGCTCAACTGATCCAACTACAGACCAGCGAATCCCCTCTAACATTTAAGCAATT
CCTTGCATTGCATAAGCAATTAACTCTATTTTTAAATTCCCCTAAGGAATTTTATGACTCTGTTAAAGTGTTAGAGA -continued

SEQUENCE LISTING

CAGCTATCGTCTTACGTCACTTAGGCTGTTCAACTAAGGCTGTTGCTGCGTTTAAACCTTATTTCTCAGAAATGCAA
AGAGAGGCTTTTTACACTAAGGCTCTGCATGTACTACACACCTTCCCAGAGCTAAGCCCATCATTTGCTCGCCTCTC
TCCGGAGCAGAAAACTCTCTTCTTCTCCTTGAGAAAATTGGCGAATTACGATGAGTTACTCTCGCTGACGAACACCC
CAAGTTTTCAGCTTCTGTCTGCTGGGCGCTCGCAACGAGCTCTTTTAGCTCTGGACTTGTACCTCTATGCTTTGGAT
TCCTGTGGAGAACAGGGGATGTCCTCTCAATTCCACACAAACTTCGCACCTCTACAGTCCATGTTGCAACAATACGC
TACTGTAGAAGAGGCCTTTTCTCGTTATTTTACTTACCGAGCTAATCGATTAGGATTTGATGGCTCTTCTCGATCCG
AGATGGCTTTAGTAAGAATGGCCACCTTGATGAACTTGTCTCCTTCCGAAGCTGCGATTTTAACCACAAGCTTCAAA
ACCCTTCCTACAGAAGAAGCGGATACTTTGATCAATAGTTTCTATACCAATAAGGGCGATTCGTTGGCTCTTTCTCT
GCGAGGGTTGCCTACACTTGTATCCGAACTGACGCGAACTGCCCATGGCAATACCAATGCAGAAGCTCGATCTCAGC
AAATTTATGCAACTACCCTATCGCTAGTAGTAAAGAGTCTGAAAGCGCACAAAGAAATGCTAAACAAGCAAATTCTT
TCTAAGGAAATTGTTTTAGATTTCTCAGAAACTGCAGCTTCTTGCCAAGGATTGGATATCTTTTCCGAGAATGTCGC
TGTTCAAATTCACTTAAATGGAACCGTTAGTATCCATTTA

SEQ ID NO: 64 - CT733 fragment protein sequence
APQPRGTLPSSTTKIGSEVWIEQKVRQYPELLWLVEPSSTGASLKSPSGAIFSPTLFQKKVPAFDIAVRSLIHLHLL
IQGSRQAYAQLIQLQTSESPLTFKQFLALHKQLTLFLNSPKEFYDSVKVLETAIVLRHLGCSTKAVAAFKPYFSEMQ
REAFYTKALHVLHTFPELSPSFARLSPEQKTLFFSLRKLANYDELLSLTNTPSFQLLSAGRSQRALLALDLYLYALD
SCGEQGMSSQFHTNFAPLQSMLQQYATVEEAFSRYFTYRANRLGFDGSSRSEMALVRMATLMNLSPSEAAILTTSFK
TLPTEEADTLINSFYTNKGDSLALSLRGLPTLVSELTRTAHGNTNAEARSQQIYATTLSLVVKSLKAHKEMLNKQIL
SKEIVLDFSETAASCQGLDIFSENVAVQIHLNGTVSIHL SEQ ID NO: 65 - CT153 fragment nucleotide sequence
ACTAAGCCTTCTTTCTTATACGTTATTCAACCTTTTTCCGTATTTAATCCACGATTAGGACGTTTCTCTACAGACTC
AGATACTTATATCGAAGAAGAAAACCGCCTAGCATCGTTCATTGAGAGTTTGCCACTGGAGATCTTCGATATACCTT
CTTTCATGGAAACCGCGATTTCCAATAGCCCCTATATTTTATCTTGGGAGACAACTAAAGACGGCGCTCTGTTCACT
ATTCTTGAACCCAAACTCTCAGCTTGCGCAGCCACTTGCCTGGTAGCCCCTTCTATACAAATGAAATCCGATGCGGA
GCTCCTAGAAGAAATTAAGCAAGCGTTATTACGCAGCTCTCATGACGGTGTGAAATATCGCATCACCAGAGAATCCT
TCTCTCCAGAAAAGAAAACTCCTAAGGTTGCTCTAGTCGATGACGATATTGAATTGATTCGCAATGTCGACTTTTTG
GGTAGAGCTGTTGACATTGTCAAATTAGACCCTATTAATATTCTGAATACCGTAAGCGAAGAGAATATTCTAGATTA
CTCTTTTACAAGAGAAACGGCTCAGCTGAGCGCGGATGGTCGTTTTGGTATTCCTCCAGGGACTAAGCTATTCCCTA
AACCTTCTTTTGATGTAGAAATCAGTACCTCCATTTTCGAAGAAACAACTTCATTTACTCGAAGTTTTTCTGCATCG
GTTACTTTTAGTGTACCAGACCTCGCGGCGACTATGCCTCTTCAAAGCCCTCCCATGGTAGAAAATGGTCAAAAAGA
AATTTGTGTCATTCAAAAACACTTATTCCCAAGCTACTCTCCTAAACTAGTCGATATTGTTAAACGATACAAAAGAG
AGGCTAAGATCTTGATTAACAAGCTTGCCTTTGGAATGTTATGGCGACATCGGGCTAAAAGCCAAATCCTCACCGAG
GGAAGCGTACGTCTAGACTTACAAGGATTCACAGAATCGAAGTACAATTACCAGATTCAAGTAGGATCCCATACGAT
TGCAGCTGTATTAATCGATATGGATATTTCCAAGATTCAATCCAAATCAGAACAAGCTTATGCAATTAGGAAAATCA
AATCAGGCTTTCAACGTAGCTTGGATGACTATCATATTTATCAAATTGAAAGAAAACAAACCTTTTCTTTTTCTCCG
AAGCATCGCAGCCTCTCATCCACATCCCATTCCGAAGATTCTGATTTGGATCTTTCTGAAGCAGCCGCCTTTTCAGG
AAGTCTTACCTGCGAGTTTGTAAAAAAAAGCACTCAACATGCCAAGAATACCGTCACATGTTCCACAGCCGCTCATT
CCCTATACACACTCAAAGAAGATGACAGCTCGAACCCCTCTGAAAAACGATTAGATAGTTGTTTCCGCAATTGGATT
GAAAACAAACTAAGCGCCAATTCTCCAGATTCCTGGTCAGCGTTTATTCAAAAATTCGGAACACACTATATTGCATC
AGCAACTTTTGGAGGGATAGGTTTCCAAGTGCTCAAACTATCTTTTGAACAGGTGGAGGATCTACATAGCAAAAAGA
TCTCCTTAGAAACCGCAGCAGCCAACTCTCTATTAAAAGGTTCTGTATCCAGCAGCACAGAATCTGGATACTCCAGC
TATAGCTCCACGTCTTCTTCTCATACGGTATTTTTAGGAGGAACGGTCTTACCTTCGGTTCATGATGAACGTTTAGA
CTTTAAAGATTGGTCGGAAAGTGTGCACCTGGAACCTGTTCCTATCCAGGTTTCTTTACAACCTATAACGAATTTAC
TAGTTCCTCTCCATTTTCCTAATATCGGTGCTGCAGAGCTCTCTAATAAACGAGAATCTCTTCAACAAGCGATTCGA
GTCTATCTCAAAGAACATAAAGTAGATGAGCAAGGAGAACGTACTACATTTACATCAGGAATCGATAATCCTTCTTC
CTGGTTTACCTTAGAAGCTGCCCACTCTCCTCTTATAGTCAGTACTCCTTACATTGCTTCGTGGTCTACGCTTCCTT
ATTTGTTCCCAACATTAAGAGAACGTTCTTCGGCAACCCCTATCGTTTTCTATTTTTGTGTAGATAATAATGAACAT
GCTTCGCAAAAAATATTAAACCAATCGTATTGCTTCCTCGGGTCCTTGCCTATTCGACAAAAAATTTTTGGTAGCGA
ATTTGCTAGTTTCCCCTATCTATCTTTCTATGGAAATGCAAAAGAGGCGTACTTTGATAACACGTACTACCCAACGC
GTTGTGGGTGGATTGTTGAAAAGTTAAATACTACACAAGATCAATTCCTCCGGGATGGAGACGAGGTGCGACTAAAA
CATGTTTCCAGCGGAAAGTATCTAGCAACAACTCCTCTTAAGGATACCCATGGTACACTCACGCGTACAACGAACTG
TGAAGATGCTATCTTTATTATTAAAAAATCTTCAGGTTAT SEQ ID NO: 66 - CT153 fragment protein sequence
TKPSFLYVIQPFSVFNPRLGRFSTDSDTYIEEENRLASFIESLPLEIFDIPSFMETAISNSPYILSWETTKDGALFT
ILEPKLSACAATCLVAPSIQMKSDAELLEEIKQALLRSSHDGVKYRITRESFSPEKKTPKVALVDDDIELIRNVDFL
GRAVDIVKLDPINILNTVSEENILDYSFTRETAQLSADGRFGIPPGTKLFPKPSFDVEISTSIFEETTSFTRSFSAS
VTFSVPDLAATMPLQSPPMVENGQKEICVIQKHLFPSYSPKLVDIVKRYKREAKILINKLAFGMLWRHRAKSQILTE
GSVRLDLQGFTESKYNYQIQVGSHTIAAVLIDMDISKIQSKSEQAYAIRKIKSGFQRSLDDYHIYQIERKQTFSFSP
KHRSLSSTSHSEDSDLDLSEAAAFSGSLTCEFVKKSTQHAKNTVTCSTAAHSLYTLKEDDSSNPSEKRLDSCFRNWI
ENKLSANSPDSWSAFIQKFGTHYIASATFGGIGFQVLKLSFEQVEDLHSKKISLETAAANSLLKGSVSSSTESGYSS
YSSTSSSHTVFLGGTVLPSVHDERLDFKDWSESVHLEPVPIQVSLQPITNLLVPLHFPNIGAAELSNKRESLQQAIR
VYLKEHKVDEQGERTTFTSGIDNPSSWFTLEAAHSPLIVSTPYIASWSTLPYLFPTLRERSSATPIVFYFCVDNNEH
ASQKILNQSYCFLGSLPIRQKIFGSEFASFPYLSFYGNAKEAYFDNTYYPTRCGWIVEKLNTTQDQFLRDGDEVRLK
HVSSGKYLATTPLKDTHGTLTRTTNCEDAIFIIKKSSGY SEQ ID NO: 67 - CT601 fragment nucleotide sequence
GGTAAAGCACCGTCTTTGCAGGCTATTCTAGCCGAAGTCGAAGACACCTCCTCTCGTCTACACGCTCATCACAATGA
GCTTGCTATGATCTCTGAACGCCTCGATGAGCAAGACACGAAACTACAGCAACTTTCGTCAACACAAGATCATAACC
TACCTCGACAAGTTCAGCGACTAGAAACGGACCAAAAAGCTTTGGCAAAAACACTGGCGATTCTTTCGCAATCCGTC
CAAGATATTCGGTCTTCTGTACAAAATAAATTACAAGAAATCCAACAAGAACAAAAAAAATTAGCACAAAATTTGCG
AGCGCTTCGTAACTCTTTACAAGCTCTCGTTGATGGCTCTTCTCCAGAAAATTATATTGATTTCCTAACTGGTGAAA
CCCCGGAACATATTCATATTGTTAAACAAGGAGAGACCCTGAGCAAGATCGCGAGTAAATATAACATCCCCGTCGTA
GAATTAAAAAAACTTAATAAACTAAATTCGGATACTATTTTTACAGATCAAAGAATTCGCCTTCCGAAAAAGAAA -continued

SEQUENCE LISTING

SEQ ID NO: 68 - CT601 fragment protein sequence
GKAPSLQAILAEVEDTSSRLHAHHNELAMISERLDEQDTKLQQLSSTQDHNLPRQVQRLETDQKALAKTLAILSQSV
QDIRSSVQNKLQEIQQEQKKLAQNLRALRNSLQALVDGSSPENYIDFLTGETPEHIHIVKQGETLSKIASKYNIPVV
ELKKLNKLNSDTIFTDQRIRLPKKK SEQ ID NO: 69 - CT279 fragment nucleotide sequence
GCACAAGTAATTTCTTCCGATAACACATTCCAAGTCTATGAAAAGGGAGATTGGCACCCAGCCCTATATAATACTAA
AAAGCAGTTGCTAGAGATCTCCTCTACTCCTCCTAAAGTAACCGTGACAACTTTAAGCTCATATTTTCAAAACTTTG
TTAGAGTCTTGCTTACAGATACACAAGGAAATCTTTCTTCATTCGAAGACCATAATCTCAATCTAGAAGAATTTTTA
TCTCAACCAACTCCTGTAATACATGGTCTTGCCCTTTATGTGGTCTACGCTATCCTACACAACGATGCAGCTTCCTC
TAAATTATCTGCTTCCCAAGTAGCGAAAAATCCAACAGCTATAGAATCTATAGTTCTTCCTATAGAAGGTTTTGGTT
TGTGGGGACCTATCTATGGATTCCTTGCTCTAGAAAAAGACGGGAATACTGTTCTTGGTACTTCTTGGTATCAACAT
GGCGAGACTCCTGGATTAGGAGCAAATATCGCTAACCCTCAATGGCAAAAAAATTTCAGAGGCAAAAAAGTATTTCT
AGTCTCAGCTTCTGGAGAAACAGATTTTGCTAAGACAACCCTAGGACTGGAAGTTATAAAAGGATCTGTATCTGCAG
CATTAGGAGACTCACCTAAAGCTGCTTCTTCCATCGACGGAATTTCAGGAGCTACTTTGACTTGTAATGGTGTTACC
GAATCCTTCTCTCATTCTCTAGCTCCCTACCGCGCTTTGTTGACTTTCTTCGCCAACTCTAAACCTAGTGGAGAGTC
TCATGACCAC SEQ ID NO: 70 - CT279 fragment protein sequence
AQVISSDNTFQVYEKGDWHPALYNTKKQLLEISSTPPKVTVTTLSSYFQNFVRVLLTDTQGNLSSFEDHNLNLEEFL
SQPTPVIHGLALYVVYAILHNDAASSKLSASQVAKNPTAIESIVLPIEGFGLWGPIYGFLALEKDGNTVLGTSWYQH
GETPGLGANIANPQWQKNFRGKKVFLVSASGETDFAKTTLGLEVIKGSVSAALGDSPKAASSIDGISGATLTCNGVT
ESFSHSLAPYRALLTFFANSKPSGESHDH SEQ ID NO: 71 - CT443 fragment nucleotide sequence
GGGGTGTTAGAGACCTCTATGGCAGAGTCTCTCTCTACAAACGTTATTAGCTTAGCTGACACCAAAGCGAAAGACAA
CACTTCTCATAAAAGCAAAAAAGCAAGAAAAAACCACAGCAAAGAGACTCCCGTAGACCGTAAAGAGGTTGCTCCGG
TTCATGAGTCTAAAGCTACAGGACCTAAACAGGATTCTTGCTTTGGCAGAATGTATACAGTCAAAGTTAATGATGAT
CGCAATGTTGAAATCACACAAGCTGTTCCTGAATATGCTACGGTAGGATCTCCCTATCCTATTGAAATTACTGCTAC
AGGTAAAAGGGATTGTGTTGATGTTATCATTACTCAGCAATTACCATGTGAAGCAGAGTTCGTACGCAGTGATCCAG
CGACAACTCCTACTGCTGATGGTAAGCTAGTTTGGAAAATTGACCGCTTAGGACAAGGCGAAAAGAGTAAAATTACT
GTATGGGTAAAACCTCTTAAAGAAGGTTGCTGCTTTACAGCTGCAACAGTATGCGCTTGTCCAGAGATCCGTTCGGT
TACAAAATGTGGACAACCTGCTATCTGTGTTAAACAAGAAGGCCCAGAGAATGCTTGTTTGCGTTGCCCAGTAGTTT
ACAAAATTAATATAGTGAACCAAGGAACAGCAACAGCTCGTAACGTTGTTGTTGAAAATCCTGTTCCAGATGGTTAC
GCTCATTCTTCTGGACAGCGTGTACTGACGTTTACTCTTGGAGATATGCAACCTGGAGAGCACAGAACAATTACTGT
AGAGTTTTGTCCGCTTAAACGTGGTCGTGCTACCAATATAGCAACGGTTTCTTACTGTGGAGGACATAAAAATACAG
CAAGCGTAACAACTGTGATCAACGAGCCTTGCGTACAAGTAAGTATTGCAGGAGCAGATTGGTCTTATGTTTGTAAG
CCTGTAGAATATGTGATCTCCGTTTCCAATCCTGGAGATCTTGTGTTGCGAGATGTCGTCGTTGAAGACACTCTTTC
TCCCGGAGTCACAGTTCTTGAAGCTGCAGGAGCTCAAATTTCTTGTAATAAAGTAGTTTGGACTGTGAAAGAACTGA
ATCCTGGAGAGTCTCTACAGTATAAAGTTCTAGTAAGAGCACAAACTCCTGGACAATTCACAAATAATGTTGTTGTG
AAGAGCTGCTCTGACTGTGGTACTTGTACTTCTTGCGCAGAAGCGACAACTTACTGGAAAGGAGTTGCTGCTACTCA
TATGTGCGTAGTAGATACTTGTGACCCTGTTTGTGTAGGAGAAAATACTGTTTACCGTATTTGTGTCACCAACAGAG
GTTCTGCAGAAGATACAAATGTTTCTTTAATGCTTAAATTCTCTAAAGAACTGCAACCTGTATCCTTCTCTGGACCA
ACTAAAGGAACGATTACAGGCAATACAGTAGTATTCGATTCGTTACCTAGATTAGGTTCTAAAGAAACTGTAGAGTT
TTCTGTAACATTGAAAGCAGTATCAGCTGGAGATGCTCGTGGGGAAGCGATTCTTTCTTCCGATACATTGACTGTTC
CAGTTTCTGATACAGAGAATACACACATCTAT SEQ ID NO: 72 - CT443 fragment protein sequence
GVLETSMAESLSTNVISLADTKAKDNTSHKSKKARKNHSKETPVDRKEVAPVHESKATGPKQDSCFGRMYTVKVNDD
RNVEITQAVPEYATVGSPYPIEITATGKRDCVDVIITQQLPCEAEFVRSDPATTPTADGKLVWKIDRLGQGEKSKIT
VWVKPLKEGCCFTAATVCACPEIRSVTKCGQPAICVKQEGPENACLRCPVVYKINIVNQGTATARNVVVENPVPDGY
AHSSGQRVLTFTLGDMQPGEHRTITVEFCPLKRGRATNIATVSYCGGHKNTASVTTVINEPCVQVSIAGADWSYVCK
PVEYVISVSNPGDLVLRDVVVEDTLSPGVTVLEAAGAQISCNKVVWTVKELNPGESLQYKVLVRAQTPGQFTNNVVV
KSCSDCGTCTSCAEATTYWKGVAATHMCVVDTCDPVCVGENTVYRICVTNRGSAEDTNVSLMLKFSKELQPVSFSGP
TKGTITGNTVVFDSLPRLGSKETVEFSVTLKAVSAGDARGEAILSSDTLTVPVSDTENTHIY SEQ ID NO: 73 - CT372 fragment nucleotide sequence
CAGGCTGCACACCATCACTATCACCGCTACACAGATAAACTGCACAGACAAAACCATAAAAAAGATCTCATCTCTCC
CAAACCTACCGAACAAGAGGCGTGCAATACTTCTTCCCTTAGTAAGGAATTAATCCCTCTATCAGAACAAAGAGGCC
TTTTATCCCCCATCTGTGACTTTATTTCGGAACGCCCTTGCTTACACGGAGTTTCTGTTAGAAATCTCAAGCAAGCG
CTAAAAAATTCTGCAGGAACCCAAATTGCACTGGATTGGTCTATTCTCCCTCAATGGTTCAATCCTCGGGTCTCTCA
TGCCCCTAAGCTTTCTATCCGAGACTTTGGGTATAGCGCACACCAAACTGTTACCGAAGCCACTCCTCCTTGCTGGC
AAAACTGCTTTAATCCATCTGCGGCCGTTACTATCTATGATTCCTCATATGGGAAAGGGGTCTTTCAAATATCCTAT
ACCCTTGTCCGCTATTGGAGAGAGAATGCTGCGACTGCTGGCGATGCTATGATGCTCGCAGGGAGTATCAATGATTA
TCCCTCTCGTCAGAACATTTTCTCTCAGTTTACTTTCTCCCAAAACTTCCCAAATGAACGGGTGAGTCTGACAATTG
GTCAGTACTCACTCTATGCAATAGACGGAACATTATACAATAACGATCAACAACTTGGATTCATTAGTTACGCATTA
TCACAAAATCCAACAGCAACTTATTCCTCTGGAAGTCTTGGAGCTTACCTACAAGTCGCTCCTACCGCAAGCACAAG
TCTTCAAATAGGATTTCAAGACGCTTATAATATCTCCGGATCCTCTATCAAATGGAGTAACCTTACAAAAAATAGAT
ACAATTTTCACGGTTTTGCTTCCTGGGCTCCCCGCTGTTGCTTAGGATCTGGCCAGTACTCCGTGCTTCTTTATGTG
ACTAGACAAGTTCCAGAACAGATGGAACAAACAATGGGATGGTCAGTCAATGCGAGTCAACACATATCTTCTAAACT
GTATGTGTTTGGAAGATACAGCGGTGTTACAGGACATGTGTTCCCGATTAACCGCACGTATTCATTCGGTATGGCCT
CTGCAAATTTATTTAACCGTAACCCACAAGATTTATTTGGAATTGCTTGCGCATTCAATAATGTACACCTCTCTGCT
TCTCCAAATACTAAAAGAAAATACGAAACTGTAATCGAAGGGTTTGCAACTATCGGTTGCGGCCCCTATCTTTCTTT
CGCTCCAGACTTCCAACTCTACCTCTACCCAGCTCTTCGTCCAAACAAACAATCTGCCCGTGTTTATAGCGTGCGAG
CTAATTTAGCTATC -continued

SEQUENCE LISTING

SEQ ID NO: 74 - CT372 fragment protein sequence
QAAHNHYHRYTDKLHRQNHKKDLISPKPTEQEACNTSSLSKELIPLSEQRGLLSPICDFISERPCLHGVSVRNLKQA
LKNSAGTQIALDWSILPQWFNPRVSHAPKLSIRDFGYSAHQTVTEATPPCWQNCFNPSAAVTIYDSSYGKGVFQISY
TLVRYWRENAATAGDAMMLAGSINDYPSRQNIFSQFTFSQNFPNERVSLTIGQYSLYAIDGTLYNNDQQLGFISYAL
SQNPTATYSSGSLGAYLQVAPTASTSLQIGFQDAYNISGSSIKWSNLTKNRYNFHGFASWAPRCCLGSGQYSVLLYV
TRQVPEQMEQTMGWSVNASQHISSKLYVFGRYSGVTGHVFPINRTYSFGMASANLFNRNPQDLFGIACAFNNVHLSA
SPNTKRKYETVIEGFATIGCGPYLSFAPDFQLYLYPALRPNKQSARVYSVRANLAI SEQ ID NO: 75 - CT456 fragment nucleotide sequence
ACAAATTCAGCGGCTACATCTTCTATCCAAACGACTGGAGAGACTGTAGTAAACTATACGAATTCAGCCTCCGCCCC
CAATGTAACTGTATCGACCTCCTCTTCTTCCACACAAGCCACAGCCACTTCGAATAAAACTTCCCAAGCCGTTGCTG
GAAAAATCACTTCTCCAGATACTTCAGAAAGCTCAGAAACTAGCTCTACCTCATCAAGCGATCATATCCCTAGCGAT
TACGATGACGTTGGTAGCAATAGTGGAGATATTAGCAACAACTACGATGACGTAGGTAGTAACAACGGAGATATCAG
TAGCAATTATGACGATGCTGCTGCTGATTACGAGCCGATAAGAACTACTGAAAATATTTATGAGAGTATTGGTGGCT
CTAGAACAAGTGGCCCAGAAAATACAAGTGGTGGTGCAGCAGCAGCACTCAATTCTCTAAGAGGCTCCTCCTACAGC
AATTATGACGATGCTGCTGCTGATTACGAGCCGATAAGAACTACTGAAAATATTTATGAGAGTATTGGTGGCTCTAG
AACAAGTGGCCCAGAAAATACGAGTGGTGGTGCAGCAGCAGCACTCAATTCTCTAAGAGGCTCCTCCTACAGCAATT
ATGACGATGCTGCTGCTGATTACGAGCCGATAAGAACTACTGAAAATATTTATGAGAGTATTGGTGGCTCTAGAACA
AGTGGCCCAGAAAATACGAGTGATGGTGCAGCAGCAGCAGCACTCAATTCTCTAAGAGGCTCCTCCTACACAACAGG
GCCTCGTAACGAGGGTGTATTCGGCCCTGGACCGGAAGGACTACCAGACATGTCTCTTCCTTCATACGATCCTACAA
ATAAAACCTCGTTATTGACTTTCCTCTCCAACCCTCATGTAAAGTCGAAAATGCTTGAAAACTCGGGGCATTTCGTC
TTCATTGATACAGATAGAAGTAGTTTCATTCTTGTTCCTAACGGAAATTGGGACCAAGTCTGTTCAATTAAAGTTCA
AAATGGAAAGACCAAAGAAGATCTCGACATCAAAGACTTGGAAAACATGTGTGCAAAATTCTGTACAGGGTTTAGCA
AATTCTCTGGTGACTGGGACAGTCTTGTAGAACCTATGGTGTCAGCCAAAGCTGGAGTGGCCAGCGGAGGCAATCTT
CCCAATACAGTGATTATCAATAATAAATTCAAAACTTGCGTTGCTTATGGTCCTTGGAATAGCCAGGAAGCAAGTTC
TGGTTATACACCTTCTGCTTGGAGACGTGGTCATCGAGTAGATTTTGGAGGAATTTTTGAGAAAGCCAACGACTTTA
ATAAAATCAACTGGGGAACTCAAGCCGGGCCTAGTAGCGAAGACGATGGCATTTCCTTCTCCAATGAAACTCCTGGA
GCTGGTCCTGCAGCTGCTCCATCACCAACGCCATCCTCTATTCCTATCATCAATGTCAATGTCAATGTTGGCGGAAC
TAATGTGAATATTGGAGATACGAATGTCAACACGACTAACACCACACCAACAACTCAATCTACAGACGCCTCTACAG
ATACAAGCGATATCGATGACATAAATACCAACAACCAAACTGATGATATCAATACGACAGACAAAGACTCTGACGGA
GCTGGTGGAGTCAATGGCGATATATCCGAAACAGAATCCTCTTCTGGAGATGATTCAGGAAGTGTCTCTTCCTCAGA
ATCAGACAAGAATGCCTCTGTCGGAAATGACGGACCTGCTATGAAAGATATCCTTTCTGCCGTGCGTAAACACCTAG
ACGTCGTTTACCCTGGCGAAAATGGCGGTTCTACAGAAGGGCCTCTCCCAGCTAACCAAACTCTCGGAGACGTAATC
TCTGATGTAGAGAATAAAGGCTCCGCTCAGGATACAAAATTGTCAGGAAATACAGGAGCTGGGGATGACGATCCAAC
AACCACAGCTGCTGTAGGTAATGGAGCGGAAGAGATCACTCTTTCCGACACAGATTCTGGTATCGGAGATGATGTAT
CCGATACAGCGTCTTCATCTGGGGATGAATCCGGAGGAGTCTCCTCTCCCTCTTCAGAATCCAATAAAAATACTGCC
GTTGGAAATGACGGACCTTCTGGACTAGATATCCTCGCTGCCGTACGTAAACATTTAGATAAGGTTTACCCTGGCGA
CAATGGTGGTTCTACAGAAGGGCCTCTCCAAGCTAACCAAACTCTTGGAGATATCGTCCAGGATATGGAAACAACAG
GGACATCCCAAGAAACCGTTGTATCCCCATGGAAAGGAAGCACTTCTTCAACGGAATCAGCAGGAGGAAGTGGTAGC
GTACAAACACTACTGCCTTCACCACCTCCAACCCCGTCAACTACAACATTAAGAACGGGCACAGGAGCTACCACCAC
ATCCTTGATGATGGGAGGACCAATCAAAGCTGACATAATAACAACTGGTGGCGGAGGACGAATTCCTGGAGGAGGAA
CGTTAGAAAAGCTGCTCCCTCGTATACGTGCGCACTTAGACATATCCTTTGATGCGCAAGGCGATCTCGTAAGTACT
GAAGAGCCTCAGCTTGGCTCGATTGTAAACAAATTCCGCCAAGAAACTGGTTCAAGAGGAATCTTAGCTTTCGTTGA
GAGTGCTCCAGGCAAGCCGGGATCTGCACAGGTCTTAACGGGTACAGGGGGAGATAAAGGCAACCTATTCCAAGCAG
CTGCCGCAGTCACCCAAGCCTTAGGAAATGTTGCAGGGAAAGTCAACCTTGCGATACAAGGCCAAAAACTATCATCC
CTAGTCAATGACGACGGGAAGGGGTCTGTTGGAAGAGATTTATTCCAAGCAGCAGCCCAAACAACTCAAGTGCTAAG
CGCACTGATTGATACCGTAGGA SEQ ID NO: 76 - CT456 fragment protein sequence
TNSAATSSIQTTGETVVNYTNSASAPNVTVSTSSSSTQATATSNKTSQAVAGKITSPDTSESSETSSTSSSDHIPSD
YDDVGSNSGDISNNYDDVGSNNGDISSNYDDAAADYEPIRTTENIYESIGGSRTSGPENTSGGAAAALNSLRGSSYS
NYDDAAADYEPIRTTENIYESIGGSRTSGPENTSGGAAAALNSLRGSSYSNYDDAAADYEPIRTTENIYESIGGSRT
SGPENTSDGAAAAALNSLRGSSYTTGPRNEGVFGPGPEGLPDMSLPSYDPTNKTSLLTFLSNPHVKSKMLENSGHFV
FIDTDRSSFILVPNGNWDQVCSIKVQNGKTKEDLDIKDLENMCAKFCTGFSKFSGDWDSLVEPMVSAKAGVASGGNL
PNTVIINNKFKTCVAYGPWNSQEASSGYTPSAWRRGHRVDFGGIFEKANDFNKINWGTQAGPSSEDDGISFSNETPG
AGPAAAPSPTPSSIPIINVNVNVGGTNVNIGDTNVNTTNTTPTTQSTDASTDTSDIDDINTNNQTDDINTTDKDSDG
AGGVNGDISETESSSGDDSGSVSSSESDKNASVGNDGPAMKDILSAVRKHLDVVYPGENGGSTEGPLPANQTLGDVI
SDVENKGSAQDTKLSGNTGAGDDDPTTTAAVGNGAEEITLSDTDSGIGDDVSDTASSSGDESGGVSSPSSESNKNTA
VGNDGPSGLDILAAVRKHLDKVYPGDNGGSTEGPLQANQTLGDIVQDMETTGTSQETVVSPWKGSTSSTESAGGSGS
VQTLLPSPPPTPSTTTLRTGTGATTTSLMMGGPIKADIITTGGGGRIPGGGTLEKLLPRIRAHLDISFDAQGDLVST
EEPQLGSIVNKFRQETGSRGILAFVESAPGKPGSAQVLTGTGGDKGNLFQAAAAVTQALGNVAGKVNLAIQGQKLSS
LVNDDGKGSVGRDLFQAAAQTTQVLSALIDTVG SEQ ID NO: 77: CT381 fragment nucleotide sequence
TGTTTAAAAGAAGGGGGAGACTCCAATAGTGAAAAATTTATTGTAGGGACTAATGCAACCTACCCTCCTTTTGAGTT
TGTTGATAAGCGAGGAGAGGTTGTAGGCTTCGATATAGACTTGGCTAGAGAGATTAGTAACAAGCTGGGGAAAACGC
TGGACGTTCGGGAGTTTTCCTTTGATGCACTCATTCTAAACCTAAAACAGCATCGGATTGATGCGGTTATAACAGGG
ATGTCCATTACTCCTTCTAGATTGAAGGAAATTCTTATGATTCCCTATTATGGGGAGGAAATAAAACACTTGGTTTT
AGTGTTTAAAGGAGAGAATAAGCATCCATTGCCACTCACTCAATATCGTTCTGTAGCTGTTCAAACAGGAACCTATC
AAGAGGCCTATTTACAGTCTCTTTCTGAAGTTCATATTCGCTCTTTTGATAGCACTCTAGAAGTACTCATGGAAGTC
ATGCATGGTAAATCTCCCGTCGCTGTTTTAGAGCCATCTATCGCTCAAGTTGTCTTGAAAGATTTCCCGGCTCTTTC
TACAGCAACCATAGATCTCCCTGAAGATCAGTGGGTTTTAGGATACGGGATTGGCGTTGCTTCAGATCGCCCAGCTT
TAGCCTTGAAAATCGAGGCAGCTGTGCAAGAGATCCGAAAAGAAGGAGTGCTAGCAGAGTTGGAACAGAAGTGGGGT
TTGAACAAC -continued

SEQUENCE LISTING

SEQ ID NO: 78: CT381 fragment protein sequence
CLKEGGDSNSEKFIVGTNATYPPFEFVDKRGEVVGFDIDLAREISNKLGKTLDVREFSFDALILNLKQHRIDAVITG
MSITPSRLKEILMIPYYGEEIKHLVLVFKGENKHPLPLTQYRSVAVQTGTYQEAYLQSLSEVHIRSFDSTLEVLMEV
MHGKSPVAVLEPSIAQVVLKDFPALSTATIDLPEDQWVLGYGIGVASDRPALALKIEAAVQEIRKEGVLAELEQKWG
LNN SEQ ID NO: 79: CT043 fragment nucleotide sequence
TCCAGGCAGAATGCTGAGGAAAATCTAAAAAATTTTGCTAAAGAGCTTAAACTCCCCGACGTGGCCTTCGATCAGAA
TAATACGTGCATTTTGTTTGTTGATGGAGAGTTTCTCTTCACCTGACCTACGAAGAACACTCTGATCGCCTTTATG
TTTACGCACCTCTTCTTGACGGACTGCCAGACAATCCGCAAAGAAGGTTAGCTCTATATGAGAAGTTGTTAGAAGGC
TCTATGCTCGGAGGCCAAATGGCTGGTGGAGGGGTAGGAGTCGCTACTAAGGAACAGTTGATCTTAATGCACTGCGT
GTTAGACATGAAGTATGCAGAGACCAACCTACTCAAAGCTTTTGCACAGCTTTTTATTGAAACCGTTGTGAAATGGC
GAACTGTTTGTTCTGATATCAGCGCTGGACGAGAACCCACTGTTGATACCATGCCACAAATGCCTCAAGGGGGTGGC
GGAGGAATTCAACCTCCTCCAGCAGGAATCCGTGCA SEQ ID NO: 80: CT043 fragment protein sequence
SRQNAEENLKNFAKELKLPDVAFDQNNTCILFVDGEFSLHLTYEEHSDRLYVYAPLLDGLPDNPQRRLALYEKLLEG
SMLGGQMAGGGVGVATKEQLILMHCVLDMKYAETNLLKAFAQLFIETVVKWRTVCSDISAGREPTVDTMPQMPQGGG
GGIQPPPAGIRA SEQ ID NO: 81: CT711 fragment nucleotide.seq Length: 2298
TCAATACAACCTACATCCATTTCTTTAACTAAGAATATAACGGCAGCTTTAGCCGGAGAGCAGGTCGATGCTGCTGC
AGTGTATATGCCGCAGGCTGTTTTTTTCTTTCAGCAACTGGATGAAAAAAGCAAGGGGCTGAAACAGGCTTTAGGAT
TGCTCGAAGAGGTTGATCTAGAAAAATTTATACCGTCTTTAGAAAAATCACCTACACCTATCACTACGGGAACAACG
AGTAAAATTTCCGCTGATGGGATTGAGATTGTTGGAGAGCTTTCTTCAGAAACAATTTTGGCAGATCCTAATAAAGC
TGCAGCTCAGGTTTTTGGAGAGGGGCTTGCAGATAGTTTTGATGATTGGCTCAGATTATCTGAAAATGGGGGGATTC
AAGATCCTACAGCAATAGAAGAAGAGATTGTTACTAAGTATCAAACAGAACTCAATACTCTGCGCAATAAACTCAAG
CAACAATCTTTAACAGACGATGAGTATACGAAGCTTTATGCTATTCCTCAAAACTTTGTTAAAGAGATAGAAAGCTT
AAAGAATGAAAATAATGTGAGGTTAATTCCCAAAAGTAAAGTCACTAACTTTTGGCAGAATATCATGCTCACTTACA
ACTCGGTAACCTCGTTATCAGAACCTGTTACCGATGCGATGAATACGACTATGGCGGAGTACTCTCTTTATATTGAG
AGAGCTACAGAGGCTGCCAAGTTGATACGGGAGATAACCAACACGATCAAAGACATTTTCAATCCAGTTTGGGATGT
GCGTGAACAAACAGGAATTTTTGGGTTAAAGGGAGCTGAGTATAACGCTTTAGAAGGCAATATGATTCAAAGCTTGC
TTAGCTTTGCGGGTCTATTCCGGCAGTTAATGAGTCGTACTGCAACAGTTGATGAGATAGGCGCACTTTATCCTAAA
AATGATAAAAACGAAGACGTCATTCATACTGCTATTGATGATTATGTGAATTCTTTAGCTGATTTGAAAGCCAATGA
ACAGGTCAAACTCAACGGTCTGTTGAGTTTAGTATATGCTTATTATGCTAGTACTTTAGGTTTTGCTAAGAAGGATG
TATTCAATAATGCACAAGCTTCTTTTACAGATTATACTAATTTTCTAAACCAAGAGATCCAATATTGGACGCCTAGA
GAGACTTCAAGTTTTAATATCTCCAATCAAGCATTGCAAACCTTTAAAAATAAGCCTTCGGCTGATTATAACGGCGT
ATATCTTTTTGATAATAAAGGATTAGAGACTAATCTCTTTAATCCTACGTTCTTCTTTGATGTTGTGAGTCTCATGA
CAGCTGATCCTACGAAGACTATGTCTCGACAGGATTACAATAAGGTGATTACAGCCTCGGAATCCAGTATTCAGAAG
ATTAATCAGGCTATTACCGCTTGGGAACTAGCTATTGCAGAATGTGGGACTAAAAAAGCGAAGCTCGAACCATCCAG
TTTAAATTATTTTAATGCTATGGTCGAAGCGAAGAAGACCTTCGTAGAGACCTCTCCAATACAGATGGTCTATTCAT
CTTTGATGTTGGATAAGTATCTTCCGAATCAGCAGTACATATTAGAGACATTAGGAAGTCAGATGACTTTCTCTAAC
AAGGCTGCTCGGTATTTAAATGATATCATTGCGTATGCAGTTAGCTTCCAAACAGCTGACGTCTATTATTCTTTAGG
GATGTATCTTCGACAAATGAACCAGCAGGAATTTCCTGAGGTGATTTCTCGTGCTAACGATACTGTGAAAAAAGAGA
TAGATCGGAGTCGTGCGGATCTCTTTCACTGTAAAAAAGCTATCGAAAAGATTAAAGAATTAGTGACTTCTGTAAAT
GCGGATACTGAATTGACCTCATCTCAGCGTGCAGAGTTATTAGAGACGTTAGCTAGTTATGCTTTTGAATTTGAGAA
TCTCTATCACAACCTCTCTAATGTTTACGTCATGGTTTCTAAGGTACAGATTTCTGGCGTAAGCAAGCCTGATGAAG
TGGATGAGGCTTTTACTGCTAAGATTGGATCGAAGGAATTCGATACTTGGATTCAGCAGCTTACAACATTTGAAAGT
GCTGTGATTGAAGGTGGGCGTAATGGTGTGATGCCTGGGGGAGAGCAGCAGGTTTTACAGAGTTTAGAGAGCAAGCA
GCAAGATTACACGTCGTTCAACCAGAATCAGCAATTAGCTCTACAAATGGAGTCCGCAGCGATTCAACAAGAGTGGA
CTATGGTAGCAGCAGCCTTAGCATTAATGAATCAGATTTTTGCTAAGTTGATCCGTAGATTTAAA SEQ ID NO: 82: CT711 fragment protein sequence (AAC68306)
SIQPTSISLTKNITAALAGEQVDAAAVYMPQAVFFFQQLDEKSKGLKQALGLLEEVDLEKFIPSLEKSPTPITTGTT
SKISADGIEIVGELSSETILADPNKAAAQVFGEGLADSFDDWLRLSENGGIQDPTAIEEEIVTKYQTELNTLRNKLK
QQSLTDDEYTKLYAIPQNFVKEIESLKNENNVRLIPKSKVTNFWQNIMLTYNSVTSLSEPVTDAMNTTMAEYSLYIE
RATEAAKLIREITNTIKDIFNPVWDVREQTGIFGLKGAEYNALEGNMIQSLLSFAGLFRQLMSRTATVDEIGALYPK
NDKNEDVIHTAIDDYVNSLADLKANEQVKLNGLLSLVYAYYASTLGFAKKDVFNNAQASFTDYTNFLNQEIQYWTPR
ETSSFNISNQALQTFKNKPSADYNGVYLFDNKGLETNLFNPTFFFDVVSLMTADPTKTMSRQDYNKVITASESSIQK
INQAITAWELAIAECGTKKAKLEPSSLNYFNAMVEAKKTFVETSPIQMVYSSLMLDKYLPNQQYILETLGSQMTFSN
KAARYLNDIIAYAVSFQTADVYYSLGMYLRQMNQQEFPEVISRANDTVKKEIDRSRADLFHCKKAIEKIKELVTSVN
ADTELTSSQRAELLETLASYAFEFENLYHNLSNVYVMVSKVQISGVSKPDEVDEAFTAKIGSKEFDTWIQQLTTFES
AVIEGGRNGVMPGGEQQVLQSLESKQQDYTSFNQNQQLALQMESAAIQQEWTMVAAALALMNQIFAKLIRRFK SEQ ID NO: 83: CT114 fragment nucleotide sequence - Length: 1296
GATCCTTTGAGTGCAAAACAGTTAATGTATCTGTTTCCTCAGCTCTCAGAAGAGGATGTATCTGTTTTTGCTCGATG
CATTTTGTCTTCAAAGCGTCCAGAATACCTCTTTTCAAAATCGGAGGAAGAGCTCTTTGCAAAATTGATTTTGCCAA
GGGTTTCTCTAGGTGTTCATCGGGACGATGATTTAGCGAGAGTGTTGGTGTTAGCGGAGCCTTCTGCAGAAGAGCAG
AAGGCTCGATACTATTCATTGTATCTGGATGTTTTAGCTTTGCGTGCATACGTTGAAAGAGAGCGTTTGGCGAGTGC
TGCACACGGAGATCCTGAGCGGATAGATTTGGCAACCATAGAAGCTATTAATACCATCCTTTTTCAGGAAGAAGGAT
GGAGGTATCCTTCAAAACAAGAGATGTTTGAAAACAGGTTTTCTGAGTTAGCTGCTGTTACAGATAGTAAGTTTGGA
GTTTGCTTGGGAACTGTAGTGCTTTATCAAGCTGTCGCCCAGCGGCTTGATTTGTCTCTGGACCCTGTCACCCCTCC
TGGACATATTTACTTACGCTATAAGGACAAGGTGAATATTGAAACCACTTCTGGAGGAAGGCATCTTCCTACTGAAA
GGTATTGTGAATGCATAAAAGAGTCGCAGTTAAAGGTGCGTTCGCAGATGGAGCTTATAGGGTTAACTTTTATGAAT
AGAGGAGCTTTCTTTTTGCAAAAAGGAGAGTTTCTTCAGGCGTCCTTAGCTTATGAGCAAGCTCAATCATATTTATC
AGACGAGCAGATTTCTGATTTGTTAGGGATTACTTATGTTCTTTTAGGAAAGAAGGCGGCGGGAGAGGCTCTTTTAA -continued

SEQUENCE LISTING

AGAAATCTGCAGAAAAGACTCGGCGAGGGTCATCTATCTATGACTATTTCCAAGGATATATTTCCCCCGAAATCCTA
GGGGTGTTGTTTGCCGATTCAGGGGTGACCTATCAAGAAACTTTGGAGTATCGAAAAAAACTAGTGATGCTTTCCAA
GAAGTATCCAAAAAGTGGATCTCTTAGGTTGAGGTTGGCGACAACAGCATTGGAGCTAGGGCTGGTCAAGGAGGGGG
TGCAGTTGTTAGAAGAGAGTGTTAAGGATGCCCCAGAGGACCTCTCTTTACGTCTGCAGTTTTGTAAAATTCTTTGC
AATCGACATGATTATGTCCGAGCAAAATATCATTTTGATCAAGCGCAAGCTCTTCTCATTAAAGAAGGGTTGTTTTC
CGAAAAAACTTCCTATACTCTCTTAAAAACTATCGGGAAAAAGCTATCTCTTTTTGCTCCGAGT

SEQ ID NO: 84: CT114 fragment protein sequence (AAC67705)
DPLSAKQLMYLFPQLSEEDVSVFARCILSSKRPEYLFSKSEEELFAKLILPRVSLGVHRDDDLARVLVLAEPSAEEQ
KARYYSLYLDVLALRAYVERERLASAAHGDPERIDLATIEAINTILFQEEGWRYPSKQEMFENRFSELAAVTDSKFG
VCLGTVVLYQAVAQRLDLSLDPVTPPGHIYLRYKDKVNIETTSGGRHLPTERYCECIKESQLKVRSQMELIGLTFMN
RGAFFLQKGEFLQASLAYEQAQSYLSDEQISDLLGITYVLLGKKAAGEALLKKSAEKTRRGSSIYDYFQGYISPEIL
GVLFADSGVTYQETLEYRKKLVMLSKKYPKSGSLRLRLATTALELGLVKEGVQLLEESVKDAPEDLSLRLQFCKILC
NRHDYVRAKYHFDQAQALLIKEGLFSEKTSYTLLKTIGKKLSLFAPS SEQ ID NO: 85: CT480 fragment nucleotide sequence
TCTTCAGATCTACTTGAAAAAGATGTGAAATCGATCAAAAGAGAACTCAAGGCTTTACATGAAGATGTTCTTGAGTT
AGTCCGGATCTCGCATCAGCAAAAAAATTGGGTCCAGTCTACAGATTTTTCTGTTTCTCCAGAGATCAGTGTATTGA
AGGATTGCGGAGATCCTGCGTTCCCTAATTTATTATGCGAAGACCCTTATGTTGAAAAAGTGGTCCCTTCGTTGTTA
AAGGAAGGTTTTGTTCCGAAAGGTATTTTGCGTACAGCTCAAGTAGGAAGGCCTGATAACCTAAGTCCGTTTAATGG
CTTTGTTAATATCGTTCGATTTTATGAATTGTGCGTTCCTAATTTGGCTGTTGAGCATGTTGGTAAATACGAGGAGT
TTGCGCCTAGTTTAGCCTTAAAGATAGAAGAGCATTATGTAGAGGATGGGTCTGGGGATAAAGAATTTCATATTTAT
TTGCGTCCTAATATGTTTTGGGAGCCGATAGATCCTACGCTGTTCCCTAAAAATATAACTTTAGCAGACAGCTTCTT
AAGACCACATCCTGTCACCGCTCATGATGTGAAGTTCTATTACGATGTAGTCATGAATCCCTATGTTGCAGAAATGC
GTGCAGTGGCTATGAGATCTTATTTTGAGGATATGGTTTCGGTTCGGGTAGAAAACGATTTGAAATTAATCGTTCGT
TGGAGAGCTCATACTGTACGTAATGAACAGGGAGAGGAAGAGAAAAAAGTGCTCTATTCTGCTTTCGCGAATACATT
GGCACTCCAACCGTTACCTTGTTTCGTGTATCAGCATTTCGCAAATGGAGAGAAGATCGTTCCAGAAGATTCTGATC
CCGATACGTATCGCAAAGATTCGGTATGGGCGCAAAACTTTTCTTCACATTGGGCGTATAATTACATAGTGAGCTGT
GGAGCATTCCGATTTGCAGGGATGGATGATGAGAAAATTACTTTAGTTCGTAATCCTAATTATCATAATCCGTTTGC
GGCTCTTGTGGAGAAGCGCTATATCTATATGAAAGATAGTACAGATTCTCTCTTCCAAGATTTCAAAGCTGGGAAGG
TGGATATTGCGTATTTCCCTCCTAACCATGTCGATAATCTAGCGAGCTTCATGCAAACCTCTGCTTATAAGGAACAA
GCTGCTAGAGGAGAGGCAATTTTAGAAAAAAATTCATCAGACCGGTCCTATTCTTACATCGGATGGAATTGTCTTTC
TCTTTTCTTTAACAATCGTTCGGTACGACAAGCCATGAATATGTTGATCGATCGGGATCGCATTATTGAGCAGTGCT
TGGATGGTCGTGGAGTCTCTGTGAGTGGGCCTTTTTCTCTCTGCTCTCCATCATACAACAGAGATGTAGAGGGATGG
CAATACTCTCCGGAAGAGGCCGCACGTAAATTAGAGGAAGAGGGCTGGATCGATGCTGATGGAGATGGTATTCGTGA
GAAAGTAATCGATGGAGTTGTAGTGCCTTTCCGTTTCCGGTTATGCTACTATGTGAAAAGTGTAACAGCACGAACGA
TTGCCGAATATGTAGCTACGGTATGTAAAGAGGTGGGTATCGAGTGTTGCTTACTCGGGTTAGATATGGCGGATTAT
TCACAAGCCCTCGAGGAGAAAAATTTCGATGCTATTCTTTCCGGATGGTGTTTAGGAACCCCTCCAGAAGATCCTCG
TGCTCTATGGCATTCGGAAGGAGCTTTGGAGAAAGGATCTGCCAATGCTGTTGGATTTTGTAATGAGGAAGCAGACC
GTATCATCGAACAGCTCAGTTACGAGTATGATTCTAATAAGCGCCAAGCCTTGTATCACCGTTTTCACGAGGTGATT
CATGAGGAATCTCCTTACGCGTTTCTCTATTCAAGACAGTACTCCCTTGTCTATAAGGAGTTTGTAAAAAATATTTT
TGTGCCAACAGAACATCAGGATTTGATTCCTGGAGCTCAAGATGAGACAGTGAATTTATCCATGTTGTGGGTAGATA
AAGAGGAGGGTCGATGCTCCGCTATATCT SEQ ID NO: 86: CT480/oppA_4 fragment protein sequence (AAC68080)
SSDLLEKDVKSIKRELKALHEDVLELVRISHQQKNWVQSTDFSVSPEISVLKDCGDPAFPNLLCEDPYVEKVVPSLL
KEGFVPKGILRTAQVGRPDNLSPFNGFVNIVRFYELCVPNLAVEHVGKYEEFAPSLALKIEEHYVEDGSGDKEFHIY
LRPNMFWEPIDPTLFPKNITLADSFLRPHPVTAHDVKFYYDVVMNPYVAEMRAVAMRSYFEDMVSVRVENDLKLIVR
WRAHTVRNEQGEEEKKVLYSAFANTLALQPLPCFVYQHFANGEKIVPEDSDPDTYRKDSVWAQNFSSHWAYNYIVSC
GAFRFAGMDDEKITLVRNPNYHNPFAALVEKRYIYMKDSTDSLFQDFKAGKVDIAYFPPNHVDNLASFMQTSAYKEQ
AARGEAILEKNSSDRSYSYIGWNCLSLFFNNRSVRQAMNMLIDRDRIIEQCLDGRGVSVSGPFSLCSPSYNRDVEGW
QYSPEEAARKLEEEGWIDADGDGIREKVIDGVVVPFRFRLCYYVKSVTARTIAEYVATVCKEVGIECCLLGLDMADY
SQALEEKNFDAILSGWCLGTPPEDPRALWHSEGALEKGSANAVGFCNEEADRIIEQLSYEYDSNKRQALYHRFHEVI
HEESPYAFLYSRQYSLVYKEFVKNIFVPTEHQDLIPGAQDETVNLSMLWVDKEEGRCSAIS SEQ ID NO: 87: CT089 fragment nucleotide.sequence-Length: 1194
GCTGCAGCTACTCAAGATGCACAAGAGGTTATCGGCTCTCAGGAAGCTTCTGAGGCAAGTATGCTCAAAGGATGTGA
GGATCTCATAAATCCTGCAGCTGCAACCCGAATCAAAAAAAAAGGAGAGAAGTTTGAATCATTAGAAGCTCGTCGCA
AACCAACAGCGGATAAAGCAGAAAAGAAATCCGAGAGCACAGAGGAAAAAGGCGATACTCCTCTTGAAGATCGTTTC
ACAGAAGATCTTTCCGAAGTCTCCGGAGAAGATTTTCGAGGATTGAAAAATTCGTTCGATGATGATTCTTCTCCTGA
CGAAATTCTCGATGCGCTCACAAGTAAATTTTCTGATCCCACAATAAAGGATCTAGCTCTTGATTATCTAATTCAAA
CAGCTCCCTCTGATGGGAAACTTAAGTCCACTCTCATTCAGGCAAAGCATCAACTGATGAGCCAGAATCCTCAGGCG
ATTGTTGGAGGACGCAATGTTCTGTTAGCTTCAGAAACCTTTGCTTCCAGAGCAAATACATCTCCTTCATCGCTTCG
CTCCTTATATTTCCAAGTAACCTCATCCCCCTCTAATTGCGCTAATTTACATCAAATGCTTGCTTCTTACTTGCCAT
CAGAGAAAACCGCTGTTATGGAGTTTCTAGTAAATGGCATGGTAGCAGATTTAAAATCGGAGGGCCCTTCCATTCCT
CCTGCAAAATTGCAAGTATATATGACGGAACTAAGCAATCTCCAAGCCTTACACTCTGTAAATAGCTTTTTTGATAG
AAATATTGGGAACTTGGAAAATAGCTTAAAGCATGAAGGACATGCCCCTATTCCATCCTTAACGACAGGAAATTTAA
CTAAAACCTTCTTACAATTAGTAGAAGATAAATTCCCTTCCTCTTCCAAAGCTCAAAAGGCATTAAATGAACTGGTA
GGCCCAGATACTGGTCCTCAAACTGAAGTTTTAAACTTATTCTTCCGCGCTCTTAATGGCTGTTCGCCTAGAATATT
CTCTGGAGCTGAAAAAAAACAGCAGCTGGCATCGGTTATCACAAATACGCTAGATGCGATAAATGCGGATAATGAGG
ATTATCCTAAACCAGGTGACTTCCCACGATCTTCCTTCTCTAGTACGCCTCCTCATGCTCCAGTACCTCAATCTGAG
ATTCCAACGTCACCTACCTCAACACAGCCTCCATCACCC SEQ ID NO: 88: CT089/lcrE fragment protein sequence (AAC67680)
AAATQDAQEVIGSQEASEASMLKGCEDLINPAAATRIKKKGEKFESLEARRKPTADKAEKKSESTEEKGDTPLEDRF
TEDLSEVSGEDFRGLKNSFDDDSSPDEILDALTSKFSDPTIKDLALDYLIQTAPSDGKLKSTLIQAKHQLMSQNPQA
IVGGRNVLLASETFASRANTSPSSLRSLYFQVTSSPSNCANLHQMLASYLPSEKTAVMEFLVNGMVADLKSEGPSIP -continued

SEQUENCE LISTING

PAKLQVYMTELSNLQALHSVNSFFDRNIGNLENSLKHEGHAPIPSLTTGNLTKTFLQLVEDKFPSSSKAQKALNELV
GPDTGPQTEVLNLFFRALNGCSPRIFSGAEKKQQLASVITNTLDAINADNEDYPKPGDFPRSSFSSTPPHAPVPQSE
IPTSPTSTQPPSP

SEQ ID NO: 89: CT734 fragment nucleotide sequence-Length: 591
TGTTGCGCCAACTCTTATGGATCGACTCTTGCAAAAAATACAGCCGAGATAAAAGAAGAATCTGTTACACTTCGCGA
GAAGCCGGATGCCGGCTGTAAAAAGAAATCTTCTTGTTACTTGAGAAAATTTTTCTCGCGCAAGAAACCTAAAGAGA
AGACAGAGCCTGTGTTGCCGAACTTTAAGTCTTACGCAGATCCAATGACAGATTCCGAAAGAAAAGACCTTTCTTTC
GTAGTATCTGCTGCTGCTGATAAGTCTTCTATTGCTTTGGCTATGGCTCAGGGGGAAATTAAAGGCGCATTATCGCG
TATTAGAGAGATCCATCCTCTTGCATTGTTACAAGCTCTTGCAGAAGATCCTGCTTTAATTGCTGGAATGAAAAAGA
TGCAAGGACGGGATTGGGTCTGGAATATCTTTATCACAGAATTAAGCAAAGTTTTTTCTCAAGCAGCATCTTTAGGG
GCTTTCAGCGTTGCAGACGTTGCCGCGTTCGCGTCGACCTTAGGATTAGACTCGGGGACCGTTACCTCAATTGTTGA
TGGGGAAAGGTGGGCTGAGCTGATCGATGTCGTGATTCAGAACCCTGCTATA SEQ ID NO: 90: CT734 fragment protein sequence (AAC68329)
CCANSYGSTLAKNTAEIKEESVTLREKPDAGCKKKSSCYLRKFFSRKKPKEKTEPVLPNFKSYADPMTDSERKDLSF
VVSAAADKSSIALAMAQGEIKGALSRIREIHPLALLQALAEDPALIAGMKKMQGRDWVWNIFITELSKVFSQAASLG
AFSVADVAAFASTLGLDSGTVTSIVDGERWAELIDVVIQNPAI SEQ ID NO: 91: CT016 fragment nucleotide sequence
AAAGTTAAAATTAATGATCAGTTCATTTGTATTTCCCCATACATTTCTGCTCGATGGAATCAGATAGCTTTCATAGA
GTCTTGTGATGGAGGGACGGAAGGGGGTATTACTTTGAAACTCCATTTAATTGATGGAGAGACAGTCTCTATACCTA
ATCTAGGACAAGCGATTGTTGATGAGGTGTTCCAAGAGCACTTGCTATATTTAGAGTCCACAGCTCCTCAGAAAAAC
AAGGAAGAGGAAAAAATTAGCTCTTTGTTAGGAGCTGTTCAACAAATGGCTAAAGGATGCGAAGTACAGGTTTTTTC
TCAAAAGGGCTTGGTTTCTATGTTACTAGGAGGAGCTGGTTCGATTAATGTGTTGTTGCAACATTCTCCAGAACATA
AGGATCATCCTGATCTTCCTACCGATTTACTGGAGAGGATAGCGCAAATGATGCGTTCATTATCTATAGGACCAACT
TCTATTTTAGCTAAGCCAGAGCCTCATTGCAACTGTTTGCATTGTCAAATTGGACGAGCTACAGTGGAAGAAGAGGA
TGCCGGAGTATCGGATGAGGATCTTACTTTTCGTTCATGGGATATCTCTCAAAGTGGAGAAAAGATGTACACTGTTA
CAGATCCTTTGAATCCAGAAGAGCAGTTTAATGTGTATTTAGGAACGCCGATTGGATGCACATGTGGGCAGCCATAC
TGTGAACACGTGAAAGCTGTTCTTTATACT SEQ ID NO: 92: CT016 fragment protein sequence (AAC67606)
KVKINDQFICISPYISARWNQIAFIESCDGGTEGGITLKLHLIDGETVSIPNLGQAIVDEVFQEHLLYLESTAPQKN
KEEEKISSLLGAVQQMAKGCEVQVFSQKGLVSMLLGGAGSINVLLQHSPEHKDHPDLPTDLLERIAQMMRSLSIGPT
SILAKPEPHCNCLHCQIGRATVEEEDAGVSDEDLTFRSWDISQSGEKMYTVTDPLNPEEQFNVYLGTPIGCTCGQPY
CEHVKAVLYT SEQ ID NO: 93: CM homolog of CT279 = TC_0551 fragment nucleotide sequence
GCATCCAAGTCTCGTCATTATCTTAACCAGCCTTGGTACATTATCTTATTCATCTTTGTTCTTAGTCTGGTTGCTGG
TACCCTTCTTTCTTCAGTTTCCTATGTTCTATCTCCAATCCAAAAACAAGCTGCAGAATTTGATCGTAATCAGCAAA
TGTTGATGGCCGCACAAATTATTTCCTATGACAATAAATTCCAAATATATGCTGAAGGGGATTGGCAACCTGCTGTC
TATAATACAAAAAAACAGATACTAGAAAAAAGCTCTTCCACTCCACCACAAGTGACTGTGGCGACTCTATGCTCTTA
TTTTCAAAATTTTGTTAGAGTTTTGCTTACAGACTCCCAAGGGAATCTTTCTTCTTTTGAAGATCACAATCTTAACC
TAGAAGAGTTCTTATCCCACCCCACATCTTCAGTACAAGATCACTCTCTGCATGTAATTTATGCTATTCTAGCAAAC
GATGAATCCTCTAAAAAGTTATCATCCTCCCAAGTAGCAAAAAATCCGGTATCCATAGAGTCTATTATTCTTCCTAT
AAAAGGATTTGGTTTATGGGGACCAATCTATGGATTTCTTGCTTTAGAAAAGGACGGTAATACGGTTCTAGGGACAT
GCTGGTATCAACATGGTGAGACTCCAGGATTAGGAGCAAATATAACTAATCCCCAATGGCAACAAAATTTCAGAGGA
AAAAAAGTATTTCTCGCTTCCTCTTCCGGAGAAACCGATTTTGCTAAAACAACTCTAGGACTAGAAGTTATAAAAGG
ATCTGTTTCTGCATTATTAGGGGACTCTCCCAAAGCTAATTCCGCTGTTGATGGAATTTCAGGAGCTACACTGACCT
GTAATGGAGTTACTGAAGCTTTTGCTAATTCGCTAGCTCCTTACCGCCCCTTATTGACTTTCTTCGCCAATCTTAAC
TCTAGTGGAGAATCTCATGACAACCAA SEQ ID NO: 94: CM homologue of CT279 = TC_0551 fragment protein sequence
ASKSRHYLNQPWYIILFIFVLSLVAGTLLSSVSYVLSPIQKQAAEFDRNQQMLMAAQIISYDNKFQIYAEGDWQPAV
YNTKKQILEKSSSTPPQVTVATLCSYFQNFVRVLLTDSQGNLSSFEDHNLNLEEFLSHPTSSVQDHSLHVIYAILAN
DESSKKLSSSQVAKNPVSIESIILPIKGFGLWGPIYGFLALEKDGNTVLGTCWYQHGETPGLGANITNPQWQQNFRG
KKVFLASSSGETDFAKTTLGLEVIKGSVSALLGDSPKANSAVDGISGATLTCNGVTEAFANSLAPYRPLLTFFANLN
SSGESHDNQ SEQ ID NO: 95: CM homologue of CT372 = TC_0651 fragment nucleotide sequence
AATGGAAAAGTTCTGTGTGAGGTTTCTGTGTCCTTCCGTTCGATTCTGCTGACGGCTCTGCTTTCACTTTCTTTTAC
AAACACTATGCAGGCTGCACACCATCATTATCACCGTTATGATGATAAACTACGCAGACAATACCATAAAAAGGACT
TGCCCACTCAAGAGAATGTTCGGAAAGAGTTTTGTAATCCCTACTCTCATAGTAGTGATCCTATCCCTTTGTCACAA
CAACGAGGAGTCCTATCTCCTATCTGTGATTTAGTCTCAGAGTGCTCGTTTTTGAACGGGATTTCCGTTAGGAGTCT
TAAACAAACACTGAAAAATTCTGCTGGGACTCAAGTTGCTTTAGACTGGTCTATCCTTCCTCAATGGTTCAATCCTA
GATCCTCTTGGGCTCCTAAGCTCTCTATTCGAGATCTTGGATATGGTAAACCCCAGTCCCTTATTGAAGCAGATTCC
CCTTGTTGTCAAACCTGCTTCAACCCATCTGCTGCTATTACGATTTACGATTCTTCATGTGGGAAGGGTGTTGTCCA
AGTGTCATACACCCTTGTTCGTTATTGGAGAGAAACGGCTGCACTTGCAGGGCAAACTATGATGCTTGCAGGAAGTA
TTAATGATTATCCTGCTCGCCAAAACATATTCTCTCAACTTACATTTTCCCAAACTTTCCCTAATGAGAGAGTAAAT
CTAACTGTTGGTCAATACTCTCTTTACTCGATAGACGGAACGCTGTACAACAATGATCAGCAGCTAGGATTTATTAG
TTATGCGTTGTCGCAAAATCCAACAGCGACTTATTCCTCTGGAAGCCTTGGCGCCTATCTACAAGTCGCTCCAACAG
AAAGCACCTGTCTTCAAGTTGGGTTCCAAGATGCCTATAATATTTCAGGTTCCTCGATCAAATGGAATAATCTTACA
AAAAATAAGTATAACTTCCATGGCTATGCATCTTGGGCTCCACACTGTTGCTTAGGACCTGGACAATACTCTGTTCT
TCTTTATGTAACCAGAAAGGTTCCTGAGCAAATGATGCAGACAATGGGCTGGTCTGTGAATGCAAGTCAATACATCT
CTTCTAAACTTTATGTATTTGGAAGATACAGCGGAGTCACAGGCCAATTGTCTCCTATTAACCGAACCTATTCATTT
GGCTTAGTCTCTCCTAATTTATTGAACCGTAACCCACAAGACTTATTTGGAGTAGCTTGCGCATTCAATAATATACA
CGCCTCCGCCTTTCAAAATGCTCAAAGAAAATATGAAACTGTGATCGAGGGATTTGCAACTATTGGTTGCGGACCTT -continued

SEQUENCE LISTING

ACATCTCCTTTGCTCCAGATTTCCAACTTTACCTCTATCCTGCTCTGCGTCCAAATAAACAAAGCGCCCGAGTCTAT
AGCGTTCGCGCAAACCTAGCTATT

SEQ ID NO: 96: CM homologue of CT372 = TC_0651 fragment protein sequence
NGKVLCEVSVSFRSILLTALLSLSFTNTMQAAHHHYHRYDDKLRRQYHKKDLPTQENVRKEFCNPYSHSSDPIPLSQ
QRGVLSPICDLVSECSFLNGISVRSLKQTLKNSAGTQVALDWSILPQWFNPRSSWAPKLSIRDLGYGKPQSLIEADS
PCCQTCFNPSAAITIYDSSCGKGVVQVSYTLVRYWRETAALAGQTMMLAGSINDYPARQNIFSQLTFSQTFPNERVN
LTVGQYSLYSIDGTLYNNDQQLGFISYALSQNPTATYSSGSLGAYLQVAPTESTCLQVGFQDAYNISGSSIKWNNLT
KNKYNFHGYASWAPHCCLGPGQYSVLLYVTRKVPEQMMQTMGWSVNASQYISSKLYVFGRYSGVTGQLSPINRTYSF
GLVSPNLLNRNPQDLFGVACAFNNIHASAFQNAQRKYETVIEGFATIGCGPYISFAPDFQLYLYPALRPNKQSARVY
SVRANLAI SEQ ID NO: 97: CM homologue of CT443 = TC_0727 fragment nucleotide sequence
AGCGGGGTGTTAGAGACCTCTATGGCAGAGTCTCTCTCTACCAACGTTATTAGCTTAGCTGACACCAAAGCGAAAGA
GACCACTTCTCATCAAAAGACAGAAAAGCAAGAAAAAATCATCAAAATAGGACTTCCGTAGTCCGTAAAGAGGTTA
CTGCAGTTCGTGATACTAAAGCTGTAGAGCCTAGACAGGATTCTTGCTTTGGCAAAATGTATACAGTCAAAGTTAAT
GATGATCGTAATGTAGAAATCGTGCAGTCCGTTCCTGAATATGCTACGGTAGGATCTCCATATCCTATTGAGATTAC
TGCTATAGGGAAAAGAGACTGTGTTGATGTAATCATTACACAGCAATTACCATGCGAAGCAGAGTTTGTTAGCAGTG
ATCCAGCTACTACTCCTACTGCTGATGGTAAGCTAGTTTGGAAAATTGATCGGTTAGGACAGGGCGAAAAGAGTAAA
ATTACTGTATGGGTAAAACCTCTTAAAGAAGGTTGCTGCTTTACAGCTGCAACGGTTTGTGCTTGTCCAGAGATCCG
TTCGGTTACGAAATGTGGCCAGCCTGCTATCTGTGTTAAACAGGAAGGTCCAGAAAGCGCATGTTTGCGTTGCCCAG
TAACTTATAGAATTAATGTAGTCAACCAAGGAACAGCAACAGCACGTAATGTTGTTGTGGAAAATCCTGTTCCAGAT
GGCTATGCTCATGCATCCGGACAGCGTGTATTGACATATACTCTTGGGGATATGCAACCTGGAGAACAGAGAACAAT
CACCGTGGAGTTTTGTCCGCTTAAACGTGGTCGAGTCACAAATATTGCTACAGTTTCTTACTGTGGTGGACACAAAA
ATACTGCTAGCGTAACAACAGTGATCAATGAGCCTTGCGTGCAAGTTAACATCGAGGGAGCAGATTGGTCTTATGTT
TGTAAGCCTGTAGAATATGTTATCTCTGTTTCTAACCCTGGTGACTTAGTTTTACGAGACGTTGTAATTGAAGATAC
GCTTTCTCCTGGAATAACTGTTGTTGAAGCAGCTGGAGCTCAGATTTCTTGTAATAAATTGGTTTGGACTTTGAAGG
AACTCAATCCTGGAGAGTCTTTACAATATAAGGTTCTAGTAAGAGCTCAAACTCCAGGGCAATTCACAAACAACGTT
GTTGTGAAAAGTTGCTCTGATTGCGGTATTTGTACTTCTTGCGCAGAAGCAACAACTTACTGGAAAGGAGTTGCTGC
TACTCATATGTGCGTAGTAGATACTTGTGATCCTATTTGCGTAGGAGAGAACACTGTTTATCGTATCTGTGTGACAA
ACAGAGGTTCTGCTGAAGATACAAATGTGTCCTTAATTTTGAAATTCTCTAAAGAATTACAACCTATATCTTTCTCT
GGACCAACTAAAGGAACCATTACAGGAAACACGGTAGTGTTTGATTCGTTACCTAGATTAGGTTCTAAAGAAACTGT
AGAGTTTTCTGTAACGTTGAAAGCAGTATCCGCTGGAGATGCTCGTGGGGAAGCTATTCTTTCTTCCGATACATTGA
CAGTTCCTGTATCTGATACGGAGAATACACATATCTAT SEQ ID NO: 98: CM homologue of CT443 = TC_0727 fragment protein sequence
SGVLETSMAESLSTNVISLADTKAKETTSHQKDRKARKNHQNRTSVVRKEVTAVRDTKAVEPRQDSCFGKMYTVKVN
DDRNVEIVQSVPEYATVGSPYPIEITAIGKRDCVDVIITQQLPCEAEFVSSDPATTPTADGKLVWKIDRLGQGEKSK
ITVWVKPLKEGCCFTAATVCACPEIRSVTKCGQPAICVKQEGPESACLRCPVTYRINVVNQGTATARNVVVENPVPD
GYAHASGQRVLTYTLGDMQPGEQRTITVEFCPLKRGRVTNIATVSYCGGHKNTASVTTVINEPCVQVNIEGADWSYV
CKPVEYVISVSNPGDLVLRDVVIEDTLSPGITVVEAAGAQISCNKLVWTLKELNPGESLQYKVLVRAQTPGQFTNNV
VVKSCSDCGICTSCAEATTYWKGVAATHMCVVDTCDPICVGENTVYRICVTNRGSAEDTNVSLILKFSKELQPISFS
GPTKGTITGNTVVFDSLPRLGSKETVEFSVTLKAVSAGDARGEAILSSDTLTVPVSDTENTHIY SEQ ID NO: 99: CM homologue of CT043 = TC_0313 fragment nucleotide sequence
TCCAGACAGAATGCTGAGGAAAATCTAAAAAATTTTGCTAAAGAGCTCAAGCTCCCCGACGTGGCCTTCGATCAGAA
TAATACGTGCATTTTGTTTGTTGATGGAGAGTTTTCTCTTCACCTGACCTACGAAGAGCACTCTGATCGCCTTTATG
TTTACGCACCTCTCCTTGACGGACTCCCAGATAATCCGCAAAGAAAGTTGGCTCTGTATGAGAAATTGTTGGAAGGC
TCTATGCTCGGAGGCCAAATGGCTGGTGGAGGAGTAGGAGTTGCTACTAAAGAACAGTTGATCCTAATGCATTGCGT
GTTAGATATGAAATATGCAGAGACTAATCTATTGAAAGCTTTTGCACAGCTTTTCATTGAAACTGTTGTGAAATGGC
GAACGGTCTGTTCTGATATCAGCGCTGGACGAGAACCTTCCGTTGACACTATGCCTCAAATGCCTCAAGGAGGCAGC
GGAGGAATTCAACCTCCTCCAACAGGAATTCGTGCG SEQ ID NO: 100: CM homologue of CT043 = TC_0313 fragment protein sequence
SRQNAEENLKNFAKELKLPDVAFDQNNTCILFVDGEFSLHLTYEEHSDRLYVYAPLLDGLPDNPQRKLALYEKLLEG
SMLGGQMAGGGVGVATKEQLILMHCVLDMKYAETNLLKAFAQLFIETVVKWRTVCSDISAGREPSVDTMPQMPQGGS
GGIQPPPTGIRA SEQ ID NO: 101: CM homologue of CT601 = TC_0890 fragment nucleotide sequence
CTCGCTAATCGGTTATTTCTAATCACCCTTATAGGTTTTGGCTATTCTGCTTACGGTGCCAGCACAGGGAAATCACC
TTCTTTACAGGTTATTTTAGCTGAAGTCGAGGATACATCTTCGCGCTTACAAGCTCATCAGAATGAGCTTGTTATGC
TCTCGGAACGTTTAGATGAGCAAGACACAAAACTTCAACAACTCTCGTCAACTCAGGCCCGTAATCTTCCTCAACAA
GTTCAACGGCTTGAGATTGATCTGAGAGCTCTGGCTAAAACAGCTGCTGTGCTCTCGCAATCTGTTCAGGATATCCG
ATCATCCGTGCAAAATAAATTACAAGAAATCCAACAAGAACAAAAAAATTTAGCTCAAAATTTACGAGCGCTTCGCA
ACTCCTTACAAGCACTAGTTGATGGCTCTTCCCCAGAAAATTATATTGATTTTTTGGCCGGGGAGACACCTGAACAT
ATTCACGTTGTTAAACAAGGAGAAACCCTGAGTAAAATCGCTAGTAAGTACAATATCCCTGTCGCAGAATTGAAAAA
ACTTAATAAATTAAATTCCGATACTATTTTTACTGATCAAAGAATCCGACTTCCAAAAAAGAAA SEQ ID NO: 102: CM homologue of CT601 = TC_0890 fragment protein sequence
LANRLFLITLIGFGYSAYGASTGKSPSLQVILAEVEDTSSRLQAHQNELVMLSERLDEQDTKLQQLSSTQARNLPQQ
VQRLEIDLRALAKTAAVLSQSVQDIRSSVQNKLQEIQQEQKNLAQNLRALRNSLQALVDGSSPENYIDFLAGETPEH
IHVVKQGETLSKIASKYNIPVAELKKLNKLNSDTIFTDQRIRLPKKK SEQ ID NO: 103: CM homologue of CT456 = TC_0741 fragment nucleotide sequence
ACGACTCCAATAAGTAATTCTCCATCTTCTATTCCAACTGTTACAGTATCAACTACTACAGCATCTTCTGGATCTCT
CGGAACTTCTACTGTATCATCAACGACTACAAGTACTTCAGTCGCACAAACAGCAACAACAACATCTTCTGCTTCTA
CATCTATAATTCAGTCTAGTGGAGAAAACATCCAATCCACTACAGGTACCCCTTCTCCTATTACGTCTAGTGTTTCA -continued

SEQUENCE LISTING

ACATCCGCTCCATCTCCTAAAGCCTCCGCCACTGCAAACAAAACTTCAAGCGCTGTTTCTGGGAAAATTACCTCACA
AGAAACTTCTGAGGAATCCGAAACCCAAGCCACTACATCTGATGGAGAAGTTAGTAGTAATTACGATGATGTTGATA
CCCCGACCAATTCGTCCGATTCGACAGTTGATAGTGATTACCAAGATGTTGAGACTCAGTACAAAACAATTAGCAAC
AATGGTGAAAACACTTATGAAACAATCGGAAGTCATGGTGAGAAAAACACACACGTCCAGGAAAGCCATGCATCCGG
AACAGGAAATCCCATAAATAATCAGCAAGAAGCTATTAGACAGCTCCGATCATCTACCTATACAACCAGCCCTCGTA
ATGAGAATATATTTAGTCCAGGACCGGAAGGTCTACCTAATATGTCTCTTCCTAGTTACAGCCCTACAGATAAAAGT
TCTCTACTAGCTTTCCTATCTAATCCCAATACAAAAGCAAAAATGCTCGAACACTCCGGGCATTTAGTCTTTATAGA
CACAACTAGAAGTAGCTTTATCTTTGTTCCGAATGGAAATTGGGATCAAGTCTGTTCCATGAAGGTTCAGAATGGGA
AAACTAAAGAAGACCTTGGCTTAAAGGACTTAGAAGATATGTGTGCAAAGTTTTGCACAGGATACAATAAATTCTCC
TCTGATTGGGGAAATCGAGTTGACCCCTTGGTCTCTTCTAAGGCCGGGATAGAAAGTGGGGGGCACCTCCCAAGCTC
AGTTATCATCAACAACAAATTTAGAACCTGTGTTGCCTATGGGCCGTGGAACCCCAAAGAAAACGGCCCCAATTATA
CTCCTTCAGCCTGGAGACGTGGGCATCGAGTAGATTTTGGAAAGATCTTTGATGGAACAGCGCCGTTTAATAAAATC
AACTGGGGCTCTTCCCCTACCCCTGGTGATGACGGCATCTCCTTCTCTAATGAAACTATTGGGTCTGAACCATTCGC
GACACCTCCCTCATCCCCATCGCAAACCCCCGTTATCAACGTCAATGTTAATGTCGGTGGAACCAATGTTAATATTG
GGGATACAAACGTATCTAAAGGATCCGGCACACCAACATCTTCTCAATCTGTGGACATGTCTACAGATACTAGCGAT
TTAGATACCAGTGATATTGATACAAACAACCAAACTAACGGCGATATCAACACGAATGACAACTCCAATAATGTCGA
TGGAAGTTTATCTGACGTTGATTCAAGGGTGGAAGACGATGACGGTGTATCGGATACAGAGTCCACTAATGGCAATG
ACTCTGGTAAAACTACTTCCACAGAAGAAAATGGTGACCCAAGCGGACCAGACATCCTGGCTGCTGTACGTAAACAC
CTAGACACTGTCTATCCAGGAGAAAATGGCGGATCTACAGAAGGACCTCTCCCTGCTAATCAAAATCTGGGGAACGT
TATCCATGATGTGGAGCAGAATGGATCTGCTAAAGAAACTATTATCACTCCAGGAGATACAGGGCCTACAGACTCAA
GCTCCTCTGTAGATGCTGATGCAGACGTTGAAGATACTTCTGATACTGACTCTGGAATCGGAGACGACGACGGTGTA
TCGGATACAGAGTCCACTAATGGTAATAACTCTGGTAAAACTACTTCCACAGAAGAAAATGGTGACCCAAGCGGACC
AGACATCCTGGCTGCTGTACGTAAACACCTAGACACTGTCTATCCAGGAGAAAATGGCGGATCTACAGAAGGACCTC
TCCCTGCTAATCAAAATCTGGGGAACGTTATCCATGATGTAGAACAAAACGGAGCCGCTCAAGAAACTATTATCACT
CCAGGAGATACGGAATCTACAGACACAAGCTCTAGTGTAAATGCTAATGCAGACTTAGAAGATGTTTCTGATGCTGA
TTCAGGATTCGGGGATGATGACGGTATATCGGATACAGAGTCCACTAATGGTAACGACTCTGGAAAAAATACTCCTG
TAGGGGATGGTGGTACACCAAGCGGACCAGATATCCTAGCTGCTGTACGCAAACATCTAGACACTGTCTATCCAGGA
GAAAATGGTGGATCTACAGAGAGACCTTTACCCGCTAATCAAAATTTAGGAGATATCATTCATGATGTAGAACAAAA
CGGAAGCGCTAAAGAAACTGTAGTATCGCCTTATCGAGGAGGAGGAGGAAATACATCTTCCCCAATTGGATTAGCCT
CCCTGCTTCCAGCAACACCATCCACACCTTTGATGACAACACCTAGAACAAATGGGAAAGCTGCAGCTTCTTCTTTG
ATGATAAAAGGAGGAGAAACTCAAGCCAAGCTAGTTAAGAATGGCGGCAATATCCCTGGAGAAACCACATTAGCAGA
ATTACTCCCTCGTTTAAGAGGACACCTTGACAAAGTCTTTACTTCAGACGGGAAGTTTACAAATCTTAATGGACCTC
AACTTGGAGCCATCATAGACCAATTCCGCAAAGAAACGGGTTCCGGAGGAATCATAGCTCATACAGATAGTGTTCCA
GGAGAGAACGGAACAGCCTCTCCTCTCACAGGAAGTTCAGGGGAAAAAGTCTCTCTCTATGATGCAGCGAAAAACGT
CACTCAAGCTTTAACAAGTGTTACGAACAAAGTAACCCTAGCAATGCAAGGACAAAAACTGGAAGGAATTATAAACA
ACAACAATACCCCCTCTTCTATTGGACAAAATCTTTTCGCAGCAGCGAGGGCAACGACACAATCCCTCAGTTCATTA
ATTGGAACCGTACAA

SEQ ID NO: 104: CM homologue of CT456 = TC_0741 fragment protein sequence
TTPISNSPSSIPTVTVSTTTASSGSLGTSTVSSTTTSTSVAQTATTSSASTSIIQSSGENIQSTTGTPSPITSSVS
TSAPSPKASATANKTSSAVSGKITSQETSEESETQATTSDGEVSSNYDDVDTPTNSSDSTVDSDYQDVETQYKTISN
NGENTYETIGSHGEKNTHVQESHASGTGNPINNQQEAIRQLRSSTYTTSPRNENIFSPGPEGLPNMSLPSYSPTDKS
SLLAFLSNPNTKAKMLEHSGHLVFIDTTRSSFIFVPNGNWDQVCSMKVQNGKTKEDLGLKDLEDMCAKFCTGYNKFS
SDWGNRVDPLVSSKAGIESGGHLPSSVIINNKFRTCVAYGPWNPKENGPNYTPSAWRRGHRVDFGKIFDGTAPFNKI
NWGSSPTPGDDGISFSNETIGSEPFATPPSSPSQTPVINVNVNVGGTNVNIGDTNVSKGSGTPTSSQSVDMSTDTSD
LDTSDIDTNNQTNGDINTNDNSNNVDGSLSDVDSRVEDDDGVSDTESTNGNDSGKTTSTEENGDPSGPDILAAVRKH
LDTVYPGENGGSTEGPLPANQNLGNVIHDVEQNGSAKETIITPGDTGPTDSSSSVDADADVEDTSDTDSGIGDDDGV
SDTESTNGNNSGKTTSTEENGDPSGPDILAAVRKHLDTVYPGENGGSTEGPLPANQNLGNVIHDVEQNGAAQETIIT
PGDTESTDTSSSVNANADLEDVSDADSGFGDDDGISDTESTNGNDSGKNTPVGDGGTPSGPDILAAVRKHLDTVYPG
ENGGSTERPLPANQNLGDIIHDVEQNGSAKETVVSPYRGGGGNTSSPIGLASLLPATPSTPLMTTPRTNGKAAASSL
MIKGGETQAKLVKNGGNIPGETTLAELLPRLRGHLDKVFTSDGKFTNLNGPQLGAIIDQFRKETGSGGIIAHTDSVP
GENGTASPLIGSSGEKVSLYDAAKNVTQALTSVTNKVTLAMQGQKLEGIINNNNTPSSIGQNLFAAARATTQSLSSL
IGTVQ SEQ ID NO: 105: CM homologue of CT381 = TC_0660 fragment nucleotide sequence
TGTTCAAAAGAGAGCAAAGACTCTGTTAGTGAAAAATTTATTGTAGGAACTAACGCAACGTATCCTCCTTTTGAGTT
TGTTGATGAAAGAGGTGAGACGGTTGGCTTTGATATTGATTTAGCTAGGGAGATTAGTAAAAAGCTAGGGAAAAAAT
TAGAAGTCCGAGAATTTGCTTTTGATGCACTCGTTCTCAATTTAAAACAGCATCGTATTGATGCAATTATGGCAGGG
GTGTCCATTACGTCTTCTCGATTGAAAGAAATTTTGATGATTCCCTACTATGGCGAAGAAATAAAGAGTTTGGTTTT
AGTGTTTAAGGATGGAGACTCAAAGTCTTTACCACTAGATCAGTATAATTCTGTTGCTGTTCAAACTGGCACGTACC
AAGAGGAATATTTACAGTCTCTTCCAGGGGTGCGTATTCGCTCTTTTGATAGTACTTTAGAAGTGCTTATGGAAGTT
TTGCATAGCAAGTCTCCTATAGCTGTTTTAGAACCGTCTATTGCGCAGGTCGTTTTAAAAGATTTTCCGACGCTCAC
TACTGAAACGATAGATCTTCCTGAAGATAAATGGGTTTTAGGGTATGGAATTGGAGTTGCTTCTGATCGACCATCTC
TAGCTTCTGATATAGAAGCTGCTGTACAAGAGATCAAGAAAGAAGGAGTGTTAGCAGAGTTAGAGCAAAAATGGGGT
TTGAACGGC SEQ ID NO: 106: CM homologue of CT381 = TC_0660 fragment protein sequence
CSKESKDSVSEKFIVGTNATYPPFEFVDERGETVGFDIDLAREISKKLGKKLEVREFAFDALVLNLKQHRIDAIMAG
VSITSSRLKEILMIPYYGEEIKSLVLVFKDGDSKSLPLDQYNSVAVQTGTYQEEYLQSLPGVRIRSFDSTLEVLMEV
LHSKSPIAVLEPSIAQVVLKDFPTLTTETIDLPEDKWVLGYGIGVASDRPSLASDIEAAVQEIKKEGVLAELEQKWG
LNG SEQ ID NO: 107 - CT255 fragment nucleotide sequence
GAAGAAAAAGGCATCTTACAATTGGTTGAAATTTCGCGAGCAATGGCTTTACAGGGAGTTTGTCCTTGGACTAATTT
ACAGAGTGTGGAGTCTATGTTGCAGTATATAGCAGGGGAGTGTCAGGAGTTGGCTGATGCTGTACAAGAAAATAAAG
CTTCGTTGGAAATCGCTTCGGAAGCCGGAGACGTACTTACTTTAGTATTGACCTTGTGTTTCTTGCTAGAAAGAGAA
GGAAAGCTTAAAGCTGAAGAAGTATTTGTAGAAGCTTTGGCTAAGTTGCGTCGTCGATCTCCTCATGTTTTTGATCC -continued

SEQUENCE LISTING

TCATAATCAAATTTCTTTAGAACAGGCTGAAGAATACTGGGCTCGTATGAAACAGCAAGAAAAAATTTCT

SEQ ID NO: 108 - CT255 fragment protein sequence
EEKGILQLVEISRAMALQGVCPWTNLQSVESMLQYIAGECQELADAVQENKASLEIASEAGDVLTLVLTLCFLLERE
GKLKAEEVFVEALAKLRRRSPHVFDPHNQISLEQAEEYWARMKQQEKIS SEQ ID NO: 109 - CT341 fragment nucleotide sequence
GATTACTACACGATATTGGGTGTAGCGAAGACTGCTACTCCTGAAGAAATAAAGAAAGCTTACCGTAAGCTCGCTGT
AAAGTACCATCCAGATAAGAATCCTGGGGATGCTGAAGCGGAGCGACGCTTTAAAGAAGTTTCTGAAGCCTATGAAG
TATTAGGTGATGCGCAGAAGCGGGAGTCATATGATCGTTACGGCAAAGACGGTCCATTTGCTGGTGCTGGAGGATTC
GGTGGCGCTGGCATGGGGAATATGGAAGACGCTTTGCGAACATTTATGGGAGCTTTTGGCGGCGATTTCGGTGGTAA
TGGAGGCGGTTTCTTTGAAGGGCTTTTTGGAGGACTTGGAGAAGCTTTCGGAATGCGTGGAGGCTCAGAAAGTTCTC
GACAAGGAGCTAGTAAGAAGGTGCATATTACGCTGTCCTTCGAGGAGGCGGCAAAAGGTGTTGAAAAAGAACTTCTT
GTTTCAGGCTATAAATCTTGTGATGCTTGTTCTGGTAGTGGAGCCAATACTGCTAAAGGTGTAAAAGTTTGTGATCG
ATGCAAGGGCTCTGGTCAGGTAGTGCAAAGCCGAGGCTTTTTCTCCATGGCTTCTACTTGCCCTGATTGTAGTGGTG
AAGGTCGGGTTATCACAGATCCTTGTTCAGTTTGTCGTGGGCAGGGACGTATCAAGGATAAACGTAGCGTCCATGTT
AATATCCCAGCTGGAGTCGATTCTGGGATGAGATTAAAGATGGAAGGCTATGGAGATGCTGGCCAAAATGGAGCGCC
TGCAGGGGATCTGTATGTTTTTATTGATGTAGAGCCTCATCCTGTTTTCGAGCGCCATGGGGATGATTTAGTTTTAG
AGCTTCCTATTGGATTTGTTGATGCGGCTTTAGGGATCAAGAAGGAAATCCCTACACTCTTAAAAGAAGGTACTTGC
CGTTTGAGTATCCCAGAAGGGATTCAGAGCGGAACAGTTCTTAAAGTTAGAGGGCAGGGATTCCCTAATGTGCATGG
GAAATCCAGAGGAGATCTTTTAGTAAGAGTATCTGTGGAGACTCCCCAGCACCTATCTAATGAACAAAAAGATTTAT
TGAGACAGTTTGCTGCTACGGAGAAGGCTGAAAATTTCCCTAAGAAACGGAGTTTCTTAGACAAAATCAAAGGTTTT
TTTTCTGACTTTGCTGTA SEQ ID NO: 110 - CT341 fragment protein sequence
DYYTILGVAKTATPEEIKKAYRKLAVKYHPDKNPGDAEAERRFKEVSEAYEVLGDAQKRESYDRYGKDGPFAGAGGF
GGAGMGNMEDALRTFMGAFGGDFGGNGGGFFEGLFGGLGEAFGMRGGSESSRQGASKKVHITLSFEEAAKGVEKELL
VSGYKSCDACSGSGANTAKGVKVCDRCKGSGQVVQSRGFFSMASTCPDCSGEGRVITDPCSVCRGQGRIKDKRSVHV
NIPAGVDSGMRLKMEGYGDAGQNGAPAGDLYVFIDVEPHPVFERHGDDLVLELPIGFVDAALGIKKEIPTLLKEGTC
RLSIPEGIQSGTVLKVRGQGFPNVHGKSRGDLLVRVSVETPQHLSNEQKDLLRQFAATEKAENFPKKRSFLDKIKGF
FSDFAV SEQ ID NO: 111 - CT716 fragment nucleotide sequence
AATAAAAAACTCCAAGATCTGTCTAAACTGCTCACTATTGAGCTTTTCAAGAAACGTACACGGTTGGAAACAGTAAA
AAAAGCGCTCTCCACAATAGAACATCGCTTACAACAAATACAGGAGCACATCGCGAAAATTTCCTTAACAAGGCACA
AACAATTCCTATGTCGGTCATATACCCATGAATATGACCAACATTTAGAACATTTACAAAGAGAGCAAACTTCTCTA
TATAAACAGCATCAGACCCTGAAAACGTCTTTGAAAGATGCTTATGGCGACATACAAAAACAACTAGACCAAAGAAA
AATTATCGAAAAGATCCATGACAGTAAATATCCTATAAAGAGCGCGAATAAC
SEQ ID NO: 112 - CT716 fragment protein sequence
NKKLQDLSKLLTIELFKKRTRLETVKKALSTIEHRLQQIQEHIAKISLTRHKQFLCRSYTHEYDQHLEHLQREQTSL
YKQHQTLKTSLKDAYGDIQKQLDQRKIIEKIHDSKYPIKSANN
SEQ ID NO: 113 - CT745 fragment nucleotide sequence
GCGTGGTGGCTACACAAACGATTCCCTCATGTGCAGCTGTCTATTCTAGAAAAAGAGTCTCGATCTGGAGGGCTAAT
TGTCACAGAGAAACAACAAGGGTTTTCCCTCAATATGGGCCCTAAAGGTTTTGTTTTAGCTCATGATGGGCAACACA
CCCTTCACCTCATTCAGTCTTTAGGCCTAGCAGACGAGCTATTATATAGCTCTCCAGAGGCTAAAAACCGCTTTATC
CACTATAATAATAAAACCCGAAAAGTCTCGCCTTGGACTATTTTCAAACAAAATCTCCCTCTCTCTTTTGCTAAGGA
TTTCTTTGCGCGTCCTTACAAACAAGACAGCTCCGTGGAAGCCTTCTTTAAAAGACACAGTTCTTCCAAGCTTAGAA
GAAATCTTTTAAATCCCATTAGCATTGCTATTCGTGCAGGACATAGTCATATATTGTCTGCACAGATGGCTTACCCA
GAATTAACACGAAGAGAAGCTCAAACAGGATCGTTGTTACGTAGTTATCTCAAAGATTTTCCTAAAGAGAAACGCAC
AGGCCCTTATTTAGCTACCTTGCGGTCTGGGATGGGAATGCTAACCCAGGCTTTGCATGATAAATTGCCTGCTACCT
GGTATTTTTCTGCACCCGTCAGCAAAATCCGTCAGTTGGCGAATGGGAAAATTTCTCTTTCATCTCCTCAAGGAGAA
ATAACGGGAGATATGCTCATTTATGCTGGGTCCGTGCACGATCTCCCTTCCTGTCTAGAAGGGATCCCTGAAACCAA
GCTTATCAAGCAAACGACTTCATCTTGGGATCTCTCTTGTGTATCTTTAGGATGGCATGCATCCTTCCCTATCCCTC
ATGGATATGGCATGCTTTTCGCTGATACGCCTCCCTTATTAGGGATCGTGTTTAATACGGAAGTGTTCCCTCAACCC
GAGCGGCCTAATACAATAGTCTCTCTTCTTTTAGAAGGTCGATGGCACCAAGAAGAAGCGTATGCTTTCTCACTAGC
AGCTATTTCTGAGTACCTGCAAATTTACACTCCTCCCCAAGCTTTCTCACTATTCTCTCCTCGAGAGGGACTTCCCC
AACACCATGTTGGATTTATCCAATCCCGCCAACGCCTTCTATCTAAACTTCCTCACAATATAAAAATTGTAGGGCAG
AATTTTGCAGGTCCAGGTCTCAACCGCGCTACAGCGTCTGCTTATAAAGCTATAGCTTCTTTACTATCA SEQ ID NO: 114 - CT745 fragment protein sequence
AWWLHKRFPHVQLSILEKESRSGGLIVTEKQQGFSLNMGPKGFVLAHDGQHTLHLIQSLGLADELLYSSPEAKNRFI
HYNNKTRKVSPWTIFKQNLPLSFAKDFFARPYKQDSSVEAFFKRHSSSKLRRNLLNPISIAIRAGHSHILSAQMAYP
ELTRREAQTGSLLRSYLKDFPKEKRTGPYLATLRSGMGMLTQALHDKLPATWYFSAPVSKIRQLANGKISLSSPQGE
ITGDMLIYAGSVHDLPSCLEGIPETKLIKQTTSSWDLSCVSLGWHASFPIPHGYGMLFADTPPLLGIVFNTEVFPQP
ERPNTIVSLLLEGRWHQEEAYAFSLAAISEYLQIYTPPQAFSLFSPREGLPQHHVGFIQSRQRLLSKLPHNIKIVGQ
NFAGPGLNRATASAYKAIASLLS SEQ ID NO: 115 - CT387 fragment nucleotide sequence
ACGCTCTTTCATTCTCATCATGATGCCGTCTCTCCAGACAGCTACCTATGTTCTTCCCTTCAGTTAGTTGGTACTGG
CGTATACGAAGGAGAAATCGAGATTCAAAATATCCCCTCTTATTTCCTTGGATTCCAATTACCCTCTCATTGCATAC
ACCTTAATTTAAAGAGCTCTCTAGCTCAATTAGGAATAGATGCCTCCCTTCTTCACTGCGAATTGAGCAAAAATCAA
CATCGAGCACATATACATGCTCAATTTACCGGTCATGGCCCCATTGCTGAATCTATGCTAGCCCTTCTCCAACCAGG
AGATCGTGTAGCAAAACTATTTGCTGCAGACGATCGCAGACTGGTCCGATCTCCAGATTACCTCGAAAGCATGCTGA
AAAATACAGATAAAGCTGGCCATCCTTTGCTCTGTTTTGGGAAAAAAATTAGAACACTTGATTTCTTTTGATGTGGTA
GATGATCGCCTTGTCGTCTCCCTTCCTACCCTGCCGGGAGTTGTTCGTTATGATTCGGATATTTATGGACTCCTTCC
TCTTATTCAAAAATCACTCAGTAATCCCAAACTCAGCATTCGTCACTTTTTAGCTCTGTACCAACAGATTGTGGAAG
GGCAACATGTCTCTTGCGGAAACCATATTCTTCTGATCAAAACAGAACCGCTGCACATCCGCACTGTATTTGCTCGC -continued

SEQUENCE LISTING

GTGGTAAATCAACTCCTCCCTCAAGGTCTCTCCCACACTTCTGCCAATATTTGGAACCAACCACTCGAGAATCCGG
GGATATCTTTGAATTTTTTGGGAACCCTTCTGCACAGATAGAAAGAATTCCTTTAGAATTTTTCACTATCGAACCCT
ATAAAGAACATTCTTACTTCTGTAATCGGGATTTATTACAAACCATCTTACAATCAGAAAGCGAAATCAAAAAAATA
TTCGAAACAGCGCCCAAAGAACCTGTCAAAGCTGCCACCTATTTATCAAAAGGCAGTGAAATCTCTTCCCTGCACAC
AGACTCTTGGCTCACAGGATCCGCAGCTGCCTATCAATATAGTGAGCAAGCAGATAAAAACGAGTACACTCATGCTC
AACCTTGCTATCCTTTCTTAGAAGCAATGGAAATGGGCCTGATCAATAGCGAAGGAGCCTTACTCACTCGTTATTTC
CCTTCAGCTAGCTTAAAAGGAATGTTGATTTCCTACCATGTGCGCCACTATCTCAAACAAATCTACTTTCAAGTTCC
CTCTTATACACATGGAAACTATTTCTCTCATAATGACAGAGGTTTGCTATTAGATCTGCAGCAAGCAGATATTGATG
TTTTCTGGGCAGATGAAGAAAGCGGCCGTGTGTTGCAATATACAAAACGACGCGATAAGAATAGCGGTATGTTCGTG
ATCAAAAATCGTGTTGAAGAGTTTCGATCAGCTTATTTTATTGCTATTTATGGCTCTCGTCTCCTTGAGAATAATTT
CTCTGCTCAGCTCCATACCCTCCTAGCGGGCTTACAGCAAGCAGCACATACTCTCGGCATTCCTGGATTCTCAAAGC
CTACCCCACTTGCAGTCATCACCGGAGGCGGCACTGGAGTTATGGCCACAGGAAATCGTGTAGCTAAAGAACTAGGA
ATCCTATCTTGTGGAACCGTTCTTGATTTAGAAGCTTCTCCAGCACAAATCGACCAACCTACCAATGAATTCTTAGA
TGCTAAAATGACATACCGCCTACCTCAACTTATAGAAAGGCAAGAACACTTTTATGCAGACCTTCCTATCCTTGTAG
TTGGCGGTGTAGGAACCGATTTCGAACTCTACCTAGAACTTGTCTATCTCAAAACAGGAGCTAAACCACCGACTCCC
ATTTTCCTAATTGGACCTATTGAATACTGGAAAGAAAAAGTGGCCCACGCCTACGAGATCAACCTCAAAGCAGGAAC
CATCCGTGGATCCGAATGGATCAGCAACTGCCTATATTGTATCACTTCTCCGGAAGCTGGAATTGCCGTATTCGAAC
AATTCCTAGCTGGAGAACTCCCTATAGGATACGACTATCCTCCAGCTCCAGATGGATTAGTGATCGTC

SEQ ID NO: 116 - CT387 fragment protein sequence
TLFHSHHDAVSPDSYLCSSLQLVGTGVYEGEIEIQNIPSYFLGFQLPSHCIHLNLKSSLAQLGIDASLLHCELSKNQ
HRAHIHAQFTGHGPIAESMLALLQPGDRVAKLFAADDRRLVRSPDYLESMLKNTDKAGHPLLCFGKKLEHLISFDVV
DDRLVVSLPTLPGVVRYDSDIYGLLPLIQKSLSNPKLSIRHFLALYQQIVEGQHVSCGNHILLIKTEPLHIRTVFAR
VVNQLLPQGLSHTSANILEPTTRESGDIFEFFGNPSAQIERIPLEFFTIEPYKEHSYFCNRDLLQTILQSESEIKKI
FETAPKEPVKAATYLSKGSEISSLHTDSWLTGSAAAYQYSEQADKNEYTHAQPCYPFLEAMEMGLINSEGALLTRYF
PSASLKGMLISYHVRHYLKQIYFQVPSYTHGNYFSHNDIRGLLLDLQQADIDVFWADEESGRVLQYTKRRDKNSGMFV
IKNRVEEFRSAYFIAIYGSRLLENNFSAQLHTLLAGLQQAAHTLGIPGFSKPTPLAVITGGGTGVMATGNRVAKELG
ILSCGTVLDLEASPAQIDQPTNEFLDAKMTYRLPQLIERQEHFYADLPILVVGGVGTDFELYLELVYLKTGAKPPTP
IFLIGPIEYWKEKVAHAYEINLKAGTIRGSEWISNCLYCITSPEAGIAVFEQFLAGELPIGYDYPPAPDGLVIV SEQ ID NO: 117 - CT812 fragment nucleotide sequence
TGCGTAGATCTTCATGCTGGAGGACAGTCTGTAAATGAGCTGGTATATGTAGGCCCTCAAGCGGTTTTATTGTTAGA
CCAAATTCGAGATCTATTCGTTGGGTCTAAAGATAGTCAGGCTGAAGGACAGTATAGGTTAATTGTAGGAGATCCAA
GTTCTTTCCAAGAGAAAGATGCGGATACTCTTCCCGGGAAGGTAGAGCAAAGTACTTTGTTCTCAGTAACCAATCCC
GTGGTTTTCCAAGGTGTGGACCAACAGGATCAAGTCTCTTCCCAAGGGTTAATTTGTAGTTTTACGAGCAGCAACCT
TGATTCTCCTCGTGACGGAGAATCTTTTTTAGGTATTGCTTTTGTTGGGGATAGTAGTAAGGCTGGAATCACATTAA
CTGACGTGAAAGCTTCTTTGTCTGGAGCGGCTTTATATTCTACAGAAGATCTTATCTTTGAAAAGATTAAGGGTGGA
TTGGAATTTGCATCATGTTCTTCTCTAGAACAGGGGGGAGCTTGTGCAGCTCAAAGTATTTTGATTCATGATTGTCA
AGGATTGCAGGTTAAACACTGTACTACAGCCGTGAATGCTGAGGGGTCTAGTGCGAATGATCATCTTGGATTTGGAG
GAGGCGCTTTCTTTGTTACGGGTTCTCTTTCTGGAGAGAAAAGTCTCTATATGCCTGCAGGAGATATGGTAGTTGCG
AATTGTGATGGGGCTATATCTTTTGAAGGAAACAGCGCGAACTTTGCTAATGGAGGAGCGATTGCTGCCTCTGGGAA
AGTGCTTTTTGTCGCTAATGATAAAAAGACTTCTTTTATAGAGAACCGAGCTTTGTCTGGAGGAGCGATTGCAGCCT
CTTCTGATATTGCCTTTCAAAACTGCGCAGAACTAGTTTTCAAAGGCAATTGTGCAATTGGAACAGAGGATAAAGGT
TCTTTAGGTGGAGGGGCTATATCTTCTCTAGGCACCGTTCTTTTGCAAGGGAATCACGGGATAACTTGTGATAAGAA
TGAGTCTGCTTCGCAAGGAGGCGCCATTTTTGGCAAAAATTGTCAGATTTCTGACAACGAGGGGCCAGTGGTTTTCA
GAGATAGTACAGCTTGCTTAGGAGGAGGCGCTATTGCAGCTCAAGAAATTGTTTCTATTCAGAACAATCAGGCTGGG
ATTTCCTTCGAGGGAGGTAAGGCTAGTTTCGGAGGAGGTATTGCGTGTGGATCTTTTTCTTCCGCAGGTGGTGCTTC
TGTTTTAGGGACCATTGATATTTCGAAGAATTTAGGCGCGATTTCGTTCTCTCGTACTTTATGTACGACCTCAGATT
TAGGACAAATGGAGTACCAGGGAGGAGGAGCTCTATTTGGTGAAAATATTTCTCTTTCTGAGAATGCTGGTGTGCTC
ACCTTTAAAGACAACATTGTGAAGACTTTTGCTTCGAATGGGAAAATTCTGGGAGGAGGAGCGATTTTAGCTACTGG
TAAGGTGGAAATTACTAATAATTCCGAAGGAATTTCTTTTACAGGAAATGCGAGAGCTCCACAAGCTCTTCCAACTC
AAGAGGAGTTTCCTTTATTCAGCAAAAAAGAAGGGCGACCACTCTCTTCAGGATATTCTGGGGGAGGAGCGATTTTA
GGAAGAGAAGTAGCTATTCTCCACAACGCTGCAGTAGTATTTGAGCAAAATCGTTTGCAGTGCAGCGAAGAAGAAGC
GACATTATTAGGTTGTTGTGGAGGAGGCGCTGTTCATGGGATGGATAGCACTTCGATTGTTGGCAACTCTTCAGTAA
GATTTGGTAATAATTACGCAATGGGACAAGGAGTCTCAGGAGGAGCTCTTTTATCTAAAACAGTGCAGTTAGCTGGG
AATGGAAGCGTCGATTTTTCTCGAAATATTGCTAGTTTGGGAGGAGGAGCTCTTCAAGCTTCTGAAGGAAATTGTGA
GCTAGTTGATAACGGCTATGTGCTATTCAGAGATAATCGAGGGAGGGTTTATGGGGGTGCTATTTCTTGCTTACGTG
GAGATGTAGTCATTTCTGGAAACAAGGGTAGAGTTGAATTTAAAGACAACATAGCAACACGTCTTTATGTGGAAGAA
ACTGTAGAAAAGGTTGAAGAGGTAGAGCCAGCTCCTGAGCAAAAAGACAATAATGAGCTTTCTTTCTTAGGGAGAGC
AGAACAGAGTTTTATTACTGCAGCTAATCAAGCTCTTTTCGCATCTGAAGATGGGGATTTATCACCTGAGTCATCCA
TTTCTTCTGAAGAACTTGCGAAAAGAAGAGAGTGTGCTGGAGGAGCTATTTTTGCAAAACGGGTTCGTATTGTAGAT
AACCAAGAGGCCGTTGTATTCTCGAATAACTTCTCTGATATTTATGGCGGCGCCATTTTTACAGGTTCTCTTCGAGA
AGAGGATAAGTTAGATGGGCAAATCCCTGAAGTCTTGATCTCAGGCAATGCAGGGGATGTTGTTTTTTCCGGAAATT
CCTCGAAGCGTGATGAGCATCTTCCTCATACAGGTGGGGGAGCCATTTGTACTCAAAATTTGACGATTTCTCAGAAT
ACAGGGAATGTTCTGTTTTATAACAACGTGGCCTGTTCGGGAGGAGCTGTTCGTATAGAGGATCATGGTAATGTTCT
TTTAGAAGCTTTTGGAGGAGATATTGTTTTTAAAGGAAATTCTTCTTTCAGAGCACAAGGATCCGATGCTATCTATT
TTGCAGGTAAAGAATCGCATATTACAGCCCTGAATGCTACGGAAGGACATGCTATTGTTTTCCACGACGCATTAGTT
TTTGAAAATCTAGAAGAAAGGAAATCTGCTGAAGTATTGTTAATCAATAGTCGAGAAAATCCAGGTTACACTGGATC
TATTCGATTTTTAGAAGCAGAAAGTAAAGTTCCTCAATGTATTCATGTACAACAAGGAAGCCTTGAGTTGCTAAATG
GAGCCACATTATGTAGTTATGGTTTTAAACAAGATGCTGGAGCTAAGTTGGTATTGGCTGCTGGAGCTAAACTGAAG
ATTTTAGATTCAGGAACTCCTGTACAACAAGGGCATGCTATCAGTAAACCTGAAGCAGAAATCGAGTCATCTTCTGA
ACCAGAGGGTGCACATTCTCTTTGGATTGCGAAGAATGCTCAAACAACAGTTCCTATGGTTGATATCCATACTATTT
CTGTAGATTTAGCCTCCTTCTCTTCTAGTCAACAGGAGGGGACAGTAGAAGCTCCTCAGGTTATTGTTCCTGGAGGA
AGTTATGTTCGATCTGGAGAGCTTAATTTGGAGTTAGTTAACACAACAGGTACTGGTTATGAAAATCATGCTTTATT
GAAGAATGAGGCTAAAGTTCCATTGATGTCTTTCGTTGCTTCTGGTGATGAAGCTTCAGCCGAAATCAGTAACTTGT
CGGTTTCTGATTTACAGATTCATGTAGTAACTCCAGAGATTGAAGAAGACACATACGGCCATATGGGAGATTGGTCT
GAGGCTAAAATTCAAGATGGAACTCTTGTCATTAGTTGGAATCCTACTGGATATCGATTAGATCCTCAAAAAGCAGG -continued

SEQUENCE LISTING

GGCTTTAGTATTTAATGCATTATGGGAAGAAGGGGCTGTCTTGTCTGCTCTGAAAAATGCACGCTTTGCTCATAATC
TCACTGCTCAGCGTATGGAATTCGATTATTCTACAAATGTGTGGGGATTCGCCTTTGGTGGTTTCCGAACTCTATCT
GCAGAGAATCTGGTTGCTATTGATGGATACAAAGGAGCTTATGGTGGTGCTTCTGCTGGAGTCGATATTCAATTGAT
GGAAGATTTTGTTCTAGGAGTTAGTGGAGCTGCTTTCCTAGGTAAAATGGATAGTCAGAAGTTTGATGCGGAGGTTT
CTCGGAAGGGAGTTGTTGGTTCTGTATATACAGGATTTTTAGCTGGATCCTGGTTCTTCAAAGGACAATATAGCCTT
GGAGAAACACAGAACGATATGAAAACGCGTTATGGAGTACTAGGAGAGTCGAGTGCTTCTTGGACATCTCGAGGAGT
ACTGGCAGATGCTTTAGTTGAATACCGAAGTTTAGTTGGTCCTGTGAGACCTACTTTTTATGCTTTGCATTTCAATC
CTTATGTCGAAGTATCTTATGCTTCTATGAAATTCCCTGGCTTTACAGAACAAGGAAGAGAAGCGCGTTCTTTTGAA
GACGCTTCCCTTACCAATATCACCATTCCTTTAGGGATGAAGTTTGAATTGGCGTTCATAAAAGGACAGTTTTCAGA
GGTGAACTCTTTGGGAATAAGTTATGCATGGGAAGCTTATCGAAAAGTAGAAGGAGGCGCGGTGCAGCTTTTAGAAG
CTGGGTTTGATTGGGAGGGAGCTCCAATGGATCTTCCTAGACAGGAGCTGCGTGTCGCTCTGGAAAATAATACGGAA
TGGAGTTCTTACTTCAGCACAGTCTTAGGATTAACAGCTTTTTGTGGAGGATTTACTTCTACAGATAGTAAACTAGG
ATATGAGGCGAATACTGGATTGCGATTGATCTTT

SEQ ID NO: 118 - CT812 fragment protein sequence
CVDLHAGGQSVNELVYVGPQAVLLLDQIRDLFVGSKDSQAEGQYRLIVGDPSSFQEKDADTLPGKVEQSTLFSVTNP
VVFQGVDQQDQVSSQGLICSFTSSNLDSPRDGESFLGIAFVGDSSKAGITLTDVKASLSGAALYSTEDLIFEKIKGG
LEFASCSSLEQGGACAAQSILIHDCQGLQVKHCTTAVNAEGSSANDHLGFGGGAFFVTGSLSGEKSLYMPAGDMVVA
NCDGAISFEGNSANFANGGAIAASGKVLFVANDKKTSFIENRALSGGAIAASSDIAFQNCAELVFKGNCAIGTEDKG
SLGGGAISSLGTVLLQGNHGITCDKNESASQGGAIFGKNCQISDNEGPVVFRDSTACLGGGAIAAQEIVSIQNNQAG
ISFEGGKASFGGGIACGSFSSAGGASVLGTIDISKNLGAISFSRTLCTTSDLGQMEYQGGGALFGENISLSENAGVL
TFKDNIVKTFASNGKILGGGAILATGKVEITNNSEGISFTGNARAPQALPTQEEFPLFSKKEGRPLSSGYSGGGAIL
GREVAILHNAAVVFEQNRLQCSEEEATLLGCCGGGAVHGMDSTSIVGNSSVRFGNNYAMGQGVSGGALLSKTVQLAG
NGSVDFSRNIASLGGGALQASEGNCELVDNGYVLFRDNRGRVYGGAISCLRGDVVISGNKGRVEFKDNIATRLYVEE
TVEKVEEVEPAPEQKDNNELSFLGRAEQSFITAANQALFASEDGDLSPESSISSEELAKRRECAGGAIFAKRVRIVD
NQEAVVFSNNFSDIYGGAIFTGSLREEDKLDGQIPEVLISGNAGDVVFSGNSSKRDEHLPHTGGGAICTQNLTISQN
TGNVLFYNNVACSGGAVRIEDHGNVLLEAFGGDIVFKGNSSFRAQGSDAIYFAGKESHITALNATEGHAIVFHDALV
FENLEERKSAEVLLINSRENPGYTGSIRFLEAESKVPQCIHVQQGSLELLNGATLCSYGFKQDAGAKLVLAAGAKLK
ILDSGTPVQQGHAISKPEAEIESSSEPEGAHSLWIAKNAQTTVPMVDIHTISVDLASFSSSQQEGTVEAPQVIVPGG
SYVRSGELNLELVNTTGTGYENHALLKNEAKVPLMSFVASGDEASAEISNLSVSDLQIHVVTPEIEEDTYGHMGDWS
EAKIQDGTLVISWNPTGYRLDPQKAGALVFNALWEEGAVLSALKNARFAHNLTAQRMEFDYSTNVWGFAFGGFRTLS
AENLVAIDGYKGAYGGASAGVDIQLMEDFVLGVSGAAFLGKMDSQKFDAEVSRKGVVGSVYTGFLAGSWFFKGQYSL
GETQNDMKTRYGVLGESSASWTSRGVLADALVEYRSLVGPVRPTFYALHFNPYVEVSYASMKFPGFTEQGREARSFE
DASLTNITIPLGMKFELAFIKGQFSEVNSLGISYAWEAYRKVEGGAVQLLEAGFDWEGAPMDLPRQELRVALENNTE
WSSYFSTVLGLTAFCGGFTSTDSKLGYEANTGLRLIF SEQ ID NO: 119 - CT812N nucleotide sequence
TGCGTAGATCTTCATGCTGGAGGACAGTCTGTAAATGAGCTGGTATATGTAGGCCCTCAAGCGGTTTTATTGTTAGA
CCAAATTCGAGATCTATTCGTTGGGTCTAAAGATAGTCAGGCTGAAGGACAGTATAGGTTAATTGTAGGAGATCCAA
GTTCTTTCCAAGAGAAAGATGCGGATACTCTTCCCGGGAAGGTAGAGCAAAGTACTTTGTTCTCAGTAACCAATCCC
GTGGTTTTCCAAGGTGTGGACCAACAGGATCAAGTCTCTTCCCAAGGGTTAATTTGTAGTTTTACGAGCAGCAACCT
TGATTCTCCTCGTGACGGAGAATCTTTTTTAGGTATTGCTTTTGTTGGGGATAGTAGTAAGGCTGGAATCACATTAA
CTGACGTGAAAGCTTCTTTGTCTGGAGCGGCTTTATATTCTACAGAAGATCTTATCTTTGAAAAGATTAAGGGTGGA
TTGGAATTTGCATCATGTTCTTCTCTAGAACAGGGGGGAGCTTGTGCAGCTCAAAGTATTTTGATTCATGATTGTCA
AGGATTGCAGGTTAAACACTGTACTACAGCCGTGAATGCTGAGGGGTCTAGTGCGAATGATCATCTTGGATTTGGAG
GAGGCGCTTTCTTTGTTACGGGTTCTCTTTCTGGAGAGAAAAGTCTCTATATGCCTGCAGGAGATATGGTAGTTGCG
AATTGTGATGGGGCTATATCTTTTGAAGGAAACAGCGCGAACTTTGCTAATGGAGGAGCGATTGCTGCCTCTGGGAA
AGTGCTTTTTGTCGCTAATGATAAAAAGACTTCTTTTATAGAGAACCGAGCTTTGTCTGGAGGAGCGATTGCAGCCT
CTTCTGATATTGCCTTTCAAAACTGCGCAGAACTAGTTTTCAAAGGCAATTGTGCAATTGGAACAGAGGATAAAGGT
TCTTTAGGTGGAGGGGCTATATCTTCTCTAGGCACCGTTCTTTTGCAAGGGAATCACGGGATAACTTGTGATAAGAA
TGAGTCTGCTTCGCAAGGAGGCGCCATTTTTGGCAAAAATTGTCAGATTTCTGACAACGAGGGGCCAGTGGTTTTCA
GAGATAGTACAGCTTGCTTAGGAGGAGGCGCTATTGCAGCTCAAGAAATTGTTTCTATTCAGAACAATCAGGCTGGG
ATTTCCTTCGAGGGAGGTAAGGCTAGTTTCGGAGGAGGTATTGCGTGTGGATCTTTTTCTTCCGCAGGTGGTGCTTC
TGTTTTAGGGACCATTGATATTTCGAAGAATTTAGGCGCGATTTCGTTCTCTCGTACTTTATGTACGACCTCAGATT
TAGGACAAATGGAGTACCAGGGAGGAGGAGCTCTATTTGGTGAAAATATTTCTCTTTCTGAGAATGCTGGTGTGCTC
ACCTTTAAAGACAACATTGTGAAGACTTTTGCTTCGAATGGGAAAATTCTGGGAGGAGGAGCGATTTTAGCTACTGG
TAAGGTGGAAATTACTAATAATTCCGAAGGAATTTCTTTTACAGGAAATGCGAGAGCTCCACAAGCTCTTCCAACTC
AAGAGGAGTTTCCTTTATTCAGCAAAAAAGAAGGGCGACCACTCTCTTCAGGATATTCTGGGGGAGGAGCGATTTTA
GGAAGAGAAGTAGCTATTCTCCACAACGCTGCAGTAGTATTTGAGCAAAATCGTTTGCAGTGCAGCGAAGAAGAAGC
GACATTATTAGGTTGTTGTGGAGGAGGCGCTGTTCATGGGATGGATAGCACTTCGATTGTTGGCAACTCTTCAGTAA
GATTTGGTAATAATTACGCAATGGGACAAGGAGTCTCAGGAGGAGCTCTTTTATCTAAAACAGTGCAGTTAGCTGGG
AATGGAAGCGTCGATTTTTCTCGAAATATTGCTAGTTTGGGAGGAGGAGCTCTTCAAGCTTCTGAAGGAAATTGTGA
GCTAGTTGATAACGGCTATGTGCTATTCAGAGATAATCGAGGGAGGGTTTATGGGGGTGCTATTTCTTGCTTACGTG
GAGATGTAGTCATTTCTGGAAACAAGGGTAGAGTTGAATTTAAAGACAACATAGCAACACGTCTTTATGTGGAAGAA
ACTGTAGAAAAGGTTGAAGAGGTAGAGCCAGCTCCTGAGCAAAAAGACAATAATGAGCTTTCTTTCTTAGGGAGAGC
AGAACAGAGTTTTATTACTGCAGCTAATCAAGCTCTTTTCGCATCTGAAGATGGGGATTTATCACCTGAGTCATCCA
TTTCTTCTGAAGAA SEQ ID NO: 120: CT812N protein sequence
CVDLHAGGQSVNELVYVGPQAVLLLDQIRDLFVGSKDSQAEGQYRLIVGDPSSFQEKDADTLPGKVEQSTLFSVTNP
VVFQGVDQQDQVSSQGLICSFTSSNLDSPRDGESFLGIAFVGDSSKAGITLTDVKASLSGAALYSTEDLIFEKIKGG
LEFASCSSLEQGGACAAQSILIHDCQGLQVKHCTTAVNAEGSSANDHLGFGGGAFFVTGSLSGEKSLYMPAGDMVVA
NCDGAISFEGNSANFANGGAIAASGKVLFVANDKKTSFIENRALSGGAIAASSDIAFQNCAELVFKGNCAIGTEDKG
SLGGGAISSLGTVLLQGNHGITCDKNESASQGGAIFGKNCQISDNEGPVVFRDSTACLGGGAIAAQEIVSIQNNQAG
ISFEGGKASFGGGIACGSFSSAGGASVLGTIDISKNLGAISFSRTLCTTSDLGQMEYQGGGALFGENISLSENAGVL
TFKDNIVKTFASNGKILGGGAILATGKVEITNNSEGISFTGNARAPQALPTQEEFPLFSKKEGRPLSSGYSGGGAIL
GREVAILHNAAVVFEQNRLQCSEEEATLLGCCGGGAVHGMDSTSIVGNSSVRFGNNYAMGQGVSGGALLSKTVQLAG -continued

SEQUENCE LISTING

NGSVDFSRNIASLGGGALQASEGNCELVDNGYVLFRDNRGRVYGGAISCLRGDVVISGNKGRVEFKDNIATRLYVEE
TVEKVEEVEPAPEQKDNNELSFLGRAEQSFITAANQALFASEDGDLSPESSISSEE

SEQ ID NO: 121: CT812C nucleotide sequence
GAAGAACTTGCGAAAAGAAGAGAGTGTGCTGGAGGAGCTATTTTTGCAAAACGGGTTCGTATTGTAGATAACCAAGA
GGCCGTTGTATTCTCGAATAACTTCTCTGATATTTATGGCGGCGCCATTTTTACAGGTTCTCTTCGAGAAGAGGATA
AGTTAGATGGGCAAATCCCTGAAGTCTTGATCTCAGGCAATGCAGGGGATGTTGTTTTTTCCGGAAATTCCTCGAAG
CGTGATGAGCATCTTCCTCATACAGGTGGGGGAGCCATTTGTACTCAAAATTTGACGATTTCTCAGAATACAGGGAA
TGTTCTGTTTTATAACAACGTGGCCTGTTCGGGAGGAGCTGTTCGTATAGAGGATCATGGTAATGTTCTTTTAGAAG
CTTTTGGAGGAGATATTGTTTTTAAAGGAAATTCTTCTTTCAGAGCACAAGGATCCGATGCTATCTATTTTGCAGGT
AAAGAATCGCATATTACAGCCCTGAATGCTACGGAAGGACATGCTATTGTTTTCCACGACGCATTAGTTTTTGAAAA
TCTAGAAGAAAGGAAATCTGCTGAAGTATTGTTAATCAATAGTCGAGAAAATCCAGGTTACACTGGATCTATTCGAT
TTTTAGAAGCAGAAAGTAAAGTTCCTCAATGTATTCATGTACAACAAGGAAGCCTTGAGTTGCTAAATGGAGCCACA
TTATGTAGTTATGGTTTTAAACAAGATGCTGGAGCTAAGTTGGTATTGGCTGCTGGAGCTAAACTGAAGATTTTAGA
TTCAGGAACTCCTGTACAACAAGGGCATGCTATCAGTAAACCTGAAGCAGAAATCGAGTCATCTTCTGAACCAGAGG
GTGCACATTCTCTTTGGATTGCGAAGAATGCTCAAACAACAGTTCCTATGGTTGATATCCATACTATTTCTGTAGAT
TTAGCCTCCTTCTCTTCTAGTCAACAGGAGGGGACAGTAGAAGCTCCTCAGGTTATTGTTCCTGGAGGAAGTTATGT
TCGATCTGGAGAGCTTAATTTGGAGTTAGTTAACACAACAGGTACTGGTTATGAAAATCATGCTTTATTGAAGAATG
AGGCTAAAGTTCCATTGATGTCTTTCGTTGCTTCTGGTGATGAAGCTTCAGCCGAAATCAGTAACTTGTCGGTTTCT
GATTTACAGATTCATGTAGTAACTCCAGAGATTGAAGAAGACACATACGGCCATATGGGAGATTGGTCTGAGGCTAA
AATTCAAGATGGAACTCTTGTCATTAGTTGGAATCCTACTGGATATCGATTAGATCCTCAAAAAGCAGGGGCTTTAG
TATTTAATGCATTATGGGAAGAAGGGGCTGTCTTGTCTGCTCTGAAAAATGCACGCTTTGCTCATAATCTCACTGCT
CAGCGTATGGAATTCGATTATTCTACAAATGTGTGGGGATTCGCCTTTGGTGGTTTCCGAACTCTATCTGCAGAGAA
TCTGGTTGCTATTGATGGATACAAAGGAGCTTATGGTGGTGCTTCTGCTGGAGTCGATATTCAATTGATGGAAGATT
TTGTTCTAGGAGTTAGTGGAGCTGCTTTCCTAGGTAAAATGGATAGTCAGAAGTTTGATGCGGAGGTTTCTCGGAAG
GGAGTTGTTGGTTCTGTATATACAGGATTTTTAGCTGGATCCTGGTTCTTCAAAGGACAATATAGCCTTGGAGAAAC
ACAGAACGATATGAAAACGCGTTATGGAGTACTAGGAGAGTCGAGTGCTTCTTGGACATCTCGAGGAGTACTGGCAG
ATGCTTTAGTTGAATACCGAAGTTTAGTTGGTCCTGTGAGACCTACTTTTTATGCTTTGCATTTCAATCCTTATGTC
GAAGTATCTTATGCTTCTATGAAATTCCCTGGCTTTACAGAACAAGGAAGAGAAGCGCGTTCTTTTGAAGACGCTTC
CCTTACCAATATCACCATTCCTTTAGGGATGAAGTTTGAATTGGCGTTCATAAAAGGACAGTTTTCAGAGGTGAACT
CTTTGGGAATAAGTTATGCATGGGAAGCTTATCGAAAAGTAGAAGGAGGCGCGGTGCAGCTTTTAGAAGCTGGGTTT
GATTGGGAGGGAGCTCCAATGGATCTTCCTAGACAGGAGCTGCGTGTCGCTCTGGAAAATAATACGGAATGGAGTTC
TTACTTCAGCACAGTCTTAGGATTAACAGCTTTTTGTGGAGGATTTACTTCTACAGATAGTAAACTAGGATATGAGG
CGAATACTGGATTGCGATTGATCTTT SEQ ID NO: 122: CT812C protein sequence
EELAKRRECAGGAIFAKRVRIVDNQEAVVFSNNFSDIYGGAIFTGSLREEDKLDGQIPEVLISGNAGDVVFSGNSSK
RDEHLPHTGGGAICTQNLTISQNTGNVLFYNNVACSGGAVRIEDHGNVLLEAFGGDIVFKGNSSFRAQGSDAIYFAG
KESHITALNATEGHAIVFHDALVFENLEERKSAEVLLINSRENPGYTGSIRFLEAESKVPQCIHVQQGSLELLNGAT
LCSYGFKQDAGAKLVLAAGAKLKILDSGTPVQQGHAISKPEAEIESSSPEPEGAHSLWIAKNAQTTVPMVDIHTISVD
LASFSSSQQEGTVEAPQVIVPGGSYVRSGELNLELVNTTGTGYENHALLKNEAKVPLMSFVASGDEASAEISNLSVS
DLQIHVVTPEIEEDTYGHMGDWSEAKIQDGTLVISWNPTGYRLDPQKAGALVFNALWEEGAVLSALKNARFAHNLTA
QRMEFDYSTNVWGFAFGGFRTLSAENLVAIDGYKGAYGGASAGVDIQLMEDFVLGVSGAAFLGKMDSQKFDAEVSRK
GVVGSVYTGFLAGSWFFKGQYSLGETQNDMKTRYGVLGESSASWTSRGVLADALVEYRSLVGPVRPTFYALHFNPYV
EVSYASMKFPGFTEQGREARSFEDASLTNITIPLGMKFELAFIKGQFSEVNSLGISYAWEAYRKVEGGAVQLLEAGF
DWEGAPMDLPRQELRVALENNTEWSSYFSTVLGLTAFCGGFTSTDSKLGYEANTGLRLIF SEQ ID NO: 123: CT869 fragment nucleotide sequence
AGAGAGGTTCCTTCTAGAATCTTTCTTATGCCCAACTCAGTTCCAGATCCTACGAAAGAGTCGCTATCAAATAAAAT
TAGTTTGACAGGAGACACTCACAATCTCACTAACTGCTATCTCGATAACCTACGCTACATACTGGCTATTCTACAAA
AAACTCCCAATGAAGGAGCTGCTGTCACAATAACAGATTACCTAAGCTTTTTTGATACACAAAAAGAAGGTATTTAT
TTTGCAAAAAATCTCACCCCTGAAAGTGGTGGTGCGATTGGTTATGCGAGTCCCAATTCTCCTACCGTGGAGATTCG
TGATACAATAGGTCCTGTAATCTTTGAAAATAATACTTGTTGCAGACTATTTACATGGAGAAATCCTTATGCTGCTG
ATAAAATAAGAGAAGGCGGAGCCATTCATGCTCAAAATCTTTACATAAATCATAATCATGATGTGGTCGGATTTATG
AAGAACTTTTCTTATGTCCAAGGAGGAGCCATTAGTACCGCTAATACCTTTGTTGTGAGCGAGAATCAGTCTTGTTT
TCTCTTTATGGACAACATCTGTATTCAAACTAATACAGCAGGAAAAGGTGGCGCTATCTATGCTGGAACGAGCAATT
CTTTTGAGAGTAATAACTGCGATCTCTTCTTCATCAATAACGCCTGTTGTGCAGGAGGAGCGATCTTCTCCCCTATC
TGTTCTCTAACAGGAAATCGTGGTAACATCGTTTTCTATAACAATCGCTGCTTTAAAAATGTAGAAACAGCTTCTTC
AGAAGCTTCTGATGGAGGAGCAATTAAAGTAACTACTCGCCTAGATGTTACAGGCAATCGTGGTAGGATCTTTTTTA
GTGACAATATCACAAAAAATTATGGCGGAGCTATTTACGCTCCTGTAGTTACCCTAGTGGATAATGGCCCTACCTAC
TTTATAAACAATATCGCCAATAATAAGGGGGGCGCTATCTATATAGACGGAACCAGTAACTCCAAAATTTCTGCCGA
CCGCCATGCTATTATTTTTAATGAAAATATTGTGACTAATGTAACTAATGCAAATGGTACCAGTACGTCAGCTAATC
CTCCTAGAAGAAATGCAATAACAGTAGCAAGCTCCTCTGGTGAAATTCTATTAGGAGCAGGGAGTAGCCAAAATTTA
ATTTTTTATGATCCTATTGAAGTTAGCAATGCAGGGGTCTCTGTGTCCTTCAATAAGGAAGCTGATCAAACAGGCTC
TGTAGTATTTTCAGGAGCTACTGTTAATTCTGCAGATTTTCATCAACGCAATTTACAAACAAAAACACCTGCACCCC
TTACTCTCAGTAATGGTTTTCTATGTATCGAAGATCATGCTCAGCTTACAGTGAATCGATTCACACAAACTGGGGGT
GTTGTTTCTCTTGGGAATGGAGCAGTTCTGAGTTGCTATAAAAATGGTACAGGAGATTCTGCTAGCAATGCCTCTAT
AACACTGAAGCATATTGGATTGAATCTTTCTTCCATTCTGAAAAGTGGTGCTGAGATTCCTTTATTGTGGGTAGAGC
CTACAAATAACAGCAATAACTATACAGCAGATACTGCAGCTACCTTTTCATTAAGTGATGTAAAACTCTCACTCATT
GATGACTACGGGAACTCTCCTTATGAATCCACAGATCTGACCCATGCTCTGTCATCACAGCCTATGCTATCTATTTC
TGAAGCTAGCGATAACCAGCTACAATCAGAAAATATAGATTTTTCGGGACTAAATGTCCCTCATTATGGATGGCAAG
GACTTTGGACTTGGGGCTGGGCAAAAACTCAAGATCCAGAACCAGCATCTTCAGCAACAATCACTGATCCACAAAAA
GCCAATAGATTTCATAGAACCTTACTACTAACATGGCTTCCTGCCGGGTATGTTCCTAGCCCAAAACACAGAAGTCC
CCTCATAGCTAACACCTTATGGGGGAATATGCTGCTTGCAACAGAAAGCTTAAAAAATAGTGCAGAGCTGACACCTA
GTGGTCATCCTTTCTGGGGAATTACAGGAGGAGGACTAGGCATGATGGTTTACCAAGATCCTCGAGAAAATCATCCT
GGATTCCATATGCGCTCTTCCGGATACTCTGCGGGGATGATAGCAGGGCAGACACACACCTTCTCATTGAAATTCAG
TCAGACCTACACCAAACTCAATGAGCGTTACGCAAAAAACAACGTATCTTCTAAAAATTACTCATGCCAAGGAGAAA -continued

SEQUENCE LISTING

TGCTCTTCTCATTGCAAGAAGGTTTCTTGCTGACTAAATTAGTTGGGCTTTACAGCTATGGAGACCATAACTGTCAC
CATTTCTATACTCAAGGAGAAAATCTAACATCTCAAGGGACGTTCCGCAGTCAAACGATGGGAGGTGCTGTCTTTTT
TGATCTCCCTATGAAACCCTTTGGATCAACGCATATACTGACAGCTCCCTTTTTAGGTGCTCTTGGTATTTATTCTA
GCCTGTCTCACTTTACTGAGGTGGAGCCTATCCGCGAAGCTTTTCTACAAAGACTCCTTTGATCAATGTCCTAGTC
CCTATTGGAGTTAAAGGTAGCTTTATGAATGCTACCCACAGACCTCAAGCCTGGACTGTAGAATTGGCATACCAACC
CGTTCTGTATAGACAAGAACCAGGGATCGCAGCCCAGCTCCTAGCCAGTAAGGGTATTTGGTTCGGTAGTGGAAGCC
CCTCATCGCGTCATGCCATGTCCTATAAAATCTCACAGCAAACACAACCTTTGAGTTGGTTAACTCTCCATTTCCAG
TATCATGGATTCTACTCCTCTTCAACCTTCTGTAATTATCTCAATGGGGAAATTGCTCTGCGATTC

SEQ ID NO: 124: CT869 fragment protein sequence
REVPSRIFLMPNSVPDPTKESLSNKISLTGDTHNLTNCYLDNLRYILAILQKTPNEGAAVTITDYLSFFDTQKEGIY
FAKNLTPESGGAIGYASPNSPTVEIRDTIGPVIFENNTCCRLFTWRNPYAADKIREGGAIHAQNLYINHNHDVVGFM
KNFSYVQGGAISTANTFVVSENQSCFLFMDNICIQTNTAGKGGAIYAGTSNSFESNNCDLFFINNACCAGGAIFSPI
CSLTGNRGNIVFYNNRCFKNVETASSEASDGGAIKVTTRLDVTGNRGRIFFSDNITKNYGGAIYAPVVTLVDNGPTY
FINNIANNKGGAIYIDGTSNSKISADRHAIIFNENIVTNVTNANGTSTSANPPRRNAITVASSSGEILLGAGSSQNL
IFYDPIEVSNAGVSVSFNKEADQTGSVVFSGATVNSADFHQRNLQTKTPAPLTLSNGFLCIEDHAQLTVNRFTQTGG
VVSLGNGAVLSCYKNGTGDSASNASITLKHIGLNLSSILKSGAEIPLLWVEPTNNSNNYTADTAATFSLSDVKLSLI
DDYGNSPYESTDLTHALSSQPMLSISEASDNQLQSENIDFSGLNVPHYGWQGLWTWGWAKTQDPEPASSATITDPQK
ANRFHRTLLLTWLPAGYVPSPKHRSPLIANTLWGNMLLATESLKNSAELTPSGHPFWGITGGGLGMMVYQDPRENHP
GFHMRSSGYSAGMIAGQTHTFSLKFSQTYTKLNERYAKNNVSSKNYSCQGEMLFSLQEGFLLTKLVGLYSYGDHNCH
HFYTQGENLTSQGTFRSQTMGGAVFFDLPMKPFGSTHILTAPFLGALGIYSSLSHFTEVGAYPRSFSTKTPLINVLV
PIGVKGSFMNATHRPQAWTVELAYQPVLYRQEPGIAAQLLASKGIWFGSGSPSSRHAMSYKISQQTQPLSWLTLHFQ
YHGFYSSSTFCNYLNGEIALRF SEQ ID NO: 125: CT166 fragment nucleotide sequence
AACGTTCGTACGTACTCTGTTCAGAGGGGGGGGGTAAAAACGATTTCTGCTAGTGCAGTTCCTCCTACAGCAGCTGT
TTTATCGAGAAAAAAGCGTGCTATAGAAGAGAAGAAGGAGGAAGCTTCTTCTGGAAAGATAGAAAATCTTGATGCTA
GCAAATACGATCTTACTCCCAAGAACATAGAAGAAAAACTAGGAATTACTCCTGAACAGAAATCTACTGTTAAAGAC
CTATTAAATAAACTGAAAAAGGTCATTAGTGCTTACAACTCTATGCCAGATAAAAATTCGGAAGCGGGACAGAATTC
CTTGATTCAACAAGGAAAATACGTCGATGCCATTCAGAAGAAGCTTCCAGCATCATCGCAGGCTCAGCCTAAACAGG
CAAAAGCTAAGGAACAGAAAGCCGAAGAAAAACCTAAGACGACTCCGATTGAAGGTGTTCTTGAAACCATCAAAACA
GAATTTAAAGGCCATCGTGTACCTGTTGAGAAAATCATCCATGGAATATGGATCGCAGGAGCGCCTCCGGATGGTAT
CGAAGATTATATGCGAGTCTTTTTAGATACTTATGAAGGTTTTGACTTCTACTTCTGGGTAGATGAGAATGCTTATG
CAGCAGCTAAATTTTCTAGCATTTTGAAGAAGGTCGCTTTCGATGCGGCTATTCAAGATCTACGATCTGCCACAGAT
GAGTCTACGAAGGCCTTTGTTAAAGACTACGATGAATTAAAACAGAAATATGAAAAGAAAGTTGCGGAGACGACTTC
TCAAGCAGAAAAAGACCAATATCTCAAAGATCTAAAGGATCTTTTAGAGAAATTTACAAAAATCAGTGATGAGATTC
GTGGAAAATTTGATCGGCTGTTTCTTAAGAATGTGATTGTTGCTCAGAACGGATTCTTTAATTTCTGCTTGCTGAAA
GGCCTCGGCAATATCAATGACGAAACGCGTGCAGAGTATTTAGAGAAAGAACTCAAACTTCCTACTGAGGAGATCGA
ACAGTATAAAAAGCTTAAAGAGACGAACAAAGAGAAGATAGCCGCTATTGTAAAACAACTAAACGAGAAACTTGGAT
CGGATCGGGTAAAAATCAAAGACATTAAAGAGCTGCAATCTATGAAGCAAGCTCGAAATGTCTACAATTATGAACAG
GAAATGTTTCTGCGCTGGAACTATGCAGCCGCAACAGATCAGATTCGTATGTATATGTTGGAGGAACTTGGAGGTCT
TTATACTGATCTGGATATGATGCCTTCATACTCTCAGGAAGTATTGGAGCTTATCAAAAAGCACAGTGATGGAAACC
GAATGTTTGAGGATATGAGCTCTAGACGGGCGATTTCTGATGCGGTTTTAAAGATGGCTGTAGGTAAGGCGACAACA
GTTTCCATGGAAGAGGTAGCAAAGGATATCGATGTTTCTCGCTTAACAGAAGAGGATAAGACAAAATTAAATGCTCT
ATTTAAGGATCTAGAGCCATTTGCAAAACCGGATTCTAAAGGAGCTGAAGCAGAAGGGGGTGAAGGAGCAAAAGGTA
TGAAAAAGAGCTTTTTCCAGCCCATAGATCTGAATATTGTCAGAAATACCATGCCTATCTTGAGACGCTATCATCAC
TATCCTGAGTTAGGATGGTTTATTCGAGGATTGAACGGATTGATGGTCTCTCATAAGGGAAGCACTGCGGTTTCTGC
TGTCATTGTAGGGCAACAGGCTGCCTACCAGGAACTAGCAGCACTTAGACAAGATGTCCTTTCAGGGGAGTTTTTCC
ATTCTTTAGAAAATTTGACACATAGAAACCATAAGGAGCGTATTGGAAATCATCTCGTCGCTAATTATTTGGCTAAA
AGTCTCTTTTTTGATTACTGCCAAGATTCAGTGATGCCGGAGGCTGTAAGTACCTTAGGTATTAGA SEQ ID NO: 126 - CT166 fragment protein sequence
NVRTYSVQRGGVKTISASAVPPTAAVLSRKKRAIEEKKEEASSGKIENLDASKYDLTPKNIEEKLGITPEQKSTVKD
LLNKLKKVISAYNSMPDKNSEAGQNSLIQQGKYVDAIQKKLPASSQAQPKQAKAKEQKAEEKPKTTPIEGVLETIKT
EFKGHRVPVEKIIHGIWIAGAPPDGIEDYMRVFLDTYEGFDFYFWVDENAYAAAKFSSILKKVAFDAAIQDLRSATD
ESTKAFVKDYDELKQKYEKKVAETTSQAEKDQYLKDLKDLLEKFTKISDEIRGKFDRLFLKNVIVAQNGFFNFCLLK
GLGNINDETRAEYLEKELKLPTEEIEQYKKLKETNKEKIAAIVKQLNEKLGSDRVKIKDIKELQSMKQARNVYNYEQ
EMFLRWNYAAATDQIRMYMLEELGGLYTDLDMMPSYSQEVLELIKKHSDGNRMFEDMSSRRAISDAVLKMAVGKATT
VSMEEVAKDIDVSRLTEEDKTKLNALFKDLEPFAKPDSKGAEAEGGEGAKGMKKSFFQPIDLNIVRNTMPILRRYHH
YPELGWFIRGLNGLMVSHKGSTAVSAVIVGQQAAYQELAALRQDVLSGEFFHSLENLTHRNHKERIGNHLVANYLAK
SLFFDYCQDSVMPEAVSTLGIR SEQ ID NO: 127 - CT175 fragment nucleotide sequence
TGTTATCATAAAAAAGAAGAACCAAAAGATGTTTTGCGGATTGCGATCTGTCATGATCCAATGTCTTTAGATCCGCG
TCAGGTTTTTTTAAGCAAAGATGTTTCTATTGTAAAAGCTCTCTATGAAGGGTTAGTCCGGGAAAAAGAAGCTGCGT
TCCAGCTAGCTTTGGCAGAAAGATATCATCAATCTGATGATGGTTGTGTTTATACTTTTTTTCTAAAAAATACATTC
TGGAGCAACGGAGATGTTGTAACAGCATATGATTTTGAAGAGTCTATTAAACAAATTTATTTCCGAGAAATTGATAA
CCCTTCGTTACGCTCTCTTGCATTAATTAAAAATTCTCATGCTGTTTTAACAGGAGCTCTCCCTGTTGAAGATTTAG
GTGTTAGAGCTTTGAATGCGAAAACTCTAGAAATTGTTTTAGAAAACCCGTTTCCTTATTTTCTAGAGATATTGGCG
CACCCGGTTTTTTATCCGGTGCACACCTCTTTACGAGAATATTACAAAGATAAGCGTAACAAACGCGTTTTCCCGAT
AATTTCTAATGGTCCTTTTGCGATTCAATGTTATGAGCCGCAAAGATATTTACTAATCAACAAAAACCCCTCTGTATC
ATGCCAAGCACGATGTTCTGTTAAATTCGGTATGTTTGCAGATAGTTCCTGATATCCATACAGCTATGCAGTTATTC
CAAAAAAATCATATCGATTTAGTTGGGTTACCCTGGAGCTCCTCCTTTTCTTTAGAAGAACAAAGAAATCTCCCTAG
AGAAAAATTATTTGATTATCCTGTATTGAGTTGCTCTGTTTTATTCTGTAACATTCATCAAACACCTTTAAATAATC
CCTCGCTGAGAACAGCCCTCTCTTTAGCAATCAATCGAGAAACTTTATTAAAACTAGCAGGTAAAGGCTGTAGCGCT
ACGAGCTTTGTTCACCCACAATTATCTCAGATACCTGCTACTACTTGTCTCAAGATGAGCGGATTGCTTTAGCAAA
AGGCTACTTGACCGAAGCTTTAAAGACTTTATCTCAAGAAGATTTAGAAAAAATTACATTAATTTATCCTATAGAAT -continued

SEQUENCE LISTING

CTGTTTGCTTACGAGCCGTTGTTCAAGAAATTCGCCAACAATTATTTGATGTACTGGGATTTAAAATTTCTACATTA
GGATTAGAATATCATTGTTTTTAGACAAACGTTCCAGAGGAGAATTCTCCTTAGCAACTGGTAATTGGATTGCAGA
CTATCATCAAGCTAGTGCTTTCCTGTCTGTCCTAGGTAATGGGACAAGATATAAAGACTTTCAATTGATTAACTGGC
AGAACCAAAAGTACACAAATATAGTTGCTCAACTTCTGATTCAAGAATCAAGCGACCTACAGCTTATGGCAGAGCAG
TTGTTGCTTAAAGAAAGTCCTCTTATTCCTCTATACCACCTCGATTATGTGTATGCGAAACAGCCTCGGGTGTCTGA
TCTCCAAACCTCTTCTCGTGGAGAAATTGATTTAAAAAGAGTTTCATTAGCTGAAGGATAG

SEQ ID NO: 128 - CT175 fragment protein sequence
CYHKKEEPKDVLRIAICHDPMSLDPRQVFLSKDVSIVKALYEGLVREKEAAFQLALAERYHQSDDGCVYTFFLKNTF
WSNGDVVTAYDFEESIKQIYFREIDNPSLRSLALIKNSHAVLTGALPVEDLGVRALNAKTLEIVLENPFPYFLEILA
HPVFYPVHTSLREYYKDKRNKRVFPIISNGPFAIQCYEPQRYLLINKNPLYHAKHDVLLNSVCLQIVPDIHTAMQLF
QKNHIDLVGLPWSSSFSLEEQRNLPREKLFDYPVLSCSVLFCNIHQTPLNNPSLRTALSLAINRETLLKLAGKGCSA
TSFVHPQLSQIPATTLSQDERIALAKGYLTEALKTLSQEDLEKITLIYPIESVCLRAVVQEIRQQLFDVLGFKISTL
GLEYHCFLDKRSRGEFSLATGNWIADYHQASAFLSVLGNGTRYKDFQLINWQNQKYTNIVAQLLIQESSDLQLMAEQ
LLLKESPLIPLYHLDYVYAKQPRVSDLQTSSRGEIDLKRVSLAEG SEQ ID NO: 129 - TC0666 fragment nucleotide sequence (homologue of CT387)
ATGACACTCTTTCACACTCATCACGATGCCGTCTCTCCGGACGGCTACTTATGTTCTTCCCTTCAGTTAGTTGGCTC
TGGCACATATGAAGGAGAAATCGAAATCCAAAATATTCCTTCTTATTTCCTTGGATTCCGATTACCCACCCATTGCG
TTCATCTTAATTTGAAGAGTTCTCTAGCCCAGTTAGGAGTAGATGCATCTCTTCTTCACTGCGAACTAAGCAAAAAT
CAACAACGTGCACATATGCACGTGCAGTTCACCGGCTATGGCCCTATCGCTGAGTCCATGCTATCTCTTCTCAAACC
CGGAGATCGAGTAGCCAAACTGTTTGCTGCAGATGATCGTAGACTAGTCCGCTCCCCTGATTATCTTGAAAGCATGC
TAAAAAATACTGATAAGACAGGACATCCTCTGCTCCGATTTGGAAAAAAACTCGAGCATCTTATCTCTTTTGATGTG
GTGGACGATCGCCTCGTTGTATCACTCCCCACCTTGCCAGGCATAGTCAATTATGACCCAGACATCTATGGACTTCT
TCCCTTAATTCAAAAATCACTAAGCAATCCTAAATTGAGTATTCGCCACTTCTTGTCTCTCTATCAGAAGATCGTAG
AAGGACCACACATCCCTTATGAAGGAAACATTTTGTTAATCAAAACAGAGCCTCTTCATATCCGCACAGTATTTGCT
CGCGTGGTCGATCAAATGCTCCCTCAAGGTCTATTTCACACTTCTGCCAACATTTTAGAACCCACAACGCGAGAGTC
TGGAGATATTTTTGAATTTTTTGGAAATCCCTCCACTCTTGTAGAAAGAATCCCTCTAGAATTCTTCACTATCGAAC
CCTACAAAGAACACTCTTACTTCTGTAATCGAGATCTATTGCAAACTACCTTGCAATCGGAAAGTGAAATCAAAAAA
ATATTCGATACAGCTCCTCAAGAGCCTGTAAAAGCCGCCACTTATTTATCAAAAGGAAGTGAAATTTCTTCTCTTGA
TGCAGATTCTTGGCTTACGGGATCCGCAGCTGCATACCAATGTAGCGAAAAACAGGCAGCTAAAGACGAATACATCC
ACGCTCAACCCTGTTATCCATTTTTGGAAGCAATGGAAACGGGACTCATCAATAGCGAAGGAGCTTTACTCACTCGG
TTTTTCCCCTCTTCCAGCTTAAAAGGGATGTTGATCTCCTATCATGTACGCCACTATCTTAAGCAAATTTACTTTCA
AGTTCCTTCTTATACATATGGAGACTACTTCTCTCATAATGACCGAGGATTACTGTTAGATCTATATCAGGCGAACA
TTGATGTGTTCTGGGCTGATGAAGAGAGCGGCCGTGTATTGCAATATACAAAACGGCGCGACAAAAATAGTGGAATG
TTCGTCGTTAAAAATCGAGTAGAAGAGTTCCAATCAGCATATTTCGTAGCGATTTATGGATCACGTCTCCTGGAAAA
TAATTTCTCGGCCCAACTAAACACGCTTCTTGCAGGGTTACAAAAAGCTGCACACACTCTAGGCATTCCAGGCTTCT
CAAAACCCACTCCTCTTGCCGTAATCACAGGAGGAGGGACTGGCGTTATGGCTACAGGAAATCGTGTTGCAAAAGAG
TTGGGAATTCTTTCTTGCGGGACCGTTCTCGATTTGGAAGCTTCACCTGCACAAATAGATCAGCCTGCAAACGAATT
TTTAGATGCCAAAATGACATACCGTCTACCGCAACTTATAGAAAGACAAGAACATTTTTATTCAGACCTTGCCATTT
TAGTTGTTGGTGGTGTTGGAACAGATTTCGAACTTTACCTAGAACTCGTCTACTTGAAAACAGGCGCCAAACCTCCT
ACTCCAATTTTCCTTATTGGGCCTGTTGAATACTGGAAAGAGAAAGTTGCTCATGCCTATGAGATTAATCTTAAAGC
AGGAACTATTCGTGGTTCTGAGTGGATCAGCAACTGCTTATTCTGCATTACATCTCCTGAAGCAGGAATTGCTGTAT
TCGAACAGTTCCTCGCTGGAGAACTTCCCATAGGATATGATTATCCTCCAGCTCCAGACGGATTAGTTATCGTC SEQ ID NO: 130 - TC0666 fragment protein sequence (homologue of CT387)
MTLFHTHHDAVSPDGYLCSSLQLVGSGTYEGEIEIQNIPSYFLGFRLPTHCVHLNLKSSLAQLGVDASLLHCELSKN
QQRAHMHVQFTGYGPIAESMLSLLKPGDRVAKLFAADDRRLVRSPDYLESMLKNTDKTGHPLLRFGKKLEHLISFDV
VDDRLVVSLPTLPGIVNYDPDIYGLLPLIQKSLSNPKLSIRHFLSLYQKIVEGPHIPYEGNILLIKTEPLHIRTVFA
RVVDQMLPQGLFHTSANILEPTTRESGDIFEFFGNPSTLVERIPLEFFTIEPYKEHSYFCNRDLLQTTLQSESEIKK
IFDTAPQEPVKAATYLSKGSEISSLDADSWLTGSAAAYQCSEKQAAKDEYIHAQPCYPFLEAMETGLINSEGALLTR
FFPSSSLKGMLISYHVRHYLKQIYFQVPSYTYGDYFSHNDRGLLLDLYQANIDVFWADEESGRVLQYTKRRDKNSGM
FVVKNRVEEFQSAYFVAIYGSRLLENNFSAQLNTLLAGLQKAAHTLGIPGFSKPTPLAVITGGGTGVMATGNRVAKE
LGILSCGTVLDLEASPAQIDQPANEFLDAKMTYRLPQLIERQEHFYSDLAILVVGGVGTDFELYLELVYLKTGAKPP
TPIFLIGPVEYWKEKVAHAYEINLKAGTIRGSEWISNCLFCITSPEAGIAVFEQFLAGELPIGYDYPPAPDGLVIV SEQ ID NO: 131 - TC0197 fragment nucleotide sequence
AATTGTTCCGATCTTTATGCCGTAGGAAGTTCTGCAGACCATCCTGCCTACTTGATTCCTCAAGCGGGGTTATTATT
GGATCATATTAAGGATATATTCATTGGCCCTAAAGATAGTCAGGATAAGGGGCAGTATAAGTTGATTATTGGTGAGG
CTGGCTCTTTCCAAGATAGTAATGCAGAGACTCTTCCTCAAAAGGTAGAGCACAGCACTTTGTTTTCAGTTACAACA
CCTATAATTGTGCAAGGAATAGATCAACAAGATCAGGTCTCTTCGCAGGGATTGGTCTGTAATTTTTCAGGAGATCA
TTCAGAGGAGATTTTTGAGAGAGAATCCTTTTTAGGGATCGCTTTCCTAGGGAATGGTAGCAAGGATGGAATCACGT
TAACAGATATAAAATCTTCGTTATCTGGTGCTGCCTTGTATTCTTCAGATGATCTTATTTTTGAAAGAATTAAGGGA
GATATAGAGCTTTCTTCTTGTTCATCTTTAGAAAGAGGAGGAGCTTGTTCAGCTCAAAGTATTTTAATTCATGATTG
TCAAGGATTAACGGTAAAACATTGTGCCGCAGGGGTGAATGTTGAAGGAGTTAGTGCTAGCGACCATCTCGGATTTG
GGGGCGGGGCCTTCTCTACTACAAGTTCTCTTTCTGGAGAGAAGAGTTTGTATATGCCTGCAGGCGATATTGTGGTG
GCTACCTGCGATGGTCCTGTGTGTTTCGAAGGAAATAGTGCTCAGTTAGCAAATGGTGGCGCTATTGCCGCTTCTGG
TAAAGTTCTTTTTGTAGCTAACGAAAAAAAGATTTCCTTTACAGACAACCAAGCTTTGTCTGGAGGAGCTATTTCTG
CATCTTCTAGTATTTCTTTCCAAAATTGTGCTGAGCTTGTGTTCAAGAGTAATCTTGCAAAAGGAGTTAAAGATAAA
TGTTCTTTGGGAGGAGGTGCTTTAGCCTCTTTAGAATCCGTAGTTTTGAAAGATAATCTCGGTATTACTTATGAAAA
AAATCAGTCCTATTCGGAAGGAGGGGCTATTTTTGGGAAGGATTGTGAGATTTTTGAAAACAGGGGGCCTGTTGTAT
TCAGAGATAATACAGCTGCTTTAGGAGGCGGAGCTATTTTGGCGCAACAAACTGTGGCGATTTGTGGTAATAAGTCT
GGAATATCTTTTGAAGGAAGTAAGTCTAGTTTTGGAGGGGCCATTGCTTGTGGAAATTTCTCTTCTGAGAATAATTC
TTCAGCTTTGGGATCAATTGATATCTCTAACAATCTAGGAGATATCTCTTTTCTTCGGACTCTGTGTACTACTTCGG
ATTTAGGGCAAACGGATTACCAAGGGGGAGGGGCCTTATTCGCTGAAAATATTTCTCTTTCTGAGAATGCTGGTGCA
ATTACTTTCAAAGACAATATTGTGAAGACATTTGCCTCAAATGGAAAAATGTTGGGTGGAGGGGCAATTTTAGCTTC
AGGAAATGTTTTGATTAGCAAAAACTCTGGAGAGATTTCTTTTGTAGGGAATGCTCGAGCTCCTCAGGCTATTCCGA -continued

SEQUENCE LISTING

CTCGTTCATCTGACGAATTGTCTTTTGGCGCACAATTAACTCAAACTACTTCAGGATGTTCTGGAGGAGGAGCTCTT
TTTGGTAAAGAGGTTGCCATTGTTCAAAATGCCACTGTTGTATTCGAGCAAAATCGCTTACAGTGTGGCGAGCAGGA
AACACATGGTGGAGGCGGTGCTGTTTATGGTATGGAGAGTGCCTCTATTATTGGAAACTCTTTTGTGAGATTCGGAA
ATAATTACGCTGTAGGGAATCAGATTTCTGGAGGAGCTCTTTTATCCAAGAAGGTCCGTTTAGCTGAAAATACAAGG
GTAGATTTTTCTCGAAATATCGCTACTTTCTGCGGCGGGGCTGTTCAAGTTTCTGATGGAAGTTGCGAATTGATCAA
CAATGGGTATGTGCTATTCAGAGATAACCGAGGGCAGACATTTGGTGGGGCTATTTCTTGCTTGAAAGGAGATGTGA
TCATTTCCGGAAATAAAGATAGGGTTGAGTTTAGAGATAACATTGTGACGCGGCCTTATTTTGAAGAAAATGAAGAA
AAAGTTGAGACAGCAGATATTAATTCAGATAAGCAAGAAGCAGAAGAGCGCTCTTATTAGAGAACATTGAGCAGAG
CTTTATTACTGCAACTAATCAGACCTTTTTCTTAGAGGAAGAGAAACTCCCATCAGAAGCTTTTATCTCTGCTGAAG
AACTTTCAAAGAGAAGAGAATGTGCTGGTGGGGCGATTTTTGCAAAACGGGTCTACATTACGGATAATAAAGAACCT
ATCTTGTTTTCGCATAATTTTTCTGATGTTTATGGGGGAGCTATTTTTACGGGTTCTCTACAGGAAACTGATAAACA
AGATGTTGTAACTCCTGAAGTTGTGATATCAGGCAACGATGGGGATGTCATTTTTTCTGGAAATGCAGCTAAACATG
ATAAGCATTTACCTGATACAGGTGGTGGAGCCATTTGTACACAGAATTTGACGATTTCCCAAAACAATGGGAATGTC
TTGTTCTTGAACAATTTTGCTTGTTCTGGTGGAGCAGTTCGCATAGAGGATCATGGAGAAGTTCTTTTAGAGGCTTT
TGGGGGAGATATTATTTTCAATGGAAACTCTTCTTTCAGAGCTCAAGGATCGGATGCGATCTATTTTGCTGGTAAGG
ACTCTAGAATTAAAGCTTTAAATGCTACTGAAGGACATGCGATTGTGTTCCAAGATGCATTGGTGTTTGAAAATATA
GAAGAAAGAAAGTCTTCGGGACTATTGGTGATTAACTCTCAGGAAAATGAGGGTTATACGGGATCCGTCCGATTTTT
AGGATCTGAAAGTAAGGTTCCTCAATGGATTCATGTGCAACAGGGAGGTCTTGAGTTGCTACATGGAGCTATTTTAT
GTAGTTATGGGGTTAAACAAGATCCTAGAGCTAAAATAGTATTATCTGCTGGATCTAAATTGAAGATTCTAGATTCA
GAGCAAGAAAATAACGCAGAAATTGGAGATCTTGAAGATTCTGTTAATTCAGAAAAAACACCATCTCTTTGGATTGG
GAAGAACGCTCAAGCAAAAGTCCCTCTGGTTGATATCCATACTATTTCTATTGATTTAGCATCATTTTCTTCTAAAG
CTCAGGAAACCCCTGAGGAAGCTCCACAAGTCATCGTCCCTAAGGGAAGTTGTGTCCACTCGGGAGAGTTAAGTTTG
GAGTTGGTTAATACAACAGGAAAAGGTTATGAGAATCATGCGTTGTTAAAAAATGATACTCAGGTTTCTCTCATGTC
TTTCAAAGAGGAAAATGATGGATCTTTAGAAGATTTGAGTAAGTTGTCTGTTTCGGATTTACGCATTAAAGTTTCTA
CTCCAGATATTGTAGAAGAAACTTATGGCCATATGGGGGATTGGTCTGAAGCTACAATTCAAGATGGGGCTCTTGTC
ATTAATTGGCATCCTACTGGATATAAATTAGATCCGCAAAAAGCTGGTTCTTTGGTATTCAATGCATTATGGGAGGA
AGAGGCTGTATTGTCTACTCTAAAAAATGCTCGGATTGCCCATAACCTTACCATTCAGAGAATGGAATTTGATTATT
CTACAAATGCTTGGGGATTAGCTTTTAGTAGCTTTAGAGAGCTATCTTCAGAGAAGCTTGTTTCTGTTGATGGATAT
AGAGGCTCTTATATAGGGGCTTCTGCAGGCATTGATACTCAGTTGATGGAAGATTTTGTTTTGGGAATCAGCACGGC
TTCCTTCTTCGGGAAAATGCATAGTCAGAATTTTGATGCAGAGATTTCTCGACATGGTTTTGTTGGTTCGGTCTATA
CAGGCTTCCTAGCTGGGGCCTGGTTCTTCAAGGGGCAGTACAGTCTTGGCGAAACACATAACGATATGACAACTCGT
TACGGGGTTTTGGGAGAATCTAATGCTACTTGGAAGTCTCGAGGAGTACTAGCAGATGCTTTAGTTGAATATCGTAG
TTTAGTCGGTCCAGCACGACCTAAATTTTATGCTTTGCATTTTAATCCTTATGTCGAGGTATCTTATGCATCTGCGA
AGTTCCCTAGTTTTGTAGAACAAGGAGGAGAAGCTCGTGCTTTTGAAGAAACCTCTTTAACAAACATTACCGTTCCC
TTTGGTATGAAATTTGAACTATCTTTTACAAAAGGACAGTTTTCAGAGACTAATTCTCTTGGAATAGGTTGTGCATG
GGAAATGTATCGGAAAGTCGAAGGAAGATCTGTAGAGCTACTAGAAGCTGGTTTTGATTGGGAAGGATCTCCTATAG
ATCTCCCTAAACAAGAGCTGAGAGTGGCTTTAGAAAACAATACGGAATGGAGTTCGTATTTTAGTACAGCTCTAGGA
GTAACAGCATTTTGTGGAGGATTTTCTTCTATGGATAATAAACTAGGATACGAAGCGAATGCTGGAATGCGTTTGAT
TTTCTAG

SEQ ID NO: 132 - TC0197 fragment protein sequence
NCSDLYAVGSSADHPAYLIPQAGLLLDHIKDIFIGPKDSQDKGQYKLIIGEAGSFQDSNAETLPQKVEHSTLFSVTT
PIIVQGIDQQDQVSSQGLVCNFSGDHSEEIFERESFLGIAFLGNGSKDGITLTDIKSSLSGAALYSSDDLIFERIKG
DIELSSCSSLERGGACSAQSILIHDCQGLTVKHCAAGVNVEGVSASDHLGFGGGAFSTTSSLSGEKSLYMPAGDIVV
ATCDGPVCFEGNSAQLANGGAIAASGKVLFVANEKKISFTDNQALSGGAISASSSISFQNCAELVFKSNLAKGVKDK
CSLGGGALASLESVVLKDNLGITYEKNQSYSEGGAIFGKDCEIFENRGPVVFRDNTAALGGGAILAQQTVAICGNKS
GISFEGSKSSFGGAIACGNFSSENNSSALGSIDISNNLGDISFLRTLCTTSDLGQTDYQGGGALFAENISLSENAGA
ITFKDNIVKTFASNGKMLGGGAILASGNVLISKNSGEISFVGNARAPQAIPTRSSDELSFGAQLTQTTSGCSGGGAL
FGKEVAIVQNATVVFEQNRLQCGEQETHGGGGAVYGMESASIIGNSFVRFGNNYAVGNQISGGALLSKKVRLAENTR
VDFSRNIATFCGGAVQVSDGSCELINNGYVLFRDNRGQTFGGAISCLKGDVIISGNKDRVEFRDNIVTRPYFEENEE
KVETADINSDKQEAEERSLLENIEQSFITATNQTFFLEEEKLPSEAFISAEELSKRRECAGGAIFAKRVYITDNKEP
ILFSHNFSDVYGGAIFTGSLQETDKQDVVTPEVVISGNDGDVIFSGNAAKHDKHLPDTGGGAICTQNLTISQNNGNV
LFLNNFACSGGAVRIEDHGEVLLEAFGGDIIFNGNSSFRAQGSDAIYFACKDSRIKALNATEGHAIVFQDALVFENI
EERKSSGLLVINSQENEGYTGSVRFLGSESKVPQWIHVQQGGLELLHGAILCSYGVKQDPRAKIVLSAGSKLKILDS
EQENNAEIGDLEDSVNSEKTPSLWIGKNAQAKVPLVDIHTISIDLASFSSKAQETPEEAPQVIVPKGSCVHSGELSL
ELVNTTGKGYENHALLKNDTQVSLMSFKEENDGSLEDLSKLSVSDLRIKVSTPDIVEETYGHMGDWSEATIQDGALV
INWHPTGYKLDPQKAGSLVFNALWEEEAVLSTLKNARIAHNLTIQRMEFDYSTNAWGLAFSSFRELSSEKLVSVDGY
RGSYIGASAGIDTQLMEDFVLGISTASFFGKMHSQNFDAEISRHGFVGSVYTGFLAGAWFFKGQYSLGETHNDMTTR
YGVLGESNATWKSRGVLADALVEYRSLVGPARPKFYALHFNPYVEVSYASAKFPSFVEQGGEARAFEETSLTNITVP
FGMKFELSFTKGQFSETNSLGIGCAWEMYRKVEGRSVELLEAGFDWEGSPIDLPKQELRVALENNTEWSSYFSTALG
VTAFCGGFSSMDNKLGYEANAGMRLIF SEQ ID NO: 133 - TC0261 fragment nucleotide sequence
ACTCGAGAAGTCCCTCCTTCGATTCTTTTAAAGCCTATACTAAATCCATACCATATGACCGGGTTATTTTTTCCCAA
GGTTAATTTGCTTGGAGACACACATAATCTCACTGATTACCATTTGGATAATCTAAAATGCATTCTGGCTTGCCTAC
AAAGAACTCCTTATGAAGGAGCTGCTTTCACAGTAACCGATTACTTAGGTTTTTCAGATACACAAAAGGATGGTATT
TTTTGTTTTAAAAATCTTACTCCAGAGAGTGGAGGGGTTATTGGTTCCCCAACTCAAAACACTCCTACTATAAAAAT
TCATAATACAATCGGCCCCGTTCTTTTCGAAAATAATACCTGTCATAGACTGTGGACACAGACCGATCCCGAAAATG
AAGGAAACAAAGCACGCGAAGGCGGGGCAATTCATGCTGGGGACGTTTACATAAGCAATAACCAGAACCTTGTCGGA
TTCATAAAGAACTTTGCTTATGTTCAAGGTGGAGCTATTAGTGCTAATACTTTTGCCTATAAAGAAAATAAATCGAG
CTTTCTTTGCCTAAATAACTCTTGTATACAAACTAAGACGGGAGGGAAAGGTGGTGCTATTTACGTTAGTACGAGCT
GCTCTTTCGAGAACAATAACAAGGATCTGCTTTTCATCCAAAACTCCGGCTGTGCAGGAGGAGCTATCTTCTCTCCA
ACCTGTTCTCTAATAGGAAACCAAGGAGATATTGTTTTTTACAGCAACCACGGTTTTAAAAATGTTGATAATGCAAC
TAACGAATCTGGGGATGGAGGAGCTATTAAAGTAACTACCCGCTTGGACATCACCAATAATGGTAGTCAAATCTTTT
TTTCTGATAATATCTCAAGAAATTTTGGAGGAGCTATTCATGCTCCTTGTCTTCATCTTGTTGGTAATGGGCCAACC
TATTTTACAAACAATATAGCTAATCACACAGGTGGGGCTATTTATATAACAGGAACAGAAACCTCAAAGATTTCTGC
AGATCACCATGCTATTATTTTTGATAATAACATTTCTGCAAACGCCACCAATGCGGACGGATCTAGCAGCAACACTA -continued

SEQUENCE LISTING

ATCCTCCTCACAGAAATGCGATCACTATGGACAATTCCGCTGGAGGAATAGAACTTGGTGCAGGGAAGAGCCAGAAT
CTTATTTTCTATGATCCTATTCAAGTGACGAATGCTGGAGTTACCGTAGACTTCAATAAGGATGCCTCCCAAACCGG
ATGTGTAGTTTTCTCTGGAGCGACTGTCCTTTCTGCAGATATTTCTCAGGCTAATTTGCAAACTAAAACACCTGCAA
CGCTTACTCTCAGTCACGGTCTTCTGTGTATCGAAGATCGTGCTCAGCTCACAGTGAACAATTTTACACAAACAGGA
GGGATTGTAGCCTTAGGAAATGGAGCAGTTTTAAGCAGCTACCAACACAGCACTACAGACGCCACTCAAACTCCCCC
TACAACCACCACTACAGATGCTTCCGTAACTCTTAATCACATTGGATTAAATCTCCCCTCTATTCTTAAGGATGGAG
CAGAGATGCCTCTATTATGGGTAGAACCTATAAGCACAACTCAAGGTAACACTACAACATATACGTCAGATACCGCG
GCTTCCTTCTCATTAAATGGAGCCACACTCTCTCTCATTGATGAAGATGGAAATTCTCCCTATGAAAACACGGACCT
CTCTCGTGCATTGTACGCTCAACCTATGCTAGCAATTTCTGAGGCCAGTGATAACCAATTGCAATCCGAAAGCATGG
ACTTTTCTAAAGTTAATGTTCCTCACTATGGATGGCAAGGACTTTGGACCTGGGGGTGGGCAAAAACTGAAAATCCA
ACAACAACTCCTCCAGCAACAATTACTGATCCGAAAAAAGCTAATCAGTTTCATAGAACTTTATTATTAACGTGGCT
CCCTGCTGGTTATATCCCCAGCCCTAAACATAAAAGCCCTTTAATAGCTAATACCTTGTGGGGGAATATACTTTTTG
CAACGGAAAACTTAAAAAATAGCTCAGGGCAAGAACTTCTTGATCGTCCTTTCTGGGGAATTACAGGAGGGGGCTTG
GGGATGATGGTCTATCAAGAACCTAGAAAAGACCATCCTGGATTCCACATGCATACCTCCGGATATTCAGCAGGAAT
GATTACAGGAAACACACATACCTTCTCATTACGATTCAGCCAGTCCTATACAAAACTCAATGAACGTTATGCCAAGA
ACTATGTGTCTTCTAAAAATTACTCTTGCCAAGGGGAAATGCTTTTGTCCTTACAAGAAGGACTCATGCTGACTAAA
CTAATTGGTCTCTATAGTTATGGGAATCACAACAGCCACCATTTCTATACCCAAGGAGAAGACCTATCGTCTCAAGG
GGAGTTCCATAGTCAGACTTTTGGAGGGGCTGTCTTTTTTGATCTACCTCTGAAACCTTTTGGAAGAACACACATAC
TTACAGCTCCTTTCTTAGGTGCCATTGGTATGTATTCTAAGCTGTCTAGCTTTACAGAAGTAGGAGCCTATCCAAGA
ACCTTTATTACAGAAAACGCCTTTAATCAATGTCCTGATTCCTATCGGAGTAAAAGGTAGCTTCATGAATGCCACCCA
TAGACCTCAGGCCTGGACTGTAGAGCTTGCTTACCAACCTGTTCTTTACAGACAAGAACCTAGTATCTCTACCCAAT
TACTCGCTGGTAAAGGTATGTGGTTTGGGCATGGAAGTCCTGCATCTCGCCACGCTCTAGCTTATAAAATTTCACAG
AAAACACAGCTTTTGCGATTTGCAACACTTCAACTCCAGTATCACGGATACTATTCGTCTTCCACTTTCTGTAATTA
TCTGAATGGAGAGGTATCTTTACGTTTC

SEQ ID NO: 134 - TC0261 fragment protein sequence
TREVPPSILLKPILNPYHMTGLFFPKVNLLGDTHNLTDYHLDNLKCILACLQRTPYEGAAFTVTDYLGFSDTQKDGI
FCFKNLTPESGGVIGSPTQNTPTIKIHNTIGPVLFENNTCHRLWTQTDPENEGNKAREGGAIHAGDVYISNNQNLVG
FIKNFAYVQGGAISANTFAYKENKSSFLCLNNSCIQTKTGGKGGAIYVSTSCSFENNNKDLLFIQNSGCAGGAIFSP
TCSLIGNQGDIVFYSNHGFKNVDNATNESGDGGAIKVTTRLDITNNGSQIFFSDNISRNFGGAIHAPCLHLVGNGPT
YFTNNIANHTGGAIYITGTETSKISADHHAIIFDNNISANATNADGSSSNTNPPHRNAITMDNSAGGIELGAGKSQN
LIFYDPIQVTNAGVTVDFNKDASQTGCVVFSGATVLSADISQANLQTKTPATLTLSHGLLCIEDRAQLTVNNFTQTG
GIVALGNGAVLSSYQHSTTDATQTPPTTTTDASVTLNHIGLNLPSILKDGAEMPLLWVEPISTTQGNTTTYTSDTA
ASFSLNGATLSLIDEDGNSPYENTDLSRALYAQPMLAISEASDNQLQSESMDFSKVNVPHYGWQGLWTWGWAKTENP
TTTPPATITDPKKANQFHRTLLLTWLPAGYIPSPKHKSPLIANTLWGNILFATENLKNSSGQELLDRPFWGITGGGL
GMMVYQEPRKDHPGFHMHTSGYSAGMITGNTHTFSLRFSQSYTKLNERYAKNYVSSKNYSCQGEMLLSLQEGLMLTK
LIGLYSYGNHNSHHFYTQGEDLSSQGEFHSQTFGGAVFFDLPLKPFGRTHILTAPFLGAIGMYSKLSSFTEVGAYPR
TFITETPLINVLIPIGVKGSFMNATHRPQAWTVELAYQPVLYRQEPSISTQLLAGKGMWFGHGSPASRHALAYKISQ
KTQLLRFATLQLQYHGYYSSSTFCNYLNGEVSLRF SEQ ID NO: 135 - CT600 nucleotide sequence
ATGAGAAAGACTATTTTTAAAGCGTTTAATTTATTATTCTCCCTTCTTTTTCTTTCTTCATGCTCTTATCCTTGCAG
AGATTGGGAATGCCATGGTTGCGACTCCGCAAGACCTCGTAAATCCTCTTTTGGATTCGTACCTTTCTACTCCGATG
AAGAAATTCAACAAGCTTTTGTTGAAGATTTTGATTCCAAAGAAGAGCAGCTGTACAAAACGAGCGCACAGAGTACC
TCTTTCCGAAATATCACTTTCGCTACAGATAGTTATTCTATTAAAGGAGAGGATAACCTCACGATTCTTGCAAGCTT
AGTTCGTCATTTGCATAAATCTCCTAAAGCTACGCTATATATAGAGGGCCATACAGATGAACGTGGAGCTGCAGCTT
ATAACCTAGCTTTAGGAGCTCGTCGTGCGAATGCTGTAAAACAATACCTCATCAAACAGGGAATCGCTGCAGACCGC
TTATTCACTATTTCTTACGGAAAAGAACATCCTGTTCATCCAGGCCATAATGAATTAGCTTGGCAACAAAATCGTCG
TACTGAATTTAAGATCCATGCTCGCTAA SEQ ID NO: 136 - CT600 protein sequence
MRKTIFKAFNLLFSLLFLSSCSYPCRDWECHGCDSARPRKSSFGFVPFYSDEEIQQAFVEDFDSKEEQLYKTSAQST
SFRNITFATDSYSIKGEDNLTILASLVRHLHKSPKATLYIEGHTDERGAAAYNLALGARRANAVKQYLIKQGIAADR
LFTISYGKEHPVHPGHNELAWQQNRRTEFKIHAR SEQ ID NO: 137 - CT600 fragment nucleotide sequence
TGCTCTTATCCTTGCAGAGATTGGGAATGCCATGGTTGCGACTCCGCAAGACCTCGTAAATCCTCTTTTGGATTCGT
ACCTTTCTACTCCGATGAAGAAATTCAACAAGCTTTTGTTGAAGATTTTGATTCCAAAGAAGAGCAGCTGTACAAAA
CGAGCGCACAGAGTACCTCTTTCCGAAATATCACTTTCGCTACAGATAGTTATTCTATTAAAGGAGAGGATAACCTC
ACGATTCTTGCAAGCTTAGTTCGTCATTTGCATAAATCTCCTAAAGCTACGCTATATATAGAGGGCCATACAGATGA
ACGTGGAGCTGCAGCTTATAACCTAGCTTTAGGAGCTCGTCGTGCGAATGCTGTAAAACAATACCTCATCAAACAGG
GAATCGCTGCAGACCGCTTATTCACTATTTCTTACGGAAAAGAACATCCTGTTCATCCAGGCCATAATGAATTAGCT
TGGCAACAAAATCGTCGTACTGAATTTAAGATCCATGCTCGC SEQ ID NO: 138 - CT600 fragment protein sequence
CSYPCRDWECHGCDSARPRKSSFGFVPFYSDEEIQQAFVEDFDSKEEQLYKTSAQSTSFRNITFATDSYSIKGEDNL
TILASLVRHLHKSPKATLYIEGHTDERGAAAYNLALGARRANAVKQYLIKQGIAADRLFTISYGKEHPVHPGHNELA
WQQNRRTEFKIHAR SEQ ID NO: 139 - CT823 nucleotide sequence
ATGATGAAAAGATTATTATGTGTGTTGCTATCGACATCAGTTTTCTCTTCGCCAATGCTAGGCTATAGTGCGTCAAA
GAAAGATTCTAAGGCTGATATTTGTCTTGCAGTATCCTCAGGAGATCAAGAGGTTTCACAAGAAGATCTGCTCAAAG
AAGTATCCCGAGGATTTTCTCGGGTCGCTGCTAAGGCAACGCCTGGAGTTGTATATATAGAAAATTTTCCTAAAACA
GGGAACCAGGCTATTGCTTCTCCAGGAAACAAAAGAGGCTTTCAAGAGAACCCTTTTGATTATTTTAATGACGAATT
TTTTAATCGATTTTTTGGATTGCCTTCGCATAGAGAGCAGCAGCGTCCGCAGCAGCGTGATGCTGTAAGAGGAACTG
GGTTCATTGTTTCTGAAGATGGTTATGTTGTTACTAACCATCATGTAGTCGAGGATGCAGGAAAAATTCATGTTACT
CTCCACGACGGACAAAAATACACAGCTAAGATCGTGGGGTTAGATCCAAAAACAGATCTTGCTGTGATCAAAATTCA -continued

SEQUENCE LISTING

AGCGGAGAAATTACCATTTTTGACTTTTGGGAATTCTGATCAGCTGCAGATAGGTGACTGGGCTATTGCTATTGGAA
ATCCTTTTGGATTGCAAGCAACGGTCACTGTCGGGGTCATTAGTGCTAAAGGAAGAAATCAGCTACATATTGTAGAT
TTCGAAGACTTTATTCAAACAGATGCTGCCATTAATCCTGGGAATTCAGGCGGTCCATTGTTAAACATCAATGGTCA
AGTTATCGGGGTTAATACTGCCATTGTCAGTGGTAGCGGGGGATATATTGGAATAGGGTTTGCTATTCCTAGCTTGA
TGGCTAAACGAGTCATTGATCAATTGATTAGTGATGGGCAGGTAACAAGAGGCTTTTTGGGAGTTACCTTGCAACCG
ATAGATTCTGAATTGGCTACTTGTTACAAATTGGAAAAAGTGTACGGAGCTTTGGTGACGGATGTTGTTAAAGGTTC
TCCAGCAGAAAAAGCAGGGCTGCGCCAAGAAGATGTCATTGTGGCTTACAATGGAAAAGAAGTAGAGTCTTTGAGTG
CGTTGCGTAATGCCATTTCCCTAATGATGCCAGGGACTCGTGTTGTTTTAAAAATCGTTCGTGAAGGGAAAACAATC
GAGATACCTGTGACGGTTACACAGATCCCAACAGAGGATGGCGTTTCAGCGTTGCAGAAGATGGGAGTCCGTGTTCA
GAACATTACTCCAGAAATTTGTAAGAAACTCGGATTGGCAGCAGATACCCGAGGGATTCTGGTAGTTGCTGTGGAGG
CAGGCTCGCCTGCAGCTTCTGCAGGCGTCGCTCCTGGACAGCTTATCTTAGCGGTGAATAGGCAGCGAGTCGCTTCC
GTTGAAGAGTTAAATCAGGTTTTGAAAAACTCGAAAGGAGAGAATGTTCTCCTTATGGTTTCTCAAGGAGATGTGGT
GCGATTCATCGTCTTGAAATCAGACGAGTAG

SEQ ID NO: 140 - CT823 protein sequence
MMKRLLCVLLSTSVFSSPMLGYSASKKDSKADICLAVSSGDQEVSQEDLLKEVSRGFSRVAAKATPGVVYIENFPKT
GNQAIASPGNKRGFQENPFDYFNDEFFNRFFGLPSHREQQRPQQRDAVRGTGFIVSEDGYVVTNHHVVEDAGKIHVT
LHDGQKYTAKIVGLDPKTDLAVIKIQAEKLPFLTFGNSDQLQIGDWAIAIGNPFGLQATVTVGVISAKGRNQLHIVD
FEDFIQTDAAINPGNSGGPLLNINGQVIGVNTAIVSGSGGYIGIGFAIPSLMAKRVIDQLISDGQVTRGFLGVTLQP
IDSELATCYKLEKVYGALVTDVVKGSPAEKAGLRQEDVIVAYNGKEVESLSALRNAISLMMPGTRVVLKIVREGKTI
EIPVTVTQIPTEDGVSALQKMGVRVQNITPEICKKLGLAADTRGILVVAVEAGSPAASAGVAPGQLILAVNRQRVAS
VEELNQVLKNSKGENVLLMVSQGDVVRFIVLKSDE SEQ ID NO: 141 - CT823 fragment nucleotide sequence
TCGCCAATGCTAGGCTATAGTGCGTCAAAGAAAGATTCTAAGGCTGATATTTGTCTTGCAGTATCCTCAGGAGATCA
AGAGGTTTCACAAGAAGATCTGCTCAAAGAAGTATCCCGAGGATTTTCTCGGGTCGCTGCTAAGGCAACGCCTGGAG
TTGTATATATAGAAAATTTTCCTAAAACAGGGAACCAGGCTATTGCTTCTCCAGGAAACAAAAGAGGCTTTCAAGAG
AACCCTTTTGATTATTTTAATGACGAATTTTTTAATCGATTTTTTGGATTGCCTTCGCATAGAGAGCAGCAGCGTCC
GCAGCAGCGTGATGCTGTAAGAGGAACTGGGTTCATTGTTTCTGAAGATGGTTATGTTGTTACTAACCATCATGTAG
TCGAGGATGCAGGAAAAATTCATGTTACTCTCCACGACGGACAAAAATACACAGCTAAGATCGTGGGGTTAGATCCA
AAAACAGATCTTGCTGTGATCAAAATTCAAGCGGAGAAATTACCATTTTTGACTTTTGGGAATTCTGATCAGCTGCA
GATAGGTGACTGGGCTATTGCTATTGGAAATCCTTTTGGATTGCAAGCAACGGTCACTGTCGGGGTCATTAGTGCTA
AAGGAAGAAATCAGCTACATATTGTAGATTTCGAAGACTTTATTCAAACAGATGCTGCCATTAATCCTGGGAATTCA
GGCGGTCCATTGTTAAACATCAATGGTCAAGTTATCGGGGTTAATACTGCCATTGTCAGTGGTAGCGGGGGATATAT
TGGAATAGGGTTTGCTATTCCTAGCTTGATGGCTAAACGAGTCATTGATCAATTGATTAGTGATGGGCAGGTAACAA
GAGGCTTTTTGGGAGTTACCTTGCAACCGATAGATTCTGAATTGGCTACTTGTTACAAATTGGAAAAAGTGTACGGA
GCTTTGGTGACGGATGTTGTTAAAGGTTCTCCAGCAGAAAAAGCAGGGCTGCGCCAAGAAGATGTCATTGTGGCTTA
CAATGGAAAAGAAGTAGAGTCTTTGAGTGCGTTGCGTAATGCCATTTCCCTAATGATGCCAGGGACTCGTGTTGTTT
TAAAAATCGTTCGTGAAGGGAAAACAATCGAGATACCTGTGACGGTTACACAGATCCCAACAGAGGATGGCGTTTCA
GCGTTGCAGAAGATGGGAGTCCGTGTTCAGAACATTACTCCAGAAATTTGTAAGAAACTCGGATTGGCAGCAGATAC
CCGAGGGATTCTGGTAGTTGCTGTGGAGGCAGGCTCGCCTGCAGCTTCTGCAGGCGTCGCTCCTGGACAGCTTATCT
TAGCGGTGAATAGGCAGCGAGTCGCTTCCGTTGAAGAGTTAAATCAGGTTTTGAAAAACTCGAAAGGAGAGAATGTT
CTCCTTATGGTTTCTCAAGGAGATGTGGTGCGATTCATCGTCTTGAAATCAGACGAG SEQ ID NO: 142 - CT823 fragment protein sequence
SPMLGYSASKKDSKADICLAVSSGDQEVSQEDLLKEVSRGFSRVAAKATPGVVYIENFPKTGNQAIASPGNKRGFQE
NPFDYFNDEFFNRFFGLPSHREQQRPQQRDAVRGTGFIVSEDGYVVTNHHVVEDAGKIHVTLHDGQKYTAKIVGLDP
KTDLAVIKIQAEKLPFLTFGNSDQLQIGDWAIAIGNPFGLQATVTVGVISAKGRNQLHIVDFEDFIQTDAAINPGNS
GGPLLNINGQVIGVNTAIVSGSGGYIGIGFAIPSLMAKRVIDQLISDGQVTRGFLGVTLQPIDSELATCYKLEKVYG
ALVTDVVKGSPAEKAGLRQEDVIVAYNGKEVESLSALRNAISLMMPGTRVVLKIVREGKTIEIPVTVTQIPTEDGVS
ALQKMGVRVQNITPEICKKLGLAADTRGILVVAVEAGSPAASAGVAPGQLILAVNRQRVASVEELNQVLKNSKGENV
LLMVSQGDVVRFIVLKSDE SEQ ID NO: 143 - TC0106 nucleotide sequence
ATGCTAACTAACTTTACCTTTCGCAACTGTCTTTTGTTTTTCGTCACATTGTCCAGTGTCCCTGTTTTCTCGGCACC
CCAACCTCGCGTAACGCTTCCTAGTGGAGCCAATAAAATCGGATCAGAAGCTTGGATAGAGCAAAAAGTCCGTCAAT
ATCCAGAACTTTTGTGGTTAGTTGAACCTTCTCCTGCAGGAACTTCTTTAAACGCTCCTTCGGGGATGATCTTTTCT
CCCCTATTGTTCCAAAAGAAAGTCCCTGCTTTTGATATCGCAGTACGCAGTCTGATTCACCTACACCTGCTTATCCA
GGGCTCCCGCCAAGCTTATGCTCAGCTTGTCCAGCTGCAGGCTAATGAATCCCCTATGACATTTAAACAGTTCCTTA
CCCTACATAAGCAGCTCTCCTTATTCCTAAATTCTCCTAAAGAGTTTTATGATTCCGTCAAAATTTTAGAAACTGCT
ATCATCCTACGCCACTTAGGATGTTCAACAAAAGCTGTTGCCACATTTAAGCCTTATTTTTCAGAAACGCAAAAAGA
GGTCTTCTATACAAAAGCTTTGCATGTTCTGCATACTTTCCCAGAATTGAGCCCTTCGTTTGCTAGACTCTCTCCAG
AACAAAAAACGCTCTTCTTCTCATTGAGAAAGCTCGCTAATTATGATGAGTTACTTTCCCTGACAAATGCCCCTAGT
TTACAACTACTATCTGCTGTACGCTCGCGACGCGCGCTTTTGGCTCTAGACTTGTATCTCTATGCTTTAGATTTTTG
TGGAGAACAGGGGATATCCTCTCAGTTTCATATGGACTTTTCTCCTTTACAGTCCATGTTGCAACAATATGCTACGG
TTGAAGAAGCCTTCTCCCGCTACTTTACTTACCGAGCTAATCGCCTAGGATTTGCGGGTTCTTCTCGAACTGAAATG
GCCTTAGTTAGAATAGCTACTTTAATGAACCTATCCCCTTCAGAAGCTGCTATTTTAACAACAAGCTTTAAGTCTCT
TTCCTTGGAAGATGCTGAAAGCTTAGTGAATAGCTTTTATACAAATAAGGGAGACTCTTTAGCTCTTTCTTTACGAG
GACTACCAACTCTTATATCTGAACTAACACGCGCTGCGCATGGAAATACGAATGCGGAAGCTCGAGCTCAGCAAATT
TACGCCACAACGTTATCATTGGTAGCAAAAAGCTTGAAAGCTCACAAAGAGATGCAAAACAAACAAATTCTTCCCGA
AGAAGTCGTTTTAGATTTCTCTGAAACTGCTTCTTCCTGTCAAGGATTGGACATCTTCTCTGAGAACGTTGCTGTTC
AAATCCACTTGAATGGATCTGTCAGCATCCATCTATAA SEQ ID NO: 144 - TC0106 protein sequence
MLTNFTFRNCLLFFVTLSSVPVFSAPQPRVTLPSGANKIGSEAWIEQKVRQYPELLWLVEPSPAGTSLNAPSGMIFS
PLLFQKKVPAFDIAVRSLIHLHLLIQGSRQAYAQLVQLQANESPMTFKQFLTLHKQLSLFLNSPKEFYDSVKILETA
IILRHLGCSTKAVATFKPYFSETQKEVFYTKALHVLHTFPELSPSFARLSPEQKTLFFSLRKLANYDELLSLTNAPS -continued

SEQUENCE LISTING

LQLLSAVRSRRALLALDLYLYALDFCGEQGISSQFHMDFSPLQSMLQQYATVEEAFSRYFTYRANRLGFAGSSRTEM
ALVRIATLMNLSPSEAAILTTSFKSLSLEDAESLVNSFYTNKGDSLALSLRGLPTLISELTRAAHGNTNAEARAQQI
YATTLSLVAKSLKAHKEMQNKQILPEEVVLDFSETASSCQGLDIFSENVAVQIHLNGSVSIHL

SEQ ID NO: 145 - TC0106 fragment nucleotide sequence
TCAGAAGCTTGGATAGAGCAAAAAGTCCGTCAATATCCAGAACTTTTGTGGTTAGTTGAACCTTCTCCTGCAGGAAC
TTCTTTAAACGCTCCTTCGGGGATGATCTTTTCTCCCCTATTGTTCCAAAAGAAAGTCCCTGCTTTTGATATCGCAG
TACGCAGTCTGATTCACCTACACCTGCTTATCCAGGGCTCCCGCCAAGCTTATGCTCAGCTTGTCCAGCTGCAGGCT
AATGAATCCCCTATGACATTTAAACAGTTCCTTACCCTACATAAGCAGCTCTCCTTATTCCTAAATTCTCCTAAAGA
GTTTTATGATTCCGTCAAAATTTTAGAAACTGCTATCATCCTACGCCACTTAGGATGTTCAACAAAAGCTGTTGCCA
CATTTAAGCCTTATTTTTCAGAAACGCAAAAAGAGGTCTTCTATACAAAAGCTTTGCATGTTCTGCATACTTTCCCA
GAATTGAGCCCTTCGTTTGCTAGACTCTCTCCAGAACAAAAAACGCTCTTCTTCTCATTGAGAAAGCTCGCTAATTA
TGATGAGTTACTTTCCCTGACAAATGCCCCTAGTTTACAACTACTATCTGCTGTACGCTCGCGACGCGCGCTTTTGG
CTCTAGACTTGTATCTCTATGCTTTAGATTTTTGTGGAGAACAGGGGATATCCTCTCAGTTTCATATGGACTTTTCT
CCTTTACAGTCCATGTTGCAACAATATGCTACGGTTGAAGAAGCCTTCTCCCGCTACTTTACTTACCGAGCTAATCG
CCTAGGATTTGCGGGTTCTTCTCGAACTGAAATGGCCTTAGTTAGAATAGCTACTTTAATGAACCTATCCCCTTCAG
AAGCTGCTATTTTAACAACAAGCTTTAAGTCTCTTTCCTTGGAAGATGCTGAAAGCTTAGTGAATAGCTTTTATACA
AATAAGGGAGACTCTTTAGCTCTTTCTTTACGAGGACTACCAACTCTTATATCTGAACTAACACGCGCTGCGCATGG
AAATACGAATGCGGAAGCTCGAGCTCAGCAAATTTACGCCACAACGTTATCATTGGTAGCAAAAAGCTTGAAAGCTC
ACAAAGAGATGCAAAACAAACAAATTCTTCCCGAAGAAGTCGTTTTAGATTTCTCTGAAACTGCTTCTTCCTGTCAA
GGATTGGACATCTTCTCTGAGAACGTTGCTGTTCAAATCCACTTGAATGGATCTGTCAGCATCCATCTA SEQ ID NO: 146 - TC0106 fragment protein sequence
SEAWIEQKVRQYPELLWLVEPSPAGTSLNAPSGMIFSPLLFQKKVPAFDIAVRSLIHLHLLIQGSRQAYAQLVQLQA
NESPMTFKQFLTLHKQLSLFLNSPKEFYDSVKILETAIILRHLGCSTKAVATFKPYFSETQKEVFYTKALHVLHTFP
ELSPSFARLSPEQKTLFFSLRKLANYDELLSLTNAPSLQLLSAVRSRRALLALDLYLYALDFCGEQGISSQFHMDFS
PLQSMLQQYATVEEAFSRYFTYRANRLGFAGSSRTEMALVRIATLMNLSPSEAAILTTSFKSLSLEDAESLVNSFYT
NKGDSLALSLRGLPTLISELTRAAHGNTNAEARAQQIYATTLSLVAKSLKAHKEMQNKQILPEEVVLDFSETASSCQ
GLDIFSENVAVQIHLNGSVSIHL SEQ ID NO: 147 - TC0431 nucleotide sequence
ATGCCCCACTCTCCTTTTTTATATGTTGTTCAACCGCATTCTGTTTTTAATCCTAGATTGGGAGAGCGGCACCCTAT
TACTTTAGATTTCATCAAAGAAAAGAATCGATTAGCTGATTTTATTGAAAACCTACCTTTAGAAATTTTTGGAGCCC
CTTCTTTCTTGGAAAATGCTTCTTTAGAAGCCTCTTATGTCTTGTCTAGGGAATCCACAAAAGATGGCACTCTTTTT
ACCGTTCTAGAACCCAAACTATCTGCCTGCGTAGCTACTTGCCTTGTGGATTCTTCTATTCCTATGGAGCCCGATAA
CGAGCTCTTAGAAGAAATTAAACACACTTTGTTGAAAAGCTCTTGTGATGGCGTACAATATCGTGTAACCCGAGAGA
CTCTCCAAAACAAAGATGAAGCCCCCAGAGTCTCTTTAGTTGCTGATGATATCGAACTTATCCGCAATGTAGATTTT
TTAGGACGTTCCGTTGATATTGTAAAATTGGATCCCTTGAATATTCCTAATACCGTAAGCGAGGAGAATGCTCTCGA
TTACTCTTTCACAAGGGAAACCGCCAAACTTAGCCCTGACGGACGAGTTGGCATCCCTCAAGGGACAAAAATTTTGC
CAGCTCCCTCTCTTGAAGTTGAAATTAGCACCTCTATTTTTGAGGAAACCTCTTCTTTTGAACAAAACTTTTCTTCC
TCTATTACTTTTTGTGTACCACCTCTTACCTCTTTTTCTCCTTTGCAAGAACCTCCTCTAGTGGGAGCTGGACAGCA
GGAAATTCTTGTGACTAAAAAGCACTTATTCCCTAGCTATACCCCTAAACTTATTGATATTGTCAAACGACACAAAA
GAGACGCAAAGATTCTAGTAAACAAGATCCAGTTCGAGAAACTATGGAGAAGTCATGCCAAAAGTCAAATCTTAAAA
GAAGGCTCTGTTCGCTTGGATTTACAAGGATTTACAGGGGAGCTGTTTAACTACCAACTTCAAGTAGGATCTCATAC
AATTGCAGCCGTGTTAATTGATCCGGAAATTGCTAACGTCAAATCCCTCCCCGAACAAACTTACGCTGTAAGAAAAA
TTAAATCAGGGTTCCAATGTAGTTTGGATGACCAACACATTTATCAAGTCGCAGTAAAAAAACATCTTTCTCTGTCT
TCACAACCTCCGAAGATATCTCCGTTATCTCAATCCGAAAGCTCCGATTTAAGTCTCTTTGAAGCAGCAGCGTTTTC
AGCAAGCCTAACTTACGAGTTCGTAAAGAAAAATACATATCATGCTAAGAATACTGTAACTTGCTCCACGGTATCGC
ACTCTCTGTATATTCTCAAAGAAGATGACGGGGCTAATGCTGCAGAAAAACGCTTAGACAACAGTTTCCGAAACTGG
GTCGAAAATAAGTTGAACGCAAATTCTCCAGATTCTTGTACTGCATTTATTCAAAAATTCGGCACACATTACATCAC
ATCGGCAACTTTTGGAGGATCTGGGTTCCAAGTTCTTAAATTATCCTTTGAACAGGTAGAAGGCCTCCGTAGTAAGA
AGATCTCCCTAGAAGCAGCAGCAGCAAATTCCTTATTAAAAAGCTCTGTGTCAAACAGCACGGAATCTGGCTACTCT
ACTTACGATTCCTCTTCTTCTTCTCATACAGTATTCCTAGGGGGCACTGTATTACCCTCTGTTCATGATGGACAGTT
AGATTTTAAAGATTGGTCTGAAAGTGTCTGTTTAGAACCTGTTCCCATTCACATTTCTTTACTCCCCTTAACAGACT
TGCTCACCCCTCTTTATTTTCCTGAAACGGATACAACCGAACTATCTAATAAACGTAATGCTCTCCAACAAGCGGTT
CGAGTTTACCTTAAAGACCATCGTTCAGCTAAACAAAGCGAACGCTCCGTATTCACAGCGGGGATCAATAGTCCTTC
TTCCTGGTTCACATTAGAATCTGCTAATTCACCTCTTGTTGTGAGTTCTCCTTACATGACGTATTGGTCTACTCTCC
CCTATCTCTTCCCCACATTAAAAGAGCGTTCTTCAGCAGCTCCCATCGTTTTTTATTTTTGTGTGGATAATAATGAA
CACGCCTCCCAAAAAATTTTAAACCAAACATATTGCTTCATAGGTTCTTTACCTATTCGACAAAAGATTTTTGGCAG
AGAATTTGCTGAGAATCCTTATTTATCTTTCTATGGAAGGTTTGGAGAAGCTTATTTTGATGGCGGTTATCCAGAAC
GTTGTGGATGGATTGTTGAAAAGTTAAATACTACTAAAGATCAAATTCTCCGCGATGAGGATGAAGTGCAACTAAAG
CATGTTTATAGCGGAGAGTATCTGTCTACAATTCCTATTAAGGATTCCCATTGCACACTCTCGCGTACATGCACCGA
ATCGAATGCTGTTTTTATTATCAAAAAACCTTCGAGCTATTGA SEQ ID NO: 148 - TC0431 protein sequence
MPHSPFLYVVQPHSVFNPRLGERHPITLDFIKEKNRLADFIENLPLEIFGAPSFLENASLEASYVLSRESTKDGTLF
TVLEPKLSACVATCLVDSSIPMEPDNELLEEIKHTLLKSSCDGVQYRVTRETLQNKDEAPRVSLVADDIELIRNVDF
LGRSVDIVKLDPLNIPNTVSEENALDYSFTRETAKLSPDGRVGIPQGTKILPAPSLEVEISTSIFEETSSFEQNFSS
SITFCVPPLTSFSPLQEPPLVGAGQQEILVTKKHLFPSYTPKLIDIVKRHKRDAKILVNKIQFEKLWRSHAKSQILK
EGSVRLDLQGFTGELFNYQLQVGSHTIAAVLIDPEIANVKSLPEQTYAVRKIKSGFQCSLDDQHIYQVAVKKHLSLS
SQPPKISPLSQSESSDLSLFEAAAFSASLTYEFVKKNTYHAKNTVTCSTVSHSLYILKEDDGANAAEKRLDNSFRNW
VENKLNANSPDSCTAFIQKFGTHYITSATFGGSGFQVLKLSFEQVEGLRSKKISLEAAAANSLLKSSVSNSTESGYS
TYDSSSSSHTVFLGGTVLPSVHDGQLDFKDWSESVCLEPVPIHISLLPLTDLLTPLYFPETDTTELSNKRNALQQAV
RVYLKDHRSAKQSERSVFTAGINSPSSWFTLESANSPLVVSSPYMTYWSTLPYLFPTLKERSSAAPIVFYFCVDNNE
HASQKILNQTYCFIGSLPIRQKIFGREFAENPYLSFYGRFGEAYFDGGYPERCGWIVEKLNTTKDQILRDEDEVQLK
HVYSGEYLSTIPIKDSHCTLSRTCTESNAVFIIKKPSSY -continued

SEQUENCE LISTING

SEQ ID NO: 149 - TC0431 fragment nucleotide sequence
CCCCACTCTCCTTTTTATATGTTGTTCAACCGCATTCTGTTTTTAATCCTAGATTGGGAGAGCGGCACCCTATTAC
TTTAGATTTCATCAAAGAAAAGAATCGATTAGCTGATTTTATTGAAAACCTACCTTTAGAAATTTTTGGAGCCCCTT
CTTTCTTGGAAAATGCTTCTTTAGAAGCCTCTTATGTCTTGTCTAGGGAATCCACAAAAGATGGCACTCTTTTTACC
GTTCTAGAACCCAAACTATCTGCCTGCGTAGCTACTTGCCTTGTGGATTCTTCTATTCCTATGGAGCCCGATAACGA
GCTCTTAGAAGAAATTAAACACACTTTGTTGAAAAGCTCTTGTGATGGCGTACAATATCGTGTAACCCGAGAGACTC
TCCAAAACAAAGATGAAGCCCCCAGAGTCTCTTTAGTTGCTGATGATATCGAACTTATCCGCAATGTAGATTTTTTA
GGACGTTCCGTTGATATTGTAAAATTGGATCCCTTGAATATTCCTAATACCGTAAGCGAGGAGAATGCTCTCGATTA
CTCTTTCACAAGGGAAACCGCCAAACTTAGCCCTGACGGACGAGTTGGCATCCCTCAAGGGACAAAAATTTTGCCAG
CTCCCTCTCTTGAAGTTGAAATTAGCACCTCTATTTTTGAGGAAACCTCTTCTTTTGAACAAAACTTTTCTTCCTCT
ATTACTTTTTGTGTACCACCTCTTACCTCTTTTTCTCCTTTGCAAGAACCTCCTCTAGTGGGAGCTGGACAGCAGGA
AATTCTTGTGACTAAAAAGCACTTATTCCCTAGCTATACCCCTAAACTTATTGATATTGTCAAACGACACAAAAGAG
ACGCAAAGATTCTAGTAAACAAGATCCAGTTCGAGAAACTATGGAGAAGTCATGCCAAAAGTCAAATCTTAAAAGAA
GGCTCTGTTCGCTTGGATTTACAAGGATTTACAGGGGAGCTGTTTAACTACCAACTTCAAGTAGGATCTCATACAAT
TGCAGCCGTGTTAATTGATCCGGAAATTGCTAACGTCAAATCCCTCCCCGAACAAACTTACGCTGTAAGAAAAATTA
AATCAGGGTTCCAATGTAGTTTGGATGACCAACACATTTATCAAGTCGCAGTAAAAAAACATCTTTCTCTGTCTTCA
CAACCTCCGAAGATATCTCCGTTATCTCAATCCGAAAGCTCCGATTTAAGTCTCTTTGAAGCAGCAGCGTTTTCAGC
AAGCCTAACTTACGAGTTCGTAAAGAAAAATACATATCATGCTAAGAATACTGTAACTTGCTCCACGGTATCGCACT
CTCTGTATATTCTCAAAGAAGATGACGGGGCTAATGCTGCAGAAAAACGCTTAGACAACAGTTTCCGAAACTGGGTC
GAAAATAAGTTGAACGCAAATTCTCCAGATTCTTGTACTGCATTTATTCAAAAATTCGGCACACATTACATCACATC
GGCAACTTTTGGAGGATCTGGGTTCCAAGTTCTTAAATTATCCTTTGAACAGGTAGAAGGCCTCCGTAGTAAGAAGA
TCTCCCTAGAAGCAGCAGCAGCAAATTCCTTATTAAAAAGCTCTGTGTCAAACAGCACGGAATCTGGCTACTCTACT
TACGATTCCTCTTCTTCTTCTCATACAGTATTCCTAGGGGGCACTGTATTACCCTCTGTTCATGATGGACAGTTAGA
TTTTAAAGATTGGTCTGAAAGTGTCTGTTTAGAACCTGTTCCCATTCACATTTCTTTACTCCCCTTAACAGACTTGC
TCACCCCTCTTTATTTTCCTGAAACGGATACAACCGAACTATCTAATAAACGTAATGCTCTCCAACAAGCGGTTCGA
GTTTACCTTAAAGACCATCGTTCAGCTAAACAAAGCGAACGCTCCGTATTCACAGCGGGGATCAATAGTCCTTCTTC
CTGGTTCACATTAGAATCTGCTAATTCACCTCTTGTTGTGAGTTCTCCTTACATGACGTATTGGTCTACTCTCCCCT
ATCTCTTCCCCACATTAAAAGAGCGTTCTTCAGCAGCTCCCATCGTTTTTTATTTTTGTGTGGATAATAATGAACAC
GCCTCCCAAAAAATTTTAAACCAAACATATTGCTTCATAGGTTCTTTACCTATTCGACAAAAGATTTTTGGCAGAGA
ATTTGCTGAGAATCCTTATTTATCTTTCTATGGAAGGTTTGGAGAAGCTTATTTTGATGGCGGTTATCCAGAACGTT
GTGGATGGATTGTTGAAAAGTTAAATACTACTAAAGATCAAATTCTCCGCGATGAGGATGAAGTGCAACTAAAGCAT
GTTTATAGCGGAGAGTATCTGTCTACAATTCCTATTAAGGATTCCCATTGCACACTCTCGCGTACATGCACCGAATC
GAATGCTGTTTTTATTATCAAAAAACCTTCGAGCTAT SEQ ID NO: 150 - TC0431 fragment protein sequence
PHSPFLYVVQPHSVFNPRLGERHPITLDFIKEKNRLADFIENLPLEIFGAPSFLENASLEASYVLSRESTKDGTLFT
VLEPKLSACVATCLVDSSIPMEPDNELLEEIKHTLLKSSCDGVQYRVTRETLQNKDEAPRVSLVADDIELIRNVDFL
GRSVDIVKLDPLNIPNTVSEENALDYSFTRETAKLSPDGRVGIPQGTKILPAPSLEVEISTSIFEETSSFEQNFSSS
ITFCVPPLTSFSPLQEPPLVGAGQQEILVTKKHLFPSYTPKLIDIVKRHKRDAKILVNKIQFEKLWRSHAKSQILKE
GSVRLDLQGFTGELFNYQLQVGSHTIAAVLIDPEIANVKSLPEQTYAVRKIKSGFQCSLDDQHIYQVAVKKHLSLSS
QPPKISPLSQSESSDLSLFEAAAFSASLTYEFVKKNTYHAKNTVTCSTVSHSLYILKEDDGANAAEKRLDNSFRNWV
ENKLNANSPDSCTAFIQKFGTHYITSATFGGSGFQVLKLSFEQVEGLRSKKISLEAAAANSLLKSSVSNSTESGYST
YDSSSSSHTVFLGGTVLPSVHDGQLDFKDWSESVCLEPVPIHISLLPLTDLLTPLYFPETDTTELSNKRNALQQAVR
VYLKDHRSAKQSERSVFTAGINSPSSWFTLESANSPLVVSSPYMTYWSTLPYLFPTLKERSSAAPIVFYFCVDNNEH
ASQKILNQTYCFIGSLPIRQKIFGREFAENPYLSFYGRFGEAYFDGGYPERCGWIVEKLNTTKDQILRDEDEVQLKH
VYSGEYLSTIPIKDSHCTLSRTCTESNAVFIIKKPSSY SEQ ID NO: 151 - TC0210 nucleotide sequence
ATGATGAAAAGATTATTATGTGTGTTGCTATCGACATCAGTTTTCTCTTCGCCCATGTTGGGCTATAGTGCGCCAAA
GAAAGATTCCAGTACTGGCATTTGTCTTGCAGCATCTCAAAGTGATCGGGAACTTTCCCAAGAAGATTTGCTAAAAG
AAGTGTCTAGAGGATTTTCCAAAGTCGCTGCTCAGGCAACTCCAGGAGTTGTGTATATAGAAAATTTTCCTAAAACT
GGGAGTCAAGCTATTGCTTCTCCTGGGAATAAAAGGGGTTTTCAAGAGAATCCCTTTGATTATTTCAATGATGAGTT
TTTCAATCGATTTTTTGGTTTACCCTCGCATAGAGAGCAGCCTCGTCCCCAACAGCGTGATGCTGTAAGAGGAACAG
GTTTTATTGTGTCAGAAGATGGGTACGTTGTGACCAACCATCACGTAGTGGAAGATGCGGGGAAAATTCATGTTACT
TTACACGATGGACAAAAATACACCGCAAAAATCATAGGATTAGATCCTAAAACGGATCTCGCTGTGATTAAGATCCA
AGCAAAAAATCTCCCTTTTTTAACTTTTGGAAACTCTGATCAGCTTCAGATAGGGGATTGGTCAATAGCCATTGGAA
ATCCTTTCGGATTACAAGCCACAGTAACCGTTGGCGTGATTAGTGCTAAGGGAAGAAACCAATTACATATTGTTGAT
TTTGAAGATTTTATTCAGACGGATGCAGCAATTAATCCCGGGAATTCAGGTGGTCCATTATTGAACATTGATGGACA
GGTTATTGGAGTGAATACAGCAATCGTTAGCGGTAGCGGGGGATACATTGGAATAGGATTTGCCATTCCTAGCTTAA
TGGCTAAACGAGTTATTGACCAACTCATTAGCGATGGACAGGTGACGAGAGGATTTTTAGGAGTAACCTTACAGCCT
ATTGATTCGGAGCTTGCCGCTTGTTACAAATTAGAAAAGGTGTACGGAGCCTTGATTACGGATGTTGTTAAGGGATC
TCCTGCAGAAAAAGCAGGTTTGCGCCAGGAAGATGTCATTGTTGCTTACAATGGGAAAGAAGTGGAGTCTTTGAGTG
CTTTACGTAATGCGATTTCTTTGATGATGCCAGGGACTCGTGTTGTCTTAAAAGTTGTGCGTGAAGGGAAATTCATT
GAAATACCTGTCACTGTTACACAAATTCCTGCGGAGGATGGGGTATCTGCTCTTCAAAAAATGGGAGTTCGGGTACA
GAATCTTACTCCAGAGATATGCAAGAAACTAGGATTAGCGTCTGATACTCGAGGGATTTTTGTAGTGTCCGTAGAAG
CTGGTTCTCCTGCAGCTTCTGCAGGAGTGGTTCCAGGACAACTTATTCTGGCTGTAAACAGACAGAGAGTTTCTTCT
GTTGAAGAATTGAATCAGGTCTTGAAGAATGCAAAAGGAGAGAATGTTCTCCTTATGGTTTCTCAAGGAGAAGTCAT
TCGATTCGTTGTTTTAAAGTCTGATGAATAG SEQ ID NO: 152 - TC0210 protein sequence
MMKRLLCVLLSTSVFSSPMLGYSAPKKDSSTGICLAASQSDRELSQEDLLKEVSRGFSKVAAQATPGVVYIENFPKT
GSQAIASPGNKRGFQENPFDYFNDEFFNRFFGLPSHREQPRPQQRDAVRGTGFIVSEDGYVVTNHHVVEDAGKIHVT
LHDGQKYTAKIIGLDPKTDLAVIKIQAKNLPFLTFGNSDQLQIGDWSIAIGNPFGLQATVTVGVISAKGRNQLHIVD
FEDFIQTDAAINPGNSGGPLLNIDGQVIGVNTAIVSGSGGYIGIGFAIPSLMAKRVIDQLISDGQVTRGFLGVTLQP
IDSELAACYKLEKVYGALITDVVKGSPAEKAGLRQEDVIVAYNGKEVESLSALRNAISLMMPGTRVVLKVVREGKFI
EIPVTVTQIPAEDGVSALQKMGVRVQNLTPEICKKLGLASDTRGIFVVSVEAGSPAASAGVVPGQLILAVNRQRVSS
VEELNQVLKNAKGENVLLMVSQGEVIRFVVLKSDE -continued

SEQUENCE LISTING

SEQ ID NO: 153 - TC0210 fragment nucleotide sequence
TCGCCCATGTTGGGCTATAGTGCGCCAAAGAAAGATTCCAGTACTGGCATTTGTCTTGCAGCATCTCAAAGTGATCG
GGAACTTTCCCAAGAAGATTTGCTAAAAGAAGTGTCTAGAGGATTTTCCAAAGTCGCTGCTCAGGCAACTCCAGGAG
TTGTGTATATAGAAAATTTCCTAAAACTGGGAGTCAAGCTATTGCTTCTCCTGGGAATAAAAGGGGTTTTCAAGAG
AATCCCTTTGATTATTTCAATGATGAGTTTTTCAATCGATTTTTTGGTTTACCCTCGCATAGAGAGCAGCCTCGTCC
CCAACAGCGTGATGCTGTAAGAGGAACAGGTTTTATTGTGTCAGAAGATGGGTACGTTGTGACCAACCATCACGTAG
TGGAAGATGCGGGGAAAATTCATGTTACTTTACACGATGGACAAAAATACACCGCAAAAATCATAGGATTAGATCCT
AAAACGGATCTCGCTGTGATTAAGATCCAAGCAAAAAATCTCCCTTTTTTAACTTTTGGAAACTCTGATCAGCTTCA
GATAGGGGATTGGTCAATAGCCATTGGAAATCCTTTCGGATTACAAGCCACAGTAACCGTTGGCGTGATTAGTGCTA
AGGGAAGAAACCAATTACATATTGTTGATTTTGAAGATTTTATTCAGACGGATGCAGCAATTAATCCCGGGAATTCA
GGTGGTCCATTATTGAACATTGATGGACAGGTTATTGGAGTGAATACAGCAATCGTTAGCGGTAGCGGGGGATACAT
TGGAATAGGATTTGCCATTCCTAGCTTAATGGCTAAACGAGTTATTGACCAACTCATTAGCGATGGACAGGTGACGA
GAGGATTTTTAGGAGTAACCTTACAGCCTATTGATTCGGAGCTTGCCGCTTGTTACAAATTAGAAAAGGTGTACGGA
GCCTTGATTACGGATGTTGTTAAGGGATCTCCTGCAGAAAAAGCAGGTTTGCGCCAGGAAGATGTCATTGTTGCTTA
CAATGGGAAAGAAGTGGAGTCTTTGAGTGCTTTACGTAATGCGATTTCTTTGATGATGCCAGGGACTCGTGTTGTCT
TAAAAGTTGTGCGTGAAGGGAAATTCATTGAAATACCTGTCACTGTTACACAAATTCCTGCGGAGGATGGGGTATCT
GCTCTTCAAAAAATGGGAGTTCGGGTACAGAATCTTACTCCAGAGATATGCAAGAAACTAGGATTAGCGTCTGATAC
TCGAGGGATTTTTGTAGTGTCCGTAGAAGCTGGTTCTCCTGCAGCTTCTGCAGGAGTGGTTCCAGGACAACTTATTC
TGGCTGTAAACAGACAGAGAGTTTCTTCTGTTGAAGAATTGAATCAGGTCTTGAAGAATGCAAAAGGAGAGAATGTT
CTCCTTATGGTTTCTCAAGGAGAAGTCATTCGATTCGTTGTTTTAAAGTCTGATGAA SEQ ID NO: 154 - TC0210 fragment protein sequence
SPMLGYSAPKKDSSTGICLAASQSDRELSQEDLLKEVSRGFSKVAAQATPGVVYIENFPKTGSQAIASPGNKRGFQE
NPFDYFNDEFFNRFFGLPSHREQPRPQQRDAVRGTGFIVSEDGYVVTNHHVVEDAGKIHVTLHDGQKYTAKIIGLDP
KTDLAVIKIQAKNLPFLTFGNSDQLQIGDWSIAIGNPFGLQATVTVGVISAKGRNQLHIVDFEDFIQTDAAINPGNS
GGPLLNIDGQVIGVNTAIVSGSGGYIGIGFAIPSLMAKRVIDQLISDGQVTRGFLGVTLQPIDSELAACYKLEKVYG
ALITDVVKGSPAEKAGLRQEDVIVAYNGKEVESLSALRNAISLMMPGTRVVLKVVREGKFIEIPVTVTQIPAEDGVS
ALQKMGVRVQNLTPEICKKLGLASDTRGIFVVSVEAGSPAASAGVVPGQLILAVNRQRVSSVEELNQVLKNAKGENV
LLMVSQGEVIRFVVLKSDE SEQ ID NO: 155 - CT163 nucleotide sequence
ATGTTTGTGTCGTTCGATAAATCCCGTTGCAGAGCGGATGTCCCCGATTTTTTTGAAAGGACAGGAAACTTTCTTCT
CCATTGTGTGGCAAGAGGGATCAATGTTTTATATCGTGTGAAACAAATCTCTAACTATCCTTCATGCTATTTCTCAC
ATAAAGAGATTTCGTGTTGTCGTCGTATTGCAAACATTGTGATCTGTATTCTCACAGGGCCTCTGATGTTATTGGCC
ACTGTGTTAGGATTATTAGCGTATAGGTTTTCTTCTACTTACCAGACTTCTTTACAAGAACGCTTTCGTTATAAATA
TGAACAAAAGCAAGCTTTAGATGAATACCGTGATAGGGAAGAAAAAGTCATTACGCTTCAGAAGTTTTGTAGAGGAT
TTCTAGTTAGAAATCATTTGCTCAACCAAGAAACTTTAACAACGTGTAAGCAATGGGGGCAAAAACTATTAGAAGGA
GAAAAATTCCCAAGGGTCCCAGAAGGACGGTCTCTTGTATATATTTCAAAACAGTTTCCTTCTTTAGTAGCAAAACA
CGTTGGGGCTCAAGATGCCAGGTCTCGTTGGCATCATATTTTTTCTATGCGCAAAGCGCTTGCTTATTTAGATATTA
AGCGCATACGAGCACCACGCGCTAGAGTTTATCAAAACTTTATATTCGAAGAAAAACTTCCTGTTTCACGAATTTCT
GTAGATTCAATGTGTCTCTATAAAGAAAATCCACAAGCTTTCGATGAGGCGATCAAAGAACTCTTATTTCTATTTAA
AGAAGTGCATTTCAGGGATTTTGTTGTAGAAACAGAGTCTCCAACAGACGATTTCCCCTTAGCCGTGAAAGTACACA
ACTATTGGGTATGCCCACGATACGATAATTTACCTTTATTTATTCAAGAAGGAAAAGATGGCTCTCCAGAAGGGCGT
ATAGGACTGGTCGATCTAGAAACTTTTTCTTGGTCTCCACATCCATACCCCGTAGAAGAACTAGCTGTGATGTTTCC
TATGCATAAAGAGCTTCTTATGACAGAGGCGAAAAAACTACAAATCCCTTTCTCTACAAAGGAGGTCGAGCGCTCTG
TAGAGAAAGGGCTTGCTTTTTTTGAACATATGCTAGGGCATCAAGATTTTTGTTCCCAAAAAAGCGTAACGCCATTG
CGTAATTGTGCCCCTTATATTCATCTAGAAGTATGGAGATTCTCACTGAAAATTTTTGATATTTTAAAAGCTGCTAT
TCAACTAAATGGAGCACTCAATGTTCTGTTATCTCCAGATATTCGAGAGCGGTTGAGTGCTATTTCGGATAAGCAAT
GGTTGGCTATTAGCTCCCAGGTTACGTCATCGTTACTCGAGCAAGTTTCTACAAACATCTATCAGTCTCATACTGAA
GAGGCTAAACGAGTAAATTCTTCAGGGACTTTTATCATGTGTCGATCTCCTATCTTCCGGAAAAGCATCTTCATTAA
AAATCTCCCACAATTCTTAAACAAGAAATTGCAGTTGCTTCCAGAGGAGAAAGCAATCAGCGAGGCGCTTGCTTCTC
TATGTTTACGTGCAGTAATGGAAGAGCTAGTAGCAACAGGAAATATTTATTCTTATGATTCTATGGATGATTTTTTT
GAAGGGCAGTATTGTCGCATTCGTTATTAG SEQ ID NO: 156 - CT163 protein sequence
MFVSFDKSRCRADVPDFFERTGNFLLHCVARGINVLYRVKQISNYPSCYFSHKEISCCRRIANIVICILTGPLMLLA
TVLGLLAYRFSSTYQTSLQERFRYKYEQKQALDEYRDREEKVITLQKFCRGFLVRNHLLNQETLTTCKQWGQKLLEG
EKFPRVPEGRSLVYISKQFPSLVAKHVGAQDARSRWHHIFSMRKALAYLDIKRIRAPRARVYQNFIFEEKLPVSRIS
VDSMCLYKENPQAFDEAIKELLFLFKEVHFRDFVVETESPTDDFPLAVKVHNYWVCPRYDNLPLFIQEGKDGSPEGR
IGLVDLETFSWSPHPYPVEELAVMFPMHKELLMTEAKKLQIPFSTKEVERSVEKGLAFFEHMLGHQDFCSQKSVTPL
RNCAPYIHLEVWRFSLKIFDILKAAIQLNGALNVLLSPDIRERLSAISDKQWLAISSQVTSSLLEQVSTNIYQSHTE
EAKRVNSSGTFIMCRSPIFRKSIFIKNLPQFLNKKLQLLPEEKAISEALASLCLRAVMEELVATGNIYSYDSMDDFF
EGQYCRIRY SEQ ID NO: 157 - CT163 fragment nucleotide sequence
TTTGTGTCGTTCGATAAATCCCGTTGCAGAGCGGATGTCCCCGATTTTTTTGAAAGGACAGGAAACTTTCTTCTCCA
TTGTGTGGCAAGAGGGATCAATGTTTTATATCGTGTGAAACAAATCTCTAACTATCCTTCATGCTATTTCTCACATA
AAGAGATTTCGTGTTGTCGTCGTATTGCAAACATTGTGATCTGTATTCTCACAGGGCCTCTGATGTTATTGGCCACT
GTGTTAGGATTATTAGCGTATAGGTTTTCTTCTACTTACCAGACTTCTTTACAAGAACGCTTTCGTTATAAATATGA
ACAAAAGCAAGCTTTAGATGAATACCGTGATAGGGAAGAAAAAGTCATTACGCTTCAGAAGTTTTGTAGAGGATTTC
TAGTTAGAAATCATTTGCTCAACCAAGAAACTTTAACAACGTGTAAGCAATGGGGGCAAAAACTATTAGAAGGAGAA
AAATTCCCAAGGGTCCCAGAAGGACGGTCTCTTGTATATATTTCAAAACAGTTTCCTTCTTTAGTAGCAAAACACGT
TGGGGCTCAAGATGCCAGGTCTCGTTGGCATCATATTTTTTCTATGCGCAAAGCGCTTGCTTATTTAGATATTAAGC
GCATACGAGCACCACGCGCTAGAGTTTATCAAAACTTTATATTCGAAGAAAAACTTCCTGTTTCACGAATTTCTGTA
GATTCAATGTGTCTCTATAAAGAAAATCCACAAGCTTTCGATGAGGCGATCAAAGAACTCTTATTTCTATTTAAAGA
AGTGCATTTCAGGGATTTTGTTGTAGAAACAGAGTCTCCAACAGACGATTTCCCCTTAGCCGTGAAAGTACACAACT -continued

SEQUENCE LISTING

ATTGGGTATGCCCACGATACGATAATTTACCTTTATTTATTCAAGAAGGAAAAGATGGCTCTCCAGAAGGGCGTATA
GGACTGGTCGATCTAGAAACTTTTTCTTGGTCTCCACATCCATACCCCGTAGAAGAACTAGCTGTGATGTTTCCTAT
GCATAAAGAGCTTCTTATGACAGAGGCGAAAAAACTACAAATCCCTTTCTCTACAAAGGAGGTCGAGCGCTCTGTAG
AGAAAGGGCTTGCTTTTTTTGAACATATGCTAGGGCATCAAGATTTTTGTTCCCAAAAAAGCGTAACGCCATTGCGT
AATTGTGCCCCTTATATTCATCTAGAAGTATGGAGATTCTCACTGAAAATTTTTGATATTTTAAAAGCTGCTATTCA
ACTAAATGGAGCACTCAATGTTCTGTTATCTCCAGATATTCGAGAGCGGTTGAGTGCTATTTCGGATAAGCAATGGT
TGGCTATTAGCTCCCAGGTTACGTCATCGTTACTCGAGCAAGTTTCTACAAACATCTATCAGTCTCATACTGAAGAG
GCTAAACGAGTAAATTCTTCAGGGACTTTTATCATGTGTCGATCTCCTATCTTCCGGAAAAGCATCTTCATTAAAAA
TCTCCCACAATTCTTAAACAAGAAATTGCAGTTGCTTCCAGAGGAGAAAGCAATCAGCGAGGCGCTTGCTTCTCTAT
GTTTACGTGCAGTAATGGAAGAGCTAGTAGCAACAGGAAATATTTATTCTTATGATTCTATGGATGATTTTTTTGAA
GGGCAGTATTGTCGCATTCGTTAT

SEQ ID NO: 158 - CT163 fragment protein sequence
FVSFDKSRCRADVPDFFERTGNFLLHCVARGINVLYRVKQISNYPSCYFSHKEISCCRRIANIVICILTGPLMLLAT
VLGLLAYRFSSTYQTSLQERFRYKYEQKQALDEYRDREEKVITLQKFCRGFLVRNHLLNQETLTTCKQWGQKLLEGE
KFPRVPEGRSLVYISKQFPSLVAKHVGAQDARSRWHHIFSMRKALAYLDIKRIRAPRARVYQNFIFEEKLPVSRISV
DSMCLYKENPQAFDEAIKELLFLFKEVHFRDFVVETESPTDDFPLAVKVHNYWVCPRYDNLPLFIQEGKDGSPEGRI
GLVDLETFSWSPHPYPVEELAVMFPMHKELLMTEAKKLQIPFSTKEVERSVEKGLAFFEHMLGHQDFCSQKSVTPLR
NCAPYIHLEVWRFSLKIFDILKAAIQLNGALNVLLSPDIRERLSAISDKQWLAISSQVTSSLLEQVSTNIYQSHTEE
AKRVNSSGTFIMCRSPIFRKSIFIKNLPQFLNKKLQLLPEEKAISEALASLCLRAVMEELVATGNIYSYDSMDDFFE
GQYCRIRY SEQ ID NO: 159 - CT214 nucleotide sequence
ATGCGAACAGACTCTCTTTTCAATCCTCCCGACTCTACTAGAGGAGTTTTTCAGTTTTTAGAGACTCAGTGTGATCG
AGCCGTGGCTCGGTCCAGACAAAGCCAATTTATAGGGTTAGTCTCTGCTGTAGCAGCTGCAGCATTATTATTGTTGC
TTGTGGTCGCTCTATCTGTTCCAGGATTCCCAGTTGCAGCTTCAATTGTTGTAGGGGTTCTCTTTGCTTTATCGATC
GTAGCATTAACAGCTTCGTTTTTGGTATATATAGCTAATGCTAAGCTTGTTGCAATAAGAATTAAATTCTTGAGTAG
TGGTCTGCAAGATCACTTTTCGGAGTCATCTATTTTAGGGACTCTCCGTAAAGGACGTGGTGCTAGTATTCCGCTTA
TTTCCGGACAAGCAGATGATCCTCTCCCTAATCGGATTGGGATCAAAAAAAGCACTGAAATGCGTGTTCTTCAAAAA
GGAATTGGGACAGATTATAAAAAATATAAGCAGCATCTTGATAGAGTGAATAATGATTTCACTTTTGTCTGTGAGGG
GATTAGCGCTTTAATTCCTACAGAAAAAGATGCTCCATTCCCTATAGAACCTTCTCATTTAGCAGGTGTTTTTTTAG
TATCATTTTCACCAGACAAGAATCCGATTCTAAAGATTACGCGTCATGCTGAGAAGATGTTACAGCCTCCTCAAGGC
GGATTCCCTAACGGGCTGGTTTGGTTGTGTGGAGCTCTTTCTGATCCTAAGAAATTTGCAGCTCCCTTTCTATCTTT
GATTGAGAAGACTCACCAAGGGATTTTGGTGAGTAAAGACTTGAAAGACAATAAGGAAAGAAAGCTAGCTTTAGAGG
CTTCCCTTCTTTCATTGAATATTTTCTTTTCCGGTTGGTGTTTGGGGAATCCGGAGTACAATCAGTATATCACAACT
GCTGTAGCTGAGAAATATAGGGATGTCTCTGTAAGAAATTGTATTTATGATTTCCTGGATACAGGGAATGTGATTTC
AGCTCTTGCTTTAGCAAGTAGTTATTCACAAGATTCCGCTTGGGCTGCAGGGTTGCAGAAAGTTTTACGTGAAGAAG
ATAAAAAGACTAAGAAAAAGTCACGTGAAGAAGTCTCTTGTTTGTATCGTGATATAGATCCAGGCTGTTGTTTAAGA
GCCCTTCCTAAGCGATTTGAATCCAAGTCTTCAGGTAGTCAAGGTAGTCCTAAAGAGCAGTTAAGCTCTTTGTTGAA
AGCTTTAGACCAGAAAATTCCTTCAGGGATTTTAGGATTGATTGCAAAAGCTTCTTCTGCAGATCTCAAGGCTGATT
TTGCAGGTATGCTTGAAGTTATTAAGCAATTACAAGCTTTATTCGATTCTTACCCACCTTTATGCGAAGACAATATT
CTCTTGTGGTTAAGCGCTTCTTTAGAACAAGTAGGCTTGCAGAAGAAATTGAGAACCTTTTTACCTTCATCAGAAAA
AAAACTCTTAGAAAGAGTTCTCTCTACATTTTTATTAGGTTTGTATACTCGAGGAGTCTTTTCTGTAGGGCAAGTGA
ATCAGCTAGCTACTATTTGTAATACTCAGGACTCTACAGAATTCTGCCAGAGAGTAAGTGACCTTTCGTTAATTAAA
CGAGCTCTACCTGCATTATTTGGTTAA SEQ ID NO: 160 - CT214 protein sequence
MRTDSLFNPPDSTRGVFQFLETQCDRAVARSRQSQFIGLVSAVAAAALLLLLVVALSVPGFPVAASIVVGVLFALSI
VALTASFLVYIANAKLVAIRIKFLSSGLQDHFSESSILGTLRKGRGASIPLISGQADDPLPNRIGIKKSTEMRVLQK
GIGTDYKKYKQHLDRVNNDFTFVCEGISALIPTEKDAPFPIEPSHLAGVFLVSFSPDKNPILKITRHAEKMLQPPQG
GFPNGLVWLCGALSDPKKFAAPFLSLIEKTHQGILVSKDLKDNKERKLALEASLLSLNIFFSGWCLGNPEYNQYITT
AVAEKYRDVSVRNCIYDFLDTGNVISALALASSYSQDSAWAAGLQKVLREEDKKTKKKSREEVSCLYRDIDPGCCLR
ALPKRFESKSSGSQGSPKEQLSSLLKALDQKIPSGILGLIAKASSADLKADFAGMLEVIKQLQALFDSYPPLCEDNI
LLWLSASLEQVGLQKKLRTFLPSSEKKLLERVLSTFLLGLYTRGVFSVGQVNQLATICNTQDSTEFCQRVSDLSLIK
RALPALFG SEQ ID NO: 161 - CT214 fragment nucleotide sequence
CGAACAGACTCTCTTTTCAATCCTCCCGACTCTACTAGAGGAGTTTTTCAGTTTTTAGAGACTCAGTGTGATCGAGC
CGTGGCTCGGTCCAGACAAAGCCAATTTATAGGGTTAGTCTCTGCTGTAGCAGCTGCAGCATTATTATTGTTGCTTG
TGGTCGCTCTATCTGTTCCAGGATTCCCAGTTGCAGCTTCAATTGTTGTAGGGGTTCTCTTTGCTTTATCGATCGTA
GCATTAACAGCTTCGTTTTTGGTATATATAGCTAATGCTAAGCTTGTTGCAATAAGAATTAAATTCTTGAGTAGTGG
TCTGCAAGATCACTTTTCGGAGTCATCTATTTTAGGGACTCTCCGTAAAGGACGTGGTGCTAGTATTCCGCTTATTT
CCGGACAAGCAGATGATCCTCTCCCTAATCGGATTGGGATCAAAAAAAGCACTGAAATGCGTGTTCTTCAAAAAGGA
ATTGGGACAGATTATAAAAAATATAAGCAGCATCTTGATAGAGTGAATAATGATTTCACTTTTGTCTGTGAGGGGAT
TAGCGCTTTAATTCCTACAGAAAAAGATGCTCCATTCCCTATAGAACCTTCTCATTTAGCAGGTGTTTTTTTAGTAT
CATTTTCACCAGACAAGAATCCGATTCTAAAGATTACGCGTCATGCTGAGAAGATGTTACAGCCTCCTCAAGGCGGA
TTCCCTAACGGGCTGGTTTGGTTGTGTGGAGCTCTTTCTGATCCTAAGAAATTTGCAGCTCCCTTTCTATCTTTGAT
TGAGAAGACTCACCAAGGGATTTTGGTGAGTAAAGACTTGAAAGACAATAAGGAAAGAAAGCTAGCTTTAGAGGCTT
CCCTTCTTTCATTGAATATTTTCTTTTCCGGTTGGTGTTTGGGGAATCCGGAGTACAATCAGTATATCACAACTGCT
GTAGCTGAGAAATATAGGGATGTCTCTGTAAGAAATTGTATTTATGATTTCCTGGATACAGGGAATGTGATTTCAGC
TCTTGCTTTAGCAAGTAGTTATTCACAAGATTCCGCTTGGGCTGCAGGGTTGCAGAAAGTTTTACGTGAAGAAGATA
AAAAGACTAAGAAAAAGTCACGTGAAGAAGTCTCTTGTTTGTATCGTGATATAGATCCAGGCTGTTGTTTAAGAGCC
CTTCCTAAGCGATTTGAATCCAAGTCTTCAGGTAGTCAAGGTAGTCCTAAAGAGCAGTTAAGCTCTTTGTTGAAAGC
TTTAGACCAGAAAATTCCTTCAGGGATTTTAGGATTGATTGCAAAAGCTTCTTCTGCAGATCTCAAGGCTGATTTTG
CAGGTATGCTTGAAGTTATTAAGCAATTACAAGCTTTATTCGATTCTTACCCACCTTTATGCGAAGACAATATTCTC
TTGTGGTTAAGCGCTTCTTTAGAACAAGTAGGCTTGCAGAAGAAATTGAGAACCTTTTTACCTTCATCAGAAAAAAA
ACTCTTAGAAAGAGTTCTCTCTACATTTTTATTAGGTTTGTATACTCGAGGAGTCTTTTCTGTAGGGCAAGTGAATC -continued

SEQUENCE LISTING

AGCTAGCTACTATTTGTAATACTCAGGACTCTACAGAATTCTGCCAGAGAGTAAGTGACCTTTCGTTAATTAAACGA
GCTCTACCTGCATTATTTGGT

SEQ ID NO: 162 - CT214 fragment protein sequence
RTDSLFNPPDSTRGVFQFLETQCDRAVARSRQSQFIGLVSAVAAAALLLLVVALSVPGFPVAASIVVGVLFALSIV
ALTASFLVYIANAKLVAIRIKFLSSGLQDHFSESSILGTLRKGRGASIPLISGQADDPLPNRIGIKKSTEMRVLQKG
IGTDYKKYKQHLDRVNNDFTFVCEGISALIPTEKDAPFPIEPSHLAGVFLVSFSPDKNPILKITRHAEKMLQPPQGG
FPNGLVWLCGALSDPKKFAAPFLSLIEKTHQGILVSKDLKDNKERKLALEASLLSLNIFFSGWCLGNPEYNQYITTA
VAEKYRDVSVRNCIYDFLDTGNVISALALASSYSQDSAWAAGLQKVLREEDKKTKKKSREEVSCLYRDIDPGCCLRA
LPKRFESKSSGSQGSPKEQLSSLLKALDQKIPSGILGLIAKASSADLKADFAGMLEVIKQLQALFDSYPPLCEDNIL
LWLSASLEQVGLQKKLRTFLPSSEKKLLERVLSTFLLGLYTRGVFSVGQVNQLATICNTQDSTEFCQRVSDLSLIKR
ALPALFG SEQ ID NO: 163 - CT721 nucleotide sequence
ATGGACGGGACAAAAATTCACGAAACACGCTCCTTCTCTTGGTTAAACAACCAACAAGCCATCCCTCCTTCCGAAAT
GGTGAAGGAGGCTTTTCAACGTTACGCAGACGTATTTTCGTACAGCGCAAATACCTCCATTCTGACTTTACAAGCAG
AAGCTGAAGCTTCTGCCCGCAAACTCACAGGGTGTCAGGAGAAGGCTTTTACCTTTCATTTTATTCTTCATTACCCG
AATGTCACGGCCATTATCGTGGCCGCTCTTCTGGAAAACCAAAATGCCTTCCAGGGGCGTAATCACCTTCTTGTTCC
TTCTTGCGAGCAACAATTTATCATTAATGCTCTCTGCCGTCGGCAAAACTTAGGGACAACCTATGATTGGGTAACCA
GCAAAAACGGCCGCGTAAAAGAATCCGATCTAGCAGAAGCTCTTTCCCCGCGGACCTTGCTGTTTTCCATATCTGCT
GCGAATGGTATGACAGGATTTCTGGAAGCGATCCCTGAGCTTGCTGCGTTATGTAAAGAACGCGGGGTAATTTTCCA
CATAGACCTGAGTGATATCTTAGGAAGATGCGCGCTACCCGCAGAACTCTATCAAGCAGATATCCTTACTTTTTCTT
CACAGTCTCTTGGTGGGATTGGTCCCTCAGGAGCGATGTTTATTTCTCCCGCTTTAACAAAATATTTTTCCTTATGG
CTTCCTAGTAATCCACAAGTCCCTACCTGCCTGAGTTCTCTTGCAGCTTTTTCTCTTGCCTGTCAGGAACGTACAAC
CGCTTTCTCCTCTCTTGTGCTTTCTGCTATTTCTTCTCGAGCAGCTCTTAAACAGGCTCTTTCCGCTATTCCTCAAG
TCGAATTCCTTTTGGAAGACAGTGCCCCTCGTCTCCCTAATGTCGCTGTCTTTGCTATTCCTGGTATCCCTGCAGAG
TCCTTAGGATTTTTCCTTTCCCAGAAAAATATTTTTGTAGGGTTAGGCTATGAACGCTTCCAGCCTCTATCGCAGAT
TTTACAAAGTTCGGGCATCTCTCCCTTCTTATGCCACAGCGCTTTACACGTATCTTTTACTGAACGTACTCCTACTA
CACACTTCTCTGCATTAGCAACCGCCTTACAAGAAGGGATCTCTCACCTACAACCACTGGTTACTCAATCCTTATGA SEQ ID NO: 164 - CT721 protein sequence
MDGTKIHETRSFSWLNNQQAIPPSEMVKEAFQRYADVFSYSANTSILTLQAEAEASARKLTGCQEKAFTFHFILHYP
NVTAIIVAALLENQNAFQGRNHLLVPSCEQQFIINALCRRQNLGTTYDWVTSKNGRVKESDLAEALSPRTLLFSISA
ANGMTGFLEAIPELAALCKERGVIFHIDLSDILGRCALPAELYQADILTFSSQSLGGIGPSGAMFISPALTKYFSLW
LPSNPQVPTCLSSLAAFSLACQERTTAFSSLVLSAISSRAALKQALSAIPQVEFLLEDSAPRLPNVAVFAIPGIPAE
SLGFFLSQKNIFVGLGYERFQPLSQILQSSGISPFLCHSALHVSFTERTPTTHFSALATALQEGISHLQPLVTQSL SEQ ID NO: 165 - CT721 fragment nucleotide sequence
GACGGGACAAAAATTCACGAAACACGCTCCTTCTCTTGGTTAAACAACCAACAAGCCATCCCTCCTTCCGAAATGGT
GAAGGAGGCTTTTCAACGTTACGCAGACGTATTTTCGTACAGCGCAAATACCTCCATTCTGACTTTACAAGCAGAAG
CTGAAGCTTCTGCCCGCAAACTCACAGGGTGTCAGGAGAAGGCTTTTACCTTTCATTTTATTCTTCATTACCCGAAT
GTCACGGCCATTATCGTGGCCGCTCTTCTGGAAAACCAAAATGCCTTCCAGGGGCGTAATCACCTTCTTGTTCCTTC
TTGCGAGCAACAATTTATCATTAATGCTCTCTGCCGTCGGCAAAACTTAGGGACAACCTATGATTGGGTAACCAGCA
AAAACGGCCGCGTAAAAGAATCCGATCTAGCAGAAGCTCTTTCCCCGCGGACCTTGCTGTTTTCCATATCTGCTGCG
AATGGTATGACAGGATTTCTGGAAGCGATCCCTGAGCTTGCTGCGTTATGTAAAGAACGCGGGGTAATTTTCCACAT
AGACCTGAGTGATATCTTAGGAAGATGCGCGCTACCCGCAGAACTCTATCAAGCAGATATCCTTACTTTTTCTTCAC
AGTCTCTTGGTGGGATTGGTCCCTCAGGAGCGATGTTTATTTCTCCCGCTTTAACAAAATATTTTTCCTTATGGCTT
CCTAGTAATCCACAAGTCCCTACCTGCCTGAGTTCTCTTGCAGCTTTTTCTCTTGCCTGTCAGGAACGTACAACCGC
TTTCTCCTCTCTTGTGCTTTCTGCTATTTCTTCTCGAGCAGCTCTTAAACAGGCTCTTTCCGCTATTCCTCAAGTCG
AATTCCTTTTGGAAGACAGTGCCCCTCGTCTCCCTAATGTCGCTGTCTTTGCTATTCCTGGTATCCCTGCAGAGTCC
TTAGGATTTTTCCTTTCCCAGAAAAATATTTTTGTAGGGTTAGGCTATGAACGCTTCCAGCCTCTATCGCAGATTTT
ACAAAGTTCGGGCATCTCTCCCTTCTTATGCCACAGCGCTTTACACGTATCTTTTACTGAACGTACTCCTACTACAC
ACTTCTCTGCATTAGCAACCGCCTTACAAGAAGGGATCTCTCACCTACAACCACTGGTTACTCAATCCTTA SEQ ID NO: 166 - CT721 fragment protein sequence
DGTKIHETRSFSWLNNQQAIPPSEMVKEAFQRYADVFSYSANTSILTLQAEAEASARKLTGCQEKAFTFHFILHYPN
VTAIIVAALLENQNAFQGRNHLLVPSCEQQFIINALCRRQNLGTTYDWVTSKNGRVKESDLAEALSPRTLLFSISAA
NGMTGFLEAIPELAALCKERGVIFHIDLSDILGRCALPAELYQADILTFSSQSLGGIGPSGAMFISPALTKYFSLWL
PSNPQVPTCLSSLAAFSLACQERTTAFSSLVLSAISSRAALKQALSAIPQVEFLLEDSAPRLPNVAVFAIPGIPAES
LGFFLSQKNIFVGLGYERFQPLSQILQSSGISPFLCHSALHVSFTERTPTTHFSALATALQEGISHLQPLVTQSL SEQ ID NO: 167 - CT127 nucleotide sequence
ATGCCGCACCAAGTCTTATTGTCTCCTGTTTGCGATCTTTTATCGAATGCTGAAGGTATAGAGACGCAAGTACTGTT
TGGAGAAAGGATATGCAACCATAACCATCGACACTATGCCTATTCTCAACTAGTCTTTTCTTCTATATGGAAGCCAT
ACCCTGGCGACTCTCTACAGAATATTCCTCTATTCTCTTCCCAACTGCAGCCTCCTAATGCTGTTGTCTGCTCTCAA
GAAGCTTTTTTAGATCCTTGGCATATCCCCTTACCTTTTGCCGCTCCGCTCCACATAGATAACCAAAATCAAGTGTC
CCTATCTCCTGCTAGCATAGCATTATTAAATTCCAATTCCAGAAGTAACTATGCAAAAGCTTTCTGCTCTACCAAAG
AGATTCGTTTTTTAAATTCTTCATTCTCTCCAAGAGATTTAGTTTCTTTCGCAGAACAATTGATAGATACTCCGTAC
GTTTGGGGTGGCCGGTGCATTCATAAACAGCTTCCTCGTAATGGTGTAGATTGTTCGGGGTATATTCAACTACTTTA
CCAAGTCACAGGAAGAAATATCCCTCGCAATGCTAGAGATCAATACAGAGACTGTTCTCCAGTAAAAGATTTCTCGT
CTCTACCTATAGGAGGACTTATCTTCCTCAAGAAAGCAAGCACGGGACAAATCAACCATGTTATGATGAAAATCTCG
GAGCATGAATTCATTCATGCTGCGGAAAAAATAGGGAAAGTAGAAAAAGTAATCCTAGGAAATAGGGCTTTCTTTAA
AGGGAATCTATTCTGCTCATTAGGTGAACCGCCTATAGAAGCTGTTTTTGGCGTTCCTAAAAATAGAAAAGCCTTCT
TTTGA -continued

SEQUENCE LISTING

SEQ ID NO: 168 - CT127 protein sequence
MPHQVLLSPVCDLLSNAEGIETQVLFGERICNHNHRHYAYSQLVFSSIWKPYPGDSLQNIPLFSSQLQPPNAVVCSQ
EAFLDPWHIPLPFAAPLHIDNQNQVSLSPASIALLNSNSRSNYAKAFCSTKEIRFLNSSFSPRDLVSFAEQLIDTPY
VWGGRCIHKQLPRNGVDCSGYIQLLYQVTGRNIPRNARDQYRDCSPVKDFSSLPIGGLIFLKKASTGQINHVMMKIS
EHEFIHAAEKIGKVEKVILGNRAFFKGNLFCSLGEPPIEAVFGVPKNRKAFF SEQ ID NO: 169 - CT127 fragment nucleotide sequence
CCGCACCAAGTCTTATTGTCTCCTGTTTGCGATCTTTTATCGAATGCTGAAGGTATAGAGACGCAAGTACTGTTTGG
AGAAAGGATATGCAACCATAACCATCGACACTATGCCTATTCTCAACTAGTCTTTTCTTCTATATGGAAGCCATACC
CTGGCGACTCTCTACAGAATATTCCTCTATTCTCTTCCCAACTGCAGCCTCCTAATGCTGTTGTCTGCTCTCAAGAA
GCTTTTTTAGATCCTTGGCATATCCCCTTACCTTTTGCCGCTCCGCTCCACATAGATAACCAAAATCAAGTGTCCCT
ATCTCCTGCTAGCATAGCATTATTAAATTCCAATTCCAGAAGTAACTATGCAAAAGCTTTCTGCTCTACCAAAGAGA
TTCGTTTTTTAAATTCTTCATTCTCTCCAAGAGATTTAGTTTCTTTCGCAGAACAATTGATAGATACTCCGTACGTT
TGGGGTGGCCGGTGCATTCATAAACAGCTTCCTCGTAATGGTGTAGATTGTTCGGGGTATATTCAACTACTTTACCA
AGTCACAGGAAGAAATATCCCTCGCAATGCTAGAGATCAATACAGAGACTGTTCTCCAGTAAAAGATTTCTCGTCTC
TACCTATAGGAGGACTTATCTTCCTCAAGAAAGCAAGCACGGGACAAATCAACCATGTTATGATGAAAATCTCGGAG
CATGAATTCATTCATGCTGCGGAAAAAATAGGGAAAGTAGAAAAAGTAATCCTAGGAAATAGGGCTTTCTTTAAAGG
GAATCTATTCTGCTCATTAGGTGAACCGCCTATAGAAGCTGTTTTTGGCGTTCCTAAAAATAGAAAAGCCTTCTTT SEQ ID NO: 170 - CT127 fragment protein sequence
PHQVLLSPVCDLLSNAEGIETQVLFGERICNHNHRHYAYSQLVFSSIWKPYPGDSLQNIPLFSSQLQPPNAVVCSQE
AFLDPWHIPLPFAAPLHIDNQNQVSLSPASIALLNSNSRSNYAKAFCSTKEIRFLNSSFSPRDLVSFAEQLIDTPYV
WGGRCIHKQLPRNGVDCSGYIQLLYQVTGRNIPRNARDQYRDCSPVKDFSSLPIGGLIFLKKASTGQINHVMMKISE
HEFIHAAEKIGKVEKVILGNRAFFKGNLFCSLGEPPIEAVFGVPKNRKAFF

The invention claimed is:

1. An immunogenic composition comprising an effective amount of:

(a) a combination of isolated *Chlamydia* protein antigens, said combination comprising (i) a CT279 antigen comprising the sequence of SEQ ID NO: 8, an antigen with at least 95% sequence identity to SEQ ID NO: 8, or an immunogenic fragment of SEQ ID NO: 8 that comprises the sequence of SEQ ID NO: 70; and (ii) a CT601 antigen comprising the sequence of SEQ ID NO: 6, an antigen with at least 95% sequence identity to SEQ ID NO: 6, or an immunogenic fragment of SEQ ID NO: 6 that comprises the sequence of SEQ ID NO: 68; and (b) an effective amount of a TH1 and/or TH2 adjuvant.

2. The immunogenic composition of claim 1, wherein:

(a) the CT279 antigen has at least 95% sequence identity to SEQ ID NO: 8; and (b) the CT601 antigen has at least 95% sequence identity to SEQ ID NO: 6.

3. The immunogenic composition of claim 1, wherein:

(a) the CT279 antigen comprises the amino acid sequence of SEQ ID NO: 70; and/or (b) the CT601 antigen comprises the amino acid sequence of SEQ ID NO: 68.

4. The immunogenic composition of claim 1 wherein the protein antigens are in purified or substantially purified form.

5. The immunogenic composition of claim 1, wherein the protein antigens are present as individual separate polypeptides.

6. The immunogenic composition of claim 1, wherein the protein antigens are present as hybrid polypeptides.

* * * * *